(12) United States Patent
Braganza et al.

(10) Patent No.: US 8,518,952 B2
(45) Date of Patent: Aug. 27, 2013

(54) 6 SUBSTITUTED 2-HETEROCYCLYLAMINO PYRAZINE COMPOUNDS AS CHK-1 INHIBITORS

(75) Inventors: John Frederick Braganza, San Diego, CA (US); Michael Raymond Collins, San Diego, CA (US); John Charles Kath, La Mesa, CA (US); Sacha Ninkovic, La Jolla, CA (US); Hui Li, Carlsbad, CA (US); Daniel Tyler Richter, San Diego, CA (US)

(73) Assignee: Pfizer Inc., New York, NY (US)

( * ) Notice: Subject to any disclaimer, the term of this patent is extended or adjusted under 35 U.S.C. 154(b) by 221 days.

(21) Appl. No.: 13/057,558

(22) PCT Filed: Aug. 4, 2009

(86) PCT No.: PCT/IB2009/053389
§ 371 (c)(1),
(2), (4) Date: Feb. 4, 2011

(87) PCT Pub. No.: WO2010/016005
PCT Pub. Date: Feb. 11, 2010

(65) Prior Publication Data
US 2011/0144084 A1 Jun. 16, 2011

Related U.S. Application Data

(60) Provisional application No. 61/086,732, filed on Aug. 6, 2008, provisional application No. 61/229,428, filed on Jul. 29, 2009.

(51) Int. Cl.
*A61K 31/497* (2006.01)
(52) U.S. Cl.
USPC .................................. 514/255.05; 544/405
(58) Field of Classification Search
USPC ......................................................... 544/405
See application file for complete search history.

(56) References Cited

U.S. PATENT DOCUMENTS

| | | | |
|---|---|---|---|
| 6,106,864 | A | 8/2000 | Dolan et al. |
| 6,211,164 | B1 | 4/2001 | Luo et al. |
| 6,383,744 | B1 | 5/2002 | Green et al. |
| 6,413,755 | B1 | 7/2002 | Luyten et al. |
| 6,682,736 | B1 | 1/2004 | Hanson et al. |
| 6,967,198 | B2 | 11/2005 | Benedict et al. |
| 7,704,995 | B2 | 4/2010 | Buhr et al. |

FOREIGN PATENT DOCUMENTS

| | | |
|---|---|---|
| WO | WO9111172 | 8/1991 |
| WO | WO9402518 | 2/1994 |
| WO | WO9855148 | 12/1998 |
| WO | WO0016781 | 3/2000 |
| WO | WO0035298 | 6/2000 |
| WO | WO0116306 | 3/2001 |
| WO | WO0121771 | 3/2001 |
| WO | WO02053596 | 7/2002 |
| WO | WO02070494 | 9/2002 |
| WO | WO03040170 | 5/2003 |
| WO | WO2004113322 | 12/2004 |
| WO | WO2008024974 | 2/2008 |
| WO | WO2009054941 | 4/2009 |

OTHER PUBLICATIONS

Al-Khodairy, F., et al., "Identification and Characterization of New Elements Involved in Checkpoint and Feedback Controls in Fission Yeast", Molecular Biology of the Cell, 1994, 147-160, vol. 5.
Flaggs, G., et al., "Atm-Dependent Interactions of a Mammalian Chk1 Homolog with Meiotic Chromosomes", Current Biology, 1997, 977-986, vol. 7.
Liang, A., et al., "Fast-Dissolving Intraoral Drug Delivery Systems", Expert Opinion in Therapeutic Patents, 2001, 981-986, vol. 11, No. 6.
Nurse, P., "Checkpoint Pathways Come of Age", Cell, 1997, 865-867, vol. 91.
Peng, C., et al., "Mitotic and G2 Checkpoint Control: Regulation of 14-3-3 Protein Binding by Phosphorylation of Cdc25C on Serine-216", Science, 1997, 1501-1505, vol. 277.
Sanchez, Y., et al., "Conservation of the Chk1 Checkpoint Pathway in Mammals: Linkage of DNA Damage to Cdk Regulation Through Cdc25", Science, 1997, 1497-1501, vol. 277.
Tao, Z., et al., "Chk1 Inhibitors for Novel Cancer Treatment", Anti-Cancer Agents in Medicinal Chemistry, 2006, 377-388, vol. 6.
Walworth, N., et al., "Fission Yeast Chk1 Protein Kinase Links the Rad Checkpoint Pathway to Cdc2", Nature, 1993, 368-371, vol. 363.
Weinert, T., "A DNA Damage Checkpoint Meets the Cell Cycle Engine", Science, 1997, 1450-1451, vol. 277.

*Primary Examiner* — Brian McDowell
(74) *Attorney, Agent, or Firm* — Leslie A. Robinson

(57) ABSTRACT

The present invention is directed to compounds of formula (I),

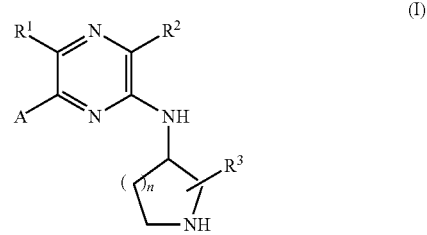

and pharmaceutically acceptable salts thereof, their synthesis, and their use as CHK-1 inhibitors.

18 Claims, No Drawings

6 SUBSTITUTED 2-HETEROCYCLYLAMINO PYRAZINE COMPOUNDS AS CHK-1 INHIBITORS

This application is a National Stage submission under 35 U.S.C. §371 from International Application No. PCT/IB2009/053389, filed Aug. 4, 2009, and claims the benefit of priority of U.S. Provisional Application No. 61/086,732, filed Aug. 6, 2008 and U.S. Provisional Application No. 61/229,428 filed Jul. 29, 2009, the contents of which are hereby incorporated by reference in their entireties.

FIELD OF THE INVENTION

The present invention is directed to compounds, and pharmaceutically acceptable salts thereof, their synthesis, and their use as modulators or inhibitors of check point kinase 1 (CHK-1). The compounds of the present invention are useful for modulating (e.g. inhibiting) CHK-1 activity and for treating diseases or conditions mediated by CHK-1, such as for example, disease states associated with abnormal cell growth such as cancer.

BACKGROUND

It has been well known in the art that check point kinase 1 (CHK-1) is one of the important enzymes that are involved in maintaining the order and fidelity of events in the cell cycle and CHK-1 inhibitors have been proposed for cancer therapy. (Science, 277, 1501-1505 (1997); Science, 277, 1497-1501 (1997)). (Cell, 91, 865-867 (1997); Science, 277, 1450-1451 (1997); Nature, 363, 368-371 (1993); Molec. Biol. Cell, 5, 147-160 (1994)). Flaggs, G. et. al. (1997) Current Biology 7:977-986; U.S. Pat. Nos. 6,967,198, 6,413,755, 6,383,744 and 6,211,164; and International Publication Nos. WO 01/16306, WO 01/21771, WO 00/16781, and WO 02/070494).

SUMMARY OF INVENTION

The current invention is directed to a compound of formula (I)

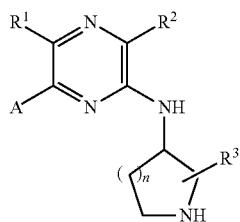

wherein, n is 0, 1 or 2; preferably n is 1 or 2, more preferably, n is 2;
A is of the structure

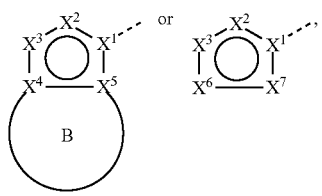

and A is optionally further substituted with 1-6 $R^4$;

$X^1, X^2, X^3, X^4$ and $X^5$ form a 5 member heteroaryl having 1-4 nitrogen ring atoms;

$X^1, X^2, X^3, X^6$ and $X^7$ form a 5 member heteroaryl having 1-4 nitrogen ring atoms;

$X^1$ is N or C; $X^2$ is N, NH or CH; $X^3$ is N; each of $X^4$ and $X^5$ is independently N or C; each of $X^6$ and $X^7$ is independently N, NH or CH;

B together with $X^4$ and $X^5$ form a ring selected from phenyl, 5-6 member heteroaryl, 5-6 member heterocyclyl, $C_5$-$C_6$ cycloalkyl and $C_5$-$C_6$ cycloalkenyl, each of the said 5-6 member heteroaryl and 5-6 member heterocyclyl has 1-3 ring heteroatoms selected from N, O and S;

each of $R^1$ and $R^2$ is independently selected from hydrogen, fluorine, chlorine, —CN, —$OR^b$, —$N(R^b)_2$, and $C_1$-$C_3$ alkyl optionally substituted with 1-6 groups selected from fluorine, chlorine and —CN;

$R^3$ represents 1-6 optional substituents independently selected from the group consisting of -oxo- and $R^0$;

two $R^3$ attached to the same ring atom, together with the ring atom attached to, may form a ring selected from $C_3$-$C_6$ cycloalkyl, $C_5$-$C_6$ cycloalkenyl and 3-6 member heterocyclyl; each of the said $C_3$-$C_6$ cycloalkyl, $C_5$-$C_6$ cycloalkenyl and 3-6 member heterocyclyl is optionally further substituted with 1-5 groups selected from -oxo- and $R^w$;

two $R^3$ attached to two adjacent ring atoms, together with the ring atoms attached to, may form a fused ring selected from $C_3$-$C_6$ cycloalkyl, $C_5$-$C_6$ cycloalkenyl, 3-6 member heterocyclyl, phenyl and 5-6 member heteroaryl; the said $C_3$-$C_6$ cycloalkyl, $C_5$-$C_6$ cycloalkenyl, 3-6 member heterocyclyl, phenyl and 5-6 member heteroaryl is optionally further substituted with 1-5 groups selected from oxo and $R^w$;

two $R^3$ attached to, two different ring atoms with at least one ring atom in between, may form a $C_1$-$C_4$ alkylene, a 2-4 member heteroalkylene, or a diradical selected from the group consisting of:

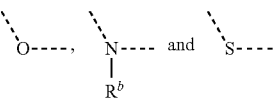

such $C_1$-$C_4$ alkylene, 2-4 member heteroalkylene and diradical together with the azetidinyl (when n is 0), pyrrolidinyl (when n is 1) or the piperidinyl (when n is 2) form a bicyclic bridged ring system, the said bicyclic bridged ring system having a total of 6-9 ring atoms with 1-3 of the ring atoms selected from O, N and S; the $C_1$-$C_4$ alkylene or a 1-4 member heteroalkylene is optionally further substituted with 1-5 groups selected from -oxo- and $R^w$;

each $R^4$ is independently $R^0$;

each $R^0$ is independently selected from the group consisting of (a) fluorine, chlorine and —CN; (b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; (c) $C_3$-$C_6$ cycloalkyl, -L-($C_3$-$C_6$ cycloalkyl), 4-6 member heterocyclyl, -L-(4-6 member heterocyclyl), phenyl, -L-phenyl, 5-6 member heteroaryl, -L-(5-6 member heteroaryl), $C_5$-$C_6$ cycloalkenyl, -L-($C_5$-$C_6$ cycloalkenyl), wherein each $C_3$-$C_6$ cycloalkyl, phenyl, 5-6 member heteroaryl, 4-6 member heterocyclyl and $C_5$-$C_6$ cycloalkenyl is independently optionally further substituted with 1-6 $R^x$; (d) —$N(R^a)_2$, -L-$N(R^a)_2$; (e) —$OR^a$, -L-$OR^a$; (f) —O-L-$N(R^a)_2$, —$N(R^b)$-L-$OR^a$, -L-O-L-$N(R^a)_2$, -L-$N(R^b)$-L-$OR^a$; (g) —C(O)$R^a$, —C(O)$OR^a$, —C(O)$N(R^a)_2$, -L-C(O)$R^a$, -L-C(O)$OR^a$, -L-C(O)$N(R^a)_2$; (h) —$N(R^b)$-(L)$_p$-C(O)$R^a$, —$N(R^b)$-(L)$_p$-C(O)$OR^a$, —$N(R^b)$-(L)$_p$-C(O)$N(R^a)_2$, -L-N ($R^b$)-(L)$_p$-C(O)R$^a$, -L-N(R$^b$)-(L)$_p$-C(O)OR$^a$, -L-N(R$^b$)-(L)$_p$-C(O)N(R$^a$)$_2$; (i) —O-(L)$_p$-C(O)R$^a$, —O-(L)$_p$-C(O)N(R$^a$)$_2$, —O-(L)$_p$-C(O)O—R$^a$, -L-O-(L)$_p$-C(O)R$^a$, -L-O-(L)$_p$-C(O)N(R$^a$)$_2$-L-O-(L)$_p$-C(O)O—R$^a$; (j) —S(O)$_2$R$^a$, —S(O)$_2$OR$^a$, —S(O)$_2$N(R$^a$)$_2$, -L-S(O)$_2$R$^a$, -L-S(O)$_2$OR$^a$, -L-S(O)$_2$N(R$^a$)$_2$; (k) —O-(L)$_p$-S(O)$_2$R$^a$, )—O-(L)$_p$-S(O)$_2$O—R$^a$, —O-(L)$_p$-S(O)$_2$N(R$^a$)$_2$, -L-O-(L)$_p$-S(O)$_2$R$^a$, -L—O-(L)$_p$-S(O)$_2$O—R$^{a'}$)-L-O-(L)$_p$-S(O)$_2$N(R$^a$)$_2$; (l) —N(R$^b$)-(L)$_p$-S(O)$_2$R$^a$, —N(R$^b$)-(L)$_p$-S(O)$_2$O—R$^a$, —N(R$^b$)-(L)$_p$-S(O)$_2$N(R$^a$)$_2$, -L-N(R$^b$)-(L)$_p$-S(O)$_2$R$^a$, -L-N(R$^b$)-(L)$_p$-S(O)$_2$O—R$^{a'}$)-L-N(R$^b$)-(L)$_p$-S(O)$_2$N(R$^a$)$_2$; and (m) —C(R$^a$)=N—CN, -L-C(R$^a$)=N—CN;

each R$^a$ is independently selected from the group consisting of (a) hydrogen, $C_1$-$C_6$ alkyl and $C_1$-$C_6$ perfluoroalkyl; (b) $C_1$-$C_6$ alkyl further substituted by 1-2 groups selected from fluorine, chlorine, —CN, —OR$^b$ and —N(R$^b$)$_2$; (c) $C_2$-$C_6$ alkenyl and $C_2$-$C_6$ alkynyl, each of which is optionally further substituted by 1-3 groups selected from fluorine, chlorine, —CN, —OR$^b$ and —N(R$^b$)$_2$; (d) —($C_1$-$C_6$ alkylene)$_p$-($C_3$-$C_6$ cycloalkyl), —($C_1$-$C_6$ alkylene)$_p$-phenyl, —($C_1$-$C_6$ alkylene)$_p$-(5-6 member heteroaryl), —($C_1$-$C_6$ alkylene)$_p$-(4-6 member heterocyclyl), —($C_1$-$C_6$ alkylene)$_p$-($C_5$-$C_6$ cycloalkenyl), wherein each $C_1$-$C_6$ alkylene is optionally further substituted with 1-3 groups selected from fluorine, chlorine and —CN, wherein each of the said $C_3$-$C_6$ cycloalkyl, phenyl, 5-6 member heteroaryl, 4-6 member heterocyclyl and $C_5$-$C_6$ cycloakenyl is independently optionally further substituted with 1-3 R$^y$;

or two R$^a$ connected to the same nitrogen form a 3-10 member heterocyclyl or 5-10 member heteroaryl, the said 3-10 member heterocyclyl and the said 5-10 member heteroaryl is optionally further substituted with 1-3 R$^z$;

each L is independently $C_1$-$C_6$ alkylene, $C_2$-$C_6$ alkenylene or $C_2$-$C_6$ alkynylene, and each L is optionally further substituted with 1-3 groups selected from fluorine, chlorine, OH and —CN;

each R$^w$, R$^x$, R$^y$ and R$^z$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; (ii) $C_1$-$C_6$ alkyl further substituted with 1-2 groups selected from fluorine, chlorine, —CN, —OR$^b$ and —N(R$^b$)$_2$; (iii) —C(O)—R$^b$, —C(O)OR$^b$, —C(O)—N(R$^b$)$_2$; (iv) —N(R$^b$)—C(O)—R$^b$, —N(R$^b$)—C(O)OR$^b$, —N(R$^b$)—C(O)—N(R$^b$)$_2$; (v) —O—C(O)—R$^b$, —o—C(O)OR$^b$, —O—C(O)—N(R$^b$)$_2$; (vi) —S(O)$_2$—R$^b$, —S(O)$_2$—O—R$^b$—S(O)$_2$—N(R$^b$)$_2$; (vii) —N(R$^b$)—S(O)$_2$—R$^b$, —N(R$^b$)—S(O)$_2$—O—R$^b$, —N(R$^b$)—S(O)$_2$—N(R$^b$)$_2$; and (viii) —O—S(O)$_2$—R$^b$, —O—S(O)$_2$—O—R$^b$—O—S(O)$_2$—N(R$^b$)$_2$;

each R$^b$ is independently selected from the group consisting of hydrogen, $C_1$-$C_3$ alkyl, $C_1$-$C_3$ perfluoroalkyl and $C_1$-$C_3$ alkyl further substituted by 1-2 groups selected from fluorine, chlorine and CN;

each p is independently 0 or 1;

or a pharmaceutically acceptable salt thereof.

In one preferred embodiment, the invention provides a compound of formula II, and pharmaceutically acceptable salt thereof.

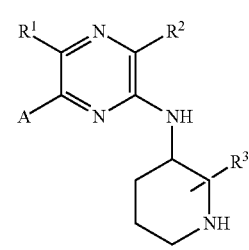

(II)

In another preferred embodiment, the invention provides a compound of formula III, or pharmaceutically acceptable salt thereof,

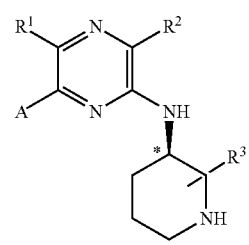

(III)

wherein the stereo chemistry of the chiral center marked by "*" is the absolute stereochemistry as indicated in formula (III). In one aspect of this embodiment, the compound has 80% or higher, preferably 90% or higher, more preferably 95% or higher, even more preferably 99% or higher, of enantiomeric excess with regard to the absolute stereo chemistry indicated in above formula III.

In another preferred embodiment, the invention provides a compound of formula IV, or pharmaceutically acceptable salt thereof.

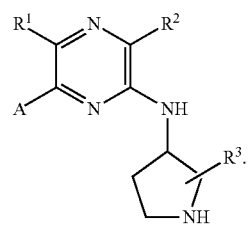

(IV)

In another preferred embodiment, the invention provides a compound of formula V, or pharmaceutically acceptable salt thereof.

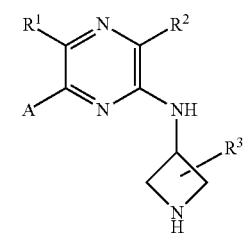

(V)

In a preferred aspect of the invention or any of the above described embodiments of the invention, and in combination with any other preferred aspects not inconsistent, A is

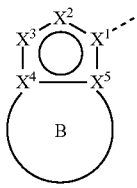

and A is optionally further substituted with 1-6 $R^4$.

In another preferred embodiment, the invention provides a compound of formula I,

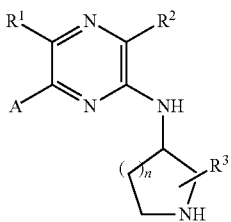

wherein, n is 0, 1 or 2, preferably, n is 1 or 2, more preferably n is 2;

A is a heteroaryl selected from the group consisting of

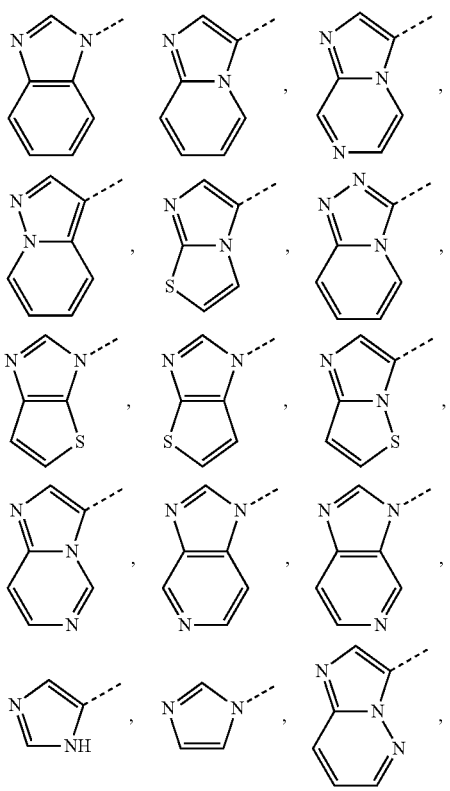

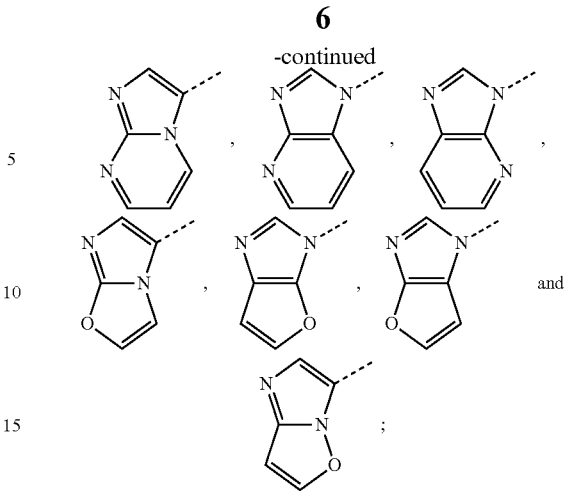

and A is optionally further substituted with 1-5 $R^4$;

each of $R^1$ and $R^2$ is independently selected from hydrogen, fluorine, chlorine, —CN, —$OR^b$, —$N(R_b)^2$, and $C_1$-$C_3$ alkyl optionally substituted with 1-6 groups selected from fluorine, chlorine and —CN;

$R^3$ represents 1-6 optional substituents independently selected from the group consisting of -oxo- and $R^0$;

each $R^4$ is independently $R^0$;

each $R^0$ is independently selected from the group consisting of (a) fluorine, chlorine and —CN; (b) $C_1$-$C_6$ alkyl, optionally further substituted with 1-6 groups selected from fluorine, chlorine and CN; (c) $C_3$-$C_6$ cycloalkyl, -L-($C_3$-$C_6$ cycloalkyl), 4-6 member heterocyclyl, -L-(4-6 member heterocyclyl), wherein each $C_3$-$C_6$ cycloalkyl and 4-6 member heterocyclyl is independently optionally further substituted with 1-6 $R^x$; (d) —$N(R^a)_2$, -L-$N(R^a)_2$; (e) —$OR^a$, -L-$OR^a$; and (g) —$C(O)R^a$, —$C(O)OR^a$, —$C(O)N(R^a)_2$, -L-$C(O)R^a$, -L-$C(O)OR^a$, -L-$C(O)N(R^a)_2$;

each $R^a$ is independently selected from the group consisting of (a) hydrogen, $C_1$-$C_6$ alkyl and $C_1$-$C_6$ perfluoroalkyl; (b) $C_1$-$C_6$ alkyl further substituted by 1-2 groups selected from fluorine, chlorine, —CN, —$OR^b$ and —$N(R^b)_2$; (d) —($C_1$-$C_6$ alkylene)$_p$-($C_3$-$C_6$ cycloalkyl), —($C_1$-$C_6$ alkylene)$_p$-(4-6 member heterocyclyl), wherein each $C_1$-$C_6$ alkylene is optionally further substituted with 1-3 groups selected from fluorine, chlorine and —CN, wherein each of the said $C_3$-$C_6$ cycloalkyl and 4-6 member heterocyclyl is independently optionally further substituted with 1-3 $R^y$;

or two $R^a$ connected to the same nitrogen form a 3-10 member heterocyclyl or 5-10 member heteroaryl, the said 3-10 member heterocyclyl and the said 5-10 member heteroaryl is optionally further substituted with 1-3 $R^z$;

each L is independently $C_1$-$C_6$ alkylene optionally further substituted with 1-3 groups selected from fluorine, chlorine, OH and —CN;

each $R^w$, $R^x$, $R^y$ and $R^z$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$;

(ii) $C_1$-$C_6$ alkyl further substituted with 1-2 groups selected from fluorine, chlorine, —CN, —$OR^b$ and —$N(R^b)_2$; (iii) —C(O)—$R^b$, —C(O)$OR^b$, —C(O)—$N(R^b)_2$; and each $R^b$ is independently selected from the group consisting of hydrogen, $C_1$-$C_3$ alkyl, $C_1$-$C_3$ perfluoroalkyl and $C_1$-$C_3$ alkyl further substituted by 1-2 groups selected from fluorine, chlorine and CN;

or a pharmaceutically acceptable salt thereof.

In another preferred embodiment, the invention provides compound of formula II,

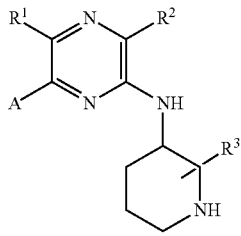

wherein,

A is a heteroaryl selected from the group consisting of

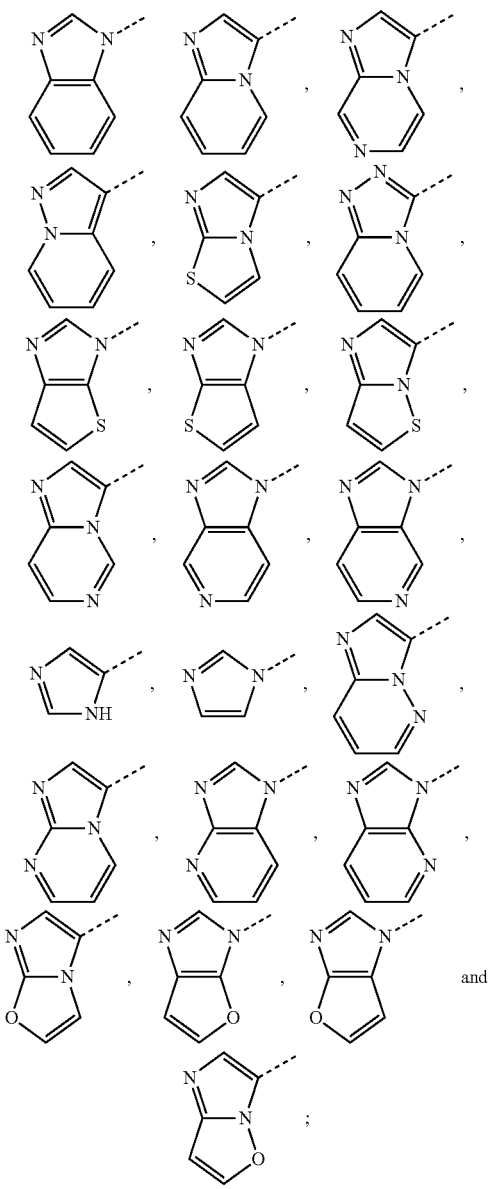

A is optionally further substituted with 1-5 $R^4$;

each of $R^1$ and $R^2$ is independently selected from hydrogen, fluorine, chlorine, —CN, —$OR^b$, —$N(R_b)^2$, and $C_1$-$C_3$ alkyl optionally substituted with 1-6 groups selected from fluorine, chlorine and —CN;

$R^3$ represents 1-6 optional substituents independently selected from the group consisting of -oxo- and $R^0$; further more, two of the $R^3$ may also (i) two $R^3$ attached to the same ring atom, together with the ring atom attached to, may also form a ring selected from $C_3$-$C_6$ cycloalkyl, $C_5$-$C_6$ cycloalkenyl and 3-6 member heterocyclyl; each of the said $C_3$-$C_6$ cycloalkyl, $C_5$-$C_6$ cycloalkenyl and 3-6 member heterocyclyl is optionally further substituted with 1-5 groups selected from -oxo- and $R^w$; or (ii) two $R^3$ attached to two adjacent ring atoms, together with the ring atoms attached to, may also form a fused ring selected from $C_3$-$C_6$ cycloalkyl, $C_5$-$C_6$ cycloalkenyl, 3-6 member heterocyclyl, phenyl, 5-6 member heteroaryl; the said $C_3$-$C_6$ cycloalkyl, $C_5$-$C_6$ cycloalkenyl, 3-6 member heterocyclyl, phenyl and 5-6 member heteroaryl is optionally further substituted with 1-5 groups selected from -oxo- and $R^w$; or (iii) two $R^3$ attached to, two different ring atoms with at least one ring atom in between, may form a $C_1$-$C_4$ alkylene, a 2-4 member heteroalkylene, or a diradical selected from the group consisting of:

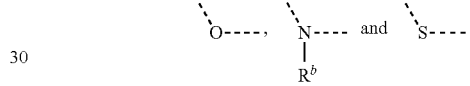

such $C_1$-$C_4$ alkylene, 2-4 member heteroalkylene and diradical together with the piperidinyl (when n is 2) form a bicyclic bridged ring system, the said bicyclic bridged ring system having a total of 6-9 ring atoms with 1-3 of the ring atoms selected from N, O and S; the $C_1$-$C_4$ alkylene or a 1-4 member heteroalkylene is optionally further substituted with 1-5 groups selected from -oxo- and $R^w$;

each $R^4$ is independently $R^0$;

each $R^0$ is independently elected from the group consisting of (a) fluorine, chlorine and —CN; (b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; (c) $C_3$-$C_6$ cycloalkyl, -L-($C_3$-$C_6$ cycloalkyl), 4-6 member heterocyclyl, -L-(4-6 member heterocyclyl), phenyl, -L-phenyl, 5-6 member heteroaryl, -L-(5-6 member heteroaryl), $C_5$-$C_6$ cycloalkenyl, -L-($C_5$-$C_6$ cycloalkenyl), wherein each $C_3$-$C_6$ cycloalkyl, phenyl, 5-6 member heteroaryl, 4-6 member heterocyclyl and $C_5$-$C_6$ cycloalkenyl is independently optionally further substituted with 1-6 $R^x$; (d) —N($R^a$)$_2$, -L-N($R^a$)$_2$; (e) —$OR^a$, -L-$OR^a$; (f) —O-L-N($R^a$)$_2$, —N($R^b$)-L-$OR^a$, -L-O-L-N($R^a$)$_2$, -L-N($R^b$)-L-$OR^a$; (g) —C(O)$R^a$, —C(O)$OR^a$, —C(O)N($R^a$)$_2$, -L-C(O)$R^a$, -L-C(O)$OR^a$, -L-C(O)N($R^a$)$_2$; (h) —N($R^b$)-(L)$_p$-C(O)$R^a$, —N($R^b$)-(L)$_p$-C(O)$OR^a$, —N($R^b$)-(L)$_p$-C(O)N($R^a$)$_2$, -L-N($R^b$)-(L)$_p$-C(O)$R^a$, -L-N($R^b$)-(L)$_p$-C(O)$OR^a$, -L-N($R^b$)-(L)$_p$-C(O)N($R^a$)$_2$; (i) —O-(L)$_p$-C(O)$R^a$, —O-(L)$_p$-C(O)N($R^a$)$_2$, —O-(L)$_p$-C(O)O—$R^a$, -L-O-(L)$_p$-C(O)$R^a$, -L-O-(L)$_p$-C(O)N($R^a$)$_2$-L-O-(L)$_p$-C(O)O—$R^a$, and (m) —C($R^a$)=N—CN, -L-C($R^a$)=N—CN;

each $R^a$ is independently selected from the group consisting of (a) hydrogen, $C_1$-$C_6$ alkyl and $C_1$-$C_6$ perfluoroalkyl; (b) $C_1$-$C_6$ alkyl further substituted by 1-2 groups selected from fluorine, chlorine, —CN, —$OR^b$ and —N($R^b$)$_2$; (c) $C_2$-$C_6$ alkenyl and $C_2$-$C_6$ alkynyl, each of which is optionally further substituted by 1-3 groups selected from fluorine, chlorine, —CN, —OR$^b$ and —N(R$^b$)$_2$; (d) —(C$_1$-C$_6$ alkylene)$_p$-(C$_3$-C$_6$ cycloalkyl), —(C$_1$-C$_6$ alkylene)$_p$-phenyl, —(C$_1$-C$_6$ alkylene)$_p$-(5-6 member heteroaryl), —(C$_1$-C$_6$ alkylene)$_p$-(4-6 member heterocyclyl), —(C$_1$-C$_6$ alkylene)$_p$-(C$_5$-C$_6$ cycloalkenyl), wherein each C$_1$-C$_6$ alkylene is optionally further substituted with 1-3 groups selected from fluorine, chlorine and —CN, wherein each of the said C$_3$-C$_6$ cycloalkyl, phenyl, 5-6 member heteroaryl, 4-6 member heterocyclyl and C$_5$-C$_6$ cycloakenyl is independently optionally further substituted with 1-3 R$^y$;

or two R$^a$ connected to the same nitrogen form a 3-10 member heterocyclyl or 5-10 member heteroaryl, the said 3-10 member heterocyclyl and the said 5-10 member heteroaryl is optionally further substituted with 1-3 R$^z$;

each L is independently C$_1$-C$_6$ alkylene and C$_2$-C$_6$ alkenylene, and each L is optionally further substituted with 1-3 groups selected from fluorine, chlorine, OH and —CN;

each R$^w$, R$^x$, R$^y$ and R$^z$ is independently selected from the group consisting of (i) fluorine, chlorine, —CN, —OR$^b$, C$_1$-C$_6$ alkyl, C$_1$-C$_3$ perfluoroalkyl, C$_2$-C$_6$ alkenyl, C$_2$-C$_6$ alkynyl and —N(R$^b$)$_2$;
(ii) C$_1$-C$_6$ alkyl further substituted with 1-2 groups selected from fluorine, chlorine, —CN, —OR$^b$ and —N(R$^b$)$_2$; (iii) —C(O)—R$^b$, —C(O)OR$^b$, —C(O)—N(R$^b$)$_2$; (iv) —N(R$^b$)—C(O)—R$^b$, —N(R$^b$)—C(O)OR$^b$, —N(R$^b$)—C(O)—N(R$^b$)$_2$; (v) —O—C(O)—R$^b$, —o—C(O)OR$^b$, —O—C(O)—N(R$^b$)$_2$;

each R$^b$ is independently selected from the group consisting of hydrogen, C$_1$-C$_3$ alkyl, C$_1$-C$_3$ perfluoroalkyl and C$_1$-C$_3$ alkyl further substituted by 1-2 groups selected from fluorine, chlorine and CN;

each p is independently 0 or 1;
or a pharmaceutically acceptable salt thereof.

In another preferred embodiment, the invention provides compound of formula I,

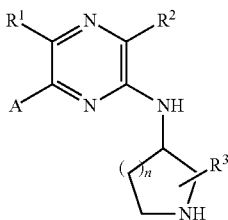

(I)

wherein,
n is 1 or 2, preferably n is 2;
A is a heteroaryl selected from the group consisting of

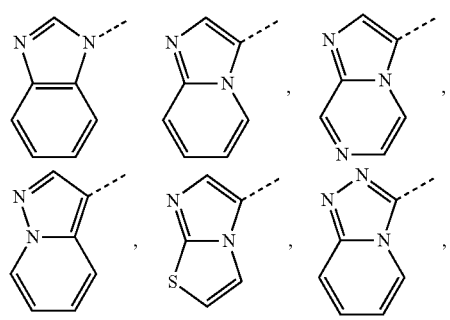

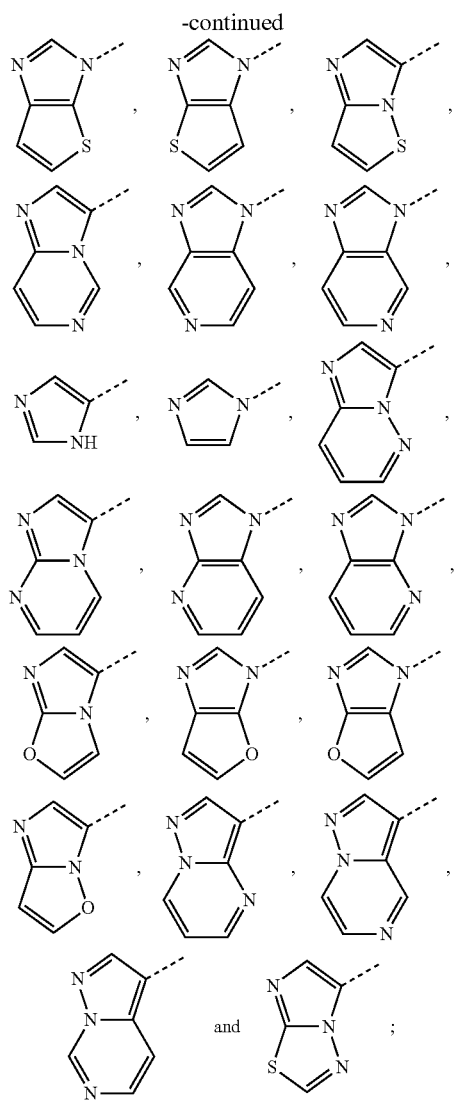

A is optionally further substituted with 1-5 R$^4$;
R$^1$ is hydrogen;
R$^2$ is selected from hydrogen, fluorine, chlorine, —CN, —OR$^b$, and C$_1$-C$_3$ alkyl;
R$^3$ represents 1-6 optional substituents independently selected from the group consisting of -oxo- and R$^0$; further more, when n is 2, two R$^3$ attached to, two different ring atoms with at least one ring atom in between, may form a C$_1$-C$_4$ alkylene, a 2-4 member heteroalkylene, or a diradical selected from the group consisting of:

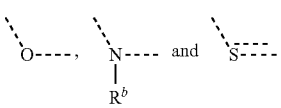

such C$_1$-C$_4$ alkylene, 2-4 member heteroalkylene and diradical together with the piperidinyl (when n is 2) form a bicyclic bridged ring system, the said bicyclic bridged ring system having a total of 6-9 ring atoms with 1-3 of the ring atoms selected from N, O and S; the C$_1$-C$_4$ alkylene or a 1-4 member heteroalkylene is optionally further substituted with 1-5 groups selected from -oxo- and $R^w$;

each $R^4$ is independently $R^0$;

each $R^0$ is independently selected from the group consisting of (a) fluorine, chlorine and —CN; (b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; (c) $C_3$-$C_6$ cycloalkyl, -L-($C_3$-$C_6$ cycloalkyl), 4-6 member heterocyclyl, -L-(4-6 member heterocyclyl), wherein each $C_3$-$C_6$ cycloalkyl and 4-6 member heterocyclyl is optionally further substituted with 1-6 $R^x$; (d) —N($R^a$)$_2$, -L-N($R^a$)$_2$; (e) —OR$^a$, -L-OR$^a$; and (f) —C(O)R$^a$, —C(O)OR$^a$, —C(O)N($R^a$)$_2$, -L-C(O)R$^a$, -L-C(O)OR$^a$, -L-C(O)N($R^a$)$_2$;

each $R^a$ is independently selected from the group consisting of (a) hydrogen, $C_1$-$C_6$ alkyl and $C_1$-$C_6$ perfluoroalkyl; and (b) $C_1$-$C_6$ alkyl further substituted by 1-2 groups selected from fluorine, chlorine, —CN, —OR$^b$ and —N(R$^b$)$_2$; (c) —($C_1$-$C_6$ alkylene)$_p$-($C_3$-$C_6$ cycloalkyl), —($C_1$-$C_6$ alkylene)$_p$-(4-6 member heterocyclyl), wherein each $C_1$-$C_6$ alkylene is optionally further substituted with 1-3 groups selected from fluorine, chlorine and —CN, wherein each of the said $C_3$-$C_6$ cycloalkyl, 4-6 member heterocyclyl is independently optionally further substituted with 1-3 $R^y$;

or two $R^a$ connected to the same nitrogen form a 3-10 member heterocyclyl or 5-10 member heteroaryl, the said 3-10 member heterocyclyl and the said 5-10 member heteroaryl is optionally further substituted with 1-3 $R^z$;

each L is independently $C_1$-$C_6$ alkylene and each L is optionally further substituted with 1-3 groups selected from fluorine, chlorine, OH and —CN;

each $R^w$, $R^x$, $R^y$ and $R^z$ is independently selected from the group consisting of (i) fluorine, chlorine, —CN, —OR$^b$, $C_1$-$C_6$ alkyl, $C_1$-$C_3$ perfluoroalkyl and —N(R$^b$)$_2$; (ii) $C_1$-$C_6$ alkyl further substituted with 1-2 groups selected from fluorine, chlorine, —CN, —OR$^b$ and —N(R$^b$)$_2$;

each $R^b$ is independently selected from the group consisting of hydrogen, $C_1$-$C_3$ alkyl, $C_1$-$C_3$ perfluoroalkyl and $C_1$-$C_3$ alkyl further substituted by 1-2 groups selected from fluorine, chlorine and CN;

each p is independently 0 or 1;

or a pharmaceutically acceptable salt thereof.

In another preferred embodiment, the invention provides compound of formula I,

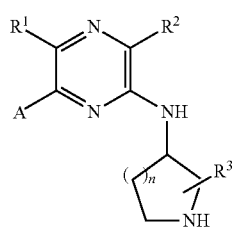
(I)

wherein,
n is 1 or 2, preferably n is 2;
A is a heteroaryl selected from the group consisting of

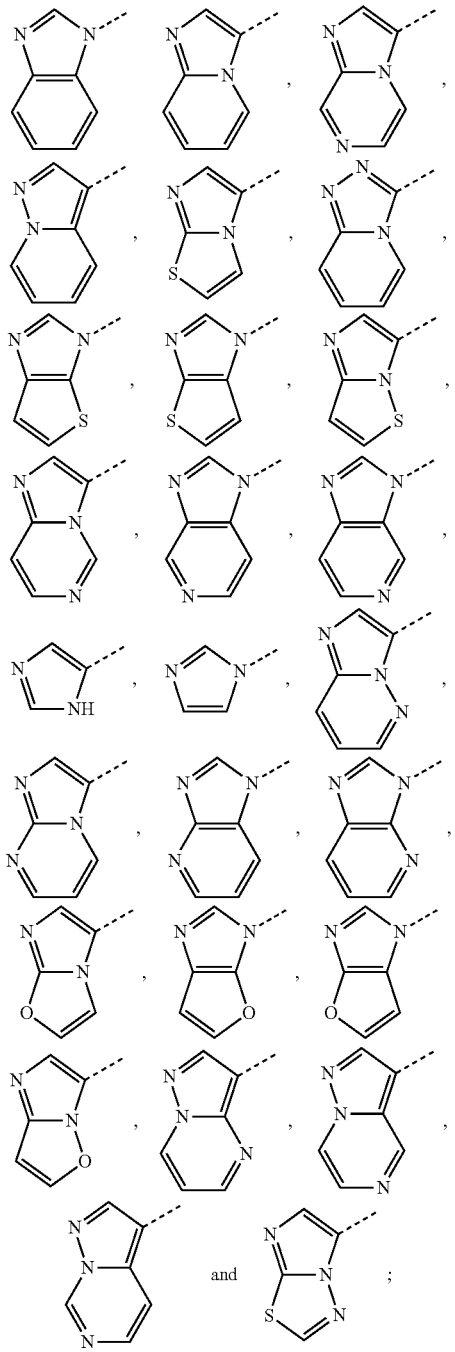

A is optionally further substituted with 1-5 $R^4$;
$R^1$ is hydrogen;
$R^2$ is selected from hydrogen, fluorine, chlorine, —CN, —OR$^b$ and $C_1$-$C_3$ alkyl;
$R^3$ represents 1-6 optional substituents independently selected from the group consisting of -oxo- and $R^0$;
each $R^4$ is independently $R^0$;
each $R^0$ is independently selected from the group consisting of (a) fluorine, chlorine and —CN; (b) $C_1$-$C_6$ alkyl optionally further substituted with 1-6 groups selected from fluorine, chlorine and CN; (c) $C_3$-$C_6$ cycloalkyl, -L-($C_3$-$C_6$ cycloalkyl), 4-6 member heterocyclyl, -L-(4-6 member heterocyclyl), wherein each $C_3$-$C_6$ cycloalkyl and 4-6 member heterocyclyl is optionally further substituted with 1-6 $R^x$; (d) —$OR^a$, -L-$OR^a$; and (e) —C(O)N($R^a$)$_2$, -L-C(O)N($R^a$)$_2$;

each $R^a$ is independently selected from the group consisting of (a) hydrogen, $C_1$-$C_6$ alkyl and $C_1$-$C_6$ perfluoroalkyl; and (b) $C_1$-$C_6$ alkyl further substituted by 1-2 groups selected from fluorine, chlorine, —CN, —$OR^b$ and —N($R^b$)$_2$; (c) —($C_1$-$C_6$ alkylene)$_p$-($C_3$-$C_6$ cycloalkyl), —($C_1$-$C_6$ alkylene)$_p$ -(4-6 member heterocyclyl), wherein each $C_1$-$C_6$ alkylene is optionally further substituted with 1-3 groups selected from fluorine, chlorine and —CN, wherein each of the said $C_3$-$C_6$ cycloalkyl, 4-6 member heterocyclyl is independently optionally further substituted with 1-3 $R^y$;

or two $R^a$ connected to the same nitrogen form a 3-10 member heterocyclyl or 5-10 member heteroaryl, the said 3-10 member heterocyclyl and the said 5-10 member heteroaryl is optionally further substituted with 1-3 $R^z$;

each L is independently $C_1$-$C_6$ alkylene and each L is optionally further substituted with 1-3 groups selected from fluorine, chlorine, OH and —CN;

each $R^w$, $R^x$, $R^y$ and $R^z$ is independently selected from the group consisting of (i) fluorine, chlorine, —CN, —$OR^b$ and $C_1$-$C_6$ alkyl; (ii) $C_1$-$C_6$ alkyl further substituted with 1-2 groups selected from fluorine, chlorine and —CN;

each $R^b$ is independently selected from the group consisting of hydrogen and $C_1$-$C_3$ alkyl;

each p is independently 0 or 1;

or a pharmaceutically acceptable salt thereof.

In a preferred aspect of the invention or any of the above described embodiments of the invention, and in combination with any other preferred aspects not inconsistent, A is

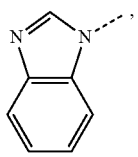

and A is optionally further substituted with 1-5 $R^4$.

In another preferred aspect of the invention or any of the above described embodiments of the invention, and in combination with any other preferred aspects not inconsistent, A is

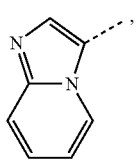

and A is optionally further substituted with 1-5 $R^4$.

In another preferred aspect of the invention or any of the above described embodiments of the invention, and in combination with any other preferred aspects not inconsistent, A is

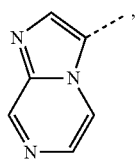

and A is optionally further substituted with 1-4 $R^4$.

In another preferred aspect of the invention or any of the above described embodiments of the invention, and in combination with any other preferred aspects not inconsistent, A is

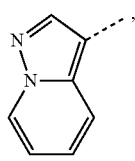

and A is optionally further substituted with 1-5 $R^4$.

In another preferred aspect of the invention or any of the above described embodiments of the invention, and in combination with any other preferred aspects not inconsistent, A is

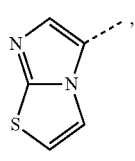

and A is optionally further substituted with 1-3 $R^4$.

In another preferred aspect of the invention or any of the above described embodiments of the invention, and in combination with any other preferred aspects not inconsistent, A is

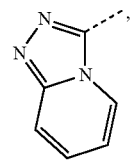

and A is optionally further substituted with 1-4 $R^4$.

In another preferred aspect of the invention or any of the above described embodiments of the invention, and in combination with any other preferred aspects not inconsistent, A is

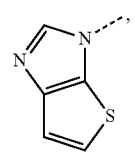

and A is optionally further substituted with 1-3 $R^4$.

In another preferred aspect of the invention or any of the above described embodiments of the invention, and in combination with any other preferred aspects not inconsistent, A is

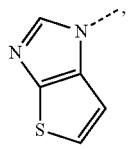

and A is optionally further substituted with 1-3 R$^4$.

In another preferred aspect of the invention or any of the above described embodiments of the invention, and in combination with any other preferred aspects not inconsistent, A is

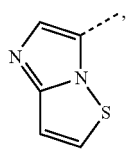

and A is optionally further substituted with 1-3 R$^4$.

In another preferred aspect of the invention or any of the above described embodiments of the invention, and in combination with any other preferred aspects not inconsistent, A is

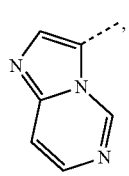

and A is optionally further substituted with 1-4 R$^4$.

In another preferred aspect of the invention or any of the above described embodiments of the invention, and in combination with any other preferred aspects not inconsistent, A is

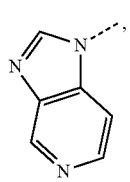

and A is optionally further substituted with 1-4 R$^4$.

In another preferred aspect of the invention or any of the above described embodiments of the invention, and in combination with any other preferred aspects not inconsistent, A is

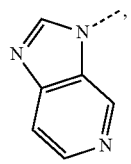

and A is optionally further substituted with 1-4 R$^4$.

In another preferred aspect of the invention or any of the above described embodiments of the invention, and in combination with any other preferred aspects not inconsistent, A is

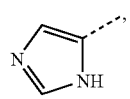

and A is optionally further substituted with 1-3 R$^4$.

In another preferred aspect of the invention or any of the above described embodiments of the invention, and in combination with any other preferred aspects not inconsistent, wherein A is

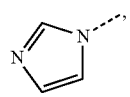

and A is optionally further substituted with 1-3 R$^4$.

In another preferred aspect of the invention or any of the above described embodiments of the invention, and in combination with any other preferred aspects not inconsistent, wherein A is

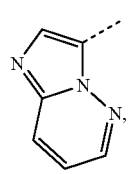

and A is optionally further substituted with 1-4 R$^4$.

In another preferred aspect of the invention or any of the above described embodiments of the invention, and in combination with any other preferred aspects not inconsistent, wherein A is

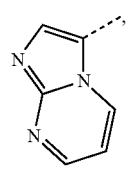

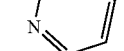

and A is optionally further substituted with 1-4 R$^4$.

In another preferred aspect of the invention or any of the above described embodiments of the invention, and in combination with any other preferred aspects not inconsistent, A is

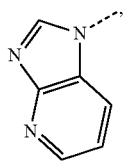

and A is optionally further substituted with 1-4 $R^4$.

In another preferred aspect of the invention or any of the above described embodiments of the invention, and in combination with any other preferred aspects not inconsistent, A is

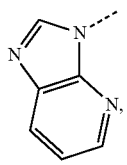

and A is optionally further substituted with 1-4 $R^4$.

In another preferred aspect of the invention or any of the above described embodiments of the invention, and in combination with any other preferred aspects not inconsistent, $R^1$ is hydrogen, In another preferred aspect of the invention or any of the above described embodiments of the invention, and in combination with any other preferred aspects not inconsistent, $R^1$ is selected from hydrogen, fluorine, chlorine and —CN.

In another preferred aspect of the invention or any of the above described embodiments of the invention, and in combination with any other preferred aspects not inconsistent, $R^1$ is $C_1$-$C_3$ alkyl.

In another preferred aspect of the invention or any of the above described embodiments of the invention, and in combination with any other preferred aspects not inconsistent, $R^1$ is $C_1$-$C_3$ alkyl further substituted with 1-6 fluorine.

In another preferred aspect of the invention or any of the above described embodiments of the invention, and in combination with any other preferred aspects not inconsistent, $R^1$ is $C_1$-$C_3$ alkyl further substituted with 1-2 groups selected from chlorine and —CN.

In another preferred aspect of the invention or any of the above described embodiments of the invention, and in combination with any other preferred aspects not inconsistent, $R^1$ is —$OR^b$.

In another preferred aspect of the invention or any of the above described embodiments of the invention, and in combination with any other preferred aspects not inconsistent, $R^1$ is —$N(R^b)_2$.

In another preferred aspect of the invention or any of the above described embodiments of the invention, and in combination with any other preferred aspects not inconsistent, $R^2$ is hydrogen, In another preferred aspect of the invention or any of the above described embodiments of the invention, and in combination with any other preferred aspects not inconsistent, $R^2$ is selected from hydrogen, fluorine, chlorine and —CN.

In another preferred aspect of the invention or any of the above described embodiments of the invention, and in combination with any other preferred aspects not inconsistent, $R^2$ is $C_1$-$C_3$ alkyl.

In another preferred aspect of the invention or any of the above described embodiments of the invention, and in combination with any other preferred aspects not inconsistent, $R^2$ is $C_1$-$C_3$ alkyl further substituted with 1-6 fluorine.

In another preferred aspect of the invention or any of the above described embodiments of the invention, and in combination with any other preferred aspects not inconsistent, $R^2$ is $C_1$-$C_3$ alkyl further substituted with 1-2 groups selected from chlorine and —CN.

In another preferred aspect of the invention or any of the above described embodiments of the invention, and in combination with any other preferred aspects not inconsistent, $R^2$ is —$OR^b$.

In another preferred aspect of the invention or any of the above described embodiments of the invention, and in combination with any other preferred aspects not inconsistent, $R^2$ is —$N(R^b)_2$.

In another preferred aspect of the invention or any of the above described embodiments of the invention, and in combination with any other preferred aspects not inconsistent, $R^1$ is hydrogen and $R^2$ is hydrogen.

In another preferred aspect of the invention or any of the above described embodiments of the invention, and in combination with any other preferred aspects not inconsistent, A is further substituted with 1-3 $R^4$ selected from the group consisting of fluorine, chlorine, $C_1$-$C_3$ alkyl, $C_1$-$C_3$ alkoxy, and $CF_3$.

In another preferred aspect of the invention or any of the above described embodiments of the invention, and in combination with any other preferred aspects not inconsistent, A is further substituted with 1-3 $R^4$ selected from the group consisting of
(a) fluorine, chlorine and —CN; and
(b) $C_1$-$C_6$ alkyl, optionally further substituted with 1-6 groups selected from fluorine, chlorine and CN.

In another preferred aspect of the invention or any of the above described embodiments of the invention, and in combination with any other preferred aspects not inconsistent, A is further substituted with 1-3 $R^4$ selected from the group consisting of
(a) fluorine, chlorine and —CN;
(b) $C_1$-$C_6$ alkyl, optionally further substituted with 1-6 groups selected from fluorine, chlorine and CN; and
(c) $C_3$-$C_6$ cycloalkyl, -L-($C_3$-$C_6$ cycloalkyl), 4-6 member heterocyclyl, -L-(4-6 member heterocyclyl), wherein each $C_3$-$C_6$ cycloalkyl and 4-6 member heterocyclyl is independently optionally further substituted with 1-6 $R^x$.

In another preferred aspect of the invention or any of the above described embodiments of the invention, and in combination with any other preferred aspects not inconsistent, A is further substituted with 1-3 $R^4$ selected from the group consisting of
(a) fluorine, chlorine and —CN;
(b) $C_1$-$C_6$ alkyl, optionally further substituted with 1-6 groups selected from fluorine, chlorine and CN; and
(d) —$N(R^a)_2$, -L-$N(R^a)_2$.

In another preferred aspect of the invention or any of the above described embodiments of the invention, and in combination with any other preferred aspects not inconsistent, A is further substituted with 1-3 $R^4$ selected from the group consisting of
(a) fluorine, chlorine and —CN;
(b) $C_1$-$C_6$ alkyl, optionally further substituted with 1-6 groups selected from fluorine, chlorine and CN; and
(e) —$OR^a$, -L-$OR^a$.

In another preferred aspect of the invention or any of the above described embodiments of the invention, and in combination with any other preferred aspects not inconsistent, A is further substituted with 1-3 $R^4$ selected from the group consisting of (a) fluorine, chlorine and —CN;

(b) $C_1$-$C_6$ alkyl, optionally further substituted with 1-6 groups selected from fluorine, chlorine and CN; and (g) —C(O)$R^a$, —C(O)O$R^a$, —C(O)N($R^a$)$_2$, -L-C(O)$R^a$, -L-C(O)O$R^a$, -L-C(O)N($R^a$)$_2$.

In another preferred aspect of the invention or any of the above described embodiments of the invention, and in combination with any other preferred aspects not inconsistent, A is further substituted with 1-3 $R^4$ selected from the group consisting of (a) fluorine, chlorine and —CN;

(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and (h) —N($R^b$)-(L)$_p$-C(O)$R^a$, —N($R^b$)-(L)$_p$-C(O)O$R^a$, —N($R^b$)-(L)$_p$-C(O)N($R^a$)$_2$, -L-N($R^b$)-(L)$_p$-C(O)$R^a$, -L-N($R^b$)-(L)$_p$-C(O)O$R^a$, -L-N($R^b$)-(L)$_p$-C(O)N($R^a$)$_2$.

In another preferred aspect of the invention or any of the above described embodiments of the invention, and in combination with any other preferred aspects not inconsistent, A is further substituted with 1-3 $R^4$ selected from the group consisting of (a) fluorine, chlorine and —CN;

(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and (i) —O-(L)$_p$-C(O)$R^a$, —O-(L)$_p$-C(O)N($R^a$)$_2$, —O-(L)$_p$-C(O)O—$R^a$, -L-O-(L)$_p$-C(O)$R^a$, -L-O-(L)$_p$-C(O)N($R^a$)$_2$-L-O-(L)$_p$-C(O)O—$R^a$.

In another preferred aspect of the invention or any of the above described embodiments of the invention, and in combination with any other preferred aspects not inconsistent, A is further substituted with 1-3 $R^4$ selected from the group consisting of (a) fluorine, chlorine and —CN;

(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and (j) —S(O)$_2$$R^a$, —S(O)$_2$O$R^a$, —S(O)$_2$N($R^a$)$_2$, -L-S(O)$_2$$R^a$, -L-S(O)$_2$O$R^a$, -L-S(O)$_2$N($R^a$)$_2$.

In another preferred aspect of the invention or any of the above described embodiments of the invention, and in combination with any other preferred aspects not inconsistent, A is further substituted with 1-3 $R^4$ selected from the group consisting of (a) fluorine, chlorine and —CN;

(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and (k) —O-(L)$_p$-S(O)$_2$$R^a$, )—O-(L)$_p$-S(O)$_2$O—$R^a$, —O-(L)$_p$-S(O)$_2$N($R^a$)$_2$, -L-O-(L)$_p$-S(O)$_2$$R^a$, -L-O-(L)$_p$-S(O)$_2$O—$R^a$)-L-O-(L)$_p$-S(O)$_2$N($R^a$)$_2$.

In another preferred aspect of the invention or any of the above described embodiments of the invention, and in combination with any other preferred aspects not inconsistent, A is further substituted with 1-3 $R^4$ selected from the group consisting of (a) fluorine, chlorine and —CN;

(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and (l) —N($R^b$)-(L)$_p$-S(O)$_2$$R^a$, —N($R^b$)-(L)$_p$-S(O)$_2$O—$R^a$, —N($R^b$)-(L)$_p$-S(O)$_2$N($R^a$)$_2$, -L-N($R^b$)-(L)$_p$-S(O)$_2$$R^a$, -L-N($R^b$)-(L)$_p$-S(O)$_2$O—$R^a$)-L-N($R^b$)-(L)$_p$-S(O)$_2$N($R^a$)$_2$.

In another preferred aspect of the invention or any of the above described embodiments of the invention, and in combination with any other preferred aspects not inconsistent, A is further substituted with 1-3 $R^4$ selected from the group consisting of (a) fluorine, chlorine and —CN;

(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and (m) —C($R^a$)=N—CN, -L-C($R^a$)=N—CN.

In another preferred aspect of the invention or any of the above described embodiments of the invention, and in combination with any other preferred aspects not inconsistent, each $R^a$ is independently selected from the group consisting of hydrogen, $C_1$-$C_6$ alkyl and $C_1$-$C_6$ perfluoroalkyl.

In another preferred aspect of the invention or any of the above described embodiments of the invention, and in combination with any other preferred aspects not inconsistent, $R^a$ is independently selected from the group consisting of hydrogen, $C_1$-$C_6$ alkyl, $C_1$-$C_6$ perfluoroalkyl and $C_1$-$C_6$ alkyl further substituted by 1-2 groups selected from fluorine, chlorine, —CN, —O$R^b$ and —N($R^b$)$_2$.

In another preferred aspect of the invention or any of the above described embodiments of the invention, and in combination with any other preferred aspects not inconsistent, each $R^a$ is independently selected from the group consisting of (a) hydrogen, $C_1$-$C_6$ alkyl, $C_1$-$C_6$ perfluoroalkyl, (b) $C_1$-$C_6$ alkyl further substituted by 1-2 groups selected from fluorine, chlorine, —CN, —O$R^b$ and —N($R^b$)$_2$ and (c) $C_2$-$C_6$ alkenyl and $C_2$-$C_6$ alkynyl, each of which is optionally further substituted by 1-3 groups selected from fluorine, chlorine, —CN, —O$R^b$ and —N($R^b$)$_2$.

In another preferred aspect of the invention or any of the above described embodiments of the invention, and in combination with any other preferred aspects not inconsistent, each $R^a$ is independently selected from the group consisting of (a) hydrogen, $C_1$-$C_6$ alkyl, $C_1$-$C_6$ perfluoroalkyl, (b) $C_1$-$C_6$ alkyl further substituted by 1-2 groups selected from fluorine, chlorine, —CN, —O$R^b$ and —N($R^b$)$_2$ and (d) —($C_1$-$C_6$ alkylene)$_p$-($C_3$-$C_6$ cycloalkyl), —($C_1$-$C_6$ alkylene)$_p$-phenyl, —($C_1$-$C_6$ alkylene)$_p$-(5-6 member heteroaryl), —($C_1$-$C_6$ alkylene)$_p$-(4-6 member heterocyclyl), —($C_1$-$C_6$ alkylene)$_p$-($C_5$-$C_6$ cycloalkenyl), wherein each $C_1$-$C_6$ alkylene is optionally further substituted with 1-3 groups selected from fluorine, chlorine and —CN, wherein each $C_3$-$C_6$ cycloalkyl, phenyl, 5-6 member heteroaryl, 4-6 member heterocyclyl and $C_5$-$C_6$ cycloakenyl is independently optionally further substituted with 1-3 $R^y$.

In another preferred aspect of the invention or any of the above described embodiments of the invention, and in combination with any other preferred aspects not inconsistent, each $R^a$ is independently selected from the group consisting of (a) hydrogen, $C_1$-$C_6$ alkyl, $C_1$-$C_6$ perfluoroalkyl, (b) $C_1$-$C_6$ alkyl further substituted by 1-2 groups selected from fluorine, chlorine, —CN, —O$R^b$ and —N($R^b$)$_2$;

or two $R^a$ connected to the same nitrogen form a 3-10 member heterocyclyl or 5-10 member heteroaryl, the said 3-10 member heterocyclyl and the said 5-10 member heteroaryl is optionally further substituted with 1-3 $R^z$.

In another preferred aspect of the invention or any of the above described embodiments of the invention, and in combination with any other preferred aspects not inconsistent, each L is —$C_1$-$C_6$ alkylene.

In another preferred aspect of the invention or any of the above described embodiments of the invention, and in combination with any other preferred aspects not inconsistent, each L is independently —$C_1$-$C_6$ alkylene or $C_2$-$C_6$ alkenylene.

In another preferred aspect of the invention or any of the above described embodiments of the invention, and in combination with any other preferred aspects not inconsistent, each L is independently —$C_1$-$C_6$ alkylene or $C_2$-$C_6$ alkynylene.

In another preferred aspect of the invention or any of the above described embodiments of the invention, and in combination with any other preferred aspects not inconsistent, each $R^w$ is independently selected from the group consisting of fluorine, chlorine, —CN and $C_1$-$C_6$ alkyl, In another preferred aspect of the invention or any of the above described embodiments of the invention, and in combination with any other preferred aspects not inconsistent, each $R^w$ is independently selected from the group consisting of fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$.

In another preferred aspect of the invention or any of the above described embodiments of the invention, and in combination with any other preferred aspects not inconsistent, each $R^w$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —N($R^b)_2$.

In another preferred aspect of the invention or any of the above described embodiments of the invention, and in combination with any other preferred aspects not inconsistent, each $R^w$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —$N(R^b)_2$ and (iii) —C(O)—$R^b$, —C(O)$OR^b$, —C(O)—$N(R^b)_2$.

In another preferred aspect of the invention or any of the above described embodiments of the invention, and in combination with any other preferred aspects not inconsistent, each $R^w$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —$N(R^b)_2$ and (iv) —$N(R^b)$—C(O)—$R^b$, —$N(R^b)$—C(O)$OR^b$, —$N(R^b)$—C(O)—$N(R^b)_2$.

In another preferred aspect of the invention or any of the above described embodiments of the invention, and in combination with any other preferred aspects not inconsistent, each $R^w$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —$OR^b$ and —$N(R^b)_2$ and (v) —O—C(O)—$R^b$, —O—C(O)$OR^b$, —O—C(O)—$N(R^b)_2$.

In another preferred aspect of the invention or any of the above described embodiments of the invention, and in combination with any other preferred aspects not inconsistent, each $R^w$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —$N(R^b)_2$ and (vi) —$S(O)_2$—$R^b$, —$S(O)_2$—O—$R^b$—$S(O)_2$—$N(R^b)_2$.

In another preferred aspect of the invention or any of the above described embodiments of the invention, and in combination with any other preferred aspects not inconsistent, each $R^w$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —$N(R^b)_2$ and (vii) —$N(R^b)$—$S(O)_2$—$R^b$, —$N(R^b)$—$S(O)_2$—O—$R^b$, —$N(R^b)$—$S(O)_2$—$N(R)_2$.

In another preferred aspect of the invention or any of the above described embodiments of the invention, and in combination with any other preferred aspects not inconsistent, each $R^w$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —$N(R^b)_2$ and (viii) —O—$S(O)_2$—$R^b$, —O—$S(O)_2$—O—$R^b$—O—$S(O)_2$—$N(R^b)_2$.

In another preferred aspect of the invention or any of the above described embodiments of the invention, and in combination with any other preferred aspects not inconsistent, each $R^x$ is independently selected from the group consisting of fluorine, chlorine, —CN and $C_1$-$C_6$ alkyl, In another preferred aspect of the invention or any of the above described embodiments of the invention, and in combination with any other preferred aspects not inconsistent, each $R^x$ is independently selected from the group consisting of fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$.

In another preferred aspect of the invention or any of the above described embodiments of the invention, and in combination with any other preferred aspects not inconsistent, each $R^x$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —$N(R^b)_2$.

In another preferred aspect of the invention or any of the above described embodiments of the invention, and in combination with any other preferred aspects not inconsistent, each $R^x$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —$N(R^b)_2$ and (iii) —C(O)—$R^b$, —C(O)$OR^b$, —C(O)—$N(R^b)_2$.

In another preferred aspect of the invention or any of the above described embodiments of the invention, and in combination with any other preferred aspects not inconsistent, each $R^x$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$; and (ii) $C_1$-$C_6$ alkyl further substituted with 1-2 groups selected from fluorine, chlorine, —CN, —$OR^b$ and —$N(R^b)_2$ and (iv) —$N(R^b)$—C(O)—$R^b$, —$N(R^b)$—C(O)$OR^b$, —$N(R^b)$—C(O)—$N(R)_2$.

In another preferred aspect of the invention or any of the above described embodiments of the invention, and in combination with any other preferred aspects not inconsistent, each $R^x$ is independently selected from the group consisting of (i) fluorine, chlorine, —CN, —$OR^b$, $C_1$-$C_6$ alkyl, $C_1$-$C_3$ perfluoroalkyl, $C_2$-$C_6$ alkenyl, $C_2$-$C_6$ alkynyl and —$N(R^b)_2$;

and (ii) $C_1$-$C_6$ alkyl further substituted with 1-2 groups selected from fluorine, chlorine, —CN, —OR$^b$ and —N(R$^b$)$_2$ and (v) —O—C(O)—R$^b$, —O—C(O)OR$^b$, —O—C(O)—N(R$^b$)$_2$.

In another preferred aspect of the invention or any of the above described embodiments of the invention, and in combination with any other preferred aspects not inconsistent, each R$^x$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (vi) —S(O)$_2$—R$^b$, —S(O)$_2$—O—R$^b$—S(O)$_2$—N(R$^b$)$_2$.

In another preferred aspect of the invention or any of the above described embodiments of the invention, and in combination with any other preferred aspects not inconsistent, each R$^x$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (vii) —N(R$^b$)—S(O)$_2$—R$^b$, —N(R$^b$)—S(O)$_2$—O—R$^b$, —N(R$^b$)—S(O)$_2$—N(R$^b$)$_2$.

In another preferred aspect of the invention or any of the above described embodiments of the invention, and in combination with any other preferred aspects not inconsistent, each R$^x$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (viii) —O—S(O)$_2$—R$^b$, —O—S(O)$_2$—O—R$^b$—O—S(O)$_2$—N(R$^b$)$_2$.

In another preferred aspect of the invention or any of the above described embodiments of the invention, and in combination with any other preferred aspects not inconsistent, each R$^y$ is independently selected from the group consisting of fluorine, chlorine, —CN and $C_1$-$C_6$ alkyl, In another preferred aspect of the invention or any of the above described embodiments of the invention, and in combination with any other preferred aspects not inconsistent, each R$^y$ is independently selected from the group consisting of fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$.

In another preferred aspect of the invention or any of the above described embodiments of the invention, and in combination with any other preferred aspects not inconsistent, each R$^y$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$.

In another preferred aspect of the invention or any of the above described embodiments of the invention, and in combination with any other preferred aspects not inconsistent, each R$^y$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (iii) —C(O)—R$^b$, —C(O)OR$^b$, —C(O)—N(R$^b$)$_2$.

In another preferred aspect of the invention or any of the above described embodiments of the invention, and in combination with any other preferred aspects not inconsistent, each R$^y$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (iv) —N(R$^b$)—C(O)—R$^b$, —N(R$^b$)—C(O)OR$^b$, —N(R$^b$)—C(O)—N(R)$_2$.

In another preferred aspect of the invention or any of the above described embodiments of the invention, and in combination with any other preferred aspects not inconsistent, each R$^y$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (v) —O—C(O)—R$^b$, —O—C(O)OR$^b$, —O—C(O)—N(R$^b$)$_2$.

In another preferred aspect of the invention or any of the above described embodiments of the invention, and in combination with any other preferred aspects not inconsistent, each R$^y$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (vi) —S(O)$_2$—R$^b$, —S(O)$_2$—O—R$^b$—S(O)$_2$—N(R$^b$)$_2$.

In another preferred aspect of the invention or any of the above described embodiments of the invention, and in combination with any other preferred aspects not inconsistent, each R$^y$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (vii) —N(R$^b$)—S(O)$_2$—R$^b$, —N(R$^b$)—S(O)$_2$—O—R$^b$, —N(R$^b$)—S(O)$_2$—N(R)$_2$.

In another preferred aspect of the invention or any of the above described embodiments of the invention, and in combination with any other preferred aspects not inconsistent, each R$^y$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$ and (viii) —O—S(O)$_2$—R$^b$, —O—S(O)$_2$—O—R$^b$—O—S(O)$_2$—N(R$^b$)$_2$.

In another preferred aspect of the invention or any of the above described embodiments of the invention, and in combination with any other preferred aspects not inconsistent, each R$^z$ is independently selected from the group consisting of fluorine, chlorine, —CN and $C_1$-$C_6$ alkyl, In another preferred aspect of the invention or any of the above described embodiments of the invention, and in combination with any other preferred aspects not inconsistent, each R$^z$ is independently selected from the group consisting of fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$.

In another preferred aspect of the invention or any of the above described embodiments of the invention, and in combination with any other preferred aspects not inconsistent, each R$^z$ is independently selected from the group consisting of (i) fluorine, chlorine, —CN, —OR$^b$, $C_1$-$C_6$ alkyl, $C_1$-$C_3$ perfluoroalkyl, $C_2$-$C_6$ alkenyl, $C_2$-$C_6$ alkynyl and —N(R$^b$)$_2$; and (ii) $C_1$-$C_6$ alkyl further substituted with 1-2 groups selected from fluorine, chlorine, —CN, —OR$^b$ and —N(R$^b$)$_2$.

In another preferred aspect of the invention or any of the above described embodiments of the invention, and in combination with any other preferred aspects not inconsistent, each $R^z$ is independently selected from the group consisting of (i) fluorine, chlorine, —CN, —OR$^b$, C$_1$-C$_6$ alkyl, C$_1$-C$_3$ perfluoroalkyl, C$_2$-C$_6$ alkenyl, C$_2$-C$_6$ alkynyl and —N(R$^b$)$_2$; and (ii) C$_1$-C$_6$ alkyl further substituted with 1-2 groups selected from fluorine, chlorine, —CN, —OR$^b$ and —N(R$^b$)$_2$ and (iii) —C(O)—R$^b$, —C(O)OR$^b$, —C(O)—N(R$^b$)$_2$.

In another preferred aspect of the invention or any of the above described embodiments of the invention, and in combination with any other preferred aspects not inconsistent, each $R^z$ is independently selected from the group consisting of (i) fluorine, chlorine, —CN, —OR$^b$, C$_1$-C$_6$ alkyl, C$_1$-C$_3$ perfluoroalkyl, C$_2$-C$_6$ alkenyl, C$_2$-C$_6$ alkynyl and —N(R$^b$)$_2$; and (ii) C$_1$-C$_6$ alkyl further substituted with 1-2 groups selected from fluorine, chlorine, —CN, —OR$^b$ and —N(R$^b$)$_2$ and (iv) —N(R$^b$)—C(O)—R$^b$, —N(R$^b$)—C(O)OR$^b$, —N(R$^b$)—C(O)—N(R$^b$)$_2$.

In another preferred aspect of the invention or any of the above described embodiments of the invention, and in combination with any other preferred aspects not inconsistent, each $R^z$ is independently selected from the group consisting of (i) fluorine, chlorine, —CN, —OR$^b$, C$_1$-C$_6$ alkyl, C$_1$-C$_3$ perfluoroalkyl, C$_2$-C$_6$ alkenyl, C$_2$-C$_6$ alkynyl and —N(R$^b$)$_2$; and (ii) C$_1$-C$_6$ alkyl further substituted with 1-2 groups selected from fluorine, chlorine, —CN, —OR$^b$ and —N(R$^b$)$_2$ and (v) —O—C(O)—R$^b$, —O—C(O)OR$^b$, —O—C(O)—N(R$^b$)$_2$.

In another preferred aspect of the invention or any of the above described embodiments of the invention, and in combination with any other preferred aspects not inconsistent, each $R^z$ is independently selected from the group consisting of (i) fluorine, chlorine, —CN, —OR$^b$, C$_1$-C$_6$ alkyl, C$_1$-C$_3$ perfluoroalkyl, C$_2$-C$_6$ alkenyl, C$_2$-C$_6$ alkynyl and —N(R$^b$)$_2$; and (ii) C$_1$-C$_6$ alkyl further substituted with 1-2 groups selected from fluorine, chlorine, —CN, —OR$^b$ and —N(R$^b$)$_2$ and (vi) —S(O)$_2$—R$^b$, —S(O)$_2$—O—R$^b$—S(O)$_2$—N(R$^b$)$_2$.

In another preferred aspect of the invention or any of the above described embodiments of the invention, and in combination with any other preferred aspects not inconsistent, each $R^z$ is independently selected from the group consisting of (i) fluorine, chlorine, —CN, —OR$^b$, C$_1$-C$_6$ alkyl, C$_1$-C$_3$ perfluoroalkyl, C$_2$-C$_6$ alkenyl, C$_2$-C$_6$ alkynyl and —N(R$^b$)$_2$; and (ii) C$_1$-C$_6$ alkyl further substituted with 1-2 groups selected from fluorine, chlorine, —CN, —OR$^b$ and —N(R$^b$)$_2$ and (vii) —N(R$^b$)—S(O)$_2$—R$^b$, —N(R$^b$)—S(O)$_2$—O—R$^b$, —N(R$^b$)—S(O)$_2$—N(R$^b$)$_2$.

In another preferred aspect of the invention or any of the above described embodiments of the invention, and in combination with any other preferred aspects not inconsistent, each $R^z$ is independently selected from the group consisting of (i) fluorine, chlorine, —CN, —OR$^b$, C$_1$-C$_6$ alkyl, C$_1$-C$_3$ perfluoroalkyl, C$_2$-C$_6$ alkenyl, C$_2$-C$_6$ alkynyl and —N(R$^b$)$_2$; and (ii) C$_1$-C$_6$ alkyl further substituted with 1-2 groups selected from fluorine, chlorine, —CN, —OR$^b$ and —N(R$^b$)$_2$ and (viii) —O—S(O)$_2$—R$^b$, —O—S(O)$_2$—O—R$^b$—O—S(O)$_2$—N(R$^b$)$_2$.

In another preferred aspect of the invention or any of the above described embodiments of the invention, and in combination with any other preferred aspects not inconsistent, each $R^b$ is hydrogen.

In another preferred aspect of the invention or any of the above described embodiments of the invention, and in combination with any other preferred aspects not inconsistent, each $R^b$ is independently selected from the group consisting of hydrogen and C$_1$-C$_3$ alkyl.

In another preferred aspect of the invention or any of the above described embodiments of the invention, and in combination with any other preferred aspects not inconsistent, each $R^b$ is independently selected from the group consisting of hydrogen, C$_1$-C$_3$ alkyl and C$_1$-C$_3$ perfluoroalkyl.

In another preferred aspect of the invention or any of the above described embodiments of the invention, and in combination with any other preferred aspects not inconsistent, each $R^b$ is independently selected from the group consisting of hydrogen, C$_1$-C$_3$ alkyl and C$_1$-C$_3$ alkyl further substituted by 1-2 groups selected from fluorine, chlorine and CN.

In another preferred aspect of the invention or any of the above described embodiments of the invention, and in combination with any other preferred aspects not inconsistent, each $R^3$ is independently selected from the group consisting of -oxo-, fluorine, chlorine, C$_1$-C$_3$ alkyl, C$_1$-C$_3$ alkoxy, and CF$_3$.

In another preferred aspect of the invention or any of the above described embodiments of the invention, and in combination with any other preferred aspects not inconsistent, each $R^3$ is independently selected from the group consisting of -oxo- and (a) fluorine, chlorine and —CN; and (b) C$_1$-C$_6$ alkyl, C$_2$-C$_6$ alkenyl and C$_2$-C$_6$ alkynyl, each of which is optionally further substituted with 1-6 groups selected from fluorine, chlorine and CN.

In another preferred aspect of the invention or any of the above described embodiments of the invention, and in combination with any other preferred aspects not inconsistent, each $R^3$ is independently selected from the group consisting of -oxo- and (a) fluorine, chlorine and —CN;

(b) C$_1$-C$_6$ alkyl, C$_2$-C$_6$ alkenyl and C$_2$-C$_6$ alkynyl, each of which is optionally further substituted with 1-6 groups selected from fluorine, chlorine and CN; and (c) C$_3$-C$_6$ cycloalkyl, -L-(C$_3$-C$_6$ cycloalkyl), 4-6 member heterocyclyl, -L-(4-6 member heterocyclyl), phenyl, -L-phenyl, 5-6 member heteroaryl, -L-(5-6 member heteroaryl), C$_5$-C$_6$ cycloalkenyl, -L-(C$_5$-C$_6$ cycloalkenyl), wherein each C$_3$-C$_6$ cycloalkyl, phenyl, 5-6 member heteroaryl, 4-6 member heterocyclyl and C$_5$-C$_6$ cycloakenyl is independently optionally further substituted with 1-6 R$^x$.

In another preferred aspect of the invention or any of the above described embodiments of the invention, and in combination with any other preferred aspects not inconsistent, each $R^3$ is independently selected from the group consisting of -oxo- and (a) fluorine, chlorine and —CN;

(b) C$_1$-C$_6$ alkyl, C$_2$-C$_6$ alkenyl and C$_2$-C$_6$ alkynyl, each of which is optionally further substituted with 1-6 groups selected from fluorine, chlorine and CN; and (d) —N(R$^a$)$_2$, -L-N(R$^a$)$_2$.

In another preferred aspect of the invention or any of the above described embodiments of the invention, and in combination with any other preferred aspects not inconsistent, each $R^3$ is independently selected from the group consisting of -oxo- and (a) fluorine, chlorine and —CN;

(b) C$_1$-C$_6$ alkyl, C$_2$-C$_6$ alkenyl and C$_2$-C$_6$ alkynyl, each of which is optionally further substituted with 1-6 groups selected from fluorine, chlorine and CN; and (e) —OR$^a$, -L-OR$^a$.

In another preferred aspect of the invention or any of the above described embodiments of the invention, and in combination with any other preferred aspects not inconsistent, each $R^3$ is independently selected from the group consisting of -oxo- and (a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and
(g) —C(O)$R^a$, —C(O)O$R^a$, —C(O)N($R^a$)$_2$, -L-C(O)$R^a$, -L-C(O)O$R^a$, -L-C(O)N($R^a$)$_2$.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and
(h) —N($R^b$)-(L)$_p$-C(O)$R^a$, —N($R^b$)-(L)$_p$-C(O)O$R^a$, —N($R^b$)-(L)$_p$-C(O)N($R^a$)$_2$, -L-N($R^b$)-(L)$_p$-C(O)$R^a$, -L-N($R^b$)-(L)$_p$-C(O)O$R^a$, -L-N($R^b$)-(L)$_p$-C(O)N($R^a$)$_2$.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and
(i) —O-(L)$_p$-C(O)$R^a$, —O-(L)$_p$-C(O)N($R^a$)$_2$, —O-(L)$_p$-C(O)O—$R^a$, -L-O-(L)$_p$-C(O)$R^a$, -L-O-(L)$_p$-C(O)N($R^a$)$_2$-L-O-(L)$_p$-C(O)O—$R^a$.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and
(j) —S(O)$_2$$R^a$, —S(O)$_2$O$R^a$, —S(O)$_2$N($R^a$)$_2$, -L-S(O)$_2$$R^a$, -L-S(O)$_2$O$R^a$, -L-S(O)$_2$N($R^a$)$_2$.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and
(k) —O-(L)$_p$-S(O)$_2$$R^a$, )—O-(L)$_p$-S(O)$_2$O—$R^a$, —O-(L)$_p$-S(O)$_2$N($R^a$)$_2$, -L-O-(L)$_p$-S(O)$_2$$R^a$, -L-O-(L)$_p$-S(O)$_2$O—$R^a$)-L-O-(L)$_p$-S(O)$_2$N($R^a$)$_2$.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and
(l) —N($R^b$)-(L)$_p$-S(O)$_2$$R^a$, —N($R^b$)-(L)$_p$-S(O)$_2$O—$R^a$, —N($R^b$)-(L)$_p$-S(O)$_2$N($R^a$)$_2$, -L-N($R^b$)-(L)$_p$-S(O)$_2$$R^a$, -L-N($R^b$)-(L)$_p$-S(O)$_2$O—$R^a$)-L-N($R^b$)-(L)$_p$-S(O)$_2$N($R^a$)$_2$.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; and
(m) —C($R^a$)=N—CN, -L-C($R^a$)=N—CN.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN;
further more, two of the $R^3$ attached to the same ring atom, together with the ring atom attached to, may also form a ring selected from $C_3$-$C_6$ cycloalkyl, $C_5$-$C_6$ cycloalkenyl and 3-6 member heterocyclyl; each of the said $C_3$-$C_6$ cycloalkyl, $C_5$-$C_6$ cycloalkenyl and 3-6 member heterocyclyl is optionally further substituted with 1-5 groups selected from -oxo- and $R^w$.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN;
further more, two of the $R^3$ attached to two adjacent ring atoms, together with the ring atoms attached to, form a fused ring selected from $C_3$-$C_6$ cycloalkyl, $C_5$-$C_6$ cycloalkenyl, 3-6 member heterocyclyl, phenyl, 5-6 member heteroaryl; the said $C_3$-$C_6$ cycloalkyl, $C_5$-$C_6$ cycloalkenyl, 3-6 member heterocyclyl, phenyl and 5-6 member heteroaryl is optionally further substituted with 1-5 groups selected from -oxo- and $R^w$.

In another preferred aspect of the invention or any of the above described embodiments of the invention, and in combination with any other preferred aspects not inconsistent, each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN;
further more, two $R^3$ attached to, two different ring atoms with at least one ring atom in between, may form a $C_1$-$C_4$ alkylene, a 2-4 member heteroalkylene, or a diradical selected from the group consisting of:

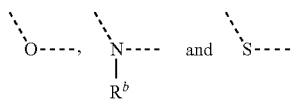

such $C_1$-$C_4$ alkylene, 2-4 member heteroalkylene and diradical together with the azetidinyl (when n is 0), pyrrolidinyl (when n is 1) or the piperidinyl (when n is 2) form a bicyclic bridged ring system, the said bicyclic bridged ring system having a total of 6-9 ring atoms with 1-3 of the ring atoms selected from O, N and S; the $C_1$-$C_4$ alkylene or a 1-4 member heteroalkylene is optionally further substituted with 1-5 groups selected from -oxo- and $R^w$.

In another preferred aspect of the invention or any of the above described embodiments of the invention, and in combination with any other preferred aspects not inconsistent, each p is 0.

In another preferred aspect of the invention or any of the above described embodiments of the invention, and in combination with any other preferred aspects not inconsistent, each p is 1.

This invention also relates to a method for the treatment of abnormal cell growth in a mammal, including a human, comprising administering to said mammal an amount of a compound of the Formula I, as defined above, or a pharmaceutically acceptable salt or solvate thereof, that is effective in treating abnormal cell growth.

In one embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In another embodiment of said method, said abnormal cell growth is a benign proliferative disease, including, but not limited to, psoriasis, benign prostatic hypertrophy or restinosis.

In a preferred embodiment of the present invention the cancer is selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkins's lymphoma, spinal axis tumors, or a combination of one or more of the foregoing cancers.

In another preferred embodiment of the present invention the cancer is selected from lung cancer (NSCLC and SCLC), ovarian cancer, colon cancer, rectal cancer, cancer of the anal region, or a combination of one or more of the foregoing cancers. In a more preferred embodiment of the present invention the cancer is selected from lung cancer (NSCLC and SCLC), ovarian cancer, colon cancer, rectal cancer, or a combination of one or more of the foregoing cancers.

In another embodiment of said method, said abnormal cell growth is a benign proliferative disease, including, but not limited to, psoriasis, benign prostatic hypertrophy or restinosis.

This invention also relates to a pharmaceutical composition for the treatment of abnormal cell growth in a mammal, including a human, comprising an amount of a compound of the Formula I, as defined above, or a pharmaceutically acceptable salt or solvate thereof, that is effective in treating abnormal cell growth, and a pharmaceutically acceptable carrier. In one embodiment of said composition, said abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

As used herein, the symbol [------] when incorporated into the chemical structure of a substituent means that the atom to which [------] is attached is the point of attachment of that substituent to some position on another molecule. For example, X in the hypothetical molecule $CH_3CH_2$—X might be defined as X is

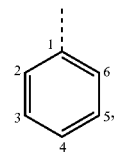

in which case, the placement of [------] attached to the arbitrarily numbered position C-1, means that C-1 of the phenyl ring is attached to the methylene carbon.

The symbols "⌿" and "⌿", when used together in a single molecule without further indication otherwise, for example, chemical name or accompanying description, merely indicate relative stereochemistry of trans or cis where applicable. The symbol "⌿" and the symbol "⌿", used together or separately, in combination with an indication of them representing the absolute stereochemistry, for example, an indication of "S" or "R" in the corresponding chemical structure or the accompanying chemical name, indicate the absolute stereochemistry of the corresponding chiral center.

"$C_m$-$C_n$ alkyl", wherein m is an integer of 1-19, n is an integer of 2 to 20 and n>m, refers to a straight chain or branched saturated hydrocarbon radical having from m to n carbon atoms, wherein n is an integer of 2 to 20. A $C_m$-$C_n$ alkyl group may be unsubstituted or further substituted by at least one substituent. Examples of $C_1$-$C_{12}$ alkyl groups include, but are not limited to methyl, ethyl, propyl, isopropyl, butyl, sec-butyl, iso-butyl, tert-butyl, pentyl, neo-pentyl, sec-pentyl, hexyl, heptyl, octyl, and the like, including substituted forms thereof. Further, the term "alkyl" refers to a straight chain or branched saturated hydrocarbon radical of 1 to 20 carbon atoms, or 1 to 12 carbon atoms, or 1 to 8 carbon atoms, or 1 to 6 carbon atoms, or 1 to 4 carbon atoms. Alkyl may be may be unsubstituted or further substituted by at least one substituent. Suitable substituents on an alkyl group are the same as those described for a $C_1$-$C_{12}$ alkyl group.

A "m to n member heteroalkyl", wherein m is an integer of 2-19, n is an integer of 3 to 20 and n>m, refers to a $C_m$-$C_n$ alkyl, as defined above, wherein 1 to 3 groups selected from

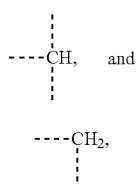

wherein the "------" indicates the point of attachment of the group with other parts of the $C_m$-$C_n$ alkyl, and wherein the above group (a) and (b) are components of the $C_m$—$C_n$ alkyl, are replaced by a group selected, respectively, from

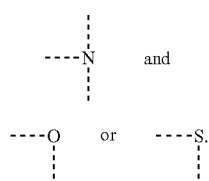

Examples of heteroalkyl include, but are not limited to: —O—$CH_3$, —NH—$CH_3$, —N($CH_3$)—$CH_3$, —S—$CH_3$, —$CH_2$—O—$CH_3$, —$CH_2$—N(H)—$CH_3$ and —$CH_2$—S—$CH_3$.

"$C_m$-$C_n$ cycloalkyl", wherein m is an integer of 3-19, n is an integer of 4 to 20 and n>m, refers to a cyclic saturated hydrocarbon radical having from m to n carbon atoms. A cycloalkyl group may be monocyclic and where permissible may be bicyclic or polycyclic. A cycloalkyl may also be a spirocyclic. A cycloalkyl group may be optionally substituted by at least one substituent. Illustrative examples of cycloalkyl are derived from, but not limited to, the following:

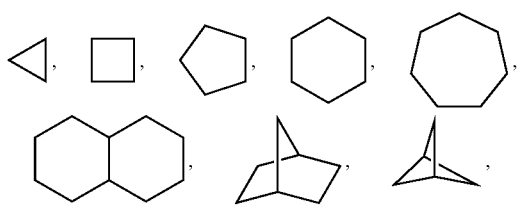

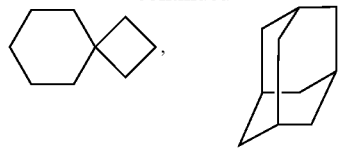

"$C_m$-$C_n$ Nonaromatic carbocyclyl", wherein m is an integer of 3-19, n is an integer of 4 to 20 and n>m, refers to a m to n member all-carbon monocyclic ring group, all-carbon bicyclic or multicyclic ring system group wherein one or more of the rings may contain one or more double bonds or an aromatic ring as part of the bicyclic or multicyclic ring system, but the monocyclic ring, the bicyclic or multicyclic ring system does not have a completely conjugated pi-electron system. Examples, without limitation, of nonaromatic carbocyclyl are cyclopropyl, cyclobutyl, cyclopentyl, cyclopentenyl, cyclohexyl, cyclohexadienyl, adamantanyl, cycloheptyl, cycloheptatrienyl and the like. A nonaromatic carbocyclyl may be substituted or unsubstituted. Illustrative examples of nonaromatic carbocyclyl are derived from, but not limited to, the following:

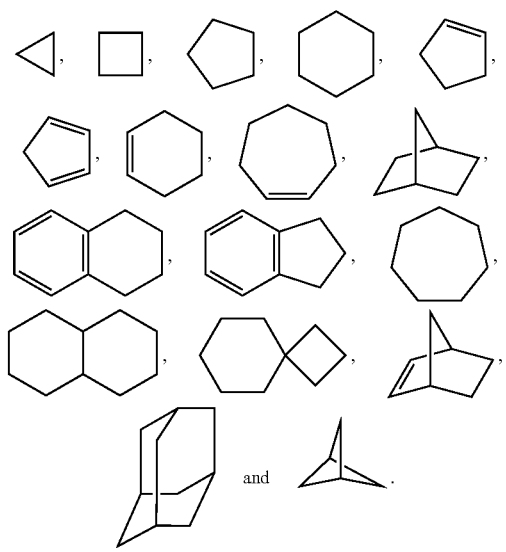

"$C_m$-$C_n$ alkenyl", wherein m is an integer of 2-19, n is an integer of 3 to 20 and n>m, refers to a straight chain or branched unsaturated hydrocarbon radical having from 2 to 12 carbon atoms. A $C_m$-$C_n$ alkenyl group have one more carbon-carbon double bonds, which can be conjugated or unconjugated, but do not form a completely conjugated pi-electron system. A $C_m$-$C_n$ cycloalkenyl group may be monocyclic, bicyclic or polycyclic. A cycloalkenyl may also be a spirocyclic. A $C_m$—$C_n$ cycloalkenyl group may be optionally substituted by at least one substituent.

"$C_m$-$C_n$ cycloalkenyl", wherein m is an integer of 4-19, n is an integer of 5 to 20 and n>m, refers to a cyclic alkenyl radical having from m to n carbon atoms, and having one or more carbon-carbon double bond. A $C_m$-$C_n$ cycloalkyl group may be monocyclic and where permissible may be bicyclic or polycyclic. A $C_m$-$C_n$ cycloalkyl may also be a spirocyclic. A cycloalkyl group may be optionally substituted by at least one substituent. Illustrative examples of cycloalkyl are derived from, but not limited to, the following:

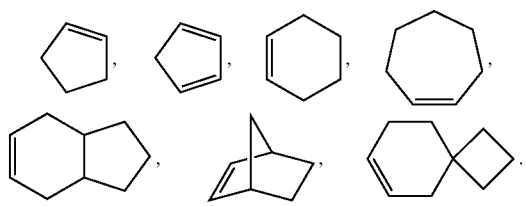

"Alkoxy" or "alkoxyl" refers to —OR$^c$ wherein R$^c$ is C$_1$-C$_{12}$ alkyl, C$_2$-C$_{12}$ alkenyl, C$_2$-C$_{12}$ alkynyl, C$_3$-C$_{12}$ cycloalkyl or (C$_1$-C$_6$ alkylene)-(C$_3$-C$_{12}$ cycloalkyl). A "C$_1$-C$_{12}$ alkoxy" or "C$_1$-C$_{12}$ alkoxyl" refers to an alkoxy group, as defined herein, wherein R$^c$ has 1 to 12 total carbon atoms.

"Alkoxyalkyl" refers to an alkyl, as defined herein, that is substituted by at least one alkoxy group as defined herein. A "C$_2$-C$_6$ alkylalkoxy" refers an alkylalkoxy wherein the total carbon number of the alkyl and its alkoxy substituents are from 2 to 6.

"Alkylamino" refers to —NR$^p$R$^q$ wherein each R$^p$ and R$^q$ is independently H, C$_1$-C$_{12}$ alkyl, C$_2$-C$_{12}$ alkenyl, C$_2$-C$_{12}$ alkynyl, C$_3$-C$_{12}$ cycloalkyl, (C$_1$-C$_6$ alkylene)-(C$_3$-C$_{12}$ cycloalkyl) provided R$^p$ and R$^q$ are not both H. A "monoalkylamino" refers to an alkylamino group, as defined herein, wherein one of R$^p$ and R$^q$ is H. A "dialkylamino" refers to an alkylamino group, as defined herein, wherein none of R$^p$ and R$^q$ is H. A "C$_{1-12}$ alkylamino" refers to an alkylamino group that contains 1 to 10 carbon atoms.

"C$_2$-C$_{12}$ alkynyl" refers to a straight chain or branched hydrocarbon radical having from 2-12 carbon atoms and at least one carbon-carbon triple bond. In the case where C$_2$-C$_{12}$ alkynyl has more than one carbon-carbon double bond, the carbon-carbon double bonds can be conjugated or unconjugated. A C$_2$-C$_{12}$ alkynyl group may be optionally substituted by at least one substituent. Further, the term "alkynyl" refers to a straight chain or branched hydrocarbon radical of 2 to 20 carbon atoms, or 2 to 12 carbon atoms, or 2 to 8 carbon atoms, or 2 to 6 carbon atoms, or 2 to 4 carbon atoms, and having at least one carbon-carbon triple bond. Alkynyl may be substituted or unsubstituted. Suitable substituents on an alkynyl group are the same as those described for a C$_1$-C$_{12}$ alkyl group.

"Amino" refers to —NH$_2$.

"C$_6$-C$_{10}$ aryl" refers to an all-carbon monocyclic ring or polycyclic ring of 6 to 10 carbon atoms having a completely conjugated pi-electron system. A C$_6$-C$_{10}$ aryl group may be optionally substituted by at least one substituent. Examples of C$_6$-C$_{10}$ aryl include, but are not limited to, phenyl and naphthyl. Further, the term "aryl" refers to an all-carbon monocyclic ring or polycyclic ring of 6 to 20 carbon atoms having a completely conjugated pi-electron system. The aryl group may be substituted or unsubstituted. Examples of aryl include, but are not limited to, anthracenyl, phenanthreneyl and perylenyl.

"Heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include C$_{1-12}$ aliphatic, 3-10 member heterocyclyl, 6-10 member aryl, halogen, —NO$_2$, NH$_2$, NR$_2$, —CN, —COR, —COOR, —CONR$_2$, —OH, —OR, —OCOR, —SR, —SOR, —SO$_2$R, —SONR$_2$, —SO$_2$NR$_2$, wherein R is a C$_{1-10}$ aliphatic, 3-10 member heterocyclyl, C$_{6-10}$ aryl, 5-10 member heteroaryl.

Examples of typical monocyclic heteroaryl groups include, but are not limited to:

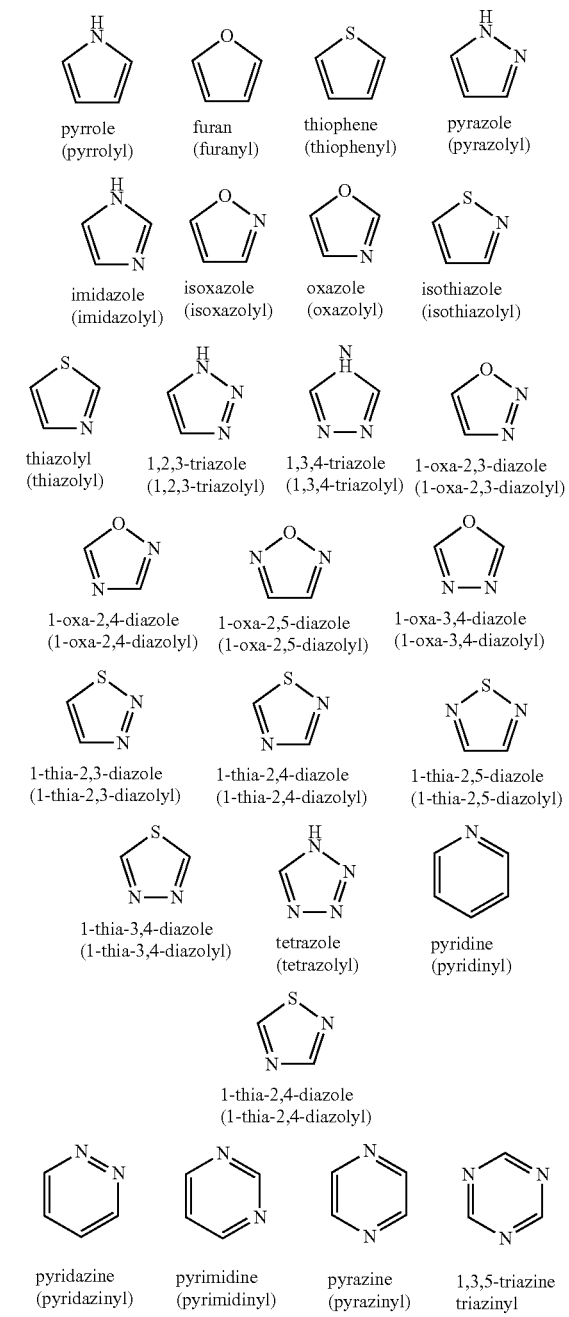

Examples of bicyclic heteroaryl groups include, but are not limited to:

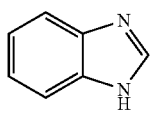
benzimidazole
(benzimidazolyl)

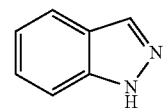
indazole
(indazolyl)

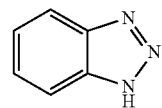
benzotriazole
(benzotriazolyl)

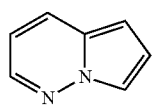
pyrrolo[1,2-b]pyridazine
(pyrrolo[1,2-b]pyridazinyl)

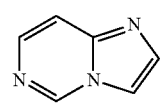
imidazol[1,2-c]pyrimidine
(imidazo[1,2-c]pyrimidinyl)

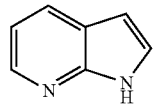
pyrrolo[2,3-b]pyridine
(pyrrolo[2,3-b]pyridinyl)

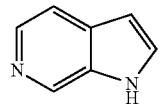
pyrrolo[2,3-c]pyridine
(pyrrolo[2,3-c]pyridinyl)

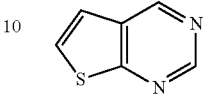
thienopyrimidine
(thienopyrimidinyl)

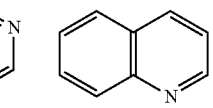
thienopyrimidine
(thienopyrimidinyl)

quinoline
(quinolinyl)

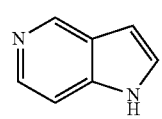
pyrrolo[3,2-c]pyridine
(pyrrolo[3,2-c]pyridinyl)

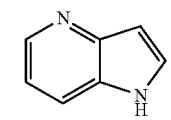
pyrrolo[3,2-b]pyridine
(pyrrolo[3,2-b]pyridinyl)

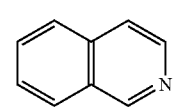
isoquinoline
(isoquinolinyl)

cinnoline
(cinnolinyl)

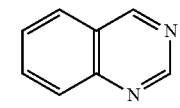
quinazoline
(azaquinazoline)

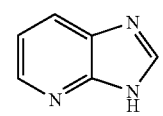
imidazo[4,5-b]pyridine
(imidazo[4,5-b]pyridinyl)

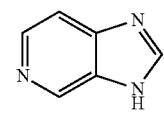
imidazo[4,5-c]pyridine
(imidazo[4,5-c]pyridinyl)

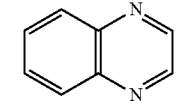
quinoxaline
(quinoxalinyl)

phthalazine
(phthalazinyl)

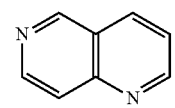
1,6-naphthyridine
(1,6-naphthyridinyl)

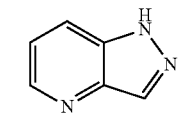
pyrazolo[4,3-d]pyridine
(pyrazolo[4,3-d]pyidinyl)

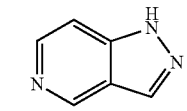
pyrazolo[4,3-c]pyridine
(pyrazolo[4,3-c]pyidinyl)

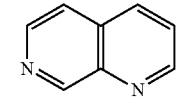
1,7-naphthyridine
(1,7-naphthyridinyl)

1,8-naphthyridine
(1,8-naphthyridinyl)

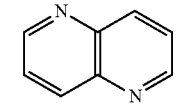
1,5-naphthyridine
(1,5-naphthyridinyl)

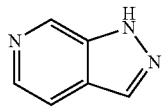
pyrazolo[3,4-c]pyridine
(pyrazolo[3,4-c]pyidinyl)

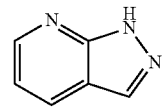
pyrazolo[3,4-b]pyridine
(pyrazolo[3,4-b]pyidinyl)

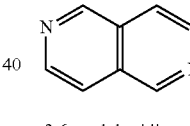
2,6-naphthyridine
(2,6-naphthyridinyl)

2,7-naphthyridine
(2,7-naphthyridinyl)

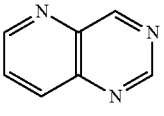
pyrido[3,2-d]pyrimidine
(pyrido[3,2-d]pyrimidinyl)

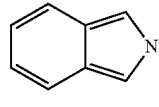
isoindole
(isoindolyl)

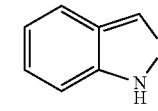
indazole
(indazolyl)

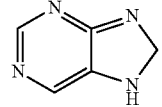
purine
(purinyl)

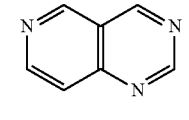
pyrido[4,3-d]pyrimidine
(pyrido[4,3-d]pyrimidinyl)

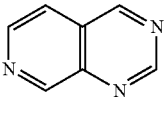
pyrido[3,4-d]pyrimidine
(pyrido[3,4-d]pyrimidinyl)

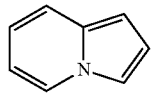
indolizine
(indolininyl)

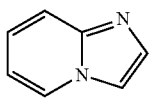
imidazo[1,2-a]pyridine
(imidazo[1,2-a]pyridinyl)

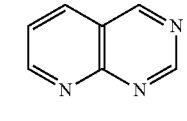
pyrido[2,3-d]pyrimidine
(pyrido[2,3-d]pyrimidinyl)

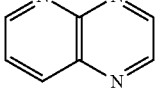
pyrido[2,3-b]pyrazine
(pyrido[2,3-b]pyrazinyl)

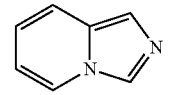
imidazo[1,5-a]pyridine
(imidazo[1,5-a]pyridinyl)

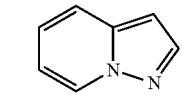
pyrazolo[1,5-a]pyridine
(pyrazolo[1,5-a]pyridinyl)

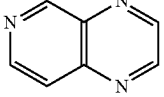
pyrido[3,4-b]pyrazine
(pyrido[3,4-b]pyrazinyl)

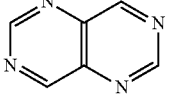
pyrimido[5,4-d]pyrimidine
(pyrimido[5,4-d]pyrimidinyl)

-continued

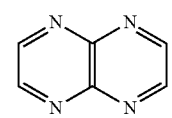
pyrazino[2,3-b]pyrazine
(pyrazino[5,4-b]pyrazinyl)

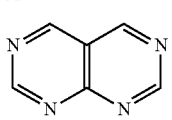
pyrimido[4,5-d]pyrimidine
(pyrimido[4,5-d]pyrimidinyl)

"Heterocyclyl" refers to a monocyclic or polycyclic group having from 3 to 12 ring atoms, wherein from 1 to 4 ring atoms are heteroatoms selected from N, O, and S. "Heteroalicyclic" or "heterocyclyl" may also have one or more double bonds. However, "Heteroalicyclic" or "heterocyclyl" do not have a completely conjugated pi-electron system. "Heteroalicyclic" or "heterocyclyl" can be substituted or unsubstituted.

Examples of saturated heterocyclyl groups include, but are not limited to:

    

oxirane (oxiranyl)    thiarane (thiaranyl)    aziridine (aziridinyl)    oxetane (oxetanyl)    thiatane (thiatanyl)

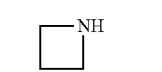  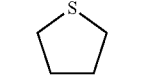

azetidine (azetidinyl)    tetrahydrofuran (tetrahydrofuranyl)    tetrahydrothiophene (tetrahydrothiophenyl)

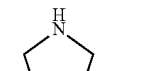  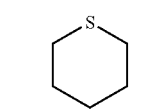

pyrrolidine (pyrrolidinyl)    tetrahydropyran (tetrahydropyranyl)    tetrahydrothiopyran (tetrahydrothiopyranyl)

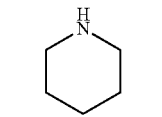  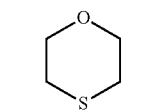

piperidine (piperidinyl)    1,4-dioxane (1,4-dioxanyl)    1,4-oxathiane (1,4-oxathianyl)

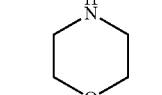  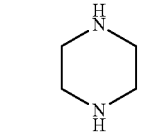

morpholine (morpholinyl)    1,4-dithiane (1,4-dithianyl)    piperazine (piperazinyl)

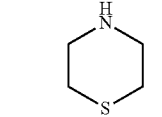  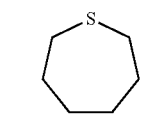

1,4-azathiane (1,4-azathianyl)    oxepane (oxepanyl)    thiepane (thiepanyl)

-continued

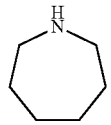 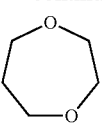 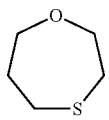

azepane (azepanyl)    1,4-dioxepane (1,4-dioxepanyl)    1,4-oxathiepane (1,4-oxathiepanyl)

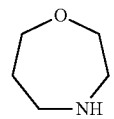 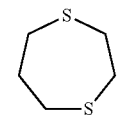 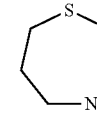

1,4-oxaazepane (1,4-oxazepanyl)    1,4-dithiepane (1,4-dithiepanyl)    1,4-thieazepane (1,4-thieazepanyl)

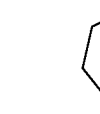 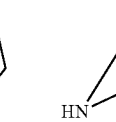

1,4-diazepane (1,4-diazepanyl)    tropane (tropanyl)

(1S,5R)-3-aza-bicyclo[3.1.0]hexane
(1S,5R)-3-aza-bicyclo[3.1.0]hexyl

Examples of partially unsaturated heterocyclyl groups include, but are not limited to:

 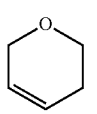

3,4-dihydro-2H-pyran (3,4-dihydro-2H-pyranyl)    5,6-dihydro-2H-pyran (5,6-dihydro-2H-pyranyl)

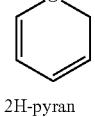 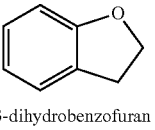

2H-pyran (2H-pyranyl)    2,3-dihydrobenzofuran 2,3-dihydrobenzofuranyl

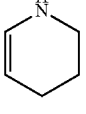 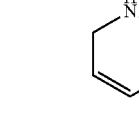

1,2,3,4-tetrahydropyridine (1,2,3,4-tetrahydropyridinyl)    1,2,5,6-tetrahydropyridine (1,2,5,6-tetrahydropyridinyl)

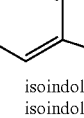 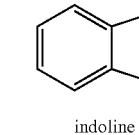

isoindoline isoindolinyl    indoline indolinyl

A "diradical" refers to a group that has two open valences and is further connected to two other groups, or forms a double bond with the same atom of one group, or forms two single bonds with the same atom of one group. Examples of diradicals are, but are not limited to —CH$_2$—, —O—, —O—CH$_2$—, —(C$_1$-C$_3$ alkylene)-NH— and —CH$_2$—

$CH_2$—. When a diradical is referred to as, for example, —O—$CH_2$— or —($C_1$-$C_3$ alkylene)-NH—, it is understood that each end of the diradical can equally connect to another moiety. For example, if K is defined as A-L-B, and L is a diradical selected from —O—$CH_2$— and —($C_1$-$C_3$ alkylene)-, it is understood that K is therefore selected from A-O—$CH_2$—B, A-$CH_2$—O—B, and A-($C_1$-$C_3$ alkylene)-B. A and B herein are referred to as different organic moieties.

When "ene" is added after the "yl" at the end of any of the previously defined terms to form a new term, the new term refers to a diradical formed by removing one hydrogen atom from the original term of which the new term derived from. For example, an alkylene refers to a diradical group formed by removing one hydrogen atom from an alkyl group and that a "methylene" refers to a divalent radical —$CH_2$-derived from removing one hydrogen atom from methyl. More examples of such diradicals include, but are not limited to: alkenylene, alkynylene, cycloalkylene, phenylene, heterocyclylene, heteroarylene and (nonaromatic unsaturated carbocyclylene), which are derived from alkenyl, alkynyl, cycloalkyl, phenyl, heterocyclyl, heteroaryl and (nonaromatic unsaturated carbocyclyl), respectively. For example, "cyclopropylene" refers to both

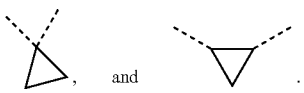

For example, "$C_1$-$C_2$ alkylene" refers to all of the following: —$CH_2$—, —$CH(CH_3)$— and —$CH_2$—$CH_2$—.

A "$C_m$-$C_n$ alkenylene", wherein m is an integer of 2-19, n is an integer of 3 to 20 and n>m, refers to a diradical formed by removing one hydrogen atom from a "$C_m$-$C_n$ alkenyl", as defined previously. Examples of an alkenylene include, but are not limited to: —CH═CH—, —CH═CH—$CH_2$—, —CH═CH($CH_3$)— and —C(═CH—$CH_3$)—.

A "$C_m$-$C_n$ alkynylene", wherein m is an integer of 2-19, n is an integer of 3 to 20 and n>m, refers to a diradical formed by removing one hydrogen atom from a "$C_m$-$C_n$ alkynyl", as defined previously. Examples of an alkenylene include, but are not limited to: —C≡C—, —C≡C—$CH_2$— and —C≡C($CH_3$)—.

A "m to n member heteroalkylene", wherein m is an integer of 2-19, n is an integer of 3 to 20 and n>m, refers to a diradical formed by removing one hydrogen atom from a "m to n member" heteroalkyl, as defined previously. Examples of heteroalkylene include, but are not limited to: —O—$CH_2$—, —NH—$CH_2$—, —N($CH_3$)—$CH_2$—, —S—$CH_2$—, —$CH_2$—O—$CH_2$—, —$CH_2$—N(H)—$CH_2$—, —$CH_2$—S—$CH_2$—, —$CH_2$—CH($OCH_3$)—, —CH($OCH_3$)— and —CH($NH_2$)—$CH_2$—.

"oxo" or "-oxo-" refers to an oxygen double bond "═O" substitution.

"Hydroxy" or "hydroxyl" both refer to —OH.

"Perfluoroalkyl" refers to an alkyl group in which all of its hydrogen atoms are replaced by fluorine atoms.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with the alkyl group.

When a group is "optionally substituted" or "optionally further substituted" by some substituents, it means a carbon or a nitrogen atom of this group wherein one or more hydrogen atoms are attached to the carbon or nitrogen atom, such carbon or nitrogen atom is optionally substituted by some other substituents. For example, "R is H, $C_1$-$C_3$ alkyl or phenyl, and R is optionally further substituted by 1-3 groups selected from —F, oxo and $C_1$-$C_3$ perfluoroalkyl", means that R is 1) H (when R is H, R cannot be further substituted); 2) $C_1$-$C_3$ alkyl optionally further substituted by 1-3 groups selected from —F, oxo and $C_1$-$C_3$ perfluoroalkyl; and 3) phenyl optionally further substituted by 1-3 groups selected from —F and $C_1$-$C_3$ perfluoroalkyl. Optional substitution of oxo does not apply when R is phenyl because no single atom of the phenyl group possess two hydrogen atoms to be substituted by oxo, i.e. ═O bond. When a group is further substituted by a "—($C_1$-$C_4$ alkylene)-", it means the "—($C_1$-$C_4$ alkylene)-", together with the nitrogen atom or the carbon atom of the group to which "$C_1$-$C_4$ alkylene" is attached to, form a carbo or hetero spiro cycle.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts that retain the biological effectiveness and properties of the parent compound. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cellular" tyrosine kinase (CTKs) and serine-threonine kinases (STKs).

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of the present teachings and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, can be determined before use of compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art. The effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

DETAILED DESCRIPTION

Compounds of the present invention may be prepared using the reaction routes and synthetic schemes described below, employing the techniques available in the art using starting materials that are readily available. The preparation of certain embodiments of the present invention is described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g. by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

Compounds of the general structure represented by I are prepared according to three general synthetic processes;

Method A and Method B described in Scheme 1, Method C and Method D in Scheme 2 and Method E and Method F described in Scheme 3.

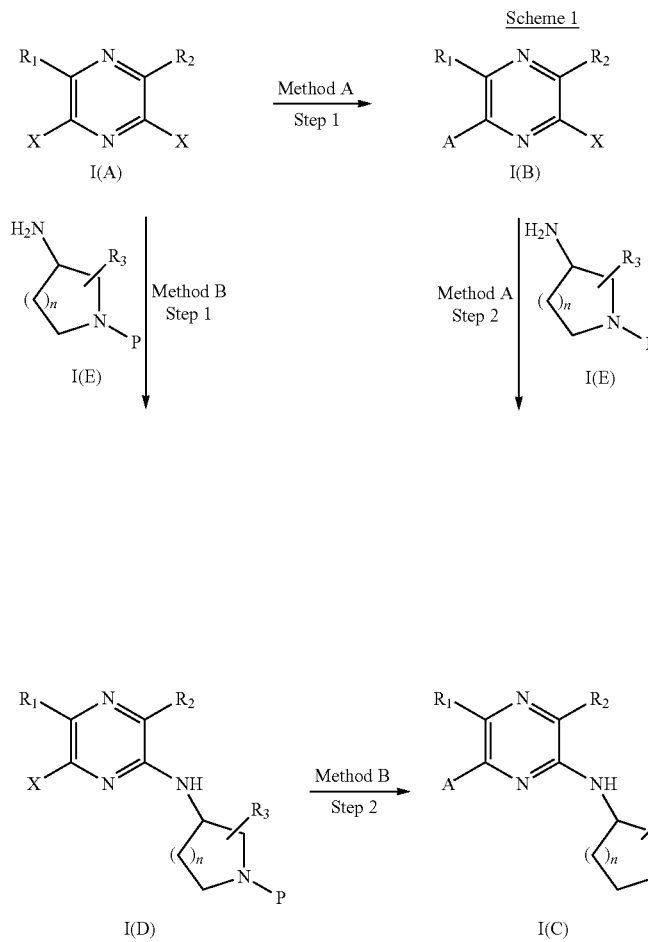

Scheme 1

Method A

Method B

Compound I(A), wherein X is Cl, Br or I, is converted to Compound I(B) by treating I(A) with a heterocycle and using the Heck reaction conditions, or with boronic acid of the formula A-B(OH)$_2$ or a corresponding boronic ester, following modified Suzuki reaction conditions known to those skilled in the art, or with a trimethylstannyl or tributylstannyl of the formula A-Sn(R)$_3$. In cases where Compound I(B) contains an N-linked heterocycle "A", it can be obtained by reacting appropriate heterocycle with Compound I(A), wherein X is F, Cl, Br or I in a suitable solvent, for example, dimethylformamide, in the presence of a base, for example, cesium carbonate, at an elevated temperature ranging from 40° C. to 220° C. for a period of time ranging from one hour to a few days. Compound I(B) is converted to Compound I(C) by treatment with an amine of the type I(E) in a suitable solvent, for example, dimethylsulfoxide, in the presence of a base, for example, cesium fluoride, at an elevated temperature ranging from 40° C. to 220° C. for a period of time ranging from one hour to a few days. Depending of the protection group P used, Compound I(C) can be converted to Compound I by either acidic conditions such as HCl in a solvent such as dioxane, methanol or water, or by hydrogenation using a catalyst such as palladium on charcoal, or under basic conditions at temperatures varying from 20° C. to 200° C.

Compound I(A), wherein X is F, Cl, Br or I is converted to Compound I(D) by treatment with an amine of the type I(E) in a suitable solvent, for example, dimethylsulfoxide, in the presence of a base, for example, cesium fluoride, at an elevated temperature ranging from 40° C. to 220° C. for a period of time ranging from one hour to a few days. Compound I(D) is converted to Compound I(C) by treatment with a heterocycle following conditions for the Heck reaction or with boronic acid of the formula R$_1$—B(OH)$_2$ or a corresponding boronic ester, following modified Suzuki reaction conditions known to those skilled in the art, or with a trimethylstannyl or tributylstannyl of the formula R1-Sn(R)$_3$. In cases where Compound I(C) contains an N-linked heterocycle "A", it can be obtained by reacting the appropriate heterocycle with Compound I(D), wherein X is F, Cl, Br or I in a suitable solvent, for example, dimethylformamide, in the presence of a base, for example, cesium carbonate, at an elevated temperature ranging from 40° C. to 220° C. for a period of time ranging from one hour to a few days. Compound I can be obtain from Compound I(C) by removing a protection group P as described in Method A.

Scheme 2

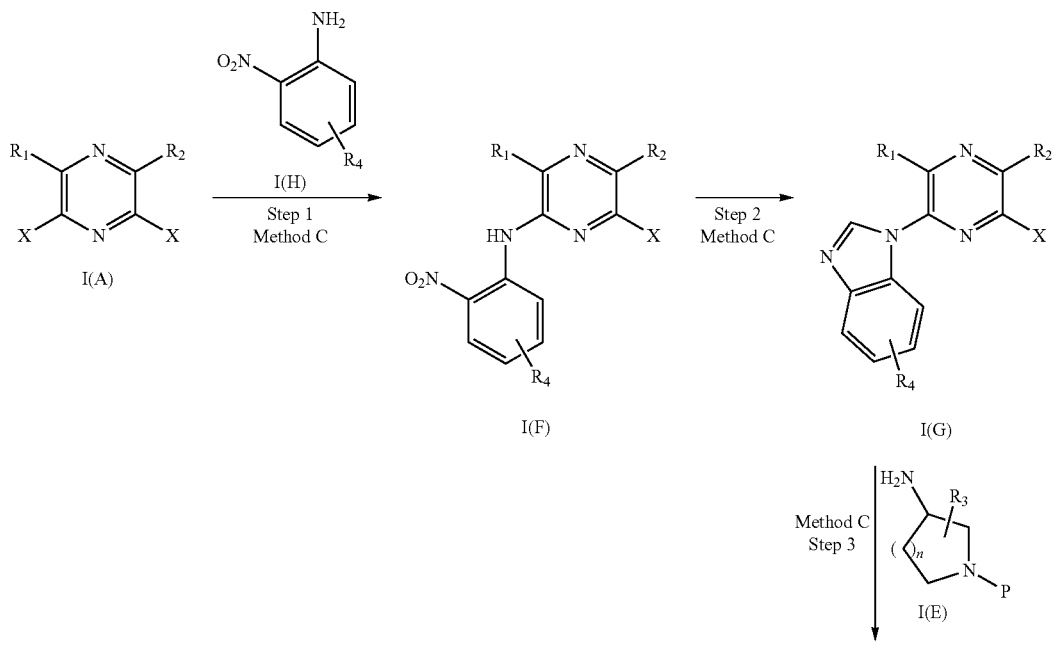

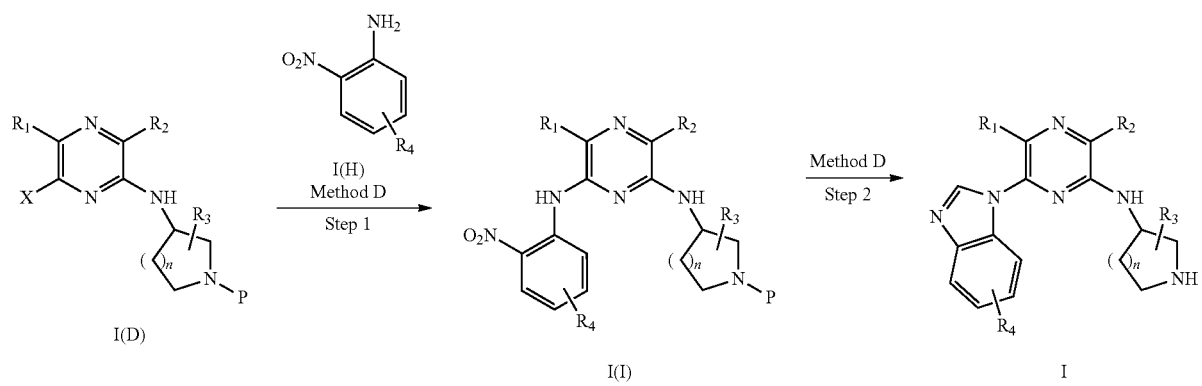

Method C

With reference to Scheme 2 above, Compound I may be prepared starting with the palladium amination reaction of Compound I(A), wherein X is F, Cl, Br or I and an appropriate 2-amino-nitrobenzene I(H) to provide Compound I(F) according to Step 1. Reduction of the nitro group followed by addition of formamidine acetate provides the benzimidazole I(G). In Step 3, Compound I(G) is converted to Compound I by treatment with an amine of the type I(E) in a suitable solvent, for example, dimethylsulfoxide, in the presence of a base, for example, cesium fluoride, at an elevated temperature ranging from 40° C. to 220° C. for a period of time ranging from one hour to a few days followed by subsequent removal of the protection group P as described in Step 3 of Method A.

Method D

Compound I(D), obtained according to step 1 of Method A as described in Scheme 1, wherein X is Cl, Br or I can be converted to Compound I(I) via a palladium amination reaction by treatment with 2-amino-nitrobenzene I(H). Reduction of the nitro group followed by addition of formamidine acetate provides the benzimidazole I after subsequent removal of the protection group P as described in Step 3 of Method A.

Scheme 3

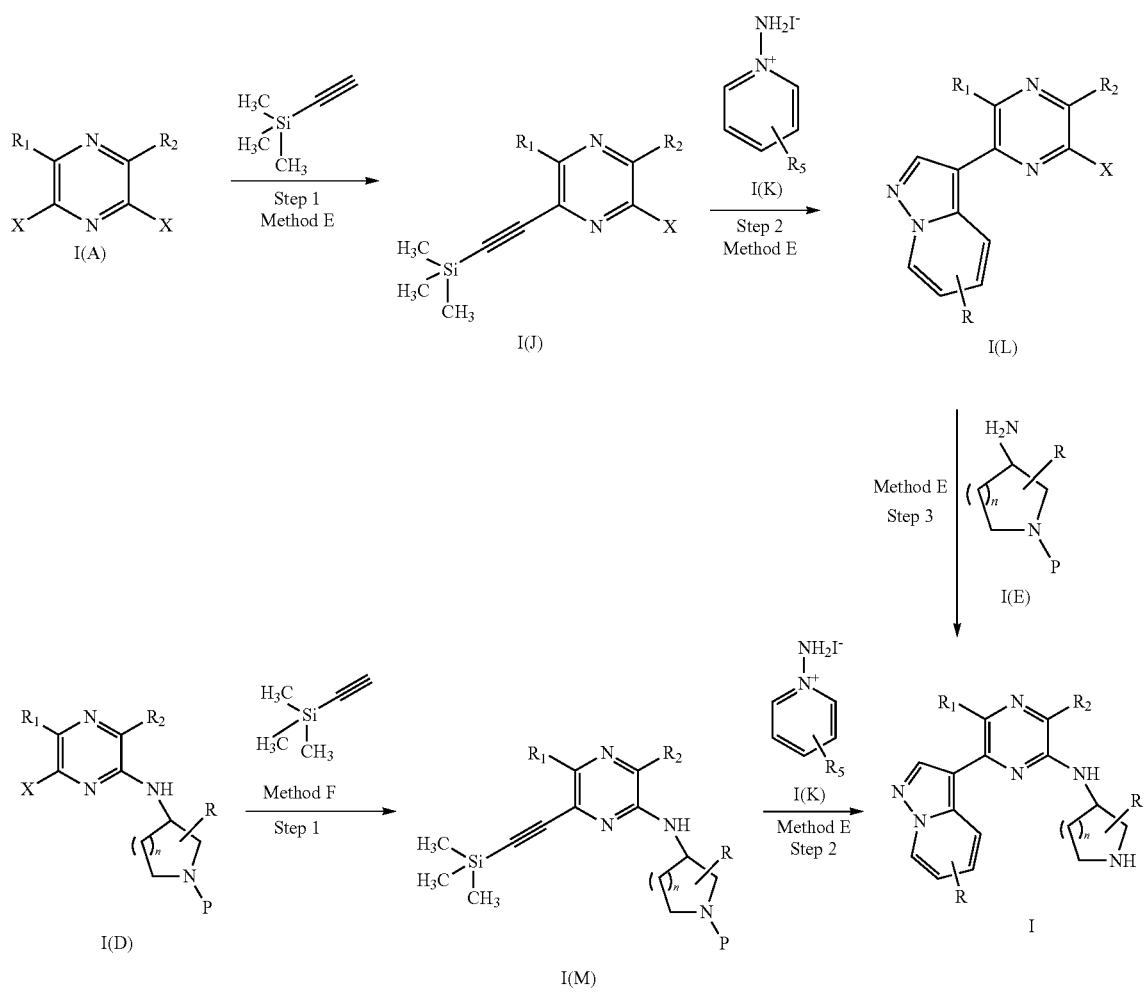

Method E

With reference to Scheme 3 above, Compound I may be prepared starting with the Sonogashira coupling reaction of compound I(A), wherein X is F, Cl, Br or I, and trimethylsilylacetylene to afford Compound I(J). Treatment of I(J) with a base such as potassium carbonate in a solvent such as methanol, followed by reaction with Compound I(K) and a base such as DBU in a solvent such as acetonitrile at an elevated temperature ranging from 40° C. to 150° C., affords compound I(L), which can be converted to Compound I in a manner described according to Step 3 of Method C in Scheme 2.

Method F

Compound I(D), obtained according to step 1 of Method A as described in Scheme 1, wherein X is F, Cl, Br or I, can be converted to compound I(M) via a palladium mediated Sonogashira coupling reaction with trimethylsilylacetylene. Treatment of I(M) with a base such as potassium carbonate in a solvent such as methanol, followed by reaction with Compound I(K) and a base such as DBU in a solvent such as acetonitrile at an elevated temperature ranging from 40° C. to 150° C., affords the desired Compound I after removal of protecting group P in a manner described according to Step 3 of Method A in Scheme 1.

We have also prepared commercially unavailable amines which were used in the synthesis of the compounds of the current invention. The synthesis of these amines is described following the Specific Examples of the current invention.

The compounds of the present invention may have asymmetric carbon atoms. The carbon-carbon bonds of the compounds of the present invention may be depicted herein using a solid line (—) a solid wedge ((━━▬), ) or a dotted wedge ((∙∙∙∙∙∙∙), ) The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the present invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art. See, e.g. "Stereochemistry of Organic Compounds" by E. L. Eliel (Wiley, New York, 1994), the disclosure of which is incorporated herein by reference in its entirety.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization. Where structural isomers are interconvertible via a low energy barrier, tautomeric isomerism ('tautomerism') can occur. This can take the form of proton tautomerism in compounds of the present invention containing, for example, an imino, keto, or oxime group, or so-called valence tautomerism in compounds which contain an aromatic moiety. It follows that a single compound may exhibit more than one type of isomerism. Included within the scope of the invention are all stereoisomers, geometric isomers and tautomeric forms of the inventive compounds, including compounds exhibiting more than one type of isomerism, and mixtures of one or more thereof.

Salts of the present invention can be prepared according to methods known to those of skill in the art. Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

In the case of compounds that are solids, it is understood by those skilled in the art that the inventive compounds and salts may exist in different crystalline or polymorphic forms, or in an amorphous form, all of which are intended to be within the scope of the present invention.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with position emitting isotopes such as, $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of the invention may exist in both unsolvated and solvated forms. The term 'solvate' is used herein to describe a molecular complex comprising a compound of the invention and an amount of one or more pharmaceutically acceptable solvent molecules. The term 'hydrate' is employed when said solvent is water. Examples of solvate forms include, but are not limited to, compounds of the invention in association with water, isopropanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'promoieties' as described, for example, in *Design of Prodrugs* by H. Bundgaard (Elsevier, 1985).

Some examples of prodrugs in accordance with the invention include:

(i) where the compounds of the present invention contain a carboxylic acid functionality (—COOH), a prodrug compound wherein the hydrogen of the carboxylic acid functionality of the compound is replaced by ($C_1$-$C_8$)alkyl to form the corresponding ester;

(ii) where the compounds of the present invention contain an alcohol functionality (—OH), a prodrug compound wherein the hydrogen of the alcohol functionality of the compound is replaced by ($C_1$-$C_6$) alkanoyloxymethyl to form the corresponding ether; and (iii) where the compounds of the present invention contain a primary or secondary amino functionality (—NH$_2$ or —NHR where R≠H), a prodrug compound wherein, as the case may be, one or both hydrogens of the amino functionality of the compound I is/are replaced by ($C_1$-$C_{10}$) alkanoyl to form the corresponding amide.

Further examples of replacement groups in accordance with the foregoing examples and examples of other prodrug types may be found in the aforementioned references. Moreover, certain compounds of the present invention may themselves act as prodrugs of other compounds of the present invention.

Also included within the scope of the invention are metabolites of compounds of the present invention, that is, compounds formed in vivo upon administration of the drug. Some examples of metabolites in accordance with the invention include:

(i) where the compounds of the present invention contain a methyl group, a hydroxymethyl derivative thereof (e.g. —CH$_3$→—CH$_2$OH);

(ii) where the compounds of the present invention contain an alkoxy group, a hydroxy derivative thereof (e.g. —OR→—OH);

(iii) where the compounds of the present invention contain a tertiary amino group, a secondary amino derivative thereof (e.g. —NR$^1$R$^2$→—NHR$^1$ or —NHR$^2$);

(iv) where the compounds of the present invention contain a secondary amino group, a primary derivative thereof (e.g. —NHR$^1$→—NH$_2$);

(v) where the compounds of the present invention contain a phenyl moiety, a phenol derivative thereof (e.g. -Ph→-PhOH); and (vi) where the compounds of the present invention contain an amide group, a carboxylic acid derivative thereof (e.g. —CONH$_2$→COOH).

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention, or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free (e.g. Powderject™ Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

This invention also relates to a method for the treatment of abnormal cell growth in a mammal which comprises administering to said mammal an amount of a compound of the present invention, or a salt or solvate thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

In one embodiment of the present invention the anti-tumor agent used in conjunction with a compound of the present invention and pharmaceutical compositions described herein is an anti-angiogenesis agent, kinase inhibitor, pan kinase inhibitor or growth factor inhibitor. Preferred pan kinase inhibitors include Sutent™ (sunitinib), described in U.S. Pat. No. 6,573,293 (Pfizer, Inc, NY, USA). Anti-angiogenesis agents, include but are not limited to the following agents, such as EGF inhibitors, EGFR inhibitors, VEGF inhibitors, VEGFR inhibitors, TIE2 inhibitors, IGF1R inhibitors, COX-II (cyclooxygenase II) inhibitors, MMP-2 (matrix-metalloprotienase 2) inhibitors, and MMP-9 (matrix-metalloprotienase 9) inhibitors.

Preferred VEGF inhibitors, include for example, Avastin (bevacizumab), an anti-VEGF monoclonal antibody of Genentech, Inc. of South San Francisco, Calif. Additional VEGF inhibitors include CP-547,632 (Pfizer Inc., NY, USA), AG13736 (Pfizer Inc.), ZD-6474 (AstraZeneca), AEE788 (Novartis), AZD-2171, VEGF Trap (Regeneron/Aventis), Vatalanib (also known as PTK-787, ZK-222584: Novartis & Schering AG), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof.

VEGF inhibitors useful in the practice of the present invention are described in U.S. Pat. Nos. 6,534,524 and 6,235,764, both of which are incorporated in their entirety for all purposes. Additional VEGF inhibitors are described in, for example in WO 99/24440, in WO 95/21613, WO 99/61422, U.S. Pat. No. 5,834,504, WO 98/50356, U.S. Pat. No. 5,883,113 U.S. Pat. No. 5,886,020, U.S. Pat. No. 5,792,783, U.S. Pat. No. 6,653,308, WO 99/10349, WO 97/32856, WO 97/22596, WO 98/54093, WO 98/02438, WO 99/16755, and WO 98/02437, all of which are herein incorporated by reference in their entirety.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain, Vitaxin and combinations thereof.

Other antiproliferative agents that may be used in combination with the compounds of the present invention include inhibitors of the enzyme farnesyl protein transferase and inhibitors of the receptor tyrosine kinase PDGFr, including the compounds disclosed and claimed in the following: U.S. Pat. No. 6,080,769; U.S. Pat. No. 6,194,438; U.S. Pat. No. 6,258,824; U.S. Pat. No. 6,586,447; U.S. Pat. No. 6,071,935; U.S. Pat. No. 6,495,564; and U.S. Pat. No. 6,150,377; U.S. Pat. No. 6,596,735; U.S. Pat. No. 6,479,513; WO 01/40217; U.S. 2003-0166675. Each of the foregoing patents and patent applications is herein incorporated by reference in their entirety.

PDGRr inhibitors include but are not limited to those disclosed in international patent application publication numbers WO01/40217 and WO2004/020431, the contents of which are incorporated in their entirety for all purposes. Preferred PDGFr inhibitors include Pfizer's CP-673,451 and CP-868,596 and its salts.

Preferred GARF inhibitors include Pfizer's AG-2037 (pelitrexol and its salts). GARF inhibitors useful in the practice of the present invention are disclosed in U.S. Pat. No. 5,608,082 which is incorporated in its entirety for all purposes.

Examples of useful COX-II inhibitors which can be used in conjunction with a compound of Formula (I) and pharmaceutical compositions disclosed herein include CELEBREX™ (celecoxib), parecoxib, deracoxib, ABT-963, MK-663 (etoricoxib), COX-189 (Lumiracoxib), BMS 347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, T-614, JTE-522, S-2474, SVT-2016, CT-3, SC-58125 and Arcoxia (etoricoxib). Additionally, COX-II inhibitors are disclosed in U.S. Patent Applications US 2005-0148627 and US 2005-0148777, the contents of which are incorporated in their entirety for all purposes.

In a particular embodiment the anti-tumor agent is celecoxib (U.S. Pat. No. 5,466,823), valdecoxib (U.S. Pat. No. 5,633,272), parecoxib (U.S. Pat. No. 5,932,598), deracoxib (U.S. Pat. No. 5,521,207), SD-8381 (U.S. Pat. No. 6,034,256, Example 175), ABT-963 (WO 2002/24719), rofecoxib (CAS No. 162011-90-7), MK-663 (or etoricoxib) as disclosed in WO 1998/03484, COX-189 (Lumiracoxib) as disclosed in WO 1999/11605, BMS-347070 (U.S. Pat. No. 6,180,651), NS-398 (CAS 123653-11-2), RS 57067 (CAS 17932-91-3), 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, or meloxicam.

Other useful inhibitors as anti-tumor agents used in combination with a compound of the present invention and pharmaceutical compositions disclosed herein include aspirin, and non-steroidal anti-inflammatory drugs (NSAIDs) which inhibit the enzyme that makes prostaglandins (cyclooxygenase I and II), resulting in lower levels of prostaglandins, include but are not limited to the following, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol), Oxaprozin (Daypro) and combinations thereof. Preferred COX-I inhibitors include ibuprofen (Motrin), nuprin, naproxen (Aleve), indomethacin (Indocin), nabumetone (Relafen) and combinations thereof.

Targeted agents used in combination with a compound of the present invention and pharmaceutical compositions disclosed herein include EGFr inhibitors such as Iressa (gefitinib, AstraZeneca), Tarceva (erlotinib or OSI-774, OSI Pharmaceuticals Inc.), Erbitux (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof. Preferred EGFr inhibitors include Iressa, Erbitux, Tarceva and combinations thereof.

Other anti-tumor agents include those selected from pan erb receptor inhibitors or ErbB2 receptor inhibitors, such as CP-724,714 (Pfizer, Inc.), CI-1033 (canertinib, Pfizer, Inc.), Herceptin (trastuzumab, Genentech Inc.), Omitarg (2C4, pertuzumab, Genentech Inc.), TAK-165 (Takeda), GW-572016 (Ionafarnib, GlaxoSmithKline), GW-282974 (GlaxoSmithKline), EKB-569 (Wyeth), PKI-166 (Novartis), dHER2 (HER2 Vaccine, Corixa and GlaxoSmithKline), APC8024 (HER2 Vaccine, Dendreon), anti-HER2/neu bispecific antibody (Decof Cancer Center), B7.her2.IgG3 (Agensys), AS HER2 (Research Institute for Rad Biology & Medicine), trifunctional bispecific antibodies (University of Munich) and mAB AR-209 (Aronex Pharmaceuticals Inc) and mAB 2B-1 (Chiron) and combinations thereof.

Preferred erb selective anti-tumor agents include Herceptin, TAK-165, CP-724,714, ABX-EGF, HER3 and combinations thereof. Preferred pan erbb receptor inhibitors include GW572016, CI-1033, EKB-569, and Omitarg and combinations thereof.

Additional erbB2 inhibitors include those disclosed in WO 98/02434, WO 99/35146, WO 99/35132, WO 98/02437, WO 97/13760, WO 95/19970, U.S. Pat. No. 5,587,458, and U.S. Pat. No. 5,877,305, each of which is herein incorporated by reference in its entirety. ErbB2 receptor inhibitors useful in the present invention are also disclosed in U.S. Pat. Nos. 6,465,449, and 6,284,764, and in WO 2001/98277 each of which are herein incorporated by reference in their entirety.

Additionally, other anti-tumor agents may be selected from the following agents, BAY-43-9006 (Onyx Pharmaceuticals Inc.), Genasense (augmerosen, Genta), Panitumumab (Abgenix/Amgen), Zevalin (Schering), Bexxar (Corixa/GlaxoSmithKline), Abarelix, Alimta, EPO 906 (Novartis), discodermolide (XAA-296), ABT-510 (Abbott), Neovastat (Aeterna), enzastaurin (Eli Lilly), Combrestatin A4P (Oxigene), ZD-6126 (AstraZeneca), flavopiridol (Aventis), CYC-202 (Cyclacel), AVE-8062 (Aventis), DMXAA (Roche/Antisoma), Thymitaq (Eximias), Temodar (temozolomide, Schering Plough) and Revilimd (Celegene) and combinations thereof.

Other anti-tumor agents may be selected from the following agents, CyPat (cyproterone acetate), Histerelin (histrelin acetate), Plenaixis (abarelix depot), Atrasentan (ABT-627), Satraplatin (JM-216), thalomid (Thalidomide), Theratope, Temilifene (DPPE), ABI-007 (paclitaxel), Evista (raloxifene), Atamestane (Biomed-777), Xyotax (polyglutamate paclitaxel), Targetin (bexarotine) and combinations thereof.

Additionally, other anti-tumor agents may be selected from the following agents, Trizaone (tirapazamine), Aposyn (exisulind), Nevastat (AE-941), Ceplene (histamine dihydrochloride), Orathecin (rubitecan), Virulizin, Gastrimmune (G17DT), DX-8951f (exatecan mesylate), Onconase (ranpirnase), BEC2 (mitumoab), Xcytrin (motexafin gadolinium) and combinations thereof.

Further anti-tumor agents may be selected from the following agents, CeaVac (CEA), NeuTrexin (trimetresate glucuronate) and combinations thereof. Additional anti-tumor agents may be selected from the following agents, OvaRex (oregovomab), Osidem (IDM-1), and combinations thereof. Additional anti-tumor agents may be selected from the following agents, Advexin (ING 201), Tirazone (tirapazamine), and combinations thereof. Additional anti-tumor agents may be selected from the following agents, RSR13 (efaproxiral), Cotara (131I chTNT 1/b), NBI-3001 (IL-4) and combinations thereof. Additional anti-tumor agents may be selected from the following agents, Canvaxin, GMK vaccine, PEG Interon A, Taxoprexin (DHA/paciltaxel), and combinations thereof.

Other anti-tumor agents include Pfizer's MEK1/2 inhibitor PD325901, Array Biopharm's MEK inhibitor ARRY-142886, Bristol Myers' CDK2 inhibitor BMS-387,032, Pfizer's CDK inhibitor PD0332991 and AstraZeneca's AXD-5438, and combinations thereof.

Additionally, mTOR inhibitors may also be utilized such as CCI-779 (Wyeth) and rapamycin derivatives RAD001 (Novartis) and AP-23573 (Ariad), HDAC inhibitors, SAHA (Merck Inc./Aton Pharmaceuticals) and combinations thereof. Additional anti-tumor agents include aurora 2 inhibitor VX-680 (Vertex), and Chk1/2 inhibitor XL844 (Exilixis).

The following cytotoxic agents, e.g., one or more selected from the group consisting of epirubicin (Ellence), docetaxel (Taxotere), paclitaxel, Zinecard (dexrazoxane), rituximab (Rituxan) imatinib mesylate (Gleevec), and combinations thereof, may be used in combination with a compound of the present invention and pharmaceutical compositions disclosed herein.

The invention also contemplates the use of the compounds of the present invention together with hormonal therapy, including but not limited to, exemestane (Aromasin, Pfizer Inc.), leuprorelin (Lupron or Leuplin, TAP/Abbott/Takeda), anastrozole (Arimidex, Astrazeneca), gosrelin (Zoladex, AstraZeneca), doxercalciferol, fadrozole, formestane, tamoxifen citrate (tamoxifen, Nolvadex, AstraZeneca), Casodex (AstraZeneca), Abarelix (Praecis), Trelstar, and combinations thereof.

The invention also relates to the use of the compounds of the present invention together with hormonal therapy agents such as anti-estrogens including, but not limited to fulvestrant, toremifene, raloxifene, lasofoxifene, letrozole (Femara, Novartis), anti-androgens such as bicalutamide, flutamide, mifepristone, nilutamide, Casodex™ (4'-cyano-3-(4-fluorophenylsulphonyl)-2-hydroxy-2-methyl-3'-(trifluoromethyl) propionanilide, bicalutamide) and combinations thereof.

Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof.

Particularly preferred cytotoxic agents include Camptosar, Erbitux, Iressa, Gleevec, Taxotere and combinations thereof.

The following topoisomerase I inhibitors may be utilized as anti-tumor agents: camptothecin; irinotecan HCl (Camptosar); edotecarin; orathecin (Supergen); exatecan (Daiichi); BN-80915 (Roche); and combinations thereof. Particularly preferred toposimerase II inhibitors include epirubicin (Ellence).

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, Paraplatin (carboplatin), eptaplatin, lobaplatin, nedaplatin, Eloxatin (oxaliplatin, Sanofi) or satrplatin and combinations thereof. Particularly preferred alkylating agents include Eloxatin (oxaliplatin).

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid and combinations thereof. Antibiotics include intercalating antibiotics and include, but are not limited to: aclarubicin, actinomycin D, amrubicin, annamycin, adriamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin, zinostatin and combinations thereof.

Plant derived anti-tumor substances include for example those selected from mitotic inhibitors, for example vinblastine, docetaxel (Taxotere), paclitaxel and combinations thereof.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, topotecan, and combinations thereof.

Preferred cytotoxic topoisomerase inhibiting agents include one or more agents selected from the group consisting of camptothecin, 10-hydroxycamptothecin, 9-aminocamptothecin, irinotecan HCl (Camptosar), edotecarin, epirubicin (Ellence), etoposide, SN-38, topotecan, and combinations thereof.

Immunologicals include interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-n1 and combinations thereof. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab (Y-muHMFG1), Provenge (Dendreon) and combinations thereof.

Biological response modifiers are agents that modify defense mechanisms of living organisms or biological responses, such as survival, growth, or differentiation of tissue cells to direct them to have anti-tumor activity. Such agents include krestin, lentinan, sizofuran, picibanil, ubenimex and combinations thereof.

Other anticancer agents that can be used in combination with a compound of the present invention include alitretinoin, ampligen, atrasentan bexarotene, bortezomib. Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, Telcyta (TLK-286, Telik Inc.), Velcade (bortemazib, Millenium), tretinoin, and combinations thereof.

Platinum-coordinated compounds include but are not limited to, cisplatin, carboplatin, nedaplatin, oxaliplatin, and combinations thereof.

Camptothecin derivatives include but are not limited to camptothecin, 10-hydroxycamptothecin, 9-aminocamptothecin, irinotecan, SN-38, edotecarin, topotecan and combinations thereof.

Other antitumor agents include mitoxantrone, I-asparaginase, procarbazine, dacarbazine, hydroxycarbamide, pentostatin, tretinoin and combinations thereof.

Anti-tumor agents capable of enhancing antitumor immune responses, such as CTLA4 (cytotoxic lymphocyte antigen 4) antibodies, and other agents capable of blocking CTLA4 may also be utilized, such as MDX-010 (Medarex) and CTLA4 compounds disclosed in U.S. Pat. No. 6,682,736; and anti-proliferative agents such as other farnesyl protein transferase inhibitors, for example the farnesyl protein transferase inhibitors. Additionally, specific CTLA4 antibodies that can be used in combination with compounds of the present invention include those disclosed in U.S. Pat. Nos. 6,682,736 and 6,682,736 both of which are herein incorporated by reference in their entirety.

Specific IGF1R antibodies that can be used in the combination methods of the present invention include those disclosed in WO 2002/053596, which is herein incorporated by reference in its entirety.

Specific CD40 antibodies that can be used in the present invention include those disclosed in WO 2003/040170 which is herein incorporated by reference in its entirety.

Gene therapy agents may also be employed as anti-tumor agents such as TNFerade (GeneVec), which express TNFalpha in response to radiotherapy.

In one embodiment of the present invention statins may be used in combination with a compound of the present invention and pharmaceutical compositions thereof. Statins (HMG-CoA reducatase inhibitors) may be selected from the group consisting of Atorvastatin (Lipitor™, Pfizer Inc.), Provastatin (Pravachol™, Bristol-Myers Squibb), Lovastatin (Mevacor™, Merck Inc.), Simvastatin (Zocor™, Merck Inc.), Fluvastatin (Lescol™, Novartis), Cerivastatin (Baycol™, Bayer), Rosuvastatin (Crestor™, AstraZeneca), Lovostatin and Niacin (Advicor™, Kos Pharmaceuticals), derivatives and combinations thereof.

In a preferred embodiment the statin is selected from the group consisting of Atovorstatin and Lovastatin, derivatives and combinations thereof. Other agents useful as anti-tumor agents include Caduet.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

In the following examples and preparations, "BOC", "Boc" or "boc" means N-tert-butoxycarbonyl, CBZ means carbobenzyloxy, DCM means $CH_2Cl_2$, DIPEA or DIEA means diisopropyl ethyl amine, DMA means N,N-dimethylacetamide, "DMF" means dimethylformamide, "DMSO" means dimethylsulfoxide, "DPPP" means 1,3-bis(diphenylphosphino)propane, "HOAc" means acetic acid, "IPA" means isopropyl alcohol, "MTBE" means methyl t-butyl ether, "NMP" means 1-methyl 2-pyrrolidinone, TEA means triethyl amine, TFA means trifluoro acetic acid.

Specific Examples

Example 1

(Method B): 6-(1H-benzimidazol-1-yl)-N-[(3R)-piperidin-3-yl]pyrazin-2-amine

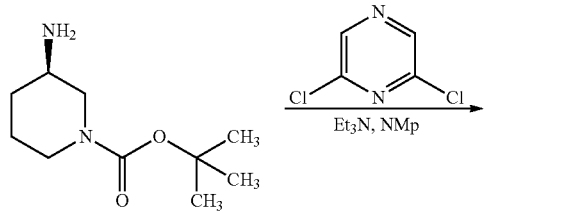

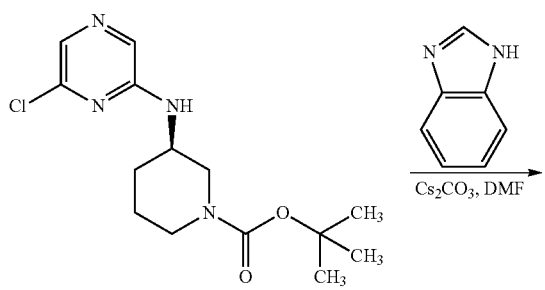

1a

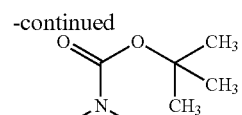

1b

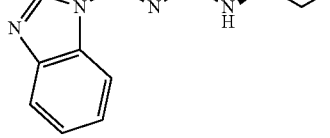

1

Preparation of Compound 1a: (R)-Tert-butyl 3-(6-chloropyrazin-2-ylamino)piperidine-1-carboxylate A mixture of (R)-1-BOC-3-aminopiperidine (200 mg, 1 mmol), 2,6-dichloropyrazine (149 mg, 1 mmol), and diisopropylethyl amine (129 mg, 1 mmol) in NMP (2 ml) was heated to 80° C. The reaction mixture was concentrated under reduced pressure, and the crude product was purified by flash chromatography on silica gel (30-100% EtOAc-hexanes) which gave the title compound 1a as a clear oil (187 mg, 60% yield). 1H NMR (400 MHz, chloroform-d) δ ppm 7.81 (br. s., 2H), 5.00 (br. s., 1H), 3.88 (br. s., 1H), 3.72 (d, J=12.6 Hz, 1H), 3.46 (br. s., 1H), 3.35 (dd, J=18.7, 6.1 Hz, 2H), 1.94 (br. s., 1H), 1.53-1.79 (m, 3H), 1.43 (br. s., 9H). LCMS M+1−Boc=213.

Preparation of Compound 1b: (3R)-Tert-butyl 3-(6-(1H-benzo[d]imidazol-1-yl)pyrazin-2-ylamino)piperidine-1-carboxylate Benzimidazole (76 mg, 0.64 mmol), 1a (200 mg, 0.639 mmol) and $Cs_2CO_3$ (312 mg, 0.959 mmol) were dissolved in DMF (2 mL). The mixture was heated at 80° C. overnight. The reaction mixture was diluted with water (25 mL) and extracted with DCM (2×20 mL). The organic layer was concentrated under reduced pressure and the crude product was purified by flash chromatography on silica gel (0-45% ethanol-EtOAc) which gave the title compound 1b as a clear oil (80 mg, 32% yield). 1H NMR (400 MHz, DMSO-d6) δ ppm 8.92 (s, 1H), 8.27 (s, 1H), 8.20 (s, 1H), 7.93-8.04 (m, 1H), 7.77 (d, J=7.3 Hz, 1H), 7.49-7.60 (m, 2H), 7.30-7.39 (m, 2H), 7.18 (t, J=8.6 Hz, 1H), 3.83 (s, 1H) 3.44 (qd, J=7.0, 5.0 Hz, 1H), 2.02 (s, 1H), 1.82 (s, 1H), 1.62 (s, 1H), 1.49 (d, J=3.8 Hz, 1H), 1.46 (s, 1H), 1.31-1.43 (m, 3H), 1.01-1.13 (m, 5H). LCMS m/z 395 (M+H).

Compound 1b (80 mg) was dissolved in 1,4-dioxanes (5 mL) and treated with 4M HCl in 1,4-dioxane (2 mL). A yellow precipitate formed after two hours. The solvent was removed under reduced pressure and the resultant yellow solid was dissolved in MeOH (1 mL). The solution was passed thru an SCX column and eluted with 4 N ammonium in MeOH. The methanolic solution was concentrated under reduced pressure which gave the desired compound 1 as a colorless oil (57 mg, 48% yield). 1H NMR (400 MHz, MeOD) δ ppm 8.82 (s, 1H), 8.16 (d, J=8.1 Hz, 1H), 8.13 (s, 1H), 7.88 (s, 1H), 7.76 (d, J=7.8 Hz, 1H), 7.44 (t, J=7.4 Hz, 1H), 7.38 (t, J=7.6 Hz, 1H), 4.01 (dd, J=13.6, 5.6 Hz, 1H), 3.09-3.22 (m, 2H), 2.97 (d, J=12.4 Hz, 1H), 2.49-2.68 (m, 2H), 2.16 (dd, J=12.0, 3.2 Hz, 1H), 1.82 (ddd, J=13.3, 3.8, 3.7 Hz, 1H), 1.60-1.73 (m, 1H), 1.48-1.60 (m, 1H). LCMS m/z 295 (M+1).

Example 2

(Method B): 6-Imidazo[1,2-a]pyridin-3-yl-N-[(3R)-piperidin-3-yl]pyrazin-2-amine

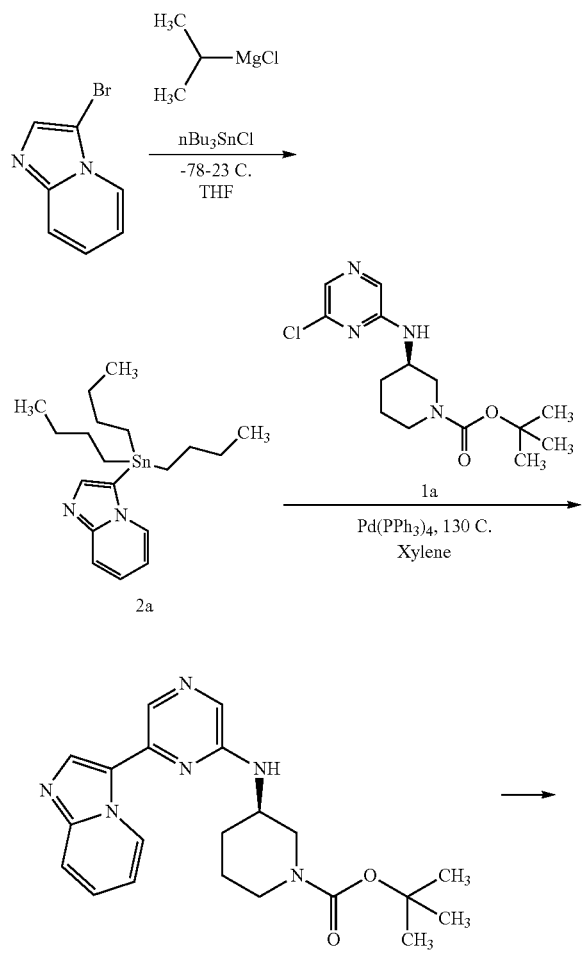

Preparation of Compound 2a: 3-(Tributylstannyl)-imidazo[1,2-a]pyridine

3-Bromoimidazo[1,2-a]pyridine (197 mg, 1 mmol) was dissolved THF (3 mL), cooled to −78° C., and treated with isopropylmagnesium chloride (108 mg, 1.05 mmol). The mixture was gradually warmed to room temperature. After 1 h, the reaction mixture was cooled to −78° C., treated with tri-n-butyltin chloride (326 mg, 1 mmol), and gradually warmed to room temperature. The reaction mixture was quenched with saturated NaHCO₃, and the aqueous layer was extracted with EtOAc. The organic layer was washed with brine, dried over Na₂SO₄, decanted and concentrated which gave the title compound 2a as an oil. The crude product was used in the next step.

Preparation of Compound 2b: (3R)-Tert-butyl 3-(6-(imidazo[1,2-a]pyridin-3-yl)pyrazin-2-ylamino)piperidine-1-carboxylate A mixture of 2a (crude), 1a (90 mg, 0.29 mmol) and tetrakis(triphenylphosphine) palladium(0) (33 mg, 0.029 mmol) in o-xylene (2 mL) was purged with nitrogen and heated to 130° C. overnight. The reaction mixture was concentrated under reduced pressure, and the crude product was purified by flash chromatography on silica gel (30-100% EtOAc-hexanes then 0-20% MeOH-EtOAc) which gave the title compound 2b as a greenish oil (89 mg, 78% yield). 1H NMR (400 MHz, MeOD) δ ppm 9.67 (br. s., 2H), 8.15 (s, 1H), 8.13 (s, 1H), 7.63-7.77 (m, 1H), 7.57 (d, J=8.6 Hz, 1H), 7.35 (t, J=7.7 Hz, 1H), 7.01 (t, J=6.9 Hz, 1H), 3.85 (d, J=3.3, Hz, 1H), 3.34 (d, J=7.3 Hz, 1H), 0.68-2.42 (m, 18H). LCMS m/z 395 (M+1).

A mixture of 2b (89 mg) and 4N HCl in dioxane (2 mL) was stirred at 23° C. for 2 h. The solvent was removed under reduced pressure and the resultant yellow solid was triturated with EtOAc which gave the dihydrochloride title compound 2 as a yellow solid (75 mg, 91% yield). 1H NMR (400 MHz, DMSO-d6) δ ppm 9.98-10.14 (m, 1H), 9.93 (d, J=7.1 Hz, 1H), 9.22 (br. s., 1H), 9.03 (s, 1H), 8.46 (s, 1H), 8.00-8.13 (m, 3H), 7.89 (d, J=7.1 Hz, 2H), 4.40 (br. s., 1H), 3.43 (d, J=10.9 Hz, 1H), 3.17 (d, J=3.8 Hz, 1H), 2.93 (br. s., 1H), 2.84 (d, J=9.8 Hz, 1H), 2.04 (d, J=12.9 Hz, 1H), 1.85-2.00 (m, 2H), 1.59 (d, J=8.8 Hz, 1H). LCMS m/z 295 (M+1).

Example 3

(Method A): 6-Imidazo[1,2-a]pyridin-3-yl-N-[(3S)-piperidin-3-yl]pyrazin-2-amine

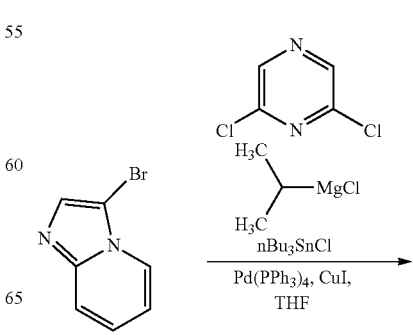

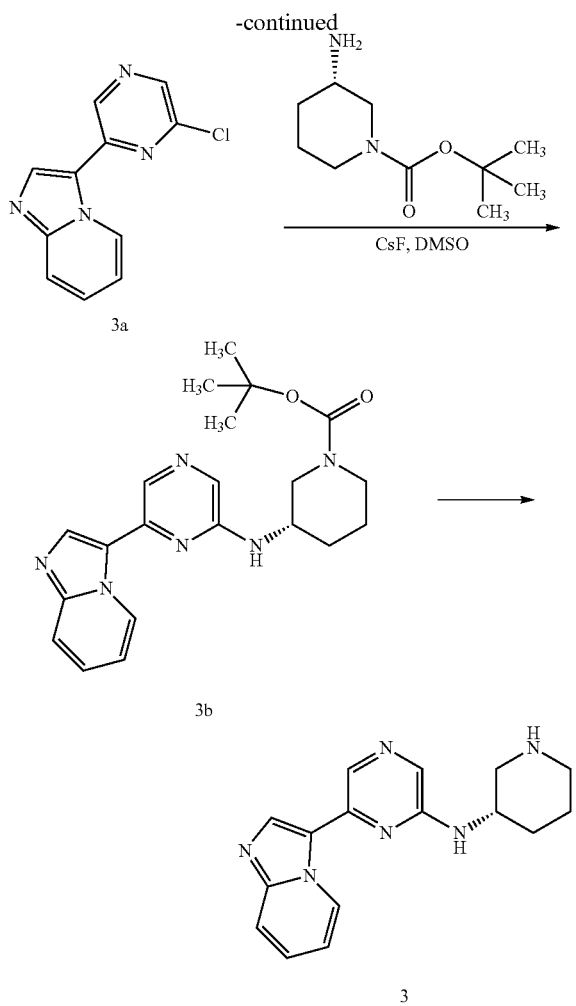

Preparation of 3a: 3-(6-Chloropyrazin-2-yl)-imidazo[1,2-a]pyridine

A solution of 3-bromoimidazo[1,2-a]pyridine (10 g, 51 mmol) in THF (100 ml) was cooled to −78° C., and treated with isopropylmagnesium chloride (26.7 mL, 53.3 mmol) over 10 minutes. The resultant yellow mixture was stirred at −78° C. to −40° C. for 60 minutes, cooled to −78° C., treated with tri-n-butyltin chloride (13.7 mL, 50.8 mmol) and warmed to room temperature. The reaction mixture became homogenous after 30 min. Next, the crude organostannane was treated with 2,6-dichloropyrazine (15.1 g, 102 mmol), tetrakis(triphenylphosphine) palladium(0) (1.76 g, 1.52 mmol), copper(I) iodide (48 mg, 0.254 mmol) and purged with nitrogen. The reaction mixture was refluxed overnight. The reaction mixture was concentrated under reduced pressure, and the crude product was purified by flash chromatography on silica gel (0-10% MeOH-DCM) which gave the title compound 3a as yellow solid (10.1 g). 1H NMR (300 MHz, DMSO-d6) δ ppm 9.55-9.63 (m, 1H), 9.33 (s, 1H), 8.70 (s, 1H), 8.55-8.61 (m, 1H), 7.76-7.84 (m, 1H), 7.46-7.59 (m, 1H), 7.20-7.31 (m, 1H).

Preparation of 3b: (3S)-Tert-butyl 3-(6-(imidazo[1,2-a]pyridin-3-yl)pyrazin-2-ylamino)piperidine-1-carboxylate A mixture of cesium fluoride in DMSO (0.9 mL) was treated with 3-(6-chloropyrazin-2-yl)-imidazo[1,2-a]pyridine 3a (100 mg, 0.434 mmol), (S)-1-BOC-3-aminopiperidine (124 mg, 0.62 mmol) and heated to 120° C. overnight. The crude reaction mixture was poured into 5% aqueous NaHCO3 and extracted with MTBE. The organic layer was washed with brine, dried over MgSO4, filtered and concentrated under reduced pressure which gave a brown oil (250 mg). The crude product was purified by radial chromatography on silica gel (2-6% MeOH-EtOAc with 0.1% NH4OH) which gave the title compound 3b as an off-white solid from MTBE-heptane (100 mg). 1H NMR (400 MHz, DMSO-d6) δ ppm 9.69 (d, J=6.8 Hz, 1H), 8.36 (s, 1H), 8.34 (s, 1H), 7.85 (s, 1H), 7.71 (d, J=8.8 Hz, 1H), 7.39 (ddd, J=8.6, 7.0, 1.3 Hz, 1H), 7.24 (d, J=6.80 Hz, 1H), 7.07 (td, J=6.9, 1.1 Hz, 1H), 3.74-3.86 (m, 2H), 1.97-2.07 (m, 1H), 1.81 (s, 1H), 1.43 (s, 4H), 1.24 (s, 3H), 1.17 (s, 1H), 1.10 (s, 5H).

A solution of 3b (75 mg, 0.19 mmol) in DCM (1 mL) was treated with TFA (1 mL). After two hours, the solvent was removed under reduced pressure and the crude product was dissolved in 10% IPA/chloroform, washed with saturated aqueous NaHCO3, brine, dried over MgSO4, filtered and concentrated under reduced pressure. The crude product was purified by preparative HPLC (water-acetonitrile with TFA), which gave the title compound 3 as a beige solid from MTBE-heptane (25 mg). 1H NMR (400 MHz, DMSO-d6) δ ppm 9.77 (d, J=7.0 Hz, 1H), 8.36 (s, 1H), 8.31 (s, 1H), 7.80 (s, 1H), 7.71 (d, J=9.1 Hz, 1H), 7.39 (dd, J=8.3, 7.3 Hz, 1H), 7.06-7.15 (m, 2H), 3.78 (s, 1H), 3.13 (s, 1H), 3.08 (s, 1H), 2.78-2.88 (m, 1H), 2.40-2.47 (m, 1H), 2.03 (s, 1H), 1.68 (s, 1H), 1.47 (d, J=8.6 Hz, 2H). LCMS m/z 295 (M+1).

Example 4

(Method A): 6-Imidazo[1,2-a]pyrazin-3-yl-N-[(3R)-piperidin-3-yl]pyrazin-2-amine

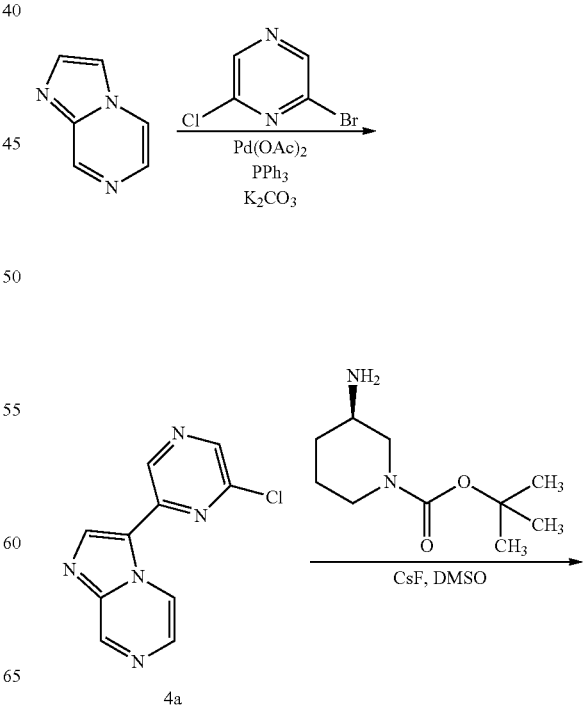

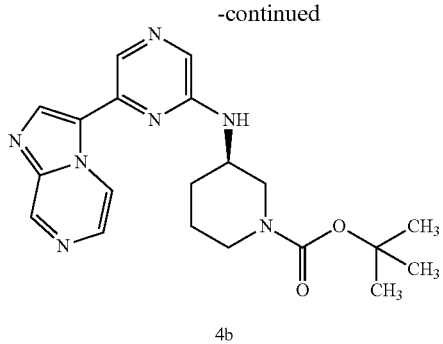

4b

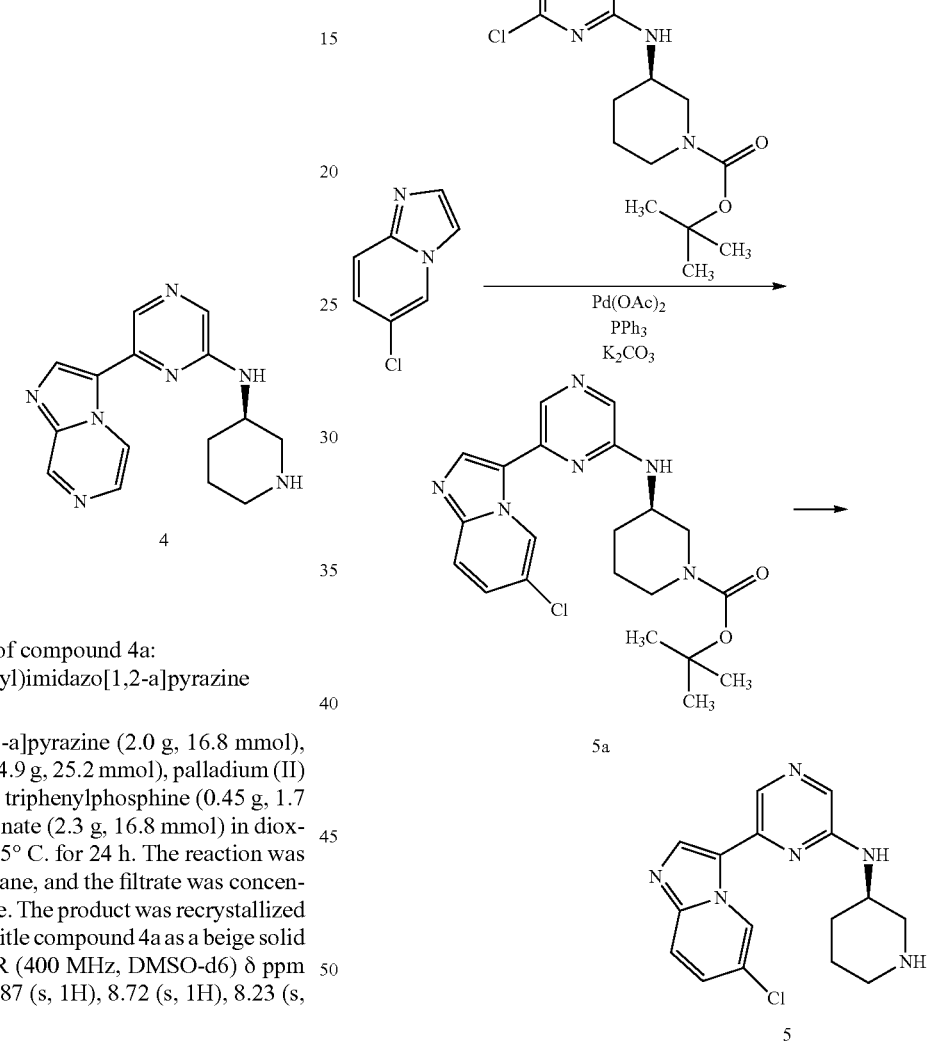

Preparation of compound 4a: 3-(6-Chloropyrazin-2-yl)imidazo[1,2-a]pyrazine

A mixture of imidazo[1,2-a]pyrazine (2.0 g, 16.8 mmol), 2-bromo-6-chloropyrazine (4.9 g, 25.2 mmol), palladium (II) acetate (0.78 g, 3.36 mmol), triphenylphosphine (0.45 g, 1.7 mmol), and potassium carbonate (2.3 g, 16.8 mmol) in dioxane (40 mL) was heated at 75° C. for 24 h. The reaction was filtered hot, rinsed with dioxane, and the filtrate was concentrated under reduced pressure. The product was recrystallized from EtOAc which gave the title compound 4a as a beige solid (2.2 g, 55% yield). 1H NMR (400 MHz, DMSO-d6) δ ppm 9.43 (s, 2H), 9.29 (s, 1H), 8.87 (s, 1H), 8.72 (s, 1H), 8.23 (s, 1H).

A mixture of cesium fluoride (178 mg, 1.17 mmol), 4a (100 mg, 0.43 mmol) and (R)-tert-butyl 3-aminopiperidine-1-carboxylate (130 mg, 0.65 mmol) in DMSO (0.9 mL) was heated to 120° C. overnight. The crude product was filtered and purified by preparative HPLC (water-acetonitrile with acetic acid). The product 4b was dissolved in MeOH (2 mL) and treated with 4N HCl in dioxane (3 mL). The reaction mixture was stirred at room temperature for 2 h and concentrated under reduced pressure. The crude product was dissolved in MeOH and passed thru an SCX column which gave the title compound 4 as a yellow solid (56 mg, 44% yield). 1H NMR (400 MHz, MeOD) δ ppm 9.59 (s, 1H), 9.12 (s, 1H), 8.47 (br. s., 1H), 8.37 (s, 1H), 8.09 (s, 1H), 7.89 (s, 1H), 4.19 (br. s., 1H), 3.48 (br. s., 1H), 3.21 (br. s., 1H), 2.90 (br. s., 2H), 2.22 (br. s., 1H), 2.03 (br. s., 1H), 1.85 (br. s., 1H), 1.69 (br. s., 1H). LCMS m/z 296 (M+1).

Example 5

(Method B): 6-(6-Chloroimidazo[1,2-a]pyridin-3-yl)-N-[(3R)-piperidin-3-yl]pyrazin-2-amine Preparation of compound 5a: (3R)-Tert-butyl 3-(6-(6-chloroimidazo[1,2-a]pyridin-3-yl)pyrazin-2-ylamino)piperidine-1-carboxylate A mixture of 6-chloroimidazo[1,2-a]pyridine (100 mg, 0.66 mmol), 1a (308 mg, 0.98 mmol), palladium (II) acetate (30 mg, 0.13 mmol), triphenylphosphine (17 mg, 0.07 mmol), and potassium carbonate (90 mg, 0.66 mmol) in dioxane (1.2 mL) was heated in a microwave at 130° C. for 30 min. The reaction was filtered and purified by preparative reverse phase HPLC (water-acetonitrile with acetic acid), which gave 5a. (3R)-Tert-butyl 3-(6-(6-chloroimidazo[1,2-a]pyridin-3-yl)

pyrazin-2-ylamino)piperidine-1-carboxylate 5a was dissolved in MeOH (2 mL) and treated with 4N HCl in dioxane (3 mL). The reaction mixture was stirred at room temperature for 2 h and diluted with 2-MeTHF (30 mL) which gave the title compound 5 as a solid (45 mg, 19% yield). 1H NMR (400 MHz, MeOD) δ ppm 9.98 (br. s., 1H), 8.78 (s, 1H), 8.39 (s, 1H), 8.10 (s, 3H), 4.30 (br. s., 1H), 3.54 (br. s., 1H), 3.36 (br. s., 1H), 3.18 (br. s., 2H), 2.29 (br. s., 1H), 2.15 (br. s., 1H), 1.97 (br. s., 1H), 1.81 (br. s., 1H). LCMS m/z 329 (M+1).

Example 6

(Method E): N-[(3R)-piperidin-3-yl]-6-pyrazolo[1,5-a]pyridin-3-ylpyrazin-2-amine

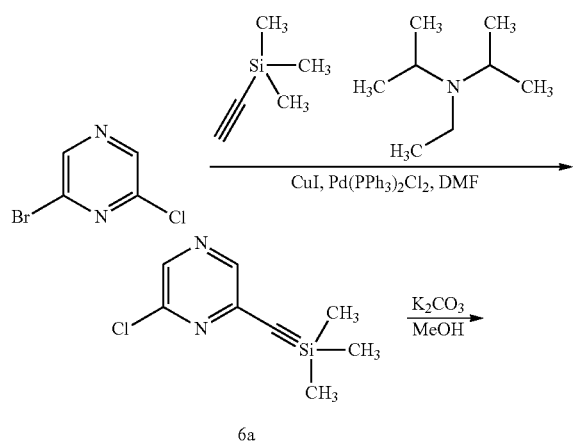

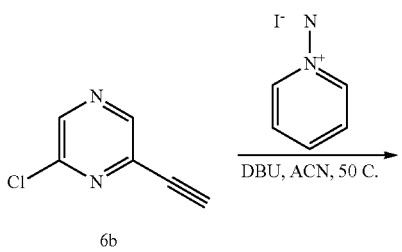

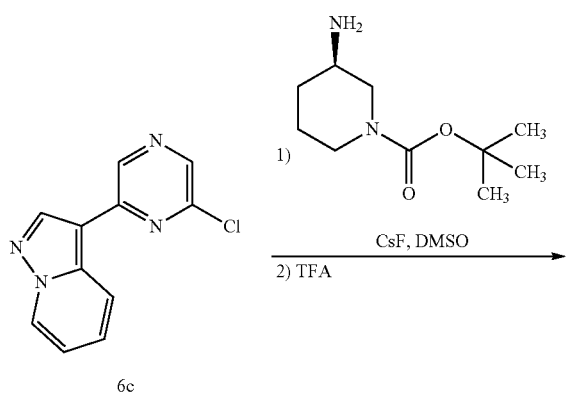

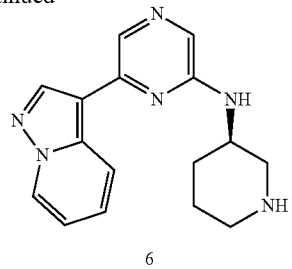

6

Preparation of compound 6a:
2-Chloro-6-(2-(trimethylsilyl)ethynyl)pyrazine

A mixture of 2-bromo-6-chloropyrazine (0.976 g, 5 mmol), Pd(PPh$_3$)$_2$Cl$_2$ (0.106 g, 0.15 mmol), DIEA (0.646 g, 5 mmol) and CuI (0.095 g, 0.5 mmol) in DMF was purged with nitrogen and treated with trimethylsilylacetylene (0.491 g, 5 mmol). The resultant mixture was stirred at 23° C. overnight. The reaction mixture was poured into saturated aqueous NaHCO$_3$ and extracted with EtOAc. The organic layer was washed with brine, dried over Na$_2$SO$_4$, decanted and concentrated under reduced pressure. The crude product was purified by flash chromatography on silica gel (0-20% EtOAc-hexanes) which gave the title compound 6a as a clear oil (861 mg, 80% yield). 1H NMR (400 MHz, MeOD) δ ppm 8.62 (s, 1H), 8.61 (s, 1H), 0.29 (s, 9H).

Preparation of compound 6b:
2-Chloro-6-ethynylpyrazine

A solution of 6a (861 mg, 4.09 mmol) in MeOH (10 mL) was cooled to 0° C. treated with potassium carbonate (565 mg, 4.09 mmol). The reaction mixture was stirred at 0° C. for 6 h. The reaction mixture was filtered and the solids washed with methanol. The filtrate was concentrated under reduced pressure. The resultant solid dissolved in ethyl acetate and washed with water, brine, dried over Na$_2$SO$_4$, decanted and concentrated under reduced pressure. The crude product was purified by flash chromatography on silica gel (0-20% EtOAc-hexanes) which gave the title compound 6b as a tan solid (91 mg, 16% yield). 1H NMR (400 MHz, MeOD) δ ppm 8.66 (s, 1H), 8.64 (s, 1H), 4.12 (s, 1H).

Preparation of compound 6c:
3-(6-Chloropyrazin-2-yl)pyrazolo[1,5-a]pyridine

A mixture of 6b (91 mg, 0.66 mmol) and 1-aminopyridinium iodide (146 mg, 0.657 mmol) in acetonitrile (5 mL) was warmed to 50° C. and treated with DBU (200 mg, 1.31 mmol). The reaction mixture turned dark purple. After 4 h, the reaction mixture was poured into saturated aqueous NaHCO$_3$ and extracted with methanolic EtOAc. The EtOAc layer was washed with brine, dried over Na$_2$SO$_4$, decanted and concentrated under reduced pressure. The crude product was purified by flash chromatography on silica gel (0-40% EtOAc-hexanes) which gave the title compound 6c as a yellow solid (48 mg, 32% yield). 1H NMR (400 MHz, DMSO-d6) δ ppm 9.21 (s, 1H), 8.91 (s, 1H), 8.87 (d, J=6.8 Hz, 1H), 8.50 (s, 1H), 8.40 (d, J=8.8 Hz, 1H), 7.55-7.57 (m, 1H), 7.14 (t, J=6.69 Hz, 1H). LCMS m/z 231 (M+1).

A mixture of 6c (92 mg, 0.4 mmol), (R)-tert-butyl 3-aminopiperidine-1-carboxylate (160 mg, 0.8 mmol) and cesium fluoride (122 mg, 0.8 mmol) in DMSO (0.8 mL) was heated to 80° C. overnight. The reaction was poured into water and extracted with EtOAc. The EtOAc layer was washed with brine, dried over Na$_2$SO$_4$, decanted and concentrated under reduced pressure to give an oil. The crude product was purified by flash chromatography on silica gel (50-100% EtOAc-hexanes) which gave the Boc protected material (133 mg). A solution of the Boc protected material in DCM (2 mL) and TFA (1 mL) was stirred for 1 h. The solvent was removed under reduced pressure and the crude product was purified by reverse phase preparative HPLC which gave the title compound 6 as a greenish oil (67 mg, 60% yield). 1H NMR (400 MHz, MeOD) δ ppm 8.61 (d, J=7.1 Hz, 1H), 8.54 (s, 1H), 8.37 (d, J=8.8 Hz, 1H), 8.21 (s, 1H), 7.73 (s, 1H), 7.43 (d, J=8.1 Hz, 1H), 7.02 (t, J=6.6 Hz, 1H), 4.36 (dq, J=8.5, 4.2 Hz, 1H), 3.64 (dd, J=12.2, 2.9 Hz, 1H), 3.37 (s, 1H), 3.05-3.20 (m, 2H), 2.25 (d, J=12.9 Hz, 1H), 2.16 (dd, J=9.7, 5.2 Hz, 1H), 1.96 (ddd, J=14.3, 3.9, 3.8 Hz, 1H), 1.71-1.85 (m, J=13.0, 9.6, 9.6, 3.4 Hz, 1H). LCMS 295 (M+1).

Example 7

(Method A): 6-(6-Methoxyimidazo[1,2-a]pyridin-3-yl)-N-[(3R)-piperidin-3-yl]pyrazin-2-amine

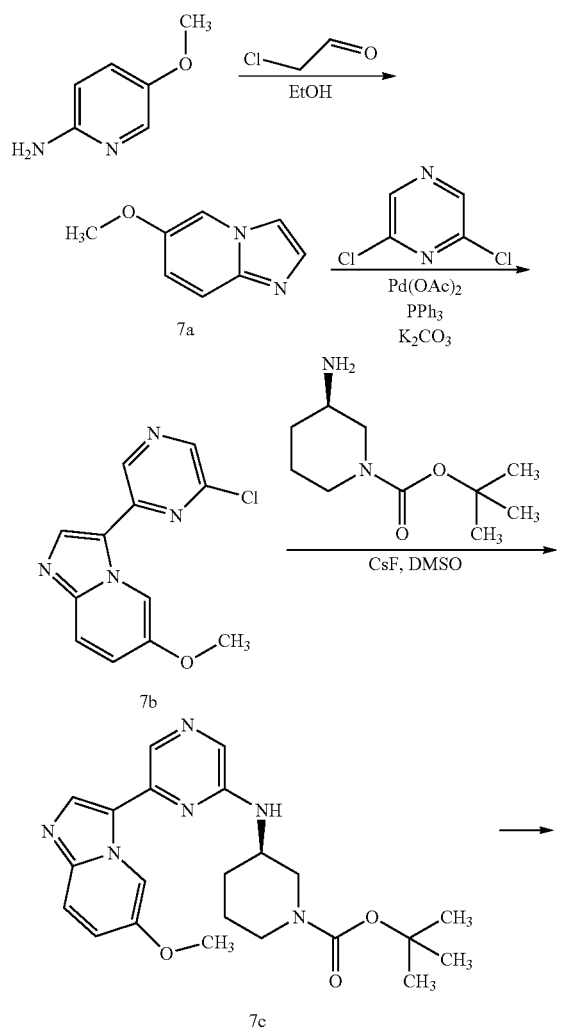

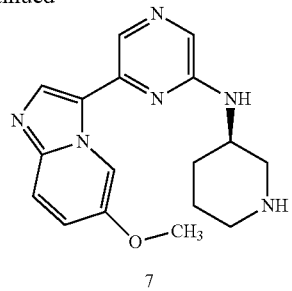

Preparation of compound 7a:
6-Methoxyimidazo[1,2-a]pyridine

A solution of 5-methoxypyridin-2-amine (5.0 g, 40.3 mmol) and chloroacetaldehyde (~55% solution in water—32 g, 200 mmol) in ethanol (200 mL) was refluxed overnight. The solvent was removed under reduced pressure and the resultant brown oil was triturated using methanolic MTBE which gave the hydrochloride of the title compound 7a as a beige solid (5.7 g, 77% yield). 1H NMR (400 MHz, DMSO-d6) δ ppm 14.62 (br, 1H), 8.70 (d, J=2.3 Hz, 1H), 8.24 (d, J=1.5 Hz, 1H), 8.15 (d, J=2.0 Hz, 1H), 7.90 (d, J=9.8 Hz, 1H), 7.71 (dd, J=9.8, 2.3 Hz, 1H), 3.89 (s, 3H). LCMS 185 (M+1).

Preparation of compound 7b: 3-(6-Chloropyrazin-2-yl)-6-methoxy-imidazo[1,2-a]pyridine A mixture of 7a (4.0 g, 20 mmol), 2,6-dichloropyrazine (3.2 g, 22 mmol), palladium(II)acetate (0.2 g, 0.87 mmol), triphenylphosphine (0.59 g, 2.2 mmol), and potassium carbonate (3.0 g, 22 mmol) in dioxane (43 mL) was degassed, purged with nitrogen and heated at 100° C. overnight. The crude reaction mixture was filtered hot and the solids were washed with dioxane. The filtrate was concentrated under reduced pressure and the crude product was purified by flash chromatography on silica gel (0-10% methanol in 1:1 EtOAc-heptane) which gave the title compound 7b as a solid (2.5 g, 40% yield). 1H NMR (400 MHz, DMSO-d6) δ ppm 9.33 (s, 2H), 8.65 (s, 1H), 8.59 (s, 1H), 7.75 (s, 1H), 7.35 (s, 1H), 3.88 (s, 3H). LCMS m/z 261 (M+1).

A mixture of cesium fluoride (110 mg, 0.72 mmol), 7b (75 mg, 0.29 mmol), (R)-tert-butyl 3-aminopiperidine-1-carboxylate (86.5 mg, 0.432 mmol) in DMF (1 mL) was heated to 120° C. overnight. The crude product was filtered and purified by reverse phase preparative HPLC (water-acetonitrile with acetic acid) to obtain 7c. The BOC protected compound 7c was dissolved in MeOH (3 mL) and 4N HCl dioxane (3 mL) and stirred at room temperature for 2 h. The solvent was removed under reduced pressure and the crude product was dissolved in MeOH. The methanolic solution was passed thru an SCX column, and the filtrate was concentrated under reduced pressure which gave the title compound 7 as a solid (34 mg, 37% yield). 1H NMR (400 MHz, DMSO-d6) δ ppm 9.41 (d, J=2.8 Hz, 1H), 8.29 (d, J=5.0 Hz, 2H), 7.80 (s, 1H), 7.63 (d, J=9.3 Hz, 1H), 7.18 (dd, J=9.8, 2.5 Hz, 2H), 4.10 (br. s., 1H), 3.94 (s, 4H), 3.17 (d, J=4.8 Hz, 3H), 2.80 (br.

s., 1H), 2.33 (d, J=2.0 Hz, 2H), 1.95 (br. s., 1H), 1.69 (br. s., 1H), 1.42 (br. s., 2H). LCMS m/z 325 (M+1).

Example 8

(Method A): N-[(3R)-piperidin-3-yl]-6-[1,2,4]triazolo[4,3-a]pyridin-3-ylpyrazin-2-amine

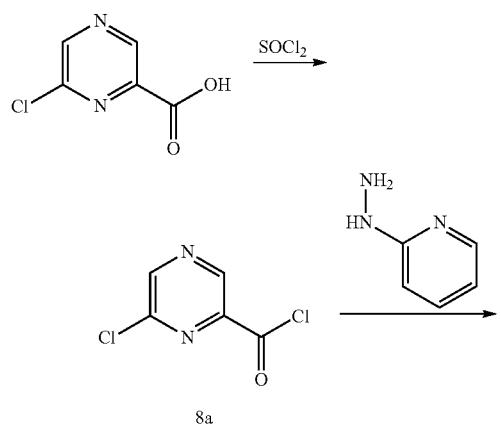

8a

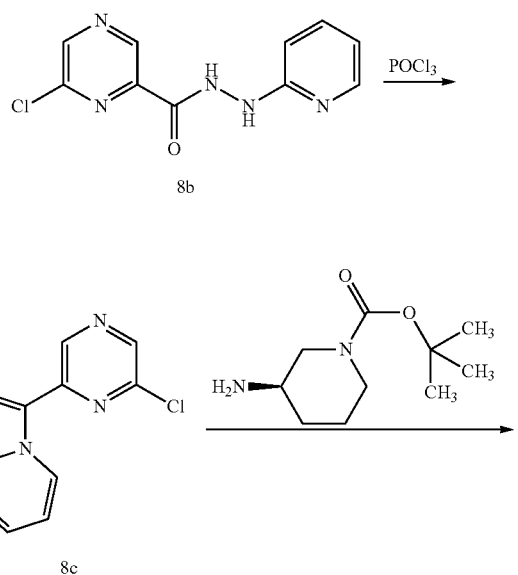

8b

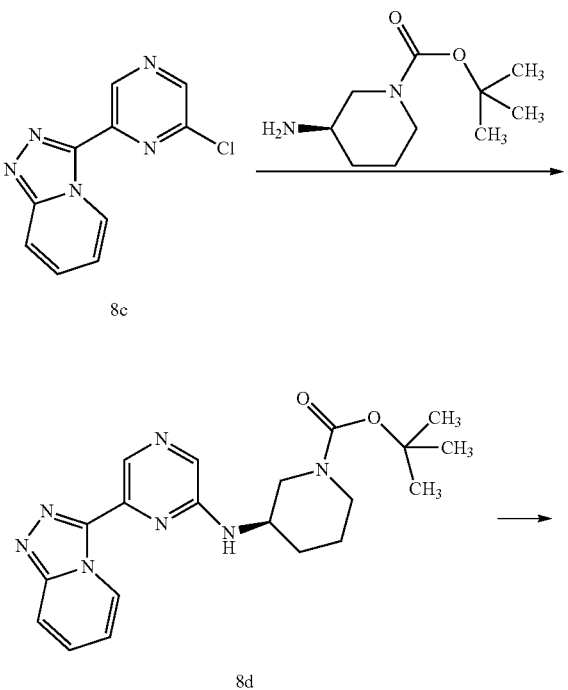

8c

8d

-continued

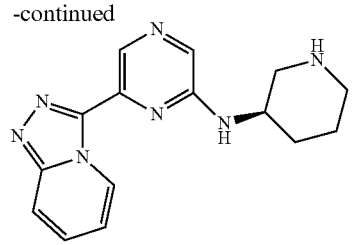

8

Preparation of compound 8a:
6-Chloropyrazine-2-carbonyl chloride

A mixture of 2-chloro-6-carboxy-pyrazine (1000 mg, 6.3 mmol) in ACN (20 mL) was treated with thionyl chloride (800 uL). The resulting mixture, which became homogeneous upon heating, was refluxed for 2 h. The solvent was removed under reduced pressure which gave an oil. The crude product was used in the next step.

Preparation of compound 8b: 6-Chloro-N'-(pyridin-2-yl)pyrazine-2-carbohydrazide

The crude product 8a was dissolved ACN (10 mL) and treated with a solution of 2-hydrazino pyridine (688 mg, 6.3 mmol) in ACN (10 mL). The reaction mixture was stirred at room temperature for 18 h and the solids were collected and washed with acetonitrile which gave the title compound 8b as an orange solid (1.2 g, 77% yield). 1H NMR (400 MHz, DMSO-d6) δ ppm 11.38 (br. s., 1H), 10.95 (br. s., 1H), 9.21 (s, 1H), 9.13 (s, 1H), 8.01-8.10 (m, 2H), 7.25 (br. s., 1H), 7.07 (t, J=6.5 Hz, 1H). LCMS m/z 250 (M+H).

Preparation of compound 8c: 3-(6-Chloropyrazin-2-yl)-[1,2,4]triazolo[4,3-a]pyridine A solution of 8b (120 mg, 0.48 mmol) and POCl₃ (1 mL) was refluxed for 8 h. The mixture was removed from heat and allowed to stand at RT for 72 h. The solvent was removed under reduced pressure and the crude product was treated with water. The mixture was extracted with DCM. The organic layer was concentrated under reduced pressure which gave the title compound 8c as an off-white solid. 1H NMR (400 MHz, DMSO-d6) δ ppm 9.69 (br. s., 1H) 8.89 (d, J=1.3 Hz, 1H), 8.36 (d, J=5.8 Hz, 1H), 8.13 (br. s., 1H), 7.73 (br. s., 1H), 7.26 (br. s., 1H). LCMS m/z 232 (M+H).

Preparation of compound 8d: Tert-butyl (3R)-3-[(6-[1,2,4]triazolo[4,3-a]pyridin-3-ylpyrazin-2-yl)amino]piperidine-1-carboxylate A mixture of 8c (30 mg, 0.13 mmol), (R)-tert-butyl 3-aminopiperidine-1-carboxylate (39 mg, 0.20 mmol) and cesium fluoride (52 mg, 0.26 mmol) in DMSO (1 mL) was heated at 120° C. for 6 h. The crude reaction mixture was filtered and the filtrate was diluted with DCM (50 mL) and washed with water (25 mL). The crude product was purified by flash chromatography on silica gel (0-45% ethanol-EtOAc) which gave the title compound 8d as an amber oil. LCMS m/z of 396 (M+H).

A solution of 8d (65 mg, 0.16 mmol), 4N HCl in dioxane (2 mL) and dioxane (2.5 mL) was stirred for 2 h. The solvent was removed under reduced pressure and the resultant yellow solid was dissolved in methanol. The methanolic solution was passed thru an SCX column and eluted with 4N ammonium in MeOH. The solvent was removed under reduced pressure, which gave rise to the title compound 8 as a brown solid (27 mg, 70% yield). 1H NMR (400 MHz, DMSO-d6) δ ppm 9.32 (br. s., 2H), 8.45 (br. s., 3H), 3.40 (d, J=7.0 Hz, 2H), 3.20 (br. s., 1H), 2.67-2.93 (m, 2H), 1.98-2.08 (m, 1H), 1.81-1.90 (m, 1H), 1.50-1.74 (m, 2H). LCMS m/z 296 (M+1).

Example 9

(Method C): 6-{5-[(3-Methyloxetan-3-yl)methoxy]-1H-benzimidazol-1-yl}-N-[(3R,6R)-6-methylpiperidin-3-yl]pyrazin-2-amine

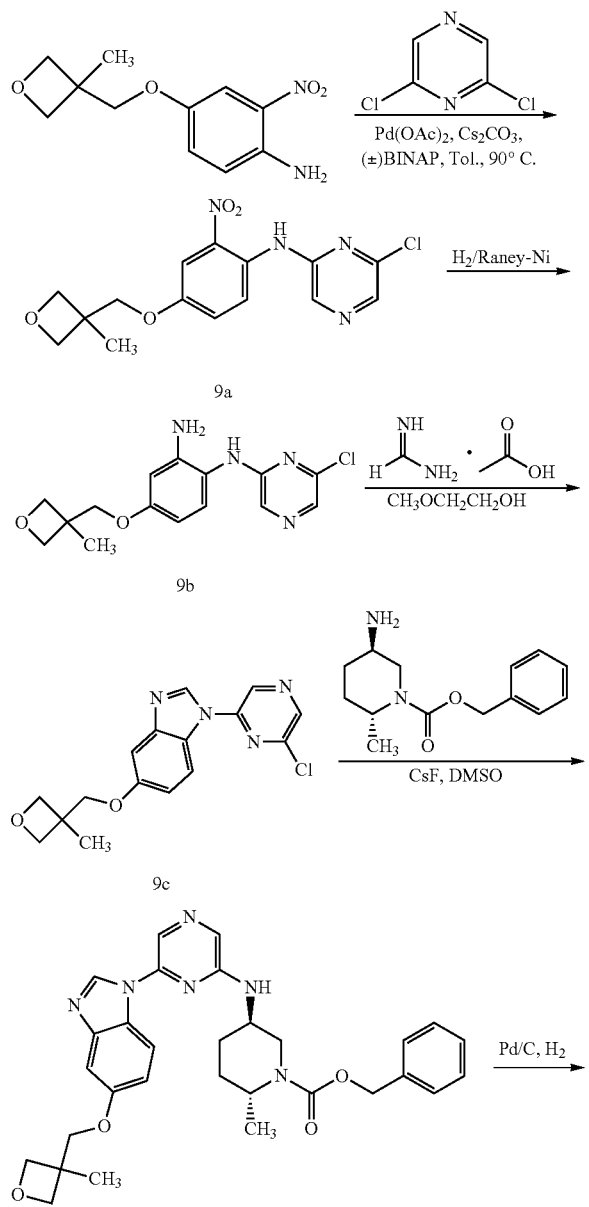

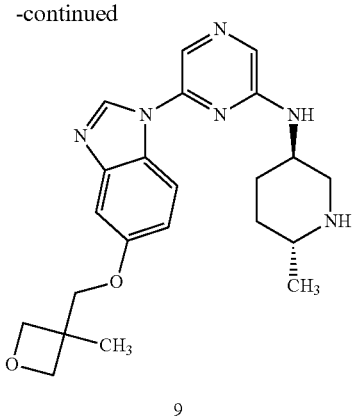

9

Preparation of compound 9a: 6-Chloro-N-(4-((3-methyloxetan-3-yl)methoxy)-2-nitrophenyl)pyrazin-2-amine A mixture of 2,6-dichloropyrazine (25 g, 168 mmol), 4-((3-methyloxetan-3-yl)methoxy)-2-nitrobenzenamine (Tom, Norma Jacqueline; Ripin, David Harold Brown; Castaldi, Michael James PCT Int. Appl. (2004), WO 2004113322 A1) (40 g, 168 mmol), palladium (II) acetate (1.5 g, 6.72 mmol), (±)-2,2-bis(diphenylphosphino)-1,1'-binaphinyl[(±)-BINAP] (4.18 g, 6.72 mmol) and cesium carbonate (76.7 g, 235.2 mmol) in toluene (800 mL) was stirred at 90° C. under N₂ for 23 h. The mixture was filtered through a pad of Celite and washed with EtOAc. The filtrate was evaporated under reduced pressure and the crude product was purified by flash chromatography on silica (EtOAc:petroleum ether=1:5) which gave the title compound 9a as a red solid (22.4 g, 37% yield).

Preparation of compound 9b: N1-(6-chloropyrazin-2-yl)-4-((3-methyloxetan-3-yl)methoxy)benzene-1,2-diamine A suspension of 9a (30 g, 86 mmol) and Raney-Ni (60 g) in MeOH (90 mL) was stirred under 1 PSI of hydrogen at room temperature for 2 h. The reaction mixture was filtered through a pad of Celite with MeOH rinses. The filtrate was evaporated under reduced pressure which gave the title compound 9b as a white solid (27 g, 98% yield).

Preparation of compound 9c: 1-(6-Chloropyrazin-2-yl)-5-((3-methyloxetan-3-yl)methoxy)-1H-benzo[d]imidazole A solution of 9b (27 g, 84 mmol) and formamidine acetate (17.6 g, 168 mmol) in 2-methoxyethanol (350 mL) was heated at reflux for 3 h. After removal of the solvent under reduced pressure, the residue was dissolved in EtOAc (2 L), and the solution was washed with water (1 L×2), dried over anhydrous Na₂SO₄ and concentrated under reduced pressure which gave the title compound 9c as a grey solid (23 g, 83%).

Preparation of compound 9d: (2R,5R)-Benzyl 2-methyl-5-(6-(5-((3-methyloxetan-3-yl)methoxy)-1H-benzo[d]imidazol-1-yl)pyrazin-2-ylamino)piperidine-1-carboxylate A mixture of 9c (150 mg, 0.45 mmol), (2R,5R)-benzyl 5-amino-2-methylpiperidine-1-carboxylate (255 mg, 10.9 mmol) and cesium fluoride (138 mg, 0.91 mmol) in DMSO (0.9 mL) was heated to 120° C. for 2.5 h. The reaction was poured into water and extracted with EtOAc. The organic layer was washed with brine, dried over Na₂SO₄, decanted and concentrated which gave an oil. The crude product was purified by flash chromatography on silica (0-100% EtOAc-hexanes) which gave the title compound 9d as an oil (100 mg, 40% yield).

A solution of 9d (100 mg, 0.18 mmol) in MeOH (1.5 mL), was purge with argon and treated with palladium on carbon (10%). The reaction mixture was stirred under an atmosphere of hydrogen at ambient temperature and pressure for 24 h. The reaction mixture was filtered thru celite and the solvent was removed under reduced pressure. The crude product was purified on MS triggered reverse phase preparative HPLC which gave the title compound 9 as white solid (25 mg, 33%). 1H NMR (400 MHz, DMSO-d6) δ ppm 8.91 (s, 1H), 8.23 (s, 1H), 8.17 (d, J=9.1 Hz, 1H), 7.88 (s, 1H), 7.43 (d, J=7.6 Hz, 1H), 7.37 (d, J=2.5 Hz, 1H), 7.05 (dd, J=9.0, 2.4 Hz, 1H), 4.54 (d, J=5.8 Hz, 2H), 4.34 (d, J=5.6 Hz, 2H), 4.13 (s, 2H), 3.77 (br s, 1H), 2.54-2.65 (m, 1H), 2.37-2.45 (m, 1H), 2.04-2.12 (m, 1H), 1.66-1.75 (m, 1H), 1.41 (s, 3H), 1.37-1.40 (m, 1H), 1.30-1.36 (m, 1H), 1.18-1.29 (m, 1H), 1.05 (d, J=8.0 Hz, 3H). LCMS m/z 409 (M+1).

Example 10

(Method B): 6-Imidazo[1,2-a]pyridin-3-yl-N-[(3R)-pyrrolidin-3-yl]pyrazin-2-amine

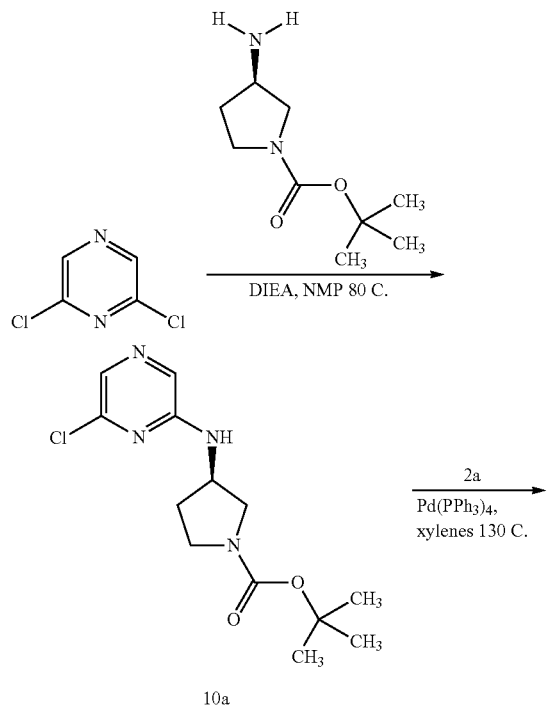

Preparation of compound 10a: (R)-Tert-butyl 3-(6-chloropyrazin-2-ylamino)pyrrolidine-1-carboxylate A mixture of 2,6-dichloropyrazine (0.149 mg, 1 mmol), (R)-3-Amino-pyrrolidine-1-carboxylic acid tert-butyl ester (0.205 g, 1.1 mmol) and diisopropylethylamine (0.19 mL, 1.1 mmol) in NMP (2 mL) was heated to 120° C. in a microwave reactor for 1 h. The crude reaction mixture was partitioned between EtOAc and water. The organic phase was washed with brine, dried over sodium sulfate, filtered and concentrated under reduced pressure which gave an oil. The crude product was purified by flash chromatography on silica gel (0-100% EtOAc-hexanes) which gave the title compound 10a as an oil (200 mg). LCMS m/z 199 (M+1-BOC).

6-Imidazo[1,2-a]pyridin-3-yl-N-[(3R)-pyrrolidin-3-yl]pyrazin-2-amine

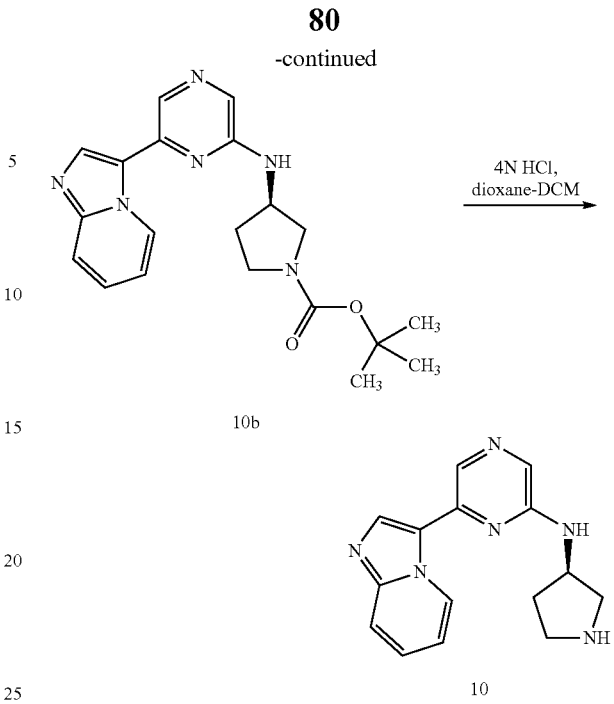

A mixture of 2a (0.204 g, 0.5 mmol), (R)-3-(6-chloropyrazin-2-ylamino)-pyrrolidine-1-carboxylic acid tert-butyl ester (75 mg, 0.25 mmol) and palladiumtetrakistriphenylphosphine (0) (29 mg, 0.025 mmol) in o-xylene (2 mL) was vacuum flushed with nitrogen then heated to 130° C. Once the reaction was completed the reaction mixture was concentrated and purified by flash chromatography on silica gel (0-100% EtOAc-hexanes then 0-20% MeOH-EtOAc) which gave the title compound 10b as a greenish oil. LCMS gave purity ~85%. The green oil 10b was dissolved in DCM (1 mL) and 4N HCl in dioxane (1 mL) and stirred at 23° C. until the reaction was determined to be complete by LCMS. The crude product was purified by reverse phase HPLC (water-acetonitrile with AcOH) and the pooled pure fractions were concentrated under reduced pressure. The product was dissolved in methanol (3 mL) and neutralized with Sili-bond Carbonate which gave the title compound 10 as an oil (26 mg). 1H NMR (400 MHz, MeOD) δ ppm 9.82 (d, J=7.1 Hz, 1H), 8.28 (s, 1H), 8.25 (s, 1H), 7.77 (s, 1H), 7.68 (d, J=9.1 Hz, 1H), 7.48 (d, J=6.8 Hz, 1H), 7.11 (t, J=6.4 Hz, 1H), 4.46-4.58 (m, 1H), 3.34-3.40 (m, 1H) 3.06-3.23 (m, 2H), 3.01 (dd, J=11.8, 4.2 Hz, 1H), 2.31 (dd, J=13.3, 7.7 Hz, 1H), 1.94 (ddd, J=12.8, 4.9, 2.8 Hz, 1H). LCMS m/z 281 (M+H).
Example 11
(Method A): N-(4,4-difluoropiperidin-3-yl)-6-(imidazo[1,2-a]pyridin-3-yl)pyrazin-2-amine
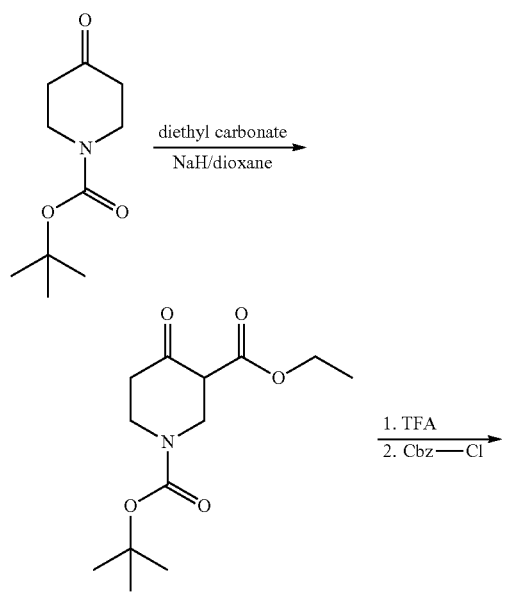
11a
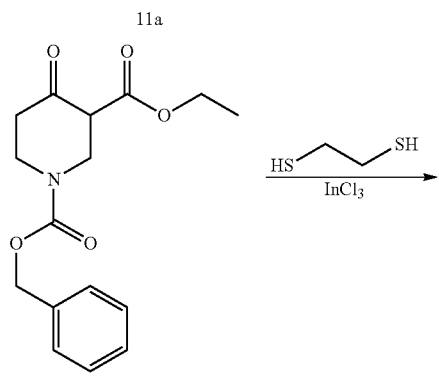
11b
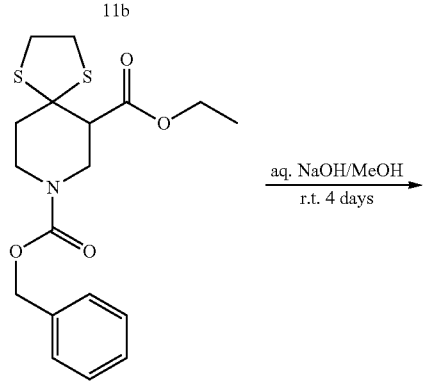
11c
-continued
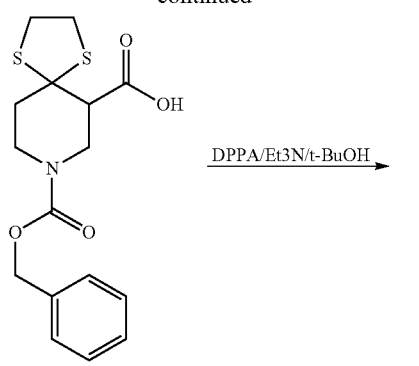
11d
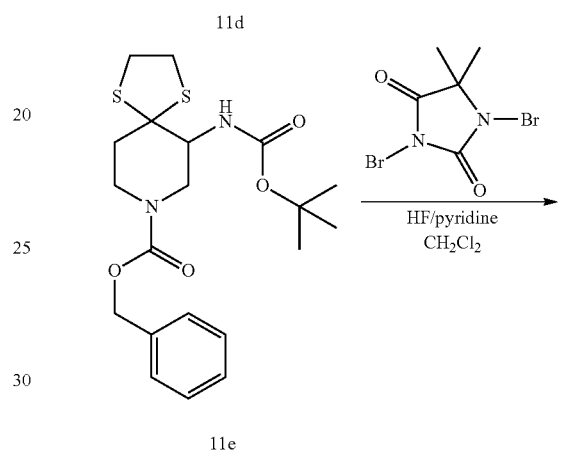
11e
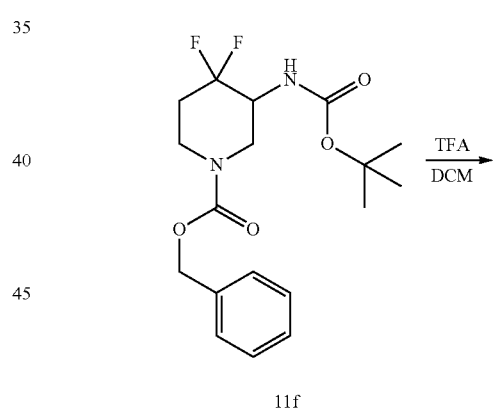
11f
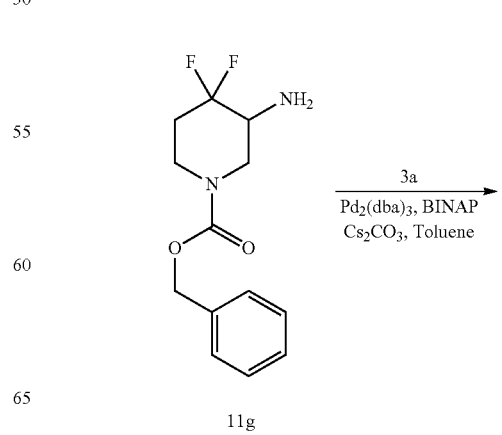
11g

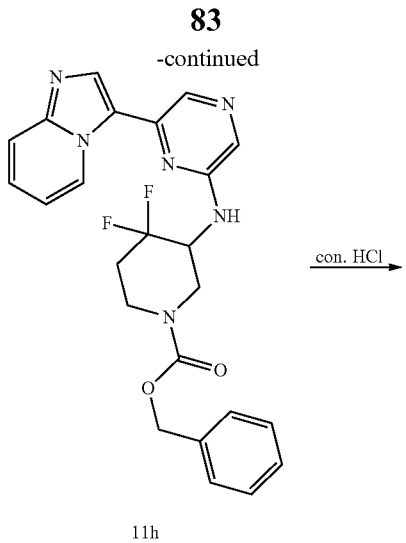

11h

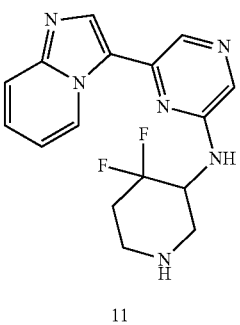

11

Preparation of compound 11a: 1-tert-butyl 3-ethyl 4-oxopiperidine-1,3-dicarboxylate NaH (60%, 60 g, 1.5 mol) was suspended in dry dioxane (500 mL) and diethyl carbonate (151 mL, 1.25 mol) was added. The mixture was heated to 90° C., then a solution of tert-butyl 4-oxopiperidine-1-carboxylate (100 g, 0.5 mol) in dry dioxane (300 mL) was added dropwise over 2 h. After addition, the mixture was continually stirred for 1 h. The cooled mixture was poured into an ice-water with stirring. The mixture was extracted with EtOAc (1 L×2). The combined extracts were washed with water (1 L), brine (500 mL), dried over $Na_2SO_4$ and concentrated in vacuo. The residue was purified by column chromatography (EtOAc/petrol ether=1:200 to 1:80) which gave the title compound 11a as a light yellow oil (115 g, 85%).

Preparation of compound 11b: 1-benzyl 3-ethyl 4-oxopiperidine-1,3-dicarboxylate To a stirred solution of 11a (115 g, 0.42 mol) in anhydrous $CH_2Cl_2$ (300 mL) was added dropwise TFA (485 g, 4.2 mol) at 5-10° C. After addition, the mixture was stirred for 1 h at that temperature. The mixture was concentrated in vacuo and the residue was used for next step without any purification. The residue (71.8 g, 0.42 mol) was dissolved in dry $CH_2Cl_2$ (300 mL), then dry TEA (129 g, 1.26 mol) was added. After that, Cbz-Cl (80 g, 0.49 mol) was added dropwise at 0° C. The mixture was stirred at r.t. for 2 h. The mixture was washed with 2 N HCl (500 mL×2), aq. $NaHCO_3$ (800 mL), brine (800 mL), dried over $Na_2SO_4$ and concentrated in vacuo to give a yellow oil, which was purified by column chromatography (EtOAc/petroleum ether=1:20) which gave the title compound 11b as light yellow oil (115 g, 89.8% in two steps). $^1$H NMR (400 MHz, $CDCl_3$): δ ppm 1.31-1.28 (m, 3H), 12.09 (s, 1H), 2.39 (s, 2H), 3.66-3.63 (m, 2H), 4.27-4.19 (m, 2H), 5.17 (s, 2H), 7.38-7.30 (m, 5H).

Preparation of compound 11c: 8-benzyl 6-ethyl 1,4-dithia-8-azaspiro[4.5]decane-6,8-dicarboxylate To a stirred solution of compound 11b (64 g, 0.21 mol) and 1,2-Ethanedithiol (21 mL, 0.25 mol) in dry $CH_2Cl_2$ (800 mL) was added quickly anhydrous $InCl_3$ (28 g, 0.127 mol) in one portion. The mixture was stirred at room temperature for 40 h. The mixture was directly purified by column chromatography (EtOAc/petrol ether=1:30 to 1:10) which gave the title compound 11c as a colorless liquid (40 g, 50%).

Preparation of compound 11d: 8-[(benzyloxy)carbonyl]-1,4-dithia-8-azaspiro[4.5]decane-6-carboxylic acid To a stirred solution of 11c (39 g, 0.1 mol) in MeOH (400 mL) was added dropwise aq. NaOH (40 g, 1.0 mol in 400 mL of $H_2O$) below 40° C. The mixture was stirred at r.t. (30° C.) for 4 days. The mixture was concentrated in vacuo to remove methanol. The residue was acidified to pH=5 with 2 N HCl and extracted with EtOAc (500 mL×4). The combined extracts were dried over $Na_2SO_4$ and concentrated in vacuo which gave the title compound 11d as yellow oil (26.3 g, 74.6%). $^1$H NMR (400 MHz, $CDCl_3$): δ ppm 1.931 (s, 1H), 2.79 (s, 1H), 2.951 (s, 1H), 3.271-3.251 (m, 1H), 3.291 (s, 4H), 3.731-3.571 (m, 2H), 4.011-3.981 (m, 2H), 4.311-4.191 (m, 1H), 5.11 (s, 2H), 7.36-7.28 (m, 5H).

Preparation of compound 11e: benzyl 6-[(tert-butoxycarbonyl)amino]-1,4-dithia-8-azaspiro[4.5]decane-8-carboxylate To a stirred solution of compound 11d (19.2 g, 54 mmol) in t-BuOH (250 mL) was added DPPA (18 g, 65 mmol) and $Et_3N$ (6.6 g, 65 mmol) dropwise at room temperature. The resulting mixture was stirred for 3 h, then heated to 85° C. and stirred overnight. The reaction mixture was concentrated to remove most of the solvent. The residue was purified by column chromatography (Petroleum Ether:EtOAc=50:1 to 10:1) which gave the title compound 11e as yellow oil (12.3 g, 54%). 1H NMR (400 MHz, CDCl3) 1.380 (s, 9H), 2.096-2.049 (m, 2H), 2.850 (m, 1H), 3.269-3.155 (m, 1H), 3.874-3.856 (m, 1H), 4.000 (m, 1H), 4.899-4.876 (d, 1H), 5.080-5.035 (m, 2H), 7.291-7.227 (m, 5H).

Preparation of compound 11f: benzyl 3-[(tert-butoxycarbonyl)amino]-4,4-difluoropiperidine-1-carboxylate 1,3-dibromo-5,5-dimethylimidazolidine-2,4-dione (4.8 g, 17 mmol) was dissolved in dry $CH_2Cl_2$ (100 mL) and allowed to stir under nitrogen. The mixture was cooled to −78° C. and pyridinium poly(hydrogen fluoride) (13 mL) was added via polyethylene syringe, followed by the dropwise addition of compound 11e (6.5 g, 15.3 mmol). After 10 min, the reaction mixture, which was deep red, was diluted with hexane (1 L) and filtered through a column of basic alumina. The organic was washed with $NaHCO_3$, brine, concentrated and purified by column chromatography (Petroleum Ether:EtOAc=50:1) which gave the title compound 11f as a colorless oil (1.2 g, 12.5%). 1H NMR (400 MHz, CDCl3) 1.380 (s, 9H), 2.133-

1.874 (m, 2H), 3.159-3.101 (m, 1H), 4.078-3.927 (m, 3H), 4.687-4.670 (d, 1H), 5.274-5.030 (m, 2H), 7.300-7.210 (m, 5H).

Preparation of compound 11g: benzyl 3-amino-4,4-difluoropiperidine-1-carboxylate To a solution of compound 11f (2.0 g, 5.4 mmol) in CH$_2$Cl$_2$ (40 mL) was added TFA (10 mL) at 0° C. The resulting mixture was stirred at room temperature for 2 h. The reaction solution was diluted with CH$_2$Cl$_2$ (400 mL), washed with NaHCO$_3$ (sat., aq.). The organic phase was washed with brine, dried over Na$_2$SO$_4$ and concentrated. The residue was purified by Chem-Flush which gave the title compound 11g as colorless oil (1.3 g, 89%). 1H NMR (400 MHz, CDCl3) 0.676-0.717 (m, 2H), 0.931-0.979 (m, 2H), 2.880-2.891 (d, 3H), 2.983-3.052 (m, 3H), 3.770-3.799 (t, 2H), 4.613-4.652 (m, 3H), 6.214 (s, 1H), 6.385-6.399 (d, 1H), 7.314-7.356 (t, 1H), 7.559-7.641 (m, 2H), 8.170-8.191 (d, 1H), 8.216-8.245 (t, 2H).

Preparation of compound 11h: benzyl 4,4-difluoro-3-{[6-(imidazo[1,2-a]pyridin-3-yl)pyrazin-2-yl]amino}piperidine-1-carboxylate A mixture of 11g (0.24 g, 0.89 mmol), compound 3a (0.218 g, 0.98 mmol), Pd$_2$(dba)$_3$ (32 mg, 0.056 mmol), BINAP (38 mg, 0.06 mmol) and Cs$_2$CO$_3$ (1.0 g, 3 mmol) in anhydrous toluene (12 mL) was heated rapidly to 120° C. and stirred for 90 min. The mixture was cooled to room temperature and was filtered. The filtrate was concentrated in vacuo and purified by pre-HPLC which gave the title compound 11h as a brown solid (0.35 g, 86%). 1H NMR (400 MHz, CDCl3) 2.321-2.194 (m, 2H), 3.161 (m, 1H), 3.441-3.332 (m, 2H), 4.545-4.497 (m, 1H), 5.160-4.850 (m, 2H), 7.133-7.005 (m, 2H), 7.392-7.359 (m, 3H), 7.942 (brs, 1H), 8.150 (s, 1H), 8.441 (s, 1H), 8.770 (s, 1H), 8.841-8.804 (m, 2H), 9.702-9.685 (d, 1H).

A solution of compound 11h (0.2 g, 0.43 mmol) in con. HCl (4 mL) was stirred at room temperature overnight. The mixture was concentrated to dryness which gave the title compound 11 hydrochloride salt as yellow solid (140 mg, 75%). 1H NMR (400 MHz, D2O) 2.373-2.294 (m, 1H), 2.531-2.509 (1, 1H), 3.265-3.157 (m, 2H), 3.597-3.497 (m, 2H), 4.898-4.818 (m, 1H), 7.446-7.412 (t, 1H), 7.928-8.847 (m, 3H), 8.122 (s, 1H), 8.300 (s, 1H), 9.349-9.332 (d, 1H).

Example 12

(Method A): 6-Imidazo[1,2-a]pyridin-3-yl-N-[(3R,4R)-4-methylpyrrolidin-3-yl]pyrazin-2-amine

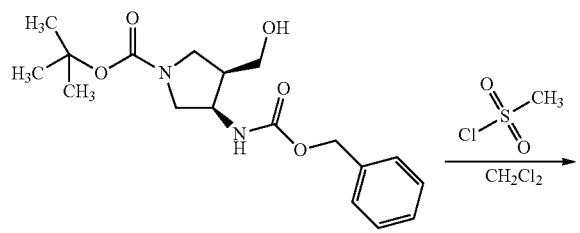

Preparation of compound 12a: (3R,4R)-Tert-butyl 3-(benzyloxycarbonyl)-4-((methylsulfonyloxy)methyl)pyrrolidine-1-carboxylate To a solution of (3R,4R)-tert-butyl 3-(benzyloxycarbonyl)-4-(hydroxymethyl)pyrrolidine-1-carboxylate (1 g, 2.8 mmol) and Et$_3$N (0.4 g, 4.2 mmol) in anhydrous CH$_2$Cl$_2$ (20 mL) was added MsCl (0.38 g, 3.36 mmol) dropwise at 0° C. under nitrogen. After the addition, the mixture was stirred at room temperature for 3 h. The crude reaction mixture was poured into water (100 mL) and extracted with CH$_2$Cl$_2$ (20 mL×3). The combined organic extracts were dried over Na$_2$SO$_4$, filtered and concentrated under reduced pressure which gave the title compound 12a (1.1 g, 92%) as a light yellow oil, which was directly utilized for the next reaction without further purification.

Preparation of compound 12b: (3R,4R)-Tert-butyl 3-(benzyloxycarbonyl)-4-methylpyrrolidine-1-carboxylate To a solution of compound 12a (1 g, 2.3 mmol) in DME (50 mL) was sequentially treated with NaI (3.5 g, 23 mmol) and Zn powder (1.5 g, 23 mmol) at room temperature under nitrogen. After the addition, the mixture was heated to reflux under nitrogen for 1 h and cooled to room temperature. The mixture was filtered thru Celite and the filtrate was partitioned between EtOAc (50 mL) and H$_2$O (50 mL). The organic layer was washed with saturated aqueous Na$_2$SO$_3$, brine, dried over anhydrous Na$_2$SO$_4$, filtered and concentrated under reduced pressure which gave the title compound 12b as a light yellow oil (0.6 g, 77.9%).

Preparation of compound 12c: (3R,4R)-Tert-butyl 3-amino-4-methylpyrrolidine-1-carboxylate A Parr reaction vessel was charged with compound 12b (0.6 g, 1.8 mmol), HOAc (0.5 g, 9 mmol), MeOH (20 mL) and 10% Pd/C (0.2 g). The reaction vessel was flushed with hydrogen (50 PSI) at room temperature for 24 h. The mixture was filtered thru Celite and the filter cake rinsed with MeOH (20 mL). The filtrate was concentrated under reduced pressure which gave the title compound 12c as a light yellow oil (0.3 g, 83%), which was used for the next reaction without further purification.

Preparation of compound 12d: (3R,4R)-Tert-butyl 3-(6-(H-imidazo[1,2-a]pyridin-3-yl)pyrazin-2-ylamino)-4-methylpyrrolidine-1-carboxylate A mixture of compound 12c (0.3 g, 1.5 mmol), compound 3a (0.35 g, 1.5 mmol) and cesium fluoride (0.45 g, 3 mmol) in anhydrous DMSO (2 mL) was heated at 80° C. under N$_2$ overnight. The reaction mixture was cooled to room temperature and diluted with water (10 mL). The mixture was extracted with EtOAc (20 mL×3) and the combined organic extracts were dried over Na$_2$SO$_4$, filtered and concentrated under reduced pressure. The crude product was purified by column chromatography on silica gel (petroleum ether-EtOAc, 2:1) which provided the title compound 12d as a light yellow oil (0.4 g, 67%).

To a solution of compound 12d (0.25 g, 0.63 mmol) in CH$_2$Cl$_2$ (20 mL) was added 5 M HCl in CH$_2$Cl$_2$ (0.6 mL, 3.1 mmol) dropwise at 0° C. under nitrogen. After the addition, the mixture was stirred at room temperature for 1 h. The mixture was concentrated under reduced pressure and the residue was dissolved in saturated aqueous Na$_2$CO$_3$ (5 mL) and MeOH (100 mL). The solvent was removed under reduced pressure and the resultant residue was treated with CH$_2$Cl$_2$ (100 mL). The mixture was filtered and the filtrate was concentrated under reduced pressure. The crude product was purified by preparative supercritical fluid chromatography, which gave the title compound 12 as a yellow oil (0.15 g, 81%). $^1$H NMR (400 MHz, DMSO) δ ppm 9.76 (d, J=6.80 Hz, 1H), 8.35 (s, 1H), 8.31 (s, 1H), 7.90 (s, 1H), 7.70 (d, J=8.8 Hz, 1H), 7.38 (dd, J=8.0, 7.6 Hz, 1H), 7.32 (d, J=7.2 Hz, 1H), 7.11 (dd, J=6.8, 6.8 Hz, 1H), 4.38 (m, 1H), 3.55-3.27 (m, 4H), 2.45-2.50 (m, 1H), 0.91 (d, J=6.8 Hz, 3H). LCMS m/z 295 (M+1).

Example 13

(Method D): N-[(3R)-pyrrolidin-3-yl]-6-[6-(trifluoromethyl)imidazo[1,2-a]pyridin-3-yl]pyrazin-2-amine

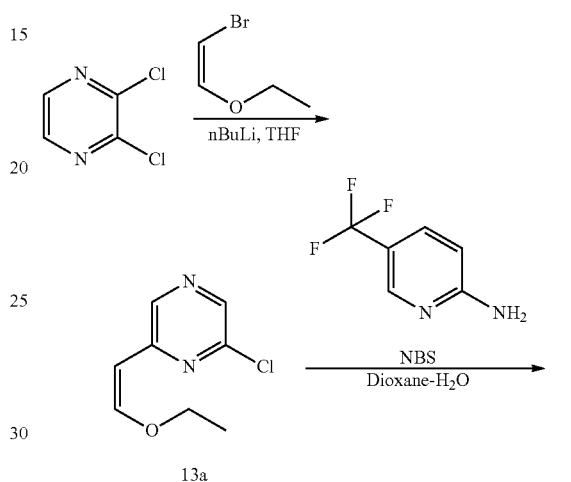

13a

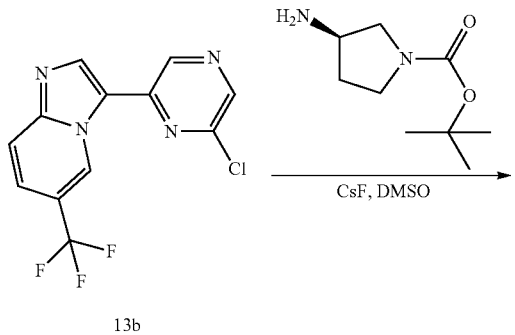

13b

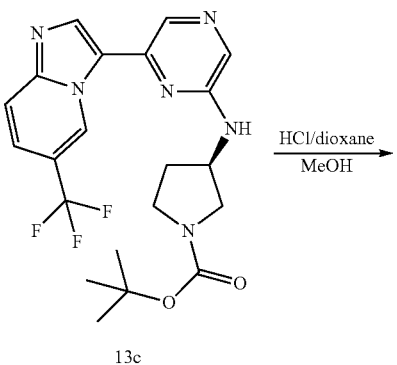

13c

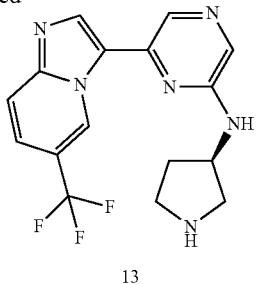

13

Preparation of compound 13a: 2-chloro-6-[(Z)-2-ethoxyethenyl]pyrazine

To a solution of (Z)-1-bromo-2-ethoxy-ethene (11.6 mL, 92.6 mmol, 1.1 eq) in THF (150 mL) at −78° C. was added nBuLi (37 mL, 2.5 M in hexane, 92.6 mmol, 1.1 eq). The mixture was stirred at −78° C. for 30 min to form a colorless solution. A solution of 2,3-dichloropyrazine (12.8 g, 84 mmol, 1.0 eq) in THF (50 mL) was added slowly. The resulting brown solution was stirred at −78° C. for 25 min to reach completion. The reaction was quenched by water and warmed to rt. The mixture was diluted with EtOAc and washed with water. The organic layer was collected and dried over $Na_2SO_4$. The crude product was purified by flash chromatography (15-30% EtOAc/Heptane) on silica gel which gave the title compound 13a (8.0 g, 51%). $^1H$ NMR (400 MHz, $CDCl_3$) δ ppm 1.41 (t, J=7.18 Hz, 3H) 4.12 (q, J=7.13 Hz, 2H) 5.44 (d, J=7.05 Hz, 1H) 6.59 (d, J=7.05 Hz, 1H) 8.28 (s, 1H) 9.12 (s, 1H).

Preparation of compound 13b: 3-(6-chloropyrazin-2-yl)-6-(trifluoromethyl)imidazo[1,2-a]pyridine 13a (328 mg, 1.92 mmol) was dissolved in dioxane-water (6 mL:3 mL) and treated with NBS (285 mg, 1.60 mmol) in one portion which gave a light yellow solution. Solution stirred for 10 min at room temperature. 2-amino-5-(trifluoromethyl)pyridine (260 mg, 1.60 mmol) was added and the reaction mixture was heated in the microwave for 10 min at 100° C. The crude reaction was diluted with EtOAc (35 mL) and $NaHCO_3$ (sat, aq) (20 mL). The aqueous phase was back extracted with EtOAc (25 mL) The combined extracts were washed with brine (35 mL) then dried ($MgSO_4$) filtered and concentrated. The crude product was purified by column chromatography (EtOAc/MeOH) which gave the title compound 13b as a beige solid (265 mg, 45%). 1H NMR (300 MHz, DMSO-d6) δ ppm 7.76 (dd, J=9.4, 1.9 Hz, 1H) 8.00 (d, J=9.4 Hz, 1H) 8.67 (s, 1H) 8.83 (s, 1H) 9.39 (s, 1H) 10.04 (s, 1H).

Preparation of compound 13c: tert-butyl (3R)-3-({6-[6-(trifluoromethyl)imidazo[1,2-a]pyridin-3-yl]pyrazin-2-yl}amino)pyrrolidine-1-carboxylate To a solution of 13b (75 mg, 0.25 mmol) and CsF (77 mg, 0.50 mmol) in DMSO ((0.5 mL) was added tert-butyl (3R)-3-aminopyrrolidine-1-carboxylate (47 mg, 0.25 mmol) and the red slurry was heated in a 120° C. oil bath for 2 h. The crude reaction mixture was diluted with $NaHCO_3$ (15 mL) and EtOAc (20 mL). The layers were separated and the aqueous phase was back extracted with EtOAC (2×15 mL). The combined organic extracts were washed with brine (25 mL) then dried ($MgSO_4$), filtered and concentrated. The crude product was purified by column chromatography (EtOAc/MeOH) which gave the title compound 13c as a dark green solid (76 mg, 67%). 1H NMR (300 MHz, DMSO-d6) δ ppm 1.39 (d, J=11.5 Hz, 9H) 1.88-2.06 (m, 1H) 2.09-2.37 (m, 1H) 3.00-3.54 (m, 3H) 3.56-3.81 (m, 1H) 4.41 (br. s., 1H) 7.56-7.73 (m, 2H) 7.88 (s, 1H) 7.92 (d, J=9.4 Hz, 1H) 8.44 (s, 1H) 8.57 (s, 1H) 10.30 (d, J=11.3 Hz, 1H).

13c (76 mg, 0.17 mmol) was dissolved in methanol (1.5 mL) to give a dark green solution. 4N HCl-dioxane solution (0.5 mL) was added and the solution quickly changed to a yellow-orange color. Stirring was continued at RT for 3 h and the crude reaction was concentrated and dried. The crude solid was taken up in MTBE and a small amount of MeOH and the solid collected which gave the title compound 13 as an orange solid (29 mg). 1H NMR (300 MHz, DMSO-d6) δ ppm 2.01-2.17 (m, 1H) 2.18-2.35 (m, 1H) 3.24-3.50 (m, 4H) 4.53 (br. s., 1H) 7.84 (dd, J=9.4, 1.7 Hz, 1H) 7.98 (s, 1H) 8.05 (d, J=9.4 Hz, 1H) 8.49 (s, 1H) 8.74 (s, 1H) 9.44 (br. s., 2H) 10.22 (s, 1H).

Example 14

(Method A): 2-[3-(6-{[(3R,4R)-4-methylpyrrolidin-3-yl]amino}pyrazin-2-yl)imidazo[1,2-a]pyridin-6-yl]propan-2-ol

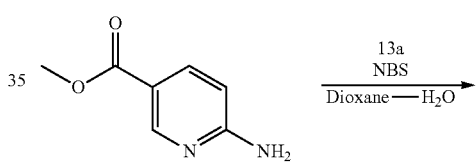

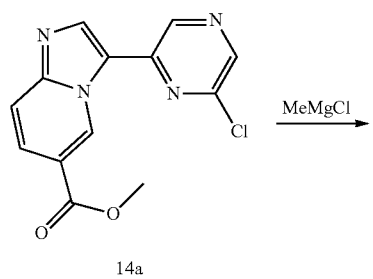

14a

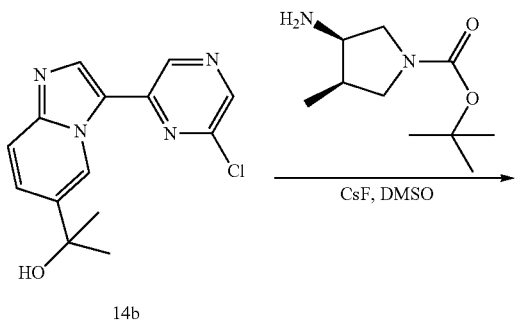

14b

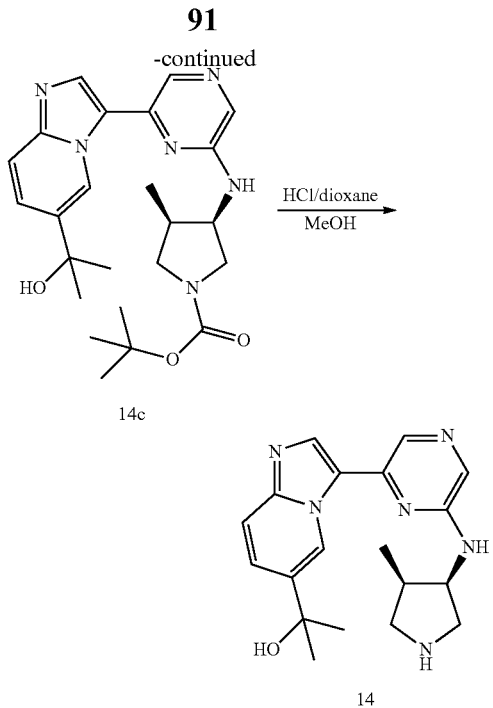

14c

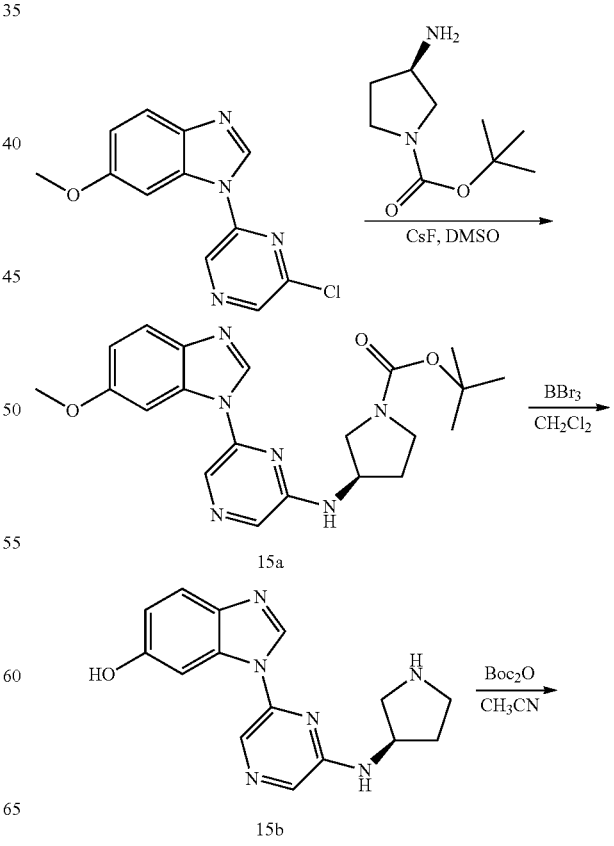

Preparation of compound 14a: methyl 3-(6-chloropyrazin-2-yl)imidazo[1,2-a]pyridine-6-carboxylate 14a (2.62 g, 15.4 mmol) was dissolved in dioxane-water (8 mL:4 mL) and treated with NBS (2.28 g, 12.8 mmol). The reaction mixture was stirred at room temperature for 10 min. Methyl 6-aminopyridine-3-carboxylate (1.95 g, 12.8 mmol) was added and the reaction mixture was heated in the microwave for 10 min at 100° C. The crude reaction mixture was diluted with EtOAc and NaHCO$_3$ (sat, aq). The aqueous phase was back extracted with EtOAc. The combined extracts were washed with brine then dried (MgSO4) filtered and concentrated. The crude product was purified by column chromatography (EtOAc/MeOH) which gave the title compound 14a as a brown solid (2.7 g, 76%). 1H NMR (300 MHz, DMSO-d6) δ ppm 7.76 (dd, J=9.4, 1.9 Hz, 1H) 8.00 (d, J=9.4 Hz, 1H) 8.67 (s, 1H) 8.83 (s, 1H) 9.39 (s, 1H) 10.04 (s, 1H).

Preparation of compound 14b: 2-[3-(6-chloropyrazin-2-yl)imidazo[1,2-a]pyridin-6-yl]propan-2-ol To a 0° C. heterogenous yellow solution of 14a (528 mg, 1.83 mmol) in anhydrous THF (36 mL) was added methylmagnesium chloride (3.0M in THF, 3.04 mL, 9.14 mmol) dropwise. The rxn mixture was warmed up to rt and allowed to stir for 2.5 h. The rxn mixture was slowly quenched with NH$_4$Cl (sat., aq.), then extracted with EtOAc (3×). Organic layer was washed with water and brine then dried over Na$_2$SO$_4$. The crude product was purified by column chromatography (EtOAc/MeOH) which gave the title compound 14b as a yellow solid (224 mg, 42%). 1H NMR (300 MHz, CHLOROFORM-d) δ ppm 1.72 (s, 6H) 7.53-7.61 (m, 1H) 7.74 (d, J=9.42 Hz, 1H) 8.33 (s, 1H) 8.39 (s, 1H) 8.96 (s, 1H) 9.82-9.92 (m, 1H).

Preparation of compound 14c: tert-butyl (3R,4R)-3-({6-[6-(2-hydroxypropan-2-yl)imidazo[1,2-a]pyridin-3-yl]pyrazin-2-yl}amino)-4-methylpyrrolidine-1-carboxylate To a solution of 14b (88.6 mg, 0.307 mmol) and CsF (93.7 mg, 0.614 mmol) in DMSO (1 mL) was added tert-butyl (3R,4R)-3-amino-4-methylpyrrolidine-1-carboxylate (61.5 mg, 0.307 mmol) and the mixture was heated in a 120° C. oil bath for 4 h. The crude reaction mixture was diluted with NaHCO$_3$ and EtOAc. The layers were separated and the aqueous phase was back extracted with EtOAc. The combined organic extracts were washed with brine then dried (MgSO$_4$), filtered and concentrated. The crude product was purified by column chromatography (EtOAc/MeOH) which gave the title compound 14c as a yellow solid (76 mg, 54% yield). 1H NMR (300 MHz, MeOD) δ ppm 1.06 (d, J=6.78 Hz, 3H) 1.47 (d, J=7.72 Hz, 9H) 1.61 (d, J=3.39 Hz, 6H) 7.50-7.57 (m, 1H) 7.59-7.65 (m, 1H) 7.82 (s, 1H) 8.24 (s, 1H) 8.27 (s, 1H) 10.11 (br. s., 1H).

14c (75 mg, 0.17 mmol) was dissolved in methanol (2 mL) to give a green solution. 4N HCl-dioxane solution (0.4 mL) was added and the solution quickly changed to a yellow-orange color. Stirring was continued at RT for 3 h and the crude reaction mixture was concentrated and dried. The crude solid was triturated with EtOAc and the solid collected which gave the title compound 14 as a yellow solid (70 mg). 1H NMR (300 MHz, DMSO-d6) δ ppm 1.01 (d, J=6.78 Hz, 3H) 1.55 (d, J=4.90 Hz, 6H) 2.58-3.76 (m, 5H) 4.83 (br. s., 1H) 7.88-8.17 (m, 4H) 8.48 (br. s., 1H) 8.97 (s, 1H) 9.50 (br. s., 2H) 10.20 (s, 1H).

Example 15

(Method A): 6-[6-(propan-2-yloxy)-1H-benzimidazol-1-yl]-N-[(3R)-pyrrolidin-3-yl]pyrazin-2-amine

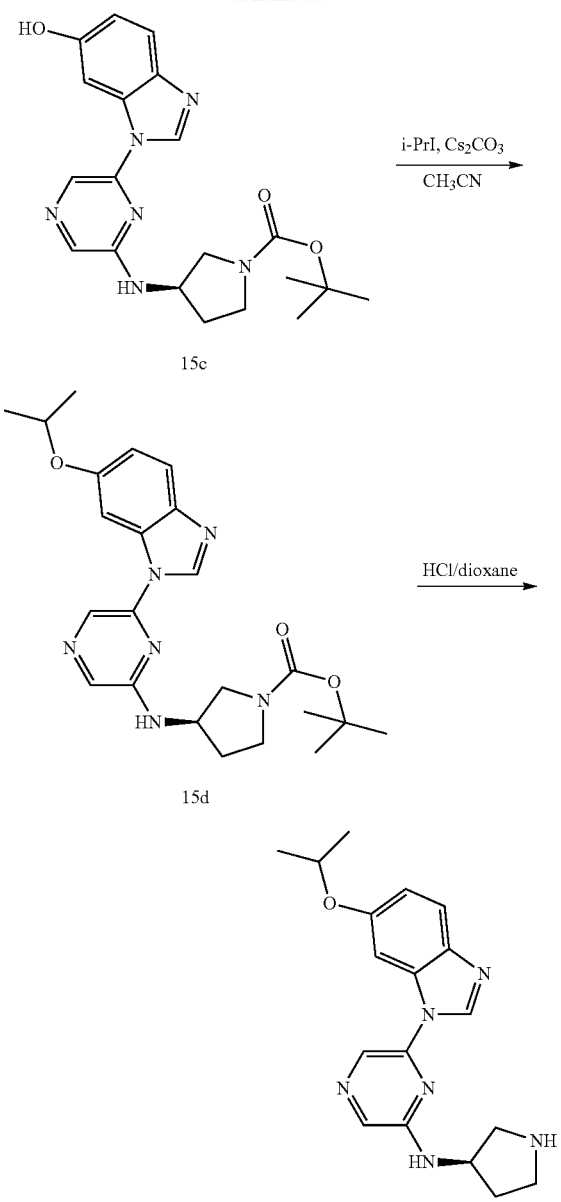

Preparation of compound 15a: tert-butyl (3R)-3-{[6-(6-methoxy-1H-benzimidazol-1-yl)pyrazin-2-yl]amino}pyrrolidine-1-carboxylate To a solution of 1-(6-chloropyrazin-2-yl)-6-methoxy-1H-benzimidazole (4.00 g, 15.3 mmol) and tert-butyl (3R)-3-aminopyrrolidine-1-carboxylate (4.00 g, 21.5 mmol) in DMSO (70 mL) was added CsF (8.0 g, 50 mmol). The mixture was stirred at 90° C. for 12 h. The mixture was quenched with water, diluted with EtOAc (400 mL). The separated organic layer was washed with brine, dried with Na₂SO₄ and concentrated. The residue was purified by column chromatography (CH₂Cl₂/MeOH=30:1) which gave the title compound 15a as a yellow solid (4.0 g, 65%).

Preparation of compound 15b: 1-{6-[(3R)-pyrrolidin-3-ylamino]pyrazin-2-yl}-1H-benzimidazol-6-ol BBr₃ (8 mL) was added to a solution of 15a (4.0 g, 9.6 mmol) in CH₂Cl₂ (200 mL) at 0° C. The mixture was stirred at room temperature for 12 h. The mixture was quenched with ice-water (100 mL), basified with Na₂CO₃ (aq.) to pH=10, filtered and separated, with 15b residing in the water phase and used in the next step directly.

Preparation of compound 15c: tert-butyl (3R)-3-{[6-(6-hydroxy-1H-benzimidazol-1-yl)pyrazin-2-yl]amino}pyrrolidine-1-carboxylate A solution of (Boc)₂O (2.0 g, 9.6 mmol) in CH₃CN (25 mL) was added to the water solution of compound. The mixture 15b was stirred at room temperature for 12 h, then filtered and the filter cake was washed with MeOH which gave the title compound 15c as a white solid (1.4 g, 35%). 1H NMR (400 MHz, DMSO): δ ppm 8.716 (s, 1H), 8.224 (s, 1H), 7.921 (s, 1H), 7.776 (d, 1H), 7.610 (s, 1H), 7.523 (d, 1H), 6.825 (d, 1H), 4.487 (s, 1H), 3.615 (t, 1H), 2.228 (t, 1H), 1.935 (t, 1H), 1.416 (d, 9H).

Preparation of compound 15d: tert-butyl (3R)-3-({6-[6-(propan-2-yloxy)-1H-benzimidazol-1-yl]pyrazin-2-yl}amino)pyrrolidine-1-carboxylate A mixture of 15c (0.2 g, 0.5 mmol), i-PrI (111 mg, 0.650 mmol), Cs₂CO₃ (0.493 g, 1.5 mmol) in CH₃CN (10 mL) was heated at 65° C. for 12 h. The resulting mixture was cooled to room temperature and filtered, the filtrate was concentrated in vacuo, the residue was purified by column chromatography (methanol/dichloromethane=1:20) which gave the title compound 15d as an oil (180 mg, 81.4%).

To a mixture of 15d (180 mg, 0.41 mmol) in dioxane (5 mL) was added HCl(g)/dioxane (10 mL) dropwise at room temperature, the resulting mixture was stirred for 1 h. The mixture was concentrated in vacuo, the residue was purified by prep-HPLC which gave the title compound 15 as a light yellow solid (98 mg, 70.6%). 1H NMR (400 MHz, DMSO): δ ppm 8.38 (s, 1H), 8.08 (s, 1H), 7.91 (s, 1H), 7.59-7.61 (m, 1H), 7.32 (m, 2H), 6.88-6.90 (d, 1H), 4.77 (m, 1H), 4.44 (m, 1H), 3.35-3.51 (m, 4H), 2.24-2.32 (m, 2H), 1.27 (d, 6H).

Example 16

(Method A): 6-(imidazo[1,2-a]pyridin-3-yl)-3-methyl-N-[(3R)-piperidin-3-yl]pyrazin-2-amine

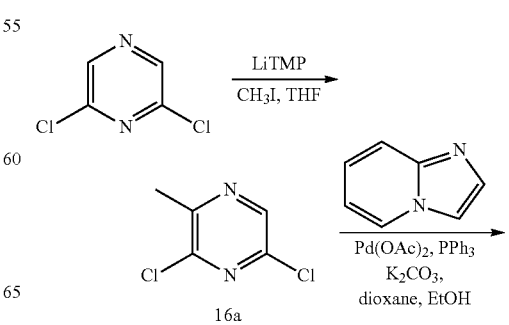

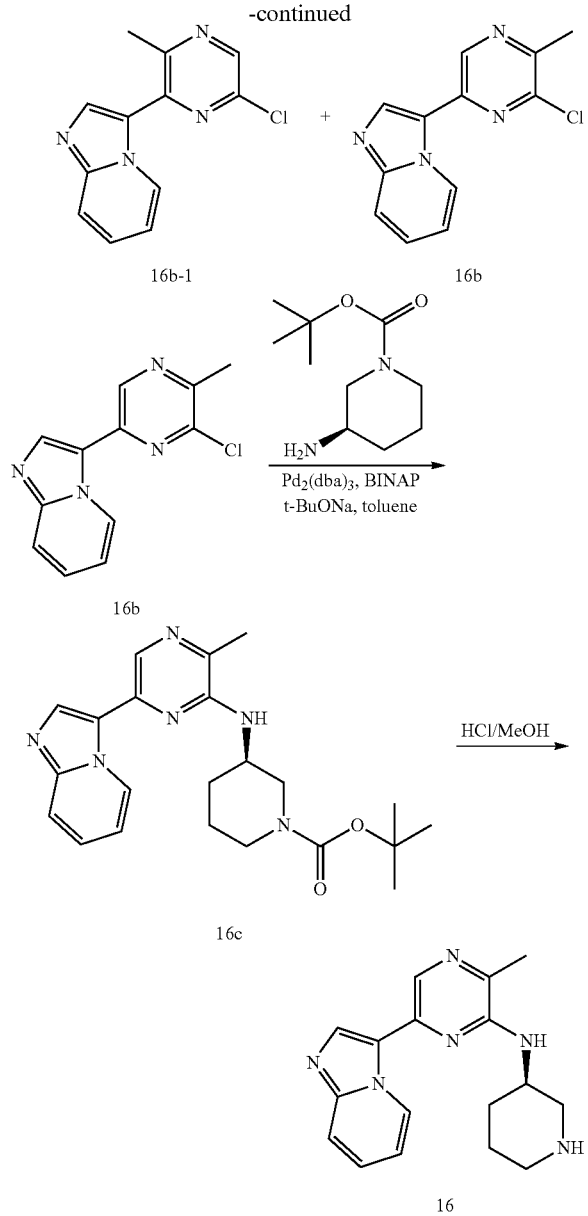

Preparation of compound 16b: 3-(6-chloro-5-methylpyrazin-2-yl)imidazo[1,2-a]pyridine A mixture of 16a (0.5 g, 3.07 mmol), imidazo[1,2-a]pyridine (0.36 g, 3.07 mmol), $K_2CO_3$ (1.48 g, 10.71 mmol), $PPh_3$ (80 mg, 0.30 mmol) and $Pd(OAc)_2$ (50 mg) in 5 mL of dioxane was heated at 120° C. under microwave irradiation for 30 min. The reaction mixture was filtered and the filtrate was concentrated in vacuo. The residue was purified by chromatography via silica gel ($CH_2Cl_2$:MeOH=80:1) to give a mixture of 16b and it's regioisomer, which were separated by prep-HPLC which gave the title compound 16b as yellow solid (0.12 g, 10%).

Preparation of compound 16c: tert-butyl (3R)-3-{[6-(imidazo[1,2-a]pyridin-3-yl)-3-methylpyrazin-2-yl]amino}piperidine-1-carboxylate A mixture of 16b (0.26 g, 1.06 mmol), tert-butyl (3R)-3-aminopiperidine-1-carboxylate (0.29 g, 1.59 mmol), t-BuONa (0.20 g, 2.12 mmol), $Pd_2(dba)_3$ (100 mg), and BINAP (150 mg) in 100 mL of toluene was refluxed overnight. The solvent was removed in vacuo and the residue was purified by chromatography via silica gel ($CH_2Cl_2$:MeOH=50:1) which gave the title compound 16c as a yellow oil (0.18 g, 42%). 16c (0.18 g, 0.44 mmol) in HCl(g)/MeOH (30 mL) was stirred overnight at room temperature. The solvent was removed in vacuo and the residue was purified by prep-HPLC which gave the title compound 16 as yellow solid (50 mg, 37%). 1H NMR (400 MHz, MeOD): δ ppm 9.476 (d, 1H), 8.104 (d, 2H), 7.582 (d, 1H), 7.354 (t, 1H), 7.023 (t, 1H), 4.280 (m, 1H), 3.408 (d, 1H), 3.162 (d, 1H), 2.886 (m, 2H), 2.336 (s, 3H), 2.147 (d, 1H), 1.926 (m, 1H), 1.688 (m, 2H).

Example 17/18

(Method A): 6-(6-methoxy-3H-imidazo[4,5-c]pyridin-3-yl)-N-[(3R)-piperidin-3-yl]pyrazin-2-amine/6-(6-methoxy-1H-imidazo[4,5-c]pyridin-1-yl)-N-[(3R)-piperidin-3-yl]pyrazin-2-amine

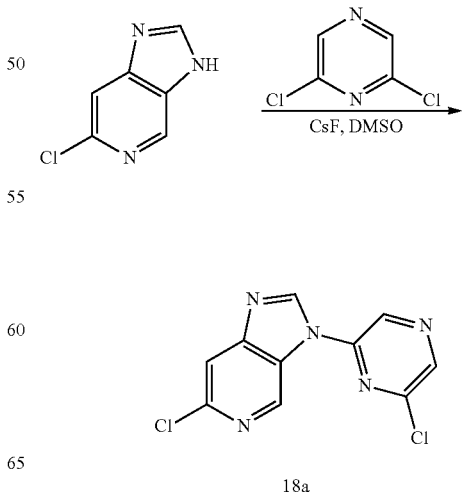

Preparation of compound 16a: 3,5-dichloro-2-methylpyrazine

To a solution of n-BuLi (78 mL, 0.195 mol) in dry THF (1.5 L) was added TMP (27.5 g, 0.195 mol) at −65° C. After the addition, the mixture was warmed to 0° C. and stirred for 30 min at this temperature, the reaction mixture was then re-cooled to −78° C. and 2,6-dichloropyrazine (20 g, 0.13 mol) in THF (50 mL) was added into the mixture dropwise. The mixture was stirred for 30 min at −78° C., then $CH_3I$ (65 g, 0.68 mol) was added and the reaction mixture was slowly warmed to rt and stirred for 3 h. The mixture was concentrated and diluted with $H_2O$ (300 mL), extracted with DCM (4×100 mL). The combined organic layer was washed with saturated $NH_4Cl$ aqueous and water, dried over $Na_2SO_4$, concentrated and the residue was purified by chromatography which gave the title compound 16a (10 g, 47.6%).

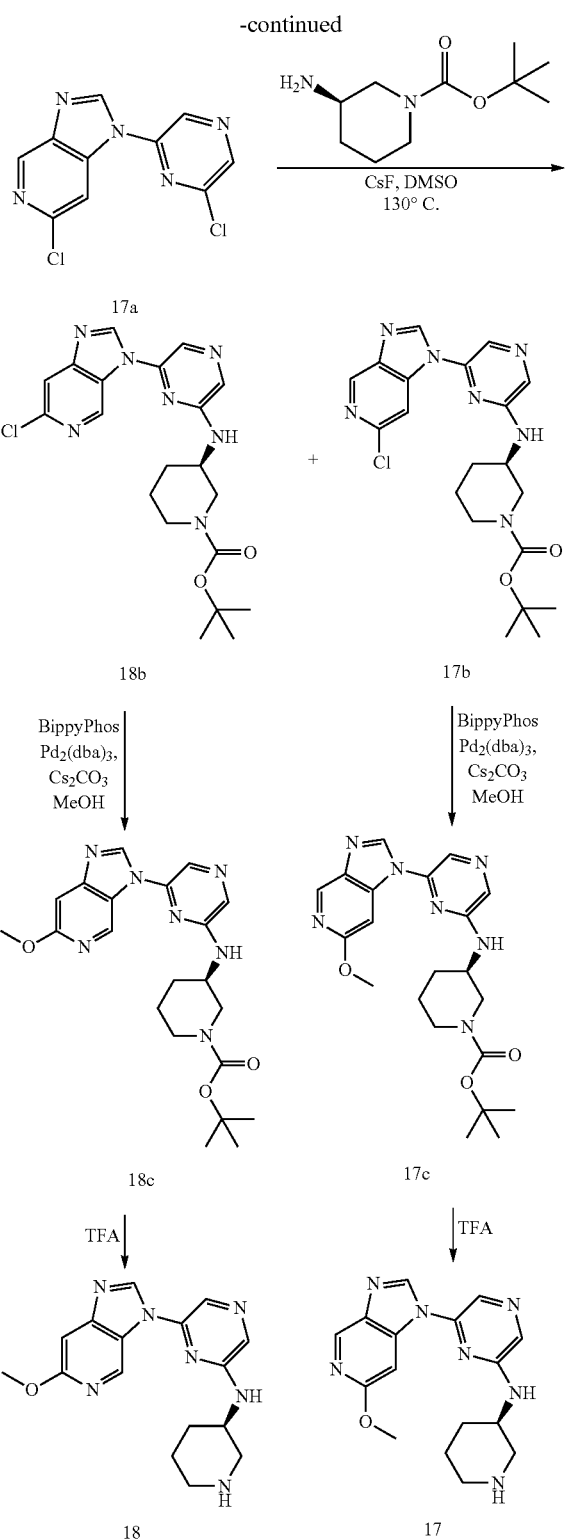

Preparation of compound 18a/17a: 6-chloro-3-(6-chloropyrazin-2-yl)-3H-imidazo[4,5-c]pyridine/6-chloro-1-(6-chloropyrazin-2-yl)-1H-imidazo[4,5-c]pyridine A mixture of 6-chloro-3H-imidazo[4,5-c]pyridine (4.6 g, 30 mmol), 2,6-dichloropyrazine (6 g, 40.5 mmol) and CsF (9.1 g, 60 mmol) in dry DMSO (80 mL) was stirred at room temperature for 20 h under $N_2$. The mixture was poured into water (50 mL) with stirring. The formed precipitate was collected by filtration. The filter cake was suspended in MeOH (20 mL) and filtered again. The filter cake was collected and dried in vacuum which gave a mixture of title compounds 18a & 17a as a white solid (5.0 g, 62.9%).

Preparation of compound 18b/17b: tert-butyl (3R)-3-{([6-(6-chloro-3H-imidazo[4,5-c]pyridin-3-yl)pyrazin-2-yl]amino}piperidine-1-carboxylate/tert-butyl (3R)-3-{[6-(6-chloro-1H-imidazo[4,5-c]pyridin-1-yl)pyrazin-2-yl]amino}piperidine-1-carboxylate A mixture of 18a & 17a (4.0 g. 15 mmol), compound tert-butyl (3R)-3-aminopiperidine-1-carboxylate (citric acid salt) (8.8 g, 22.6 mmol) and CsF (6.8 g, 45 mmol) in dry DMSO (100 mL) was heated to 130-140° C. under $N_2$ for 20 h. The cold reaction mixture was poured into ice-water (200 mL) and extracted with EtOAc (100 mL×3). The combined extracts were washed with water (100 mL×2), brine (100 mL), dried over $Na_2SO_4$ and concentrated in vacuo. The residue was purified by preparative HPLC which gave the title compound 18b as a yellow solid (1.6 g, 24.5%) and 17b as a red solid (2.15 g, 33.8%). 18b: $^1$H NMR (400 MHz, $CDCl_3$): δ ppm 1.385 (br, 9H), 1.554 (m, 1H), 1.775 (m, 2H), 1.905 (m, 1H), 3.361 (m, 1H), 3.444 (m, 2H), 3.627 (m, 1H), 3.978 (m, 1H) 5.066 (br, 1H), 7.738 (s, 1H), 7.869 (s, 1H), 8.157 (s, 1H), 8.620 (s, 1H), 9.182 (s, 1H); 17b: 1H NMR (400 MHz, $CDCl_3$): δ ppm 1.382 (br, 9H), 1.561 (m, 1H), 1.738 (m, 2H), 1.993 (m, 1H), 3.400 (br, 3H), 3.789 (m, 3H), 3.938 (m, 1H) 5.069 (br, 1H), 7.880 (s, 1H), 7.931 (s, 1H), 8.165 (s, 1H), 8.536 (s, 1H), 8.884 (s, 1H).

Preparation of compound 18c: tert-butyl (3R)-3-{[6-(6-methoxy-3H-imidazo[4,5-c]pyridin-3-yl)pyrazin-2-yl]amino}piperidine-1-carboxylate A mixture of 18b (180 mg, 0.42 mmol), $Pd_2(dba)_3$ (15.3 mg, 0.017 mmol), Bippyphos (10.6 mg, 0.02 mmol) and $Cs_2CO_3$ (136.9 mg, 0.42 mmol) in anhydrous MeOH (3 mL) was stirred at 100° C. under microwave irradiation for 1 h. The mixture was concentrated and the residue was purified by prep. HPLC which gave the title compound 18c as a yellow solid (100 mg, 56%).

TFA (0.6 ml) was added dropwise to a solution of 18c (100 mg, 0.235 mmol) in anhydrous $CH_2Cl_2$ 10 ml) at 0° C. under $N_2$. Then the solution was stirred at room temperature for 3 h. The solution was concentrated under reduced pressure. The residue was dissolved in water (50 mL) and washed with EtOAc (40 mL). The aqueous solution was basified with $Na_2CO_3$ (aq) to pH=8-9. The solution was then extracted with $CH_2Cl_2$ (30 mL×3). The combined organic layers were washed with brine (50 mL), dried over $Na_2SO_4$ and concentrated which gave the title compound 18 as a light yellow solid (72 mg, 94.3%). 1H NMR (400 MHz, CDCl3): δ ppm 1.549 (m, 1H), 1.739 (m, 2H), 1.826 (m, 1H), 2.838 (m, 2H), 3.111 (m, 1H), 3.946 (s, 3H), 4.026 (d, 1H), 5.487 (s, 1H), 7.083 (s, 1H), 7.812 (s, 1H), 8.031 (s, 1H), 8.535 (s, 1H), 8.992 (s, 1H).

Preparation of compound 271c: tert-butyl (3R)-3-{[6-(6-methoxy-1H-imidazo[4,5-c]pyridin-1-yl)pyrazin-2-yl]amino}piperidine-1-carboxylate A mixture of 17b (150 mg, 0.35 mmol), $Pd_2(dba)_3$ (13 mg, 0.014 mmol), Bippyphos (9 mg, 0.0175 mmol) and $Cs_2CO_3$ (342 mg, 1.05 mmol) in anhydrous MeOH (3 mL) was heated at 100° C. under microwave irradiation for 1 h. The mixture was concentrated and the residue was purified by preparative HPLC which gave the title compound 17c as a light yellow solid (50 mg, 33.7%).

To a stirred solution of 17c (50 mg, 0.12 mmol) in dry $CH_2Cl_2$ (5 mL) was added dropwise TFA (0.3 mL) at 0° C. under $N_2$. After addition, the mixture was stirred at the same temperature for 3 h. The reaction mixture was concentrated in vacuo. The residue was dissolved in water (40 mL) and extracted with EtOAc (20 mL). The aqueous phase was basified to pH=10 with $K_2CO_3$ and extracted with $CHCl_3$/MeOH (ratio 1:10, 30 mL×3). The combined extracts were dried over $Na_2SO_4$ and concentrated in vacuum which gave the title compound 17 as a yellow solid (25 mg, 65.8%). 1H NMR (400 MHz, $CDCl_3$) δ ppm 1.536-1.495 (m, 1H), 1.703 (m, 2H), 1.796 (m, 1H), 2.786-2.706 (m, 3H), 3.101-3.066 (m, 1H), 3.935 (s, 3H), 3.950 (m, 1H), 5.486-5.471 (br, 1H), 7.229 (s, 1H), 7.798 (s, 1H), 7.972 (s, 1H), 8.376 (s, 1H), 8.634 (s, 1H).

Example 19

(Method A): (2R,3R)—N-[6-(7-methoxyimidazo[1,2-a]pyridin-3-yl)pyrazin-2-yl]-2-methyl-1-azabicyclo[2.2.2]octan-3-amine

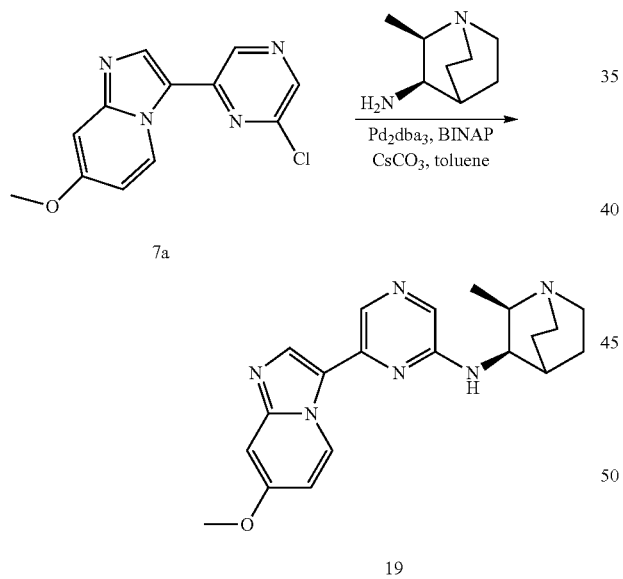

To a sealed tube was added 7a (50 mg, 019 mmol), (2R,3R)-2-methyl-1-azabicyclo[2.2.2]octan-3-amine (49 mg, 0.23 mmol), $Cs_2CO_3$ (313 mg, 0.96 mmol), $Pd_2(dba)_3$ (11 mg, 0.012 mmol), BINAP (12 mg, 0.019 mmol) and toluene (2 mL). The brown slurry was place in a 120° C. oil bath and heat for 16 h. The crude reaction concentrated and purified by prep HPLC which gave the title compound 19 as a tan solid (12 mg, 17%). 1H NMR (400 MHz, DMSO-d6) δ ppm 1.05 (d, J=7.07 Hz, 3H) 1.25-1.35 (m, 1H) 1.62-1.70 (m, 2H) 1.79-1.90 (m, 2H) 2.54-2.63 (m, 1H) 2.74-2.86 (m, 1H) 2.96-3.04 (m, 1H) 3.20-3.25 (m, 1H) 3.88 (s, 3H) 4.07-4.16 (m, 1H) 6.84 (dd, J=7.58, 2.27 Hz, 1H) 7.10 (d, J=1.77 Hz, 1H) 7.17 (d, J=8.08 Hz, 1H) 7.90 (s, 1H) 8.20 (s, 1H) 8.24 (s, 1H) 9.56 (d, J=7.58 Hz, 1H).

Example 20

(Method B): 3-(imidazo[1,2-a]pyridin-3-yl)-5-[(3R)-piperidin-3-ylamino]pyrazine-2-carbonitrile

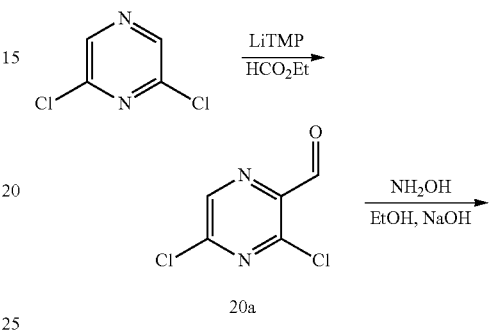

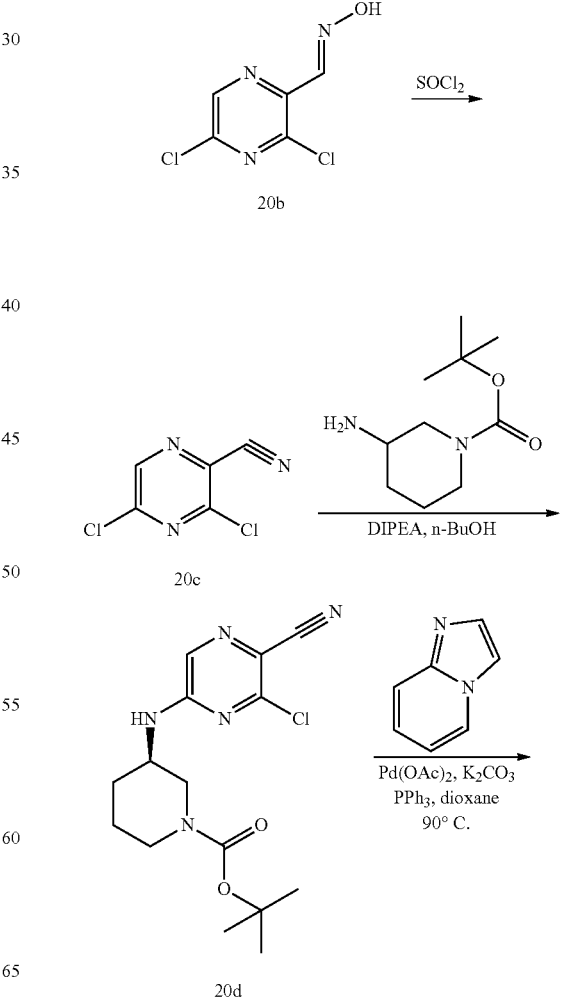

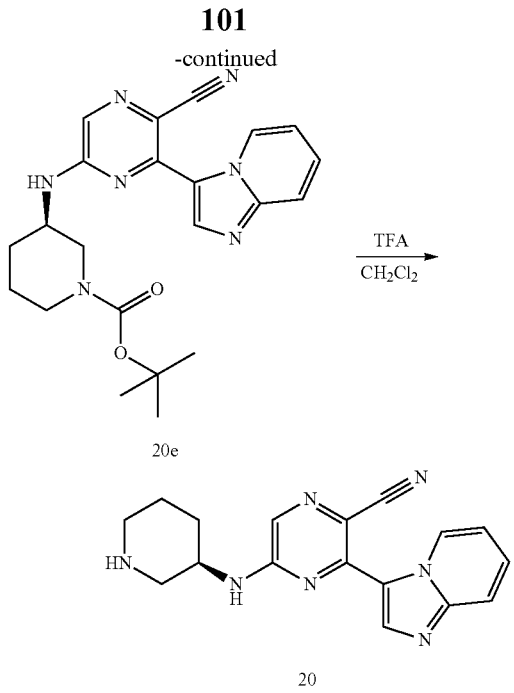

Preparation of compound 20a: 3,5-dichloropyrazine-2-carbaldehyde

To THF (100 mL) was added n-BuLi (4 mL, 10 mmol) at −30° C. under $N_2$. 2,2,6,6-tetramethylpiperidine (1.26 mL, 10.2 mol) was added dropwise. The mixture was stirred at room temperature for 15 min. Then a solution of 2,6-dichloropyrazine (1.3 g, 8.3 mmol) in THF (20 mL) was added dropwise at −78° C. The mixture was stirred at −78° C. for 1.5 h. Ethyl formate (1 mL, 12 mmol) was added and the reaction mixture was stirred at −78° C. for an additional 2 h. The reaction was quenched with saturated $NH_4Cl$ (20 mL), warmed to room temperature, and diluted with ethyl acetate (150 mL). The organic layer was separated and dried over $Na_2SO_4$ and concentrated to dryness. The residue was purified by column chromatography (PE:EA from 30:1 to 5:1) which gave the title compound 20a as an oil (0.8 g, 54%).

Preparation of compound 20b: (E)-1-(3,5-dichloro-pyrazin-2-yl)-N-hydroxymethanimine To a solution of 20a (4.2 g, 23.7 mmol) in EtOH (100 mL) was added $NH_2OH·HCl$ (1.88 g, 27 mmol) and aqueous NaOH (16 mL, 3 M). The resulting mixture was stirred at room temperature for 2 h. The mixture was concentrated to remove EtOH. Then the solid was collected by filtration, washed with ethyl acetate (15 mL) and dried in vacuo which gave the title compound 20b as yellow solid (1.6 g, 35%).

Preparation of compound 20c: 3,5-dichloropyrazine-2-carbonitrile

The solution of 20b (0.8 g, 4.1 mmol) in $SOCl_2$ (20 mL) was stirred at 80° C. for 2 h. Then the resulting mixture was stirred at room temperature for 2 h. The mixture was concentrated to dryness. The which gave the title compound 20c as light yellow solid (0.4 g, 56%).

Preparation of compound 20d: tert-butyl (3R)-3-[(6-chloro-5-cyanopyrazin-2-yl)amino]piperidine-1-carboxylate To a solution of 20c (0.6 g, 3.46 mmol) and tert-butyl (3R)-3-aminopiperidine-1-carboxylate (0.41 g, 2 mmol) in n-BuOH (20 mL) was added DIPEA (1.2 mL, 6.9 mmol) at room temperature. The resulting mixture was stirred at 50° C. for 5 h. The mixture was concentrated to dryness. The residue was purified by column chromatography ($CH_2Cl_2$:$CH_3OH$ from 500:1 to 100:1) which gave the title compound 20d as yellow solid (0.7 g, 60%). $^1$H NMR (400 MHz, CDCl3) δ ppm 1.37 (s, 9H), 1.56 (m, 1H), 1.70 (m, 2H), 1.86 (s, 1H), 3.36 (s, 3H), 3.57 (s, 1H), 3.96 (s, 1H), 5.78 (br, 1H), 7.76 (s, 1H).

Preparation of compound 20e: tert-butyl (3R)-3-{[5-cyano-6-(imidazo[1,2-a]pyridin-3-yl)pyrazin-2-yl]amino}piperidine-1-carboxylate The mixture of 20d (0.3 g, 0.89 mmol), imidazo[1,2-a]pyridine (0.115 g, 0.98 mmol), $PPh_3$ (0.024 g, 0.089 mmol), $K_2CO_3$ (0.43 g, 3.1 mmol) and $Pd(OAc)_2$ (0.03 g, 0.13 mmol) in dioxane (35 mL) was stirred at 90° C. under $N_2$ overnight. The reaction mixture was filtered and the filtrate was concentrated to dryness. The residue was purified by column chromatography ($CH_2Cl_2$:$CH_3OH$ from 200:1 to 50:1) which gave the title compound 20e as light yellow solid (0.28 g, 75%).

To a solution of 20e (0.3 g, 0.7 mmol) in DCM (10 mL) was added TFA (2 mL) at 0° C. The resulting mixture was stirred at room temperature for 5 h. The mixture was concentrated to dryness. The residue was purified by prep-HPLC which gave the title compound 20 as yellow solid (HCOOH salt, 0.1 g, 45%). 1H NMR (400 MHz, DMSO) δ ppm 1.68-1.57 (m, 2H), 1.89 (m, 1H), 2.04 (m, 1H), 2.86 (m, 2H), 3.11 (d, 2H), 4.16 (br, 1H), 7.15 (m, 1H), 7.53 (m, 1H), 7.82 (d, 1H), 7.96 (s, 1H), 8.45 (s, 2H), 9.30 (s, 1H).

Example 21

(Method A): 3-{6-[(3R)-piperidin-3-ylamino]pyrazin-2-yl}pyrazolo[1,5-a]pyridine-6-carbonitrile

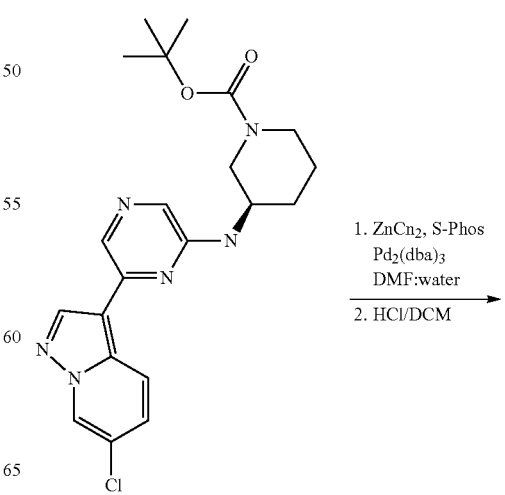

1. ZnCn₂, S-Phos
   Pd₂(dba)₃
   DMF:water
2. HCl/DCM

-continued

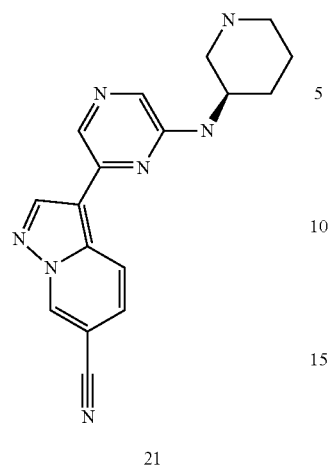

21

A mixture of (R)-3-[6-(6-Chloro-pyrazolo[1,5-a]pyridin-3-yl)-pyrazin-2-ylamino]-piperidine-1-carboxylic acid tert-butyl ester (129 mg, 0.3 mmol), zinc cyanide (40 mg, 0.342 mmol), S-Phos (11.1 mg, 0.027 mmol) and $Pd_2(dba)_3$ (11 mg, 0.012 mmol) in DMF-water (1.36 ml, 99:1 DMF:water) was degassed for 5 min then back filled with nitrogen. The reaction mixture was then heated to 150° C. in a microwave reactor for 30 min. The crude reaction mixture was diluted with 2N NaOH (1 ml) and ethyl acetate (10 ml). The aqueous layer was back extracted with ethyl acetate (10 ml), then the pooled ethyl acetate phases were washed with brine and dried with sodium sulfate and concentrated in vacuo to an oil. The crude oil was purified by column chromatography (0-100% ethyl acetate in heptane) which gave (R)-3-[6-(6-cyano-pyrazolo[1,5-a]pyridin-3-yl)-pyrazin-2-ylamino]-piperidine-1-carboxylic acid tert-butyl ester as a greenish oil (70 mg). (R)-3-[6-(6-cyano-pyrazolo[1,5-a]pyridin-3-yl)-pyrazin-2-ylamino]-piperidine-1-carboxylic acid tert-butyl ester (70 mg, 0.167 mmol) was dissolved in anhydrous DCM (2 ml) then 4 N HCl in dioxane (0.417 mL, 10 eq.) was added. The resulting mixture was capped and stirred at 23° C. After 4 h the reaction mixture was concentrated which gave the title compound 21 as a light yellow solid (64 mg). 1H NMR (400 MHz, DMSO-d6) δ ppm 1.54-1.68 (m, 1H) 1.79-2.01 (m, 2H) 2.01-2.16 (m, 1H) 2.78-3.05 (m, 2H) 3.19-3.30 (m, 1H) 3.44 (none, 1H) 4.27 (br. s., 1H) 7.68 (d, J=8.59 Hz, 1H) 7.84 (s, 1H) 8.38 (s, 1H) 8.54 (d, J=9.35 Hz, 1H) 8.98 (s, 1H) 9.67 (s, 1H); LCMS M+1 320.2.

Example 22

(Method E): 6-[6-(2,2-difluoroethoxy)pyrazolo[1,5-a]pyridin-3-yl]-N-[(3R)-piperidin-3-yl]pyrazin-2-amine

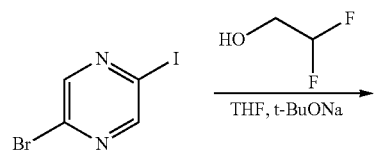

-continued

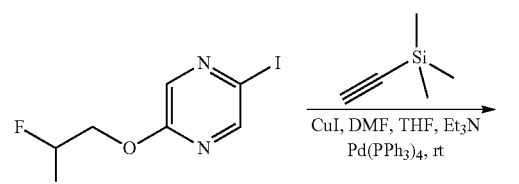

22a

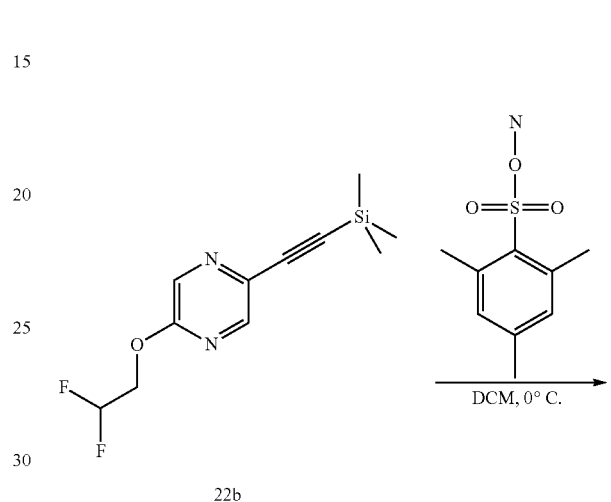

22b

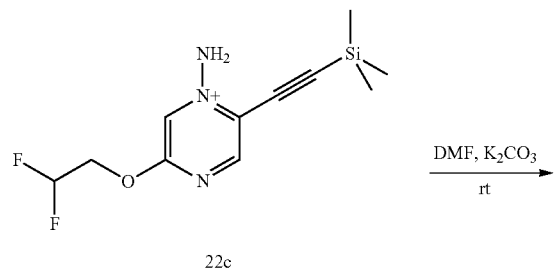

22c

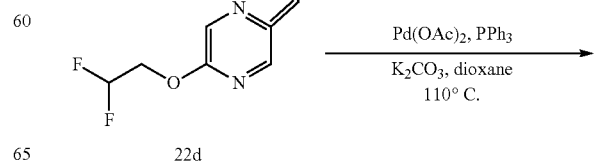

22d

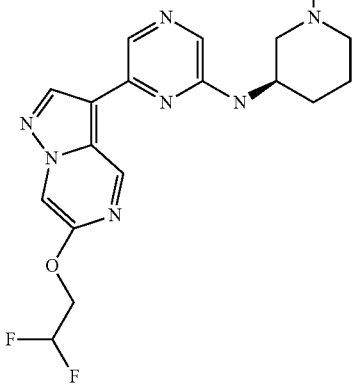

22e

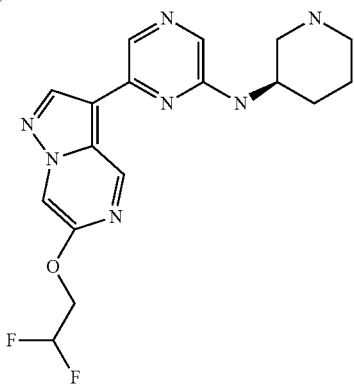

22

Preparation of compound 22a: 2-(2,2-difluoroethoxy)-5-iodopyrazine

To a solution of 2,2-difluoroethanol (0.74 g, 8.7 mmol) in THF (50 mL) at room temperature was added sodium butoxide (1.13 g, 11.4 mmol) and stirred for 15 min. The reaction mixture was cooled to 0° C. and a solution of 2-bromo-5-iodopyrazine (2.5 g, 8.7 mmol) in THF (50 mL) was added slowly over 5 min. The reaction mixture was allowed to warm to room temperature and stirred for 16 h. The mixture was diluted with ethyl acetate and washed with sat. $NH_4Cl$. The organic layer was dried over $MgSO_4$, filtered and concentrated which gave the title compound 22a (2.3 g, 90%).

Preparation of compound 22b: 2-(2,2-difluoroethoxy)-5-[(trimethylsilyl)ethynyl]pyrazine To a solution of 22a (2.3 g, 8.04 mmol), (trimethylsilyl)acetylene (1.4 mL, 9.65 mmol) and copper iodide (0.15 g, 0.8 mmol) in a mixture of THF (25 mL), DMF (25 mL) and triethylamine (10 mL) was added $Pd(PPh_3)_4$ (0.28 g, 0.24 mmol) at room temperature. After 30 min. the reaction mixture was diluted with ethyl acetate and washed with water. The organic layer was dried over $MgSO_4$, filtered and concentrated. The crude product was purified by flash chromatography (0-15% EtOAc/Heptane) which gave the title compound 22b (2.2 g, 98%); LCMS: M+1 257.

Preparation of compound 22c: 1-amino-5-(2,2-difluoroethoxy)-2-[(trimethylsilyl)ethynyl]pyrazin-1-ium To a solution of 22b (2.2 g, 6.9 mmol) in dichloromethane (10 mL) at 0° C. was added 2-[(aminooxy)sulfonyl]-1,3,5-trimethylbenzene (1.77 g, 8.24 mmol). The reaction mixture was stirred at 0° C. and warmed gradually to room temperature. After 3 h, the solution was concentrated which gave the title compound 22c. LCMS: M+1 272.

Preparation of 22d: 6-(2,2-difluoroethoxy)pyrazolo[1,5-a]pyrazine

A mixture of 22c (1.9 g, 5.6 mmol) and potassium carbonate (1.55 g, 11.2 mmol) in DMF (80 mL) was stirred at room temperature for 18 h. The reaction mixture was diluted with ethyl acetate and washed with water. The organic layer was dried over $MgSO_4$, filtered and concentrated. The crude product was purified by flash chromatography (0-30% EtOAc/Heptane) on silica gel which gave the title compound 22d (0.29 g, 26%) 1H NMR (400 MHz, DMSO-d6) δ ppm 4.57 (td, J=14.91, 3.54 Hz, 2H). 6.42 (m, 1H) 6.98 (d, J=1.52 Hz, 1H) 8.08 (d, J=2.27 Hz, 1H) 8.59 (s, 1H) 9.01 (d, J=1.01 Hz, 1H); LCMS: M+1 200.

Preparation of compound 22e: tert-butyl (3R)-3-({6-[6-(2,2-difluoroethoxy)pyrazolo[1,5-a]pyrazin-3-yl]pyrazin-2-yl}amino)piperidine-1-carboxylate A mixture of 22d (135 mg, 0.68 mmol), tert-butyl (3R)-3-[(6-bromopyrazin-2-yl)amino]piperidine-1-carboxylate (243 mg, 0.68 mmol), potassium carbonate (188 mg, 1.36 mmol), triphenylphosphine (18.4 mg, 0.068 mmol) and palladium acetate (7.9 mg, 0.034 mmol) in anhydrous 1,4-dioxane (1.5 mL, 0.5M) was heated at 110° C. for 3 h. The reaction mixture was diluted with ethyl acetate and washed with water. The organic layer was dried over $MgSO_4$, filtered and concentrated. The crude product was purified by flash chromatography (0-100% EtOAc/Heptane) on silica gel which gave the title compound 22e. LCMS: M+1 476.

To a solution of 22e (50 mg) in dichloromethane (2 mL) was added 4M HCl in 1,4-dioxane (1 mL). The reaction mixture was stirred at room temperature for 5 min. Water was added and washed with ethyl acetate. The aqueous layer was concentrated and the crude product was purified by reverse phase HPLC which gave the title compound 22. 1H NMR (400 MHz, MeOD) δ ppm 1.71 (m, 1H) 1.88 (m, 1H) 2.10 (m, 1H) 2.27 (m, 1H) 2.98 (m, 2H) 3.57 (m, 1H) 4.33 (m, 1H) 4.65 (td, J=13.89, 4.04 Hz, 3H) 6.28 (m, 1H) 7.81 (s, 1H) 8.31 (s, 1H) 8.42 (s, 1H) 8.62 (s, 1H) 9.61 (s, 1H); LCMS M+1 376.

Example 23

(Method A): N-[(3R)-piperidin-3-yl]-6-pyrazolo[1,5-a]pyrimidin-3-ylpyrazin-2-amine

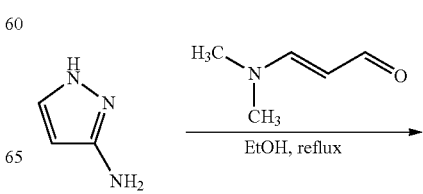

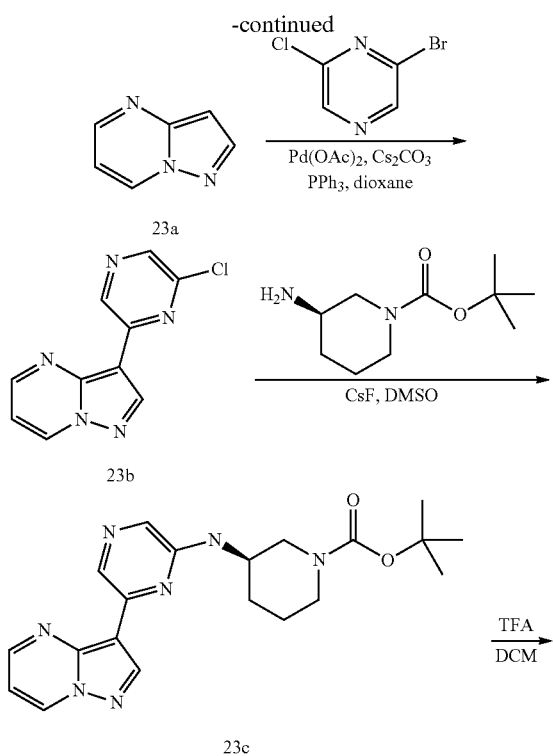

Preparation of compound 23a: pyrazolo[1,5-a]pyrimidine

A mixture of 1H-pyrazol-3-ylamine (32 g, 0.386 mol) and (E)-3-dimethylamino-propenal (38.2 g, 0.386 mol) in EtOH (500 mL) was refluxed for 6 h. The solvent was removed in vacuo and the residue was purified via column chromatography (petroleum ether/EtOAc=10:1~2:1) which gave the title compound 23a as a white solid (30 g, 65%).

Preparation of compound 23b: 3-(6-Chloro-pyrazin-2-yl)-pyrazolo[1,5-a]pyrimidine To a stirred solution of 23a (30 g, 0.252 mol), 2-bromo-6-chloro-pyrazine (58.5 g, 0.302 mol) and PPh₃ (6.6 g, 0.0252 mol) in dioxane (300 mL) was added Cs₂CO₃ (82.1 g, 0.252 mol) and Pd(OAc)₂ (11.3 g, 0.0504 mol). The mixture was purged with N₂×3 and stirred at reflux for 3 days. The reaction mixture was cooled to room temperature and filtered. The filtrate was concentrated, and the resulting residue was purified via preparative HPLC which gave the title compound 23b as a yellow solid (3.01 g, 5%).

Preparation of compound 23c: (R)-3-(6-Pyrazolo[1,5-a]pyrimidin-3-yl-pyrazin-2-ylamino)-piperidine-1-carboxylic acid tert-butyl ester A mixture of 23b (300 mg, 1.3 mmol), (R)-3-amino-piperidine-1-carboxylic acid tert-butyl ester (310 mg, 1.3 mmol) and CsF (235.4 mg, 1.55 mmol) in anhydrous DMSO (10 mL) was heated at 80° C. under N₂ and stirred overnight. The mixture was cooled to room temperature, diluted with water (20 mL) and extracted with EtOAc (15 mL×3). The combined organic layers were dried over Na₂SO₄ and concentrated. The residue was purified via column chromatography (petroleum ether/EtOAc=3:1~1:1) which gave the title compound 23c as a yellow solid (150 mg, 29%).

To a stirred solution of 23c (150 mg, 0.379 mmol) in DCM (10 mL) was added dropwise TFA (0.3 mL) at 0° C. The reaction mixture was stirred for 3 h at room temperature. The mixture was concentrated. The resulting residue was dissolved in water (10 mL) and extracted with Et₂O (5 mL×3). Then the aqueous layer was basified to a pH ~10 by 10N Na₂CO₃ and extracted with CHCl₃/IPA (3:1) (10 mL×3). Combined organic layers were washed with brine (10 mL), dried over Na₂SO₄ and concentrated. The residue was purified via preparative HPLC which gave the title compound 23 as a yellow solid (HCOOH salt, 23 mg, 21%). 1H NMR (400 MHz, DMSO): δ ppm 1.623-1.509 (m, 2H), 1.784-1.773 (m, 1H), 1.996-1.986 (m, 1H), 2.094-2.062 (m, 1H), 3.011-2.981 (m, 4H), 4.018 (m, 1H), 7.025-7.108 (d, 1H), 7.196-7.168 (m, 1H), 7.789 (s, 1H), 8.709 (s, 1H), 8.758-8.748 (m, 1H), 8.808 (s, 1H), 9.242-9.220 (m, 1H).

Example 24

(Method F): 3-{6-[(3R)-piperidin-3-ylamino]pyrazin-2-yl}imidazo[1,2-a]pyridine-7-carbonitrile

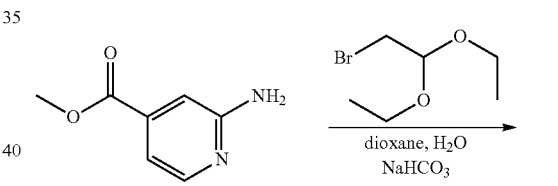

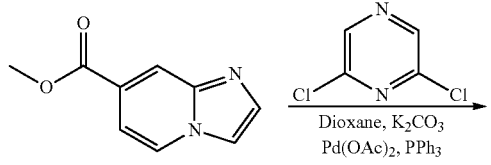

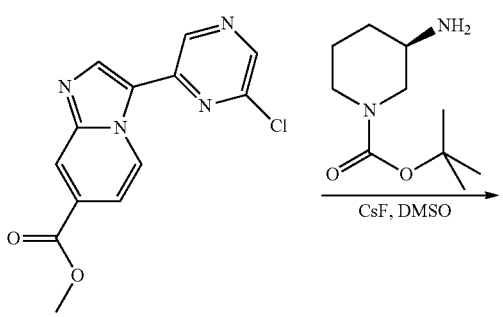

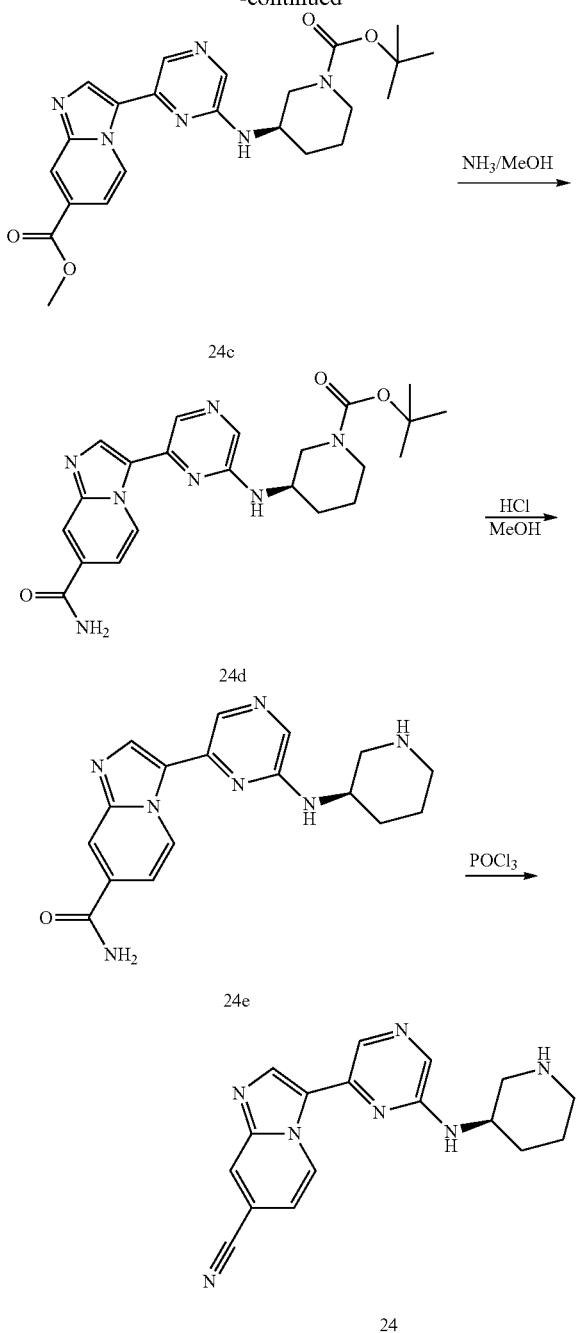

to room temperature, and the solid was collected by filtration and dried in vacuo which gave the title compound 24a as a yellow solid (9.5 g, 85.7%).

Preparation of compound 24b: 3-(6-Chloro-pyrazin-2-yl)-imidazo[1,2-a]pyridine-7-carboxylic acid methyl ester To a solution of 24a (2.6 g, 14.8 mmol) and 2,6-Dichloropyrazine (2.2 g, 14.8 mmol) in dioxane (60 mL) was added $K_2CO_3$ (2.04 g, 14.8 mmol) and $PPh_3$ (0.388 g, 1.48 mmol). The mixture was degassed under $N_2 \times 3$. Then $Pd(OAc)_2$ (0.26 g) was added, the resulting mixture was then degassed again and was allowed to reflux overnight. The mixture was concentrated to give crude product, which was purified by column chromatography which gave the title compound 24b as a yellow solid (1.9 g, 44.2%).

Preparation of compound 24c: methyl 3-(6-{[(3R)-1-(tert-butoxycarbonyl)piperidin-3-yl]amino}pyrazin-2-yl)imidazo[1,2-a]pyridine-7-carboxylate To a solution of 24b (0.814 g, 2.82 mmol) and tert-butyl (3R)-3-aminopiperidine-1-carboxylate (0.57 g, 2.82 mmol) in DMSO (10 ml) was added CsF (0.43 g, 2.82 mmol). The resulting mixture was heated to 80~100° C. overnight. $H_2O$ (50 mL) was added and the mixture was extracted with ethyl acetate (20 mL×3). The combined organic layers were dried over $Na_2SO_4$ and filtered. The filtrate was concentrated to give crude product, which was purified on $Al_2O_3$ which gave the title compound 24c as a yellow solid (0.56 g, 43.8%).

Preparation of compound 24d: tert-butyl (3R)-3-{[6-(7-carbamoylimidazo[1,2-a]pyridin-3-yl)pyrazin-2-yl]amino}piperidine-1-carboxylate 24c (0.56 g, 1.2 mmol) was dissolved in a saturated solution of $NH_3$ in $CH_3OH$ (60 mL), and the mixture was heated to 80~100° C. for 24 h. Then the mixture was concentrated which gave the title compound 24d.

Preparation of compound 24e: 3-{6-[(3R)-piperidin-3-ylamino]pyrazin-2-yl}imidazo[1,2-a]pyridine-7-carboxamide Crude 24d (0.56 g), was dissolved in a solution of 4N $HCl/CH_3OH$ (5 ml), and the mixture was stirred at rt overnight. Then aq. $Na_2CO_3$ (5 ml) was added to the mixture, the layers were separated. The aqueous layer was extracted with $CH_2Cl_2$ (50 mL×4), and the combined organic layers were dried over $Na_2SO_4$ and filtered. The filtrate was concentrated to give crude product, which was purified via prep. HPLC which gave the title compound 24e as a white solid (78 mg, 18.7% for two steps). 1H NMR (400 MHz, MeOD) δ ppm 1.801-1.727 (m, 1H), 1.975-1.860 (m, 1H), 2.162-2.2.113 (m, 1H) 2.277-2.245 (m, 1H), 3.105-3.040 (m, 2H), 3.350-3.326 (m, 1H), 3.606-3.576 (d, 3H), 4.327-4.281 (m, 1H), 7.601-7.579 (m, 1H), 7.882 (s, 1H), 8.224 (s, 1H), 8.365-8.355 (d, 2H), 8.508 (s, 1H), 9.67 (d, 1H).

Preparation of compound 24a: imidazo[1,2-a]pyridine-7-carboxylic acid methyl ester To a solution of 2-Bromo-1,1-diethoxy-ethane (18.62 g, 0.095 mol) in $H_2O$ (80 ml) was added aq. HBr (2 ml). The resulting mixture was heated to 80° C. for 1.5 h and then was cooled to 40° C. Then a solution of 2-Amino-isonicotinic acid methyl ester (9.61 g, 0.063 mol) and $NaHCO_3$ (6.615 g, 0.0788 mol) in $CH_3OH/H_2O$ (3:1 400 ml) was added dropwise to the above mixture. The resulting mixture was heated to 80° C. for 18 h. The mixture was concentrated and cooled A suspension of 24e (0.223 g, 0.51 mmol) in of $POCl_3$ (5 mL) was refluxed for 6 h. The mixture was cooled and concentrated to remove $POCl_3$. The resulting mixture was adjusted to pH=8 with 1N aq. NaOH. The resulting mixture was lyophilized and purified via prep. HPLC which gave the title compound 24 (77 mg, yield 48.1%). 1H NMR (400 MHz, DMSO) δ ppm 1.560-1.552 (m, 1H), 1.775-1.760 (m, 1H), 1.962-1.913 (m, 1H) 2.177-2.145 (m, 1H), 2.875-2.740 (m, 2H), 3.350-3.326 (m, 1H), 3.406-3.386 (m, 1H), 4.127-4.081 (m, 1H), 7.375-7.354 (m, 1H), 7.882 (s, 1H), 8.331 (s, 1H), 8.409 (d, 2H), 8.733 (s, 1H), 9.816-9.693 (d, 1H).

Example 25

(Method A): N-[(3R,5S)-5-(difluoromethyl)pyrrolidin-3-yl]-6-(imidazo[1,2-a]pyridin-3-yl)pyrazin-2-amine

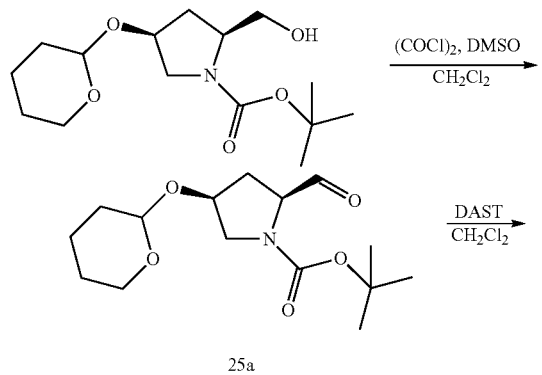

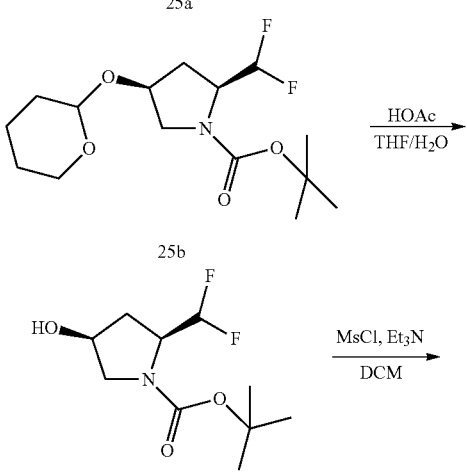

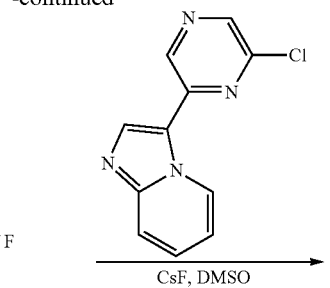

Preparation of compound 25a: tert-butyl (2S,4S)-2-formyl-4-(tetrahydro-2H-pyran-2-yloxy)pyrrolidine-1-carboxylate To a solution of oxalyl dichloride (19.0 g, 0.15 mol) in dry dichloromethane (180 mL) was added dropwise a solution of dry DMSO (22.0 g, 0.30 mol) in dry dichloromethane (60 mL) at −70° C. under nitrogen gas. After the mixture was stirred at this temperature for 30 min, a solution of tert-butyl (2S,4S)-2-(hydroxymethyl)-4-(tetrahydro-2H-pyran-2-yloxy)pyrrolidine-1-carboxylate (30.0 g, 0.1 mol) in dry dichloromethane (120 mL) was added. The mixture was stirred for at −70° C. for 1.5 h and then dry Et$_3$N (60 mL) was added. Stirring was maintained at −70° C. for about 1.5 h. The reaction mixture was quenched with water (50 mL) at −70° C. and then allowed to warm to room temperature. The aqueous layer was extracted with dichloromethane (200 mL×3). The combined organic layers were washed with 5% aqueous citric acid (400 mL×3), 5% aqueous Na$_2$CO$_3$ (400 mL×3) and brine (400 mL×3) in sequence, dried over Na$_2$SO$_4$ and concentrated in vacuo which gave the title compound 25a as brown liquid (29.0 g, 97%).

Preparation of compound 25b: tert-butyl (2S,4S)-2-(difluoromethyl)-4-(tetrahydro-2H-pyran-2-yloxy)pyrrolidine-1-carboxylate To a solution of 25a (30.0 g, 0.099 mol) in dry dichloromethane (450 mL) was added dropwise DAST (27.69.2 mL, 0.21 mol) at −63° C. The resulting mixture was stirred at room temperature overnight. The reaction mixture was quenched with 5% aqueous $Na_2CO_3$ (500 mL) at 0° C. The dichloromethane layer was separated. The aqueous layer was extracted with dichloromethane (150 mL×3). The combined dichloromethane layers were washed with brine (300 mL×3), dried over $Na_2SO_4$ and concentrated in vacuo. The crude residue was purified by column chromatography (petroleum ether/EtOAc 20:1) which gave the title compound 25b as yellow oil (6.0 g, 19%).

Preparation of compound 25c: tert-butyl (2S,4S)-2-(difluoromethyl)-4-hydroxypyrrolidine-1-carboxylate A solution of 25b (3.0 g, 0.0093 mol) in $HOAc/THF/H_2O$ (1:1:1, 150 mL) was refluxed for 4 h. The reaction mixture was basified with solid $NaHCO_3$ to pH ~8 and then extracted with EtOAc (100 mL×3). The combined organic layers were washed with brine (100 mL×3), dried over $Na_2SO_4$ and concentrated in vacuo. The crude residue was purified by column chromatography (petroleum ether/EtOAc 4:1) which gave the title compound 25c as a white solid (1.0 g, 45%).

Preparation of compound 25d: tert-butyl (2S,4S)-2-(difluoromethyl)-4-[(methylsulfonyl)oxy]pyrrolidine-1-carboxylate To a solution of 25c (1.5 g, 0.006 mol) and $Et_3N$ (1.6 g, 0.016 mol) in dry DCM (6 mL) was added dropwise MsCl (1.5 g, 0.015 mol) at 0° C. under $N_2$ gas. After the addition, the reaction mixture was stirred at room temperature overnight. The reaction mixture was diluted with EtOAc (50 mL), washed with 5% aqueous citric acid (50 mL×2), 5% aqueous $Na_2CO_3$ (50 mL×2) and brine (50 mL×2) in sequence. Then the organic layer was dried over $Na_2SO_4$ and concentrated in vacuo which gave the title compound 25d as brown oil (1.8 g, 90%).

Preparation of compound 25e: tert-butyl (2S,4R)-4-azido-2-(difluoromethyl)pyrrolidine-1-carboxylate A solution of 25d (1.8 g, 0.0057 mol) and $NaN_3$ (0.6 g, 0.0086 mol) in DMF (60 mL) was stirred at 70° C. under $N_2$ gas for 3 h. The reaction mixture was poured into 10% aqueous $NaHCO_3$ (200 mL). The mixture was extracted with methyl t-butyl ether (100 mL×3). The combined organic layers were washed with brine (50 mL×3), dried over $Na_2SO_4$ and concentrated in vacuo which gave the title compound 25e as an orange oil (1.5 g, 95%).

Preparation of compound 25f: tert-butyl (2S,4R)-4-amino-2-(difluoromethyl)pyrrolidine-1-carboxylate A solution of 25e (1.5 g, 0.0057 mol) and $PPh_3$ (3.0 g, 0.0114 mol) in THF (50 mL) and water (5 mL) was stirred at room temperature for 72 h. The reaction mixture was concentrated in vacuo to give residue, which was dissolved in EtOAc (50 mL). The EtOAc layer was acidified with 5% aqueous citric acid to pH ~4. The separated aqueous layer was extracted with EtOAc (50 mL×3) and then basified with solid $NaHCO_3$ to pH ~8, The basified aqueous layer was extracted with dichloromethane (50 mL×3). The combined dichloromethane layers were dried over $Na_2SO_4$ and concentrated in vacuo which gave the title compound 25f as yellow oil (1.0 g, 76%).

Preparation of compound 25g: tert-butyl (2S,4R)-2-(difluoromethyl)-4-{[6-(imidazo[1,2-a]pyrazin-3-yl)pyrazin-2-yl]amino}pyrrolidine-1-carboxylate A mixture of 3-(6-chloropyrazin-2-yl)imidazo[1,2-a]pyridine (0.15 g, 0.65 mmol), 25f (0.2 g, 0.85 mmol) and CsF (0.13 g, 0.85 mmol) in dry DMSO (1.3 mL) was refluxed overnight. The reaction mixture was cooled to room temperature and then poured into water (50 mL). The mixture was extracted with EtOAc (20 mL×3). The combined organic layers were washed with brine (30 mL×3), dried over $Na_2SO_4$ and concentrated in vacuo. The residue was purified by column chromatography (petroleum ether/EtOAc 1:1) which gave the title compound 25g as a yellow solid (0.11 g, 39%).

To a solution of 25g (0.11 g, 0.26 mmol) in $CHCl_3$ (3.0 mL) was added dropwise TMSI (0.1 mL) at room temperature. The resulting mixture was stirred at room temperature overnight. The reaction mixture was acidified with 1 N aq. HCl to pH ~3 and diluted with water (10 mL). The separated aqueous layer was extracted with EtOAc (1:2, 30 mL×3). The aqueous layer was lyophilized to give residue, which was purified by preparative HPLC which gave the title compound 25 as a yellow syrup (16.1 mg, 19%). 1H NMR (400 MHz, MeOD): δ ppm 2.10-2.01 (m, 1H), 2.31-2.23 (m, 1H), 3.10-3.02 (m, 1H), 3.23-3.21 (m, 1H), 3.79-3.62 (m, 1H), 4.58-4.50 (m, 1H), 5.96-5.644 (m, 1H), 7.12-7.07 (t, 1H), 7.50-7.45 (t, 1H), 7.69-7.67 (d, 1H), 7.77 (s, 1H), 8.28 (s, 1H), 8.29, (s, 1H), 9.87-9.85 (d, 1H).

Example 26

(Method A): N-[(3R,5S)-5-(fluoromethyl)pyrrolidin-3-yl]-6-pyrazolo[1,5-a]pyridin-3-ylpyrazin-2-amine

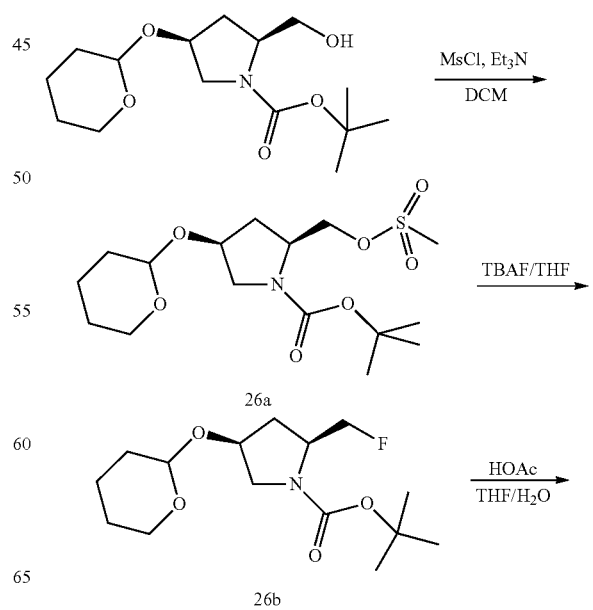

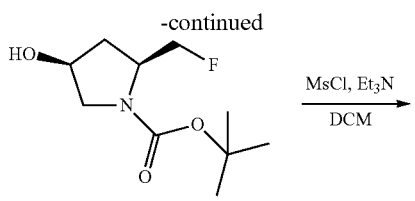

26c

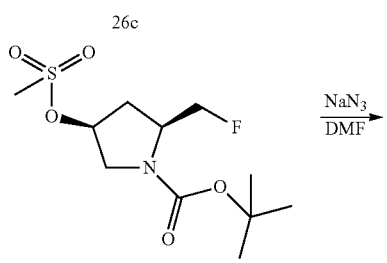

26d

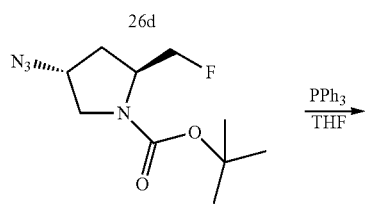

26e

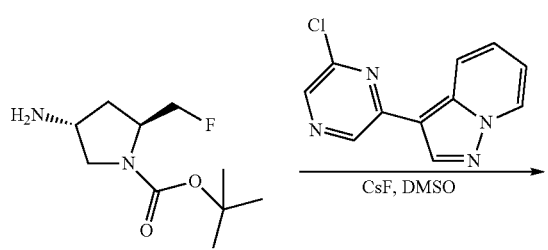

26f

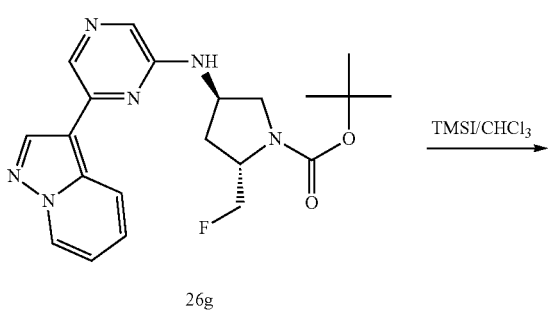

26g

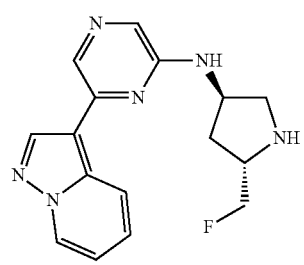

26

Preparation of compound 26a: (2S,4S)-2-Methanesulfonyloxymethyl-4-(tetrahydro-pyran-2-yloxy)-pyrrolidine-1-carboxylic acid tert-butyl ester To a solution of (2S,4S)-2-Hydroxymethyl-4-(tetrahydro-pyran-2-yloxy)-pyrrolidine-1-carboxylic acid tert-butyl ester (20.0 g, 0.066 mol) and $Et_3N$ (13.42 g, 0.133 mol) in dry DCM (50 mL) was added dropwise MsCl (11.4 g, 0.10 mol) at 0° C. under $N_2$ gas. After the addition, the reaction mixture was stirred at room temperature for 1 h. The reaction mixture was diluted with dichloromethane (300 mL) and then washed with 5% aqueous citric acid (200 mL×3), 5% aqueous $Na_2CO_3$ (200 mL×3) and brine (200 mL×3) in sequence. The organic layer was dried over $Na_2SO_4$ and concentrated in vacuum which gave the title compound 26a as a white solid (21.0 g, 50%).

Preparation of compound 26b: (2S,4S)-2-Fluoromethyl-4-(tetrahydro-pyran-2-yloxy)-pyrrolidine-1-carboxylic acid tert-butyl ester A solution of 26a (21.0 g, 0.060 mol) in TBAF/THF (1.0 M, 200 mL) was refluxed for 2 h. The reaction mixture was concentrated in vacuo. The residue was diluted with EtOAc (300 mL). The organic layer was washed with water (100 mL×3), 5% aqueous citric acid (100 mL×3), 5% aqueous $Na_2CO_3$ (100 mL×3) and brine (100 mL×3) in sequence, dried over $Na_2SO_4$ and concentrated in vacuo. The residue was purified by column chromatography (petroleum ether/EtOAc 10:1) which gave the title compound 26b as yellow oil (10.0 g, 55%).

Preparation of compound 26c: (2S,4S)-2-Fluoromethyl-4-hydroxy-pyrrolidine-1-carboxylic acid tert-butyl ester A solution of 26b (10.0 g, 0.033 mol) in HOAc/THF/$H_2O$ (1:1:1, 300 mL) was refluxed for 4 h. The reaction mixture was basified with solid $NaHCO_3$ to pH ~8 and then extracted with EtOAc (100 mL×3). The combined organic layers were washed with brine (100 mL×3), dried over $Na_2SO_4$ and concentrated in vacuo. The residue was purified by crystallization from petroleum ether (15 mL) which gave the title compound 26c as an off-white solid (5.0 g, 69%).

Preparation of compound 26d: (2S,4S)-2-Fluoromethyl-4-methanesulfonyloxy-pyrrolidine-1-carboxylic acid tert-butyl ester To a solution of 26c (1.33 g, 0.006 mol) and $Et_3N$ (1.5 g, 0.015 mol) in dry DCM (6 mL) was added dropwise MsCl (1.3 g, 0.012 mol) at 0° C. under $N_2$ gas. After the addition, the reaction mixture was stirred at room temperature overnight. The reaction mixture was diluted with EtOAc (50 mL), washed with 5% aqueous citric acid (50 mL×3), 5% aqueous $Na_2CO_3$ (50 mL×3) and brine (50 mL×3) in sequence. Then the organic layer was dried over $Na_2SO_4$ and concentrated in vacuo which gave the title compound 26d as an orange oil (1.8 g, 94%).

Preparation of compound 26e: (2S,4R)-4-Azido-2-fluoromethyl-pyrrolidine-1-carboxylic acid tert-butyl ester A solution of 26d (1.8 g, 0.006 mol) and NaN₃ (0.6 g, 0.009 mol) in DMF (6 mL) was stirred at 80° C. under N₂ gas for 3 h. The reaction mixture was poured into 10% aqueous NaHCO₃ (200 mL). The mixture was extracted with methyl t-butyl ether (100 mL×3). The combined organic layers were washed with brine (50 mL×3), dried over Na₂SO₄ and concentrated in vacuo which gave the title compound 26e as an orange oil (1.5 g, 95%).

Preparation of compound 26f: (2S,4R)-4-Amino-2-fluoromethyl-pyrrolidine-1-carboxylic acid tert-butyl ester A solution of 26e (1.5 g, 0.006 mol) and PPh₃ (3.2 g, 0.012 mol) in THF (50 mL) and water (2 mL) was stirred at room temperature for 48 h. The reaction mixture was concentrated in vacuum to give a residue, which was dissolved in EtOAc (100 mL). The EtOAc layer was acidified with 10% aqueous citric acid to pH ~4. The aqueous layer was extracted with EtOAc (100 mL×3) and then basified with solid NaHCO₃ to pH ~8. The aqueous layer was extracted with dichloromethane (100 mL×3). The combined dichloromethane layers were dried over Na₂SO₄ and concentrated in vacuo which gave the title compound 26f as a yellow oil (0.9 g, 67%).

Preparation of compound 26g: tert-butyl (2S,4R)-2-(fluoromethyl)-4-{[6-(pyrazolo[1,5-a]pyridin-3-yl)pyrazin-2-yl]amino}pyrrolidine-1-carboxylate A mixture of 3-(6-chloropyrazin-2-yl)pyrazolo[1,5-a]pyridine (0.15 g, 0.65 mmol), 26f (0.21 g, 0.97 mmol) and CsF (0.15 g, 0.97 mmol) in dry DMSO (1.2 mL) was stirred at 80° C. under N₂ gas overnight. The reaction mixture was cooled to room temperature and then poured into water (50 mL). The mixture was extracted with EtOAc (20 mL×3). The combined organic layers were washed with brine (30 mL×3), dried over Na₂SO₄ and concentrated in vacuo. The residue was purified by column chromatography (petroleum ether/EtOAc 1:1) which gave the title compound 26g as a yellow solid (0.200 g, 77%).

To a solution of 26g (0.16 g, 0.39 mmol) in CHCl₃ (3.0 mL) was added dropwise TMSI (0.093 g, 0.46 mmol) at room temperature. The resulting mixture was stirred at room temperature overnight. The reaction mixture was concentrated to give residue, which was dissolved with water (10 mL) and acidified with 1 N HCl to pH ~3. The aqueous layer was extracted with EtOAc (30 mL×3), then the aqueous layer was basified with 5% aqueous Na₂CO₃ to pH ~9 and extracted with a mixed solvent of CHCl₃ and IPA (3:1, 30 mL×3). The combined organic layers were washed with brine (30 mL×3), dried over Na₂SO₄ and concentrated which gave the title compound 26 as a brown syrup (100 mg, 83%). 1H NMR (400 MHz, MeOD): δ ppm 2.12-1.98 (m, 2H), 3.06-2.98 (m, 1H), 3.41-3.35 (m, 1H), 3.80-362 (m, 1H), 4.60-4.41 (m, 3H), 7.03-6.98 (t, 1H), 7.42-7.37 (t, 1H), 7.66 (s, 1H), 8.16, (s, 1H), 8.60-8.52 (m, 3H).

Example 27

(Method A): N-[(3S,4R)-4-fluoropiperidin-3-yl]-6-(imidazo[1,2-a]pyridin-3-yl)pyrazin-2-amine

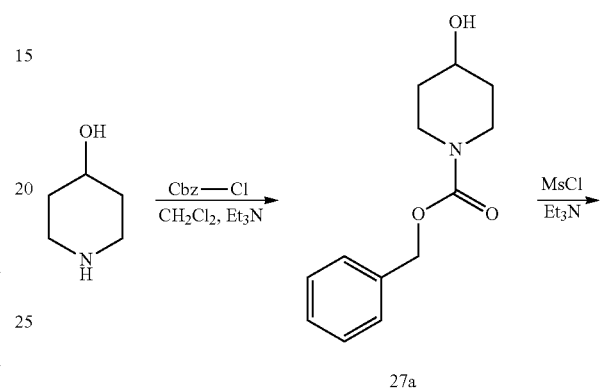

27a

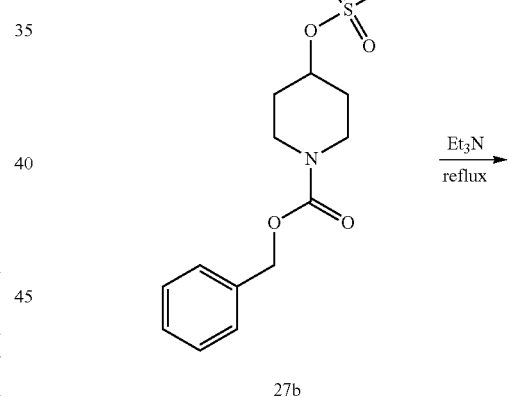

27b

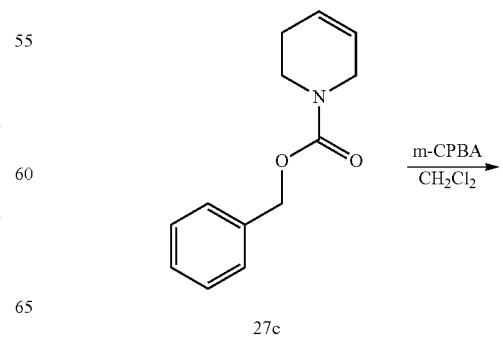

27c

119

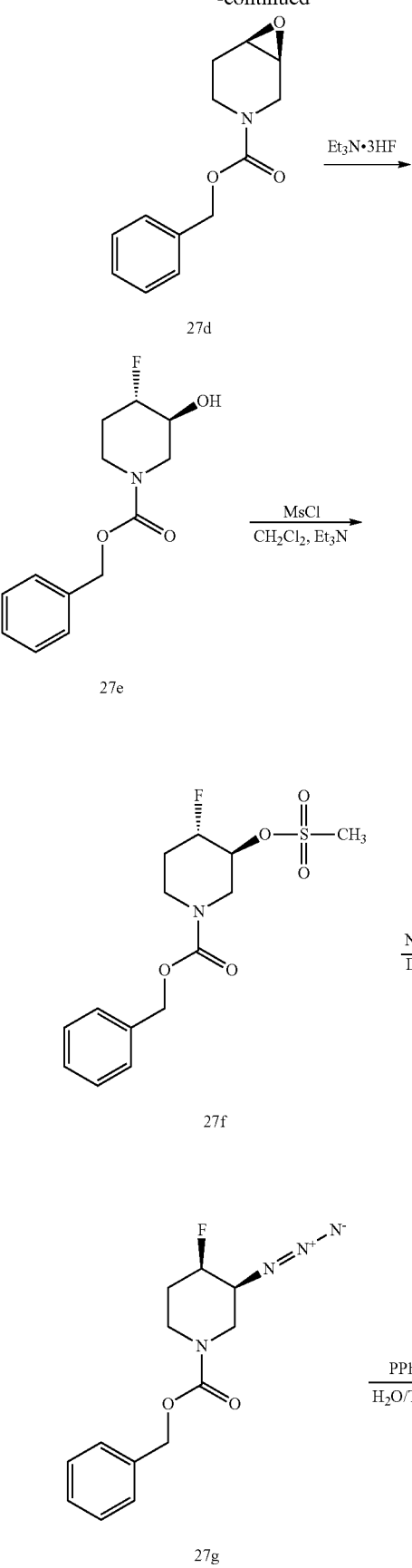

27d

27e

27f

27g

120

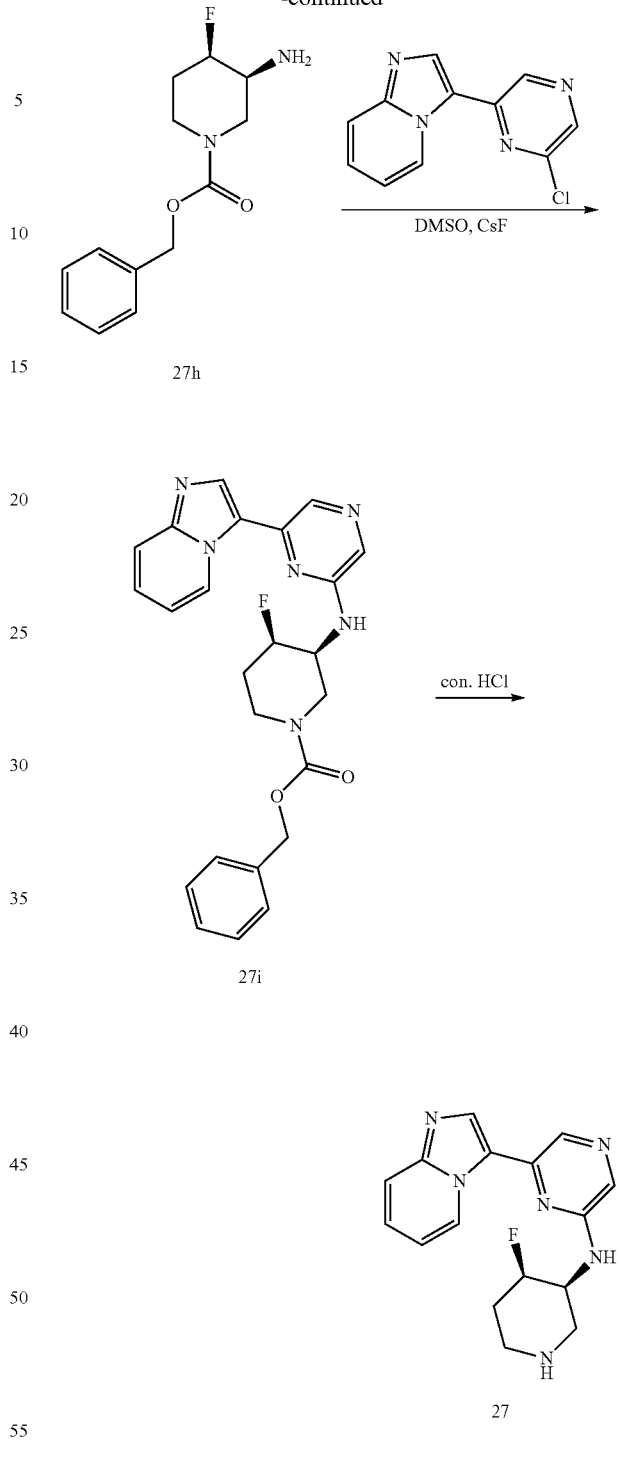

27h

27i

27

Preparation of compound 27a:
4-Hydroxy-piperidine-1-carboxylic acid benzyl ester To a stirred solution of piperidin-4-ol (50 g, 0.495 mol) in THF (200 mL) was added 2 M aqueous NaOH (1000 mL), and then CbzCl (84.16 g, 0.495 mol) was added dropwise to the above mixture at 0° C. The reaction mixture was stirred for 5 h, then extracted with EtOAc (300 mL×3). The combined organic phases were washed with saturated citric acid (100 mL), saturated NaHCO$_3$ (50 mL) and brine (100 mL), dried over Na₂SO₄ and concentrated which gave the title compound 27a as a colorless oil (123 g, >100%).

Preparation of compound 27b:
4-Methanesulfonyloxy-piperidine-1-carboxylic acid benzyl ester To a stirred solution of 27a (90 g, 0.38 mol) in CH₂Cl₂ (1.2 L) was added Et₃N (46.4 g, 0.459 mol), then methanesulfonyl chloride (43.6 g, 0.459 mol) was added dropwise at 0° C. The mixture was stirred at 0° C. for 2.5 h, and then the mixture was washed with water (200 mL), saturated aqueous NH₄Cl (200 mL) and brine (200 mL), dried over Na₂SO₄ and concentrated which gave the title compound 27b as a yellow oil (105 g, 87.6%).

Preparation of compound 27c:
3,6-Dihydro-2H-pyridine-1-carboxylic acid benzyl ester A stirred solution of 27b (210 g, 0.67 mol) in Et₃N (1500 mL) was refluxed for 72 h. The mixture was concentrated, the residue was dissolved with CH₂Cl₂ (1000 mL), washed with 1 mol/L aq. HCl (300 mL) and brine (200 mL), dried over Na₂SO₄ and concentrated. The residue was purified by column chromatography (petroleum ether/EtOAc=200:1 to 50:1) which gave the title compound 27c as yellow liquid (50 g, 35%).

Preparation of compound 27d: (1S,6R)-7-Oxa-3-aza-bicyclo[4.1.0]heptane-3-carboxylic acid benzyl ester m-CPBA (102.8 g, 0.52 mol) was added portion wise to a solution of 27c (100 g, 0.46 mol) in anhydrous CH₂Cl₂ (1.0 L) at −15° C. After addition, the reaction mixture was stirred at rt for 6 h. The mixture was washed with saturated aqueous Na₂SO₃ (300 mL) and saturated aqueous NaHCO₃ (300 mL), then concentrated in vacuo. The residue was purified by column chromatography (THF:petroleum ether=1:10) which gave the title compound 27d as off-yellow liquid (86 g, 80%).

Preparation of compound 27e:
(3S,4S)-4-Fluoro-3-hydroxy-piperidine-1-carboxylic acid benzyl ester A mixture of 27d (20 g, 85.8 mmol) and Et₃N.3HF (13.8 g, 85.8 mmol) was heated to 100° C. for 3 h. 20% BF₃.ether (30 mL) was added at room temperature, then the mixture was washed with saturated aqueous NaHCO₃ (20 mL) and extracted with CH₂Cl₂ (50 mL×2). The combined extracts were washed with brine (20 mL), dried over Na₂SO₄ and concentrated. The residue was purified by column chromatography (THF:petroleum ether=1:10) which gave the title compound 27e as a white oil (17 g, 79%).

Preparation of compound 27f: (3S,4S)-4-Fluoro-3-methanesulfonyloxy-piperidine-1-carboxylic acid benzyl ester To a stirred solution of 27e (1.8 g, 0.0071 mol) and triethylamine (1.45 g, 0.0142 mol) in anhydrous CH₂Cl₂ (20 mL) was added methanesulfonyl chloride (1.22 g, 0.0107 mol) dropwise at 0° C. After the addition, the reaction mixture was allowed to warm to room temperature over 2 h. Upon completion, the reaction mixture was washed with saturated ammonia chloride (30 mL) and brine (30 mL), dried over sodium sulfate and concentrated which gave the title compound 27f as a yellow oil (2.1 g, 87%).

Preparation of compound 27g:
(3S,4R)-3-Azido-4-fluoro-piperidine-1-carboxylic acid benzyl ester A mixture of 27f (2.1 g, 0.0063 mol) and sodium azide (1.5 g, 0.023 mol) in DMF (20 mL) was heated to 90° C. and stirred for 5 h. Upon completion, the reaction mixture was washed with 1 N aq. NaOH (300 mL×2) and brine (200 mL), dried over sodium sulfate and concentrated in vacuo. The residue was purified by column chromatography (EtOAc:petroleum ether=1:50) which gave the title compound 27g as a colorless oil (2.5 g, >100%).

Preparation of compound 27h:
(3S,4R)-3-Amino-4-fluoro-piperidine-1-carboxylic acid benzyl ester To a stirred solution of 27g (2.5 g, 8.99 mmol) in anhydrous THF (20 mL) was added triphenyl phosphane (3.5 g, 13.5 mmol) in portions over 30 min at 0° C. After the addition, the reaction mixture was stirred at room temperature overnight. 200 mL of concentrated ammonia was added. Then the reaction mixture was heated to reflux. Upon completion, the reaction mixture was cooled to room temperature, concentrated in vacuo, adjusted to pH=1-2 with 2 N HCl and washed with EtOAc (50 mL in 6 portions). The aqueous phase was made alkaline to pH=12-13 and extracted with CH₂Cl₂ (50 mL×2). The combined organic layers were washed with brine (20 mL), dried over sodium sulfate and concentrated. The residue was purified by column chromatography (CH₂Cl₂:MeOH=100:1) which gave the title compound 27h as a yellow oil (1.2 g, 35%).

Preparation of compound 27i: benzyl (3S,4R)-4-fluoro-3-{[6-(imidazo[1,2-a]pyridin-3-yl)pyrazin-2-yl]amino}piperidine-1-carboxylate A mixture of 3-(6-chloropyrazin-2-yl)imidazo[1,2-a]pyridine (115 mg, 0.49 mmol), 27h (50 mg, 0.2117 mmol) and CsF (80 mg, 0.651 mmol) in DMSO (0.5 mL) was heated to 80° C. overnight. The reaction mixture was cooled to room temperature and then partitioned with EtOAc (50 mL) and H₂O (50 mL). The combined organic layers were washed with brine (20 mL), dried over sodium sulfate and concentrated. The residue was purified by prep-HPLC which gave the title compound 27i as a yellow solid (40 mg, 25%).

A mixture of 27i (60 mg, 0.144 mmol) and conc. HCl (10 mL) was stirred at room temperature for 6 h. The mixture was evaporated in vacuo. The residue was purified via prep-HPLC which gave the title compound 27 as a brown solid (10 mg, 23%). 1H NMR: MeOD δ ppm 1.503-1.462 (m, 1H), 1.936-1.859 (m, 1H), 2.326-2.295 (m, 1H), 2.984-2.894 (m, 2H), 4.260-4.136 (m, 1H), 4.480-4.387 (m, 1H), 4.596-4.486 (m, 1H), 6.973-6.956 (t, 1H), 6.993-6.976 (t, 1H), 7.383-7.341 (t, 1H), 7.584-7.562 (d, 1H), 7.708 (s, 1H), 8.131 (s, 1H), 8.156 (s, 1H), 9.726-9.709 (d, 1H).
Example 28
(Method A): N-[(3S,4S)-4-fluoropiperidin-3-yl]-6-imidazo[1,2-a]pyridin-3-ylpyrazin-2-amine
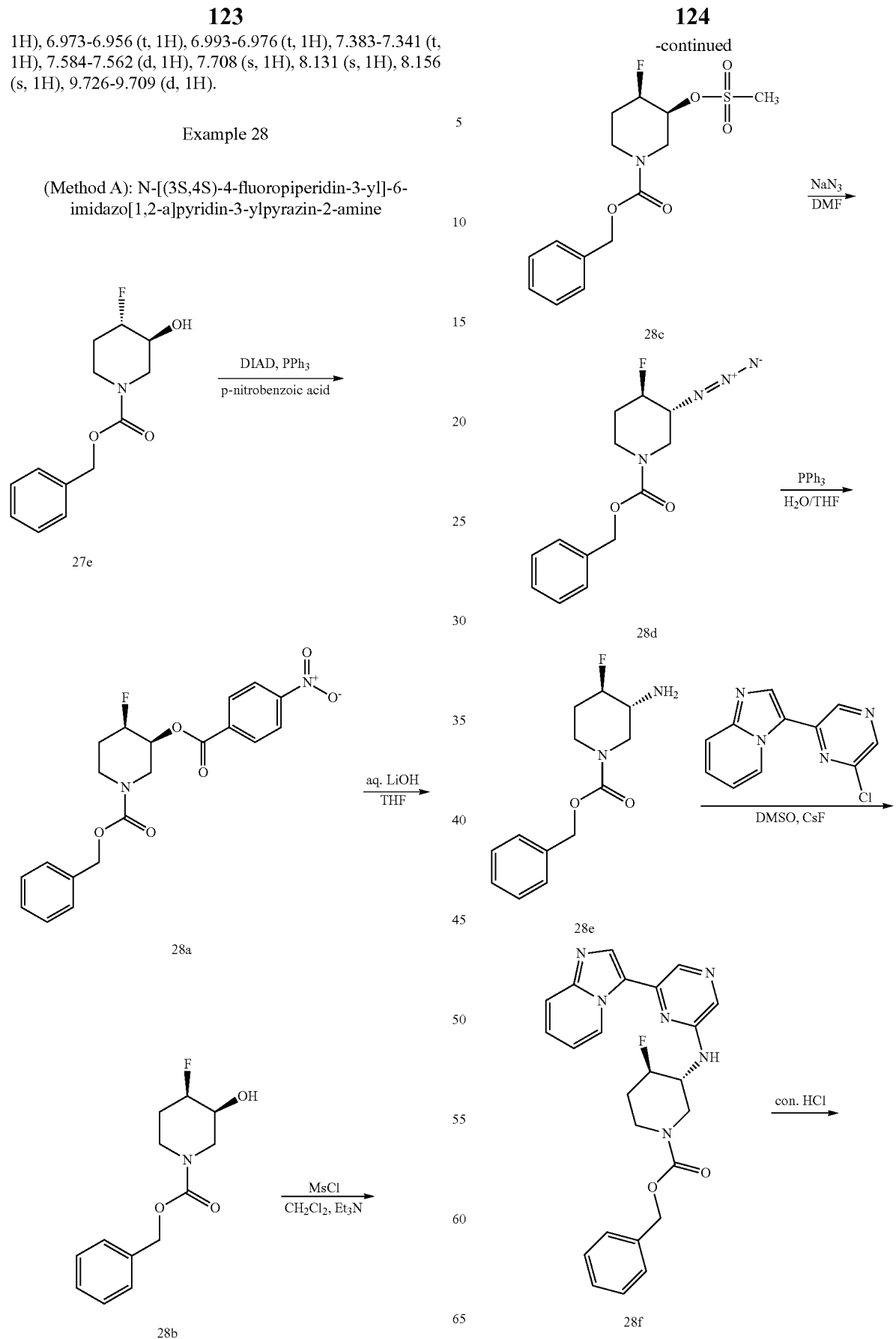

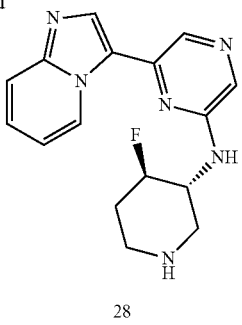

28

Preparation of compound 28a: (3S,4R)-4-Fluoro-3-(4-nitro-benzoyloxy)-piperidine-1-carboxylic acid benzyl ester To a stirred solution of triphenylphosphine (23.2 g, 0.089 mol) in THF (300 mL) was added DIAD (17.9 g, 0.089 mol) with stirring under nitrogen at 0° C. The resulting pale yellow suspension was stirred for 40 min, then a solution of 27e (15 g, 0.059 mol) and 4-nitrobenzoic acid (16.2 g, 0.089 mol) in THF (200 mL) was added slowly over 1.5 h. The resulting orange solution was warmed to room temperature and stirred for 48 h. The mixture was concentrated under reduced pressure, and the residual oil was purified by column chromatography (EtOAc:petroleum ether=1:40 to 1:10) which gave the title compound 28a as a yellow oil (30 g, 30%).

Preparation of compound 28b: (3S,4R)-4-Fluoro-3-hydroxy-piperidine-1-carboxylic acid benzyl ester To a stirred solution of 28a (30 g, 74.6 mmol) in THF (300 mL) and $H_2O$ (300 mL) was added the LiOH (12.5 g, 0.30 mol) at 0° C. The resulting orange mixture was stirred for 1.5 h. The mixture was extracted with EtOAc (100 mL×3). The combined organic phases were washed with brine (30 mL), dried over anhydrous $Na_2SO_4$ and concentrated. The residue was purified by column chromatography (EtOAc:petroleum ether=1:20) which gave the title compound 28b as a yellow oil (3.2 g, 76% purity by HPLC).

Preparation of compound 28c: (3S,4R)-4-Fluoro-3-methanesulfonyloxy-piperidine-1-carboxylic acid benzyl ester To a stirred solution of 28b (4.6 g, 0.0182 mol) and triethylamine (3.7 g, 0.0364 mol) in anhydrous $CH_2Cl_2$ (50 mL) was added methanesulfonyl chloride (3.11 g, 0.0281 mol) dropwise at 0° C. After addition, the reaction mixture was allowed to warm to room temperature for 2 h. The reaction mixture was washed with saturated ammonia chloride (30 mL) and brine (30 mL), dried over sodium sulfate and concentrated which gave the title compound 28c as a yellow oil (5.5 g, >100%).

Preparation of compound 28d: (3R,4R)-3-Azido-4-fluoro-piperidine-1-carboxylic acid benzyl ester A mixture of 28c (5.6 g, 0.166 mol) and sodium azide (2.16 g, 0.332 mol) in DMF (20 mL) was heated to 90° C. and stirred for 48 h. The reaction mixture was washed with 1 N NaOH (300 mL×2) and brine (200 mL), dried over sodium sulfate and concentrated in vacuo. The residue was purified by column chromatography (EtOAc:petroleum ether=1:50) which gave the title compound 28d as colorless oil (2.7 g, 50%).

Preparation of compound 28e: (3R,4R)-3-Amino-4-fluoro-piperidine-1-carboxylic acid benzyl ester To a stirred solution of 28d (2.7 g, 9.7 mmol) in anhydrous THF (20 mL) was added triphenyl phosphine (3.8 g, 14.57 mmol) in portions over 30 min at 0° C. After addition, the reaction mixture was stirred at room temperature overnight. 200 mL of concentrated ammonia was added. Then the reaction mixture was heated to reflux for 7 h. The reaction mixture was cooled to room temperature and concentrated in vacuo, the residue was adjusted to pH=1-2 with 2 N aq. HCl and washed with EtOAc (50 mL×2). The aqueous phase was made alkaline to pH=12-13 and extracted with $CH_2Cl_2$ (50 mL×2). The combined organic layers were washed with brine (20 mL), dried over sodium sulfate and concentrated. The residue was purified by column chromatography ($CH_2Cl_2$:MeOH=100:1) which gave the title compound 28e as a yellow oil (1.2 g, 48%).

Preparation of compound 28f: benzyl (3R,4R)-4-fluoro-3-{[6-(imidazo[1,2-a]pyridin-3-yl)pyrazin-2-yl]amino}piperidine-1-carboxylate A mixture of 3-(6-chloropyrazin-2-yl)imidazo[1,2-a]pyridine (20 mg, 0.0869 mmol), 28e (44 mg, 0.175 mmol) and CsF (40 mg, 0.262 mmol) in DMSO (0.5 mL) was heated to 80° C. overnight. The reaction mixture was cooled to room temperature and then partitioned with EtOAc (50 mL) and $H_2O$ (50 mL). The organic layers were washed with brine (20 mL), dried over sodium sulfate and concentrated. The residue was purified by prep-HPLC which gave the title compound 28f as a yellow solid (15 mg, 25%).

A mixture of 28f (60 mg, 0.144 mmol) and conc. HCl (10 mL) was stirred at room temperature for 6 h. The mixture was evaporated in vacuo. The residue was purified via prep-HPLC which gave the title compound 28 as a yellow oil (18 mg, 40%). 1H NMR: MeOD δ ppm 1.936-1.859 (m, 1H), 2.326-2.295 (m, 1H), 2.984-2.894 (m, 2H), 3.261-3.215 (m, 1H), 3.470-3438 (m, 1H), 4.360-4.308 (m, 1H), 4.660-4.610 (m, 1H), 7.017-6.983 (t, 1H), 7.368-7.351 (t, 1H), 7.596-7.564 (d, 1H), 7.744 (s, 1H) 8.098 (s, 1H), 8.184 (s, 1H), 9.549-9.532 (d, 1H).

Example 29
(Method A): 6-imidazo[1,2-a]pyridin-3-yl-N-[(3S,4S)-4-methoxypiperidin-3-yl]pyrazin-2-amine
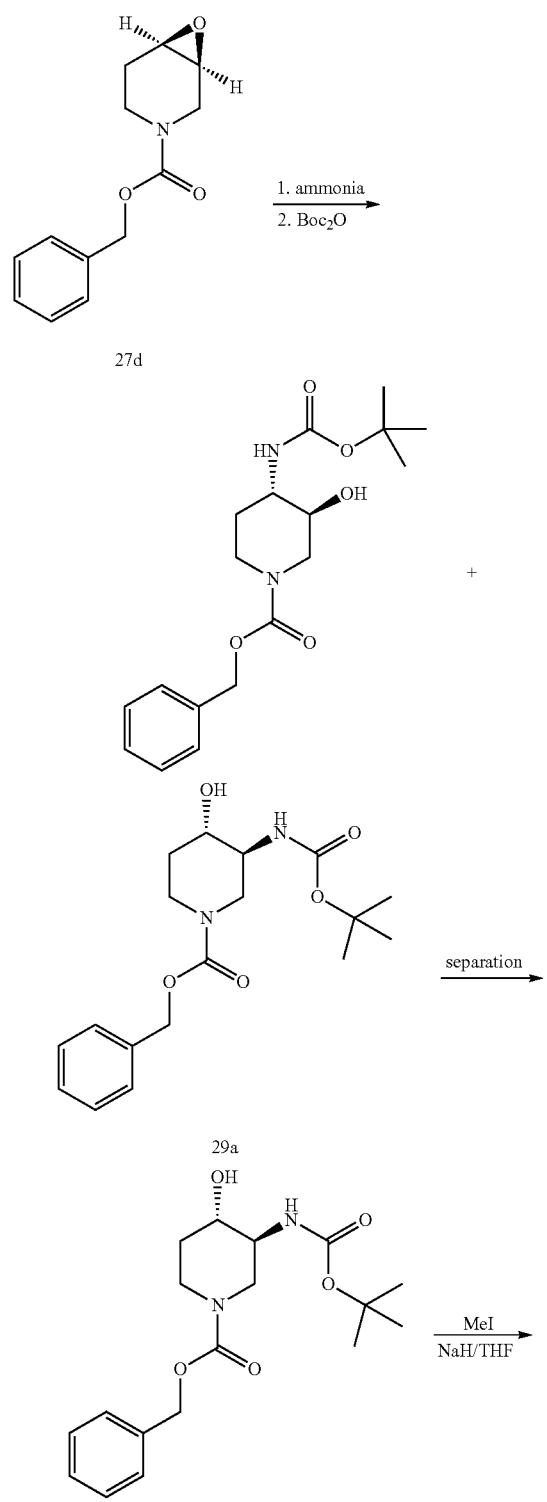
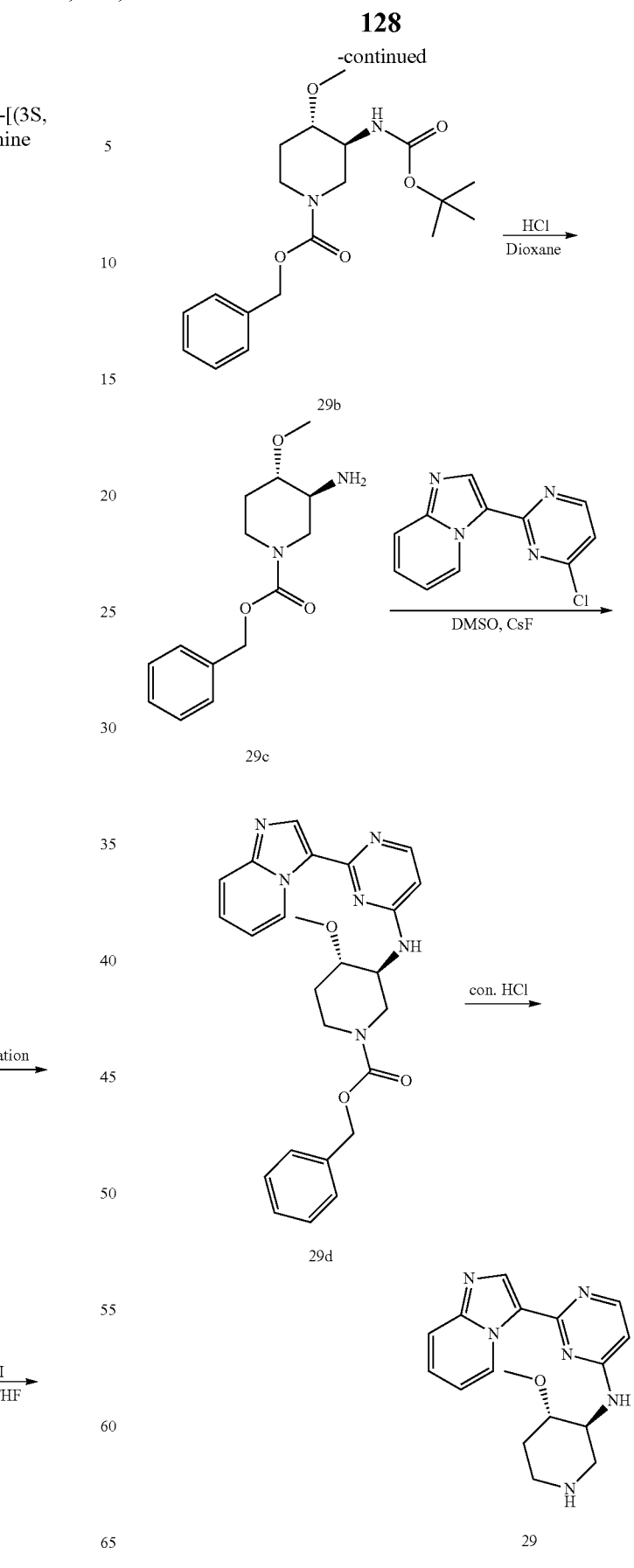

Preparation of compound 29a: benzyl (3S,4S)-3-[(tert-butoxycarbonyl)amino]-4-hydroxypiperidine-1-carboxylate To a stirred solution of 27d (3 g, 12.9 mmol) in EtOH (30 mL) was added 30% ammonia (50 mL) at room temperature. After addition, the resulting mixture was stirred at room temperature for 48 h. The reaction mixture was evaporated to dryness, and the residue was diluted with $CH_2Cl_2$ (20 mL). $(Boc)_2O$ (1.8 g, 6 mmol) was added and the mixture was stirred at room temperature overnight. The mixture was evaporated and the residue was purified by column chromatography (petroleum ether/EtOAc=40:1 to 10:1) which gave (3S,4S)-4-tert-Butoxycarbonylamino-3-hydroxy-piperidine-1-carboxylic acid benzyl ester (0.2 g, 14%) and the title compound 29a as a colorless oil (0.2 g, 14%).

Preparation of compound 29b: (3S,4S)-3-tert-Butoxycarbonylamino-4-methoxy-piperidine-1-carboxylic acid benzyl ester To a 0° C. solution of 29a (1.5 g, 4.3 mmol) in THF (50 mL) was added NaH (225 mg, 8.6 mmol) in portions. After addition, the resulting mixture was stirred at 0° C. for 0.5 h. Then $CH_3I$ (0.6 g, 8.6 mmol) was added dropwise at 0° C. After addition, the resulting mixture was allowed to warm to room temperature and stirred for 0.5 h. The mixture was concentrated and the residue was purified by column chromatography (petroleum ether/EtOAc=40:1 to 10:1) which gave the title compound 29b as a brown oil (1.3 g, 83.3%).

Preparation of compound 29c: (3S,4S)-3-Amino-4-methoxy-piperidine-1-carboxylic acid benzyl ester To a 0° C. solution of 29b (100 mg, 0.275 mmol) in anhydrous $CH_2Cl_2$ (10 mL) was added TFA (93.95 mg, 0.824 mmol). Then the resulting mixture was allowed to warm to room temperature and stirred overnight. The mixture was concentrated and the residue was adjusted to pH=9 with saturated $NaHCO_3$ (aq), then extracted with EtOAc (20 mL×3). The combined organic layers were washed with brine (50 mL), dried over $Na_2SO_4$ and concentrated which gave the title compound 29c which was used directly to next step without further purification (60 mg, 82%).

Preparation of compound 29d: benzyl (3S,4S)-3-{[2-(imidazo[1,2-a]pyridin-3-yl)pyrimidin-4-yl]amino}-4-methoxypiperidine-1-carboxylate A mixture of 3-(4-chloropyrimidin-2-yl)imidazo[1,2-a]pyridine (50 mg, 0.217 mmol), 29c (115 mg, 0.436 mmol) and CsF (99 mg, 0.651 mmol) in DMSO (0.5 mL) was heated to 80° C. overnight. The reaction mixture was cooled to room temperature and diluted with $H_2O$ (50 mL), then extracted with EtOAc (50 mL×2). The combined organic layers were washed with brine (20 mL), dried over sodium sulfate and concentrated. The residue was purified by prep-HPLC which gave the title compound 29d as a yellow solid (60 mg, 59%).

A mixture of 29d (80 mg, 0.187 mmol) in conc. HCl (10 mL) was stirred at room temperature for 6 h. The mixture was evaporated in vacuo. The residue was purified via prep-HPLC which gave the title compound 29 as a yellow solid (50 mg, 83%). 1H NMR: MeOD δ ppm 1.929-1.873 (m, 1H), 2.421-2.394 (m, 1H), 3.261-3.215 (m, 2H), 3.470-3.438 (m, 1H), 3.481 ?s, 3H), 3.624-3.537 (m, 2H), 4.395-4.349 (m, 1H), 7.130-7.096 (t, 1H), 7.497-7.459 (t, 1H), 7.696-7.673 (d, 1H), 7.885 (s, 1H) 8.222 (s, 1H), 8.319 (s, 1H), 9.676-9.659 (d, 1H).

Example 30/31

(Method A): 6-imidazo[1,2-a]pyridin-3-yl-N-[(3R,6S)-6-methylpiperidin-3-yl]pyrazin-2-amine/6-imidazo[1,2-a]pyridin-3-yl-N-[(3R,6R)-6-methylpiperidin-3-yl]pyrazin-2-amine

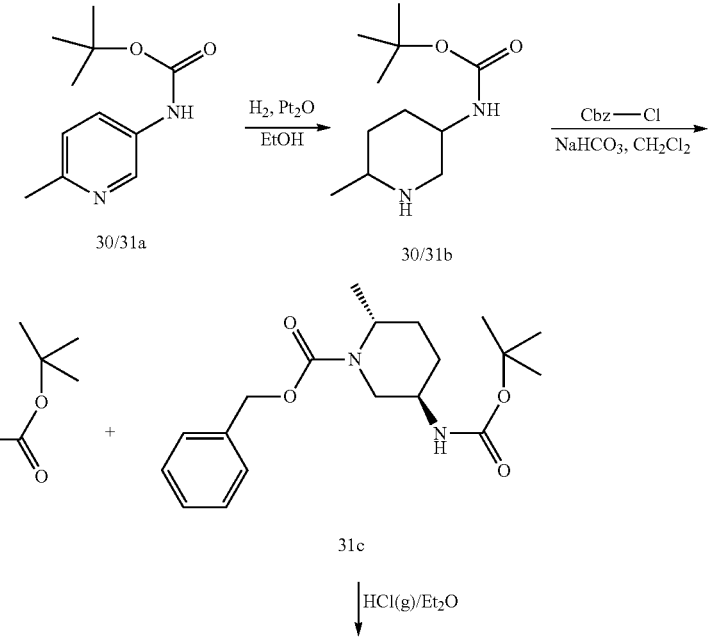

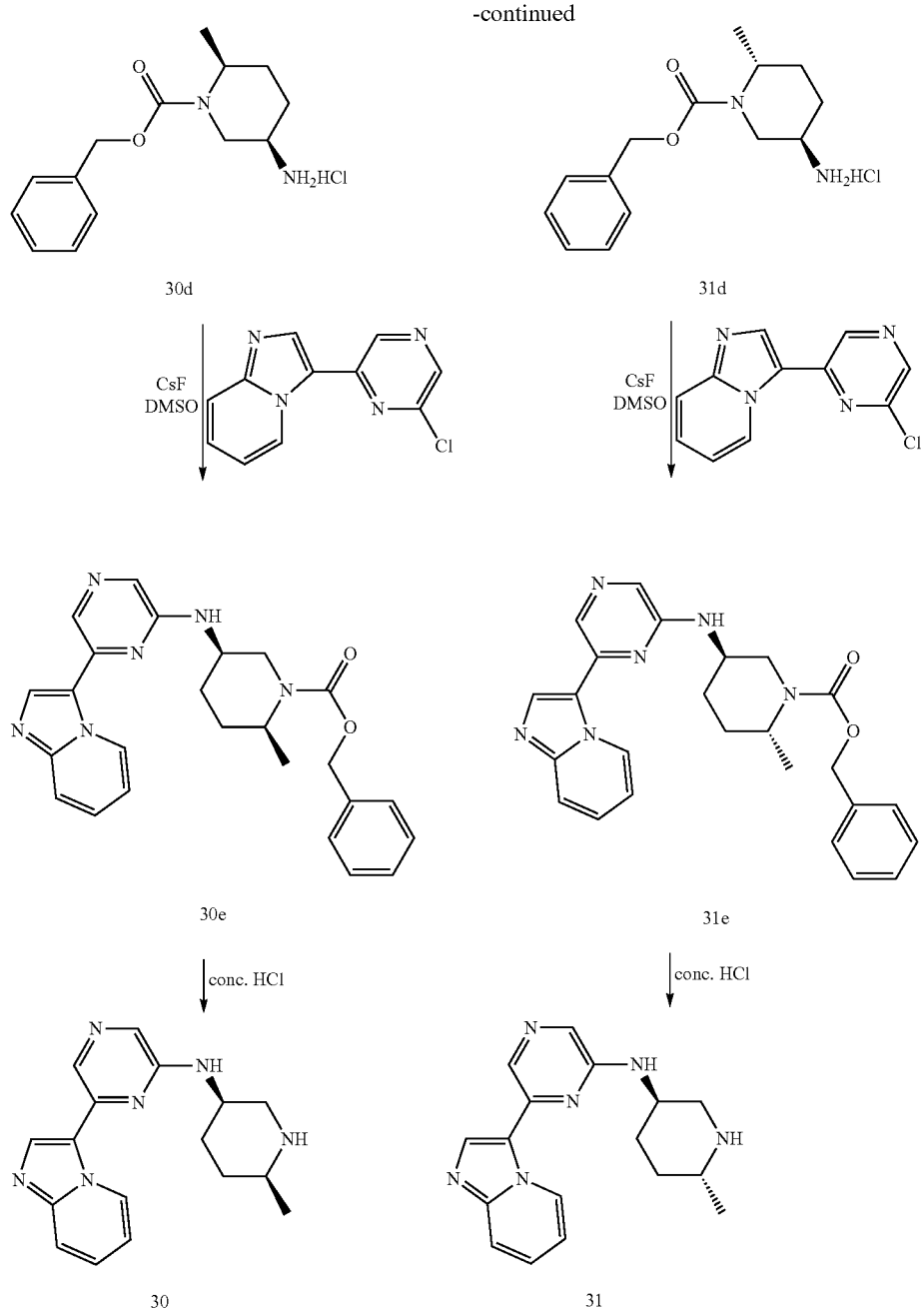

Preparation of compound 30/31a:
(6-Methyl-pyridin-3-yl)-carbamic acid tert-butyl ester To a solution of 6-Methyl-pyridin-3-ylamine (50 g, 0.46 mol) and Et₃N (80 g, 0.79 mol) in CH₂Cl₂ (800 mL) was added Boc₂O (119 g, 0.55 mol). The reaction mixture was stirred at rt overnight. The reaction mixture was extracted with CH₂Cl₂ (250 mL×3). The combined organic layers were washed with water (200 mL) and brine (200 mL), dried over Na₂SO₄ and concentrated in vacuo. The residue was purified by re-crystallization from CH₂Cl₂/petroleum ether (20 mL/100 mL) which gave the title compound 30/31a as a blue solid (40 g, 40%).

Preparation of compound 30/31b:
(6-Methyl-piperidin-3-yl)-carbamic acid tert-butyl ester To a mixture of 30/31a (25 g, 0.12 mol), EtOH (200 mL) and AcOH (25 mL) was added PtO₂ (2.6 g, 11.5 mmol). The suspension was degassed under vacuum and purged with H₂×3. The mixture was stirred under H₂ (55 psi) at 50° C. for 72 h. The mixture was filtered and the filtrate was neutralized with aqueous NaHCO₃. The solvent was removed and the residue was extracted with EtOAc (100 mL×5). The combined organic layers were washed with brine (200 mL), dried over Na₂SO₄ and concentrated in vacuo which gave the title compound 30/31 b as a red oil (24 g, 95%).

Preparation of compound 30c: benzyl (2S,5R)-5-[(tert-butoxycarbonyl)amino]-2-methylpiperidine-1-carboxylate and 31c: (2R,5R)-5-tert-Butoxycarbonylamino-2-methyl-piperidine-1-carboxylic acid benzyl ester To a stirred solution of 30/31b (24 g, 0.092 mol) and NaHCO$_3$ (48 g, 0.57 mol) in THF (300 mL) and H$_2$O (1500 mL) was added Cbz-Cl (24.5 g, 0.14 mol) dropwise. The mixture was stirred at room temperature for 2 h. The solvent was removed and the residue was extracted with EtOAc (200 mL×3). The combined organic layers were washed with brine (200 mL×2) and concentrated in vacuo. The residue was purified by chiral SFC which gave the title compound 30c as a colorless oil (10 g, 25%) and 31c as a colorless oil (5 g, 13%).

Preparation of compound 30d: (2S,5R)-5-Amino-2-methyl-piperidine-1-carboxylic acid benzyl ester HCl salt A solution of 30c (20 g, 0.057 mol) in HCl (g)/Et$_2$O (4 N, 100 mL) was stirred at room temperature for 2 h. The mixture was filtered which gave the title compound 30d as a white solid (16 g, 73%). 1H NMR (400 MHz, DMSO): δ ppm 1.097-1.080 (d, 3H), 1.627-1.573 (m, 2H), 1.849-1.749 (m, 2H), 2.991-2.978 (m, 2H), 4.158-4.139 (d, 1H), 4.317-4.292 (m, 1H), 5.072 (s, 2H), 7.386-7.305 (m, 5H), 8.392 (s, 3H).

Preparation of compound 31d: (2R,5R)-5-Amino-2-methyl-piperidine-1-carboxylic acid benzyl ester HCl salt A solution of 31c (10 g, 0.029 mol) in HCl (g)/Et$_2$O (4 N, 100 mL) was stirred at room temperature for 2 h. The mixture was filtered which gave the title compound 31d as a white solid (7 g, 64%). 1H NMR (400 MHz, DMSO): δ ppm 1.095-1.077 (d, 3H), 1.395-1.321 (m, 1H), 1.722-1.718 (m, 1H), 1.919-1.896 (m, 2H), 3.226-3.184 (d, 1H), 3.379 (s, 1H), 3.994-3.957 (d, 1H), 4.315 (s, 1H), 5.072 (s, 2H), 7.381-7.309 (m, 5H), 8.208 (s, 3H).

Preparation of compound 30e: benzyl (2S,5R)-5-{[6-(imidazo[1,2-a]pyridin-3-yl)pyrazin-2-yl]amino}-2-methylpiperidine-1-carboxylate A mixture of 3-(6-chloropyrazin-2-yl)imidazo[1,2-a]pyridine (0.1 g, 0.43 mmol), 30d (0.108 g, 0.43 mmol) and CsF (0.13 g, 0.86 mmol) in anhydrous DMSO (2 mL) was heated at 80° C. under N$_2$ and stirred overnight. The mixture was cooled to room temperature and water (10 mL) was added. The mixture was extracted with EtOAc (20 mL×3). The combined organic extracts were dried over Na$_2$SO$_4$, filtered and concentrated which gave the title compound 30e as a yellow solid (0.14 g, 73%). A mixture of 30e (0.2 g, 0.45 mmol) in concentrated HCl (20 mL) was stirred at room temperature for 4 h. The reaction mixture was diluted with water (60 mL), extracted with EtOAc (30 mL×2). The separated aqueous layer was neutralized with saturated Na$_2$CO$_3$ to pH ~7 and concentrated to give a residue. The residue was suspended in THF (80 mL) and refluxed for 30 min, then filtered. This process was repeated ×3. The filtrates were combined and concentrated to give a residue, which was purified by preparative HPLC which gave the title compound 30 as a yellow solid (formate salt, 47 mg, 33%). 1H NMR (400 MHz, DMSO): δ ppm 1.175-1.154 (d, 3H), 1.655-1.636 (m, 1H), 1.966-1.839 (m, 2H), 2.984-2.912 (m, 2H), 3.455-3.173 (m, 1H), 4.448-4.148 (d, 1H), 7.114-7.070 (t, 1H), 7.493-7.397 (m, 2H), 7.736-7.706 (d, 1H), 7.926 (s, 1H), 8.311 (s, 1H), 8.378-8.363 (d, 1H), 9.695-9.651 (d, 1H).

Preparation of compound 31e: benzyl (2R,5R)-5-{[6-(imidazo[1,2-a]pyridin-3-yl)pyrazin-2-yl]amino}-2-methylpiperidine-1-carboxylate A mixture of 3-(6-chloropyrazin-2-yl)imidazo[1,2-a]pyridine (0.1 g, 0.43 mmol), 31d (0.108 g, 0.43 mmol) and CsF (0.13 g, 0.86 mmol) in anhydrous DMSO (2 mL) was heated at 80° C. under N$_2$ and stirred overnight. The mixture was cooled to room temperature and water (10 mL) was added. The mixture was extracted with EtOAc (20 mL×3). The combined organic extracts were dried over Na$_2$SO$_4$, filtered and concentrated which gave the title compound 31e as light yellow oil (0.17 g, 89%). A mixture of 31e (0.2 g, 0.45 mmol) in concentrated HCl (20 mL) was stirred at room temperature for 4 h. The reaction mixture was diluted with water (60 mL), extracted with EtOAc (30 mL×2). The separated aqueous layer was neutralized with saturated Na$_2$CO$_3$ to pH ~7 and concentrated to give a residue. The residue was suspended in THF (80 mL) and refluxed for 30 min, then filtered. This process was repeated ×3. The filtrates were combined and concentrated to give a residue, which was purified by preparative HPLC which gave the title compound 31 as a yellow solid (formate salt, 58 mg, 41%). 1H NMR (400 MHz, DMSO): δ ppm 1.162-1.141 (d, 3H), 1.537-1.393 (m, 2H), 1.834-1.804 (m, 1H), 2.277-2.116 (m, 1H), 2.584-2.512 (d, 1H), 2.738-2.623 (m, 2H), 3.925-3.887 (d, 1H), 7.138-7.005 (t, 1H), 7.237-7.215 (d, 1H), 7.445-7.391 (t, 1H), 7.743-7.713 (d, 1H), 7.797 (s, 1H), 8.260 (s, 1H), 8.380-8.353 (d, 1H), 9.721-9.699 (d, 1H).

Example 32

(Method A): 6-(7-(2-isopropoxyethoxy)H-imidazo[1,2-a]pyridin-3-yl)-N—((R)-piperidin-3-yl)pyrazin-2-amine

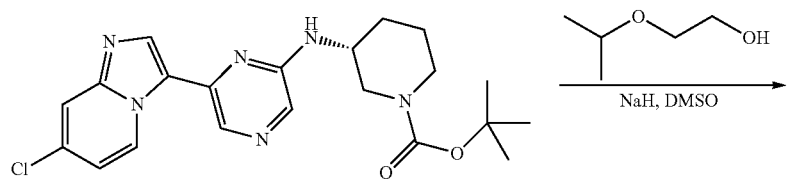

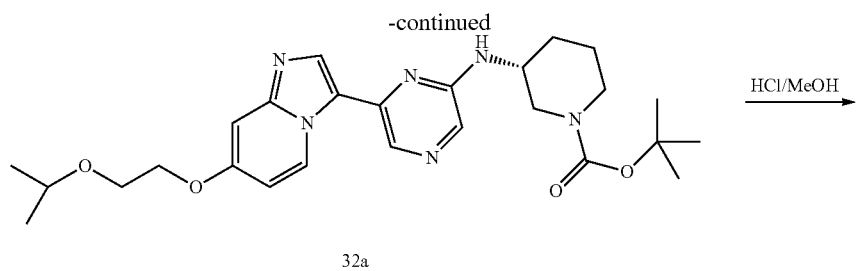

32a

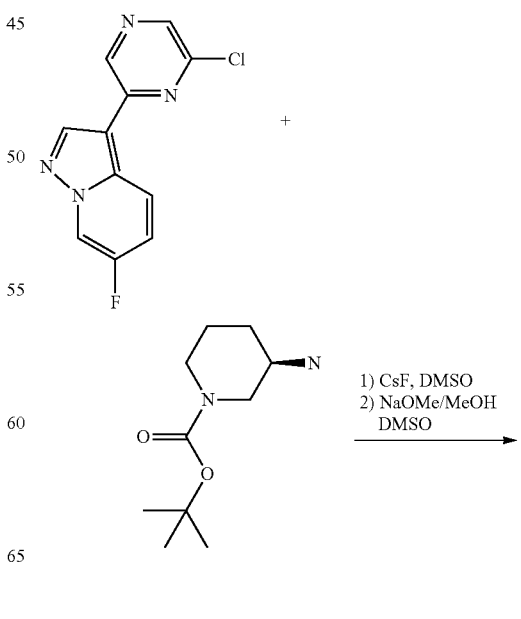

32

Preparation of compound 32a: (3R)-tert-butyl 3-(6-(7-(2-isopropoxyethoxy)H-imidazo[1,2-a]pyridin-3-yl)pyrazin-2-ylamino)piperidine-1-carboxylate To a solution of 2-isopropoxyethanol (195 mg, 1.87 mmol) in DMSO (50 ml) was added NaH (75 mg, 1.87 mmol) at room temperature. The resulting mixture was stirred at room temperature for 1 h. Then (3R)-tert-butyl 3-(6-(7-chloroH-imidazo[1,2-a]pyridin-3-yl)pyrazin-2-ylamino)piperidine-1-carboxylate (400 mg, 0.935 mmol) was added. The resulting mixture was heated to 80° C. for 24 h. The mixture was then cooled and 50 mL of H₂O was added. The resulting mixture was extracted with EtOAc (50 mL×4). The combined organic layers were washed with water (50 mL), followed by brine (50 ml), dried over Na₂SO₄ and filtered. The filtrate was concentrated which gave the title compound 32a which was used directly for the next stage without further purification (400 mg).

To a solution of 32a (420 mg, 0.84 mmol) in MeOH (50 mL) was added 4N HCl in MeOH (10 mL). The resulting mixture was stirred at room temperature overnight. The mixture was concentrated and the residue was purified via prep. HPLC which gave the title compound 32 as a white solid (39.5 mg, 10.7% for two steps). 1H NMR (400 MHz, DMSO): δ ppm 1.107-1.122 (d, 6H), 1.428-1.509 (m, 2H), 1.663-1.684 (m, 1H), 1.987-2.010 (m, 1H), 2.404-2.492 (m, 1H), 2.813-2.844 (d, 1H), 3.130-3.160 (d, 2H), 3.610-3.671 (m, 1H), 3.721-3.743 (t, 3H), 4.173-4.195 (t, 2H), 6.799-6.825 (d, 1H), 7.061-7.095 (m, 2H), 7.738 (s, 1H), 8.200-8.242 (d, 2H), 9.597-9.617 (d, 1H).

Example 33

(Method A): 6-(6-methoxypyrazolo[1,5-a]pyridin-3-yl)-N-[(3R)-piperidin-3-yl]pyrazin-2-amine

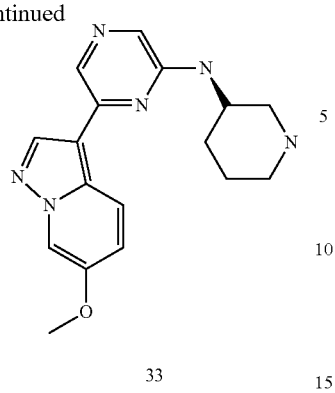

33

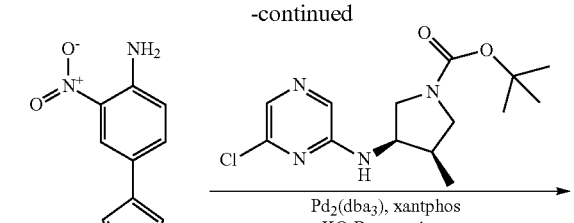

34a

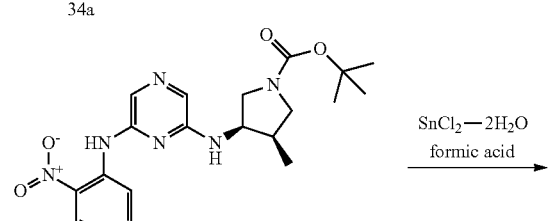

34b

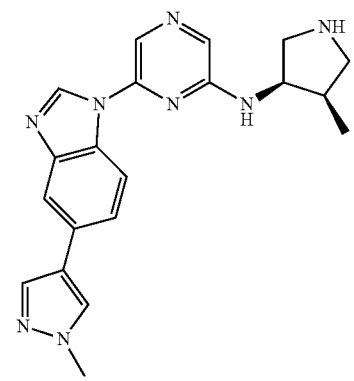

34

A mixture of 3-(6-Chloro-pyrazin-2-yl)-6-fluoro-pyrazolo [1,5-a]pyridine (124 mg, 0.5 mmol), (R)-3-Amino-piperidine-1-carboxylic acid tert-butyl ester (120 mg, 0.6 mmol) and cesium fluoride (152 mg, 0.8 mmol) in DMSO (1 mL) was heated to 120° C. When the reaction was determined to be completed by LCMS, the reaction mixture was cooled to 23° C. then diluted with ethyl acetate and water. The ethyl acetate phase was washed with brine then dried with sodium sulfate and concentrated in vacuo. The crude residue was purified by silica gel chromatography (0-30% methanol in ethylacetate). The purified material was dissolved in dimethylsulfoxide (3 ml), then a solution of sodium methoxide in methanol (1 ml) was added. The resulting mixture was heated to 120° C. for 12 h. The reaction mixture was cooled to 23° C. then diluted with ethylacetate and water. The organic phase was concentrated to an oil then purified by reverse phase prep HPLC which gave the title compound 33. 1H NMR (400 MHz, MeOD) δ ppm 1.76 (q, J=9.60 Hz, 1H) 1.93 (dt, J=13.71, 10.20 z, 1H) 2.13 (d, J=14.40 Hz, 1H) 2.23 (d, J=11.12 Hz, 1H) 3.00-3.18 (m, 2H) 3.34-3.40 (m, 1H) 3.61 (d, J=10.61 Hz, 1H) 3.89 (s, 3H) 4.22-4.43 (m, 1H) 7.21 (d, J=9.60 Hz, 1H) 7.71 (s, 1H) 8.19 (s, 1H) 8.24 (br. s., 1H) 8.27 (d, J=9.60 Hz, 1H) 8.43 (s, 1H); LCMS: M+1 325.

Example 34

(Method G): 6-[5-(1-methyl-1H-pyrazol-4-yl)-1H-benzimidazol-1-yl]-N-[(3R,4R)-4-methylpyrrolidin-3-yl]pyrazin-2-amine

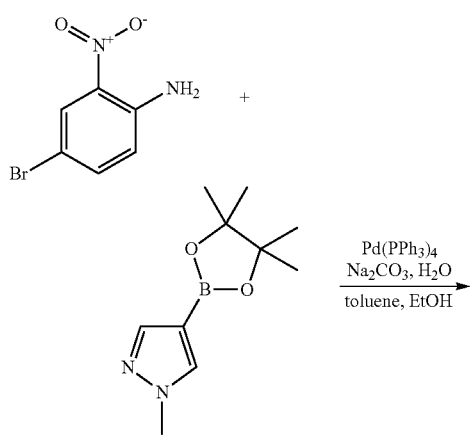

Preparation of compound 34a: 4-(1-methyl-1H-pyrazol-4-yl)-2-nitroaniline

To a round bottom flask was added sequentially 4-bromo-2-nitroaniline (500 mg, 2.30 mmol), 1-methyl-4-(4,4,5,5-tetramethyl-1,3,2-dioxaborolan-2-yl)-1H-pyrazole (575 mg, 2.76 mmol), toluene (15 mL), EtOH (8 mL), Na₂CO₃ (aq) (1250 mg, 11.5 mmol) and palladium tetrakis (106 mg, 0.0920 mmol). The red slurry was heat to reflux for 1.5 h. The solution was cooled and concentrated in vacuo. The residue was worked-up with EtOAc, NaHCO₃, brine and dried over MgSO₄. The residue was purified by column chromatography (10-30% EtOAc-DCM). The solids were triturated with MTBE which gave the title compound 34a as a red solid (341 mg, 68%).

Preparation of compound 34b: tert-butyl (3R,4R)-3-methyl-4-[(6-{[4-(1-methyl-1H-pyrazol-4-yl)-2-nitrophenyl]amino}pyrazin-2-yl)amino]pyrrolidine-1-carboxylate To a 250 mL rb flask was added 34a (200 mg, 0.917 mmol) and tert-butyl (3R,4R)-3-[(6-chloropyrazin-2-yl)amino]-4- methylpyrrolidine-1-carboxylate (287 mg, 0.917 mmol), which were dissolved in o-Xylenes (5 mL) with stirring. The mixture was degassed with N₂ for 10 min. Pd₂(dba)₃ (53.1 mg, 0.0180 mmol), xantphos (10.6 mg, 0.0180 mmol) and KO$^t$Bu (162 mg, 1.40 mmol) were added to the flask. The reaction mixture was heated at 130° C. for 2 h under N₂. The reaction mixture was filtered through a pad of Celite and washed with several volumes of toluene. Solvent was removed in vacuo. The residue was taken up in EtOAc (50 mL). The organics were then washed with H₂O (2×50 mL), filtered through a phase separator syringe, concentrated in vacuo to afford reddish residue. The residue was purified by column chromatography (Heptane/EtOAc, 0-100%) which gave the title compound 34b as a reddish oil (123 mg, 27%).

To a 2 mL microwave vial was added 34b (60 mg, 0.12 mmol) and formic Acid (2 mL). Stannous chloride-2H₂O (85 mg, 0.38 mmol) was added. The reaction vessel was sealed and heated via microwave at 130° C. for 20 min. The reaction mixture was poured into a 125 mL sep. funnel and diluted with H₂O. The aq. layer was neutralized with 10 N NaOH. The aq. layer was extracted with EtOAc (2×25 mL). The aq. layer was concentrated in vacuo which gave the title compound 34 as a purple gum (7.4 mg, 16%). 1H NMR (400 MHz, MeOD) δ ppm 0.93-1.07 (m, 7H), 3.95 (s, 5H), 3.96 (s, 1H), 7.64 (d, J=1.76 Hz, 1H), 7.87 (s, 1H), 7.90 (d, J=1.01 Hz, 1H), 7.96 (s, 1H), 8.01 (s, 1H), 8.16 (s, 1H), 8.18 (d, J=8.56 Hz, 1H), 8.55 (s, 1H), 8.80 (s, 1H); LCMS: M+1 375.2.

Example 35

(Method X): N-[(3S,4S)-4-ethoxypiperidin-3-yl]-6-(imidazo[1,2-a]pyridin-3-yl)pyrazin-2-amine

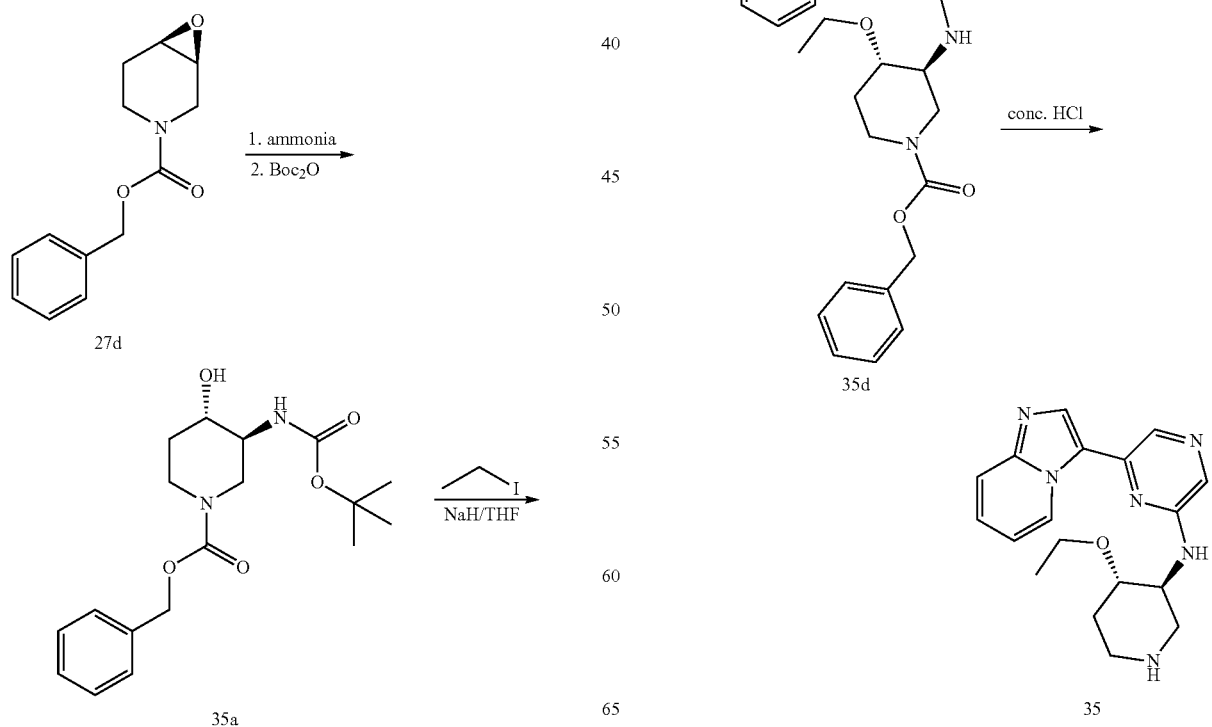

Preparation of compound 35a: benzyl (3S,4S)-3-[(tert-butoxycarbonyl)amino]-4-hydroxypiperidine-1-carboxylate A solution of 27d (75 g, 0.323 mol) in $NH_3 \cdot H_2O$ (800 mL) and EtOH (500 mL) was stirred at room temperature for 48 h. The reaction solution was evaporated to dryness, and then diluted with $CH_2Cl_2$ (2 L). To the diluted solution was added $(Boc)_2O$ (140 g, 0.646 mol) and then stirred at room temperature for 4 h. The reaction solution was evaporated and the residue was purified by column chromatography (petroleum ether/EtOAc=10:1 to 3:1) which gave the title compound 35a as a white solid (30 g, 13%).

Preparation of compound 35b: benzyl (3S,4S)-3-[(tert-butoxycarbonyl)amino]-4-ethoxypiperidine-1-carboxylate To a solution of 35a (7.5 g, 21.4 mmol) in THF (250 mL) was added NaH (60%, 1.7 g, 42.8 mmol) at 0° C. in portions. After the addition, the resulting mixture was stirred at 0° C. for 0.5 h. Then $CH_3CH_2I$ (6.6 g, 42.8 mmol) was added dropwise at the temperature. After the addition, the resulting solution was warmed to room temperature and stirred at room temperature overnight. The reaction mixture was separated between $H_2O$ (200 mL) and EtOAc (200 mL). The aqueous layer was extracted with EtOAc (200 mL). The combined organic layers were washed with brine (200 mL), dried over $Na_2SO_4$ and concentrated. The residue was purified by column chromatography (petroleum ether/EtOAc=50:1 to 10:1) which gave the title compound 35b as a yellow oil (1.7 g, 21%).

Preparation of compound 35c: benzyl (3S,4S)-3-amino-4-ethoxypiperidine-1-carboxylate To solution of 35b (1.7 g, 4.5 mmol) in $CH_2Cl_2$ (45 mL) was added TFA (9 mL) at 0° C. The resulting solution was allowed to warm room temperature and stirred for 2 h. The reaction solution was concentrated and the residue was adjusted to pH ~9 with sat. aq. $NaHCO_3$ and then extracted with EtOAc (50 mL×2). The combined organic layers were washed with brine (50 mL×2), dried over $Na_2SO_4$ and concentrated which gave the title compound 35c as a yellow oil (1.2 g, 100%).

Preparation of compound 35d: benzyl (3S,4S)-4-ethoxy-3-{[6-(imidazo[1,2-a]pyridin-3-yl)pyrazin-2-yl]amino}piperidine-1-carboxylate A mixture of 3-(6-chloropyrazin-2-yl)imidazo[1,2-a]pyridine (230 mg, 1.087 mmol), 35c (302 mg, 1.087 mmol), BINAP (28 mg) and $Cs_2CO_3$ (708 mg, 2.174 mmol) in dry toluene (1.5 mL) was added $Pd(dba)_2$ (26 mg) quickly under $N_2$. The mixture was stirred at 120° C. for 1 h. The reaction mixture was cooled to room temperature and then partitioned between EtOAc (50 mL) and $H_2O$ (50 mL). The organic layer was washed with brine (20 mL), dried over $Na_2SO_4$ and concentrated which gave the title compound 35d, which was used in the next step directly.

A mixture of 35d (500 mg, 1.05 mmol) in con.HCl (40 mL) was stirred at room temperature for 6 h. The reaction mixture was adjusted to pH ~9 with $NH_3 \cdot H_2O$. The residue was extracted with $CH_2Cl_2$ (100 mL×4). The combined organic layers were dried over $Na_2SO_4$ and concentrated. The residue was purified by prep HPLC which gave the title compound 35 as a yellow solid (67 mg, 18%). 1H NMR (400 MHz, MeOD): δ ppm 1.04 (t, 3H), 1.55-1.50 (m, 1H), 2.22-2.12 (m, 1H), 2.61-2.50 (m, 2H), 3.0.5-3.02 (m, 1H), 3.39-3.38 (m, 1H), 3.50-3.46 (m, 2H), 3.68-3.64 (m, 2H), 4.01 (m, 1H), 7.06 (t, 1H), 7.41 (t, 1H), 7.61 (d, 1H), 7.73 (s, 1H), 8.15 (d, 2H), 9.81 (d, 1H); LCMS: M+1 339.4.

Example 36

(Method B): 6-(imidazo[1,2-a]pyridin-3-yl)-3-methoxy-N-[(3R)-piperidin-3-yl]pyrazin-2-amine

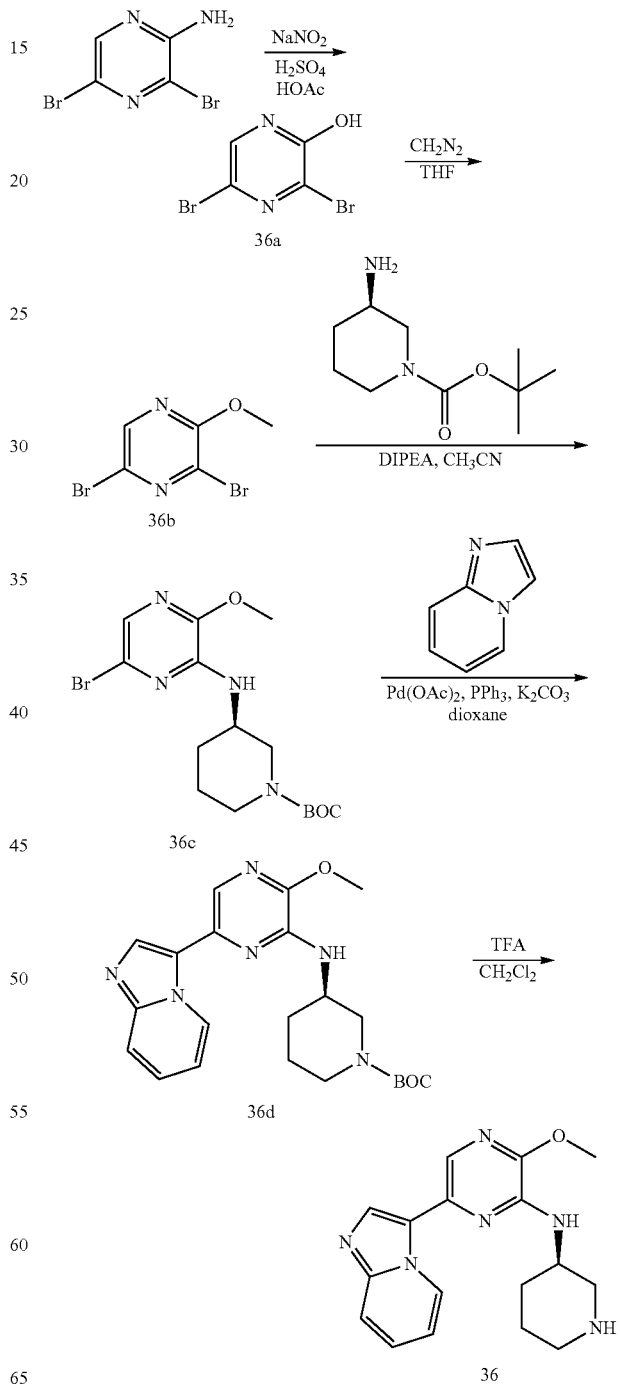

Preparation of compound 36a:
3,5-dibromopyrazin-2-ol

To a stirred solution of 3,5-dibromopyrazin-2-amine (30 g, 0.12 mol) in AcOH (300 mL) was added dropwise conc. H₂SO₄ (50 mL) at 15~25° C. To the resulting solution was then added dropwise a solution of NaNO₂ (16.6 g, 0.24 mol) in water (100 mL) at 10~15° C. during a period of 1.5 h. After the addition, the resulting mixture was stirred at 10~15° C. for 1 h. The reaction mixture was poured into water (3 L) and extracted with EtOAc (1 L×3). The combined organic layers were washed with saturated NaHCO₃ (1 L×3) and brine (1 L) in sequence, dried over Na₂SO₄ and concentrated in vacuo which gave the title compound 36a as a yellow solid (24 g, 79.4%). ¹H NMR (400 MHz, CDCl3): 7.44 (s, 1H).

Preparation of compound 36b:
3,5-dibromo-2-methoxypyrazine

To a stirred solution of 36a (8 g, 0.031 mol) in dry THF (100 mL) was added dropwise a solution of CH₂N₂ in Et₂O (0.7 N, 134 mL, 0.093 mol) at 0° C. After the addition, the resulting mixture was stirred at r.t. for 0.3 h. The reaction mixture was concentrated in vacuo and the residue was purified by column chromatography (petroleum ether/EtOAc 10:1) which gave the title compound 36b as a yellow solid (5.5 g, 32.6%). ¹H NMR (400 MHz, CDCl3) 3.963 (s, 3H), 8.060 (s, 1H).

Preparation of compound 36c: tert-butyl (3R)-3-[(6-bromo-3-methoxypyrazin-2-yl)amino]piperidine-1-carboxylate A solution of 36b (1.26 g, 4.7 mmol), DIPEA (1.22 g, 9.4 mmol) and tert-butyl (3R)-3-aminopiperidine-1-carboxylate (1.12 g, 5.64 mmol) in CH₃CN (5 mL) was stirred at reflux overnight. The reaction mixture was concentrated in vacuo and the residue was purified by column chromatography (petroleum ether/EtOAc 10:1 to 3:1) which gave the title compound 36c as yellow syrup (0.3 g, 16.5%). ¹H NMR (400 MHz, DMSO) δ ppm 1.177 (s, 9H), 1.75~1.60 (m, 2H), 1.90~1.80 (m 1H), 3.10~2.75 (m, 3H), 3.85~3.55 (m, 3H), 3.889 (s, 3H), 6.837 (s, 1H), 7.355 (s, 1H).

Preparation of compound 36d: tert-butyl (3R)-3-{[6-(imidazo[1,2-a]pyridin-3-yl)-3-methoxypyrazin-2-yl]amino}piperidine-1-carboxylate A solution of 36c (0.3 g, 0.77 mmol), imidazo[1,2-a]pyridine (0.16 g, 1.39 mmol), K₂CO₃ (0.43 g, 0.31 mmol), P(Ph)₃ (20.3 mg, 0.077 mmol) and a catalytic amount of Pd(OAc)₂ (25 mg) in dioxane (5 mL) was stirred at reflux under N₂ atmosphere overnight. The reaction mixture was cooled to r.t., diluted with EtOAc (100 mL) and the resulting mixture was washed with brine (30 mL×2), dried over Na₂SO₄ and concentrated in vacuo. The residue was purified by column chromatography (petroleum ether/EtOAc 10:1 to 2:1) which gave the title compound 36d as yellow syrup (0.12 g, 36.5%).

To a stirred solution of 36d (0.12 g, 0.28 mmol) in CH₂Cl₂ (2 mL) was added TFA (0.2 mL) at 0° C. After the addition, the resulting solution was stirred at rt for 5 h. Water (5 mL) was added and the resulting mixture was stirred at rt for 5 min. The aq. layer was separated and purified by prep. HPLC under TFA conditions which gave the title compound 36 as a white solid (TFA salt, 30.3 mg, 33.0%). ¹H NMR (400 MHz, D₂O) δ ppm 1.828~1.776 (m, 2H), 2.164~2.047 (m, 2H), 3.084~3.030 (m, 2H), 3.335~3.302 (m, 1H), 3.530~3.508 (m, 1H), 4.019 (s, 3H), 4.328 (m, 1H), 7.480~7.449 (t, 1H), 7.691 (s, 1H), 7.954~7.937 (m, 2H), 8.130 (s, 1H), 9.164~9.147 (d, 1H).

| Ex. | Structure | Name, Data and Preparation Method |
| --- | --- | --- |
| 37 | 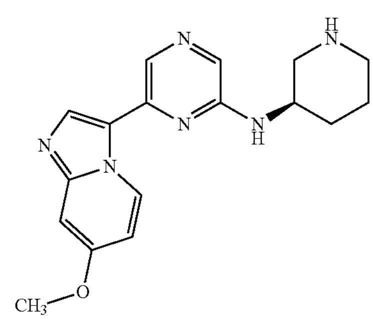 [SMILES: COc1ccn2c(-c3cncc(N[C@@H]4CCCNC4)n3)cnc2c1] | 6-(7-Methoxyimidazo[1,2-a]pyridin-3-yl)-N-[(3R)-piperidin-3-yl]pyrazin-2-amine. 1H NMR (400 MHz, MeOD) δ ppm 1.29 (br. s., 1H), 1.47-1.63 (m, 1H), 1.71 (d, J = 14.4 Hz, 1H), 1.81-1.93 (m, 1H), 2.17 (d, J = 8.1 Hz, 1H), 2.52-2.76 (m, 2H), 3.03 (d, J = 12.3 Hz, 1H), 3.93 (s, 3H), 3.97-4.12 (m, 1H), 6.85 (dd, J = 7.8, 2.5 Hz, 1H), 6.98 (d, J = 2.3 Hz, 1H), 7.69 (s, 1H), 8.09 (s, 1H), 8.19 (s, 1H), 9.62 (d, J = 7.5 Hz, 1H); LCMS: M + 1 325. Method A (Example 7) |
| 38 | 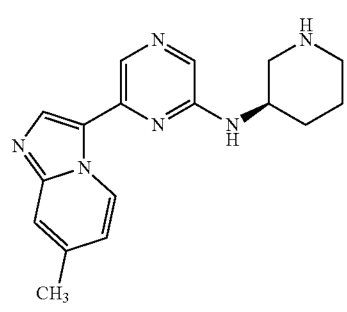 [SMILES: Cc1ccn2c(-c3cncc(N[C@@H]4CCCNC4)n3)cnc2c1] | 6-(7-Methylimidazo[1,2-a]pyridin-3-yl)-N-[(3R)-piperidin-3-yl]pyrazin-2-amine. 1H NMR (400 MHz, MeOD) δ ppm 1.77 (br. s., 1H), 1.99 (br. s., 1H), 2.11 (br. s., 1H), 2.24 (br. s., 1H), 2.66 (s, 3H), 3.09 (br. s., 2H), 3.36 (br. s., 1H), 3.58 (br. s., 1H), 4.39 (br. s., 1H), 7.59 (br. s., 1H), 7.86 (s, 1H), 8.03 (s, 1H), 8.36 (s, 1H), 8.63 (br. s., 1H), 9.70 (br. s., 1H); LCMS: M + 1 309. Method B (Example 5) |

-continued

| Ex. | Structure | Name, Data and Preparation Method |
| --- | --- | --- |
| 39 | 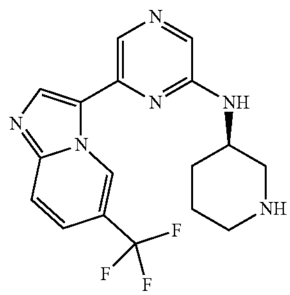 [SMILES: FC(F)(F)c1ccc2ncc(-c3cncc(N[C@@H]4CCCNC4)n3)n2c1] | N-[(3R)-piperidin-3-yl]-6-[6-(trifluoromethyl) imidazo[1,2-a]pyridin-3-yl]pyrazin-2-amine. 1H NMR (400 MHz, MeOD) δ ppm 1.80 (br. s., 2H), 1.98 (br. s., 2H), 2.19 (br. s., 1H), 3.01 (br. s., 1H), 3.15 (br. s., 2H), 4.21 (br. s., 1H), 7.65 (br. s., 1H), 7.85 (br. s., 1H), 7.90 (s, 1H), 8.35 (br. s., 2H), 10.12 (s, 1H); LCMS: M + 1 363. Method B (Example 5) |
| 40 | 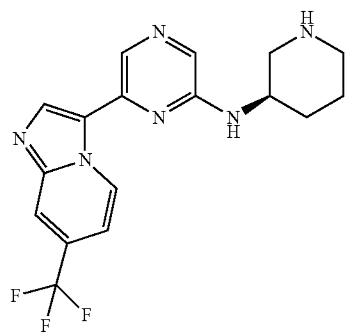 [SMILES: FC(F)(F)c1ccn2c(-c3cncc(N[C@@H]4CCCNC4)n3)cnc2c1] | N-[(3R)-piperidin-3-yl]-6-[7-(trifluoromethyl) imidazo[1,2-a]pyridin-3-yl]pyrazin-2-amine 1H NMR (400 MHz, DMSO-d6) δ ppm 1.48 (s, 2H), 1.67 (br. s., 1H), 1.88 (s, 2H), 2.02 (br. s., 1H), 2.43 (br. s., 1H), 2.83 (br. s., 1H), 3.17 (br. s.,1H), 3.80 (br. s., 1H), 7.25 (s, 1H), 7.40 (dd, J = 7.4, 1.9 Hz, 1H), 7.87 (s, 1H), 8.22 (s, 1H), 8.38 (s, 1H), 8.59 (s, 1H), 9.93 (d, J = 7.3 Hz, 1H); LCMS: M + 1 363, Method A (Example 7) |
| 41 | 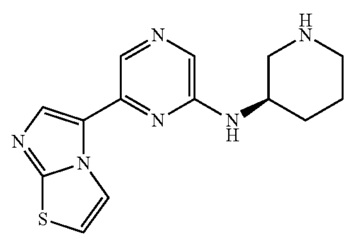 [SMILES: c1cn2c(-c3cncc(N[C@@H]4CCCNC4)n3)cnc2s1] | 6-Imidazo[2,1-b][1,3]thiazol-5-yl-N-[(3R)-piperidin-3-yl]pyrazin-2-amine. 1H NMR (400 MHz, MeOD) δ ppm 1.56 (br. s., 1H), 1.73 (br. s., 1H), 1.91 (br. s., 1H), 2.15 (br. s., 1H), 2.66 (br. s., 2H), 3.03 (br. s., 1H), 3.36 (br. s., 1H), 4.02 (br. s., 1H), 7.30 (s, 1H), 7.71 (br. s., 1H), 7.93 (s, 1H), 8.17 (br. s., 1H), 8.58 (br. s., 1H); LCMS: M + 1 301. Method A (Example 4) |
| 42 | 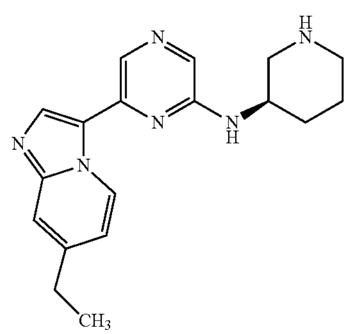 [SMILES: CCc1ccn2c(-c3cncc(N[C@@H]4CCCNC4)n3)cnc2c1] | 6-(7-Ethylimidazo[1,2-a]pyridin-3-yl)-N-[(3R)-piperidin-3-yl]pyrazin-2-amine. 1H NMR (400 MHz, DMSO-d6) δ ppm 1.30 (t, J = 7.6, Hz, 3H), 1.93 (br. s., 2H), 2.33 (s, 1H), 2.67 (s, 1H), 2.90 (q, 3H), 7.76 (br. s., 2H), 7.85 (s, 1H), 8.03 (s, 1H), 8.44 (s, 1H), 8.92 (s, 1H), 9.79 (s, 1H); LCMS: M + 1 323. Method A (Example 7) |
| 43 | 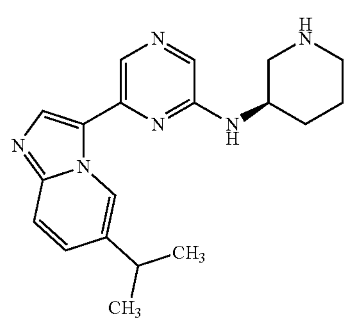 [SMILES: CC(C)c1ccc2ncc(-c3cncc(N[C@@H]4CCCNC4)n3)n2c1] | 6-(6-Isopropylimidazo[1,2-a]pyridin-3-yl)-N-[(3R)-piperidin-3-yl]pyrazin-2-amine 1H NMR (400 MHz, DMSO-d6) δ ppm 1.27-1.35 (m, 7H), 1.40-1.51 (m, 2H), 1.63-1.72 (m, 1H), 1.96-2.04 (m, 1H), 2.76-2.84 (m, 1H), 2.96-3.14 (m, 3H), 3.83-3.97 (m, 1H), 7.15 (d, J = 7.6 Hz, 1H), 7.38 (dd, J = 9.4, 1.8 Hz, 1H), 7.65 (d, J = 9.09 Hz, 1H); LCMS: M + 1 337. Method A (Example 7) |

| Ex. | Structure | Name, Data and Preparation Method |
|---|---|---|
| 44 | 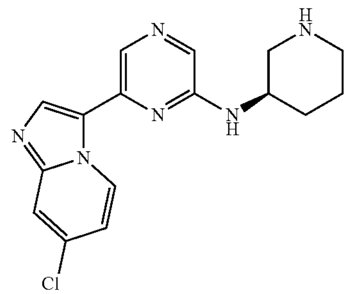 [SMILES: Clc1ccn2c(-c3cncc(N[C@@H]4CCCNC4)n3)cnc2c1] | 6-(7-Chloroimidazo[1,2-a]pyridin-3-yl)-N-[(3R)-piperidin-3-yl]pyrazin-2-amine. 1H NMR (400 MHz, DMSO-d6) δ ppm 1.49-1.66 (m, 1H), 1.88 (d, J = 13.4 Hz, 1H), 2.03 (d, J = 11.6 Hz, 2H), 2.79 (q, J = 10.2 Hz, 1H), 2.84-2.98 (m, 1H), 3.20 (d, J = 12.1 Hz, 1H), 3.44 (d, J = 10.6 Hz, 1H), 4.41 (br. s., 1H), 7.83 (br. s., 1H), 8.02 (s, 2H), 8.22 (d, J = 2.0 Hz, 1H), 8.47 (s, 1H), 8.96 (s, 1H), 9.18 (br. s., 1H), 9.92 (d, J = 7.6 Hz, 1H), 10.18 (br. s., 1H); LCMS: M + 1 329. Method A (Example 7) |
| 45 | 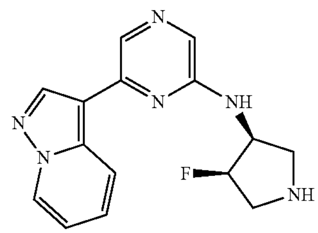 [SMILES: F[C@@H]1CNC[C@@H]1Nc1cncc(-c2cnn3ccccc23)n1] | Cis N-[4-fluoropyrrolidin-3-yl]-6-pyrazolo [1,5-a]pyridin-3-ylpyrazin-2-amine. 1H NMR (400 MHz, MeOD) δ ppm 3.25 (t, J = 11.2 Hz, 1H), 3.68-3.91 (m, 3H), 5.04 (ddd, J = 19.3, 15.8, 7.8 Hz, 1H), 5.33-5.53 (m, 1H), 7.03 (t, J = 6.7 Hz, 1H), 7.43 (d, J = 8.3 Hz, 1H), 7.82 (s, 1H), 8.28 (s, 1H), 8.37 (d, J = 8.8 Hz, 1H), 8.57 (s, 1H), 8.62 (d, J = 7.1 Hz, 1H); LCMS: M + 1 299. Method E (Example 6) |
| 46 | 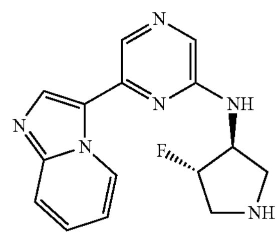 [SMILES: F[C@H]1CNC[C@@H]1Nc1cncc(-c2cnc3ccccn23)n1] | Trans N-[4-fluoropyrrolidin-3-yl]-6-imidazo[1,2-a]pyrazin-3-ylpyrazin-2-amine. 1H NMR (400 MHz, DMSO-d6) δ ppm 3.41-3.59 (m, 3H), 3.66 (d, J = 5.6 Hz, 1H), 4.22-4.51 (m, 1H), 4.91-5.23 (m, 1H), 7.03 (t, J = 6.7 Hz, 1H), 7.40 (d, J = 7.1 Hz, 1H), 7.57 (br. s., 1H), 7.71 (d, J = 9.1 Hz, 1H), 7.86 (s, 1H), 8.40 (d, J = 1.8 Hz, 2H), 9.82 (d, J = 6.8 Hz, 1H); LCMS: M + 1 299. Method E (Example 6) |
| 47 | 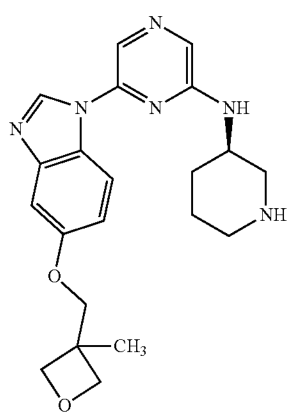 [SMILES: CC1(COc2ccc3c(c2)ncn3-c2cncc(N[C@@H]3CCCNC3)n2)COC1] | 6-{5-[(3-Methyloxetan-3-yl)methoxy]-1H-benzimidazol1-yl}-N-[(3R)-piperidin-3-yl]pyrazin-2-amine. 1H NMR (400 MHz, MeOD) 1.48 (s, 3H) 1.70-1.82 (m, 1H) 1.84-1.97 (m, 1H) 2.07-2.18 (m, 1H) 2.18-2.28 (m, 1H) 2.97-3.11 (m, 2H) 3.33-3.37 (m, 1H) 3.61 (dd, J = 12.38, 3.54 Hz, 1H) 4.13 (s, 2H) 4.23-4.33 (m, 1H) 4.49 (d, J = 5.81 Hz, 2H) 4.71 (d, J = 6.06 Hz, 2H) 7.34 (d, J = 2.27 Hz, 1H)7.15 (dd, J = 8.97, 2.40 Hz, 1H) 7.97 (s, 1H) 7.99 (d, J = 9.09 Hz, 1H) 8.24 (s, 1H) 8.45 (br. s., 1H) 8.79 (s, 1H). Method C (Example 9) |
| 48 | 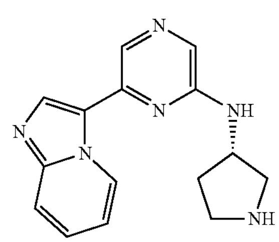 [SMILES: c1ccn2c(-c3cncc(N[C@H]4CCNC4)n3)cnc2c1] | 6-Imidazo[1,2-a]pyridin-3-yl-N-[(3S)-pyrrolidin-3-yl]pyrazin-2-amine. 1H NMR (400 MHz, DMSO-d6) δ ppm 1.87-1.95 (m, 1H), 2.19-2.28 (m, 1H), 3.03-3.07 (m, 1H), 3.12-3.24 (m, 2H), 3.35-3.40 (m, 1H), 4.43-4.48 (m, 1H), 7.09-7.12 (m, 1H), 7.39-7.45 (m, 2H), 7.73 (d, J = 9.0 Hz, 1H), 7.83 (s, 1H), 8.39 (s, 1H), 8.40 (s, 1H), 9.71 (d, J = 7.0 Hz, 1H); APCI LCMS m/z 281 (M + H). Method A (Example 3). |

| Ex. | Structure | Name, Data and Preparation Method |
|---|---|---|
| 49 | 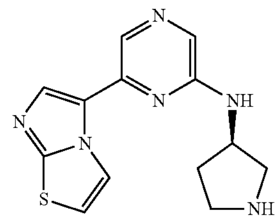 [SMILES: c1cn2c(-c3cncc(N[C@@H]4CCNC4)n3)cnc2s1] | 6-Imidazo[2,1-b][1,3]thiazol-5-yl-N-[(3R)-pyrrolidin-3-yl]pyrazin-2-amine. 1H NMR (400 MHz, MeOD) δ ppm 2.13-2.27 (m, 1H), 2.43-2.58 (m, 1H), 3.34-3.41 (m, 1H), 3.45-3.59 (m, 2H), 3.65-3.73 (m, 1H), 4.70-4.80 (m, 1H), 7.79 (d, J = 3.5 Hz, 1H), 8.03 (s, 1H), 8.40 (s, 1H), 8.49 (s, 1H), 8.85 (d, J = 4.0 Hz, 1H); APCI LCMS m/z 287 (M + H). Method A (Example 4). |
| 50 | 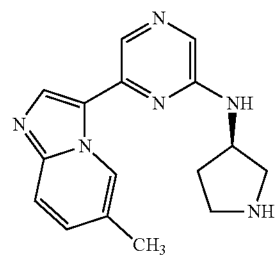 [SMILES: Cc1ccc2ncc(-c3cncc(N[C@@H]4CCNC4)n3)n2c1] | 6-(6-Methylimidazo[1,2-a]pyridin-3-yl)-N-[(3R)-pyrrolidin-3-yl]pyrazin-2-amine. 1H NMR (400 MHz, MeOD) δ ppm 1.98 (br. s., 1H), 2.33 (br. s., 1H), 2.42 (s, 3H), 3.15 (br. s., 3H), 3.37 (br. s., 1H), 4.52 (br. s., 1H), 7.32 (s, 1H), 7.56 (br. s., 1H), 7.76 (br. s., 1H), 8.17 (s, 1H), 8.25 (s, 1H), 9.63 (s, 1H). Method A (Example 4 use dichloropyrazine). |
| 51 | 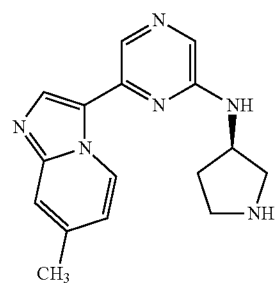 [SMILES: Cc1ccn2c(-c3cncc(N[C@@H]4CCNC4)n3)cnc2c1] | 6-(7-Methylimidazo[1,2-a]pyridin-3-yl)-N-[(3R)-pyrrolidin-3-yl]pyrazin-2-amine. 1H NMR (400 MHz, MeOD) δ ppm 1.86-1.92 (m, 1H), 2.25-2.31 (m, 1H), 2.46 (s, 3H), 2.90-2.97 (m, 1H), 3.01-3.09 (m, 1H), 3.10-3.20 (m, 1H), 4.44-4.59 (m, 1H), 6.95 (dd, J = 7.3, 1.8 Hz, 1H), 7.42 (s, 1H), 7.73 (s, 1H), 8.14 (s, 1H), 8.22 (s, 1H), 9.68 (d, J = 7.3 Hz, 1H); APCI LCMS 295 (M + H). Method A (Exmaple 4, use dichloropyrazine). |
| 52 | 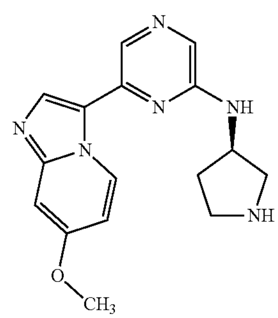 | 6-(7-Methoxyimidazo[1,2-a]pyridin-3-yl)-N-[(3R)-pyrrolidin-3-yl]pyrazin-2-amine. 1H NMR (400 MHz, MeOD) δ ppm 1.82-1.89 (m, 1H), 2.17-2.32 (m, 1H), 2.80-2.94 (m, 1H), 2.96-3.06 (m, 1H), 3.06-3.16 (m, 1H), 3.22-3.29 (m, 1H), 3.90-3.95 (m, 3H), 4.36-4.52 (m, 1H), 6.79 (dd, J = 7.7, 2.6 Hz, 1H), 6.97 (d, J = 2.5 Hz, 1H), 7.70 (s, 1H), 8.08 (s, 1H), 8.20 (s, 1H), 9.66 (d, J = 7.8 Hz, 1H). Method B (Example 10). |
| 53 | 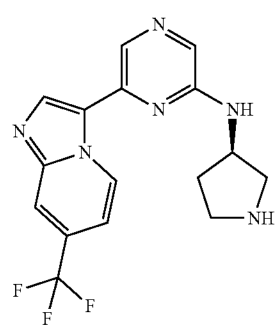 [SMILES: FC(F)(F)c1ccn2c(-c3cncc(N[C@@H]4CCNC4)n3)cnc2c1] | N-[(3R)-pyrrolidin-3-yl]-6-[7-(trifluoromethyl)imidazo[1,2-a]pyridin-3-yl]pyrazin-2-amine. 1H NMR (400 MHz, DMSO-d$_6$) δ ppm 1.63-1.78 (m, 1H), 2.05-2.18 (m, 1H), 2.74 (dd, J = 11.3, 4.0 Hz, 1H), 2.80-2.89 (m, 1H), 2.91-2.99 (m, 1H), 3.09-3.20 (m, 1H), 4.23-4.37 (m, 1H), 1.36-7.48 (m, 2H), 7.86 (s, 1H), 8.21 (s, 1H), 8.40 (s, 1H), 8.59 (s, 1H), 9.96 (d, J = 7.3 Hz, 1H); APCI LCMS m/z 349 (M + H). Method A (Example 7) |

| Ex. | Structure | Name, Data and Preparation Method |
|---|---|---|
| 54 | 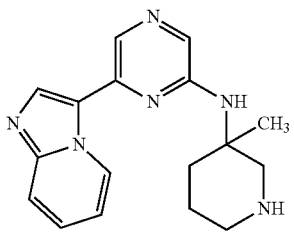 [SMILES: CC1(Nc2cncc(-c3cnc4ccccn34)n2)CCCNC1] | 6-Imidazo[1,2-a]pyridin-3-yl-N-(3-methylpiperidin-3-yl)pyrazin-2-amine. 1H NMR (400 MHz, DMSO-$d_6$) δ ppm 1.45 (s, 3H), 1.57-1.76 (m, 2H), 1.87-2.07 (m, 1H), 2.11-2.23 (m, 1H), 2.79-2.92 (m, 1H), 2.92-3.02 (m, 1H), 3.09-3.24 (m, 1H), 3.91-4.07 (m, 1H), 7.50 (s, 1H), 7.65-7.75 (m, 1H), 7.97-8.06 (m, 1H), 8.06-8.13 (m, 1H), 8.32 (s, 1H), 8.21 (s, 1H), 8.61 (d, J = 8.6 Hz, 1H), 8.80 (s, 1H), 9.36 (d, J = 6.8 Hz, 1H), 9.60 (d, J = 14.4 Hz, 1H); LCMS m/z 309. Method A (Example 4) |
| 55 | 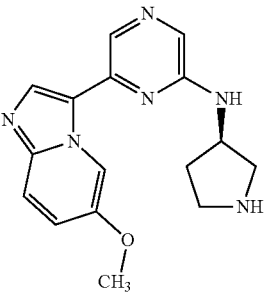 [SMILES: COc1ccc2ncc(-c3cncc(N[C@@H]4CCNC4)n3)n2c1] | 6-(6-Methoxyimidazo[1,2-a]pyridin-3-yl)-N-[(3R)-pyrrolidin-3-yl]pyrazin-2-amine. 1H NMR (400 MHz, MeOD) δ ppm 1.80-1.86 (m, 2H), 1.95-1.99 (m, 1H), 2.02-2.06 (m, 1H), 2.66 (s, 3H), 3.31-3.37 (m, 1H), 5.99 (dd, J = 9.7, 2.4 Hz, 1H), 6.31 (d, J = 9.6 Hz, 1H), 6.51 (s, 1H), 6.85 (s, 1H), 6.96 (s, 1H), 8.10 (d, J = 2.1 Hz, 1H); LCMS m/z 311 (M + H). Method A, (Example 7). |
| 56 | 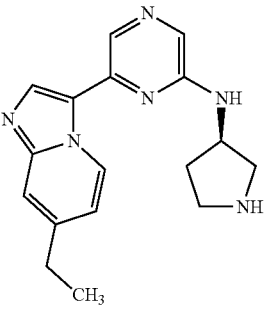 [SMILES: CCc1ccn2c(-c3cncc(N[C@@H]4CCNC4)n3)cnc2c1] | 6-(7-Ethylimidazo[1,2-a]pyridin-3-yl)-N-[(3R)-pyrrolidin-3-yl]pyrazin-2-amine 1H NMR (400 MHz, DMSO-$d_6$) δ ppm 1.26 (t, J = 7.6 Hz, 3H), 1.67-1.80 (m, 1H), 2.04-2.19 (m, 1H), 2.72 (q, J = 7.5 Hz, 2H), 2.80 (dd, J = 11.3, 4.0 Hz, 1H), 2.85-2.95 (m, 1H), 2.95-3.05 (m, 1H), 3.09-3.20 (m, 1H), 4.24-4.39 (m, 1H), 7.02 (dd, J = 7.3, 1.8 Hz, 1H), 7.36 (d, J = 6.0 Hz, 1H), 7.50 (s, 1H), 7.77 (s, 1H), 8.31 (s, 1H), 8.32 (s, 1H), 9.69 (d, J = 7.3 Hz, 1H); LCMS m/z 309 (M + H). Method A (Example 7). |
| 57 | 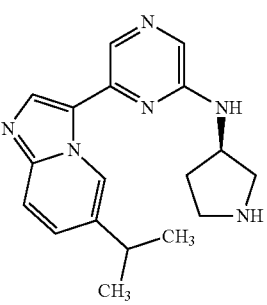 [SMILES: CC(C)c1ccc2ncc(-c3cncc(N[C@@H]4CCNC4)n3)n2c1] | 6-(6-Isopropylimidazo[1,2-a]pyridin-3-yl)-N-[(3R)-pyrrolidin-3-yl]pyrazin-2-amine. 1H NMR (400 MHz, DMSO-d6) δ ppm 1.23-1.37 (m, 6H), 2.19-2.35 (m, 2H), 3.10-3.50 (m, 4H), 4.57 (br. s., 1H), 8.01-8.13 (m, 3H), 8.42 (s, 1H), 8.85-8.95 (m, 1H), 9.59 (s, 1H). Method A (Example 7) |
| 58 | 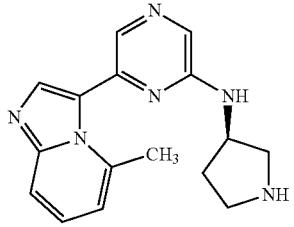 [SMILES: Cc1cccc2ncc(-c3cncc(N[C@@H]4CCNC4)n3)n12] | 6-(5-Methylimidazo[1,2-a]pyridin-3-yl)-N-[(3R)-pyrrolidin-3-yl]pyrazin-2-amine 1H NMR (400 MHz, MeOD) δ ppm 1.73-1.94 (m, 1H) 2.22 (dd, J = 13.35, 7.55 Hz, 1H) 2.46 (s, 3H) 2.88 (dd, J = 11.71, 4.91 Hz, 1H) 2.99-3.10 (m, 1H) 3.10-3.22 (m, 1H) 3.26 (dd, J = 11.96, 6.42 Hz, 1H) 4.42 (s, 1H) 6.80 (d, J = 6.80 Hz, 1H) 7.34 (dd, J = 8.81, 6.80 Hz, 1H) 7.54 (d, J = 9.06 Hz, 1H) 7.67 (s, 1H) 7.94 (s, 1H) 7.98 (s, 1H). Method A (Example 4, use dichloropyrazine). |

| Ex. | Structure | Name, Data and Preparation Method |
|---|---|---|
| 59 | 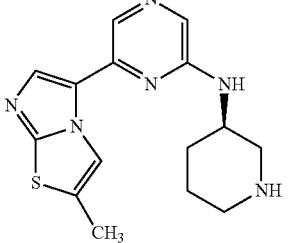 | 6-(2-Methylimidazo[2,1-b][1,3]thiazol-5-yl)-N-[(3R)-piperidin-3-yl]pyrazin-2-amine. 1H NMR (400 MHz, MeOD) δ ppm 1.63-1.83 (m, 1H), 1.87-2.03 (m, 1H), 2.08-2.20 (m, 1H), 2.20-2.35 (m, 1H), 2.67 (s, 3H), 3.06-3.19 (m, 2H), 3.55 (dd, J = 12.5, 3.4 Hz, 1H), 4.23-4.42 (m, 1H), 8.01 (s, 1H), 8.22-8.44 (m, 2H), 8.53 (s, 1H); LCMS: M + 1 315. Method A (Example 4) |
| 60 | 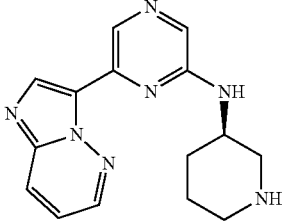 [SMILES: c1cnn2c(-c3cncc(N[C@@H]4CCCNC4)n3)cnc2c1] | 6-Imidazo[1,2-b]pyridazin-3-yl-N-[(3R)-piperidin-3-yl]pyrazin-2-amine. 1H NMR (400 MHz, DMSO-d6) δ ppm 1.59-1.72 (m, 1H), 1.74-1.89 (m, 1H), 1.92-2.06 (m, 2H), 2.69-2.81 (m, 1H), 2.83-3.01 (m, 1H), 3.21-3.30 (m, 1H), 3.53 (d, J = 11.1 Hz, 1H) 4.26 (br. s., 1H), 7.51 (dd, J = 9.1, 4.5 Hz, 1H), 7.99 (s, 1H), 8.37 (dd, J = 9.2, 1.6 Hz, 1H), 8.80 (s, 1H), 8.86 (dd, J = 4.5, 1.5 Hz, 1H), 8.95 (s, 1H), 9.19 (d, J = 10.8 Hz, 1H). Method A (Example 4). |
| 61 | 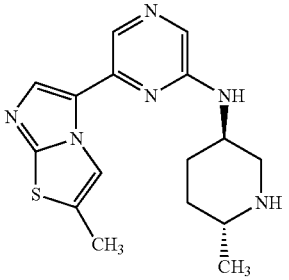 [SMILES: Cc1cn2c(-c3cncc(N[C@@H]4CC[C@@H](C)NC4)n3)cnc2s1] | Trans 6-(2-Methylimidazo[2,1-b][1,3]thiazol-5-yl)-N-(6-methylpiperidin-3-yl)pyrazin-2-amine 1H NMR (400 MHz, DMSO-d6) δ ppm 1.31 (d, J = 6.3 Hz, 3H), 1.40-1.56 (m, 1H), 1.69-1.85 (m, 1H), 1.86-1.97 (m, 1H), 2.14 (d, J = 11.6 Hz, 1H), 2.64 (s, 3H), 2.82 (q, J = 11.2 Hz, 1H), 3.13-3.29 (m, 1H), 3.41 (d, J = 11.1 Hz, 1H), 4.26-4.46 (m, 1H), 7.88 (s, 1H), 8.32 (s, 1H), 8.36 (s, 1H), 8.47 (s, 1H), 9.26 (d, J = 10.3 Hz, 1H), 9.90 (d, J = 10.6 Hz, 1H). Method A (Example 4, CBZ was used instead of Boc as the protecting group of the ring nitrogen of the 3-amino piperidine piece) |
| 62 | 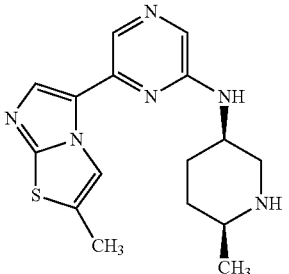 | Cis 6-(2-Methylimidazo[2,1-b][1,3]thiazol-5-yl)-N-(6-methylpiperidin-3-yl)pyrazin-2-amine 1H NMR (400 MHz, DMSO-d6) δ ppm 1.31 (d, J = 6.3 Hz, 3H), 1.71-1.85 (m, 2H), 1.86-1.98 (m, J = 4.5 Hz, 3H), 2.54 (s, 3H), 3.20-3.32 (m, 2H), 3.34-3.45 (m, 1H), 4.30 (br. s., 1H), 7.92 (s, 2H), 8.15 (br. s., 1H), 8.33 (s, 1H), 8.35-8.43 (m, 1H), 9.04-9.41 (m, 1H). Method A (Example 4, CBZ was used instead of Boc as the protecting group of the ring nitrogen of the 3-amino piperidine piece) |
| 63 | 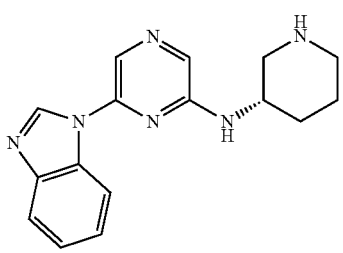 [SMILES: c1ccc2c(c1)ncn2-c1cncc(N[C@H]2CCCNC2)n1] | 6-(1H-benzimidazol-1-yl)-N-[(3S)-piperidin-3-yl]pyrazin-2-amine 1H NMR (400 MHz, MeOD) δ ppm 1.46-1.60 (m, 1H), 1.59-1.74 (m, 1H), 1.82 (ddd, J = 13.4, 3.8, 3.7 Hz, 1H), 1.89 (d, J = 3.5 Hz, 1H), 2.10-2.21 (m, 1H), 2.53 (dd, J = 11.9, 9.8 Hz, 1H), 2.57-2.64 (m, 1H), 2.96 (d, J = 12.6 Hz, 1H), 3.95-4.07 (m, 1H), 7.39 (d, J = 7.3 Hz, 1H), 7.45 (t, J = 7.3 Hz, 1H), 7.76 (d, J = 8.1 Hz, 1H), 7.88 (s, 1H), 8.14 (s, 1H), 8.17 (d, J = 8.2 Hz, 1H), 8.82 (s, 1H); LCMS: M + 1 295. Method B (Example 1). |
| 64 | 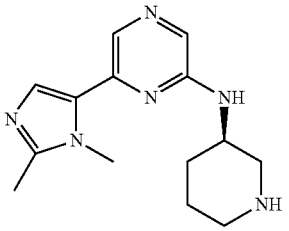 [SMILES: Cc1ncc(-c2cncc(N[C@@H]3CCCNC3)n2)n1C] | 6-(1,2-dimethyl-1H-imidazol-5-yl)-N-[(3R)-piperidin-3-yl]pyrazin-2-amine 1H NMR (400 MHz, DMSO-d6) δ ppm 1.48-1.64 (m, 1H) 2.67 (s, 3H) 2.74-2.84 (m, 1H) 2.85-2.96 (m, 1H) 3.07-3.25 (m, 2H) 3.27-3.37 (m, 1H) 3.42 (d, J = 7.55 Hz, 1H) 3.98 (s, 3H) 4.10-4.29 (m, 1H) 7.76 (d, J = 6.29 Hz, 1H) 8.03 (s, 1H) 8.15 (d, J = 3.78 Hz, 2H) 8.49 (br. s., 1H) 9.39 (br. s., 1H). Method A (Example 4). |

| Ex. | Structure | Name, Data and Preparation Method |
|---|---|---|
| 65 | 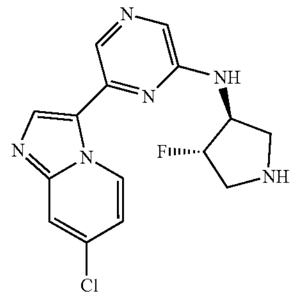 [SMILES: F[C@H]1CNC[C@@H]1Nc1cncc(-c2cnc3cc(Cl)ccn23)n1] | 6-(7-chloroimidazo[1,2-a]pyridin-3-yl)-N-[(3S,4S)-4-fluoropyrrolidin-3-yl]pyrazin-2-amine 1H NMR (400 MHz, D2O) δ ppm 3.58 (dd, J =13.26, 2.91 Hz, 1H), 3.67-3.85 (m, 2H), 3.98 (dd, J = 13.14, 6.82 Hz, 1H), 4.85 (dd, J = 14.02, 3.92 Hz, 1H), 5.39-5.56 (m, 1H), 7.55 (dd, J = 7.45, 1.89 Hz, 1H), 8.03 (s, 1H), 8.08 (d, J = 1.26 Hz, 1H), 8.43 (s, 1H), 8.31 (s, 1H), 9.67 (d, J = 7.33 Hz, 1H). Method A (Example 4). |
| 66 | 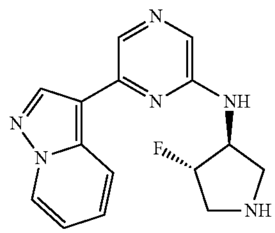 [SMILES: F[C@H]1CNC[C@@H]1Nc1cncc(-c2cnn3ccccc23)n1] | N-[(3S,4S)-4-fluoropyrrolidin-3-yl]-6-(pyrazolo[1,5-a]pyridin-3-yl)pyrazin-2-amine 1H NMR (400 MHz, MeOD) δ ppm 3.44-3.74 (m, 3H), 3.88 (dd, J = 12.4, 5.8 Hz, 1H), 4.77-4.88 (m, 1H), 5.44 (d, J = 52.0 Hz, 1H), 7.01 (t, J = 6.6 Hz, 1H), 7.36 (d, J = 8.1 Hz, 1H), 7.75 (br. s., 1H), 8.30 (s, 1H), 8.43-8.69 (m, 3H); LCMS m/z 299 (M + H). Method E (Example 6). |
| 67 | 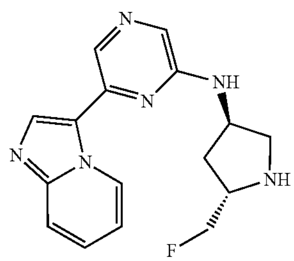 [SMILES: FC[C@@H]1C[C@@H](Nc2cncc(-c3cnc4ccccn34)n2)CN1] | N-[(3R,5S)-5-(fluoromethyl)pyrrolidin-3-yl]-6-imidazo[1,2-a]pyridin-3-ylpyrazin-2-amine 1H NMR (400 MHz, MeOD): δ ppm 2.19-2.11 (m, 2H), 3.20-3.16 (m, 1H), 3.50-3.47 (m, 1H), 3.95-3.80 (m, 1H), 4.70-4.39 (m, 3H), 7.09-7.06 (t, 1H), 7.45-7.43 (t, 1H), 7.65-7.63 (d, 1H), 7.77 (s, 1H), 8.21 (s, 1H), 8.28, (s, 1H), 9.76-9.74 (d, 1H). Method A (Example 26). |
| 68 | 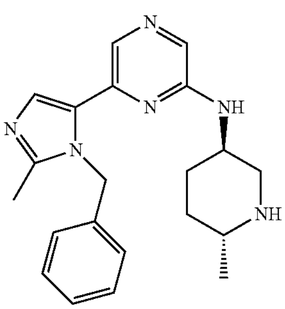 [SMILES: Cc1ncc(-c2cncc(N[C@@H]3CC[C@@H](C)NC3)n2)n1Cc1ccccc1] | 6-(1-benzyl-2-methyl-1H-imidazol-5-yl)-N-[(3R,6R)-6-methylpiperidin-3-yl]pyrazin-2-amine 1H NMR (400 MHz, MeOD) δ ppm 0.98 -1.11 (m, 1H) 1.13 (d, J = 6.55 Hz, 3H) 1.31-1.47 (m, 1H) 1.70-1.80 (m, 1H) 1.91 (s, 3H) 2.29 (s, 3H) 2.39-2.49 (m, 1H) 2.67-2.83 (m, 1H) 3.08-3.21 (m, 1H) 3.59-3.79 (m, 1H) 5.78 (dd, 2H) 7.08 (d, J = 7.05 Hz, 2H) 7.20-7.38 (m, 3H) 7.42 (s, 1H) 7.68 (s, 1H) 7.96 (s, 1H). Method A (Example 4). |
| 69 | 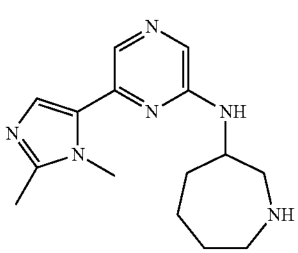 [SMILES: Cc1ncc(-c2cncc(NC3CCCCNC3)n2)n1C] | N-[6-(1,2-dimethyl-1H-imidazol-5-yl)pyrazin-2-yl]azepan-3-amine 1H NMR (400 MHz, MeOD) δ ppm 1.58-1.79 (m, 2H) 1.78-1.95 (m, 5H) 2.04-2.17 (m, 1H) 2.42 (s, 3H) 2.96-3.14 (m, 3H) 3.88 (s, 3H) 4.10-4.31 (m, 1H) 7.28 (s, 1H) 7.75 (s, 1H) 7.95 (s, 1H). Method A (Example 4). |

| Ex. | Structure | Name, Data and Preparation Method |
|---|---|---|
| 70 | 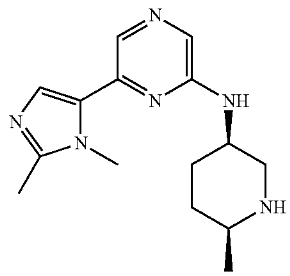 [SMILES: Cc1ncc(-c2cncc(N[C@@H]3CC[C@H](C)NC3)n2)n1C] | 6-(1,2-dimethyl-1H-imidazol-5-yl)-N-[(3R,6S)-6-methylpiperidin-3-yl]pyrazin-2-amine 1H NMR (400 MHz, MeOD) δ ppm 1.27 (d, J = 6.55 Hz, 3H) 1.89 (s, 3H) 1.92-2.07 (m, 2H) 2.41 (s, 3H) 2.99-3.17 (m, 2H) 3.43-3.55 (m, 2H) 3.86 (s, 3H) 4.08-4.18 (m, 1H) 7.27 (s, 1H) 7.83 (s, 1H) 8.01 (s, 1H) Method A (Example 4). |
| 71 | 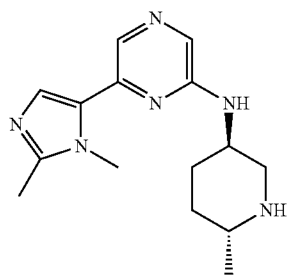 [SMILES: Cc1ncc(-c2cncc(N[C@@H]3CC[C@@H](C)NC3)n2)n1C] | 6-(1,2-dimethyl-1H-imidazol-5-yl)-N-[(3R,6R)-6-methylpiperidin-3-yl]pyrazin-2-amine 1H NMR (400 MHz, MeOD) δ ppm 1.29 (d, J = 6.29 Hz, 3H) 1.47-1.65 (m, 2H) 1.96-2.05 (m, 1H) 2.10-2.21 (m, 1H) 2.41 (s, 3H) 3.03-3.17 (m, 1H) 3.53-3.60 (m, 1H) 3.85 (s, 3H) 4.05-4.18 (m, 1H) 7.25 (s, 1H) 7.71 (s, 1H) 7.94 (s, 1H). Method A (Example 4). |
| 72 | 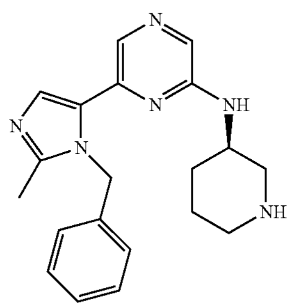 [SMILES: Cc1ncc(-c2cncc(N[C@@H]3CCCNC3)n2)n1Cc1ccccc1] | 6-(1-benzyl-2-methyl-1H-imidazol-5-yl)-N-[(3R)-piperidin-3-yl]pyrazin-2-amine 1H NMR (400 MHz, DMSO-d6) δ ppm 1.06-1.32 (m, 2H) 1.52 (d, J = 14.60 Hz, 1H) 1.61-1.72 (m, 1H) 2.20-2.23 (m, 3H) 2.63-2.73 (m, 1H) 2.81 (d, J = 12.09 Hz, 1H) 3.28-3.55 (m, 1H) 5.62-5.91 (m, 2H) 6.98 (t, J = 6.29 Hz, 3H) 7.27-7.33 (m, 2H) 7.46 (s, 1H) 7.71 (s, 1H) 7.99 (s, 1H) Method A (Example 4). |
| 73 | 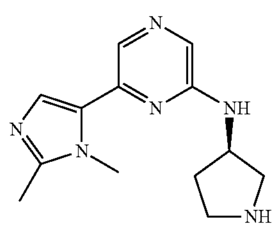 [SMILES: Cc1ncc(-c2cncc(N[C@@H]3CCNC3)n2)n1C] | 6-(1,2-dimethyl-1H-imidazol-5-yl)-N-[(3R)-pyrrolidin-3-yl]pyrazin-2-amine 1H NMR (400 MHz, DMSO-d6) δ ppm 1.90-2.05 (m, 1H) 2.17-2.30 (m, 1H) 2.30-2.36 (m, 1H) 2.66 (s, 3H) 3.04-3.19 (m, 1H) 3.20-3.31 (m, 2H) 3.95 (s, 3H) 4.38-4.53 (m, 1H) 8.04 (s, 1H) 8.13 (s, 1H) 8.17 (s, 1H) 9.36 (br. s., 1H) 9.48 (br. s., 1H). Method A (Example 4). |
| 74 | 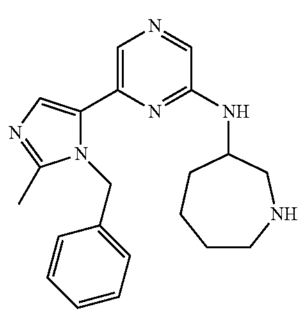 [SMILES: Cc1ncc(-c2cncc(NC3CCCCNC3)n2)n1Cc1ccccc1] | N-[6-(1-benzyl-2-methyl-1H-imidazol-5-yl)pyrazin-2-yl]azepan-3-amine 1H NMR (400 MHz, DMSO-d6) δ ppm 1.16-1.31 (m, 1H) 1.35-1.44 (m, 1H) 1.45-1.58 (m, J = 7.30 Hz, 3H) 1.58-1.67 (m, 1H) 1.87 (s, 3H) 2.56-2.64 (m, 1H) 2.64-2.77 (m, 2H) 3.56-3.66 (m, J = 8.56 Hz, 1H) 5.68-5.86 (m, 2H) 6.95 (t, J = 8.31 Hz, 3H) 7.26-7.32 (m, 2H) 7.44 (s, 1H) 7.72 (s, 1H) 7.96 (s, 1H). Method A (Example 4). |

| Ex. | Structure | Name, Data and Preparation Method |
|---|---|---|
| 75 | 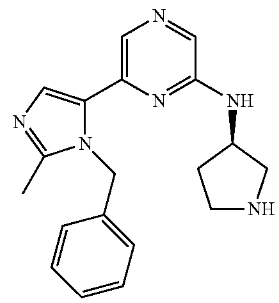 [SMILES: Cc1ncc(-c2cncc(N[C@@H]3CCNC3)n2)n1Cc1ccccc1] | 6-(1-benzyl-2-methyl-1H-imidazol-5-yl)-N-[(3R)-pyrrolidin-3-yl]pyrazin-2-amine 1H NMR (400 MHz, DMSO-d6) δ ppm 1.41-1.54 (m, 1H) 1.67-1.78 (m, 1H) 2.21-2.25 (m, 3H) 2.52-2.59 (m, 1H) 2.65-2.76 (m, 2H) 2.82-2.94 (m, 1H) 3.82-4.01 (m, J = 6.55 Hz, 1H) 5.76 (s, 2H) 6.96 (d, J = 7.05 Hz, 2H) 7.21-7.38 (m, 3H) 7.46 (s, 1H) 7.69 (s, 1H) 8.02 (s, 1H). Method A (Example 4). |
| 76 | 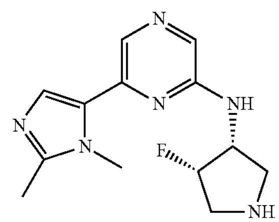 [SMILES: Cc1ncc(-c2cncc(N[C@@H]3CNC[C@@H]3F)n2)n1C] | 6-(1,2-dimethyl-1H-imidazol-5-yl)-N-[(3R,4S)-4-fluoropyrrolidin-3-yl]pyrazin-2-amine 1H NMR (400 MHz, DMSO-d6) δ ppm 1.90 (s, 1H) 2.33 (s, 3H) 3.01 (d, J = 15.61 Hz, 1H) 3.17-3.27 (m, 1H) 3.42-3.55 (m, 1H) 3.84 (s, 3H) 4.39 (d, J = 17.88 Hz, 1H) 5.13 (d, J = 52.12 Hz, 1H) 7.37 (s, 1H) 7.79 (s, 1H) 8.11 (s, 1H). Method A (Example 4). |
| 77 | 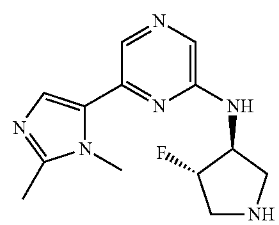 [SMILES: Cc1ncc(-c2cncc(N[C@H]3CNC[C@@H]3F)n2)n1C] | 6-(1,2-dimethyl-1H-imidazol-5-yl)-N-[(3S,4S)-4-fluoropyrrolidin-3-yl]pyrazin-2-amine 1H NMR (400 MHz, DMSO-d6) δ ppm 2.89 (s, 3H) 3.18-3.32 (m, 2H) 3.74-3.83 (m, 2H) 4.35 (s, 3H) 5.35-5.83 (m, 1H) 7.32 (d, J = 9.06 Hz, 1H) 7.79 (s, 1H) 8.43 (s, 1H) 8.54 (s, 1H). Method A (Example 4). |
| 78 | 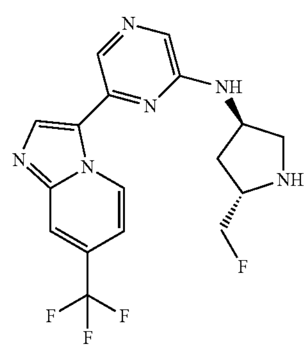 [SMILES: FC[C@@H]1C[C@@H](Nc2cncc(-c3cnc4cc(C(F)(F)F)ccn34)n2)CN1] | N-[(3R,5S)-5-(fluoromethyl)pyrrolidin-3-yl]-6-[7-(trifluoromethyl)imidazo[1,2-a]pyridin-3-yl]pyrazin-2-amine 1H NMR (400 MHz, MeOD): δ ppm 2.47-2.24 (m, 2H), 3.48-3.30 (m, 1H), 3.70-3.62 (m, 1H), 4.22-4.09 (m, 1H), 4.79-4.56 (m, 3H), 7.34-7.32 (d, 1H), 7.90 (s, 1H), 8.03 (s, 1H), 8.42-8.39 (d, 2H), 9.88-9.86 (d, 1H). Method A (Example 26). |
| 79 | 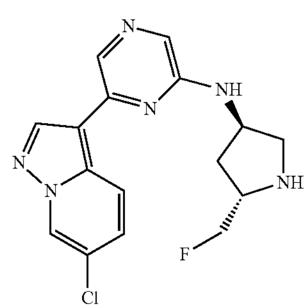 [SMILES: FC[C@@H]1C[C@@H](Nc2cncc(-c3cnn4cc(Cl)ccc34)n2)CN1] | 6-(6-chloropyrazolo[1,5-a]pyridin-3-yl)-N-[(3R,5S)-5-(fluoromethyl)pyrrolidin-3-yl]pyrazin-2-amine 1H NMR (400 MHz, MeOD): δ ppm 2.12-2.04 (m, 2H), 3.03-3.09 (m, 1H), 3.44-3.40 (m, 1H), 3.81-3.70 (m, 1H), 4.62-4.40 (m, 3H), 7.41-7.38 (d, 1H), 7.70 (s, 1H), 8.19 (s, 1H), 8.55-8.52 (m, 2H), 8.76 (s, 1H). Method A (Example 26). |

-continued

| Ex. | Structure | Name, Data and Preparation Method |
|---|---|---|
| 80 | 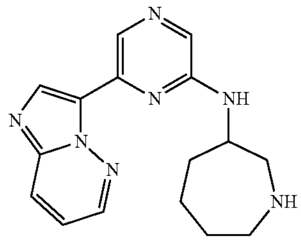 [SMILES: c1cnn2c(-c3cncc(NC4CCCCNC4)n3)cnc2c1] | N-(6-imidazo[1,2-b]pyridazin-3-ylpyrazin-2-yl)azepan-3-amine, acetate salt 1H NMR (400 MHz, DMSO-d6) δ ppm 1.43-1.75 (m, 4H) 1.88 (s, 3H) 1.90-2.02 (m, 1H) 2.63-2.73 (m, 1H) 2.79 (t, J = 5.79 Hz, 2H) 3.05 (dd, J = 13.47, 4.41 Hz, 1H) 3.93-4.14 (m, J = 7.05 Hz, 1H) 7.09 (d, J = 7.05 Hz, 1H) 7.36 (dd, J = 9.19, 4.41 Hz, 1H) 7.93 (s, 1H) 8.28 (dd, J = 9.32, 1.76 Hz, 1H) 8.39 (s, 1H) 8.74 (dd, J = 4.53, 1.51 Hz, 1H) 8.83 (s, 1H). Method A (Example 4). |
| 81 | 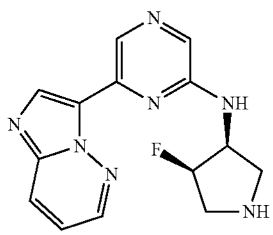 [SMILES: F[C@@H]1CNC[C@@H]1Nc1cncc(-c2cnc3cccnn23)n1] | N-[(3S,4R)-4-fluoropyrrolidin-3-yl]-6-imidazo[1,2-b]pyridazin-3-ylpyrazin-2-amine, acetate salt 1H NMR (400 MHz, DMSO-d6) δ ppm 1.83 (s, 3H) 2.52-2.67 (m, 1H) 2.94 (dd, J = 29.84, 13.47 Hz, 1H) 4.13-4.38 (m, 1H) 4.97-5.40 (m, 1H) 7.24-7.39 (m, 2H) 7.99 (s, 1H) 8.23 (dd, J = 9.19, 1.64 Hz, 1H) 8.44 (s, 1H) 8.70 (dd, J = 4.53, 1.51 Hz, 1H) 8.86 (s, 1H). Method A (Example 4). |
| 82 | 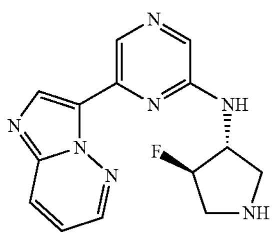 [SMILES: F[C@@H]1CNC[C@H]1Nc1cncc(-c2cnc3cccnn23)n1] | N-[(3R,4R)-4-fluoropyrrolidin-3-yl]-6-imidazo[1,2-b]pyridazin-3-ylpyrazin-2-amine 1H NMR (400 MHz, DMSO-d6) δ ppm 1.80-1.87 (m, 3H) 2.64-2.75 (m, 1H) 2.92-3.11 (m, 2H) 4.22-4.46 (m, 1H) 5.05 (d, J = 54.39 Hz, 1H) 7.38 (dd, J = 9.06, 4.53 Hz, 2H) 7.94 (s, 1H) 8.21-8.32 (m, 1H) 8.43 (s, 1H) 8.75 (dd, J = 4.66, 1.64 Hz, 1H) 8.94 (s, 1H). Method A (Example 4). |
| 83 | 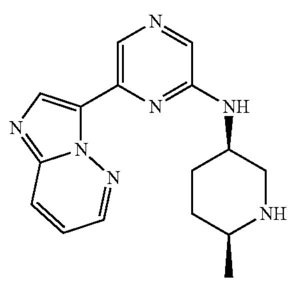 [SMILES: C[C@H]1CC[C@@H](Nc2cncc(-c3cnc4cccnn34)n2)CN1] | 6-imidazo[1,2-b]pyridazin-3-yl-N-[(3R,6S)-6-methylpiperidin-3-yl]pyrazin-2-amine, acetate salt 1H NMR (400 MHz, DMSO-d6) δ ppm 0.96-1.03 (m, 1H) 1.04 (d, J = 6.29 Hz, 3H) 1.27-1.50 (m, 2H) 1.57-1.72 (m, 1H) 1.89 (s, 3H) 1.91-1.96 (m, 1H) 2.59-2.69 (m, 1H) 2.84 (dd, J = 12.59, 2.77 Hz, 1H) 2.99 (d, J = 12.59 Hz, 1H) 3.95-4.08 (m, 1H) 7.14 (d, J = 7.05 Hz, 1H) 7.36 (dd, J = 9.19, 4.41 Hz, 1H) 8.05 (s, 1H) 8.27 (dd, J = 9.32, 1.76 Hz, 1H) 8.36 (s, 1H) 8.73 (dd, J = 4.41, 1.64 Hz, 1H) 8.83 (s, 1H). Method A (Example 4). |
| 84 | 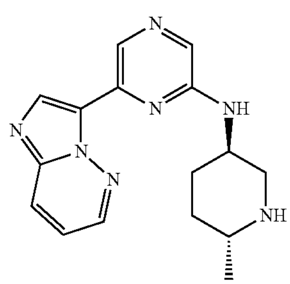 [SMILES: C[C@@H]1CC[C@@H](Nc2cncc(-c3cnc4cccnn34)n2)CN1] | 6-imidazo[1,2-b]pyridazin-3-yl-N-[(3R,6R)-6-methylpiperidin-3-yl]pyrazin-2-amine, acetate salt 1H NMR (400 MHz, DMSO-d6) δ ppm 1.02 (d, J = 6.29 Hz, 3H) 1.16-1.28 (m, 1H) 1.28-1.44 (m, 1H) 1.62-1.75 (m, 1H) 1.86 (s, 3H) 2.03 (d, J = 11.83 Hz, 1H) 2.22-2.34 (m, 1H) 3.19-3.35 (m, 1H) 3.67-3.90 (m, 1H) 7.05 (d, J = 7.30 Hz, 1H) 7.36 (dd, J = 9.19, 4.41 Hz, 1H) 7.87 (s, 1H) 8.28 (dd, J = 9.19, 1.64 Hz, 1H) 8.41 (s, 1H) 8.74 (dd, J = 4.53, 1.51 Hz, 1H) 8.83 (s, 1H). Method A (Example 4). |
| 85 | 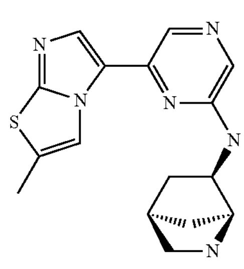 [SMILES: Cc1cn2c(-c3cncc(N[C@@H]4C[C@@H]5CN[C@H]4C5)n3)cnc2s1] | (1S,4R,6R)-2-Aza-bicyclo[2.2.1]hept-6-yl-[6-(2-methyl-imidazo[2,1-b]thiazol-5-yl)-pyrazin-2-yl]-amine 1H NMR (400 MHz, DMSO-d6) δ ppm 1.39-1.51 (m, 1H), 1.73-1.84 (m, 1H), 1.96-2.05 (m, 1H), 2.20-2.34 (m, 1H), 2.56 (s, 3H), 2.65-2.73 (m, 1H), 3.13 (br. s., 2H), 4.17 (br. s., 1H), 4.35-4.53 (m, 1H), 7.91-8.06 (m, 2H), 8.29-8.45 (m, 3H), 8.53 (br. s., 1H), 9.80 (br. s., 1H). Method A (Example 7). |

| Ex. | Structure | Name, Data and Preparation Method |
|---|---|---|
| 86 | 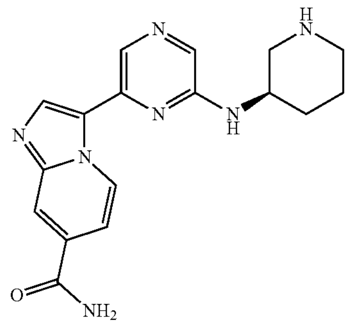 [SMILES: NC(=O)c1ccn2c(-c3cncc(N[C@@H]4CCCNC4)n3)cnc2c1] | 3-{6-[(3R)-piperidin-3-ylamino]pyrazin-2-yl}imidazo[1,2-a]pyridine-7-carboxamide 1H NMR (400 MHz, MeOD): δ ppm 1.801-1.727 (m, 1H), 1.975-1.860 (m, 1H), 2.162-2.2.113 (m, 1H), 2.277-2.245 (m, 1H), 3.105-3.040 (m, 2H), 3.350-3.326 (m, 1H), 3.606-3.576 (d, 3H), 4.327-4.281 (m, 1H), 7.601-7.579 (m, 1H), 7.882 (s, 1H), 8.224 (s, 1H), 8.365-8.355 (d, 2H), 8.508 (s, 1H), 9.67 (d, 1H). Method F (Example 24) |
| 87 | 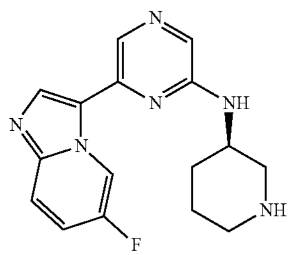 [SMILES: Fc1ccc2ncc(-c3cncc(N[C@@H]4CCCNC4)n3)n2c1] | 6-(6-fluoroimidazo[1,2-a]pyridin-3-yl)-N-[(3R)-piperidin-3-yl]pyrazin-2-amine 1H NMR (400 MHz, DMSO-d6) δ ppm 1.63 (d, J = 9.82 Hz, 1H) 1.80 (dd, J = 10.07, 3.78 Hz, 1H) 1.92-2.03 (m, 1H) 2.03-2.15 (m, 1H) 2.97 (d, J = 3.78 Hz, 2H) 3.18 (d, J = 18.38 Hz, 1H) 3.28-3.43 (m, 1H) 4.23 (s, 1H) 7.94-8.00 (m, 1H) 8.03-8.07 (m, 2H) 8.08-8.15 (m, 1H) 8.46 (s, 1H) 8.96 (s, 1H) 9.36 (d, J = 3.27 Hz, 1H) 9.88 (br. s., 1H). Method A (Example 7). |
| 88 | 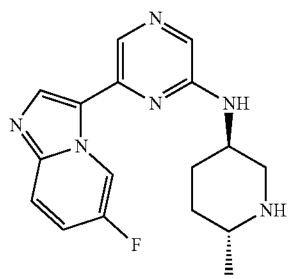 [SMILES: C[C@@H]1CC[C@@H](Nc2cncc(-c3cnc4ccc(F)cn34)n2)CN1] | 6-(6-fluoroimidazo[1,2-a]pyridin-3-yl)-N-[(3R,6R)-6-methylpiperidin-3-yl]pyrazin-2-amine 1H NMR (400 MHz, MeOD) δ ppm 1.37 (d, 3H) 1.62-1.76 (m, 2H) 2.07-2.18 (m, 1H) 2.25-2.39 (m, 1H) 2.68 (s, 1H) 2.93 (t, J = 11.96 Hz, 1H) 3.56-3.69 (m, 1H) 4.12-4.34 (m, 1H) 8.04 (s, 1H) 8.11 (dd, J = 6.04, 1.51 Hz, 2H) 8.34 (s, 1H) 8.76 (s, 1H) 9.85 (d, J = 4.28 Hz, 1H). Method A (Example 7). |
| 89 | 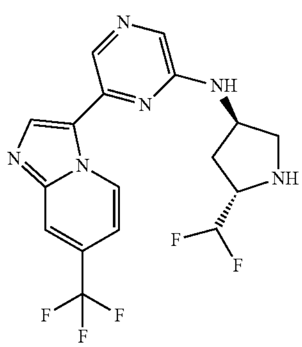 [SMILES: FC(F)[C@@H]1C[C@@H](Nc2cncc(-c3cnc4cc(C(F)(F)F)ccn34)n2)CN1] | N-[(3R,5S)-5-(difluoromethyl)pyrrolidin-3-yl]-6-[7-(trifluoromethyl)imidazo[1,2-a]pyridin-3-yl]pyrazin-2-amine 1H NMR (400 MHz, MeOD): δ ppm 2.19-2.10 (m, 1H), 2.38-2.33 (m, 1H), 3.21-3.15 (m, 1H), 3.41-3.37 (m, 1H), 3.91-3.80 (m, 1H), 4.64-4.60 (m, 1H), 6.10-5.81 (m, 1H), 7.35-7.33 (d, 1H), 7.87 (s, 1H), 8.05 (s, 1H), 8.38 (s, 1H), 8.45 (s, 1H), 9.99-9.97 (d, 1H). Method A (Example 7). |
| 90 | 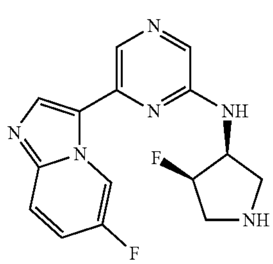 [SMILES: Fc1ccc2ncc(-c3cncc(N[C@H]4CNC[C@H]4F)n3)n2c1] | 6-(6-fluoroimidazo[1,2-a]pyridin-3-yl)-N-[(3S,4R)-4-fluoropyrrolidin-3-yl]pyrazin-2-amine 1H NMR (400 MHz, MeOD) δ ppm 3.12 (t, J = 10.83 Hz, 1H) 3.45-3.49 (m, 1H) 3.52-3.59 (m, 1H) 3.58-3.66 (m, 1H) 4.63-4.82 (m, 1H) 5.20-5.49 (m, 1H) 7.36-7.48 (m, 1H) 7.68 (dd, J = 9.69, 4.91 Hz, 1H) 7.90 (s, 1H) 8.26 (s, 1H) 8.31 (s, 1H) 9.63 (dd, J = 5.16, 1.89 Hz, 1H). Method A (Example 7). |

| Ex. | Structure | Name, Data and Preparation Method |
|---|---|---|
| 91 | 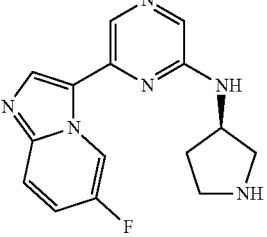 | 6-(6-fluoroimidazo[1,2-a]pyridin-3-yl)-N-[(3R)-pyrrolidin-3-yl]pyrazin-2-amine 1H NMR (400 MHz, DMSO-d6) δ ppm 1.72-1.85 (m, 1H) 2.04-2.21 (m, 1H) 2.88-2.99 (m, 2H) 3.00-3.09 (m, 1H) 3.19 (dd, J = 11.46, 6.17 Hz, 1H) 4.26-4.38 (m, 1H) 7.44-7.56 (m, 1H) 7.67 (d, J = 6.04 Hz, 1H) 7.76-7.81 (m, 1H) 7.82 (s, 1H) 8.38 (s, 1H) 8.46 (s, 1H) 9.88 (dd, J = 5.54, 2.27 Hz, 1H). Method A (Example 7). |
| 92 | 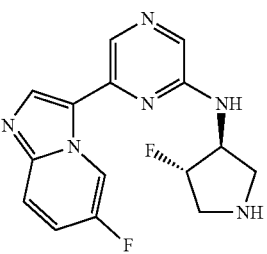 [SMILES: Fc1ccc2ncc(-c3cncc(N[C@H]4CNC[C@@H]4F)n3)n2c1] | 6-(6-fluoroimidazo[1,2-a]pyridin-3-yl)-N-[(3S,4S)-4-fluoropyrrolidin-3-yl]pyrazin-2-amine 1H NMR (400 MHz, DMSO-d6) δ ppm 2.77 (dd, J = 11.83, 4.28 Hz, 1H) 2.87-3.09 (m, 2H) 3.41 (dd, J = 11.83, 6.80 Hz, 1H) 4.15-4.39 (m, 1H) 5.06 (d, J = 52.88 Hz, 1H) 7.39 (d, J = 4.78 Hz, 1H) 7.44-7.54 (m, 1H) 7.73-7.81 (m, 1H) 7.84 (s, 1H) 8.46 (s, 1H) 8.50 (s, 1H) 9.93 (dd, J = 5.54, 2.01 Hz, 1H). Method A (Example 7). |
| 93 | 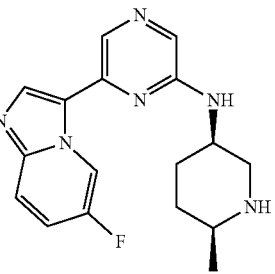 | 6-(6-fluoroimidazo[1,2-a]pyridin-3-yl)-N-[(3R,6S)-6-methylpiperidin-3-yl]pyrazin-2-amine 1H NMR (400 MHz, DMSO-d6) δ ppm 1.15 (d, J = 6.29 Hz, 3H) 1.48-1.65 (m, 2H) 1.71-1.86 (m, 1H) 1.90 (none, 1H) 1.97 (d, J = 13.09 Hz, 1H) 2.91 (br. s., 1H) 3.05 (dd, J = 12.72, 2.64 Hz, 1H) 3.22 (d, J = 12.59 Hz, 1H) 3.93-4.22 (m, 1H) 7.44-7.51 (m, 1H) 7.52-7.57 (m, 1H) 7.80 (dd, J = 9.82, 5.54 Hz, 1H) 7.94 (s, 1H) 8.37 (s, 1H) 8.46 (s, 1H) 9.75 (dd, J = 5.54, 2.27 Hz, 1H). Method A (Example 7). |
| 94 | 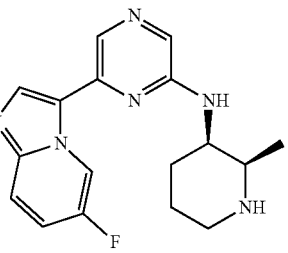 | 6-(6-fluoroimidazo[1,2-a]pyridin-3-yl)-N-[(2R,3R)-2-methylpiperidin-3-yl]pyrazin-2-amine 1H NMR (400 MHz, DMSO-d6) δ ppm 1.05 (d, J = 6.55 Hz, 3H) 1.29-1.48 (m, 1H) 1.55-1.71 (m, 2H) 2.01 (d, J = 7.81 Hz, 1H) 2.58-2.73 (m, 1H) 2.87-3.09 (m, 2H) 4.00 (d, J = 5.79 Hz, 1H) 7.28 (d, J = 8.31 Hz, 1H) 7.42-7.54 (m, 1H) 7.74-7.84 (m, 1H) 8.04 (s, 1H) 8.31 (s, 1H) 8.43 (s, 1H) 9.78 (dd, J = 5.41, 2.14 Hz, 1H). Method A (Example 7). |
| 95 | 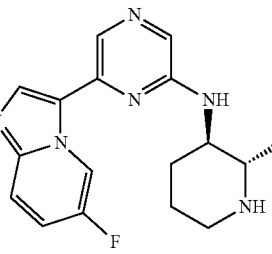 | 6-(6-fluoroimidazo[1,2-a]pyridin-3-yl)-N-[(2S,3R)-2-methylpiperidin-3-yl]pyrazin-2-amine 1H NMR (400 MHz, DMSO-d6) δ ppm 1.09 (d, J = 6.04 Hz, 3H) 1.19-1.37 (m, 1H) 1.46-1.61 (m, 1H) 1.63-1.73 (m, 1H) 2.17 (d, J = 9.57 Hz, 1H) 2.58-2.67 (m, 1H) 2.94 (d, J = 12.09 Hz, 1H) 3.48 (d, J = 8.06 Hz, 1H) 7.25 (d, J = 8.56 Hz, 1H) 7.45-7.55 (m, 1H) 7.76-7.85 (m, 2H) 8.33 (s, 1H) 8.46 (s, 1H) 9.86 (dd, J = 5.41, 2.14 Hz, 1H). Method A (Example 7). |
| 96 | 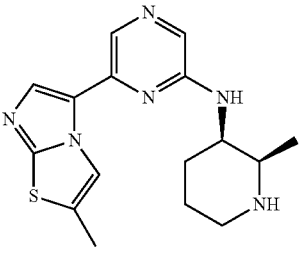 [SMILES: Cc1cn2c(-c3cncc(N[C@@H]4CCCN[C@@H]4C)n3)cnc2s1] | 6-(2-methylimidazo[2,1-b][1,3]thiazol-5-yl)-N-[(2R,3R)-2-methylpiperidin-3-yl]pyrazin-2-amine 1H NMR (400 MHz, DMSO-d6) δ ppm 1.03 (d, J = 6.55 Hz, 3H) 1.31-1.44 (m, 1H) 1.63 (d, J = 9.06 Hz, 2H) 1.89 (s, 3H) 1.90-1.98 (m, J = 5.04 Hz, 1H) 2.59-2.68 (m, 1H) 2.90-3.07 (m, 2H) 3.98 (d, J = 5.79 Hz, 1H) 7.09 (d, J = 7.81 Hz, 1H) 7.92 (s, 1H) 7.95 (s, 1H) 8.15 (s, 1H) 8.23 (br. s., 1H). Method A (Example 7). |

| Ex. | Structure | Name, Data and Preparation Method |
|---|---|---|
| 97 | 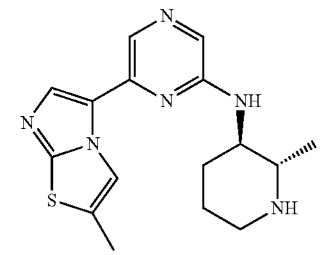 [SMILES: Cc1cn2c(-c3cncc(N[C@@H]4CCCN[C@H]4C)n3)cnc2s1] | 6-(2-methylimidazo[2,1-b][1,3]thiazol-5-yl)-N-[(2S,3R)-2-methylpiperidin-3-yl]pyrazin-2-amine 1H NMR (400 MHz, DMSO-d6) δ ppm 1.07 (d, J = 6.04 Hz, 3H) 1.16-1.32 (m, 1H) 1.45-1.61 (m, 1H) 1.65-1.75 (m, 1H) 1.89 (s, 3H) 2.07-2.21 (m, 1H) 2.56-2.63 (m, 1H) 2.95 (d, J = 12.09 Hz, 1H) 3.28-3.55 (m, 1H) 7.11 (d, J = 8.06 Hz, 1H) 7.74 (s, 1H) 7.95 (s, 1H) 8.17 (s, 1H) 8.30 (br. s., 1H). Method A (Example 7). |
| 98 | 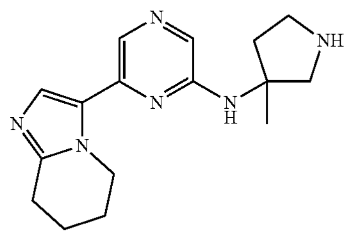 [SMILES: CC1(Nc2cncc(-c3cnc4n3CCCC4)n2)CCNC1] | N-(3-methylpyrrolidin-3-yl)-6-(5,6,7,8-tetrahydroimidazo[1,2-a]pyridin-3-yl)pyrazin-2-amine 1H NMR (400 MHz, MeOD) δ ppm 1.65 (s, 1H) 1.90 (s, 3H) 1.92-2.13 (m, 4H) 2.40-2.52 (m, 3H) 2.92 (t, J = 6.3 Hz, 2H) 3.14 (d, J = 11.8 Hz, 1H) 3.36-3.46 (m, 2H) 4.02 (d, J = 11.8 Hz, 1H) 4.25-4.43 (m, 2H) 7.37 (s, 1H) 7.78 (s, 1H) 8.02 (s, 1H). Method A (Example 7). |
| 99 | 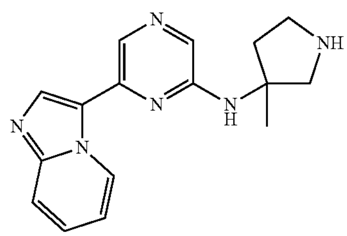 [SMILES: CC1(Nc2cncc(-c3cnc4ccccn34)n2)CCNC1] | 6-imidazo[1,2-a]pyridin-3-yl-N-(3-methylpyrrolidin-3-yl)pyrazin-2-amine 1H NMR (400 MHz, MeOD) δ ppm 1.74 (s, 2H) 1.90 (s, 3H) 2.06-2.22 (m, 2H) 3.15-3.25 (m, 1H) 3.36-3.45 (m, 2H) 3.95-4.08 (m, 1H) 7.06-7.19 (m, 1H) 7.43-7.52 (m, 1H) 7.65-7.73 (m, 1H) 7.83-7.88 (m, 1H) 8.19-8.23 (m, 1H) 8.29-8.34 (m, 1H) 9.40-9.60 (m, 1H). Method A (Example 7). |
| 100 | 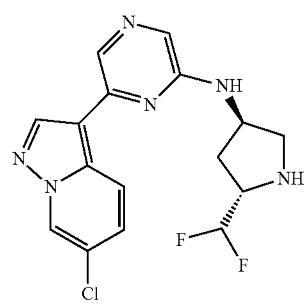 [SMILES: FC(F)[C@@H]1C[C@@H](Nc2cncc(-c3cnn4cc(Cl)ccc34)n2)CN1] | 6-(6-chloropyrazolo[1,5-a]pyridin-3-yl)-N-[(3R,5S)-5-(difluoromethyl)pyrrolidin-3-yl]pyrazin-2-amine 1H NMR (400 MHz, MeOD): δ ppm 2.00-1.95 (m, 1H), 2.24-2.17 (m, 1H), 3.03-2.98 (m, 1H), 3.23-3.18 (m, 1H), 3.72-3.65 (m, 1H), 4.49-4.47 (m, 1H), 5.91-5.63 (m, 1H), 7.30-7.28 (d, 1H), 7.61 (s, 1H), 8.10 (s, 1H), 8.44-8.39 (m, 2H), 8.64 (s, 1H). Method A (Example 7). |
| 101 | 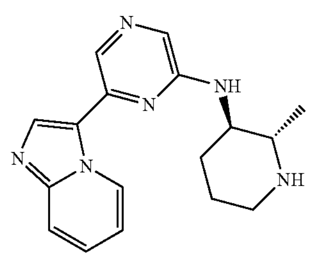 [SMILES: C[C@@H]1NCCC[C@H]1Nc1cncc(-c2cnc3ccccn23)n1] | 6-imidazo[1,2-a]pyridin-3-yl-N-[(2S,3R)-2-methylpiperidin-3-yl]pyrazin-2-amine 1H NMR (400 MHz, DEUTERIUM OXIDE) δ ppm 1.29 (d, J = 6.57 Hz, 3H) 1.45-1.63 (m, 1H) 1.67-1.86 (m, 1H) 1.97 (dd, J = 11.75, 2.91 Hz, 1H) 2.07-2.22 (m, 1H) 2.94 (td, J = 12.76, 3.03 Hz, 1H) 3.12-3.28 (m, 1H) 3.34 (d, J = 12.63 Hz, 1H) 4.08 (td, J = 10.67, 3.92 Hz, 1H) 7.37-7.56 (m, 1H) 7.90 (d, J = 5.31 Hz, 3H) 8.12 (s, 1H) 8.33 (s, 1H) 9.48 (d, J = 7.07 Hz, 1H). Method A (Example 4). |
| 102 | 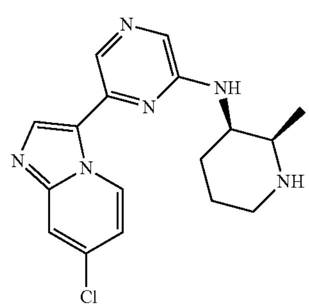 [SMILES: C[C@H]1NCCC[C@H]1Nc1cncc(-c2cnc3cc(Cl)ccn23)n1] | 6-(7-chloroimidazo[1,2-a]pyridin-3-yl)-N-[(2R,3R)-2-methylpiperidin-3-yl]pyrazin-2-amine 1H NMR (400 MHz, DEUTERIUM OXIDE) δ ppm 1.23 (d, J = 6.82 Hz, 3H) 1.73-1.87 (m, 1H) 1.93 (br. s., 3H) 2.99-3.17 (m, 1H) 3.23-3.39 (m, 1H) 3.65-3.81 (m, 1H) 4.38-4.51 (m, 1H) 7.53 (d, J = 7.07 Hz, 1H) 7.91-8.10 (m, 2H) 8.12-8.25 (m, 1H) 8.35 (s, 1H) 9.47 (d, J = 7.33 Hz, 1H). Method A (Example 7). |

-continued

| Ex. | Structure | Name, Data and Preparation Method |
|---|---|---|
| 103 | 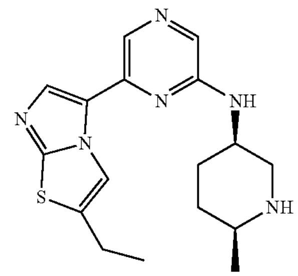 [SMILES: CCc1cn2c(-c3cncc(N[C@@H]4CC[C@H](C)NC4)n3)cnc2s1] | 6-(2-ethylimidazo[2,1-b][1,3]thiazol-5-yl)-N-[(3R,6S)-6-methylpiperidin-3-yl]pyrazin-2-amine 1H NMR (400 MHz, DMSO-d6) δ ppm 1.03 (d, J = 6.29 Hz, 3H) 1.20-1.40 (m, 6H) 1.41-1.51 (m, 1H) 1.90-2.02 (m, 1H) 2.79-2.93 (m, 3H) 3.00 (d, J = 13.09 Hz, 1H) 3.88-4.01 (m, J = 9.06 Hz, 1H) 7.09 (d, J = 7.55 Hz, 1H) 7.91 (d, J = 8.81 Hz, 2H) 8.17 (s, 1H) 8.26 (s, 1H). Method A (Example 7). |
| 104 | 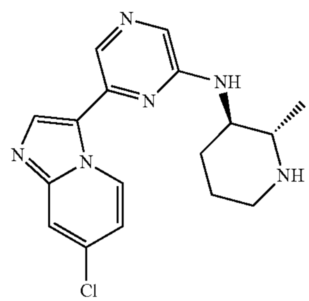 [SMILES: C[C@@H]1NCCC[C@H]1Nc1cncc(-c2cnc3cc(Cl)ccn23)n1] | 6-(7-chloroimidazo[1,2-a]pyridin-3-yl)-N-[(2S,3R)-2-methylpiperidin-3-yl]pyrazin-2-amine 1H NMR (400 MHz, DEUTERIUM OXIDE) δ ppm 1.34 (d, J = 6.57 Hz, 3H) 1.48-1.69 (m, 1H) 1.72-1.90 (m, 1H) 1.94-2.08 (m, 1H) 2.10-2.27 (m, 1H) 2.87-3.09 (m, 1H) 3.19-3.33 (m, 1H) 3.39 (d, J = 12.63 Hz, 1H) 4.01-4.22 (m, 1H) 7.49-7.68 (m, 1H) 7.95 (s, 1H) 8.08 (s, 1H) 8.17 (s, 1H) 8.39 (s, 1H) 9.52 (d, J = 7.33 Hz, 4H). Method A (Example 7). |
| 105 | 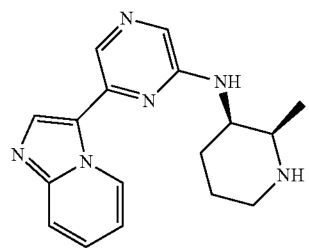 [SMILES: C[C@H]1NCCC[C@H]1Nc1cncc(-c2cnc3ccccn23)n1] | 6-imidazo[1,2-a]pyridin-3-yl-N-[(2R,3R)-2-methylpiperidin-3-yl]pyrazin-2-amine 1H NMR (400 MHz, DEUTERIUM OXIDE) δ ppm 1.21 (d, J = 7.07 Hz, 3H) 1.69-1.84 (m, 1H) 1.85-2.02 (m, 3H) 2.97-3.12 (m, 1H) 3.20-3.34 (m, 1H) 3.63-3.78 (m, 1H) 4.36-4.51 (m, 1H) 7.47 (t, J = 6.82 Hz, 1H) 7.84-8.03 (m, 3H) 8.15 (s, 1H) 8.33 (s, 1H) 9.46 (d, J = 7.07 Hz, 1H). Method A (Example 4). |
| 106 | 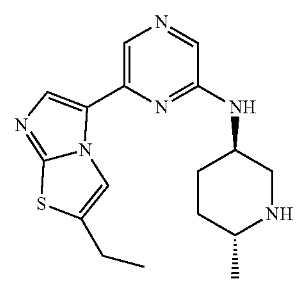 [SMILES: CCc1cn2c(-c3cncc(N[C@@H]4CC[C@@H](C)NC4)n3)cnc2s1] | 6-(2-ethylimidazo[2,1-b][1,3]thiazol-5-yl)-N-[(3R,6R)-6-methylpiperidin-3-yl]pyrazin-2-amine 1H NMR (400 MHz, DMSO-d6) δ ppm 1.29 (s, 1H) 1.30 (s, 3H) 1.32 (s, 2H) 1.41-1.58 (m, 1H) 1.67-1.84 (m, 1H) 1.86-1.99 (m, 1H) 2.15 (d, J = 13.60 Hz, 1H) 2.74-2.88 (m, J = 11.58 Hz, 1H) 3.01-3.11 (m, 2H) 3.15-3.26 (m, J = 9.57 Hz, 1H) 3.38 (d, J = 11.08 Hz, 1H) 4.32-4.43 (m, 1H) 7.89 (s, 1H) 8.31 (s, 1H) 8.35 (s, 1H) 8.46 (s, 1H) 9.24-9.42 (m, 1H) 9.90 (d, J = 12.34 Hz, 1H). Method A (Example 7). |
| 107 | 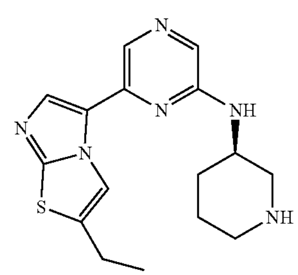 [SMILES: CCc1cn2c(-c3cncc(N[C@@H]4CCCNC4)n3)cnc2s1] | 6-(2-ethylimidazo[2,1-b][1,3]thiazol-5-yl)-N-[(3R)-piperidin-3-yl]pyrazin-2-amine 1H NMR (400 MHz, DMSO-d6) δ ppm 1.31 (t, 3H) 1.39-1.59 (m, 2H) 1.64-1.77 (m, 1H) 1.98-2.05 (m, J = 9.06 Hz, 1H) 2.45 (dd, J = 11.46, 8.94 Hz, 1H) 2.81-2.91 (m, 3H) 3.16 (d, J = 11.58 Hz, 1H) 3.69-3.90 (m, J = 3.02 Hz, 1H) 7.13 (d, J = 7.30 Hz, 1H) 7.76 (s, 1H) 7.94 (s, 1H) 8.18 (s, 1H) 8.32 (s, 1H). Method A (Example 7). |

| Ex. | Structure | Name, Data and Preparation Method |
|---|---|---|
| 108 | 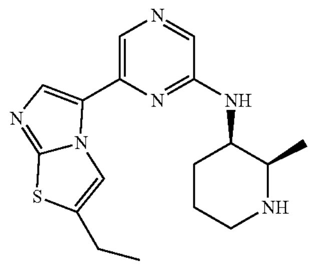 [SMILES: CCc1cn2c(-c3cncc(N[C@@H]4CCCN[C@@H]4C)n3)cnc2s1] | 6-(2-ethylimidazo[2,1-b][1,3]thiazol-5-yl)-N-[(2R,3R)-2-methylpiperidin-3-yl]pyrazin-2-amine 1H NMR (400 MHz, DMSO-d6) δ ppm 1.01 (d, J = 6.55 Hz, 3H) 1.30 (t, J = 7.43 Hz, 3H) 1.34-1.42 (m, 1H) 1.51-1.68 (m, 2H) 1.91-2.03 (m, 1H) 2.56-2.65 (m, 1H) 2.84 (q, 2H) 2.90-3.00 (m, 2H) 3.97 (d, J = 2.52 Hz, 1H) 6.99 (d, J = 8.06 Hz, 1H) 7.91 (s, 1H) 7.97 (s, 1H) 8.14 (s, 1H) 8.25 (s, 1H). Method A (Example 7). |
| 109 | 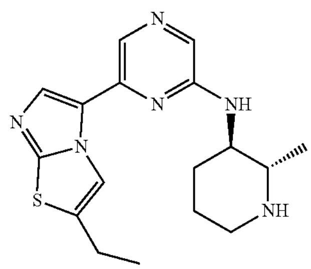 [SMILES: CCc1cn2c(-c3cncc(N[C@@H]4CCCN[C@H]4C)n3)cnc2s1] | 6-(2-ethylimidazo[2,1-b][1,3]thiazol-5-yl)-N-[(2S,3R)-2-methylpiperidin-3-yl]pyrazin-2-amine 1H NMR (400 MHz, DMSO-d6) δ ppm 1.14 (d, J = 6.29 Hz, 3H) 1.32 (t, J = 7.43 Hz, 3H) 1.48-1.68 (m, 1H) 1.69-1.82 (m, 1H) 2.08-2.18 (m, J = 12.34 Hz, 1H) 2.61-2.71 (m, 1H) 2.73-2.82 (m, 1H) 2.87 (q, 2H) 3.05 (d, J = 12.34 Hz, 1H) 3.67 (d, J = 12.34 Hz, 1H) 7.15 (d, J = 8.31 Hz, 1H) 7.76 (s, 1H) 7.93 (s, 1H) 8.19 (s, 1H) 8.28 (s, 1H). Method A (Example 7). |
| 110 | 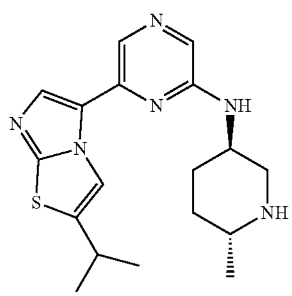 [SMILES: CC(C)c1cn2c(-c3cncc(N[C@@H]4CC[C@@H](C)NC4)n3)cnc2s1] | 6-(2-isopropylimidazo[2,1-b][1,3]thiazol-5-yl)-N-[(3R,6R)-6-methylpiperidin-3-yl]pyrazin-2-amine 1H NMR (400 MHz, DMSO-d6) δ ppm 1.03 (d, J = 6.29 Hz, 3H) 1.14-1.28 (m, J = 13.85 Hz, 1H) 1.27-1.35 (m, 1H) 1.37 (d, J = 6.80 Hz, 6H) 1.73 (d, J = 12.59 Hz, 1H) 2.05 (d, J = 13.35 Hz, 1H) 2.38 (t, J = 10.70 Hz, 1H) 2.58-2.70 (m, 1H) 3.09-3.23 (m, 1H) 3.69-3.85 (m, 1H) 7.10 (d, J = 7.55 Hz, 1H) 7.73 (s, 1H) 7.95 (s, 1H) 8.19 (s, 1H) 8.33 (s, 1H). Method A (Example 7). |
| 111 | 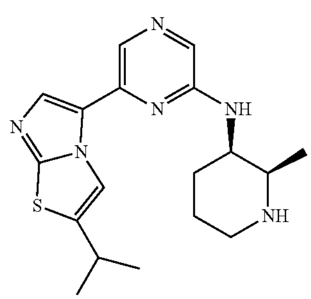 [SMILES: CC(C)c1cn2c(-c3cncc(N[C@@H]4CCCN[C@@H]4C)n3)cnc2s1] | 6-(2-isopropylimidazo[2,1-b][1,3]thiazol-5-yl)-N-[(2R,3R)-2-methylpiperidin-3-yl]pyrazin-2-amine 1H NMR (400 MHz, DMSO-d6) δ ppm 1.24 (d, J = 6.80 Hz, 3H) 1.33 (d, 6H) 1.59-1.69 (m, J = 6.04 Hz, 1H) 1.70-1.82 (m, 1H) 1.83-2.00 (m, 2H) 2.95 (t, J = 11.83 Hz, 1H) 3.14-3.27 (m, 3H) 3.46-3.59 (m, 1H) 4.15-4.39 (m, 1H) 7.61 (d, J = 8.06 Hz, 1H) 7.90 (s, 1H) 7.96 (s, 1H) 8.25 (s, 2H). Method A (Example 7). |
| 112 | 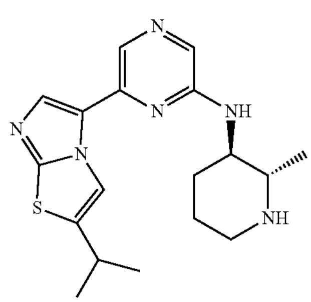 [SMILES: CC(C)c1cn2c(-c3cncc(N[C@@H]4CCCN[C@H]4C)n3)cnc2s1] | 6-(2-isopropylimidazo[2,1-b][1,3]thiazol-5-yl)-N-[(2S,3R)-2-methylpiperidin-3-yl]pyrazin-2-amine 1H NMR (400 MHz, DMSO-d6) δ ppm 1.31 (d, J = 6.55 Hz, 3H) 1.34 (d, 6H) 1.38-1.51 (m, 1H) 1.66-1.97 (m, 2H) 2.07-2.25 (m, 1H) 2.76-3.00 (m, 1H) 3.05-3.21 (m, 1H) 3.34-3.42 (m, 1H) 3.90-4.10 (m, 1H) 7.32 (d, J = 8.31 Hz, 1H) 7.80 (s, 1H) 7.95 s, 1H) 8.17 (s, 1H) 8.24 (s, 1H). Method A (Example 7). |

-continued

| Ex. | Structure | Name, Data and Preparation Method |
|---|---|---|
| 113 | 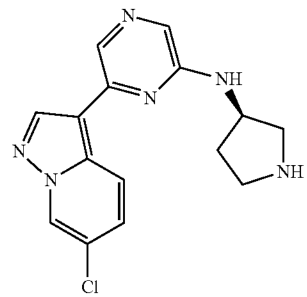 [SMILES: Clc1ccc2c(-c3cncc(N[C@@H]4CCNC4)n3)cnn2c1] | 6-(6-chloropyrazolo[1,5-a]pyridin-3-yl)-N-[(3R)-pyrrolidin-3-yl]pyrazin-2-amine 1H NMR (400 MHz, CDCl3): δ ppm 1.820-1.711 (m, 1H), 2.308-2.289 (m, 1H), 3.041-2.958 (m, 2H), 3.167-3.132 (m, 1H), 3.302-3.259 (m, 1H), 4.433-4.417 (m, 1H), 4.778-4.763 (d, 1H), 7.237-7.233 (d, 1H), 7.713 (s, 1H), 8.229 (s, 1H), 8.386 (s, 1H), 8.417-8.393 (d, 1H), 8.552-8.549 (d, 1H). Method A (Example 7). |
| 114 | 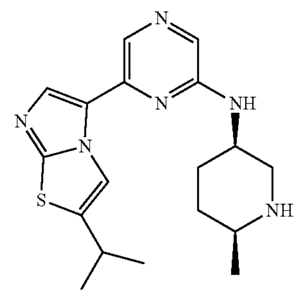 [SMILES: CC(C)c1cn2c(-c3cncc(N[C@@H]4CC[C@H](C)NC4)n3)cnc2s1] | 6-(2-isopropylimidazo[2,1-b][1,3]thiazol-5-yl)-N-[(3R,6S)-6-methylpiperidin-3-yl]pyrazin-2-amine 1H NMR (400 MHz, DMSO-d6) δ ppm 1.04 (d, J = 6.29 Hz, 3H) 1.33 (d, J = 6.80 Hz, 6H) 1.42-1.52 (m, 1H) 1.59-1.78 (m, 1H) 1.93-2.03 (m, 1H) 2.59-2.74 (m, 1H) 2.87 (dd, J = 12.46, 2.64 Hz, 1H) 3.05 (d, J = 12.34 Hz, 1H) 3.11-3.22 (m, 1H) 3.90-4.03 (m, 1H) 7.13 (d, J = 7.30 Hz, 1H) 7.91 (s, 1H) 7.93 (s, 1H) 8.18 (s, 1H) 8.24 (d, J = 1.26 Hz, 1H). Method A (Example 7). |
| 115 | 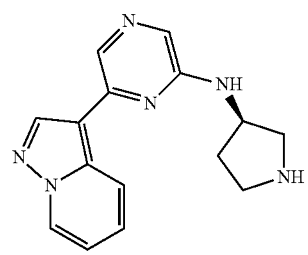 [SMILES: c1ccn2ncc(-c3cncc(N[C@@H]4CCNC4)n3)c2c1] | 6-pyrazolo[1,5-a]pyridin-3-yl-N-[(3R)-pyrrolidin-3-yl]pyrazin-2-amine 1H NMR (400 MHz, MeOD): δ ppm 2.231-2.199 (m, 1H), 2.510-2.459 (m, 1H), 3.570-3.306 (m, 3H), 3.710-3.665 (m, 1H), 4.773-4.732 (m, 1H), 7.037-7.000 (m, 1H), 7.442-7.403 (m, 1H), 7.734 (s, 1H), 8.239 (s, 1H), 8.435-8.413 (d, 1H), 8.533 (s, 1H), 8.614-8.596 (d, 1H). Method A (Example 4). |
| 116 | 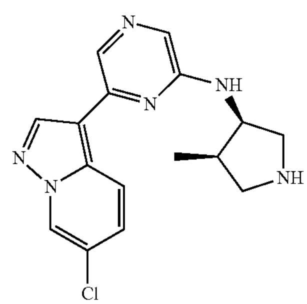 [SMILES: C[C@@H]1CNC[C@@H]1Nc1cncc(-c2cnn3cc(Cl)ccc23)n1] | 6-(6-chloropyrazolo[1,5-a]pyridin-3-yl)-N-[(3R,4R)-4-methylpyrrolidin-3-yl]pyrazin-2-amine 1H NMR (400 MHz, CDCl3): δ ppm 1.059-1.041 (m, 3H), 2.544-2.488 (m, 1H), 2.764-2.743 (m, 1H), 2.991-2.952 (m, 1H), 3.355-3.308 (m, 1H), 3.469-3.426 (m, 1H), 4.552-4.524 (m, 1H), 4.919-4.902 (m, 1H), 7.239-7.234 (d, 1H), 7.756 (s, 1H) 8.211 (s, 1H), 8.384-8.358 (m, 2H), 8.549-8.547 (d, 1H). Method A (Example 4). |
| 117 | 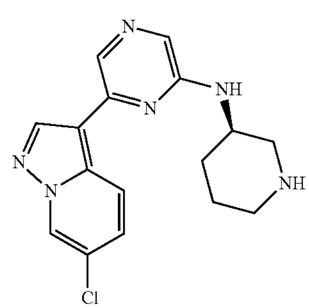 [SMILES: Clc1ccc2c(-c3cncc(N[C@@H]4CCCNC4)n3)cnn2c1] | 6-(6-chloropyrazolo[1,5-a]pyridin-3-yl)-N-[(3R)-piperidin-3-yl]pyrazin-2-amine 1H NMR (400 MHz, CDCl3): δ ppm 1.719-1.700 (m, 2H), 2.012-1.910 (m, 1H), 2.898-2.760 (m, 3H), 3.249-3.220 (d, 1H), 4.015-4.007 (m, 1H), 5.004-4.996 (m, 1H), 7.240-7.236 (d, 1H), 7.717 (s, 1H), 8.184 (s, 1H), 8.409-8.380 (m, 2H), 8.543 (s, 1H). Method A (Example 4). |

-continued

| Ex. | Structure | Name, Data and Preparation Method |
|---|---|---|
| 118 | 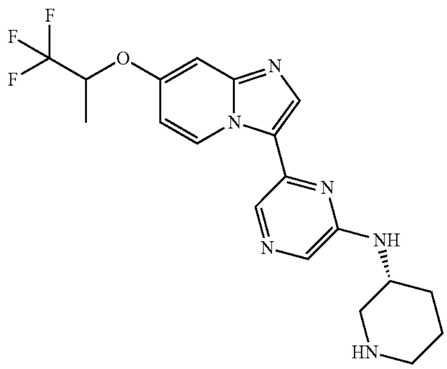 [SMILES: CC(Oc1ccn2c(-c3cncc(N[C@@H]4CCCNC4)n3)cnc2c1)C(F)(F)F] | N-[(3R)-piperidin-3-yl]-6-[7-(2,2,2-trifluoro-1-methylethoxy)imidazo[1,2-a]pyridin-3-yl]pyrazin-2-amine 1H NMR (400 MHz, DMSO): δ ppm 1.220-1.375 (m, 5H), 1.648 (m, 1H), 1.922-2.022 (m, 1H), 2.402-2.492 (m, 1H), 2.824-2.898 (d, 1H), 3.116-3.158 (d, 2H), 3.726 (s, 1H), 4.093 (s, 0.32H), 5.467-5.531 (m, 1H), 6.892-6.917 (dd, 1H), 7.083-7.102 (d, 1H), 7.406-7.412 (s, 1H), 7.755 (s, 1H), 8.210-8.252 (d, 2H), 9.654-9.673 (d, 1H). Method A (Example 32). |
| 119 | 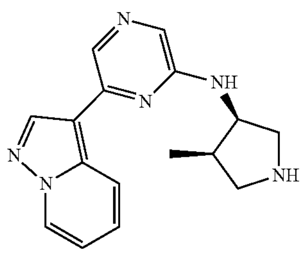 [SMILES: C[C@@H]1CNC[C@@H]1Nc1cncc(-c2cnn3ccccc23)n1] | N-[(3R,4R)-4-methylpyrrolidin-3-yl]-6-pyrazolo[1,5-a]pyridin-3-ylpyrazin-2-amine 1H NMR (400 MHz, CDCl3): δ ppm 1.061-1.043 (m, 3H), 2.547-2.511 (m, 1H), 2.748-2.700 (m, 1H), 2.970-2.930 (m, 1H), 3.349-3.303 (m, 1H), 3.475-3.433 (m, 1H), 4.559-4.529 (m, 1H), 4.788-4.469 (m, 1H), 6.885-6.851 (m, 1H), 7.303-7.286 (d, 1H), 7.730 (s, 1H) 8.233 (s, 1H), 8.410 (s, 1H), 8.410-8.394 (d, 1H), 8.521-8.504 (d, 1H). Method A (Example 4). |
| 120 | 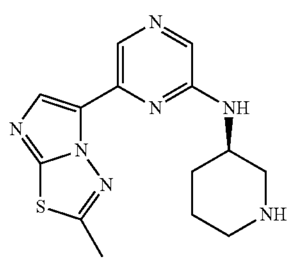 [SMILES: Cc1nn2c(-c3cncc(N[C@@H]4CCCNC4)n3)cnc2s1] | 6-(2-methylimidazo[2,1-b][1,3,4]thiadiazol-5-yl)-N-[(3R)-piperidin-3-yl]pyrazin-2-amine 1H NMR (400 MHz, DMSO-d6) δ ppm 1.50-1.71 (m, 1H) 1.72-1.88 (m, 1H) 1.88-2.06 (m, 2H) 2.72-2.81 (m, 1H) 2.83 (s, 3H) 2.91 (d, J = 14.60 Hz, 1H) 3.22 (d, J = 10.58 Hz, 1H) 3.41 (d, J = 20.40 Hz, 1H) 3.46-3.60 (m, J = 11.83 Hz, 1H) 4.09-4.23 (m, 1H) 7.90 (s, 1H) 8.03 (s, 1H) 8.51 (s, 1H). Method A (Example 7). |
| 121 | 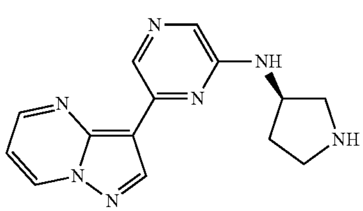 [SMILES: c1cnc2c(-c3cncc(N[C@@H]4CCNC4)n3)cnn2c1] | 6-pyrazolo[1,5-a]pyrimidin-3-yl-N-[(3R)-pyrrolidin-3-yl]pyrazin-2-amine 1H NMR (400 MHz, DMSO): δ ppm 1.945-1.929 (m, 1H), 2.332-2.241 (m, 1H), 3.093-3.052 (m, 1H), 3.236-3.172 (m, 2H), 3.552-3.506 (m, 1H), 4.486-4.473 (m, 1H), 7.209-7.181 (m, 1H), 7.699-7.386 (d, 1H), 7.818 (s, 1H), 8.771-8.758 (m, 2H), 8.816 (s, 1H), 9.250-9.229 (m, 1H). Method A (Example 23). |
| 122 | 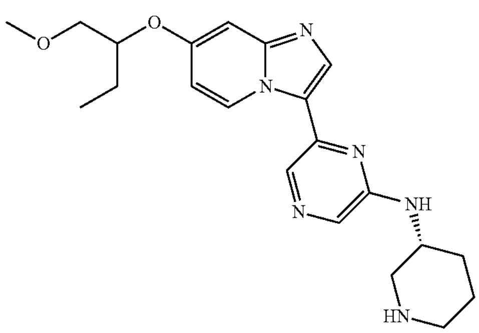 [SMILES: CCC(COC)Oc1ccn2c(-c3cncc(N[C@@H]4CCCNC4)n3)cnc2c1] | 6-{7-[1-(methoxymethyl)propoxy]imidazo[1,2-a]pyridin-3-yl}-N-[(3R)-piperidin-3-yl]pyrazin-2-amine 1H NMR (400 MHz, DMSO): δ ppm 0.902-0.996 (t, 3H), 1.467-1.888 (m, 8H), 1.998-2.067 (d, 2H), 2.926-2.957 (m, 2H), 3.510-3.557 (m, 3H), 3.959 (s, 1H), 4.625-4.649 (m, 1H), 6.792-6.812 (d, 1H), 7.144 (s, 2H), 7.716 (s, 1H), 8.206-8.369 (m, 3H), 9.545-9.565 (d, 1H). Method A (Example 32). |

| Ex. | Structure | Name, Data and Preparation Method |
|---|---|---|
| 123 | 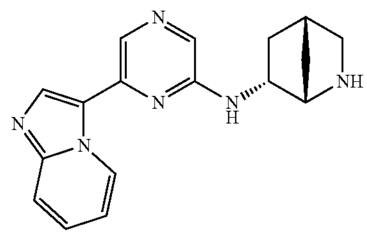 [SMILES: c1ccn2c(-c3cncc(N[C@@H]4C[C@@H]5CN[C@H]4C5)n3)cnc2c1] | (1S,4R,6R)-N-(6-imidazo[1,2-a]pyridin-3-ylpyrazin-2-yl)-2-azabicyclo[2.2.1]heptan-6-amine 1H NMR (400 MHz, DMSO-d6) δ ppm 1.21 (d, J = 9.82 Hz, 1H) 1.64 (d, J = 1.26 Hz, 1H) 1.79 (d, J = 10.07 Hz, 1H) 2.19 (t, J = 11.71 Hz, 1H) 2.79 (d, J = 9.57 Hz, 1H) 2.96 (d, J = 9.57 Hz, 1H) 3.75 (s, 1H) 4.22 (d, J = 7.05 Hz, 1H) 7.11 (t, J = 6.80 Hz, 1H) 7.29-7.54 (m, 2H) 7.72 (d, J = 9.06 Hz, 1H) 7.89 (s, 1H) 8.36 (d, J = 3.27 Hz, 2H) 9.69 (d, J = 6.80 Hz, 1H). Method A (Example 7). |
| 124 | 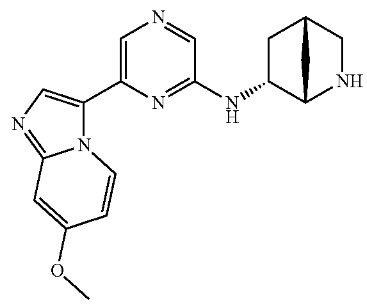 [SMILES: COc1ccn2c(-c3cncc(N[C@@H]4C[C@@H]5CN[C@H]4C5)n3)cnc2c1] | (1S,4R,6R)-N-[6-(7-methoxyimidazo[1,2-a]pyridin-3-yl)pyrazin-2-yl]-2-azabicyclo[2.2.1]heptan-6-amine 1H NMR (400 MHz, DMSO-d6) δ ppm 1.11-1.28 (m, 1H) 1.60 (d, J = 11.58 Hz, 1H) 1.79 (d, J = 10.32 Hz, 1H) 2.10-2.25 (m, 1H) 2.77 (d, J = 9.57 Hz, 1H) 2.96 (d, J = 9.57 Hz, 1H) 3.73 (s, 1H) 3.89 (s, 3H) 4.10-4.22 (m, 1H) 6.82 (dd, J = 7.68, 2.64 Hz, 1H) 7.10 (d, J = 2.52 Hz, 1H) 7.22 (d, J = 6.04 Hz, 1H) 7.84 (s, 1H) 8.21 (s, 1H) 8.32 (s, 1H) 9.54 (d, J = 7.81 Hz, 1H) Method A (Example 7). |
| 125 | 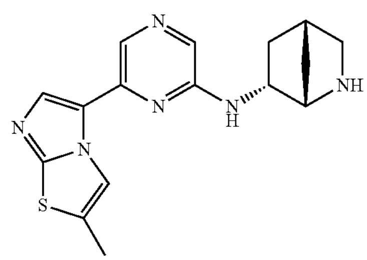 [SMILES: Cc1cn2c(-c3cncc(N[C@@H]4C[C@@H]5CN[C@H]4C5)n3)cnc2s1] | (1S,4R,6R)-N-[6-(2-methylimidazo[2,1-b][1,3]thiazol-5-yl)pyrazin-2-yl]-2-azabicyclo[2.2.1]heptan-6-amine 1H NMR (400 MHz, DMSO-d6) δ ppm 1.09 (d, J=15.61 Hz, 1H) 1.45-1.62 (m, 1H) 1.68-1.78 (m, J=9.32 Hz, 1H) 2.06-2.20 (m, 1H) 2.48 (d, J=1.26 Hz, 3H) 2.64-2.71 (m, 1H) 2.82-2.94 (m, J=9.82 Hz, 1H) 3.51-3.63 (m, 1H) 4.09-4.22 (m, J = 9.82 Hz, 1H) 7.15 (d, 1H) 7.84 (s, 1H) 7.94 (s, 1H) 8.23 (s, 1H) 8.28 (d, J=1.51 Hz, 1H). Method A (Example 7). |
| 126 | 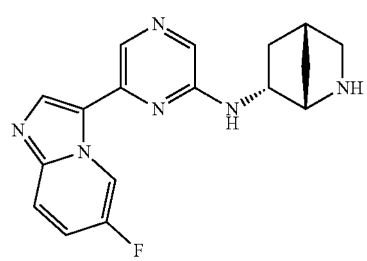 [SMILES: Fc1ccc2ncc(-c3cncc(N[C@@H]4C[C@@H]5CN[C@H]4C5)n3)n2c1] | (1S,4R,6R)-N-[6-(6-fluoroimidazo[1,2-a]pyridin-3-yl)pyrazin-2-yl]-2-azabicyclo[2.2.1]heptan-6-amine 1H NMR (400 MHz, DMSO-d6) δ ppm 1.05-1.21 (m, 1H) 1.51-1.68 (m, 2H) 2.07-2.23 (m, 1H) 2.39-2.46 (m, 1H) 2.59-2.70 (m, 1H) 2.83-2.94 (m, 1H) 3.53-3.60 (m, 1H) 3.99-4.18 (m, 1H) 7.29 (d, J = 6.55 Hz, 1H) 7.45-7.56 (m, 1H) 7.79 (dd, J = 9.82, 5.54 Hz, 1H) 7.91 (s, 1H) 8.37 (s, 1H) 8.45 (s, 1H) 9.85 (dd, J = 5.67, 2.14 Hz, 1H) Method A (Example 7). |
| 127 | 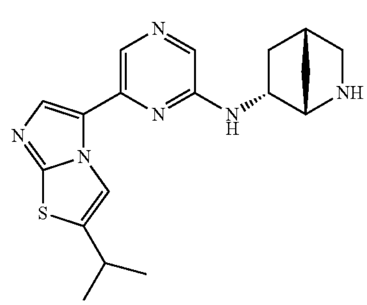 [SMILES: CC(C)c1cn2c(-c3cncc(N[C@@H]4C[C@@H]5CN[C@H]4C5)n3)cnc2s1] | (1S,4R,6R)-N-[6-(2-isopropylimidazo[2,1-b][1,3]thiazol-5-yl)pyrazin-2-yl]-2-azabicyclo[2.2.1]heptan-6-amine 1H NMR (400 MHz, DMSO-d6) δ ppm 0.88-1.00 (m, 1H) 1.25 (d, J = 6.55 Hz, 6H) 1.39-1.51 (m, 2H) 2.03 (t, J = 15.23 Hz, 1H) 2.20-2.35 (m, 1H) 2.49-2.55 (m, 1H) 2.68-2.82 (m, 1H) 3.95-4.14 (m, 1H) 7.08 (d, J = 7.05 Hz, 1H) 7.76 (s, 1H) 7.85 (s, 1H) 8.11 (s, 1H) 8.19 (s, 1H). Method A (Example 7). |

-continued

| Ex. | Structure | Name, Data and Preparation Method |
|---|---|---|
| 128 | 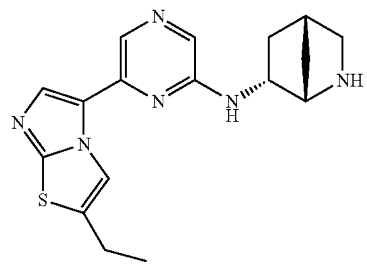 [SMILES: CCc1cn2c(-c3cncc(N[C@@H]4C[C@@H]5CN[C@H]4C5)n3)cnc2s1] | (1S,4R,6R)-N-[6-(2-ethylimidazo[2,1-b][1,3]thiazol-5-yl)pyrazin-2-yl]-2-azabicyclo[2.2.1]heptan-6-amine 1H NMR (400 MHz, DMSO-d6) δ ppm 0.94-1.05 (m, 1H) 1.27 (t, J = 7.43 Hz, 3H) 1.44-1.51 (m, 1H) 1.53-1.62 (m, 1H) 1.98-2.14 (m, 1H) 2.32-2.36 (m, 1H) 2.56 (d, J = 8.81 Hz, 1H) 2.74-2.87 (m, 3H) 4.08 (d, J = 6.80 Hz, 1H) 7.10 (d, J = 7.30 Hz, 1H) 7.80 (s, 1H) 7.89 (s, 1H) 8.16 (s, 1H) 8.25 (s, 1H). Method A (Example 7). |
| 129 | 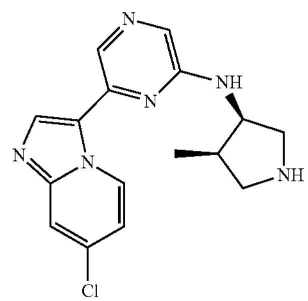 [SMILES: C[C@@H]1CNC[C@@H]1Nc1cncc(-c2cnc3cc(Cl)ccn23)n1] | 6-(7-chloroimidazo[1,2-a]pyridin-3-yl)-N-[(3R,4R)-4-methylpyrrolidin-3-yl]pyrazin-2-amine 1H NMR (400 MHz, DEUTERIUM OXIDE) δ ppm 1.06 (d, J = 7.07 Hz, 3H) 2.59-2.83 (m, 1H) 3.04-3.23 (m, 1H) 3.31-3.50 (m, 1H) 3.50-3.62 (m, 1H) 3.63-3.75 (m, 1H) 4.08 (d, J = 7.33 Hz, 0H) 7.53 (dd, J = 7.45, 1.89 Hz, 1H) 8.02 (s, 1H) 8.07 (d, J = 1.52 Hz, 1H) 8.20 (s, 1H) 8.37 (s, 1H) 9.53 (d, J = 7.58 Hz, 1H). Method A (Example 7). |
| 130 | 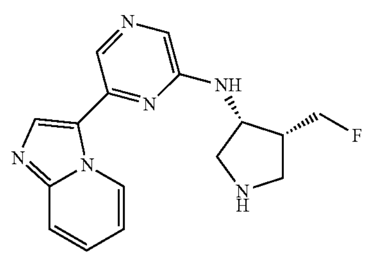 [SMILES: FC[C@@H]1CNC[C@@H]1Nc1cncc(-c2cnc3ccccn23)n1] | N-[(3R,4R)-4-(fluoromethyl)pyrrolidin-3-yl]-6-imidazo[1,2-a]pyridin-3-ylpyrazin-2-amine 1H NMR (400 MHz, MeOD) δ ppm 2.99-3.18 (m, 1H) 3.42 (dd, J = 11.37, 7.33 Hz, 1H) 3.56 (dd, J = 12.13, 6.82 Hz, 1H) 3.70-3.88 (m, 2H) 4.57-4.82 (m, 2H) 5.15 (q, J = 7.07 Hz, 1H) 7.75 (t, J = 6.82 Hz, 1H) 8.02-8.19 (m, 2H) 8.21 (br. s., 1H) 8.48 (br. s., 1H) 8.78 (s, 1H) 9.91 (d, J = 6.82 Hz, 1H). Method A (Example 4). |
| 131 | 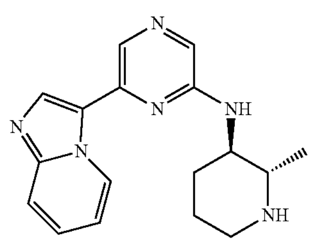 [SMILES: C[C@@H]1NCCC[C@H]1Nc1cncc(-c2cnc3ccccn23)n1] | 6-imidazo[1,2-a]pyridin-3-yl-N-[(2S,3R)-2-methylpiperidin-3-yl]pyrazin-2-amine $^1$H NMR (400 MHz, DMSO-d$_6$) d ppm 1.11 (d, J = 6.29 Hz, 3H) 1.19-1.38 (m, 2H) 1.48-1.64 (m, 1H) 1.71 (d, J = 12.59 Hz, 1H) 2.11 (d, J = 9.06 Hz, 1H) 2.55-2.73 (m, 2H) 2.99 (d, J = 11.58 Hz, 1H) 7.05-7.20 (m, 2H) 7.31-7.48 (m, 1H) 7.72 (d, J = 9.06 Hz, 1H) 7.79 (s, 1H) 8.29 (s, 1H) 8.36 (s, 1H) 9.75 (d, J = 6.80 Hz, 1H). Method A (Example 4). |
| 132 | 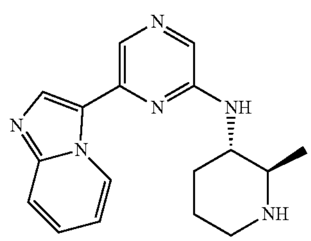 [SMILES: C[C@H]1NCCC[C@@H]1Nc1cncc(-c2cnc3ccccn23)n1] | 6-imidazo[1,2-a]pyridin-3-yl-N-[(2R,3S)-2-methylpiperidin-3-yl]pyrazin-2-amine 1H NMR (400 MHz, DMSO-d6) δ ppm 1.09 (d, J = 6.04 Hz, 3H) 1.18-1.38 (m, 1H) 1.47-1.60 (m, 1H) 1.69 (d, J = 12.59 Hz, 1H) 1.99-2.26 (m, 1H) 2.54-2.77 (m, 2H) 2.96 (d, J = 11.58 Hz, 1H) 6.87-7.17 (m, 2H) 7.40 (dd, J = 8.31, 7.30 Hz, 1H) 7.72 (d, J = 9.06 Hz, 1H) 7.78 (s, 1H) 8.29 (s, 1H) 8.36 (s, 1H) 9.76 (d, J = 7.30 Hz, 1H). Method A (Example 4). |
| 133 | 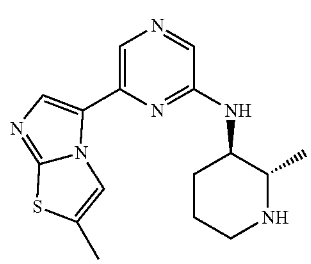 [SMILES: Cc1cn2c(-c3cncc(N[C@@H]4CCCN[C@H]4C)n3)cnc2s1] | 6-(2-methylimidazo[2,1-b][1,3]thiazol-5-yl)-N-[(2S,3R)-2-methylpiperidin-3-yl]pyrazin-2-amine 1H NMR (400 MHz, DMSO-d6) δ ppm 1.05 (d, J = 6.29 Hz, 3H) 1.16-1.33 (m, 1H) 1.42-1.58 (m, 1H) 1.67 (d, J = 12.84 Hz, 1H) 2.01-2.18 (m, 1H) 2.52-2.59 (m, 2H) 2.91 (d, J = 11.83 Hz, 1H) 3.26 (s, 3H) 3.38-3.47 (m, 2H) 6.92-7.18 (m, 1H) 7.73 (s, 1H) 7.92 (s, 1H) 8.14 (s, 1H) 8.31 (d, 1H). Method A (Example 7). |

| Ex. | Structure | Name, Data and Preparation Method |
|---|---|---|
| 134 | 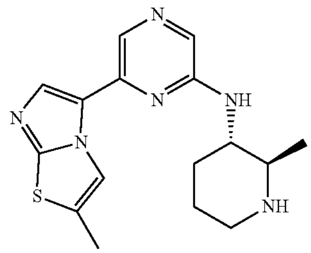 [SMILES: Cc1cn2c(-c3cncc(N[C@H]4CCCN[C@@H]4C)n3)cnc2s1] | 6-(2-methylimidazo[2,1-b][1,3]thiazol-5-yl)-N-[(2R,3S)-2-methylpiperidin-3-yl]pyrazin-2-amine 1H NMR (400 MHz, DMSO-d6) δ ppm 1.05 (d, J = 6.29 Hz, 3H) 1.16-1.30 (m, 1H) 1.45-1.58 (m, 1H) 1.63-1.78 (m, 1H) 2.04-2.20 (m, 1H) 2.92 (d, J = 13.60 Hz, 1H) 7.04 (d, J = 8.56 Hz, 1H) 7.74 (s, 1H) 7.93 (s, 1H) 8.15 (s, 1H) 8.31 (s, 1H). Method A (Example 7). |
| 135 | 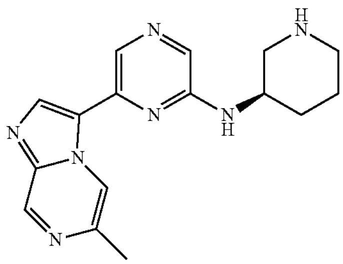 [SMILES: Cc1cn2c(-c3cncc(N[C@@H]4CCCNC4)n3)cnc2cn1] | 6-(6-methylimidazo[1,2-a]pyrazin-3-yl)-N-[(3R)-piperidin-3-yl]pyrazin-2-amine 1H NMR (400 MHz, DMSO-d6) δ ppm 1.53-1.70 (m, 1H), 1.74-1.89 (m, 1H), 1.92-2.04 (m, 1H), 2.08-2.20 (m, 1H), 2.58 (s, 3H), 2.92-3.07 (m, 2H), 3.13-3.25 (m, 1H), 3.38-3.41 (m, 1H), 4.26 (br. s., 1H), 7.73 (br. s., 1H), 7.96 (s, 1H), 8.47 (s, 1H), 8.63 (s, 1H), 9.20 (s, 2H), 9.35 (s, 1H). Method A (Example 7). |
| 136 | 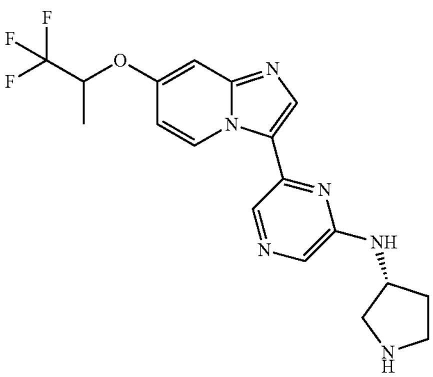 [SMILES: CC(Oc1ccn2c(-c3cncc(N[C@@H]4CCNC4)n3)cnc2c1)C(F)(F)F] | N-[(3R)-pyrrolidin-3-yl]-6-[7-(2,2,2-trifluoro-1-methylethoxy)imidazo[1,2-a]pyridin-3-yl]pyrazin-2-amine 1H NMR (400 MHz, DMSO): δ ppm 1.541-1.556 (d, 3H), 1.753-1.844 (m, 1H), 2.171-2.393 (m, 1H), 2.910-3.276 (m, 4H), 4.476 (s, 1H), 5.540-5.602 (m, 1H), 6.934-6.992 (m, 1H), 7.402-7.564 (m, 2H), 7.841-7.859 (m, 1H), 8.339-8.403 (m, 2H), 9.711-9.730 (d, 1H). Method A (Example 32). |
| 137 | 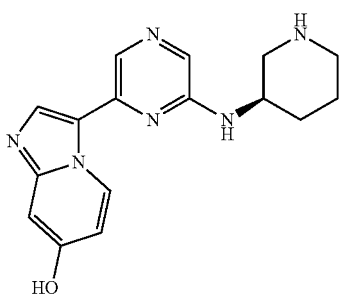 [SMILES: Oc1ccn2c(-c3cncc(N[C@@H]4CCCNC4)n3)cnc2c1] | 3-{6-[(3R)-piperidin-3-ylamino]pyrazin-2-yl}imidazo[1,2-a]pyridin-7-ol 1H NMR (400 MHz, DMSO): δ ppm 1.435-1.523 (m, 2H), 1.692-1.702 (s, 1H), 2.0240-2.029 (d, 1H), 2.840-2.870 (d, 2H), 3.182-3.341 (m, 2H), 3.930 (s, 1H), 6.706-6.724 (d, 1H), 6.828 (s, 1H), 7.033-7.050 (d, 1H), 7.724 (s, 1H), 8.159 (s, 1H), 8.236 (s, 1H), 9.514-9.609 (d, 1H). Method A (Example 7). |
| 138 | 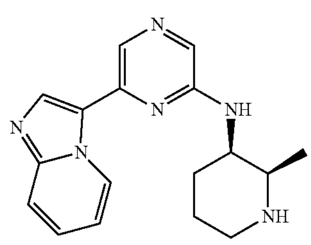 [SMILES: C[C@H]1NCCC[C@H]1Nc1cncc(-c2cnc3ccccn23)n1] | 6-imidazo[1,2-a]pyridin-3-yl-N-[(2R,3R)-2-methylpiperidin-3-yl]pyrazin-2-amine 1H NMR (400 MHz, DMSO-d6) δ ppm 1.16 (t, J = 7.30 Hz, 2H) 1.22 (d, J = 6.55 Hz, 3H) 1.60-1.73 (m, 1H) 1.76-1.97 (m, 2H) 2.80-3.01 (m, 2H) 4.18-4.43 (m, 1H) 7.14 (d, J = 7.05 Hz, 1H) 7.42 (d, J = 6.80 Hz, 1H) 7.49 (d, J = 7.81 Hz, 1H) 7.71 (d, J = 9.32 Hz, 1H) 7.93 (s, 1H) 8.36 (s, 2H) 9.64 (d, J = 7.05 Hz, 1H). Method A (Example 4). |

-continued

| Ex. | Structure | Name, Data and Preparation Method |
|---|---|---|
| 139 | 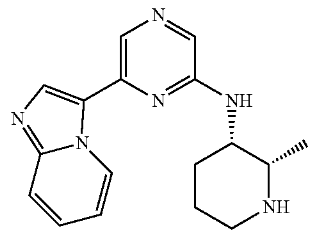 [SMILES: C[C@@H]1NCCC[C@@H]1Nc1cncc(-c2cnc3ccccn23)n1] | 6-imidazo[1,2-a]pyridin-3-yl-N-[(2S,3S)-2-methylpiperidin-3-yl]pyrazin-2-amine 1H NMR (400 MHz, DMSO-d6) δ ppm 1.10-1.23 (m, 5H) 1.48-1.64 (m, 1H) 1.67-1.83 (m, 2H) 1.84-1.94 (m, J = 8.31 Hz, 1H) 2.88 (q, J = 7.30 Hz, 2H) 3.10 (d, J = 12.59 Hz, 1H) 4.23 (s, 1H) 7.10 (t, J = 6.80 Hz, 1H) 7.24-7.44 (m, 2H) 7.68 (d, J = 9.06 Hz, 1H) 7.91 (s, 1H) 8.32 (d, J = 5.79 Hz, 2H) 9.62 (d, J = 7.05 Hz, 1H). Method A (Example 4). |
| 140 | 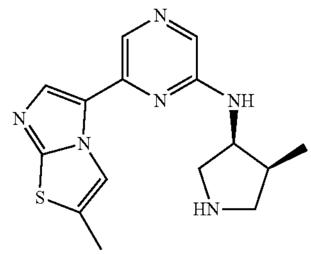 [SMILES: Cc1cn2c(-c3cncc(N[C@@H]4CNC[C@@H]4C)n3)cnc2s1] | 6-(2-methylimidazo[2,1-b][1,3]thiazol-5-yl)-N-[(3S,4S)-4-methylpyrrolidin-3-yl]pyrazin-2-amine 1H NMR (400 MHz, MeOD) δ ppm 1.14 (d, J = 7.05 Hz, 3H) 2.54 (d, J = 1.51 Hz, 3H) 2.68-2.81 (m, 1H) 3.05-3.16 (m, 1H) 3.54 (dd, J = 11.58, 7.55 Hz, 1H) 3.66 (dd, J = 12.09, 6.55 Hz, 1H) 4.71-4.80 (m, 1H) 7.85 (s, 1H) 7.87 (s, 1H) 8.23 (s, 1H) 8.26 (d, J = 1.51 Hz, 1H). Method A (Example 7). |
| 141 | 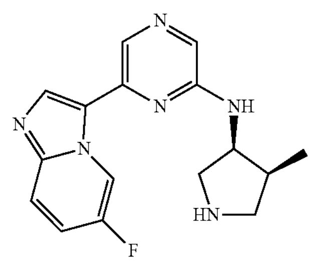 [SMILES: C[C@H]1CNC[C@H]1Nc1cncc(-c2cnc3ccc(F)cn23)n1] | 6-(6-fluoroimidazo[1,2-a]pyridin-3-yl)-N-[(3S,4S)-4-methylpyrrolidin-3-yl]pyrazin-2-amine 1H NMR (400 MHz, MeOD) δ ppm 1.14 (d, J = 7.05 Hz, 3H) 2.54 (d, J = 1.51 Hz, 3H) 2.68-2.81 (m, 1H) 3.05-3.16 (m, 1H) 3.54 (dd, J = 11.58, 7.55 Hz, 1H) 3.66 (dd, J = 12.09, 6.55 Hz, 1H) 4.71-4.80 (m, 1H) 7.85 (s, 1H) 7.87 (s, 1H) 8.23 (s, 1H) 8.26 (d, J = 1.51 Hz, 1H). Method A (Example 7). |
| 142 | 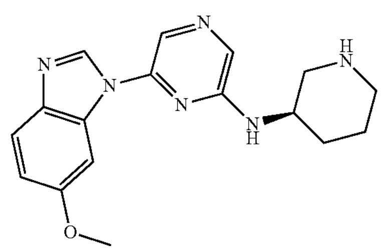 [SMILES: COc1ccc2ncn(-c3cncc(N[C@@H]4CCCNC4)n3)c2c1] | 6-(6-methoxy-1H-benzimidazol-1-yl)-N-[(3R)-piperidin-3-yl]pyrazin-2-amine 1H NMR (400 MHz, CDCl3): δ ppm 1.610 (s, 1H), 1.858 (m, 9H), 2.886-2.831 (m, 3H), 3.195 (d, 3H) 3.892 (s, 3H), 4.118 (s, 1H), 5.551 (s, 1H), 7.012 (d, 1H), 7.550 (s, 1H), 7.735-7.713 (d, 1H), 7.885 (s, 1H), 8.099 (s, 1H), 8.425 (s, 1H). Method A (Example 7). |
| 143 | 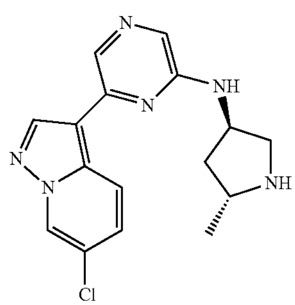 [SMILES: C[C@@H]1C[C@@H](Nc2cncc(-c3cnn4cc(Cl)ccc34)n2)CN1] | 6-(6-chloropyrazolo[1,5-a]pyridin-3-yl)-N-[(3R,5R)-5-methylpyrrolidin-3-yl]pyrazin-2-amine 1H NMR (400 MHz, DMSO): δ ppm 1.40-1.32 (d, 3H), 2.029-1.987 (m, 1H), 2.225-2.181 (m, 1H), 3.242-3.140 (m, 1H), 3.3.972-3.653 (m, 2H), 4.605-4.508 (m, 1H), 7.457-7.430 (m, 2H), 8.366 (s, 1H), 8.439-8.415 (d, 1H), 8.618-8.523 (m, 1H), 8.757 (s, 1H), 8.788 (s, 1H), 9.002 (m, 1H), 9.152 (s, 1H). Method A (Example 4). |
| 144 | 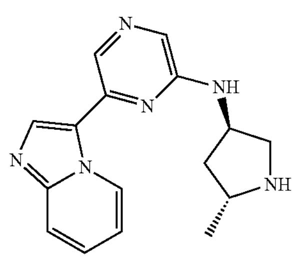 [SMILES: C[C@@H]1C[C@@H](Nc2cncc(-c3cnc4ccccn34)n2)CN1] | 6-imidazo[1,2-a]pyridin-3-yl-N-[(3R,5R)-5-methylpyrrolidin-3-yl]pyrazin-2-amine 1H NMR (400 MHz, MeOD): δ ppm 1.589-1.573 (d, 3H), 2.273-2.196 (m, 1H), 2.499-2.454 (m, 1H), 3.518-3.432 (m, 1H), 3.892-3.845 (m, 1H), 4.119-4.061 (m, 1H), 4.973-4.861 (m, 1H), 7.618-7.580 (m, 1H), 8.095-8.019 (m, 3H) 8.472 (s, 1H), 8.689 (s, 1H), 9.927-9.909 (d, 1H). Method A (Example 4). |

| Ex. | Structure | Name, Data and Preparation Method |
|---|---|---|
| 145 | 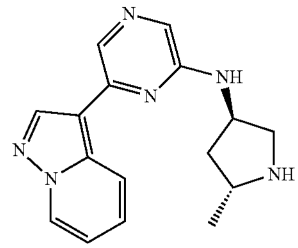 [SMILES: C[C@@H]1C[C@@H](Nc2cncc(-c3cnn4ccccc34)n2)CN1] | N-[(3R,5R)-5-methylpyrrolidin-3-yl]-6-pyrazolo[1,5-a]pyridin-3-ylpyrazin-2-amine 1H NMR (400 MHz, MeOD): δ ppm 1.524-1.425 (d, 3H), 2.207-2.130 (m, 1H), 2.418-2.372 (m, 1H), 3.471-3.433 (m, 1H), 3.845-3.800 (m, 1H), 4.067-3.976 (m, 1H), 4.811-4.789 (m, 1H), 7.058-7.025 (t, 1H), 7.458-7.440 (t, 1H), 7.740 (s, 1H), 8.335 (s, 1H) 8.464-8.418 (d, 1H), 8.569 (s, 1H), 8.643-8.626 (d, 1H). Method A (Example 4). |
| 146 | 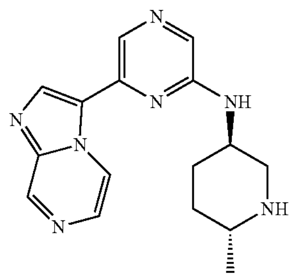 [SMILES: C[C@@H]1CC[C@@H](Nc2cncc(-c3cnc4cnccn34)n2)CN1] | 6-imidazo[1,2-a]pyrazin-3-yl-N-[(3R,6R)-6-methylpiperidin-3-yl]pyrazin-2-amine 1H NMR (400 MHz, DMSO-d6) δ ppm 1.03 (d, J = 6.29 Hz, 3H) 1.13-1.27 (m, 1H) 1.30-1.42 (m, 1H) 1.62-1.74 (m, 1H) 2.04-2.13 (m, 1H) 2.34-2.42 (m, 1H) 2.53-2.59 (m, 1H) 3.19-3.28 (m, 1H) 3.63-3.79 (m, 1H) 7.21 (d, J = 7.30 Hz, 1H) 7.85 (s, 1H) 8.06 (d, J = 4.78 Hz, 1H) 8.39 (s, 1H) 8.58 (s, 1H) 9.19 (d, J = 1.26 Hz, 1H) 9.61 (dd, J = 4.53, 1.26 Hz, 1H). Method A (Example 4). |
| 147 | 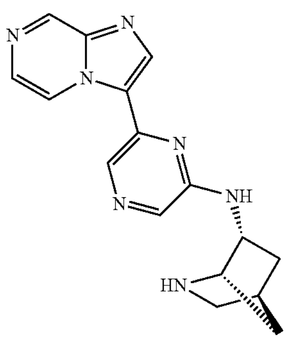 [SMILES: c1cn2c(-c3cncc(N[C@@H]4C[C@@H]5CN[C@H]4C5)n3)cnc2cn1] | (1S,4R,6R)-N-(6-imidazo[1,2-a]pyrazin-3-ylpyrazin-2-yl)-2-azabicyclo[2.2.1]heptan-6-amine 1H NMR (400 MHz, DMSO-d6) δ ppm 1.02-1.09 (m, 1H) 1.48-1.58 (m, J = 2.77 Hz, 1H) 1.67 (d, J = 9.82 Hz, 1H) 2.09-2.20 (m, 1H) 2.40 (br. s., 1H) 2.61 (d, J = 9.06 Hz, 1H) 2.80-2.92 (m, 1H) 3.46 (br. s., 1H) 3.93-4.20 (m, 1H) 7.33 (d, J = 7.05 Hz, 1H) 7.97 (s, 1H) 8.09 (d, J = 4.78 Hz, 1H) 8.40 (s, 1H) 8.57 (s, 1H) 9.18 (d, J = 1.26 Hz, 1H) 9.57 (dd, J = 4.66, 1.38 Hz, 1H). Method A (Example 4). |
| 148 | 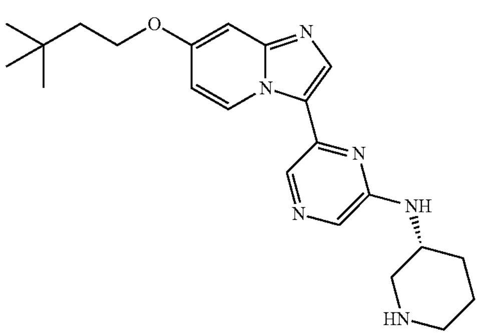 [SMILES: CC(C)(C)CCOc1ccn2c(-c3cncc(N[C@@H]4CCCNC4)n3)cnc2c1] | 6-[7-(3,3-dimethylbutoxy)imidazo[1,2-a]pyridin-3-yl]-N-[(3R)-piperidin-3-yl]pyrazin-2-amine 1H NMR (400 MHz, DMSO): δ ppm 0.984 (s, 9H), 1.566-1.785 (m, 4H), 1.954-2.087 (m, 2H), 2.873-2.979 (m, 2H), 3.202-3.233 (d, 1H), 3.459 (d, 1H), 4.130-4.165 (t, 1H), 6.754-6.779 (dd, 2H), 7.171-7.1771 (d, 1H), 7.298-7.314 (d, 1H), 7.789 (s, 1H), 8.129 (s, 0.2H), 8.250 (s, 1H), 8.346 (s, 1H), 8.661 (s, 1H), 9.452-9.471 (d, 1H). Method A (Example 32). |
| 149 | 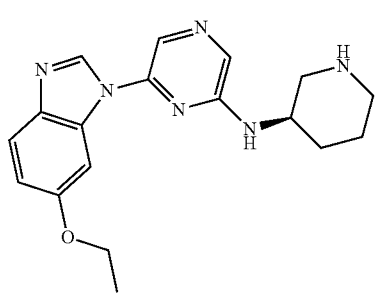 [SMILES: CCOc1ccc2ncn(-c3cncc(N[C@@H]4CCCNC4)n3)c2c1] | 6-(6-ethoxy-1H-benzimidazol-1-yl)-N-[(3R)-piperidin-3-yl]pyrazin-2-amine 1H NMR (400 MHz, MeOD): δ ppm 1.407 (t, 3H), 2.296-1.749 (m, 4H), 3.056 (m, 2H), 3.807-3.709 (m, 2H), 4.216-4.199 (m, 2H), 4.396 (m, 1H), 7.387 (d, 1H), 7.623-7.618 (d, 1H), 7.867-7.844 (d, 1H), 8.247 (s, 1H), 8.362 (s, 1H), 10.006 (s, 1H). Method A (Example 7). |

-continued

| Ex. | Structure | Name, Data and Preparation Method |
|---|---|---|
| 150 | 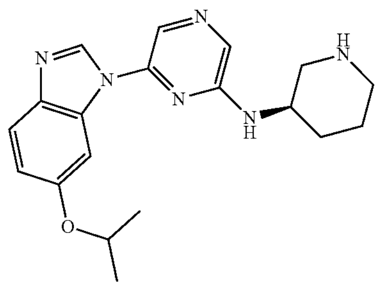 [SMILES: CC(C)Oc1ccc2ncn(-c3cncc(N[C@@H]4CCCNC4)n3)c2c1] | 6-(6-isopropoxy-1H-benzimidazol-1-yl)-N-[(3R)-piperidin-3-yl]pyrazin-2-amine 1H NMR (400 MHz, MeOD): δ ppm 1.407 (d, 6H), 2.296-1.749 (m, 4H), 3.210-3.056 (m, 2H), 3.807-3.547 (m, 3H), 4.396 (m, 1H), 4.807-4.723 (m, 1H), 7.357 (d, 1H), 7.605 (s, 1H), 7.854 (d, 1H), 8.228 (s, 1H), 8.375 (s, 1H), 9.987 (s, 1H). Method A (Example 7). |
| 151 | 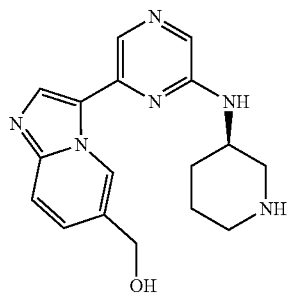 [SMILES: OCc1ccc2ncc(-c3cncc(N[C@@H]4CCCNC4)n3)n2c1] | (3-{6-[(3R)-piperidin-3-ylamino]pyrazin-2-yl}imidazo[1,2-a]pyridin-6-yl)methanol 1H NMR (400 MHz, DMSO-d6): δ ppm 1.63-1.66 (m, 1H), 1.88-2.04 (m, 3H), 2.94 (m, 2H), 3.16 (m, 1H), 3.39 (m, 1H), 3.86 (br m, 1H), 4.32 (br s, 1H), 4.76 (s, 2H), 7.87 (d, J = 6.8 Hz, 1H), 7.93-8.06 (m, 3H), 8.42 (s, 1H), 8.94 (s, 1H), 9.21 (br s, 2H), 9.81 (s, 1H). LCMS: M + 1 325.2. Method B (Example 5). |
| 152 | 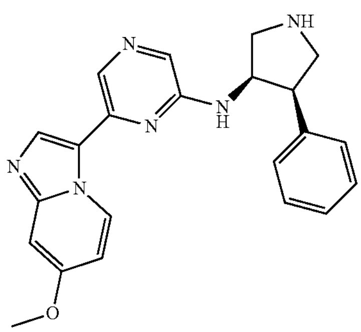 [SMILES: COc1ccn2c(-c3cncc(N[C@H]4CNC[C@H]4c4ccccc4)n3)cnc2c1] | 6-(7-methoxyimidazo[1,2-a]pyridin-3-yl)-N-[(3R,4R)-4-phenylpyrrolidin-3-yl]pyrazin-2-amine 1H NMR (400 MHz, DMSO-d6) δ ppm 2.90 (s, 1H) 3.06 (s, 1H) 3.31 (s, 3H) 3.50 (s, 1H) 3.89 (s, 3H) 4.66 (s, 1H) 6.88 (s, 1H) 6.98-7.08 (m, 5H) 7.21 (d, J = 7.05 Hz, 2H) 7.53 (s, 1H) 8.08 (d, J = 15.61 Hz, 2H) 9.51 (d, J = 7.81 Hz, 1H); LCMS: M + 1 387.2. Method A (Example 7). |
| 153 | 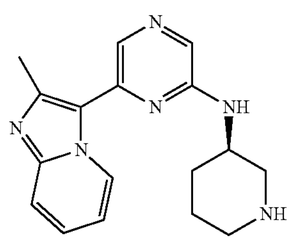 [SMILES: Cc1nc2ccccn2c1-c1cncc(N[C@@H]2CCCNC2)n1] | 6-(2-methylimidazo[1,2-a]pyridin-3-yl)-N-[(3R)-piperidin-3-yl]pyrazin-2-amine 1H NMR (400 MHz, DMSO-d6) δ ppm 1.53 (s, 1H) 1.64 (s, 1H) 1.85 (s, 1H) 2.02 (s, 1H) 2.55 (s, 3H) 2.79 (s, 2H) 3.06 (s, 1H) 3.29 (s, 1H) 4.04 (s, 1H), 6.99 (s, 1H) 7.35 (s, 2H) 7.57 (s, 1H) 7.91 (s, 1H) 8.00 (s, 1H) 9.13 (s, 1H); LCMS: M + 1 309.1. Method B (Example 5). |
| 154 | 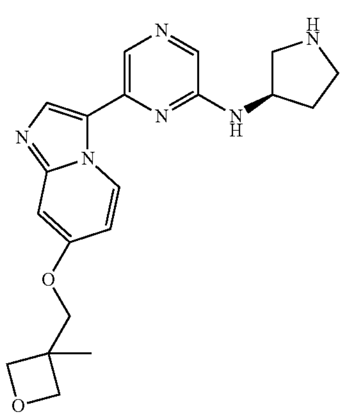 [SMILES: CC1(COc2ccn3c(-c4cncc(N[C@@H]5CCNC5)n4)cnc3c2)COC1] | 6-{7-[(3-methyloxetan-3-yl)methoxy]imidazo[1,2-a]pyridin-3-yl}-N-[(3R)-pyrrolidin-3-yl]pyrazin-2-amine 1H NMR (400 MHz, DMSO-d6) δ ppm 1.40 (s, 3H) 1.89-2.18 (m, 1H) 2.31 (dd, J = 13.26, 6.69 Hz, 1H) 3.15-3.21 (m, 1H) 3.31-3.40 (m, 2H) 3.52 (dd, J = 12.00, 6.19 Hz, 1H) 4.20 (s, 2H) 4.35 (d, J = 5.81 Hz, 2H) 4.53 (d, J = 5.81 Hz, 3H) 6.87 (dd, J = 7.58, 2.27 Hz, 1H) 7.19 (d, J = 2.02 Hz, 1H) 7.61 (d, J = 5.31 Hz, 1H) 7.80 (s, 1H) 8.12-8.32 (m, 2H) 8.39 (s, 1H) 9.55 (d, J = 7.83 Hz, 1H). Method A (Example 32). |

-continued

| Ex. | Structure | Name, Data and Preparation Method |
|---|---|---|
| 155 | 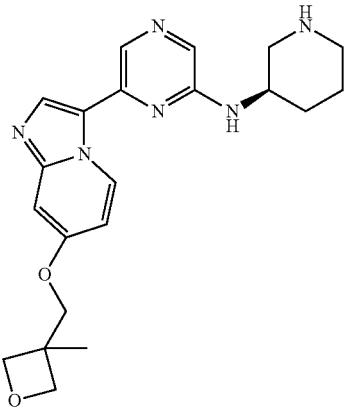 [SMILES: CC1(COc2ccn3c(-c4cncc(N[C@@H]5CCCNC5)n4)cnc3c2)COC1] | 6-{7-[(3-methyloxetan-3-yl)methoxy]imidazo[1,2-a]pyridin-3-yl}-N-[(3R)-piperidin-3-yl]pyrazin-2-amine 1H NMR (400 MHz, DMSO-d6) δ ppm 1.39 (s, 3H) 1.46-1.56 (m, 1H) 1.55-1.66 (m, 1H) 1.73-1.85 (m, 1H) 1.97-2.12 (m, 1H) 2.54-2.56 (m, 1H) 2.60-2.77 (m, 2H) 2.93-3.06 (m, 1H) 3.86-3.97 (m, 1H) 4.19 (s, 2H) 4.34 (d, J = 5.81 Hz, 2H) 4.52 (d, J = 5.56 Hz, 2H) 6.87 (d, J = 1.77 Hz, 1H) 7.09-7.27 (m, 2H) 7.77 (s, 1H) 8.23 (s, 1H) 8.30 (s, 1H) 9.58 (d, J = 7.58 Hz, 1H). Method A (Example 32). |
| 156 | 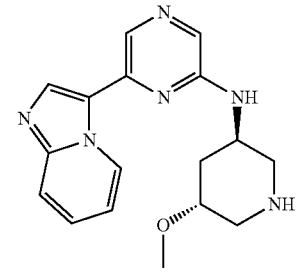 [SMILES: CO[C@H]1CNC[C@H](Nc2cncc(-c3cnc4ccccn34)n2)C1] | 6-(imidazo[1,2-a]pyridin-3-yl)-N-[(3R,5R)-5-methoxypiperidin-3-yl]pyrazin-2-amine 1H NMR (400 MHz, METHANOL-d4) δ ppm 1.75-1.80 (m, 1H) 2.42-2.56 (m, 1H) 2.91-3.04 (m, 1H) 3.14 (d, J = 12.63 Hz, 1H) 3.43-3.50 (m, 3H) 3.56 (d, J = 13.14 Hz, H) 3.66 (s, 3H) 3.92 (br. s., 1H) 4.54-4.70 (m, 1H) 7.63 (t, J = 6.69 Hz, 1H) 7.98-8.17 (m, 3H) 8.39 (br. s., 1H) 8.72 (s, 1H) 9.88 (d, J = 6.82 Hz, 1H). Method A (Example 7). |
| 157 | 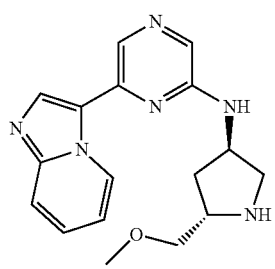 [SMILES: COC[C@@H]1C[C@@H](Nc2cncc(-c3cnc4ccccn34)n2)CN1] | 6-(imidazo[1,2-a]pyridin-3-yl)-N-[(3R,5S)-5-(methoxymethyl)pyrrolidin-3-yl]pyrazin-2-amine 1H NMR (400 MHz, DMSO-d6) δ ppm 2.05-2.24 (m, 2H), 3.24 (dd, J = 10.6, 4.8 Hz, 1H), 3.36 (s, 3H), 3.54-3.77 (m, 3H), 4.05 (br. s., 1H), 4.70 (br. s., 1H), 7.70 (t, J = 6.8 Hz, 1H), 7.99-8.15 (m, 3H), 8.22 (br. s., 1H), 8.49 (s, 1H), 9.02 (s, 1H), 9.58 (br. s., 1H), 9.79-9.98 (m, 2H); LCMS: M + 1 325. Method A (Example 7). |
| 158 | 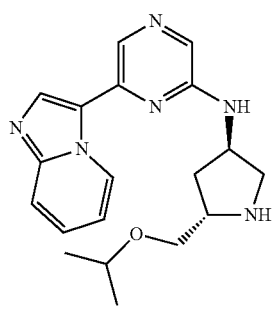 [SMILES: CC(C)OC[C@@H]1C[C@@H](Nc2cncc(-c3cnc4ccccn34)n2)CN1] | 6-(imidazo[1,2-a]pyridin-3-yl)-N-{(3R,5S)-5-[(propan-2-yloxy)methyl]pyrrolidin-3-yl}pyrazin-2-amine 1H NMR (500 MHz, DMSO-d6) δ ppm 1.14 (d, J = 5.9 Hz, 6H), 1.99-2.22 (m, 2H), 3.53-3.72 (m, 5H), 3.97 (br. s., 1H), 4.65 (br. s., 1H), 7.22 (t, J = 6.8 Hz, 1H), 7.56 (t, J = 7.8 Hz, 1H), 7.73 (d, J = 4.9 Hz, 1H), 7.80 (d, J = 8.8 Hz, 1H), 7.90 (s, 1H), 8.43 (s, 1H), 8.50 (s, 1H), 9.02 (br. s., 1H), 9.57 (br. s., 1H), 9.70 (d, J = 6.8 Hz, 1H); LCMS: M + 1 353. Method A (Example 7). |
| 159 | 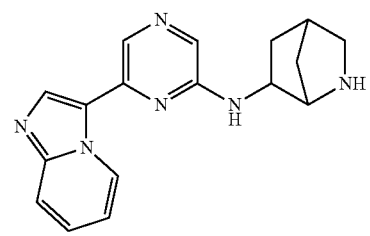 [SMILES: c1ccn2c(-c3cncc(NC4CC5CNC4C5)n3)cnc2c1] | N-[6-(imidazo[1,2-a]pyridin-3-yl)pyrazin-2-yl]-2-azabicyclo[2.2.1]heptan-6-amine 1H NMR (400 MHz, DMSO-d6) δ ppm 1.43-1.56 (m, 1H), 1.71-1.82 (m, 1H), 1.94-2.03 (m, 1H), 2.13-2.33 (m, 1H), 2.63-2.70 (m, 1H), 2.94-3.20 (m, 2H), 4.18 (br. s., 1H), 4.32-4.50 (m, 1H), 7.53-7.70 (m, 1H), 7.96-8.16 (m, 4H), 8.34 (br. s., 1H), 8.46 (s, 1H), 8.94 (s, 1H), 9.74-9.89 (m, 2H); LCMS: M + 1 307. Method A (Example 7). |

| Ex. | Structure | Name, Data and Preparation Method |
|---|---|---|
| 160 | 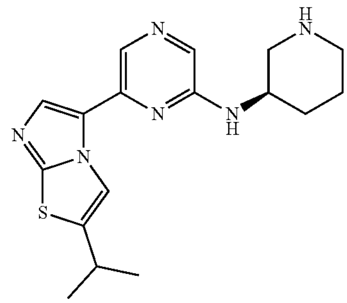 [SMILES: CC(C)c1cn2c(-c3cncc(N[C@@H]4CCCNC4)n3)cnc2s1] | N-[(3R)-piperidin-3-yl]-6-[2-(propan-2-yl)imidazo[2,1-b][1,3]thiazol-5-yl]pyrazin-2-amine 1H NMR (400 MHz, DMSO-d6) δ ppm 1.36 (d, J = 6.8 Hz, 6H), 1.54-1.69 (m, 1H), 1.75-1.88 (m, 1H), 1.90-2.01 (m, 1H), 2.01-2.12 (m, 1H), 2.89-3.05 (m, 2H), 3.12-3.22 (m, 1H), 3.30-3.39 (m, 1H), 3.39-3.50 (m, 1H), 4.31 (br. s., 1H), 7.75 (br. s., 1H), 7.92 (s, 1H), 8.27 (s, 1H), 8.34 (s, 1H), 8.37 (s, 1H), 9.21 (br. s., 1H), 9.51 (br. s., 1H); LCMS: M + 1 343. Method A (Example 7). |
| 161 | 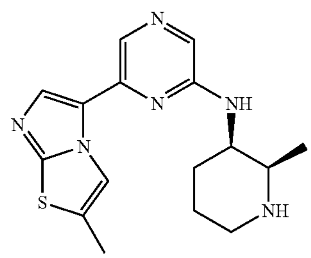 [SMILES: Cc1cn2c(-c3cncc(N[C@@H]4CCCN[C@@H]4C)n3)cnc2s1] | 6-(2-methylimidazo[2,1-b][1,3]thiazol-5-yl)-N-[(2R,3R)-2-methylpiperidin-3-yl]pyrazin-2-amine H NMR (400 MHz, DMSO-d6) δ ppm 1.30 (d, J = 6.8 Hz, 3H), 1.63-2.04 (m, 4H), 2.58 (d, J = 1.3 Hz, 3H), 2.92-3.02 (m, 1H), 3.19-3.28 (m, 1H), 3.60 (s, 1H), 4.36 (br. s., 1H), 7.99 (s, 1H), 8.20 (d, J = 9.1 Hz, 1H), 8.39 (s, 2H), 9.46 (br. s., 2H); LCMS: M + 1 329. Method A (Example 7). |
| 162 | 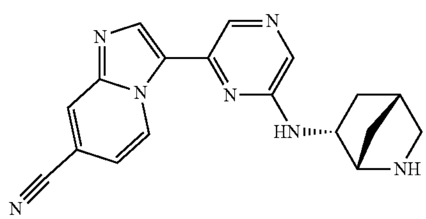 [SMILES: N#Cc1ccn2c(-c3cncc(N[C@@H]4C[C@@H]5CN[C@H]4C5)n3)cnc2c1] | 3-{6-[(1S,4R,6R)-2-azabicyclo[2.2.1]hept-6-ylamino]pyrazin-2-yl}imidazo[1,2-a]pyridine-7-carbonitrile 1H NMR (400 MHz, DMSO-d6) δ ppm 0.96-1.09 (m, 1H), 1.46-1.57 (m, 1H), 1.62-1.70 (m, 1H), 1.81 (s, 2H), 2.00-2.21 (m, 1H), 2.85 (br. s., 1H), 4.09 (br. s., 1H), 7.27-7.37 (m, 1H), 7.43 (dd, J = 7.3, 1.0 Hz, 1H), 7.97 (s, 1H), 8.39 (s, 1H), 8.47 (s, 1H), 8.61 (s, 1H), 9.82 (d, J = 7.1 Hz, 1H); LCMS: M + 1 332. Method A (Example 7). |
| 163 | 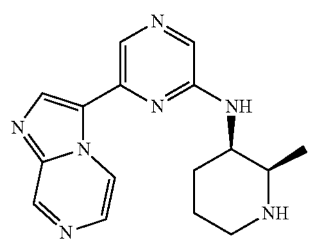 [SMILES: C[C@H]1NCCC[C@H]1Nc1cncc(-c2cnc3cnccn23)n1] | 6-(imidazo[1,2-a]pyrazin-3-yl)-N-[(2R,3R)-2-methylpiperidin-3-yl]pyrazin-2-amine 1H NMR (400 MHz, DMSO-d6) δ ppm 1.02 (d, J = 6.55 Hz, 3H) 1.25-1.44 (m, 1H) 1.51-1.69 (m, 2H) 1.93-2.05 (m, 1H) 2.59-2.70 (m, 1H) 2.94 (dd, J = 6.55, 2.27 Hz, 2H) 4.00 (d, J = 6.29 Hz, 1H) 7.13 (d, J = 8.31 Hz, 1H) 8.05-8.12 (m, 2H) 8.35 (s, 1H) 8.58 (s, 1H) 9.17 (d, J = 1.51 Hz, 1H) 9.53 (d, J = 4.03 Hz, 1H); LCMS: M + 1 310.2. Method A (Example 7). |
| 164 | 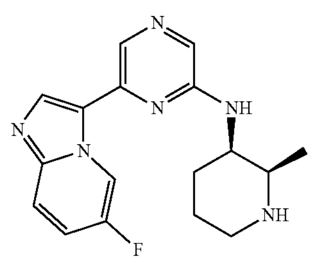 [SMILES: C[C@H]1NCCC[C@H]1Nc1cncc(-c2cnc3ccc(F)cn23)n1] | 6-(6-fluoroimidazo[1,2-a]pyridin-3-yl)-N-[(2R,3R)-2-methylpiperidin-3-yl]pyrazin-2-amine 1H NMR (400 MHz, DMSO-d6) δ ppm 1.03 (d, J = 6.55 Hz, 4H) 1.39 (dd, J = 5.92, 2.90 Hz, 1H) 1.53-1.68 (m, 2H) 2.00 (d, J = 8.06 Hz, 1H) 2.57-2.70 (m, 1H) 2.88-3.04 (m, 2H) 3.98 (d, J = 5.79 Hz, 1H) 7.20 (d, J = 8.31 Hz, 1H) 7.41-7.52 (m, 1H) 7.70-7.85 (m, 1H) 8.03 (s, 1H) 8.30 (s, 1H) 8.42 (s, 1H) 9.78 (dd, J = 5.54, 2.27 Hz, 1H); LCMS: M + 1 327.2. Method A (Example 7). |
| 165 | 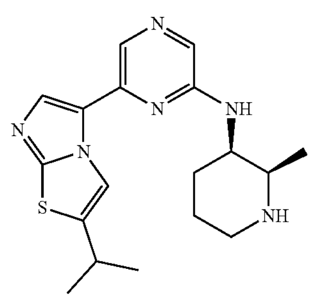 [SMILES: CC(C)c1cn2c(-c3cncc(N[C@@H]4CCCN[C@@H]4C)n3)cnc2s1] | N-[(2R,3R)-2-methylpiperidin-3-yl]-6-[2-(propan-2-yl)imidazo[2,1-b][1,3]thiazol-5-yl]pyrazin-2-amine 1H NMR (400 MHz, DMSO-d6) δ ppm 1.00 (d, J = 6.55 Hz, 3H) 1.33 (d, J = 6.80 Hz, 3H) 1.34-1.39 (m, 1H) 1.51-1.62 (m, 1H) 1.98 (d, J = 9.32 Hz, 1H) 2.55-2.69 (m, 2H) 2.84-2.97 (m, 2H) 3.12-3.22 (m, 2H) 3.96 (d, J = 11.58 Hz, 1H) 6.97 (d, J = 8.81 Hz, 1H) 7.91 (s, 1H) 7.98 (s, 1H) 8.14 (s, 1H) 8.26 (d, J = 1.51 Hz, 1H); LCMS: M + 1 357.2. Method A (Example 7). |

| Ex. | Structure | Name, Data and Preparation Method |
|---|---|---|
| 166 | 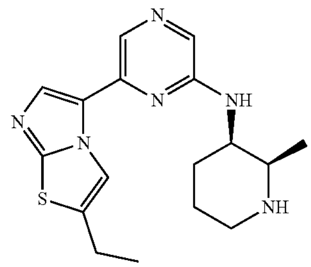 [SMILES: CCc1cn2c(-c3cncc(N[C@@H]4CCCN[C@@H]4C)n3)cnc2s1] | 6-(2-ethylimidazo[2,1-b][1,3]thiazol-5-yl)-N-[(2R,3R)-2-methylpiperidin-3-yl]pyrazin-2-amine 1H NMR (400 MHz, DMSO-d6) δ ppm 1.03 (d, J = 6.55 Hz, 3H) 1.31 (t, 3H) 1.39 (dd, J = 9.06, 3.02 Hz, 1H) 1.52-1.70 (m, 2H) 1.92-2.02 (m, 1H) 2.58-2.70 (m, 1H) 2.79-2.88 (m, 2H) 2.91-3.05 (m, 2H) 4.00 (d, J = 5.54 Hz, 1H) 7.17 (d, J = 7.81 Hz, 1H) 7.91 (s, 1H) 7.97 (s, 1H) 8.15 (s, 1H) 8.26 (br. s., 1H); LCMS: M + 1 343.2. Method A (Example 7). |
| 167 | 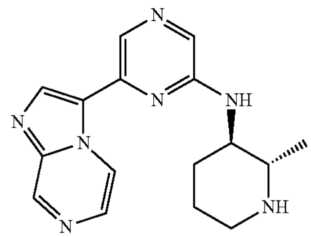 [SMILES: C[C@@H]1NCCC[C@H]1Nc1cncc(-c2cnc3cnccn23)n1] | 6-(imidazo[1,2-a]pyrazin-3-yl)-N-[(2S,3R)-2-methylpiperidin-3-yl]pyrazin-2-amine 1H NMR (400 MHz, DMSO-d6) δ ppm 1.07 (d, J = 6.04 Hz, 3H) 1.16-1.34 (m, J = 11.08, 4.03 Hz, 1H) 1.44-1.60 (m, 1H) 1.62-1.70 (m, 1H) 2.05-2.18 (m, J = 13.09 Hz, 1H) 2.54-2.60 (m, 1H) 2.83-2.99 (m, 1H) 3.33-3.56 (m, J = 11.08 Hz, 1H) 7.24 (d, J = 8.81 Hz, 1H) 7.87 (s, 1H) 8.09 (d, J = 4.78 Hz, 1H) 8.37 (s, 1H) 8.59 (s, 1H) 9.19 (d, J = 1.51 Hz, 1H) 9.60 (d, J = 4.53 Hz, 1H); LCMS: M + 1 310.2. Method A (Example 7). |
| 168 | 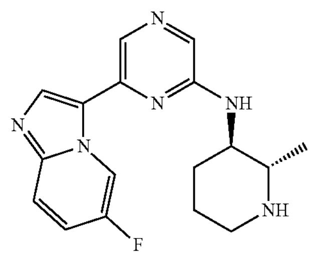 [SMILES: C[C@@H]1NCCC[C@H]1Nc1cncc(-c2cnc3ccc(F)cn23)n1] | 6-(6-fluoroimidazo[1,2-a]pyridin-3-yl)-N-[(2S,3R)-2-methylpiperidin-3-yl]pyrazin-2-amine 1H NMR (400 MHz, DMSO-d6) δ ppm 1.07 (d, J = 6.29 Hz, 3H) 1.18-1.32 (m, 1H) 1.46-1.58 (m, J = 12.34 Hz, 1H) 1.60-1.71 (m, 1H) 2.17 (d, J = 12.09 Hz, 1H) 2.55-2.61 (m, 2H) 2.92 (d, J = 11.83 Hz, 1H) 7.19 (d, J = 8.56 Hz, 1H) 7.44-7.56 (m, 1H) 7.73-7.85 (m, 2H) 7.81 (s, 1H) 8.31 (s, 1H) 8.44 (s, 1H) 9.86 (dd, J = 5.67, 2.39 Hz, 1H); LCMS: M + 1 327.2. Method A (Example 7). |
| 169 | 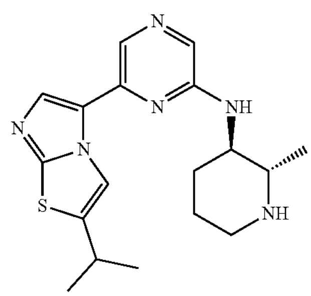 [SMILES: CC(C)c1cn2c(-c3cncc(N[C@@H]4CCCN[C@H]4C)n3)cnc2s1] | N-[(2S,3R)-2-methylpiperidin-3-yl]-6-[2-(propan-2-yl)imidazo[2,1-b][1,3]thiazol-5-yl]pyrazin-2-amine 1H NMR (400 MHz, DMSO-d6) δ ppm 1.04 (d, J = 6.04 Hz, 3H) 1.14-1.30 (m, 1H) 1.29-1.35 (m, 1H) 1.36 (dd, J = 6.80, 1.01 Hz, 6H) 1.40-1.53 (m, 1H) 1.60-1.70 (m, 1H) 2.01-2.11 (m, J = 10.32 Hz, 1H) 2.84-2.96 (m, J = 11.83 Hz, 1H) 3.09-3.24 (m, 1H) 3.33-3.57 (m, 1H) 7.06 (d, J = 8.81 Hz, 1H) 7.74 (s, 1H) 7.93 (s, 1H) 8.14 (s, 1H) 8.31 (d, J = 1.26 Hz, 1H); LCMS: M + 1 357.2. Method A (Example 7). |
| 170 | 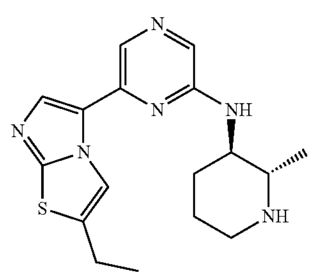 [SMILES: CCc1cn2c(-c3cncc(N[C@@H]4CCCN[C@H]4C)n3)cnc2s1] | 6-(2-ethylimidazo[2,1-b][1,3]thiazol-5-yl)-N-[(2S,3R)-2-methylpiperidin-3-yl]pyrazin-2-amine 1H NMR (400 MHz, DMSO-d6) δ ppm 1.04 (d, J = 6.04 Hz, 3H) 1.15-1.30 (m, 1H) 1.33 (t, J = 7.43 Hz, 3H) 1.41-1.55 (m, 1H) 1.61-1.73 (m, 1H) 2.03-2.16 (m, J = 15.86 Hz, 1H) 2.75-2.86 (m, 2H) 2.88-2.94 (m, J = 11.83 Hz, 1H) 7.05 (d, J = 8.31 Hz, 1H) 7.74 (s, 1H) 7.93 (s, 1H) 8.15 (s, 1H) 8.32 (s, 1H); LCMS: M + 1 343.2. Method A (Example 7). |
| 171 | 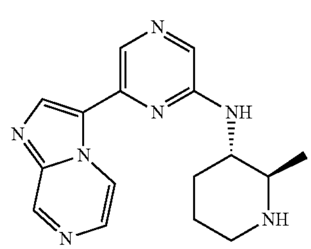 [SMILES: C[C@H]1NCCC[C@@H]1Nc1cncc(-c2cnc3cnccn23)n1] | 6-(imidazo[1,2-a]pyrazin-3-yl)-N-[(2R,3S)-2-methylpiperidin-3-yl]pyrazin-2-amine 1H NMR (400 MHz, DMSO-d6) δ ppm 1.07 (d, J = 6.29 Hz, 3H) 1.18-1.35 (m, 1H) 1.44-1.60 (m, J = 11.83 Hz, 1H) 1.62-1.70 (m, 1H) 2.11 (d, J = 10.58 Hz, 1H) 2.93 (d, J = 11.83 Hz, 1H) 3.39-3.57 (m, 1H) 7.23 (d, J = 8.56 Hz, 1H) 7.86 (s, 1H) 8.09 (d, J = 4.53 Hz, 1H) 8.37 (s, 1H) 8.58 (s, 1H) 9.19 (d, J = 1.51 Hz, 1H) 9.60 (d, J = 3.78 Hz, 1H); LCMS: M + 1 310.2. Method A (Example 7). |

| Ex. | Structure | Name, Data and Preparation Method |
|---|---|---|
| 172 | 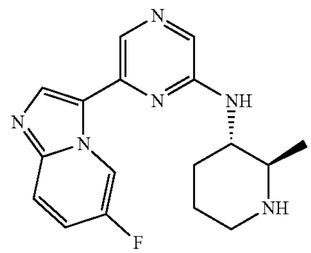 [SMILES: C[C@H]1NCCC[C@@H]1Nc1cncc(-c2cnc3ccc(F)cn23)n1] | 6-(6-fluoroimidazo[1,2-a]pyridin-3-yl)-N-[(2R,3S)-2-methylpiperidin-3-yl]pyrazin-2-amine 1H NMR (400 MHz, DMSO-d6) δ ppm 1.07 (d, J = 6.29 Hz, 3H) 1.15-1.33 (m, 1H) 1.41-1.59 (m, J = 11.83 Hz, 1H) 1.61-1.70 (m, 1H) 2.10-2.23 (m, 1H) 2.54-2.62 (m, 1H) 2.83-3.00 (m, 1H) 3.31-3.51 (m, 1H) 7.19 (d, J = 8.56 Hz, 1H) 7.41-7.53 (m, 1H) 7.75-7.85 (m, 1H) 7.80 (s, 1H) 8.31 (s, 1H) 8.44 (s, 1H) 9.86 (dd, J = 5.79, 2.27 Hz, 1H); LCMS: M + 1 327.2. Method A (Example 7). |
| 173 | 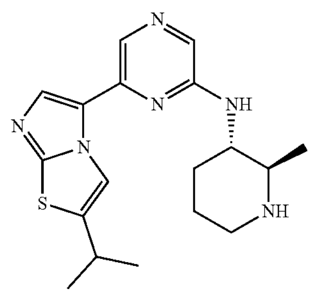 [SMILES: CC(C)c1cn2c(-c3cncc(N[C@H]4CCCN[C@@H]4C)n3)cnc2s1] | N-[(2R,3S)-2-methylpiperidin-3-yl]-6-[2-(propan-2-yl)imidazo[2,1-b][1,3]thiazol-5-yl]pyrazin-2-amine 1H NMR (400 MHz, DMSO-d6) δ ppm 1.03 (d, J = 6.29 Hz, 3H) 1.17-1.32 (m, 1H) 1.36 (dd, J = 6.80, 1.26 Hz, 6H) 1.40-1.54 (m, 1H) 1.59-1.72 (m, 1H) 2.02-2.12 (m, J = 15.86 Hz, 1H) 2.79-2.94 (m, 1H) 3.11-3.21 (m, 1H) 3.43-3.56 (m, 1H) 7.05 (d, J = 9.06 Hz, 1H) 7.74 (s, 1H) 7.93 (s, 1H) 8.14 (s, 1H) 8.32 (d, J = 1.26 Hz, 1H); LCMS: M + 1 357.2. Method A (Example 7). |
| 174 | 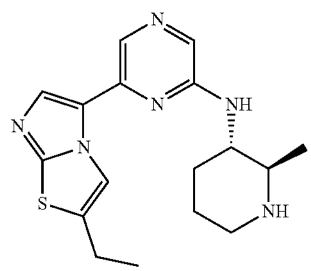 [SMILES: CCc1cn2c(-c3cncc(N[C@H]4CCCN[C@@H]4C)n3)cnc2s1] | 6-(2-ethylimidazo[2,1-b][1,3]thiazol-5-yl)-N-[(2R,3S)-2-methylpiperidin-3-yl]pyrazin-2-amine 1H NMR (400 MHz, DMSO-d6) δ ppm 1.04 (d, J = 6.29 Hz, 3H) 1.16-1.28 (m, 1H) 1.33 (t, 3H) 1.39-1.56 (m, 1H) 1.58-1.73 (m, 1H) 2.01-2.14 (m, J = 14.86 Hz, 1H) 2.80-2.86 (m, 2H) 2.86-2.93 (m, 1H) 3.40-3.50 (m, 2H) 7.05 (d, J = 8.56 Hz, 1H) 7.74 (s, 1H) 7.93 (s, 1H) 8.15 (s, 1H) 8.32 (s, 1H); LCMS: M + 1 343.2. Method A (Example 7). |
| 175 | 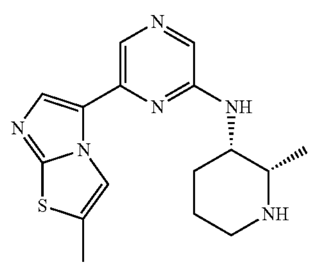 [SMILES: Cc1cn2c(-c3cncc(N[C@H]4CCCN[C@H]4C)n3)cnc2s1] | 6-(2-methylimidazo[2,1-b][1,3]thiazol-5-yl)-N-[(2S,3S)-2-methylpiperidin-3-yl]pyrazin-2-amine 1H NMR (400 MHz, DMSO-d6) δ ppm 1.00 (d, J = 6.55 Hz, 3H) 1.29-1.43 (m, 1H) 1.55-1.67 (m, 2H) 1.90-2.04 (m, 1H) 2.47 (s, 3H) 2.55-2.70 (m, 1H) 2.88-2.99 (m, 2H) 3.94 (d, J = 6.29 Hz, 1H) 6.92 (d, J = 7.55 Hz, 1H) 7.91 (s, 1H) 7.96 (s, 1H) 8.14 (s, 1H) 8.23 (br. s., 1H); LCMS: M + 1 329.2. Method A (Example 7). |
| 176 | 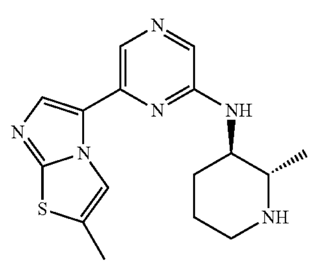 [SMILES: Cc1cn2c(-c3cncc(N[C@@H]4CCCN[C@H]4C)n3)cnc2s1] | 6-(2-methylimidazo[2,1-b][1,3]thiazol-5-yl)-N-[(2S,3R)-2-methylpiperidin-3-yl]pyrazin-2-amine 1H NMR (400 MHz, DMSO-d6) δ ppm 1.05 (d, J = 6.04 Hz, 3H) 1.15-1.30 (m, 1H) 1.43-1.60 (m, 1H) 1.67 (d, J = 3.02 Hz, 1H) 2.05-2.18 (m, 1H) 2.93 (d, J = 14.35 Hz, 1H) 3.37-3.50 (m, J = 28.96 Hz, 1H) 7.05 (d, J = 8.06 Hz, 1H) 7.74 (s, 1H) 7.93 (s, 1H) 8.15 (s, 1H) 8.31 (br. s., 1H); LCMS: M + 1 329.2. Method A (Example 7). |
| 177 | 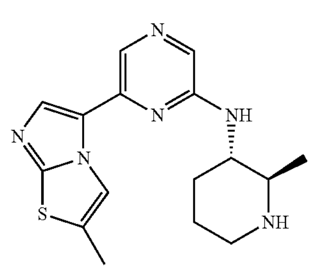 [SMILES: Cc1cn2c(-c3cncc(N[C@H]4CCCN[C@@H]4C)n3)cnc2s1] | 6-(2-methylimidazo[2,1-b][1,3]thiazol-5-yl)-N-[(2R,3S)-2-methylpiperidin-3-yl]pyrazin-2-amine 1H NMR (400 MHz, DMSO-d6) δ ppm 1.05 (d, J = 6.29 Hz, 3H) 1.15-1.30 (m, 1H) 1.39-1.57 (m, 1H) 1.63-1.72 (m, 1H) 2.01-2.19 (m, 1H) 2.53-2.59 (m, 1H) 2.92 (d, J = 12.09 Hz, 1H) 3.41 (d, J = 10.58 Hz, 1H) 7.04 (d, J = 8.31 Hz, 1H) 7.74 (s, 1H) 7.93 (s, 1H) 8.15 (s, 1H) 8.31 (br. s., 1H); LCMS: M + 1 329.2. Method A (Example 7). |

-continued

| Ex. | Structure | Name, Data and Preparation Method |
|---|---|---|
| 178 | 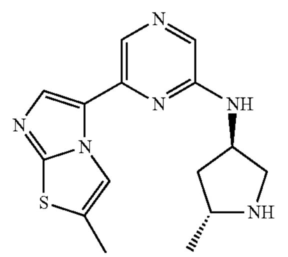 [SMILES: Cc1cn2c(-c3cncc(N[C@H]4CN[C@H](C)C4)n3)cnc2s1] | 6-(2-methylimidazo[2,1-b][1,3]thiazol-5-yl)-N-[(3R,5R)-5-methylpyrrolidin-3-yl]pyrazin-2-amine 1H NMR (400 MHz, DMSO-d6) δ ppm 1.28-1.36 (m, 1H) 1.40 (d, J = 6.55 Hz, 3H) 1.90-2.06 (m, 1H) 2.14-2.24 (m, J = 2.77 Hz, 1H) 2.58 (s, 3H) 3.61-3.73 (m, J = 7.30 Hz, 1H) 3.79-3.93 (m, 1H) 4.55-4.72 (m, 1H) 7.92 (s, 1H) 8.33 (s, 1H) 8.38 (s, 1H) 8.46 (s, 1H) 9.38 (br. s., 1H) 9.71 (br. s., 1H); LCMS: M + 1 315.2. Method A (Example 7). |
| 179 | 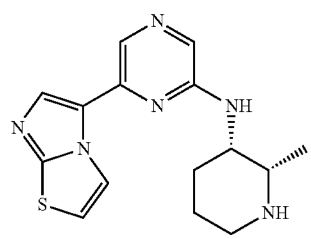 [SMILES: C[C@@H]1NCCC[C@@H]1Nc1cncc(-c2cnc3sccn23)n1] | 6-(imidazo[2,1-b][1,3]thiazol-5-yl)-N-[(2S,3S)-2-methylpiperidin-3-yl]pyrazin-2-amine 1H NMR (400 MHz, DMSO-d6) δ ppm 0.98 (d, J = 6.67 Hz, 3H) 1.18-1.27 (m, 2H) 1.29-1.40 (m, 1H) 1.52-1.65 (m, J = 4.28 Hz, 1H) 1.83-1.98 (m, 1H) 2.85-2.97 (m, J = 13.85 Hz, 2H) 3.84-3.99 (m, 1H) 6.91 (s, 1H) 7.44 (dd, J = 4.41, 1.13 Hz, 1H) 7.95-8.01 (m, 1H) 8.16 (s, 1H) 8.47 (s, 1H); LCMS: M + 1 315.2. Method A (Example 7). |
| 180 | 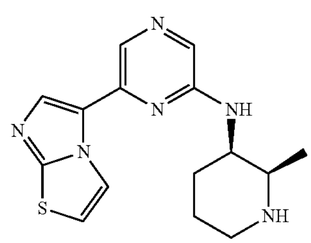 [SMILES: C[C@H]1NCCC[C@H]1Nc1cncc(-c2cnc3sccn23)n1] | 6-(imidazo[2,1-b][1,3]thiazol-5-yl)-N-[(2R,3R)-2-methylpiperidin-3-yl]pyrazin-2-amine 1H NMR (400 MHz, DMSO-d6) δ ppm 0.99 (d, J = 6.55 Hz, 3H) 1.28-1.44 (m, 1H) 1.52-1.64 (m, 1H) 1.88-1.97 (m, 1H) 2.85-2.99 (m, 2H) 3.87-4.05 (m, 1H) 6.93 (d, J = 7.55 Hz, 1H) 7.44 (dd, J = 4.41, 1.13 Hz, 1H) 7.89-8.03 (m, 2H) 8.16 (s, 1H) 8.48 (d, J = 2.27 Hz, 1H); LCMS: M + 1 315.2. Method A (Example 7). |
| 181 | 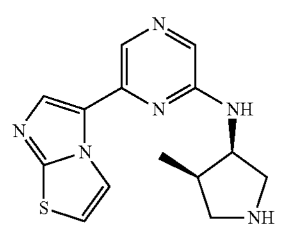 [SMILES: C[C@@H]1CNC[C@@H]1Nc1cncc(-c2cnc3sccn23)n1] | 6-(imidazo[2,1-b][1,3]thiazol-5-yl)-N-[(3R,4R)-4-methylpyrrolidin-3-yl]pyrazin-2-amine 1H NMR (400 MHz, DMSO-d6) δ ppm 0.86 (d, 3H) 2.33 (t, J = 1.89 Hz, 1H) 2.64-2.75 (m, 1H) 3.03-3.14 (m, 1H) 7.16 (d, J = 8.56 Hz, 1H) 7.46 (dd, J = 4.53, 1.01 Hz, 1H) 7.83 (s, 1H) 8.01 (s, 1H) 8.21 (s, 1H) 8.55 (d, J = 4.03 Hz, 1H); LCMS: M + 1 301.2. Method A (Example 7). |
| 182 | 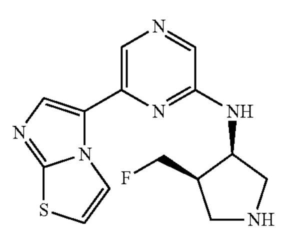 [SMILES: FC[C@@H]1CNC[C@@H]1Nc1cncc(-c2cnc3sccn23)n1] | N-[(3R,4R)-4-(fluoromethyl)pyrrolidin-3-yl]-6-(imidazo[2,1-b][1,3]thiazol-5-yl)pyrazin-2-amine 1H NMR (400 MHz, MeOD) δ ppm 2.93-3.12 (m, 1H) 3.38 (dd, J = 7.55, 1.01 Hz, 1H) 3.55 (dd, J = 12.21, 6.67 Hz, 1H) 3.69-3.81 (m, 2H) 4.58-4.62 (m, 1H) 4.70-4.75 (m, 1H) 5.05 (q, J = 7.39 Hz, 1H) 7.39 (d, J = 4.53 Hz, 1H) 7.91 (s, 1H) 8.05 (s, 1H) 8.31 (s, 1H) 8.56 (d, J = 4.53 Hz, 1H); LCMS: M + 1 319.2. Method A (Example 7). |
| 183 | 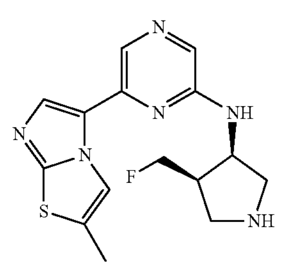 [SMILES: Cc1cn2c(-c3cncc(N[C@H]4CNC[C@H]4CF)n3)cnc2s1] | N-[(3R,4R)-4-(fluoromethyl)pyrrolidin-3-yl]-6-(2-methylimidazo[2,1-b][1,3]thiazol-5-yl)pyrazin-2-amine 1H NMR (400 MHz, MeOD) δ ppm 2.55 (s, 3H) 2.94-3.14 (m, 1H) 3.37 (dd, J = 11.20, 7.93 Hz, 1H) 3.56 (dd, J = 12.34, 6.55 Hz, 1H) 3.68-3.79 (m, 1H) 4.61 (t, J = 3.90 Hz, 1H) 4.73 (t, J = 3.90 Hz, 1H) 5.01 (q, J = 7.47 Hz, 1H) 7.90 (s, 1H) 7.95 (s, 1H) 8.26 (d, J = 1.51 Hz, 1H) 8.28 (s, 1H); LCMS: M + 1 333.2. Method A (Example 7). |

| Ex. | Structure | Name, Data and Preparation Method |
|---|---|---|
| 184 | 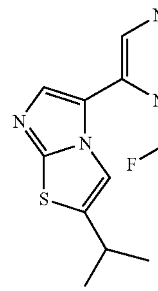 | N-[(3R,4R)-4-(fluoromethyl)pyrrolidin-3-yl]-6-[2-(propan-2-yl)imidazo[2,1-b][1,3]thiazol-5-yl]pyrazin-2-amine 1H NMR (400 MHz, MeOD) δ ppm 1.44 (d, J = 6.80 Hz, 6H) 2.97-3.16 (m, 1H) 3.33-3.37 (m, 1H) 3.37-3.46 (m, 1H) 3.54 (dd, J = 12.21, 7.18 Hz, 1H) 3.69 (dd, J = 12.21, 8.18 Hz, 1H) 3.76 (dd, J = 11.96, 7.43 Hz, 1H) 4.61 (dd, J = 4.78, 1.76 Hz, 1H) 4.73 (dd, J = 4.78, 1.76 Hz, 1H) 5.03 (q, J = 6.80 Hz, 1H) 7.98 (s, 1H) 8.14 (br. s., 1H) 8.32 (s, 1H) 8.39 (s, 1H); LCMS: M + 1 361.2. Method A (Example 7). |
| 185 | 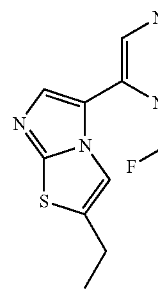 | 6-(2-ethylimidazo[2,1-b][1,3]thiazol-5-yl)-N-[(3R,4R)-4-(fluoromethyl)pyrrolidin-3-yl]pyrazin-2-amine 1H NMR (400 MHz, MeOD) δ ppm 1.40 (t, J = 7.43 Hz, 3H) 2.93 (q, 2H) 2.97-3.16 (m, 1H) 3.40 (dd, J = 11.83, 1.26 Hz, 1H) 3.52-3.60 (m, 1H) 3.65-3.80 (m, 2H) 4.62 (dd, J = 4.41, 3.15 Hz, 1H) 4.74 (t, 1H) 5.01 (q, J = 7.30 Hz, 1H) 7.89 (s, 1H) 7.93 (s, 1H) 8.26 (s, 1H) 8.29 (s, 1H); LCMS: M + 1 347.2. Method A (Example 7). |
| 186 | 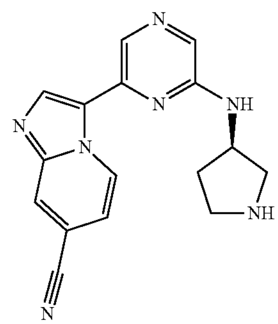 [SMILES: N#Cc1ccn2c(-c3cncc(N[C@@H]4CCNC4)n3)cnc2c1] | 3-{6-[(3R)-pyrrolidin-3-ylamino]pyrazin-2-yl}imidazo[1,2-a]pyridine-7-carbonitrile 1H NMR (400 MHz, DMSO-d6) δ ppm 1.59-1.77 (m, 1H) 2.02-2.17 (m, 1H) 2.70-2.78 (m, 1H) 2.80-2.89 (m, 1H) 2.89-2.99 (m, 1H) 3.06-3.18 (m, J = 6.04 Hz, 1H) 4.19-4.32 (m, 1H) 7.41 (dd, J = 7.30, 1.76 Hz, 1H) 7.46 (d, J = 6.04 Hz, 1H) 7.87 (s, 1H) 8.40 (s, 1H) 8.48 (d, J = 1.01 Hz, 1H) 8.63 (s, 1H) 9.88 (d, J = 7.30 Hz, 1H); LCMS: M + 1 306.2. Method A (Example 7). |
| 187 | 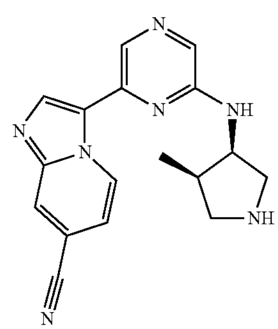 [SMILES: C[C@@H]1CNC[C@@H]1Nc1cncc(-c2cnc3cc(C#N)ccn23)n1] | 3-(6-{[(3R,4R)-4-methylpyrrolidin-3-yl]amino}pyrazin-2-yl)imidazo[1,2-a]pyridine-7-carbonitrile 1H NMR (400 MHz, DMSO-d6) δ ppm 0.87 (d, J = 6.80 Hz, 3H) 2.26-2.39 (m, 1H) 2.73 (dd, J = 11.20, 5.67 Hz, 1H) 3.11 (dd, J = 10.58, 7.05 Hz, 1H) 3.19-3.26 (m, 2H) 4.26-4.44 (m, 1H) 7.31 (d, J = 7.30 Hz, 1H) 7.41 (dd, J = 7.30, 1.51 Hz, 1H) 7.95 (s, 1H) 8.39 (s, 1H) 8.47 (d, J = 1.01 Hz, 1H) 8.62 (s, 1H) 9.84 (d, J = 7.55 Hz, 1H); LCMS: M + 1 320.2. Method A (Example 7). |
| 188 | 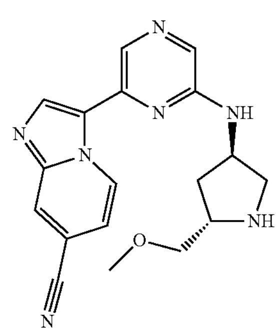 [SMILES: COC[C@@H]1C[C@@H](Nc2cncc(-c3cnc4cc(C#N)ccn34)n2)CN1] | 3-(6-{[(3R,5S)-5-(methoxymethyl)pyrrolidin-3-yl]amino}pyrazin-2-yl)imidazo[1,2-a]pyridine-7-carbonitrile 1H NMR (400 MHz, ACETONITRILE-d3) δ ppm 1.73-1.79 (m, 1H), 1.81-1.88 (m, 2H), 2.08-2.12 (m, 2H), 2.83 (dd, J = 11.08, 4.03 Hz, 1H), 3.27 (dd, J = 11.08, 5.79 Hz, 1H), 3.30 (s, 1H), 3.32 (s, 3H), 3.41-3.49 (m, J = 5.79 Hz, 1H), 4.25-4.46 (m, 1H), 5.75-5.96 (m, 1H), 7.17 (dd, J = 7.30, 1.76 Hz, 1H), 7.83 (s, 1H), 8.14 (s, 1H), 8.31 (s, 1H), 9.88 (dd, J = 7.30, 1.01 Hz, 1H); LCMS: M + 1 350.2. Method A (Example 7). |

| Ex. | Structure | Name, Data and Preparation Method |
|---|---|---|
| 189 | 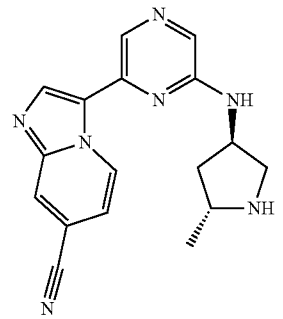 [SMILES: C[C@@H]1C[C@@H](Nc2cncc(-c3cnc4cc(C#N)ccn34)n2)CN1] | 3-(6-{[(3R,5R)-5-methylpyrrolidin-3-yl]amino}pyrazin-2-yl)imidazo[1,2-a]pyridine-7-carbonitrile 1H NMR (400 MHz, DMSO-d6) δ ppm 1.15 (d, J = 6.29 Hz, 3H), 1.52-1.73 (m, 1H), 1.84-1.96 (m, 1H), 2.25-2.35 (m, 1H), 2.72-2.80 (m, J = 16.37 Hz, 1H), 3.41 (dd, J = 4.78 Hz, 1H), 4.20-4.44 (m, 1H), 7.42 (dd, J = 7.43, 1.64 Hz, 1H), 7.55 (d, J = 6.04 Hz, 1H), 7.87 (s, 1H), 8.42 (s, 1H), 8.50 (d, J = 1.76 Hz, 1H), 8.64 (s, 1H), 9.87 (d, J = 7.05 Hz, 1H); LCMS: M + 1 320.2. Method A (Example 7). |
| 190 | 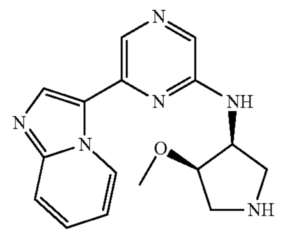 [SMILES: CO[C@@H]1CNC[C@@H]1Nc1cncc(-c2cnc3ccccn23)n1] | 6-(imidazo[1,2-a]pyridin-3-yl)-N-[(3S,4R)-4-methoxypyrrolidin-3-yl]pyrazin-2-amine 1H NMR (400 MHz, MeOD) δ ppm 2.94 (dd, J = 11.08, 8.06 Hz, 1H), 3.13-3.28 (m, 2H), 3.34-3.37 (m, 2H), 3.43 (s, 3H), 4.01-4.09 (m, 1H), 4.48-4.60 (m, 1H), 7.11-7.18 (m, 1H), 7.45-7.53 (m, 1H), 7.69 (d, J = 9.06 Hz, 1H), 7.92 (s, 1H), 8.25 (s, 1H), 8.29 (s, 1H), 9.75 (d, J = 7.05 Hz, 1H); LCMS: M + 1 311.2. Method A (Example 7). |
| 191 | 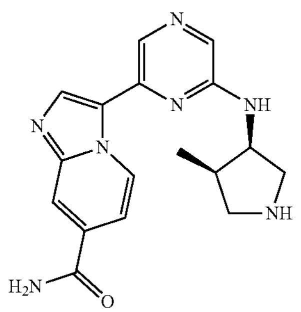 [SMILES: C[C@@H]1CNC[C@@H]1Nc1cncc(-c2cnc3cc(C(N)=O)ccn23)n1] | 3-(6-{[(3R,4R)-4-methylpyrrolidin-3-yl]amino}pyrazin-2-yl)imidazo[1,2-a]pyridine-7-carboxamide 1H NMR (400 MHz, MeOD) δ ppm 1.16 (d, J = 7.05 Hz, 3H), 2.69-2.83 (m, 1H), 3.14 (dd, J = 11.71, 9.19 Hz, 1H), 3.34-3.39 (m, 1H), 3.57 (dd, J = 11.58, 7.30 Hz, 1H), 3.69 (dd, J = 12.09, 6.29 Hz, 1H), 4.77-4.84 (m, J = 5.04 Hz, 1H), 7.56 (dd, J = 7.30, 1.76 Hz, 1H), 7.94 (s, 1H), 8.22 (d, J = 1.76 Hz, 1H), 8.39 (s, 1H), 8.52 (s, 1H), 9.73 (d, J = 7.30 Hz, 1H); LCMS: M + 1 338.2. Method A (Example 7). |
| 192 | 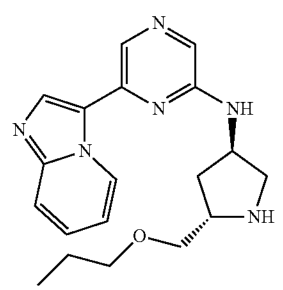 [SMILES: CCCOC[C@@H]1C[C@@H](Nc2cncc(-c3cnc4ccccn34)n2)CN1] | 6-(imidazo[1,2-a]pyridin-3-yl)-N-[(3R,5S)-5-(propoxymethyl)pyrrolidin-3-yl]pyrazin-2-amine 1H NMR (400 MHz, MeOD) δ ppm 0.86-0.98 (m, 3H), 1.47-1.65 (m, 2H), 1.91-2.08 (m, 2H), 2.90 (dd, J = 11.33, 5.04 Hz, 1H), 3.37-3.59 (m, 6H), 4.32-4.59 (m, 1H), 7.02-7.11 (m, 1H), 7.39-7.48 (m, 1H), 7.62-7.68 (m, 1H), 7.74 (s, 1H), 8.22 (s, 1H), 8.24 (s, 1H), 9.82 (d, J = 7.05 Hz, 1H); LCMS: M + 1 353.2. Method A (Example 7). |
| 193 | 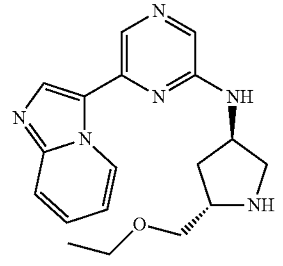 [SMILES: CCOC[C@@H]1C[C@@H](Nc2cncc(-c3cnc4ccccn34)n2)CN1] | N-[(3R,5S)-5-(ethoxymethyl)pyrrolidin-3-yl]-6-(imidazo[1,2-a]pyridin-3-yl)pyrazin-2-amine 1H NMR (400 MHz, MeOD) δ ppm 1.18 (dd, 6H), 1.91-2.13 (m, 2H), 2.91 (dd, J = 11.46, 4.91 Hz, 1H), 3.41-3.56 (m, 4H), 3.60-3.70 (m, 1H), 4.34-4.61 (m, 1H), 7.02-7.16 (m, 1H), 7.41-7.52 (m, 1H), 7.63-7.72 (m, 1H), 7.76 (s, 1H), 8.25 (s, 1H), 8.27 (s, 1H), 9.85 (d, J = 7.05 Hz, 1H); LCMS: M + 1 339.2. Method A (Example 7). |

-continued

| Ex. | Structure | Name, Data and Preparation Method |
|---|---|---|
| 194 | 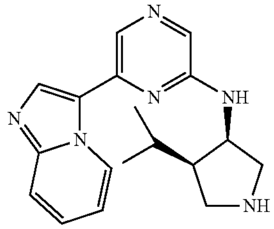 [SMILES: CC(C)[C@@H]1CNC[C@@H]1Nc1cncc(-c2cnc3ccccn23)n1] | 6-(imidazo[1,2-a]pyridin-3-yl)-N-[(3R,4R)-4-(propan-2-yl)pyrrolidin-3-yl]pyrazin-2-amine 1H NMR (400 MHz, MeOD) δ ppm 0.89-1.03 (m, 6H), 2.12-2.30 (m, 1H), 3.22-3.25 (m, 1H), 3.26-3.32 (m, 1H), 3.40-3.48 (m, 1H), 3.48-3.58 (m, 2H), 4.75 (t, J = 4.53 Hz, 1H), 6.94-7.07 (m, 1H), 7.26-7.43 (m, 1H), 7.57 (d, J = 8.81 Hz, 1H), 7.83 (s, 1H), 8.12 (s, 1H), 8.21 (s, 1H), 9.56 (d, J = 7.05 Hz, 1H); LCMS: M + 1 323.2. Method A (Example 7). |
| 195 | 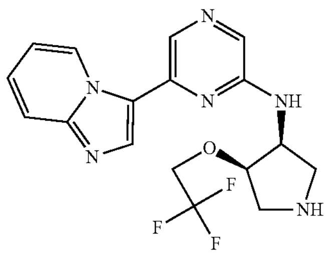 [SMILES: FC(F)(F)CO[C@@H]1CNC[C@@H]1Nc1cncc(-c2cnc3ccccn23)n1] | 6-(imidazo[1,2-a]pyridin-3-yl)-N-[(3S,4R)-4-(2,2,2-trifluoroethoxy)pyrrolidin-3-yl]pyrazin-2-amine 1H NMR (400 MHz, MeOD) δ ppm 3.21-3.34 (m, 2H), 3.48-3.66 (m, 2H), 3.67-3.79 (m, 1H), 4.04-4.18 (m, 2H), 4.53 (br. s., 1H), 4.80-4.91 (m, 1H), 7.11 (t, J = 6.80 Hz, 1H), 7.35-7.52 (m, 1H), 7.65 (d, J = 9.06 Hz, 1H), 7.92 (s, 1H), 8.20 (s, 1H), 8.28 (s, 1H), 9.59 (d, J = 7.05 Hz, 1H); LCMS: M + 1 379.1. Method A (Example 7). |
| 196 | 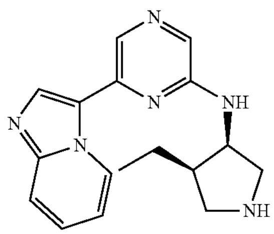 [SMILES: CC[C@@H]1CNC[C@@H]1Nc1cncc(-c2cnc3ccccn23)n1] | N-[(3R,4R)-4-ethylpyrrolidin-3-yl]-6-(imidazo[1,2-a]pyridin-3-yl)pyrazin-2-amine 1H NMR (400 MHz, MeOD) δ ppm 0.90-0.97 (m, 3H), 1.37-1.50 (m, 1H), 1.51-1.64 (m, 1H), 2.23-2.36 (m, J = 8.06 Hz, 1H), 2.71-2.85 (m, 1H), 2.95 (dd, J = 11.58, 4.28 Hz, 1H), 3.25 (dd, J = 10.95, 7.68 Hz, 2H), 4.52-4.71 (m, 1H), 7.10 (t, J = 6.42 Hz, 1H), 7.36-7.53 (m, 1H), 7.59-7.76 (m, 1H), 7.84 (s, 1H), 8.19-8.28 (m, 2H), 9.79 (d, J = 7.05 Hz, 1H); LCMS: M + 1 309.2. Method A (Example 7). |
| 197 | 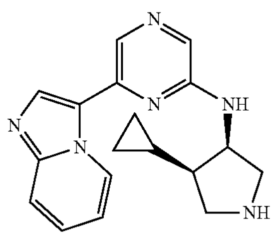 [SMILES: c1ccn2c(-c3cncc(N[C@H]4CNC[C@H]4C4CC4)n3)cnc2c1] | N-[(3R,4R)-4-cyclopropylpyrrolidin-3-yl]-6-(imidazo[1,2-a]pyridin-3-yl)pyrazin-2-amine 1H NMR (400 MHz, METHANOL-d4) δ ppm 9.68 (d, J = 7.1 Hz, 1H), 8.28 (s, 1H), 8.15 (s, 1H), 7.84 (s, 1H), 7.72-7.62 (m, J = 9.1 Hz, 1H), 7.33-7.18 (m, 1H), 6.91 (t, J = 6.4 Hz, 1H), 5.83 (d, J = 7.1 Hz, 1H), 4.57-4.40 (m, 1H), 3.44 (dd, J = 5.7, 10.7 Hz, 1H), 3.29 (dd, J = 8.3, 10.3 Hz, 1H), 3.13-2.93 (m, 1H), 1.76-1.59 (m, 1H), 0.86-0.70 (m, 1H), 0.54-0.39 (m, 2H), 0.26-0.12 (m, 2H); LCMS: M + 1 321.1. Method A (Example 7). |
| 198 | 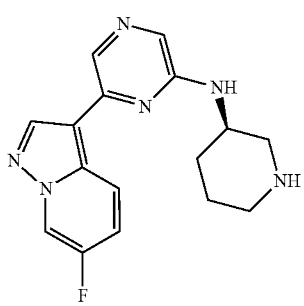 [SMILES: Fc1ccc2c(-c3cncc(N[C@@H]4CCCNC4)n3)cnn2c1] | 6-(6-fluoropyrazolo[1,5-a]pyridin-3-yl)-N-[(3R)-piperidin-3-yl]pyrazin-2-amine 1H NMR (400 MHz, MeOD) δ ppm 1.71-1.90 (m, 1H) 2.02 (dd, J = 10.48, 4.17 Hz, 1H) 2.14 (br. s., 1H) 2.26 (br. s., 1H) 3.04-3.23 (m, 2H) 3.38 (d, J = 12.88 Hz, 1H) 3.57-3.73 (m, 1H) 4.40-4.57 (m, 1H) 7.54-7.69 (m, 1H) 7.78 (s, 1H) 8.37 (s, 1H) 8.50 (dd, J = 9.60, 5.56 Hz, 1H) 8.71 (s, 1H) 8.79-8.90 (m, 1H); LCMS: M + 1 313. Method E (Example 6). |
| 199 | 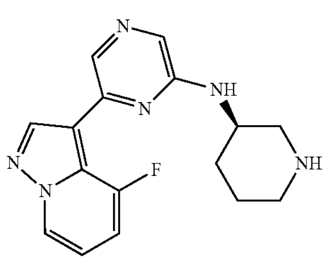 [SMILES: Fc1cccn2ncc(-c3cncc(N[C@@H]4CCCNC4)n3)c12] | 6-(4-fluoropyrazolo[1,5-a]pyridin-3-yl)-N-[(3R)-piperidin-3-yl]pyrazin-2-amine 1H NMR (400 MHz, D2O) δ ppm 2.76 (br. s., 1H) 2.92 (br. s., 1H) 3.14 (br. s., 2H) 3.94-4.18 (m, 2H) 4.36 (br. s., 1H) 4.56 (br. s., 1H) 5.24 (br. s., 1H) 7.94-8.05 (m, 1H) 8.13-8.24 (m, 1H) 8.65 (s, 1H) 8.95 (s, 1H) 9.34-9.45 (m, 2H); LCMS: M + 1 313. Method E (Example 6). |

| Ex. | Structure | Name, Data and Preparation Method |
|---|---|---|
| 200 | 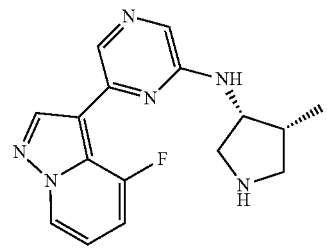 [SMILES: C[C@@H]1CNC[C@@H]1Nc1cncc(-c2cnn3cccc(F)c23)n1] | 6-(4-fluoropyrazolo[1,5-a]pyridin-3-yl)-N-[(3R,4R)-4-methylpyrrolidin-3-yl]pyrazin-2-amine 1H NMR (400 MHz, MeOD) δ ppm 1.19 (d, J = 6.82 Hz, 3H) 2.72-2.87 (m, 1H) 3.19-3.28 (m, 1H) 3.45 (dd, J = 12.51, 3.92 Hz, 1H) 3.61 (dd, J = 11.62, 7.33 Hz, 1H) 3.75 (dd, J = 12.51, 6.44 Hz, 1H) 4.95-5.08 (m, 1H) 7.05-7.17 (m, 1H) 7.27-7.39 (m, 1H) 8.00 (br. s., 1H) 8.29 (s, 1H) 8.62 (d, J = 6.82 Hz, 1H) 8.69 (s, 1H); LCMS: M + 1 313. Method E (Example 6). |
| 201 | 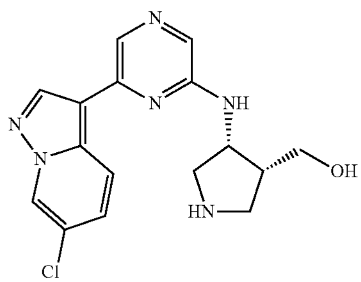 [SMILES: OC[C@@H]1CNC[C@@H]1Nc1cncc(-c2cnn3cc(Cl)ccc23)n1] | [(3R,4R)-4-{[6-(6-chloropyrazolo[1,5-a]pyridin-3-yl)pyrazin-2-yl]amino}pyrrolidin-3-yl]methanol 1H NMR (400 MHz, DMSO-d6) δ ppm 2.66 (br. s., 1H) 3.14-3.37 (m, 2H) 3.38-3.64 (m, 5H) 4.74-4.92 (m, 1H) 7.52 (d, J = 9.60 Hz, 1H) 7.55-7.66 (m, 1H) 7.89 (s, 1H) 8.37 (s, 1H) 8.48 (d, J = 9.35 Hz, 1H) 8.78 (s, 1H) 9.14 (s, 1H) 9.26 (br. s., 1H) 9.61 (br. s., 1H); LCMS: M + 1 345. Method A (Example 7). |
| 202 | 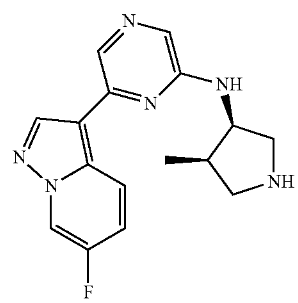 [SMILES: C[C@@H]1CNC[C@@H]1Nc1cncc(-c2cnn3cc(F)ccc23)n1] | 6-(6-fluoropyrazolo[1,5-a]pyridin-3-yl)-N-[(3R,4R)-4-methylpyrrolidin-3-yl]pyrazin-2-amine 1H NMR (400 MHz, DMSO-d6) δ ppm 1.02 (d, J = 6.57 Hz, 3H) 2.61 (d, J = 7.07 Hz, 1H) 2.99-3.13 (m, 1H) 3.13-3.29 (m, 1H) 3.35-3.50 (m, 1H) 3.51-3.64 (m, 1H) 4.64-4.80 (m, 1H) 7.44-7.71 (m, 2H) 7.89 (s, 1H) 8.37 (s, 1H) 8.42-8.59 (m, 1H) 8.77 (s, 1H) 9.12 (br. s., 1H) 9.39 (br. s., 1H) 9.55 (br. s., 1H); LCMS: M + 1 313. Method E (Example 6). |
| 203 | 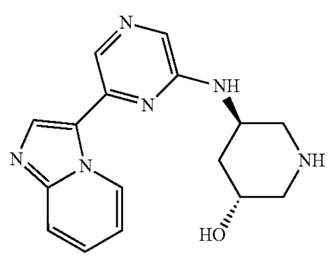 [SMILES: O[C@H]1CNC[C@H](Nc2cncc(-c3cnc4ccccn34)n2)C1] | (3R,5R)-5-{[6-(imidazo[1,2-a]pyridin-3-yl)pyrazin-2-yl]amino}piperidin-3-ol 1H NMR (400 MHz, MeOD) δ ppm 1.25-1.48 (m, 1H) 1.68-1.93 (m, 1H) 2.17-2.50 (m, 1H) 2.60-2.84 (m, 1H) 2.98 (br. s., 1H) 3.11-3.28 (m, 1H) 3.48-3.67 (m, 1H) 4.22-4.52 (m, 1H) 4.69-4.84 (m, 1H) 6.99-7.23 (m, 1H) 7.37-7.56 (m, 1H) 7.59-7.72 (m, 1H) 7.79 (br. s., 1H) 8.20-8.38 (m, 2H) 8.53 (br. s, 1H) 9.69-9.93 (m, 1H); LCMS: M + 1 311. Method A (Example 7). |
| 204 | 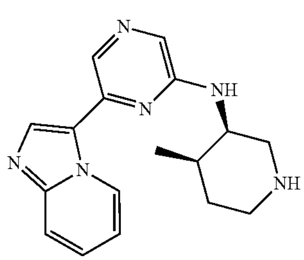 [SMILES: C[C@@H]1CCNC[C@@H]1Nc1cncc(-c2cnc3ccccn23)n1] | 6-(imidazo[1,2-a]pyridin-3-yl)-N-[(3R,4R)-4-methylpiperidin-3-yl]pyrazin-2-amine 1H NMR (400 MHz, CD3OD) δ ppm 1.17 (d, J = 7.07 Hz, 3H) 1.82-2.13 (m, 2H) 2.34 (d, J = 3.54 Hz, 1H) 3.05-3.23 (m, 1H) 3.35-3.48 (m, 2H) 3.63 (dd, J = 12.88, 3.54 Hz, 1H) 4.51 (br. s., 1H) 7.70 (t, J = 6.69 Hz, 1H) 8.00-8.19 (m, 2H) 8.29 (br. s., 1H) 8.45 (br. s., 1H) 8.77 (s, 1H) 9.86 (d, J = 6.82 Hz, 1H); LCMS: M + 1 309. Method A (Example 7). |

| Ex. | Structure | Name, Data and Preparation Method |
|---|---|---|
| 205 | 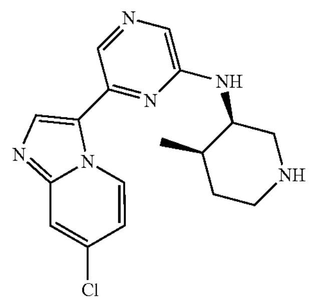 [SMILES: C[C@@H]1CCNC[C@@H]1Nc1cncc(-c2cnc3cc(Cl)ccn23)n1] | 6-(7-chloroimidazo[1,2-a]pyridin-3-yl)-N-[(3R,4R)-4-methylpiperidin-3-yl]pyrazin-2-amine 1H NMR (400 MHz, MeOD) δ ppm 1.19 (d, J = 7.07 Hz, 3H) 1.87-2.11 (m, 2H) 2.27-2.45 (m, 1H) 3.10-3.24 (m, 1H) 3.36-3.48 (m, 2H) 3.55-3.71 (m, 1H) 4.40-4.60 (m, 1H) 7.60-7.84 (m, 1H) 8.20 (s, 1H) 8.27 (s, 1H) 8.44 (s, 1H) 8.77 (s, 1H) 9.87 (d, J = 7.33 Hz, 1H); LCMS: M + 1 343/345. Method A (Example 7). |
| 206 | 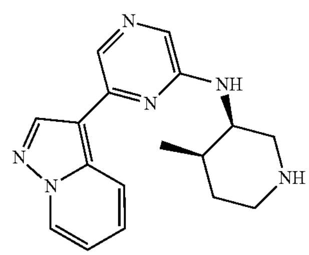 [SMILES: C[C@@H]1CCNC[C@@H]1Nc1cncc(-c2cnn3ccccc23)n1] | N-[(3R,4R)-4-methylpiperidin-3-yl]-6-(pyrazolo[1,5-a]pyridin-3-yl)pyrazin-2-amine 1H NMR (400 MHz, MeOD) δ ppm 1.20 (d, J = 6.82 Hz, 3H) 1.83-2.08 (m, 2H) 2.26-2.45 (m, 1H) 3.09-3.22 (m, 1H) 3.36-3.45 (m, 2H) 3.73 (dd, J = 12.63, 3.54 Hz, 1H) 4.50 (d, J = 2.02 Hz, 1H) 7.04 (t, J = 6.69 Hz, 1H) 7.45 (t, J = 7.83 Hz, 1H) 7.90 (s, 1H) 8.27 (s, 1H) 8.40 (d, J = 9.09 Hz, 1H) 8.57 (s, 1H) 8.63 (d, J = 7.07 Hz, 1H); LCMS: M + 1 309. Method A (Example 7). |
| 207 | 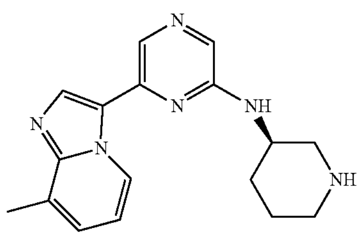 [SMILES: Cc1cccn2c(-c3cncc(N[C@@H]4CCCNC4)n3)cnc12] | 6-(8-methylimidazo[1,2-a]pyridin-3-yl)-N-[(3R)-piperidin-3-yl]pyrazin-2-amine 1H NMR (400 MHz, DMSO-d6) δ ppm 1.48 (br. s., 2H), 1.71 (br. s., 2H), 2.02 (br. s., 1H), 2.53-2.57 (m, 4H), 2.86 (br. s., 1H), 3.18 (br. s., 1H), 3.81 (br. s., 1H), 7.00 (s, 1H), 7.15 (br. s., 1H), 7.23 (s, 1H), 7.80 (s, 1H), 8.32 (d, J = 7.81 Hz, 2H), 9.61 (br. s., 1H); LCMS: M + 1 309.2. Method A (Example 4). |
| 208 | 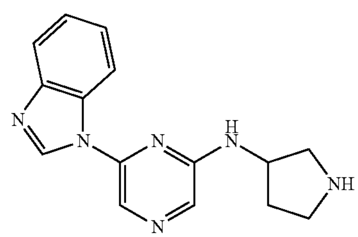 [SMILES: c1ccc2c(c1)ncn2-c1cncc(NC2CCNC2)n1] | 6-(1H-benzimidazol-1-yl)-N-(pyrrolidin-3-yl)pyrazin-2-amine 1H NMR (400 MHz, MeOD) δ ppm 1.90 (br. s., 1H) 2.30 (br. s., 1H) 2.95 (br. s., 1H) 3.11 (br. s., 2H) 3.35 (s, 1H) 4.52 (br. s., 1H) 7.41 (br. s, 2H) 7.76 (br. s., 1H) 7.92 (s, 1H) 8.18 (s, 2H) 8.81 (s, 1H); LCMS: M + 1 281.2. Method B (Example 1). |
| 209 | 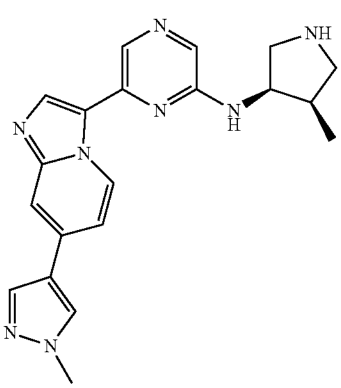 [SMILES: C[C@@H]1CNC[C@@H]1Nc1cncc(-c2cnc3cc(-c4cnn(C)c4)ccn23)n1] | 6-[7-(1-methyl-1H-pyrazol-4-yl)imidazo[1,2-a]pyridin-3-yl]-N-[(3R,4R)-4-methylpyrrolidin-3-yl]pyrazin-2-amine 1H NMR (400 MHz, MeOD) δ ppm 1.17 (d, J = 7.05 Hz, 3H), 2.80 (t, J = 5.79 Hz, 1H), 3.22 (dd, J = 11.58, 9.06 Hz, 1H), 3.42 (dd, J = 12.34, 4.78 Hz, 1H), 3.57-3.68 (m, 3H), 3.77 (dd, J = 12.09, 6.55 Hz, 1H), 4.01 (s, 3H), 4.89 (q, J = 5.88 Hz, 1H), 7.94 (dd, J = 7.30, 1.76 Hz, 1H), 8.08 (d, J = 1.01 Hz, 1H), 8.16 (d, J = 11.08 Hz, 2H), 8.42 (d, J = 13.60 Hz, 2H), 8.64 (s, 1H), 9.81 (d, J = 7.55 Hz, 1H); LCMS: M + 1 375.2. Method B (Example 5). |

-continued

| Ex. | Structure | Name, Data and Preparation Method |
|---|---|---|
| 210 | 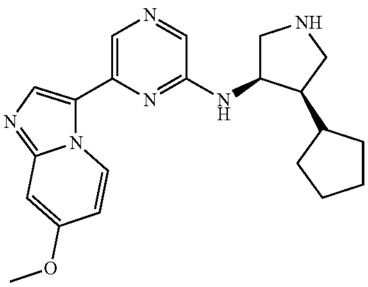 [SMILES: COc1ccn2c(-c3cncc(N[C@H]4CNC[C@H]4C4CCCC4)n3)cnc2c1] | N-[(3R,4R)-4-cyclopentylpyrrolidin-3-yl]-6-(7-methoxyimidazo[1,2-a]pyridin-3-yl)pyrazin-2-amine 1H NMR (400 MHz, MeOD) δ ppm 1.18-1.31 (m, 8H), 1.56 (br. s., 2H), 1.79 (br. s., 1H), 3.05 (s, 1H), 3.94 (s, 4H) 3.13 (s, 1H), 6.81 (dd, J = 7.81, 2.52 Hz, 1H), 7.00 (d, J = 2.52 Hz, 1H), 7.83 (s, 1H), 8.10 (s, 1H), 8.26 (s, 1H), 9.58 (d, J = 8.06 Hz, 1H); LCMS: M + 1 379.2. Method A (Example 7). |
| 211 | 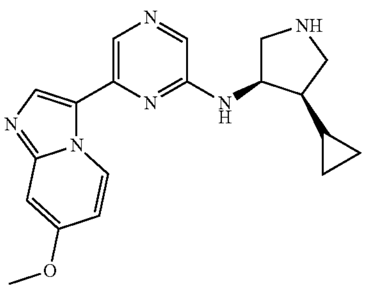 [SMILES: COc1ccn2c(-c3cncc(N[C@H]4CNC[C@H]4C4CC4)n3)cnc2c1] | N-[(3R,4R)-4-cyclopropylpyrrolidin-3-yl]-6-(7-methoxyimidazo[1,2-a]pyridin-3-yl)pyrazin-2-amine 1H NMR (400 MHz, MeOD) δ ppm 0.25 (br. s., 2H), 0.58 (br. s., 2H), 3.48-3.68 (m, 2H), 3.94 (s, 4H), 6.80 (dd, J = 7.68, 2.64 Hz, 1H), 7.00 (d, J = 2.77 Hz, 1H), 7.87 (s, 1H), 8.12 (s, 1H), 8.31 (s, 1H), 9.56 (d, J = 8.31 Hz, 1H); LCMS: M + 1 351.2. Method A (Example 7). |
| 212 | 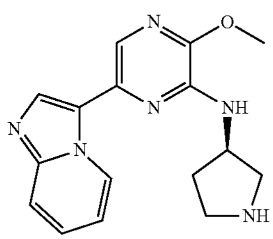 [SMILES: COc1ncc(-c2cnc3ccccn23)nc1N[C@@H]1CCNC1] | 6-(imidazo[1,2-a]pyridin-3-yl)-3-methoxy-N-[(3R)-pyrrolidin-3-yl]pyrazin-2-amine 1H NMR (400 MHz, D2O) δ ppm 2.270~2.160 (m, 1H), 2.501~2.381 (m, 1H), 3.650~3.361 (m, 4H), 3.998 (s, 3H), 4.65 (m, 1H), 7.431~7.365 (t, 1H), 7.640 (s, 1H), 7.921~7.830 (m, 2H), 8.069 (s, 1H), 9.201~9.150 (d, 1H). Method B (Example 36). |
| 213 | 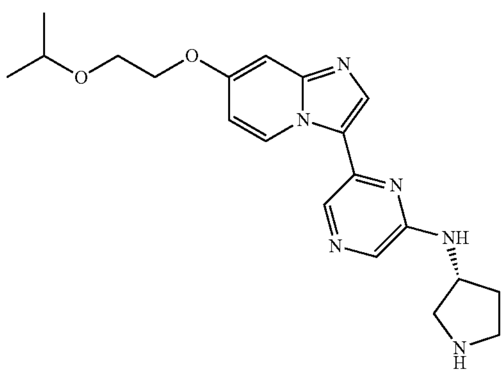 [SMILES: CC(C)OCCOc1ccn2c(-c3cncc(N[C@@H]4CCNC4)n3)cnc2c1] | 6-{7-[2-(propan-2-yloxy)ethoxy]imidazo[1,2-a]pyridin-3-yl}-N-[(3R)-pyrrolidin-3-yl]pyrazin-2-amine 1H NMR (400 MHz, DMSO): δ ppm 1.241-1.275 (m, 6H), 1.670-1.682 (m, 1H), 2.049-2.137 (m, 1H), 2.677-3.125 (m, 3H), 3.624-3.685 (m, 2H), 3.698-3.758 (m, 2H), 4.200-4.412 (m, 3H), 6.831-6.850 (d, 1H), 7.113 (s, 1H), 7.244-7.260 (d, 2H), 7.742-7.779 (m, 1H), 8.219-8.331 (m, 2H), 9.663-9.731 (d, 1H); LCMS: M + 1 383.5. Method A (Example 32). |
| 214 | 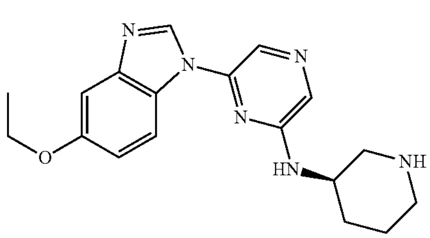 [SMILES: CCOc1ccc2c(c1)ncn2-c1cncc(N[C@@H]2CCCNC2)n1] | 6-(5-ethoxy-1H-benzimidazol-1-yl)-N-[(3R)-piperidin-3-yl]pyrazin-2-amine 1H NMR (400 MHz, MeOD): δ ppm 1.913-1.684 (m, 2H), 2.110-2.056 (m, 2H), 2.957 (m, 2H), 3.584 (d, 1H), 3.854 (s, 3H), 4.259 (m, 1H), 4.605 (s, 1H), 7.056 (d, 1H), 7.256 (s, 1H), 7.942-7.935 (d, 2H), 8.211 (s, 1H), 8.495 (s, 1H), 8.758 (s, 1H); LCMS: M + 1 339.3. Method A (Example 15). |

| Ex. | Structure | Name, Data and Preparation Method |
|---|---|---|
| 215 | 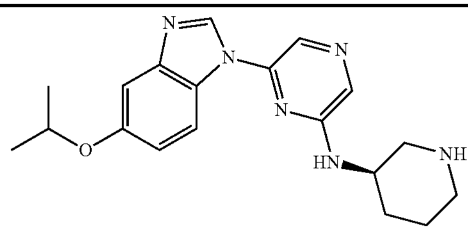 | N-[(3R)-piperidin-3-yl]-6-[5-(propan-2-yloxy)-1H-benzimidazol-1-yl]pyrazin-2-amine 1H NMR (400 MHz, MeOD): δ ppm 1.407 (d, 6H), 2.296-1.749 (m, 4H), 3.056 (m, 2H), 3.807-3.609 (m, 3H), 4.396 (s, 1H), 4.875-4.723 (m, 1H), 7.389 (d, 2H), 8.228 (t, 2H), 8.375 (s, 1H), 10.064 (s, 1H); LCMS: M + 1 353.4. Method A (Example 15). |
| 216 | 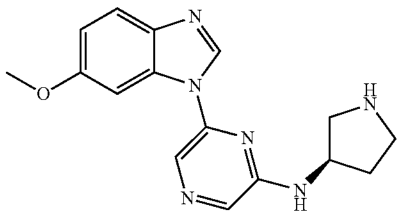 [SMILES: COc1ccc2ncn(-c3cncc(N[C@@H]4CCNC4)n3)c2c1] | 6-(6-methoxy-1H-benzimidazol-1-yl)-N-[(3R)-pyrrolidin-3-yl]pyrazin-2-amine 1H NMR (400 MHz, DMSO): δ ppm 1.81 (m, 1H), 2.19 (m, 1H), 3.23-3.32 (m, 4H), 3.82 (s, 3H), 4.40 (m, 1H), 6.90-7.00 (d, 1H), 7.63 (d, 1H), 7.76 (m, 2H), 7.92 (s, 1H), 8.25 (s, 1H), 8.78 (s, 1H); LCMS: M + 1 311.1. Method A (Example 15). |
| 217 | 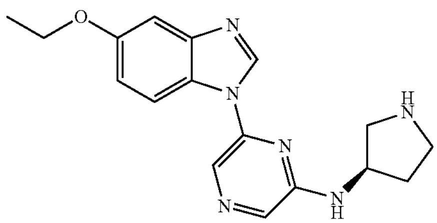 [SMILES: CCOc1ccc2c(c1)ncn2-c1cncc(N[C@@H]2CCNC2)n1] | 6-(5-ethoxy-1H-benzimidazol-1-yl)-N-[(3R)-pyrrolidin-3-yl]pyrazin-2-amine 1H NMR (400 MHz, DMSO): δ ppm 1.3 (m, 3H), 1.5-2.0 (m, 1H), 2.2 (m, 1H), 2.7-3.4 (m, 4H), 4.0 (m, 2H), 4.34 (m, 1H), 7.0 (m, 1H), 7.3 (m, 1H), 7.88 (s, 1H), 8.0-8.4 (m, 2H), 8.8 (s, 1H); LCMS: M + 1 325.1. Method A (Example 15). |
| 218 | 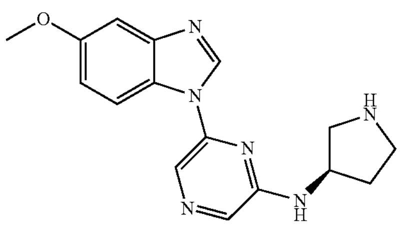 [SMILES: COc1ccc2c(c1)ncn2-c1cncc(N[C@@H]2CCNC2)n1] | 6-(5-methoxy-1H-benzimidazol-1-yl)-N-[(3R)-pyrrolidin-3-yl]pyrazin-2-amine 1H NMR (400 MHz, DMSO): δ ppm 1.5-2.3 (m, 2H), 2.5-3.2 (m, 4H), 3.8 (s, 3H), 4.0-4.3 (d, 1H), 7.0 (m, 1H), 7.3 (m, 1H), 7.5-8.0 (d, 2H), 8.0-8.4 (m, 2H), 8.8 (s, 1H); LCMS: M + 1 311.1. Method A (Example 15). |
| 219 | 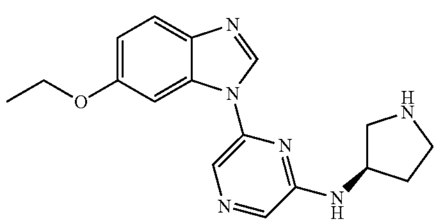 [SMILES: CCOc1ccc2ncn(-c3cncc(N[C@@H]4CCNC4)n3)c2c1] | 6-(6-ethoxy-1H-benzimidazol-1-yl)-N-[(3R)-pyrrolidin-3-yl]pyrazin-2-amine 1H NMR (400 MHz, DMSO): δ ppm 1.35 (m, 3H), 1.78 (m, 1H), 2.15 (m, 1H), 2.78-3.26 (m, 4H), 4.10 (m, 2H), 4.40 (m, 1H), 6.95 (d, 1H), 7.63 (d, 1H), 7.74 (m, 2H), 7.94 (s, 1H), 8.28 (s, 1H), 8.77 (s, 1H); LCMS: M + 1 325.1. Method A (Example 15). |
| 220 | 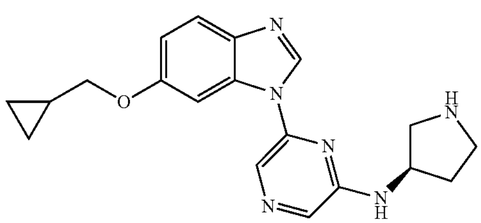 [SMILES: c1cc2ncn(-c3cncc(N[C@@H]4CCNC4)n3)c2cc1OCC1CC1] | 6-[6-(cyclopropylmethoxy)-1H-benzimidazol-1-yl]-N-[(3R)-pyrrolidin-3-yl]pyrazin-2-amine 1H NMR (400 MHz, DMSO): δ ppm 0.32 (m, 2H), 0.58 (m, 2H), 1.22 (m, 1H), 1.65 (m, 1H), 2.12 (m, 1H), 2.70-3.26 (m, 4H), 3.89 (m, 2H), 4.40 (m, 1H), 6.95 (d, 1H), 7.61 (d, 1H), 7.74 (m, 2H), 7.93 (s, 1H), 8.31 (s, 1H), 8.79 (s, 1H); LCMS: M + 1 351.2. Method A (Example 15). |
| 221 | 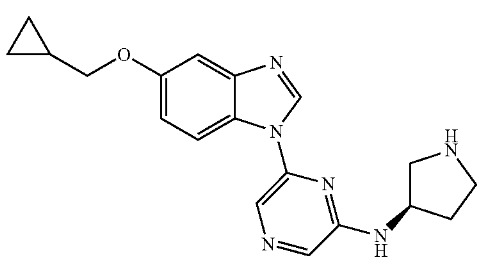 [SMILES: c1cc2c(cc1OCC1CC1)ncn2-c1cncc(N[C@@H]2CCNC2)n1] | 6-[5-(cyclopropylmethoxy)-1H-benzimidazol-1-yl]-N-[(3R)-pyrrolidin-3-yl]pyrazin-2-amine 1H NMR (400 MHz, DMSO): δ ppm 0.35 (d, 2H), 0.59 (d, 2H), 1.3 (m, 1H), 1.5-2.0 (m, 1H), 2.2 (m, 1H), 2.7-3.4 (m, 4H), 3.5-3.9 (m, 4H), 4.4 (m, 1H), 7.0 (m, 1H), 7.3 (m, 1H), 7.7-8.0 (m, 2H), 8.0-8.4 (m, 2H), 8.8 (s, 1H); LCMS: M + 1 351.1. Method A (Example 15). |

| Ex. | Structure | Name, Data and Preparation Method |
|---|---|---|
| 222 | 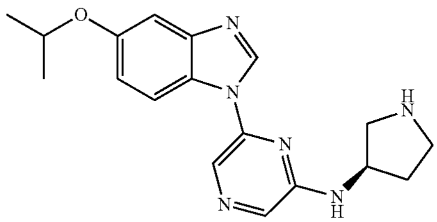 [SMILES: CC(C)Oc1ccc2c(c1)ncn2-c1cncc(N[C@@H]2CCNC2)n1] | 6-[5-(propan-2-yloxy)-1H-benzimidazol-1-yl]-N-[(3R)-pyrrolidin-3-yl]pyrazin-2-amine 1H NMR (400 MHz, DMSO): δ ppm 1.3 (d, 6H), 1.5-2.0 (m, 1H), 2.2 (m, 1H), 2.7-3.4 (m, 5H), 4.4 (m, 1H), 4.6 (m, 1H), 7.0 (m, 1H), 7.3 (m, 1H), 7.7-8.0 (m, 2H), 8.0-8.4 (m, 2H), 8.8 (s, 1H); LCMS: M + 1 339.1. Method A (Example 15). |
| 223 | 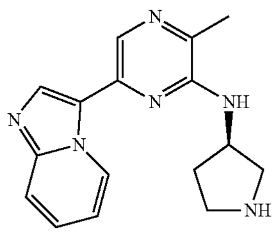 [SMILES: Cc1ncc(-c2cnc3ccccn23)nc1N[C@@H]1CCNC1] | 6-(imidazo[1,2-a]pyridin-3-yl)-3-methyl-N-[(3R)-pyrrolidin-3-yl]pyrazin-2-amine 1H NMR (400 MHz, MeOD): δ ppm 2.228 (m, 1H), 2.423 (m, 4H), 3.555 (m, 4H), 4.569 (s, 1H), 7.107 (t, 1H), 7.447 (t, 1H), 7.681 (d, 1H), 8.249 (d, 2H), 9.631 (d, 1H); LCMS: M + 1 295.3. Method A (Example 16). |
| 224 | 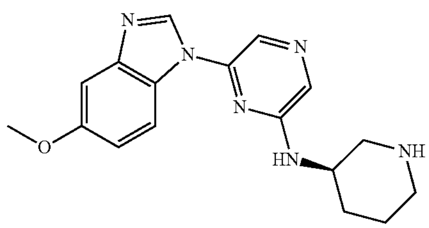 | 6-(5-methoxy-1H-benzimidazol-1-yl)-N-[(3R)-piperidin-3-yl]pyrazin-2-amine 1H NMR (400 MHz, MeOD): δ ppm 1.913-1.684 (m, 2H), 2.110-2.056 (m, 2H), 2.957 (m, 2H), 3.584 (d, 1H), 3.854 (s, 3H), 4.259 (m, 1H), 4.605 (s, 1H), 7.056 (d, 1H), 7.256 (s, 1H), 7.942-7.935 (d, 2H), 8.211 (s, 1H), 8.495 (s, 1H), 8.758 (s, 1H); LCMS: M + 1 325. Method A (Example 15). |
| 225 | 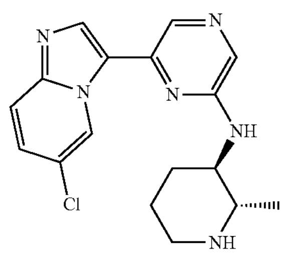 [SMILES: C[C@@H]1NCCC[C@H]1Nc1cncc(-c2cnc3ccc(Cl)cn23)n1] | 6-(6-chloroimidazo[1,2-a]pyridin-3-yl)-N-[(2S,3R)-2-methylpiperidin-3-yl]pyrazin-2-amine 1H NMR (300 MHz, DMSO-d6) δ ppm 1.35 (d, J = 6.2 Hz, 3H) 1.42-1.61 (m, 1H) 1.93 (br. s., 2H) 2.13-2.30 (m, 1H) 2.80-3.03 (m, 1H) 3.19-3.33 (m, 2H) 3.87-4.07 (m, 1H) 7.77 (d, J = 8.1 Hz, 1H) 7.84 (dd, J = 9.6, 1.1 Hz, 1H) 7.94-8.08 (m, 1H) 8.39 (s, 1H) 8.76 (s, 1H) 8.98-9.26 (m, 1H) 9.60 (d, J = 12.6 Hz, 1H) 9.78 (s, 1H). Method D (Example 13). |
| 226 | 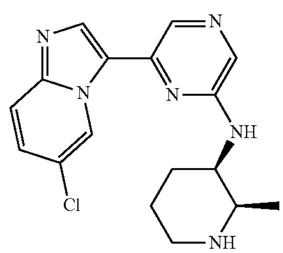 [SMILES: C[C@H]1NCCC[C@H]1Nc1cncc(-c2cnc3ccc(Cl)cn23)n1] | 6-(6-chloroimidazo[1,2-a]pyridin-3-yl)-N-[(2R,3R)-2-methylpiperidin-3-yl]pyrazin-2-amine 1H NMR (300 MHz, DMSO-d6) δ ppm 1.07 (d, J = 6.0 Hz, 3H) 1.22-1.40 (m, 1H) 1.42-1.62 (m, 1H) 1.64-1.76 (m, 1H) 2.02-2.16 (m, 1H) 2.59-2.73 (m, 2H) 2.90-3.06 (m, 2H) 7.29 (d, J = 8.9 Hz, 1H) 7.63 (d, J = 9.4 Hz, 1H) 7.86 (s, 1H) 7.93 (d, J = 9.4 Hz, 1H) 8.28 (br. s., 1H) 8.31 (s, 1H) 8.50 (s, 1H) 10.15 (s, 1H). Method D (Example 13). |
| 227 | 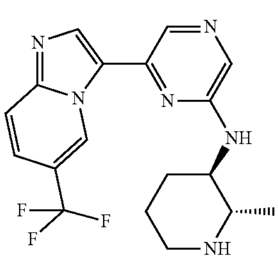 [SMILES: C[C@@H]1NCCC[C@H]1Nc1cncc(-c2cnc3ccc(C(F)(F)F)cn23)n1] | N-[(2S,3R)-2-methylpiperidin-3-yl]-6-[6-(trifluoromethyl)imidazo[1,2-a]pyridin-3-yl]pyrazin-2-amine 1H NMR (300 MHz, DMSO-d6) δ ppm 1.07 (d, J = 6.0 Hz, 3H) 1.22-1.40 (m, 1H) 1.42-1.62 (m, 1H) 1.64-1.76 (m, 1H) 2.02-2.16 (m, 1H) 2.59-2.73 (m, 2H) 2.90-3.06 (m, 2H) 7.29 (d, J = 8.9 Hz, 1H) 7.63 (d, J = 9.4 Hz, 1H) 7.86 (s, 1H) 7.93 (d, J = 9.4 Hz, 1H) 8.28 (br. s., 1H) 8.31 (s, 1H) 8.50 (s, 1H) 10.15 (s, 1H). Method D (Example 13). |

-continued

| Ex. | Structure | Name, Data and Preparation Method |
|---|---|---|
| 228 | 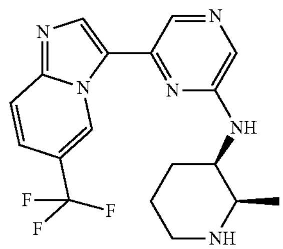 [SMILES: C[C@H]1NCCC[C@H]1Nc1cncc(-c2cnc3ccc(C(F)(F)F)cn23)n1] | N-[(2R,3R)-2-methylpiperidin-3-yl]-6-[6-(trifluoromethyl)imidazo[1,2-a]pyridin-3-yl]pyrazin-2-amine 1H NMR (300 MHz, DMSO-d6) δ ppm 1.30 (d, J = 6.4 Hz, 3H) 1.59-1.91 (m, 2H) 2.01 (d, J = 13.2 Hz, 2H) 3.02 (d, J = 14.1 Hz, 1H) 3.28 (d, J = 10.4 Hz, 1H) 3.59 (br. s., 1H) 4.35 (br. s., 1H) 7.91-8.04 (m, 1H) 8.04-8.21 (m, 2H) 8.45 (s, 1H) 8.56 (d, J = 9.2 Hz, 1H) 8.84 (s, 1H) 9.26-9.41 (m, 1H) 9.43-9.76 (m, 1H) 10.23 (s, 1H). Method D (Example 13). |
| 229 | 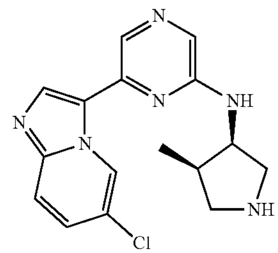 [SMILES: C[C@@H]1CNC[C@@H]1Nc1cncc(-c2cnc3ccc(Cl)cn23)n1] | 6-(6-chloroimidazo[1,2-a]pyridin-3-yl)-N-[(3R,4R)-4-methylpyrrolidin-3-yl]pyrazin-2-amine 1H NMR (300 MHz, DMSO-d6) δ ppm 1.04 (d, J = 7.0 Hz, 3H) 2.56-2.83 (m, 1H) 2.98-3.20 (m, 1H) 3.22-3.48 (m, 2H) 3.47-3.71 (m, 1H) 4.45-4.72 (m, 1H) 7.95-8.02 (m, 1H) 8.04-8.11 (m, 2H) 8.13 (s, 1H) 8.47 (s, 1H) 8.94 (s, 1H) 9.68 (br. s., 2H) 9.99 (d, J = 1.3 Hz, 1H). Method D (Example 13). |
| 230 | 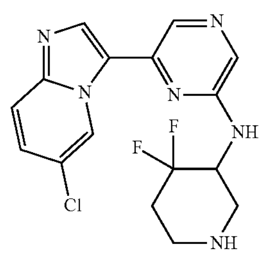 [SMILES: FC1(F)CCNCC1Nc1cncc(-c2cnc3ccc(Cl)cn23)n1] | 6-(6-chloroimidazo[1,2-a]pyridin-3-yl)-N-(4,4-difluoropiperidin-3-yl)pyrazin-2-amine 1H NMR (300 MHz, DMSO-d6) δ ppm 2.54-2.72 (m, 2H) 2.87-3.29 (m, 2H) 3.32-3.61 (m, 2H) 4.85-5.21 (m, 1H) 7.93-8.03 (m, 1H) 8.04-8.11 (m, 1H) 8.12 (s, 1H) 8.28 (d, J = 8.7 Hz, 1H) 8.51 (s, 1H) 8.94 (s, 1H) 9.84 (s, 1H) 9.96 (br. s., 1H). Method D (Example 13). |
| 231 | 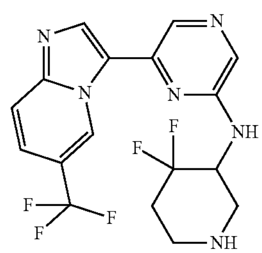 [SMILES: FC(F)(F)c1ccc2ncc(-c3cncc(NC4CNCCC4(F)F)n3)n2c1] | N-(4,4-difluoropiperidin-3-yl)-6-[6-(trifluoromethyl)imidazo[1,2-a]pyridin-3-yl]pyrazin-2-amine 1H NMR (300 MHz, DMSO-d6) δ ppm 2.25-2.66 (m, 2H) 3.00-3.29 (m, 2H) 3.29-3.54 (m, 2H) 4.84-5.19 (m, 1H) 7.99-8.06 (m, 1H) 8.13 (s, 1H) 8.13-8.18 (m, 1H) 8.30 (d, J = 8.9 Hz, 1H) 8.49 (s, 1H) 8.87 (s, 1H) 9.72-9.94 (m, 2H) 9.97 (s, 1H). Method D (Example 13). |
| 232 | 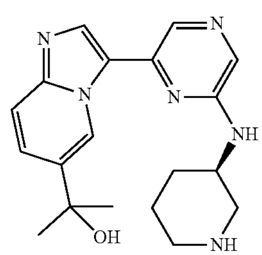 [SMILES: CC(C)(O)c1ccc2ncc(-c3cncc(N[C@@H]4CCCNC4)n3)n2c1] | 2-(3-{6-[(3R)-piperidin-3-ylamino]pyrazin-2-yl}imidazo[1,2-a]pyridin-6-yl)propan-2-ol 1H NMR (300 MHz, DMSO-d6) δ ppm 1.57 (d, J = 1.70 Hz, 6H) 1.62-2.13 (m, 4H) 2.99 (br. s., 2H) 3.08-3.45 (m, 2H) 4.36 (br. s., 1H) 7.91 (d, J = 6.22 Hz, 1H) 7.99-8.16 (m, 3H) 8.42 (s, 1H) 8.95 (s, 1H) 9.15 (br. s., 1H) 9.33 (br. s., 1H) 10.00 (s, 1H). Method A (Example 14). |
| 233 | 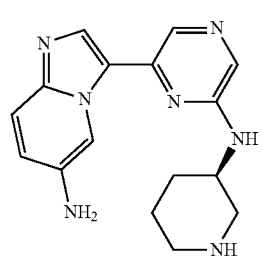 [SMILES: Nc1ccc2ncc(-c3cncc(N[C@@H]4CCCNC4)n3)n2c1] | 3-{6-[(3R)-piperidin-3-ylamino]pyrazin-2-yl}imidazo[1,2-a]pyridin-6-amine 1H NMR (300 MHz, DMSO-d6) δ ppm 1.37-1.63 (m, 1H) 1.79-1.97 (m, 2H) 2.01-2.18 (m, 1H) 2.85-3.06 (m, 2H) 3.11-3.27 (m, 2H) 3.30-3.47 (m, 1H) 4.44 (br. s., 1H) 7.54 (dd, J = 9.5, 2.0 Hz, 1H) 7.81 (s, 1H) 7.84 (s, 1H) 8.00 (s, 1H) 8.38 (s, 1H) 8.79 (s, 1H) 9.13 (br. s., 1H) 9.22 (br. s., 1H) 9.79 (br. s., 1H). Method D (Example 13). |

-continued

| Ex. | Structure | Name, Data and Preparation Method |
|---|---|---|
| 234 | 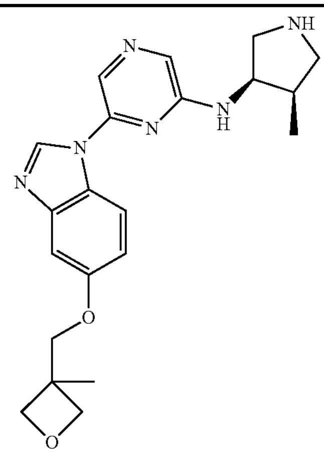 | 6-{5-[(3-methyloxetan-3-yl)methoxy]-1H-benzimidazol-1-yl}-N-[(3R,4R)-4-methylpyrrolidin-3-yl]pyrazin-2-amine 1H NMR (400 MHz, METHANOL-d4) δ ppm 0.96 (d, J = 7.1 Hz, 3H), 1.40 (s, 3H), 2.44-2.53 (m, 1H), 2.62-2.70 (m, 1H), 2.83-2.91 (m, 1H), 3.17-3.22 (m, 1H), 3.32-3.38 (m, 1H), 4.06 (s, 2H), 4.41 (d, J = 5.8 Hz, 2H), 4.57 (q, J = 6.7 Hz, 1H), 4.64 (d, J = 5.8 Hz, 2H), 7.05 (dd, J = 9.0, 2.4 Hz, 1H), 7.25 (d, J = 2.3 Hz, 1H), 7.89 (s, 1H), 8.03 (d, J = 8.8 Hz, 1H), 8.10 (s, 1H), 8.70 (s, 1H); LCMS: M + 1 395. Method A (Example 7). |
| 235 | 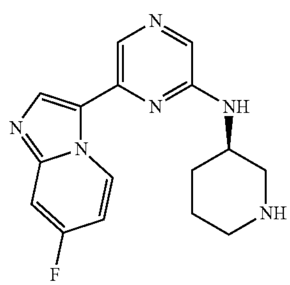 [SMILES: Fc1ccn2c(-c3cncc(N[C@@H]4CCCNC4)n3)cnc2c1] | 6-(7-fluoroimidazo[1,2-a]pyridin-3-yl)-N-[(3R)-piperidin-3-yl]pyrazin-2-amine 1H NMR (400 MHz, DMSO-d6) δ ppm 1.60-1.70 (m, 1H), 1.74-1.87 (m, 1H), 1.90-2.02 (m, 1H), 2.05-2.18 (m, 1H), 2.89-3.03 (m, 2H), 3.14-3.21 (m, 1H), 3.31-3.40 (m, 1H), 4.24 (br. s., 1H), 8.02 (br. s., 1H), 8.07 (s, 1H), 8.09-8.20 (m, 2H), 8.46 (s, 1H), 9.02 (s, 1H), 9.41 (br. s., 2H), 9.90 (br. s., 1H); LCMS: M + 1 313. Method D (Example 13). |
| 236 | 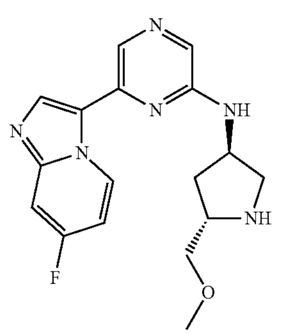 [SMILES: COC[C@@H]1C[C@@H](Nc2cncc(-c3cnc4cc(F)ccn34)n2)CN1] | 6-(7-fluoroimidazo[1,2-a]pyridin-3-yl)-N-[(3R,5S)-5-(methoxymethyl)pyrrolidin-3-yl]pyrazin-2-amine 1H NMR (400 MHz, DMSO-d6) δ ppm 2.04-2.25 (m, 2H), 3.28-3.40 (m, 4H) 3.58 (s, 1H) 3.64 (d, J = 5.6 Hz, 2H) 3.97-4.11 (m, 1H) 4.63 (br. s., 1H) 8.00-8.11 (m, 2H) 8.11-8.17 (m, 1H) 8.21 (br. s., 1H) 8.50 (s, 1H) 8.97 (s, 1H) 9.35 (br. s., 1H) 9.92 (br. s., 1H) 9.98 (br. s., 1H); LCMS: M + 1 343.2. Method D (Example 13). |
| 237 | 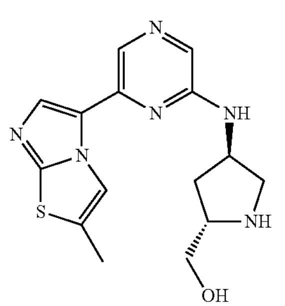 [SMILES: Cc1cn2c(-c3cncc(N[C@H]4CN[C@H](CO)C4)n3)cnc2s1] | [(2S,4R)-4-{[6-(2-methylimidazo[2,1-b][1,3]thiazol-5-yl)pyrazin-2-yl]amino}pyrrolidin-2-yl]methanol 1H NMR (400 MHz, DMSO-d6) δ ppm 2.01-2.13 (m, 1H), 2.13-2.24 (m, 1H), 2.59 (s, 3H), 3.19-3.28 (m, 1H), 3.54-3.59 (m, 2H), 3.61-3.68 (m, 1H), 3.72-3.80 (m, 1H), 3.90 (br. s., 1H), 4.68 (br. s., 1H), 7.95 (s, 1H), 8.10 (br. s., 1H), 8.41 (s, 1H), 8.44 (s, 1H), 8.50 (br. s., 1H), 9.33 (br. s., 1H), 9.86 (br. s., 1H); LCMS: M + 1 331. Method A (Example 7). |

| Ex. | Structure | Name, Data and Preparation Method |
|---|---|---|
| 238 | 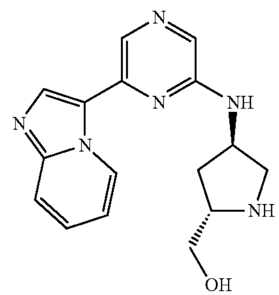 [SMILES: OC[C@@H]1C[C@@H](Nc2cncc(-c3cnc4ccccn34)n2)CN1] | [(2S,4R)-4-{[6-(imidazo[1,2-a]pyridin-3-yl)pyrazin-2-yl]amino}pyrrolidin-2-yl]methanol 1H NMR (400 MHz, DMSO-d6) δ ppm 2.03-2.23 (m, 2H), 3.17-3.25 (m, 1H), 3.50-3.67 (m, 2H), 3.71-3.79 (m, 1H), 3.88 (br. s., 1H), 4.67 (br. s., 1H), 7.59-7.72 (m, 1H), 7.96-8.15 (m, 4H), 8.47 (s, 1H), 8.97 (s, 1H), 9.24 (br. s., 1H), 9.73 (br. s., 1H), 9.89 (d, J = 7.1 Hz, 1H); LCMS: M + 1 310. Method A (Example 7). |
| 239 | 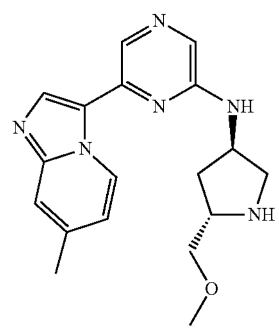 [SMILES: COC[C@@H]1C[C@@H](Nc2cncc(-c3cnc4cc(C)ccn34)n2)CN1] | N-[(3R,5S)-5-(methoxymethyl)pyrrolidin-3-yl]-6-(7-methylimidazo[1,2-a]pyridin-3-yl)pyrazin-2-amine 1H NMR (500 MHz, DMSO-d6) δ ppm 1.87-2.15 (m, 2H), 2.46 (s, 3H), 3.09 (s, 3H), 3.30-3.50 (m, 1H), 3.36-3.62 (m, 3H), 3.93 (br. s., 1H), 4.55 (br. s., 1H), 7.10 (d, J = 6.8 Hz, 1H), 7.59 (br. s., 1H), 7.62 (d, J = 5.9 Hz, 1H), 7.84 (s, 1H), 8.34 (s, 1H), 8.47 (s, 1H), 8.91 (br. s., 1H), 9.39 (br. s., 1H), 9.52 (d, J = 6.8 Hz, 1H); LCMS: M + 1 339. Method A (Example 7). |
| 240 | 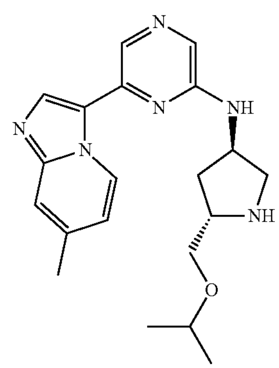 [SMILES: Cc1ccn2c(-c3cncc(N[C@H]4CN[C@H](COC(C)C)C4)n3)cnc2c1] | 6-(7-methylimidazo[1,2-a]pyridin-3-yl)-N-{(3R,5S)-5-[(propan-2-yloxy)methyl]pyrrolidin-3-yl}pyrazin-2-amine H NMR (500 MHz, DMSO-d6) δ ppm 1.14 (d, J = 5.9 Hz, 6H), 1.96-2.21 (m, 2H), 2.50-2.54 (m, 3H), 3.49-3.76 (m, 5H), 3.97 (br. s., 1H), 4.65 (br. s., 1H), 7.25 (d, J = 6.8 Hz, 1H), 7.71 (s, 1H), 7.84 (d, J = 4.9 Hz, 1H), 7.95 (s, 1H), 8.42 (s, 1H), 8.61 (s, 1H), 9.12 (br. s., 1H), 9.60 (br. s, 1H), 9.63 (d, J = 7.8 Hz, 1H); LCMS: M + 1 367. Method A (Example 7). |
| 241 | 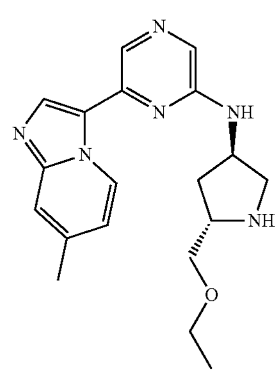 [SMILES: CCOC[C@@H]1C[C@@H](Nc2cncc(-c3cnc4cc(C)ccn34)n2)CN1] | N-[(3R,5S)-5-(ethoxymethyl)pyrrolidin-3-yl]-6-(7-methylimidazo[1,2-a]pyridin-3-yl)pyrazin-2-amine 1H NMR (500 MHz, DMSO-d6) δ ppm 1.16 (t, J = 6.8 Hz, 3H), 2.01-2.21 (m, 2H), 2.50 (s, 3H), 3.47-3.68 (m, 6H), 4.01 (br. s., 1H), 4.64 (br. s., 1H), 7.26 (d, J = 6.8 Hz, 1H), 7.71 (s, 1H), 7.85 (d, J=5.9 Hz, 1H), 7.95 (s, 1H), 8.42 (s, 1H), 8.62 (s, 1H), 9.19 (br. s., 1H), 9.64 (d, J=6.8 Hz, 2H); LCMS: M + 1 353. Method A (Example 7). |

| Ex. | Structure | Name, Data and Preparation Method |
|---|---|---|
| 242 | 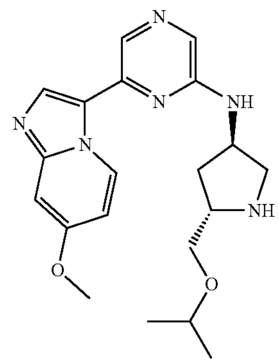 [SMILES: COc1ccn2c(-c3cncc(N[C@H]4CN[C@H](COC(C)C)C4)n3)cnc2c1] | 6-(7-methoxyimidazo[1,2-a]pyridin-3-yl)-N-{(3R,5S)-5-[(propan-2-yloxy)methyl]pyrrolidin-3-yl}pyrazin-2-amine 1H NMR (500 MHz, DMSO-d6) δ ppm 1.12 (br. s., 6H), 1.95-2.19 (m, 2H), 3.19 (br. s., 1H), 3.53-3.72 (m, 4H), 3.87-4.08 (m, 4H), 4.65 (s, 1H), 7.33 (br. s., 2H), 8.03 (br. s., 1H), 8.43 (br. s., 1H), 8.74 (br. s., 1H), 9.36 (br. s., 1H), 9.69 (br. s., 2H); LCMS: M + 1 383. Method A (Example 7). |
| 243 | 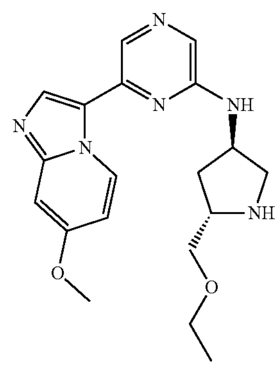 [SMILES: CCOC[C@@H]1C[C@@H](Nc2cncc(-c3cnc4cc(OC)ccn34)n2)CN1] | N-[(3R,5S)-5-(ethoxymethyl)pyrrolidin-3-yl]-6-(7-methoxyimidazo[1,2-a]pyridin-3-yl)pyrazin-2-amine 1H NMR (500 MHz, DMSO-d6) δ ppm 1.15 (t, J = 7.3 Hz, 3H), 2.04-2.19 (m, 2H), 3.15-3.24 (m, 1H), 3.28-3.38 (m, 1H), 3.49-3.61 (m, 3H), 3.63-3.71 (m, 2H), 4.01 (s, 3H), 4.65 (br. s., 1H), 7.25-7.35 (m, 2H), 7.94-8.07 (m, 1H), 8.43 (br. s., 1H), 8.73 (br. s., 1H), 9.39 (br. s., 1H), 9.68 (d, J = 6.8 Hz, 1H), 9.73 (br. s., 1H); LCMS: M + 1 369. Method A (Example 7). |
| 244 | 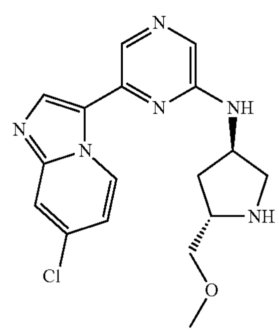 [SMILES: COC[C@@H]1C[C@@H](Nc2cncc(-c3cnc4cc(Cl)ccn34)n2)CN1] | 6-(7-chloroimidazo[1,2-a]pyridin-3-yl)-N-[(3R,5S)-5-(methoxymethyl)pyrrolidin-3-yl]pyrazin-2-amine 1H NMR (500 MHz, DMSO-d6) δ ppm 2.03-2.19 (m, 2H), 3.17-3.28 (m, 4H), 3.53-3.59 (m, 1H), 3.61 (d, J = 4.9 Hz, 2H), 3.93-4.04 (m, 1H), 4.62 (br. s., 1H), 7.19 (d, J = 7.8 Hz, 1H), 7.69 (d, J = 4.9 Hz, 1H), 7.88 (s, 2H), 8.43 (s, 2H), 9.67 (d, J = 6.8 Hz, 1H); LCMS: M + 1 359. Method D (Example 13). |
| 245 | 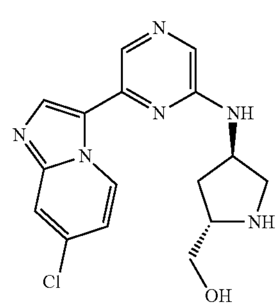 [SMILES: OC[C@@H]1C[C@@H](Nc2cncc(-c3cnc4cc(Cl)ccn34)n2)CN1] | [(2S,4R)-4-{[6-(7-chloroimidazo[1,2-a]pyridin-3-yl)pyrazin-2-yl]amino}pyrrolidin-2-yl]methanol 1H NMR (500 MHz, DMSO-d6) δ ppm 1.96-2.22 (m, 2H), 3.11-3.26 (m, 2H), 3.53-3.69 (m, 2H), 3.74-3.76 (m, 1H), 3.85-3.93 (m, 1H), 4.60-4.69 (m, 1H), 5.41 (br. s., 1H), 7.19 (d, J = 5.9 Hz, 1H), 7.68 (d, J = 5.9 Hz, 1H), 7.88 (s, 2H), 8.44 (s, 2H), 9.68 (d, J = 6.8 Hz, 1H); LCMS: M + 1 345. Method D (Example 13). |

-continued

| Ex. | Structure | Name, Data and Preparation Method |
|---|---|---|
| 246 | 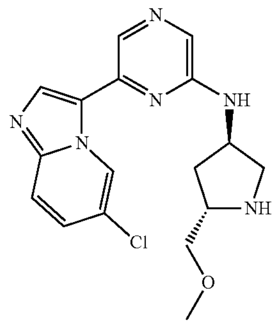 [SMILES: COC[C@@H]1C[C@@H](Nc2cncc(-c3cnc4ccc(Cl)cn34)n2)CN1] | 6-(6-chloroimidazo[1,2-a]pyridin-3-yl)-N-[(3R,5S)-5-(methoxymethyl)pyrrolidin-3-yl]pyrazin-2-amine 1H NMR (500 MHz, DMSO-d6) δ ppm 2.09-2.27 (m, 2H.), 3.28 (br. s, 3H), 3.51-3.69 (m, 4H), 3.96-4.08 (m, 1H), 4.57 (br. s., 1H), 7.46 (d, J = 7.8 Hz, 1H), 7.73-7.82 (m, 2H), 7.90 (s, 1H), 8.42-8.50 (m, 2H), 9.82 (s, 1H); LCMS: M + 1 359. Method D (Example 13). |
| 247 | 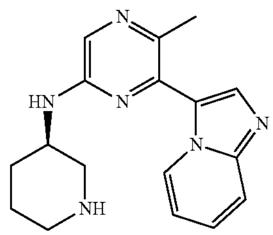 [SMILES: Cc1ncc(N[C@@H]2CCCNC2)nc1-c1cnc2ccccn12] | 6-(imidazo[1,2-a]pyridin-3-yl)-5-methyl-N-[(3R)-piperidin-3-yl]pyrazin-2-amine 1H NMR (400 MHz, MeOD) δ ppm 1.810 (m, 2H), 2.116 (m, 2H), 2.608 (s, 3H), 3.076 (m, 2H), 3.284 (m, 1H), 3.518 (m, 1H), 4.236 (m, 1H), 7.665 (t, 1H), 8.117 (m, 3H), 8.523 (s, 1H), 9.234 (d, 1H). Method A (Example 16, use 16b-1). |
| 248 | 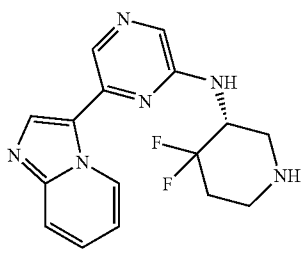 [SMILES: FC1(F)CCNC[C@H]1Nc1cncc(-c2cnc3ccccn23)n1] | N-[(3R)-4,4-difluoropiperidin-3-yl]-6-(imidazo[1,2-a]pyridin-3-yl)pyrazin-2-amine 1H NMR (400 MHz, MeOD) δ ppm 1.93-2.16 (m, 1H) 2.16-2.35 (m, 1H) 2.71-2.97 (m, 2H) 3.00-3.16 (m, 1H) 3.16-3.25 (m, 1H) 4.40-4.70 (m, 1H) 6.98-7.22 (m, 1H) 7.47 (t, J = 7.83 Hz, 1H) 7.67 (d, J = 9.09 Hz, 1H) 7.86 (s, 1H) 8.22 (s, 1H) 8.28 (s, 1H) 9.71 (d, J = 6.82 Hz, 1H); LCMS: M + 1 331. Method A (Example 11). |
| 249 | 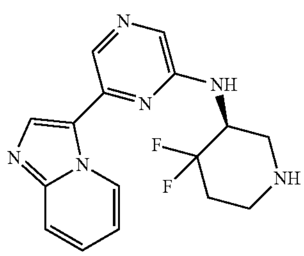 [SMILES: FC1(F)CCNC[C@@H]1Nc1cncc(-c2cnc3ccccn23)n1] | N-[(3S)-4,4-difluoropiperidin-3-yl]-6-(imidazo[1,2-a]pyridin-3-yl)pyrazin-2-amine 1H NMR (400 MHz, MeOD) δ ppm 1.96-2.19 (m, 1H) 2.18-2.38 (m, 1H) 2.71-3.00 (m, 2H) 3.02-3.18 (m, 1H) 3.17-3.27 (m, 1H) 4.44-4.69 (m, 1H) 7.04-7.28 (m, 1H) 7.44-7.56 (m, 1H) 7.62-7.76 (m, 1H) 7.88 (s, 1H) 8.25 (s, 1H) 8.30 (s, 1H) 9.73 (d, J = 6.82 Hz, 1H); LCMS: M + 1 331. Method A (Example 11). |
| 250 | 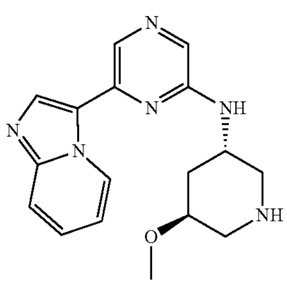 [SMILES: CO[C@@H]1CNC[C@@H](Nc2cncc(-c3cnc4ccccn34)n2)C1] | 6-(imidazo[1,2-a]pyridin-3-yl)-N-[(3S,5S)-5-methoxypiperidin-3-yl]pyrazin-2-amine 1H NMR (400 MHz, DMSO-d6) δ ppm 0.79-0.93 (m, 1H) 1.22-1.29 (m, 1H) 1.61-1.77 (m, 1H) 2.23-2.36 (m, 1H) 2.79-2.92 (m, 1H) 3.06-3.15 (m, 1H) 3.37 (s, 3H) 3.78-3.90 (m, 1H) 4.33-4.47 (m, 1H) 7.31-7.53 (m, 1H) 7.62-7.75 (m, 1H) 7.81-7.93 (m, 1H) 7.98 (br. s., 1H) 8.44 (s, 1H) 8.81 (br. s., 2H) 9.38 (br. s., 1H) 9.71-9.87 (m, 1H). Method A (Example 7). |
| 251 | 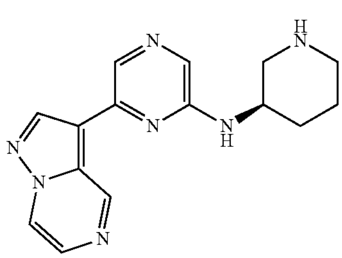 [SMILES: c1cn2ncc(-c3cncc(N[C@@H]4CCCNC4)n3)c2cn1] | N-[(3R)-piperidin-3-yl]-6-(pyrazolo[1,5-a]pyrazin-3-yl)pyrazin-2-amine, acetate salt 1H NMR (400 MHz, DMSO-d6) δ ppm 1.43-1.54 (m, 1H) 1.54-1.70 (m, 1H) 1.73-1.86 (m, 1H) 1.92 (s, 3H) 2.00-2.14 (m, 1H) 2.57-2.73 (m, 2H) 2.95-3.05 (m, 1H) 3.21-3.23 (m, 1H) 3.92-4.06 (m, 1H) 7.11-7.26 (m, 1H) 7.85 (s, 1H) 8.03 (d, J = 4.80 Hz, 1H) 8.37 (s, 1H) 8.81-8.92 (m, 2H) 9.85 (s, 1H). Method E (Example 6). |

| Ex. | Structure | Name, Data and Preparation Method |
|---|---|---|
| 252 | 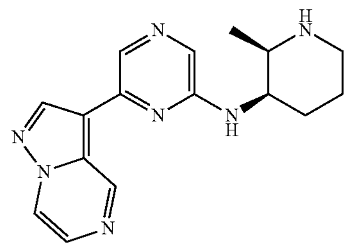 [SMILES: C[C@H]1NCCC[C@H]1Nc1cncc(-c2cnn3ccncc23)n1] | N-[(2R,3R)-2-methylpiperidin-3-yl]-6-(pyrazolo[1,5-a]pyrazin-3-yl)pyrazin-2-amine, acetate salt 1H NMR (400 MHz, DMSO-d6) δ ppm 1.04 (d, J = 6.32 Hz, 3H) 1.32-1.47 (m, 1H) 1.56-1.68 (m, 2H) 1.91 (s, 3H) 1.94-2.04 (m, 1H) 2.58-2.73 (m, 1H) 2.95-3.05 (m, 2H) 4.07-4.16 (m, 1H) 6.96-7.12 (m, 1H) 7.96-8.05 (m, 2H) 8.30 (s, 1H) 8.79-8.88 (m, 2H) 9.82 (s, 1H). Method E (Example 6). |
| 253 | 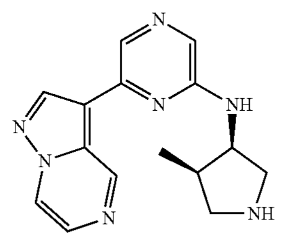 [SMILES: C[C@@H]1CNC[C@@H]1Nc1cncc(-c2cnn3ccncc23)n1] | N-[(3R,4R)-4-methylpyrrolidin-3-yl]-6-(pyrazolo[1,5-a]pyrazin-3-yl)pyrazin-2-amine, acetate salt 1H NMR (400 MHz, DMSO-d6) δ ppm 0.89 (d, J = 7.07 Hz, 3H) 1.89 (s, 3H) 2.35-2.45 (m, 1H) 2.55-2.58 (m, 1H) 2.74-2.85 (m, 1H) 3.13-3.19 (m, 2H) 3.20-3.30 (m, 2H) 4.44-4.58 (m, 1H) 7.32 (br. s., 1H) 7.89 (s, 1H) 8.02 (d, J = 4.80 Hz, 1H) 8.34 (s, 1H) 8.80-8.89 (m, 2H) 9.88 (s, 1H). Method E (Example 6). |
| 254 | 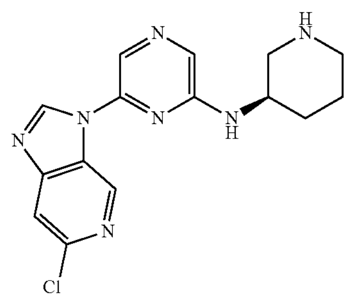 [SMILES: Clc1cc2ncn(-c3cncc(N[C@@H]4CCCNC4)n3)c2cn1] | 6-(6-chloro-3H-imidazo[4,5-c]pyridin-3-yl)-N-[(3R)-piperidin-3-yl]pyrazin-2-amine 1H NMR (400 MHz, DMSO-d6) δ ppm 1.43-1.54 (m, 2H) 1.66-1.72 (m, 1H) 1.85-1.92 (m, 4H) 1.98-2.03 (m, 1H) 2.42-2.47 (m, 1H) 2.80-2.85 (m, 1H) 3.11-3.15 (m, 1H) 3.78-3.85 (m, 1H) 7.55-7.63 (m, 1H) 7.96 (d, J = 13.89 Hz, 2H) 8.33 (s, 1H) 9.30 (s, 1H) 9.40 (s, 1H). Method A (Example 17/18). |
| 255 | 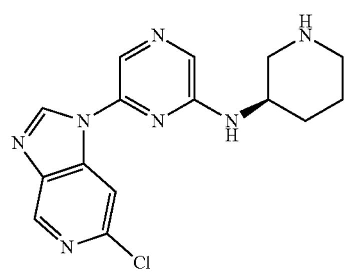 [SMILES: Clc1cc2c(cn1)ncn2-c1cncc(N[C@@H]2CCCNC2)n1] | 6-(6-chloro-1H-imidazo[4,5-c]pyridin-1-yl)-N-[(3R)-piperidin-3-yl]pyrazin-2-amine 1H NMR (400 MHz, DMSO-d6) δ ppm 1.40-1.58 (m, 2H) 1.65-1.70 (m, 1H) 1.82-1.91 (m, 4H) 1.99-2.07 (m, 1H) 2.44-2.47 (m, 1H) 2.78-2.87 (m, 1H) 3.09 (dd, J = 11.87, 3.03 Hz, 1H) 3.72-3.82 (m, 1H) 7.60 (d, J = 7.33 Hz, 1H) 7.97 (s, 1H) 8.29 (s, 2H) 8.89 (s, 1H) 9.17 (s, 1H). Method A (Example 17/18). |
| 256 | 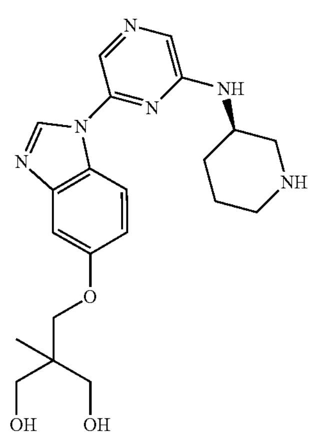 [SMILES: CC(CO)(CO)COc1ccc2c(c1)ncn2-c1cncc(N[C@@H]2CCCNC2)n1] | 2-methyl-2-{[(1-{6-[(3R)-piperidin-3-ylamino]pyrazin-2-yl}-1H-benzimidazol-5-yl)oxy]methyl}propane-1,3-diol 1H NMR (400 MHz, DMSO-d6) δ ppm 0.92 (s, 3H) 1.42-1.62 (m, 2H) 1.67-1.79 (m, 1H) 1.91 (s, 3H) 1.95-2.07 (m, 1H) 2.79-2.94 (m, 1H) 3.12-3.22 (m, 1H) 3.23-3.29 (m, 1H) 3.34-3.47 (m, 5H) 3.84 (s, 3H) 4.47 (t, J = 5.31 Hz, 2H) 6.99 (dd, J = 9.09, 2.27 Hz, 1H) 7.24 (d, J = 2.53 Hz, 1H) 7.44 (s, 1H) 7.90 (s, 1H) 8.14 (d, J = 9.09 Hz, 1H) 8.22 (s, 1H) 8.88 (s, 1H). Method C (Example 9, then treat with 0.25N HCl to open ring). |

| Ex. | Structure | Name, Data and Preparation Method |
|---|---|---|
| 257 | 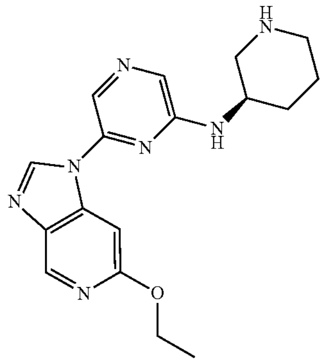 [SMILES: CCOc1cc2c(cn1)ncn2-c1cncc(N[C@@H]2CCCNC2)n1] | 6-(6-ethoxy-1H-imidazo[4,5-c]pyridin-1-yl)-N-[(3R)-piperidin-3-yl]pyrazin-2-amine 1H NMR (400 MHz, METHANOL-d4) δ ppm 1.43 (t, J = 6.69 Hz, 3H) 1.49-1.65 (m, 1H) 1.65-1.77 (m, 1H) 1.77-1.88 (m, 1H) 2.10-2.22 (m, 1H) 2.49-2.71 (m, 2H) 2.90-3.07 (m, 1H) 3.22-3.29 (m, 1H) 3.92-4.07 (m, 1H) 4.34-4.44 (m, 2H) 7.45 (s, 1H) 7.89 (s, 1H) 8.11 (s, 1H) 8.57 (s, 1H) 8.80 (s, 1H). Method A (Example 17/18). |
| 258 | 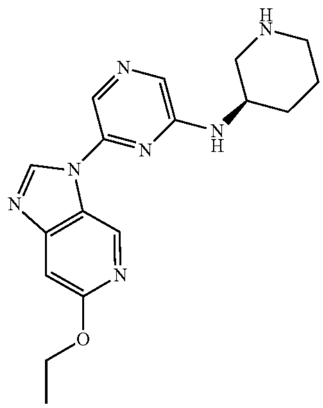 [SMILES: CCOc1cc2ncn(-c3cncc(N[C@@H]4CCCNC4)n3)c2cn1] | 6-(6-ethoxy-3H-imidazo[4,5-c]pyridin-3-yl)-N-[(3R)-piperidin-3-yl]pyrazin-2-amine 1H NMR (400 MHz, METHANOL-d4) δ ppm 1.22-1.37 (m, 1H) 1.45 (t, J = 7.07 Hz, 3H) 1.52-1.67 (m, 1H) 1.66-1.76 (m, 1H) 1.81-1.97 (m, 1H) 2.12-2.23 (m, 1H) 2.50-2.75 (m, 2H) 3.01 (d, J = 12.88 Hz, 1H) 3.92-4.10 (m, 1H) 4.37 (q, J = 7.07 Hz, 2H) 7.08 (s, 1H) 7.89 (s, 1H) 8.20 (s, 1H) 9.03 (s, 1H) 9.16 (s, 1H). Method A (Example 17/18). |
| 259 | 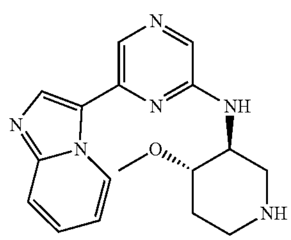 [SMILES: CO[C@H]1CCNC[C@@H]1Nc1cncc(-c2cnc3ccccn23)n1] | 6-(imidazo[1,2-a]pyridin-3-yl)-N-[(3S,4S)-4-methoxypiperidin-3-yl]pyrazin-2-amine 1H NMR (400 MHz, DMSO-d6) δ ppm 1.79-1.95 (m, 1H) 2.19-2.36 (m, 1H) 2.87-3.09 (m, 2H) 3.18-3.29 (m, 1H) 3.32 (s, 3H) 3.35-3.52 (m, 3H) 3.69 (dd, J = 13.64, 5.31 Hz, 1H) 4.38-4.47 (m, 1H) 7.81 (t, J = 6.32 Hz, 1H) 7.99-8.13 (m, 4H) 8.44 (s, 1H) 8.99 (s, 1H) 9.29 (br. s., 1H) 9.82-10.01 (m, 2H). Method A (Example 7). |
| 260 | 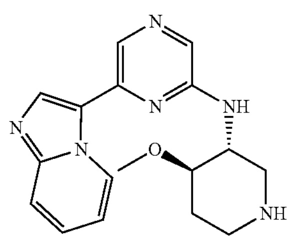 [SMILES: CO[C@@H]1CCNC[C@H]1Nc1cncc(-c2cnc3ccccn23)n1] | 6-(imidazo[1,2-a]pyridin-3-yl)-N-[(3R,4R)-4-methoxypiperidin-3-yl]pyrazin-2-amine (HCl salt) 1H NMR (400 MHz, DMSO-d6) δ ppm 1.80-1.93 (m, 1H) 2.18-2.34 (m, 1H) 2.88-3.10 (m, 2H) 3.16-3.30 (m, 1H) 3.32 (s, 3H) 3.37-3.44 (m, 1H) 3.44-3.54 (m, 2H) 3.66-3.73 (m, 1H) 4.38-4.46 (m, 1H) 7.80 (t, J = 6.32 Hz, 1H) 7.96-8.20 (m, 4H) 8.45 (s, 1H) 8.99 (s, 1H) 9.28 (br. s., 1H) 9.92 (d, J = 6.82 Hz, 2H). Method A (Example 7). |
| 261 | 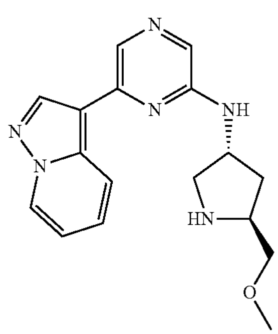 [SMILES: COC[C@@H]1C[C@@H](Nc2cncc(-c3cnn4ccccc34)n2)CN1] | N-[(3R,5S)-5-(methoxymethyl)pyrrolidin-3-yl]-6-(pyrazolo[1,5-a]pyridin-3-yl)pyrazin-2-amine 1H NMR (400 MHz, DMSO-d6) δ ppm 1.81-1.93 (m, 5H) 2.83-2.91 (m, 1H) 3.23-3.34 (m, 6H) 3.43-3.48 (m, 1H) 4.25-4.33 (m, 1H) 7.42-7.54 (m, 2H) 7.72-7.85 (m, 2H) 8.37 (s, 1H) 8.46 (s, 1H) 9.88 (d, J = 2.02 Hz, 1H). Method E (Example 6). |

| Ex. | Structure | Name, Data and Preparation Method |
|---|---|---|
| 262 | 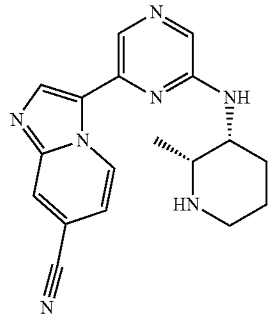 [SMILES: C[C@H]1NCCC[C@H]1Nc1cncc(-c2cnc3cc(C#N)ccn23)n1] | 3-(6-{[(2R,3R)-2-methylpiperidin-3-yl]amino}pyrazin-2-yl)imidazo[1,2-a]pyridine-7-carbonitrile 1H NMR (400 MHz, METHANOL-d4) δ ppm 1.35 (d, J=6.82 Hz, 3H) 1.84-2.20 (m, 5H) 3.16-3.20 (m, 1H) 3.81 (br. s., 1H) 4.40-4.53 (m, 1H) 7.33 (s, 1H) 7.99 (s, 1H) 8.24 (s, 1H) 8.41 (s, 1H) 8.44-8.55 (m, 1H) 9.73 (s, 1H). Method A (Example 7). |
| 263 | 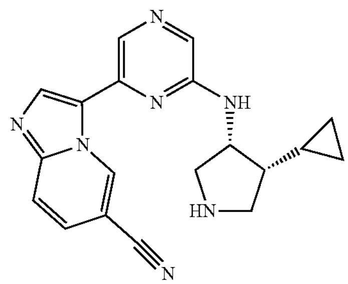 [SMILES: N#Cc1ccc2ncc(-c3cncc(N[C@H]4CNC[C@H]4C4CC4)n3)n2c1] | 3-(6-{[(3R,4R)-4-cyclopropylpyrrolidin-3-yl]amino}pyrazin-2-yl)imidazo[1,2-a]pyridine-6-carbonitrile 1H NMR (400 MHz, METHANOL-d4) δ ppm 0.11 (s, 1H) 0.16-0.23 (m, 1H) 0.43 (br. s., 1H) 0.53 (br. s., 1H) 0.87 (br. s., 2H) 1.73-1.85 (m, 1H) 3.04-3.13 (m, 1H) 3.20-3.28 (m, 1H) 3.37-3.43 (m, 1H) 3.65 (br. s., 1H) 4.66-4.74 (m, 1H) 7.57-7.66 (m, 1H) 7.82 (d, J = 9.85 Hz, 1H) 7.96 (s, 1H) 8.37 (s, 1H) 8.45 (s, 1H) 10.47 (s, 1H). Method A (Example 7). |
| 264 | 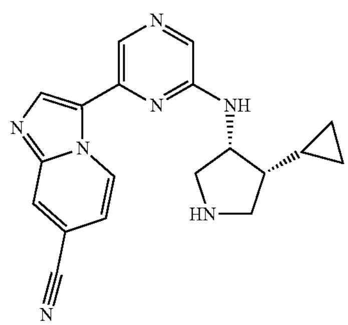 [SMILES: N#Cc1ccn2c(-c3cncc(N[C@H]4CNC[C@H]4C4CC4)n3)cnc2c1] | 3-(6-{[(3R,4R)-4-cyclopropylpyrrolidin-3-yl]amino}pyrazin-2-yl)imidazo[1,2-a]pyridine-7-carbonitrile 1H NMR (400 MHz, METHANOL-d4) δ ppm 0.00-0.11 (m, 1H) 0.11-0.23 (m, 1H) 0.39 (m, 1H) 0.44-0.58 (m, 1H) 0.74-0.90 (m, 1H) 1.75-1.82 (m, 1H) 3.2-3.25 (m, 1H) 3.30-3.33 (m, 1H) 3.42-3.49 (m, 1H) 3.51-3.60 (m, 1H) 4.67-4.74 (m, 1H) 7.22 (d, J = 7.33 Hz, 1H) 7.92 (s, 1H) 8.15 (s, 1H) 8.35 (s, 1H) 8.43 (s, 1H) 9.78 (d, J = 7.07 Hz, 1H). Method A (Example 7). |
| 265 | 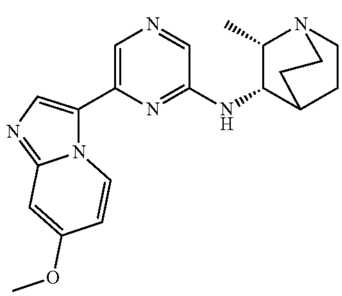 [SMILES: COc1ccn2c(-c3cncc(N[C@H]4C5CCN(CC5)[C@H]4C)n3)cnc2c1] | (2S,3S)-N-[6-(7-methoxyimidazo[1,2-a]pyridin-3-yl)pyrazin-2-yl]-2-methyl-1-azabicyclo[2.2.2]octan-3-amine 1H NMR (400 MHz, DMSO-d6) δ ppm 1.05 (d, J = 7.07 Hz, 3H) 1.25-1.35 (m, 1H) 1.62-1.70 (m, 2H) 1.79-1.90 (m, 2H) 2.54-2.63 (m, 1H) 2.74-2.86 (m, 1H) 2.96-3.04 (m, 1H) 3.20-3.25 (m, 1H) 3.88 (s, 3H) 4.07-4.16 (m, 1H) 6.84 (dd, J = 7.58, 2.27 Hz, 1H) 7.10 (d, J = 1.77 Hz, 1H) 7.17 (d, J = 8.08 Hz, 1H) 7.90 (s, 1H) 8.20 (s, 1H) 8.24 (s, 1H) 9.56 (d, J = 7.58 Hz, 1H). Method A (Example 19). |
| 266 | 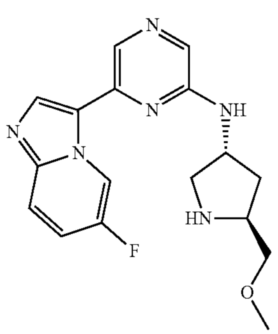 [SMILES: COC[C@@H]1C[C@@H](Nc2cncc(-c3cnc4ccc(F)cn34)n2)CN1] | 6-(6-fluoroimidazo[1,2-a]pyridin-3-yl)-N-[(3R,5S)-5-(methoxymethyl)pyrrolidin-3-yl]pyrazin-2-amine 1H NMR (400 MHz, DMSO-d6) δ ppm 1.81-1.93 (m, 5H) 2.83-2.91 (m, 1H) 3.23-3.34 (m, 6H) 3.43-3.48 (m, 1H) 4.25-4.33 (m, 1H) 7.42-7.54 (m, 2H) 7.72-7.85 (m, 2H) 8.37 (s, 1H) 8.46 (s, 1H) 9.88 (d, J = 2.02 Hz, 1H). Method E (Example 6). |

-continued

| Ex. | Structure | Name, Data and Preparation Method |
|---|---|---|
| 267 | 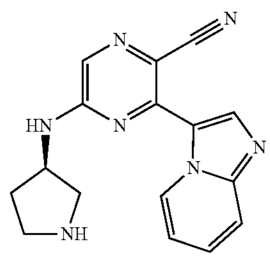 [SMILES: N#Cc1ncc(N[C@@H]2CCNC2)nc1-c1cnc2ccccn12] | 3-(imidazo[1,2-a]pyridin-3-yl)-5-[(3R)-pyrrolidin-3-ylamino]pyrazine-2-carbonitrile 1H NMR (400 MHz, DMSO) δ ppm 2.05 (m, 1H), 2.25 (m, 1H), 3.3-3.1 (m, 2H), 3.5-3.3 (m, 2H), 4.62 (m, 1H), 7.61 (m, 1H), 8.01 (m, 1H), 8.08 (m, 1H), 8.17 (s, 1H), 8.55 (s, 1H), 9.38 (s, 2H), 9.58 (s, 1H), 9.71 (s, 1H). Method A (Example 19). |
| 268 | 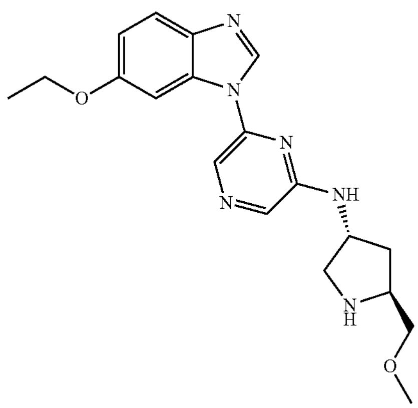 [SMILES: CCOc1ccc2ncn(-c3cncc(N[C@H]4CN[C@H](COC)C4)n3)c2c1] | 6-(6-ethoxy-1H-benzimidazol-1-yl)-N-[(3R,5S)-5-(methoxymethyl)pyrrolidin-3-yl]pyrazin-2-amine 1H NMR (400 MHz, D2O): δ ppm 1.429-1.394 (m, 3H), 2.344-2.237 (m, 2H), 3.419 (m, 3H), 3.516-3.447 (m, 1H), 3.715-3.625 (m, 2H), 3.798-3.761 (m, 2H), 4.223-4.109 (m, 3H), 4.652-4.621 (m, 3H), 7.297-7.269 (m, 1H), 7.470 (s, 1H), 7.782-7.759 (d, 1H) 8.119 (s, 1H), 8.161 (s, 1H), 9.530 (s, 1H). Method A (Example 15). |
| 269 | 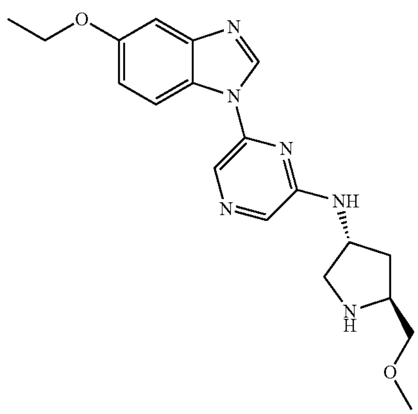 [SMILES: CCOc1ccc2c(c1)ncn2-c1cncc(N[C@H]2CN[C@H](COC)C2)n1] | 6-(5-ethoxy-1H-benzimidazol-1-yl)-N-[(3R,5S)-5-(methoxymethyl)pyrrolidin-3-yl]pyrazin-2-amine 1H NMR (400 MHz, D2O): δ ppm 1.459-1.424 (m, 3H), 2.334-2.281 (m, 2H), 3.507-3.41 (m, 4H), 3.733-3.636 (m, 2H), 3.807-3.771 (m, 1H), 4.222-4.170 (m, 3H), 7.282-7.253 (m, 1H), 7.365 (s, 1H), 8.011-7.988 (d, 1H) 8.112 (s, 1H), 8.195 (s, 1H), 9.556 (s, 1H). Method A (Example 15). |
| 270 | 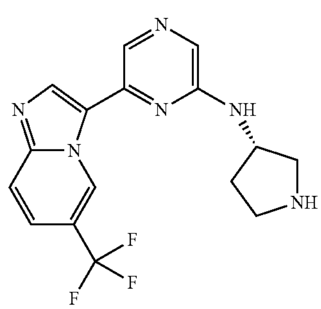 [SMILES: FC(F)(F)c1ccc2ncc(-c3cncc(N[C@H]4CCNC4)n3)n2c1] | N-[(3S)-pyrrolidin-3-yl]-6-[6-(trifluoromethyl)imidazo[1,2-a]pyridin-3-yl]pyrazin-2-amine 1H NMR (400 MHz, DMSO-d6) δ ppm 1.59-1.76 (m, 1H), 2.05 (dd, J = 12.99, 6.77 Hz, 1H), 2.72-2.84 (m, 2H), 2.94 (ddd, J = 10.43, 7.32, 7.14 Hz, 1H), 3.03 (dd, J = 11.35, 6.22 Hz, 1H), 4.26 (dt, J = 6.68, 3.43 Hz, 1H), 7.45 (d, J = 6.22 Hz, 1H), 7.62 (dd, J = 9.33, 1.65 Hz, 1H), 7.84 (s, 1H), 7.91 (d, J = 9.52 Hz, 1H), 8.38 (s, 1H), 8.55 (s, 1H), 10.34 (s, 1H); LCMS: M + 1 349.1. Method A (Example 7). |

-continued

| Ex. | Structure | Name, Data and Preparation Method |
|---|---|---|
| 271 | 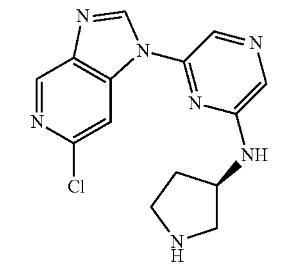 [SMILES: Clc1cc2c(cn1)ncn2-c1cncc(N[C@@H]2CCNC2)n1] | 6-(6-chloro-1H-imidazo[4,5-c]pyridin-1-yl)-N-[(3R)-pyrrolidin-3-yl]pyrazin-2-amine 1H NMR (400 MHz, MeOD) δ ppm 1.799 (m, 1H), 2.195 (m, 1H), 2.872 (m, 1H), 2.948 (m, 1H), 3.189 (m, 1H), 3.038 (m, 1H), 4.343 (m, 1H), 7.847 (s, 1H), 8.095 (s, 1H), 8.207 (s, 1H), 8.698 (s, 1H), 8.912 (s, 1H). Method A (Example 17/18). |
| 272 | 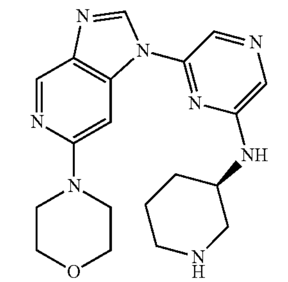 [SMILES: c1ncc(-n2cnc3cnc(N4CCOCC4)cc32)nc1N[C@@H]1CCCNC1] | 6-[6-(morpholin-4-yl)-1H-imidazo[4,5-c]pyridin-1-yl]-N-[(3R)-piperidin-3-yl]pyrazin-2-amine 1H NMR (400 MHz, MeOD) δ ppm 1.668 (m, 2H), 1.900 (m, 1H), 2.854-2.804 (m, 2H), 2.900 (m, 1H), 3.115 (m, 1H), 3.426-3.370 (m, 5H), 3.769-3.745 (m, 4H), 4.100 (m, 1H), 7.121 (s, 1H), 7.887 (s, 1H), 8.084 (s, 1H), 8.531 (s, 1H), 8.587 (s, 1H). Method A (Example 17/18). |
| 273 | 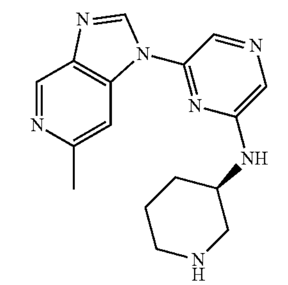 [SMILES: Cc1cc2c(cn1)ncn2-c1cncc(N[C@@H]2CCCNC2)n1] | 6-(6-methyl-1H-imidazo[4,5-c]pyridin-1-yl)-N-[(3R)-piperidin-3-yl]pyrazin-2-amine 1H NMR (400 MHz, MeOD) δ ppm 1.604-1.547 (m, 1H), 1.704-1.644 (m, 1H), 1.870-1.837 (m, 2H), 2.202-2.179 (m, 1H), 2.702-2.588 (m, 5H), 3.015-2.984 (m, 1H), 3.285 (m, 1H), 4.006-3.959 (m, 1H), 7.915 (s, 1H), 8.013 (s, 1H), 8.171 (s, 1H), 8.855 (s, 1H), 8.898 (s, 1H). Method A (Example 17/18). |
| 274 | 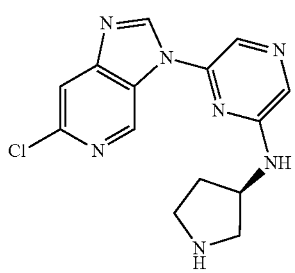 [SMILES: Clc1cc2ncn(-c3cncc(N[C@@H]4CCNC4)n3)c2cn1] | 6-(6-chloro-3H-imidazo[4,5-c]pyridin-3-yl)-N-[(3R)-pyrrolidin-3-yl]pyrazin-2-amine 1H NMR (400 MHz, MeOD) δ ppm 1.817-1.766 (m, 1H), 2.218-2.166 (m, 1H), 2.842-2.802 (m, 1H), 3.042-2.940 (m, 2H), 3.239 (m, 1H), 4.373 (m, 1H), 7.704 (s, 1H), 7.842 (s, 1H), 8.146 (s, 1H), 9.020 (s, 1H), 9.298 (s, 1H). Method A (Example 17/18). |
| 275 | 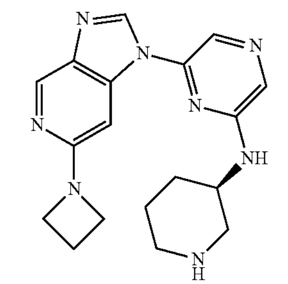 [SMILES: c1ncc(-n2cnc3cnc(N4CCC4)cc32)nc1N[C@@H]1CCCNC1] | 6-[6-(azetidin-1-yl)-1H-imidazo[4,5-c]pyridin-1-yl]-N-[(3R)-piperidin-3-yl]pyrazin-2-amine 1H NMR (400 MHz, MeOD) δ ppm 1.549 (m, 2H), 1.719 (m, 1H), 2.027-2.005 (m, 1H), 2.357-2.301 (m, 2H), 2.579-2.471 (m, 2H), 2.861-2.830 (m, 1H), 3.162 (m, 1H), 3.901 (m, 1H), 4.008 (m, 4H), 6.793 (s, 1H), 7.795 (s, 1H), 7.970 (s, 1H), 8.412 (s, 1H), 8.539 (s, 1H). Method A (Example 17/18). |

| Ex. | Structure | Name, Data and Preparation Method |
|---|---|---|
| 276 | 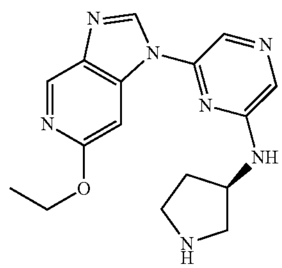 [SMILES: CCOc1cc2c(cn1)ncn2-c1cncc(N[C@@H]2CCNC2)n1] | 6-(6-ethoxy-1H-imidazo[4,5-c]pyridin-1-yl)-N-[(3R)-pyrrolidin-3-yl]pyrazin-2-amine 1H NMR (400 MHz, CDCl3) δ ppm 1.384 (m, 3H), 1.778 (m, 2H), 2.296 (m, 1H), 3.041 (m, 2H), 3.143 (m, 1H), 3.246 (m, 1H), 4.395 (m, 3H), 5.284 (m, 1H), 7.244 (s, 1H), 7.817 (s, 1H), 8.048 (s, 1H), 8.393 (s, 1H), 8.644 (s, 1H). Method A (Example 17/18). |
| 277 | 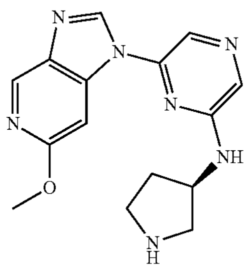 [SMILES: COc1cc2c(cn1)ncn2-c1cncc(N[C@@H]2CCNC2)n1] | 6-(6-methoxy-1H-imidazo[4,5-c]pyridin-1-yl)-N-[(3R)-pyrrolidin-3-yl]pyrazin-2-amine 1H NMR (400 MHz, CDCl3) δ ppm 1.940 (m, 1H), 2.250 (m, 1H), 2.923 (m, 2H), 3.086 (m, 1H), 3.245 (m, 1H), 3.957 (s, 3H), 4.390 (s, 1H), 5.232 (d, 1H), 7.266 (s, 1H), 7.811 (s, 1H), 8.044 (s, 1H), 8.393 (s, 1H), 8.664 (s, 1H). Method A (Example 17/18). |
| 278 | 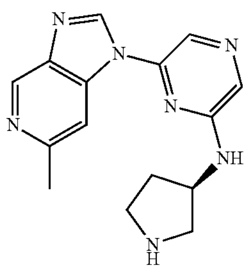 [SMILES: Cc1cc2c(cn1)ncn2-c1cncc(N[C@@H]2CCNC2)n1] | 6-(6-methyl-1H-imidazo[4,5-c]pyridin-1-yl)-N-[(3R)-pyrrolidin-3-yl]pyrazin-2-amine 1H NMR (400 MHz, MeOD) δ ppm 1.794-1.766 (m, 1H), 2.200-2.148 (m, 1H), 2.592 (s, 3H), 2.829-2.790 (m, 1H), 3.160-2.910 (m, 2H), 4.382-4.367 (m, 1H), 7.841 (s, 1H), 8.001 (s, 1H), 8.085 (s, 1H), 8.762 (s, 1H), 8.807 (s, 1H). Method A (Example 17/18). |
| 279 | 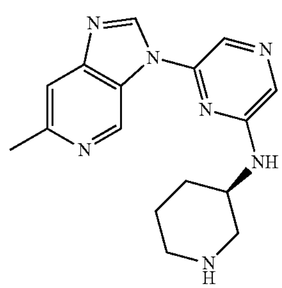 [SMILES: Cc1cc2ncn(-c3cncc(N[C@@H]4CCCNC4)n3)c2cn1] | 6-(6-methyl-3H-imidazo[4,5-c]pyridin-3-yl)-N-[(3R)-piperidin-3-yl]pyrazin-2-amine 1H NMR (400 MHz, Methanol-d4) δ ppm 1.715 (m, 2H), 1.895 (m, 1H), 2.212 (m, 1H), 2.640 (m, 2H), 2.710 (s, 3H), 3.032 (m, 1H), 3.312 (m, 1H), 4.043 (m, 1H), 7.677 (s, 1H), 7.929 (s, 1H), 8.245 (s, 1H), 9.100 (s, 1H), 9.472 (s, 1H). Method A (Example 17/18). |
| 280 | 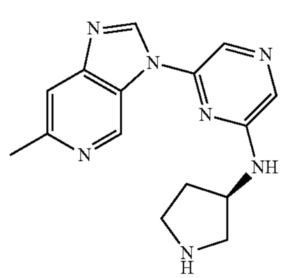 [SMILES: Cc1cc2ncn(-c3cncc(N[C@@H]4CCNC4)n3)c2cn1] | 6-(6-methyl-3H-imidazo[4,5-c]pyridin-3-yl)-N-[(3R)-pyrrolidin-3-yl]pyrazin-2-amine 1H NMR (400 MHz, Methanol-d4) δ ppm 1.814 (m, 1H), 2.223 (m, 1H), 2.593 (s, 3H), 2.975 (m, 1H), 3.031 (m, 2H), 3.209 (m, 1H), 4.405 (m, 1H), 7.553 (s, 1H), 7.826 (s, 1H), 8.147 (s, 1H), 8.965 (s, 1H), 9.392 (s, 1H). Method A (Example 17/18). |

| Ex. | Structure | Name, Data and Preparation Method |
|---|---|---|
| 281 | 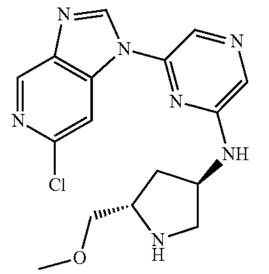 [SMILES: COC[C@@H]1C[C@@H](Nc2cncc(-n3cnc4cnc(Cl)cc43)n2)CN1] | 6-(6-chloro-1H-imidazo[4,5-c]pyridin-1-yl)-N-[(3R,5S)-5-(methoxymethyl)pyrrolidin-3-yl]pyrazin-2-amine 1H NMR (400 MHz, MeOD) δ ppm 1.970-1.836 (m, 2H), 2.826-2.786 (m, 1H), 3.393-3.323 (m, 1H), 3.4573.249 (m, 7H) 4.358-4.304 (m, 1H), 7.827 (s, 1H), 8.087 (s, 1H), 8.209 (s, 1H), 8.692 (s, 1H), 8.883 (s, 1H). Method A (Example 17/18). |
| 282 | 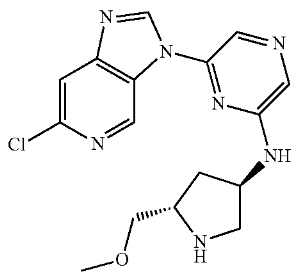 [SMILES: COC[C@@H]1C[C@@H](Nc2cncc(-n3cnc4cc(Cl)ncc43)n2)CN1] | 6-(6-chloro-3H-imidazo[4,5-c]pyridin-3-yl)-N-[(3R,5S)-5-(methoxymethyl)pyrrolidin-3-yl]pyrazin-2-amine $^1$H NMR (400 MHz, MeOD) δ ppm 2.072-1.988 (m, 2H), 2.922-2.882 (m, 1H), 3.542-3.400 (m, 7H), 4.502 (m, 1H), 7.834 (s, 1H), 7.952 (s, 1H), 8.264 (s, 1H), 9.142 (s, 1H), 9.413 (s, 1H). Method A (Example 17/18). |
| 283 | 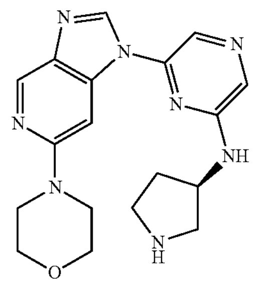 [SMILES: c1ncc(-n2cnc3cnc(N4CCOCC4)cc32)nc1N[C@@H]1CCNC1] | 6-[6-(morpholin-4-yl)-1H-imidazo[4,5-c]pyridin-1-yl]-N-[(3R)-pyrrolidin-3-yl]pyrazin-2-amine 1H NMR (400 MHz, MeOD) δ ppm 1.774-1.762 (m, 1H), 2.165-2.150 (m, 1H), 2.826-2.787 (m, 1H), 2.910-2.896 (m, 1H), 3.030-3.002 (m, 1H), 3.192-3.147 (m, 1H), 3.413-3.390 (t, 4H), 3.772-3.749 (t, 4H), 4.368 (m, 1H), 7.311 (s, 1H), 7.813 (s, 1H), 8.036 (s, 1H), 8.523 (s, 1H), 8.588 (s, 1H). Method A (Example 17/18). |
| 284 | 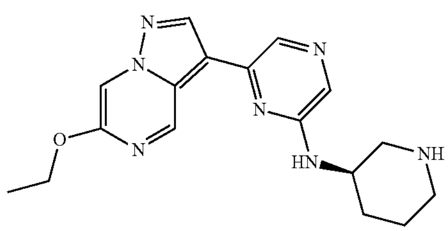 [SMILES: CCOc1cn2ncc(-c3cncc(N[C@@H]4CCCNC4)n3)c2cn1] | 6-(6-ethoxypyrazlo[1,5-a]pyrazin-3-yl)-N-[(3R)-piperidin-3-yl]pyrazin-2-amine 1H NMR (400 MHz, METHANOL-d4) δ ppm 1.46 (t, J = 7.07 Hz, 3H) 1.72 (m, 1H) 1.88 (m, 2H) 2.11 (m, 1H) 2.25 (m, 1H) 3.04 (t, J = 8.59 Hz, 2H) 3.58 (dd, J = 12.00, 4.67 Hz, 1H) 4.35 (q, J = 7.07 Hz, 3H) 7.79 (s, 1H) 8.25 (s, 1H) 8.28 (s, 1H) 8.55 (s, 1H) 9.55 (s, 1H); LCMS: M + 1 340. Method E (Example 22). |
| 285 | 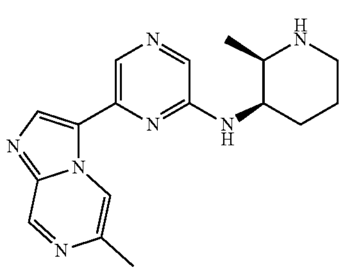 [SMILES: Cc1cn2c(-c3cncc(N[C@@H]4CCCN[C@@H]4C)n3)cnc2cn1] | 6-(6-methylimidazo[1,2-a]pyrazin-3-yl)-N-[(2R,3R)-2-methylpiperidin-3-yl]pyrazin-2-amine 1H NMR (400 MHz, DMSO-d6) δ ppm 1.15-1.25 (m, 1H) 1.32 (d, J = 6.57 Hz, 3H) 1.67-1.73 (m, 1H) 1.80-1.87 (m, 1H) 1.95-2.01 (m, 2H) 2.57 (s, 3H) 2.95-3.03 (m, 1H) 3.22-3.29 (m, 1H) 4.33-4.39 (m, 1H) 8.00 (s, 1H) 8.18-8.25 (m, 1H) 8.47 (s, 1H) 8.63 (s, 1H) 9.19 (br. s., 2H) 9.46 (br. s., 1H). Method D (Example 13). |

-continued

| Ex. | Structure | Name, Data and Preparation Method |
|---|---|---|
| 286 | 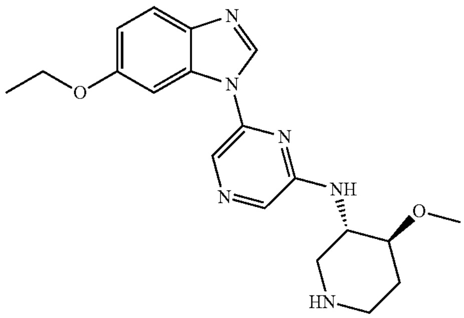 [SMILES: CCOc1ccc2ncn(-c3cncc(N[C@H]4CNCC[C@@H]4OC)n3)c2c1] | 6-(6-ethoxy-1H-benzimidazol-1-yl)-N-[(3S,4S)-4-methoxypiperidin-3-yl]pyrazin-2-amine 1H NMR (400 MHz, D2O): δ ppm 1.425-1.391 (m, 3H), 1.832-1.701 (m, 1H), 2.595-2.498 (m, 1H), 3.139-3.046 (m, 2H), 3.615-3.409 (m, 5H), 3.708-3.698 (m, 1H), 4.188-4.157 (m, 2H), 4.368-4.358 (m, 1H), 7.308-7.285 (d, 1H), 7.550 (s, 1H), 7.807-7.784 (d, 1H), 8.134 (s, 1H), 8.194 (s, 1H), 9.500 (s, 1H). Method A (Example 15). |
| 287 | 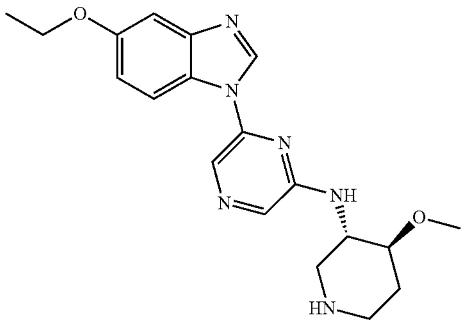 [SMILES: CCOc1ccc2c(c1)ncn2-c1cncc(N[C@H]2CNCC[C@@H]2OC)n1] | 6-(5-ethoxy-1H-benzimidazol-1-yl)-N-[(3S,4S)-4-methoxypiperidin-3-yl]pyrazin-2-amine 1H NMR (400 MHz, D2O): δ ppm 1.425-1.391 (m, 3H), 1.813-1.785 (m, 1H), 2.530-2.484 (m, 1H), 3.182-3.041 (m, 2H), 3.525-3.414 (m, 4H), 3.656-3.615 (m, 1H), 3.740-3.684 (m, 1H), 4.218-4.166 (m, 2H), 4.352-4.316 (m, 1H), 7.279-7.251 (m, 1H), 7.366 (s, 1H), 8.019-7.996 (d, 1H), 8.110 (s, 1H), 8.191 (s, 1H), 9.493 (s, 1H). Method A (Example 15). |
| 288 | 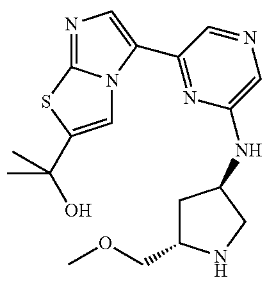 [SMILES: COC[C@@H]1C[C@@H](Nc2cncc(-c3cnc4sc(C(C)(C)O)cn34)n2)CN1] | 2-[5-(6-{[(3R,5S)-5-(methoxymethyl)pyrrolidin-3-yl]amino}pyrazin-2-yl)imidazo[2,1-b][1,3]thiazol-2-yl]propan-2-ol 1H NMR (300 MHz, MeOD) δ ppm 1.68 (s, 6H), 1.93-2.13 (m, 2H), 2.83-3.01 (m, 1H), 3.39 (s, 3H), 3.41-3.62 (m, 3H), 4.17-4.36 (m, 1H), 4.38-4.52 (m, 1H), 7.60-7.78 (m, 1H), 7.83 (s, 1H), 8.05-8.18 (m, 1H), 8.45 (s, 1H). Method A (Example 14). |
| 289 | 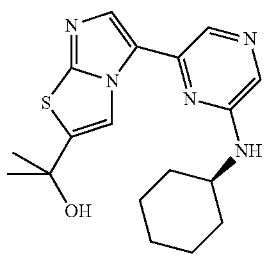 | 2-(5-{6-[(3R)-piperidin-3-ylamino]pyrazin-2-yl}imidazo[2,1-b][1,3]thiazol-2-yl)propan-2-ol 1H NMR (300 MHz, MeOD) δ ppm 1.50-1.67 (m, 2H), 1.67 (s, 6H), 1.78-1.92 (m, 1H), 2.07-2.29 (m, 1H), 2.48-2.81 (m, 2H), 2.91-3.07 (m, 1H), 3.28 (d, J = 3.20 Hz, 1H), 3.90-4.03 (m, 1H), 7.68 (s, 1H), 7.83 (s, 1H), 8.09 (s, 1H), 8.48 (s, 1H). Method A (Example 14). |
| 290 | 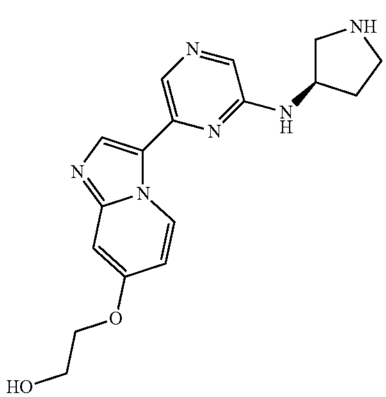 [SMILES: OCCOc1ccn2c(-c3cncc(N[C@@H]4CCNC4)n3)cnc2c1] | 2-[(3-{6-[(3R)-pyrrolidin-3-ylamino]pyrazin-2-yl}imidazo[1,2-a]pyridin-7-yl)oxy]ethanol 1H NMR (300 MHz, MeOD) δ ppm 2.07-2.25 (m, 2H) 2.35-2.54 (m, 1H) 3.38-3.52 (m, 3H) 3.54-3.66 (m, 1H) 3.95 (t, J = 4.43 Hz, 2H) 4.19 (t, J = 4.52 Hz, 2H) 4.67 (d, J = 3.20 Hz, 1H) 6.86 (d, J = 5.46 Hz, 1H) 7.01 (s, 1H) 7.78 (s, 1H) 8.10 (br. s., 1H) 8.28 (s, 1H) 9.56 (d, J = 7.72 Hz, 1H); LCMS: M + H 341. Method A (Example 32). |

-continued

| Ex. | Structure | Name, Data and Preparation Method |
|---|---|---|
| 291 | 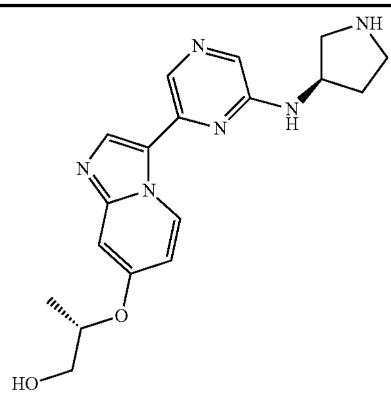 | (2S)-2-[(3-{6-[(3R)-pyrrolidin-3-ylamino]pyrazin-2-yl}imidazo[1,2-a]pyridin-7-yl)oxy]propan-1-ol 1H NMR (300 MHz, MeOD) δ ppm 1.31 (d, J = 6.40 Hz, 3H) 2.10-2.26 (m, 1H) 2.36-2.55 (m, 1H) 3.33-3.42 (m, 1H) 3.42-3.55 (m, 2H) 3.55-3.68 (m, 1H) 3.89-4.06 (m, 2H) 4.10-4.26 (m, 1H) 4.60-4.74 (m, 1H) 6.85 (dd, J = 7.63, 2.54 Hz, 1H) 6.97 (d, J = 2.45 Hz, 1H) 7.77 (s, 1H) 8.07 (s, 1H) 8.26 (s, 1H) 9.51 (d, J = 7.72 Hz, 1H); LCMS: M + H 355. Method A (Example 32). |
| 292 | 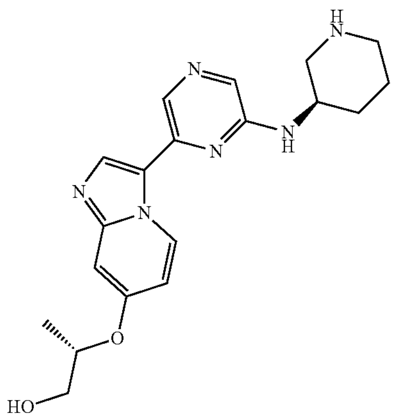 [SMILES: C[C@@H](CO)Oc1ccn2c(-c3cncc(N[C@@H]4CCCNC4)n3)cnc2c1] | (2S)-2-[(3-{6-[(3R)-piperidin-3-ylamino]pyrazin-2-yl}imidazo[1,2-a]pyridin-7-yl)oxy]propan-1-ol 1H NMR (300 MHz, MeOD) δ ppm 1.37 (d, J = 6.03 Hz, 3H) 1.67-1.81 (m, 1H) 1.82-1.93 (m, 1H) 2.04-2.17 (m, 1H) 2.19-2.32 (m, 1H) 2.94-3.15 (m, 2H) 3.47-3.61 (m, 1H) 3.74 (d, J = 5.09 Hz, 2H) 4.14-4.33 (m, 1H) 4.56-4.74 (m, 1H) 4.96 (d, J = 19.03 Hz, 1H) 6.78-6.91 (m, 1H) 7.04 (d, J = 2.26 Hz, 1H) 7.78 (s, 1H) 8.09 (s, 1H) 8.27 (s, 1H) 9.48 (d, J = 7.54 Hz, 1H); LCMS: M + H 369. Method A (Example 32). |
| 293 | 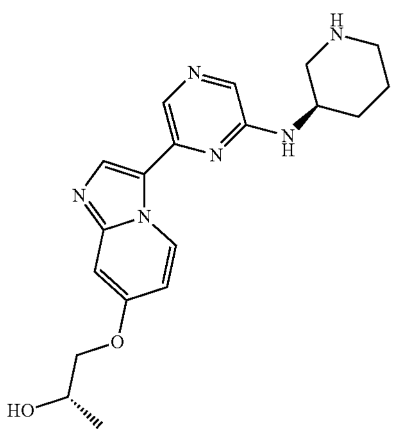 [SMILES: C[C@H](O)COc1ccn2c(-c3cncc(N[C@@H]4CCCNC4)n3)cnc2c1] | (2S)-1-[(3-{6-[(3R)-piperidin-3-ylamino]pyrazin-2-yl}imidazo[1,2-a]pyridin-7-yl)oxy]propan-2-ol 1H NMR (300 MHz, MeOD) δ ppm 1.31 (d, J = 6.40 Hz, 3H) 1.63-1.81 (m, 1H) 1.80-1.90 (m, 1H) 1.99-2.14 (m, 1H) 2.17-2.31 (m, 1H) 2.91-3.10 (m, 2H) 3.27 (br. s., 1H) 3.44-3.61 (m, 1H) 3.90-4.08 (m, 2H) 4.11-4.31 (m, 2H) 6.88 (dd, J = 7.72, 1.88 Hz, 1H) 6.99 (s, 1H) 7.77 (s, 1H) 8.08 (br. s., 1H) 8.24 (s, 1H) 9.49 (d, J = 7.54 Hz, 1H); LCMS: M + H 369. Method A (Example 32). |
| 294 | 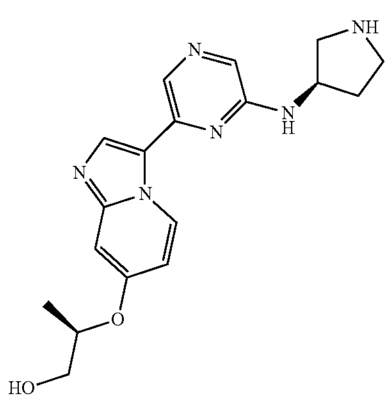 [SMILES: C[C@H](CO)Oc1ccn2c(-c3cncc(N[C@@H]4CCNC4)n3)cnc2c1] | (2R)-2-[(3-{6-[(3R)-pyrrolidin-3-ylamino]pyrazin-2-yl}imidazo[1,2-a]pyridin-7-yl)oxy]propan-1-ol 1H NMR (300 MHz, MeOD) δ ppm 1.27-1.36 (m, 3H) 3.38 (dd, J = 12.90, 4.80 Hz, 1H) 3.47-3.60 (m, 2H) 3.67 (dd, J = 12.06, 6.22 Hz, 1H) 4.06-4.15 (m, 1H) 4.16-4.27 (m, 2H) 4.67-4.79 (m, 1H) 7.31 (s, 1H) 8.02 (s, 1H) 8.36 (s, 1H) 8.46 (s, 1H) 9.65-9.71 (m, 1H); LCMS: M + H 355. Method A (Example 32). |

| Ex. | Structure | Name, Data and Preparation Method |
|---|---|---|
| 295 | 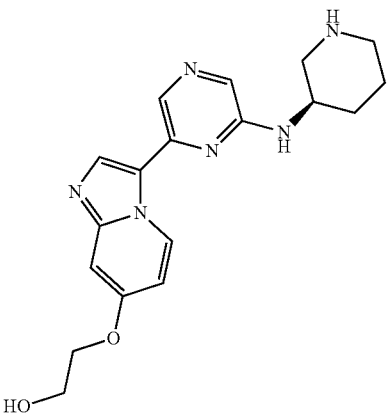 [SMILES: OCCOc1ccn2c(-c3cncc(N[C@@H]4CCCNC4)n3)cnc2c1] | 2-[(3-{6-[(3R)-piperidin-3-ylamino]pyrazin-2-yl}imidazo[1,2-a]pyridin-7-yl)oxy]ethanol 1H NMR (300 MHz, MeOD) δ ppm 1.73 (t, J = 10.83 Hz, 1H) 1.79-1.90 (m, 1H) 2.00-2.13 (m, 1H) 2.16-2.29 (m, 1H) 2.92-3.05 (m, 2H) 3.23 (br. s., 1H) 3.43-3.60 (m, 1H) 3.95 (t, J = 4.52 Hz, 2H) 4.19 (t, J = 4.52 Hz, 3H) 6.88 (d, J = 7.72 Hz, 1H) 7.01 (s, 1H) 7.77 (s, 1H) 8.09 (s, 1H) 8.25 (s, 1H) 9.50 (d, J = 7.54 Hz, 1H); LCMS M + H 356. Method A (Example 32). |
| 296 | 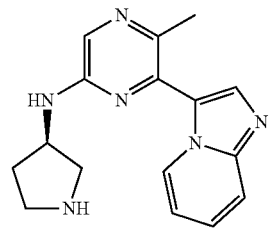 [SMILES: Cc1ncc(N[C@@H]2CCNC2)nc1-c1cnc2ccccn12] | 6-(imidazo[1,2-a]pyridin-3-yl)-5-methyl-N-[(3R)-pyrrolidin-3-yl]pyrazin-2-amine 1H NMR (400 MHz, MeOD) δ ppm 1.928 (m, 1H), 2.290 (m, 1H), 2.588 (s, 3H), 3.002 (m, 1H), 3.109 (m, 1H), 3.212 (m, 1H), 3.230 (m, 1H), 4.441 (m, 1H), 7.050 (t, 1H), 7.445 (t, 1H), 7.651 (s, 1H), 7.841 (s, 1H), 7.963 (s, 1H), 9.189 (d, 1H). Method A (Example 16, use 16b-1). |
| 297 | 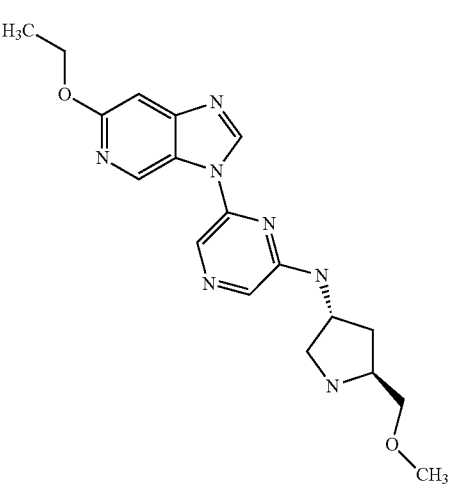 [SMILES: CCOc1cc2ncn(-c3cncc(N[C@H]4CN[C@H](COC)C4)n3)c2cn1] | [6-(6-Ethoxy-imidazo[4,5-c]pyridin-3-yl)-pyrazin-2-yl]-((3R,5S)-5-methoxymethyl-pyrrolidin-3-yl)-amine. 1H NMR (400 MHz, MeOD) δ ppm 1.43 (t, J = 7.07 Hz, 3H), 2.16-2.33 (m, 2H), 3.26 (d, J = 4.29 Hz, 1H), 3.46 (s, 3H), 3.57 (d, J = 6.82 Hz, 1H), 3.61-3.70 (m, 2H), 3.97 (dd, J = 7.07, 3.28 Hz, 1H), 4.36 (q, J = 7.07 Hz, 2H), 4.70 (d, J = 4.29 Hz, 1H), 7.08 (s, 1H), 7.96 (s, 1H), 8.31 (s, 1H), 9.02 (s, 1H), 9.15 (s, 1H). LCMS: M + 1 370. Method A (Example 298) |

Additional Specific Examples

Example 298

(Method A): [6-(6-Ethoxy-imidazo[4,5-c]pyridin-3-yl)-pyrazin-2-yl]-((3S,4S)-4-methoxy-piperidin-3-yl)-amine

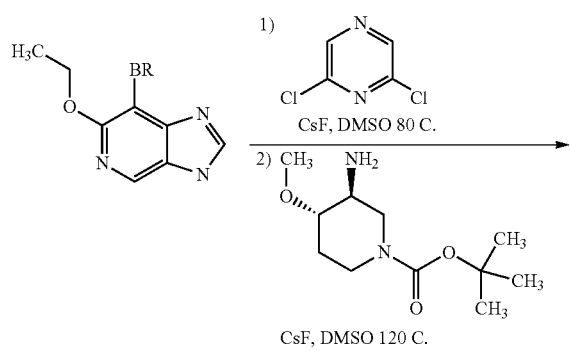

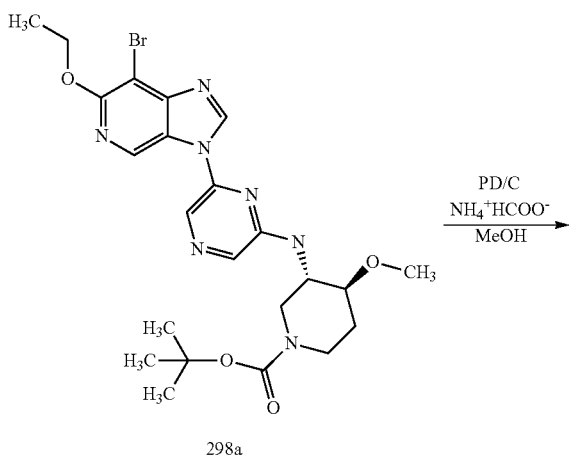

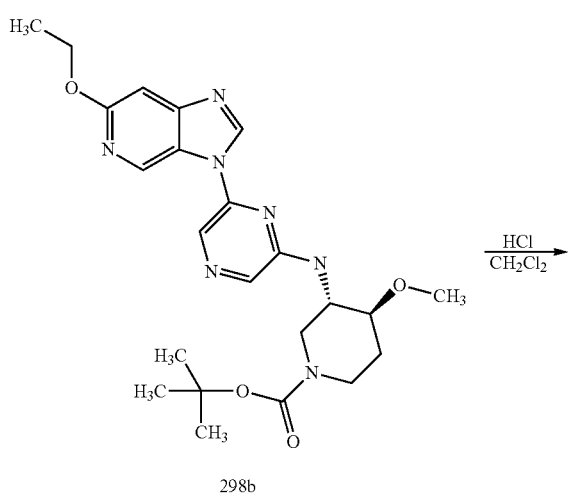

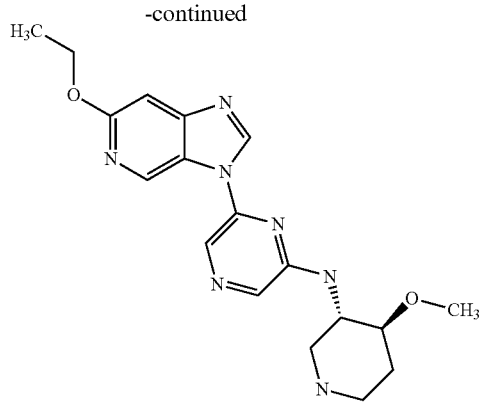

Preparation of compound 298a: (3S,4S)-3-[6-(7-Bromo-6-ethoxy-imidazo[4,5-c]pyridin-3-yl)-pyrazin-2-ylamino]-4-methoxy-piperidine-1-carboxylic acid tert-butyl ester A mixture of 7-bromo-6-ethoxy-3H-imidazo[4,5-c]pyridine (100 mg, 0.413 mmol), 2,6-dichloro pyrazine (61.5 mg, 0.413 mmol) and CsF (126 mg, 0.826 mmol) in 1 mL DMSO was heated at 80° C. for 6 hrs. The reaction mixture was cooled to room temperature, (3S,4S)-3-Amino-4-methoxy-piperidine-1-carboxylic acid tert-butyl ester (100 mg, 0.434 mmol) was added, continued to heat at 120° C. overnight. The reaction mixture was cooled to room temperature and poured into 15 mL H$_2$O, solid crashed out. The solid was filtered and added 20 mL MeOH, the insoluble material was filtered and rinsed with 10 mL MeOH. The filtrate was concentrated and chromatographed on an ISCO with 100% EtOAc to give the title compound 298a as a brown oil (90 mg, 40%).

Preparation of compound 298b: (3S,4S)-3-[6-(6-Ethoxy-imidazo[4,5-c]pyridin-3-yl)-pyrazin-2-ylamino]-4-methoxy-piperidine-1-carboxylic acid tert-butyl ester A mixture of 298a (89 mg, 0.16 mmol), 10% Pd/C wet (41 mg, 0.39 mmol) and ammonium formate (89 mg, 1.3 mmol) was heated to reflux for 1.5 hrs. The reaction was filtered, the solvent was evaporated and the crude product was chromatographed on an ISCO with 100% EtOAc to give the title compound 298b as an oil (46 mg, 60%). 298b (46 mg, 0.098 mmol) was dissolved in 1 mL CH$_2$Cl$_2$ anhydrous, 0.5 mL 4M HCl in dioxane was added, the reaction mixture was stirred at room temperature for 1 hr. The solvent was evaporated; the residue was dried over vacuum. The residue was dissolved in 15 mL 5% MeOH/CH$_2$Cl$_2$, 10 mL H$_2$O and 1 mL std NaHCO$_3$ was added, the aqueous layer was extracted with 5% MeOH/CH$_2$Cl$_2$, the organic layers were combined and dried over vacuum to give the title compound 298 as a grey solid (32 mg, 88%). 1H NMR (400 MHz, MeOD) δ ppm 1.43 (t, J=7.07 Hz, 3H), 1.83 (q, J=9.68 Hz, 1H), 2.42 (br. s., 1H), 3.02-3.13 (m, 1H), 3.07 (d, J=9.09 Hz, 1H), 3.39 (d, J=13.89 Hz, 1H), 3.47 (s, 3H), 3.58 (ddd, J=8.21, 4.04, 3.92 Hz, 2H), 4.34 (q, J=7.07 Hz, 2H), 4.29 (dt, J=8.15, 4.14 Hz, 1H), 7.06 (s, 1H), 8.01 (s, 1H), 8.27 (s, 1H), 9.01 (s, 1H), 9.09 (br. s., 1H). LCMS: M+1 370.

Example 299

(Method H): (R)-Piperidin-3-yl-(6-pyrazolo[1,5-c]pyrimidin-3-yl-pyrazin-2-yl)-amine

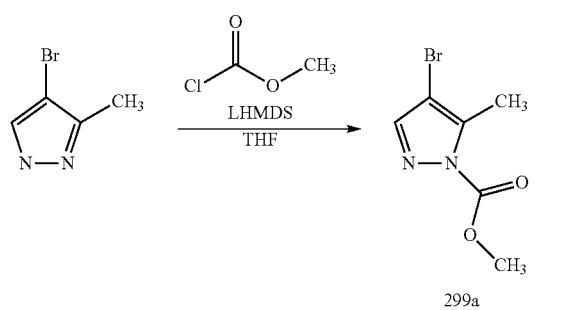
299a

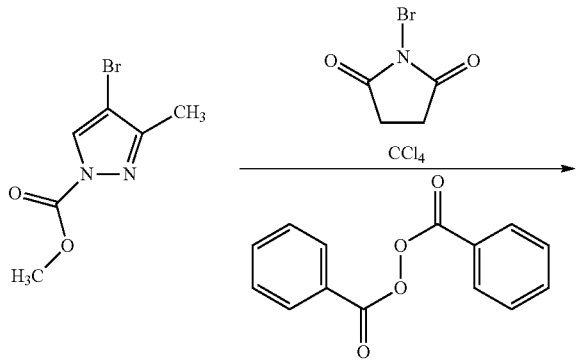
299c

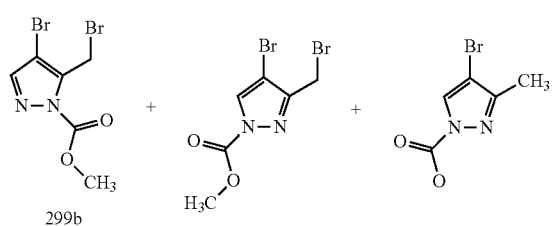
299b

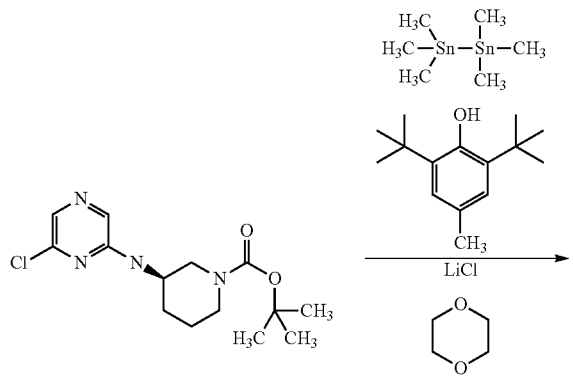

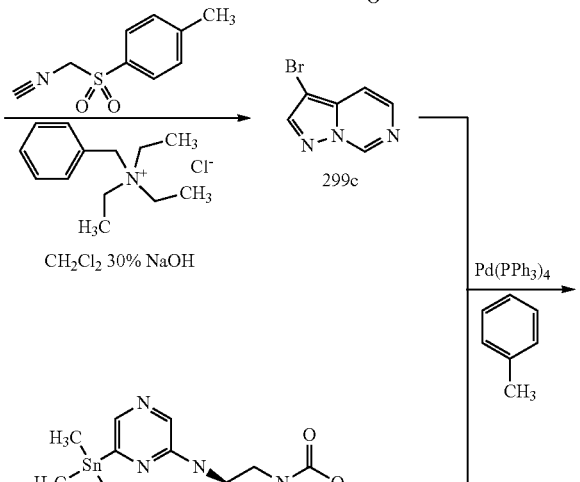
299d

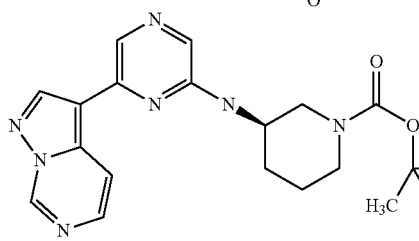
299e

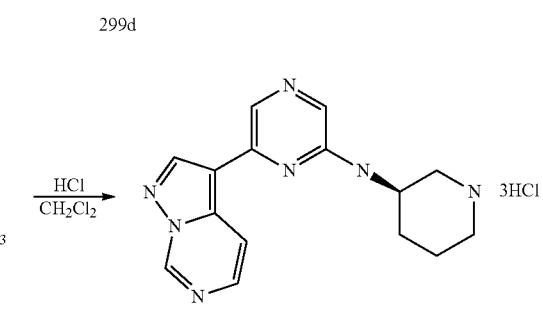
299

Preparation of compound 299a: 4-Bromo-5-methyl-pyrazole-1-carboxylic acid methyl ester Lithium bis(trimethylsilyl)amide in hexane (0.7 mL, 0.7 mmol, 1M) was added to a solution of 4-bromo-3-methyl-1H-pyrazole (100 mg, 0.62 mmol) under the $N_2$ at −78° C., and the mixture was allowed to warm to room temperature for a period of 2 hrs. The mixture was cooled again to −78° C., methyl chloroformate (0.7 mmol, 0.054 mL) was added dropwise, stirring was continued at −78° C., and the reaction was allowed to warm to room temperature and stirred for overnight. The reaction mixture was treated with $NH_4Cl$, extracted with ethyl acetate, and the combined organic layers were washed with brine and dried over $Na_2SO_4$. The solvent was evaporated and the crude product was chromatographed on an ISCO with 10% EtOAc/Heptane, got 128 mg white solid as a 1:1 mixture of the title compound 299a and 4-bromo-3-methyl-pyrazole-1-carboxylic acid methyl ester.

Preparation of compound 299b: 4-Bromo-5-bromomethyl-pyrazole-1-carboxylic acid methyl ester Bromo-N-succinimide (105 mg, 0.59 mmol) and benzoyl peroxide (2 mg, 0.008 mmol) were added to a solution of the 1:1 mixture of 299a and 4-bromo-3-methyl-pyrazole-1-carboxylic acid methyl ester (128 mg, 0.58 mmol) in CCl$_4$ (6 mL), and the mixture was stirred and heated to reflux for 6 hrs. The succinimide formed was filtered off, and the solvent was evaporated under reduced pressure. The residue was chromatographed on an ISCO with 10% EtOAc/Heptane, got 110 mg white solid as a mixture of 1:0.4:0.6 title compound 299b:4-bromo-3-bromomethyl-pyrazole-1-carboxylic acid methyl ester:4-bromo-3-methyl-pyrazole-1-carboxylic acid methyl ester. The mixture was used for next step without further separation.

Preparation of compound 299c:
3-Bromo-pyrazolo[1,5-c]pyrimidine

To a mixture of 30 mg above 299b, (p-tolylsulfonyl)methyl isocyanide (20 mg, 0.1 mmol) and benzyl triethylammonium chloride (4.8 mg, 0.02 mmol) at −10° C. was added 1 mL 1:1 CH$_2$Cl$_2$: 30% aqueous NaOH solution. After stirred for 20 min, the reaction mixture was poured into water and extracted with CH$_2$Cl$_2$. The organic phase was washed with brine, dried over Na$_2$SO$_4$, concentrated under reduced pressure to give a crude product, which was chromatographed on an ISCO with 20% EtOAc/Heptane to give 3 mg title compound 299c as white solid. 1H NMR (400 MHz, CHLOROFORM-d) δ ppm 7.43 (d, J=6.32 Hz, 1H), 7.90 (d, J=6.32 Hz, 1H), 8.06 (s, 1H), 9.20 (s, 1H). LCMS: M+1 198, 200.

Preparation of compound 299d: (R)-3-(6-Trimethyl-stannanyl-pyrazin-2-ylamino)-piperidine-1-carboxylic acid tert-butyl ester A mixture of (R)-3-(6-Chloro-pyrazin-2-ylamino)-piperidine-1-carboxylic acid tert-butyl ester (200 mg, 0.64 mmol), hexamethyldistannane (419 mg, 1.28 mmol), 2,6-bis(1,1-dimethylethyl)-4-methylphenol (7.1 mg, 0.032 mmol), lithium chloride (81.3 mg, 1.92 mmol) and tetrakis(triphenylphosphine)palladium(0) (74 mg, 0.064 mmol) in 5 mL 1,4-dioxane was degassed and purged with nitrogen and heated to reflux overnight. The reaction was filtered and the solvent was removed under reduced pressure. The crude product was chromatographed on an ISCO with 50% EtOAc/Heptane to give 180 mg oil as a 1:1 mixture of the title compound 299d and (R)-3-(6-Chloro-pyrazin-2-ylamino)-piperidine-1-carboxylic acid tert-butyl ester which was used for next step without further separation.

Preparation of compound 299e: (R)-3-(6-Pyrazolo[1,5-c]pyrimidin-3-yl-pyrazin-2-ylamino)-piperidine-1-carboxylic acid tert-butyl ester A mixture of 299c (25 mg, 0.13 mmol), 167 mg 299d and tetrakis(triphenylphosphine)palladium(0) (15 mg, 0.013 mmol) in 4 mL toluene was heated in a microwave at 160° C. for 10 min. The reaction was filtered and the solvent was removed under reduced pressure. The crude product was loaded into prep TLC plate (60% EtOAc/Heptane) which gave a mixture of the title compound 299e and the dimmer of pyrazine. The title compound 299e was further purified by a mass triggered prep HPLC as an oil (13.7 mg, 28%). 1H NMR (400 MHz, CHLOROFORM-d) δ ppm 1.42 (br. s., 9H), 1.64 (br. s., 2H), 1.71 (br. s., 1H), 1.80 (br. s., 1H), 2.06 (dd, J=11.49, 7.45 Hz, 1H), 3.31 (br. s., 1H), 3.60 (br. s., 1H), 4.01 (d, J=3.54 Hz, 1H), 4.76 (d, J=6.57 Hz, 1H), 7.76 (br. s., 1H), 7.97 (d, J=6.32 Hz, 1H), 8.22 (br. s., 2H), 8.52 (s, 1H), 9.29 (s, 1H). LCMS: M+1 396.

299e (13.7 mg, 0.035 mmol) was dissolved in 1 mL CH$_2$Cl$_2$ anhydrous, 1 mL 4M HCl in dioxane was added, the reaction mixture was stirred at room temperature for 1 hr. 6 mL CH$_2$Cl$_2$ anhydrous was added, the mixture was sonicated. The solid was filtered and rinsed with 6 mL CH$_2$Cl$_2$, dried over vacuum to give the title compound 299 as a yellow solid (10.7 mg, 75%). 1H NMR (400 MHz, MeOD) δ ppm 1.83 (br. s., 1H), 2.00 (br. s., 1H), 2.14 (br. s., 1H), 2.25 (br. s., 1H), 3.09-3.21 (m, 2H), 3.36 (br. s., 2H), 3.67 (d, J=4.29 Hz, 1H), 4.52 (br. s., 1H), 7.87 (br. s., 1H), 8.18 (d, J=5.81 Hz, 1H), 8.34 (d, J=6.06 Hz, 1H), 8.41 (br. s., 1H), 8.87 (s, 1H), 9.56 (s, 1H). LCMS: M+1 296.

Synthesis of Commercial Unavailable Amines

Example I cis-(racemic)-3-Amino-4-phenyl-pyrrolidine-1-carboxylic acid tert-butyl ester

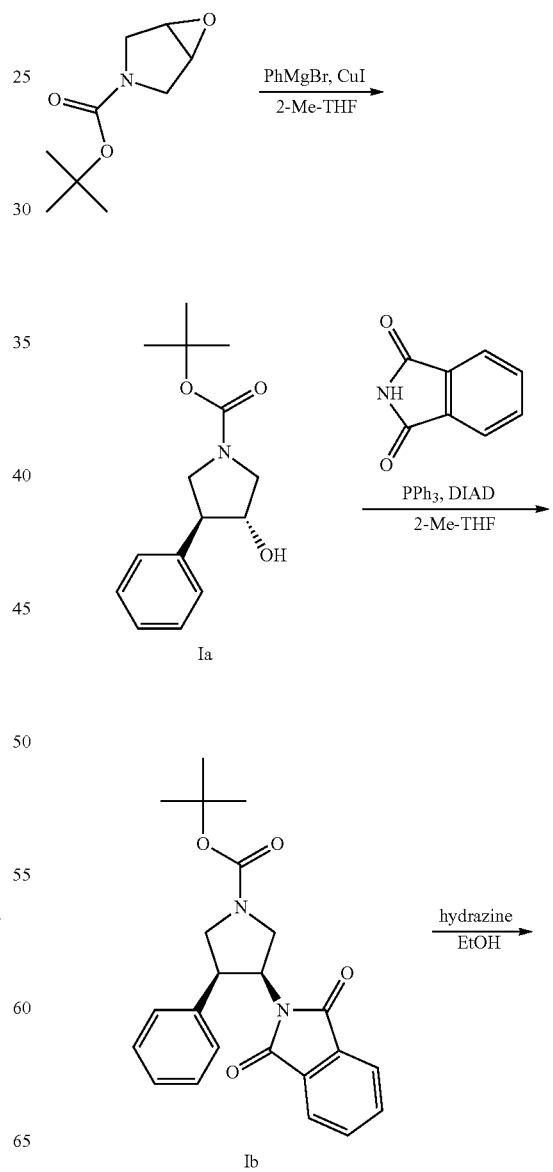

J=7.05, 4.78 Hz, 4H) 4.32 (s, 1H) 4.77 (s, 1H) 7.24 (d, J=1.76 Hz, 3H) 7.33 (d, J=7.30 Hz, 2H).

Example II

Cis-(racemic)-3-Amino-4-methoxy-pyrrolidine-1-carboxylic acid tert-butyl ester

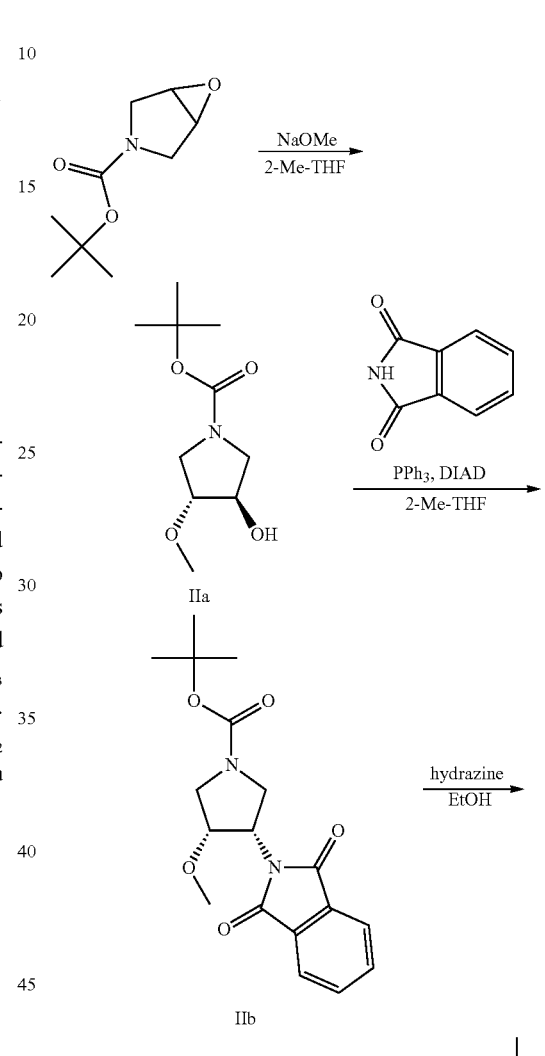

Preparation of compound Ia: trans-(racemic)-3-hydroxy-4-phenyl-pyrrolidine-1-carboxylic acid tert-butyl ester

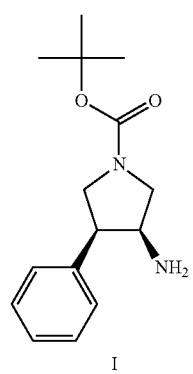

Oxa-3-aza-bicyclo[3.1.0]hexane-3-carboxylic acid tert-butyl ester (3 g, 16 mmol), was dissolved in 2-methyl-tetrahydrofuran (5 mL) and added dropwise to a solution of phenylmagnesium bromide (1.5 eq, 24.3 mL of a 1.0 M solution) and copper iodide (0.05 eq) at 0° C. The reaction was allowed to warm to room temperature and stir for 18 h. Reaction was cooled to 0° C. and quenched with sat. NH$_4$Cl solution and extracted with EtOAc. Organic was washed with NaHCO$_3$ and brine and dried over Na$_2$SO$_4$ and the solvent removed. Residue was purified by column chromatography on SiO$_2$ (15-40% EtOAc/HEptane) which gave the title compound Ia as a yellow oil (3.59 g).

Preparation of compound Ib: cis-(racemic)-3-(1,3-dioxo-1,3-dihydro-isoindol-2-yl)-4-phenyl-pyrrolidine-1-carboxylic acid tert-butyl ester Ia (3.59 g) was dissolved in 2-Me-THF and Phthalimide (2.35 g, 1.2 eq) and PPh$_3$ (4.23 g, 1.2 eq) were added and stirred for 1 h. The reaction was cooled to 0° C., and DIAD (3.4 g, 1.2 eq) was added slowly and the reaction was allowed to warm to RT and stir overnight. Reaction was concentrated and dissolved in EtOAc, washed with 2M NaOH, brine and dried over Na$_2$SO$_4$. Solvent was removed and residue purified by column chromatography on SiO$_2$ (25% EtOAc/heptane) which gave the title compound 1b as a white solid (3.8 g).

Ib (800 mg) was dissolved in ethanol (20 mL) and treated with hydrazine (10 eq) at room temperature for 24 h. The reaction was filtered to remove solids and the filtrate concentrated from ethanol (3×10 mL) which gave the title compound I as a clear oil (440 mg, 50%). 1H NMR (400 MHz, DMSO-d6) δ ppm 1.43 (s, 9H) 3.11 (s, 1H) 3.35 (s, 1H) 3.44 (dd,

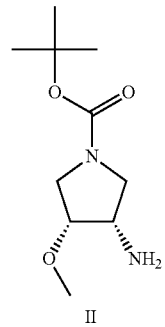

Preparation of compound IIa: trans-(racemic)-3-Hydroxy-4-methoxy-pyrrolidine-1-carboxylic acid tert-butyl ester 6-Oxa-3-aza-bicyclo[3.1.0]hexane-3-carboxylic acid tert-butyl ester (3 g, 16 mmol) was dissolved in 2-Me-THF (10 mL) and a solution of sodium methoxide in methanol (10 mL of a 25% solution) was added and the reaction stirred at rt overnight. Reaction was quenched with sat. NH4Cl and concentrated, then after extraction with EtOAc, residue was purified by column chromatography on SiO$_2$ (35% EtOAc/heptane) which gave the title compound IIa as a clear oil (1.05 g).

Preparation of compound IIb: cis-(racemic)-3-(1,3-Dioxo-1,3-dihydro-isoindol-2-yl)-4-methoxy-pyrrolidine-1-carboxylic acid tert-butyl ester IIa (1.05 g) was dissolved in 2-Me-THF and Phthalimide (853 mg, 1.2 eq) and PPh$_3$ (1.54 g, 1.2 eq) were added and stirred for 1 h. The reaction was cooled to 0° C., and DIAD (1.24 g, 1.2 eq) was added slowly and the reaction was allowed to warm to RT and stir overnight. Reaction was concentrated and dissolved in EtOAc, washed with 2M NaOH, brine and dried over Na$_2$SO$_4$. Solvent was removed and residue purified by column chromatography on SiO$_2$ (30% EtOAc/heptane) which gave the title compound IIb as a clear oil (1.886 g).

IIb (1.886 g) was dissolved in ethanol (20 mL) and treated with hydrazine (10 eq) at room temperature for 24 h. The reaction was filtered to remove solids and the filtrate concentrated from ethanol (3×10 mL) which gave the title compound II as a clear oil (570 mg, 25%). 1H NMR (400 MHz, CDCl$_3$) δ ppm 1.45 (s, 10H) 3.06 (s, 1H) 3.39 (s, 6H) 3.56 (s, 2H) 3.65 (s, 1H).

Example III (3R,5R)-3-Amino-5-methoxy-piperidine-1-carboxylic acid benzyl ester

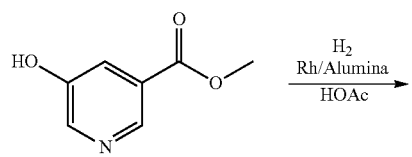

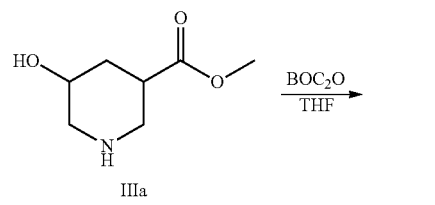
IIIa

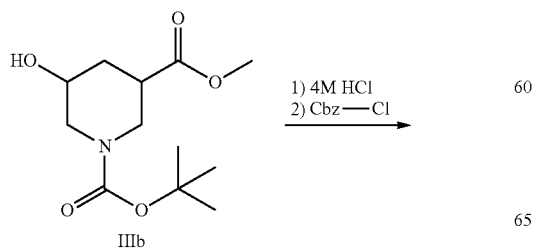
IIIb

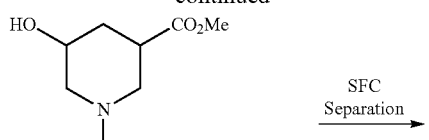
IIIc

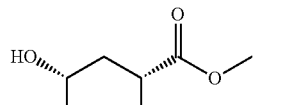

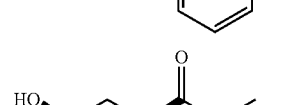

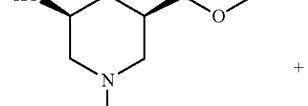

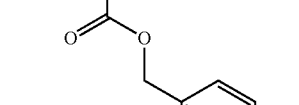

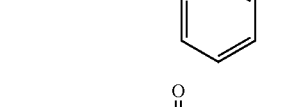
IIId-1

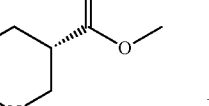

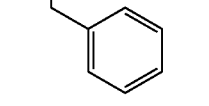

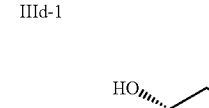

IIId

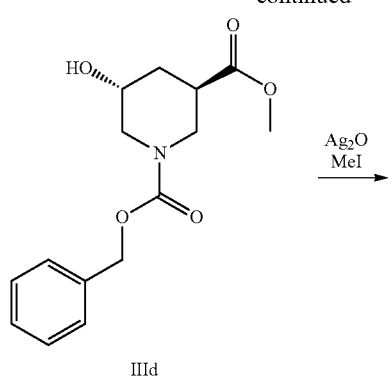

IIId

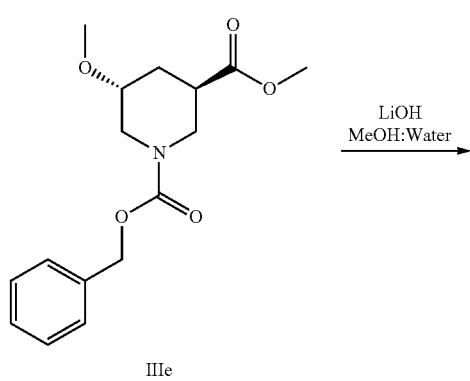

IIIe

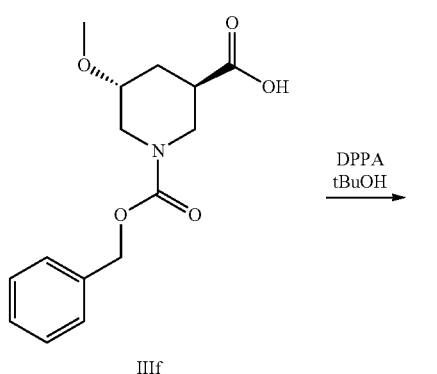

IIIf

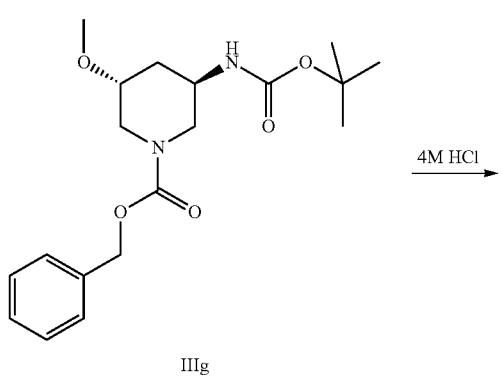

IIIg

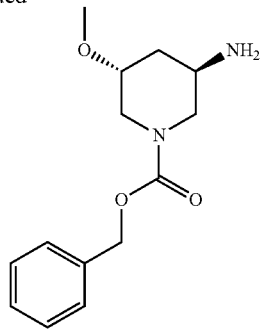

III

Preparation of compound IIIa:
5-Hydroxy-piperidine-3-carboxylic acid methyl ester (racemic)

Methyl 5-hydroxypyridine-3-carboxylate (22 g, 140 mmol), acetic acid (250 mL) and rhodium on alumina (2.2 g, 21 mmol) were added to a 1 L reactor. The mixture was hydrogenated at 200 psi and 50° C. for 18 h. The reaction was allowed to cool, then filtered through a microfiber filter paper, and concentrated in vacuo which afforded a viscous colorless residue. The residue was azeotroped with toluene and dried which gave the title compound IIIa (25.4 g, 78%).

Preparation of compound IIIb:
5-Hydroxy-piperidine-1,3-dicarboxylic acid 1-tert-butyl ester 3-methyl ester (racemic)

IIIa (25.4 g) was dissolved in THF (250 mL). Sat. aqueous sodium bicarbonate was added followed by dropwise addition of Boc anhydride (28.5 g, 130.6 mmol). The mixture was stirred for 24 h. Ethyl acetate was added and the organic layer extracted, washed with brine, and dried over sodium sulfate. The residue was concentrated and purified by column chromatography (20% ethyl acetate in heptanes to 50%). Collected KMnO4/PMA active spot which gave the title compound IIIb as a colorless oil (19.7 g).

Preparation of compound IIIc: 5-Hydroxy-piperidine-1,3-dicarboxylic acid 1-benzyl ester 3-methyl ester (racemic) IIIb (19.7 g) was dissolved in ethyl acetate (250 mL), and 4M HCl in dioxane (125 mL) was added. The mixture was stirred overnight. The mixture as concentrated and the residue dissolved in THF (250 mL), the mixture cooled to 0° C., then dilute with saturated sodium bicarbonate. Benzyl chloroformate (15 g, 84 mmoL) was added in a dropwise manner. The mixture was stirred overnight. The organic layers were separated and the aqueous layer extracted with ethyl acetate. The organic layer was washed with brine, dried over sodium sulfate, and concentrated. The residue was purified by column chromatography (20% to 50% ethyl acetate in heptanes). The major PMA/uv active spot was collected which gave the title compound IIIc as a colorless oil (14.1 g).

Preparation of compound IIId:
(3R,5R)-5-Hydroxy-piperidine-1,3-dicarboxylic acid 1-benzyl ester 3-methyl ester Separated 14.1 g of mixture of diastereomers using chiral SFC methods which gave the title compound IIId. $^1$H NMR (400 MHz, DMSO-d6) δ ppm 1.78-1.87 (m, 1H) 2.76-2.89 (m, 1H) 3.07-3.22 (m, 1H) 3.28-3.45 (m, 2H) 3.56 (br. s., 3H) 3.73-3.81 (m, 1H) 3.83-4.04 (m, 1H) 4.83-4.96 (m, 1H) 4.99-5.13 (m, 2H) 7.26-7.44 (m, 5H).

Preparation of compound IIIe: (3R,5R)-5-Methoxy-piperidine-1,3-dicarboxylic acid 1-benzyl ester 3-methyl ester To a sealed vessel was added IIId (300 mg, 1.02 mmol), silver (II) oxide (237 mg, 1.02 mmol), and iodomethane (2.05 mL, 0.5M). The mixture was refluxed 16 h. The reaction was filtered and concentrated in vacuo. The crude material was purified by silica gel column chromatography (0-100% EtOAc/Heptanes) which gave the title compound IIIe as a clear oil (186 mg, 59%). $^1$H NMR (400 MHz, CHLOROFORM-d) ppm 1.57 (s, 3H) 1.70-1.90 (m, 1H) 2.10-2.26 (m, 1H) 2.80-2.95 (m, 1H) 2.98-3.09 (m, 1H) 3.25-3.32 (m, 1H) 3.37-3.41 (m, 1H) 3.41-3.54 (m, 1H) 3.64-3.69 (m, 2H) 4.10-4.17 (m, 1H) 4.20-4.35 (m, 1H) 5.13 (d, 2H) 7.29-7.44 (m, 5H). LCMS m/z 308 (M+1).

Preparation of compound IIIf: (3R,5R)-5-Methoxy-piperidine-1,3-dicarboxylic acid 1-benzyl ester In a flask was added IIIe (182 mg, 0.592 mmol), LiOH (28 mg, 1.18 mmol), and 3:1 MeOH:water (6 mL). The mixture was stirred at room temperature for 16 h. The mixture was concentrated and neutralized to pH 5 with 1 N HCl. The compound was purified by prep HPLC which gave the title compound IIIf as a clear oil (140 mg, 80% yield). LCMS m/z 294 (M+1)

Preparation of compound IIIg: (3R,5R)-3-tert-Butoxycarbonylamino-5-methoxy-piperidine-1-carboxylic acid benzyl ester IIIf (140 mg) was dissolved in tBuOH (2.5 mL, 0.2M) and treated with TEA (93 uL, 0.67 mmol). The mixture was then treated with DPPA (0.124 mL, 0.572 mmol) and heated at 90° C. for 16 h. Dilute with water and EtOAc. Extract aqueous with EtOAc 5×20 mL. Dry over Na2SO4, filter and concentrate. Purify by biotage 0-100% EtOAc/Heptanes which gave the title compound IIIf as a clear oil (100 mg, 58%). 1H NMR (400 MHz, CHLOROFORM-d) ppm 1.21-1.33 (m, 1H) 1.35-1.53 (m, 9H) 1.84-1.92 (m, 1H) 2.90-3.16 (m, 1H) 3.28-3.50 (m, 5H) 3.50-3.71 (m, 1H) 3.74-4.27 (m, 2H) 5.08-5.27 (m, 2H) 7.28-7.40 (m, 5H). LCMS m/z 365 (M+1).

A solution of the IIIf (100 mg, 0.274 mmol) in dichloromethane (5 mL) was added 4M HCl in dioxane (0.137 mL, 0.548 mol) and stirred at room temperature for 16 hours. The reaction was concentrated in vacuo which gave the title compound III as a tan gum (44 mg, 61%). LCMS m/z 265 (M+1)

Example IV tert-Butyl (2S,4R)-4-amino-2-(hydroxymethyl)pyrrolidine-1-carboxylate

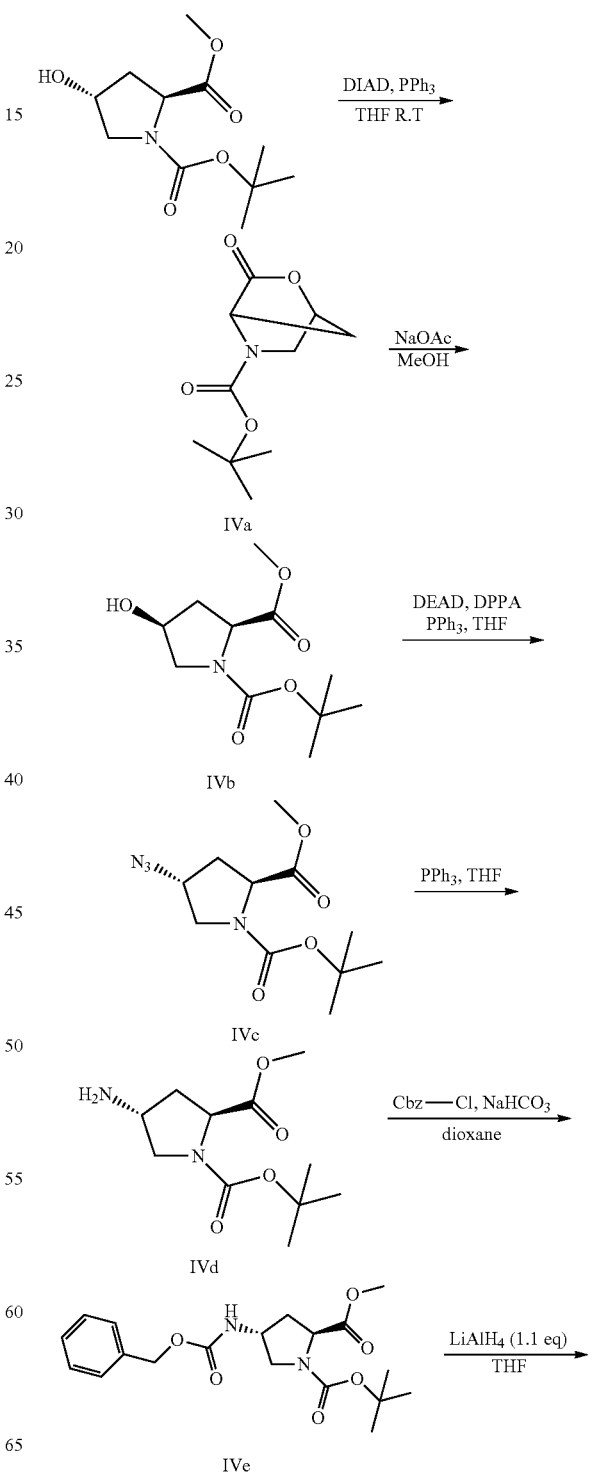

-continued

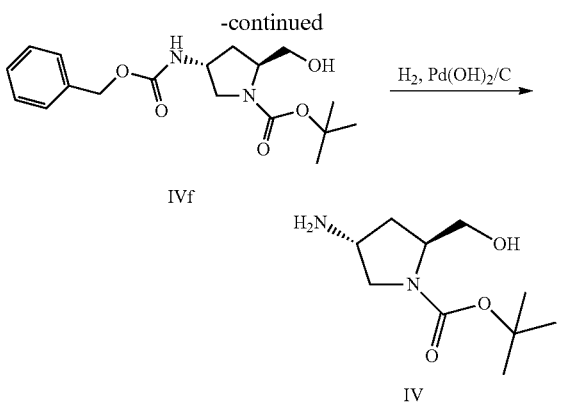

Preparation of compound IVa: tert-Butyl 3-oxo-2-oxa-5-azabicyclo[2.2.1]heptane-5-carboxylate To a solution of 1-tert-butyl 2-methyl (2S,4R)-4-hydroxypyrrolidine-1,2-dicarboxylate (170.0 g, 0.736 mol) and PPh$_3$ (237.0 g, 0.88 mol) in dry THF (1.5 L) was added dropwise DIAD (178.35 g, 0.88 mol) at 0° C. under N$_2$ gas. After addition, the resulting reaction mixture was stirred at room temperature overnight. TLC (petroleum ether/EtOAc 3:1) indicated the complete consumption of compound 1A. The solvent was removed in vacuo. The residue was purified by column chromatography (silica gel, petroleum ether/EtOAc 6:1) which gave the title compound IVa as a white solid (110.0 g, yield: 72.0%).

Preparation of compound IVb: 1-tert-Butyl 2-methyl (2S,4S)-4-hydroxypyrrolidine-1,2-dicarboxylate A solution of IVa (47.0 g, 0.22 mol) and NaOAc (36.0 g, 0.44 mol) in dry MeOH (1.0 L) was stirred at 40° C. under N$_2$ gas overnight. The solvent was removed in vacuo. The residue was partitioned between water (1.0 L) and EtOAc (1.0 L). The organic layer was separated. The aqueous layer was extracted with EtOAc (500 mL×2). The combined EtOAc layers were washed with brine (600 mL), dried over Na$_2$SO$_4$ and concentrated in vacuo which gave the title compound IVb as a white solid (53.0 g, yield: 98.0%).

Preparation of compound IVc: 1-tert-Butyl 2-methyl (2S,4R)-4-azidopyrrolidine-1,2-dicarboxylate To a solution of IVb (70.0 g, 0.286 mol) in dry THF (700 mL) were added PPh$_3$ (75.0 g, 0.286 mol) and DEAD (59.5 g, 0.342 mol) at 0° C. After stirring at this temperature for 0.5 hour, to the reaction mixture was added dropwise DPPA (93.89 g, 0.342 mol) at 0° C. The resulting mixture was stirred at room temperature for 5 days. The solution of IVc was used for next step without any purification.

Preparation of compound IVd: 1-tert-Butyl 2-methyl (2S,4R)-4-aminopyrrolidine-1,2-dicarboxylate To a stirred solution of IVc (77.3 g, 0.286 mol) in THF (0.7 L) was added PPh$_3$ (80.0 g, 0.684 mol) in portions, followed by addition of water (12.87 mL, 0.75 mol). The reaction mixture was stirred at 65° C. overnight. The reaction mixture was concentrated in vacuo. The residue was diluted with dichloromethane (1.0 L). The dichloromethane layer was acidified with 10% aqueous citric acid to pH 4~5, and then extracted with dichloromethane (500 mL×2) to removed impurity. The aqueous layer was basified with saturated aqueous Na$_2$CO$_3$ to pH 8~9 and then extracted with CH$_2$Cl$_2$ (500 mL×3). The combined organic layers were washed with brine, dried over Na$_2$SO$_4$ and concentrated in vacuo which gave the title compound as yellow oil (37.0 g, yield: 53%).

Preparation of compound IVe: 1-tert-Butyl 2-methyl (2S,4R)-4-{[(benzyloxy)carbonyl]amino}pyrrolidine-1,2-dicarboxylate To a solution of IVd (37.0 g, 0.15 mol) and Cbz-Cl (30.7 g, 0.18 mol) in dioxane (370 mL) was added aqueous NaOH (10%, 370 mL). The mixture was stirred at room temperature overnight. The reaction mixture was concentrated in vacuo. The residue was partitioned between water (1.0 L) and EtOAc (1.0 L). The aqueous layer was extracted with EtOAc (1.0 L×3). The combined organic layers were washed with brine (500 mL), dried over Na2SO4 and concentrated in vacuo to give crude product, which was purified by column chromatography (silica gel, petroleum ether/EtOAc from 3:1) which gave the title compound IVe as a colorless syrup (45.0 g, yield: 79.2%). $^1$H NMR (400 MHz, CDCl$_3$) 7.38-7.32 (m, 5H), 5.10 (s, 2H), 4.95-4.86 (m, 1H), 4.37-4.26 (m, 2H), 3.79-3.73 (m, 4H), 3.39-3.28 (m, 1H), 2.31-2.19 (m, 2H), 1.45-1.40 (d, 9H).

Preparation of compound IVf: tert-Butyl (2S,4R)-4-{[(benzyloxy)carbonyl]amino}-2-(hydroxymethyl)pyrrolidine-1-carboxylate To a stirred suspension of LiAlH$_4$ (1.2 g, 31.73 mmol) in dry THF (100 mL) was added dropwise a solution of IVe (8.0 g, 21.15 mmol) in dry THF (20 mL) at 0° C. The resulting mixture was stirred at room temperature for three hours. The reaction mixture was quenched with 10% aqueous NaOH (10 mL) at 0° C. and then diluted with EtOAc (500 mL). The resulting mixture was filtered and washed with EtOAc (300 mL). The organic layer was washed with brine (200 mL), dried over Na$_2$SO$_4$ and concentrated in vacuo to yield crude product, which was purified by column chromatography (silica gel, petroleum ether/EtOAc from 4:1 to 2:1) which gave the title compound IVf as a colorless syrup (3.0 g, 41%). 1H NMR (400 MHz, DMSO): 7.51-7.47 (m, 1H), 7.36-7.33 (m, 5H), 5.05 (s, 2H), 4.79-4.71 (m, 1H), 4.15-4.08 (m, 1H), 3.76-3.56 (m, 1H), 3.42-3.33 (m, 3H), 3.11-3.06 (m, 1H), 2.12-1.99 (m, 1H), 1.83-1.70 (m, 1H), 1.37 (s, 9H).

IVf (800 mg, 2.3 mmol) was dissolved in EtOAc (30 mL) and MeOH (10 mL) and the resultant clear solution was treated w/20% Pd(OH)$_2$ on carbon (80 mg) and hydrogen (1 atm). After 18 hours, the reaction mixture was filtered and the filtrate was concentrated under reduced pressure which gave the title compound IV as a white solid (490 mg, 99% yield) $^1$H NMR (400 MHz, DMSO-d$_6$) 4.66 (br. s., 1H), 3.63-3.77 (m, 1H), 3.40-3.51 (m, 2H), 3.15-3.36 (m, 3H), 2.82-2.96 (m, 1H), 1.89-2.04 (m, 1H), 1.78 (br. s., 1H), 1.51-1.64 (m, 1H), 1.39 (s, 9H). LCMS m/z 117 (M-BOC+1).

Example V tert-Butyl (2S,4R)-4-amino-2-(methoxymethyl)pyrrolidine-1-carboxylate

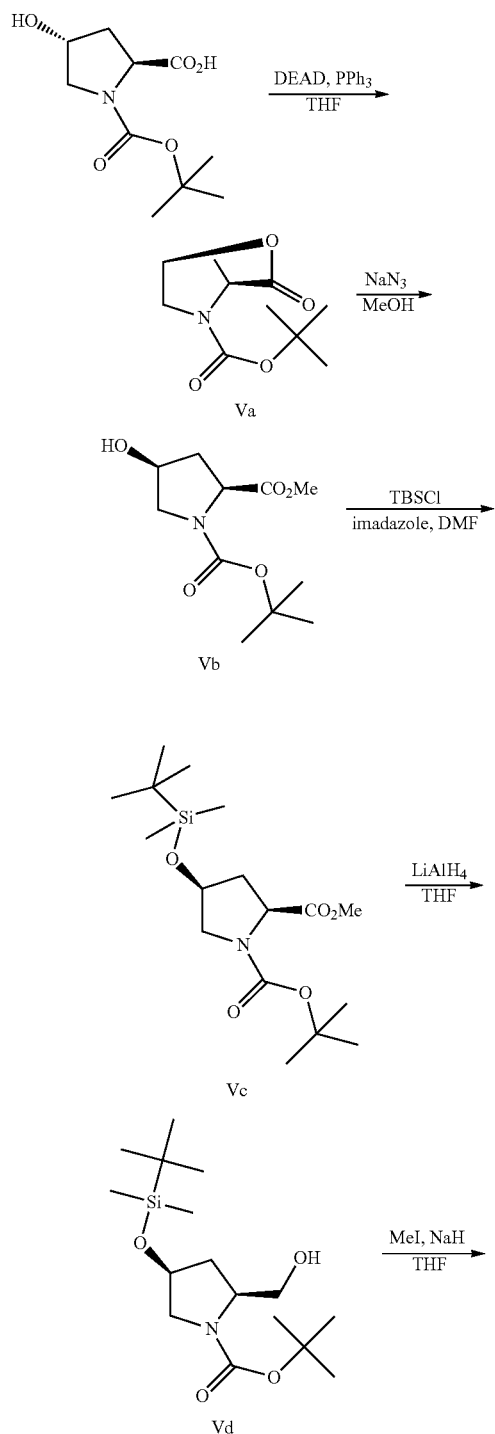

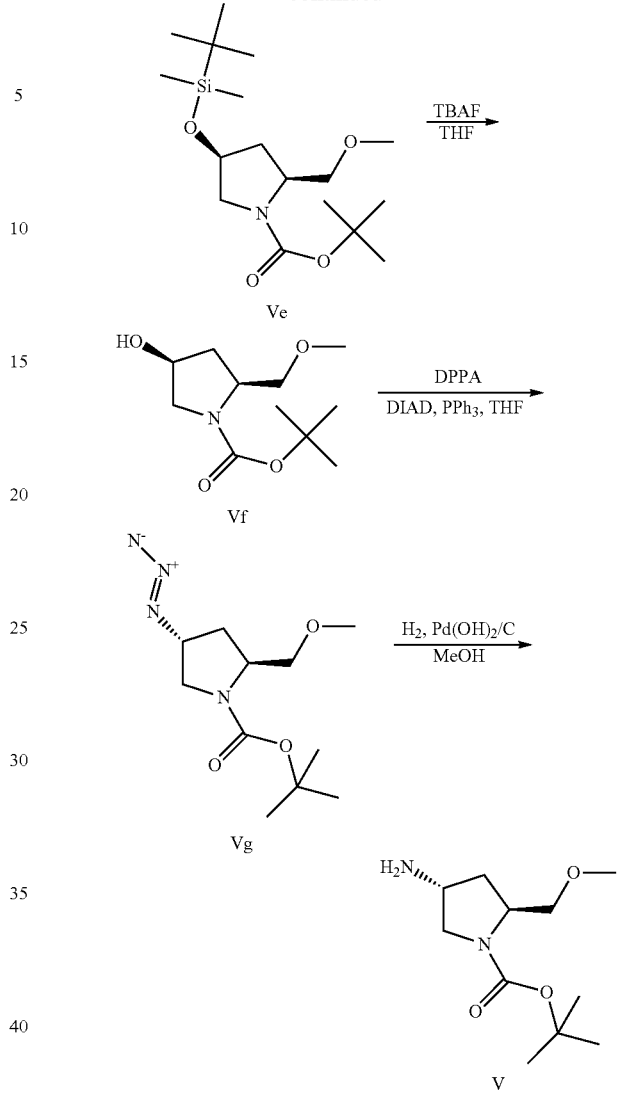

Preparation of compound Va: tert-Butyl (1S,4S)-3-oxo-2-oxa-5-azabicyclo[2.2.1]heptane-5-carboxylate To a solution of (4R)-1-(tert-butoxycarbonyl)-4-hydroxy-L-proline (100 g, 0.443 mol) and PPh$_3$ (227 g, 0.866 mol) in dry THF (1 L) was added dropwise DEAD (151 g, 0.866 mol) at 0° C. under nitrogen. After the addition, the reaction was allowed to warm up to room temperature and stirred overnight. The reaction was concentrated in vacuo and the residue was purified by column chromatography (petroleum ether: ethyl acetate=20:1~5:1) which gave the title compound Va as a yellow solid (106.5 g).

Preparation of compound Vb: 1-tert-Butyl 2-methyl (2S,4S)-4-hydroxypyrrolidine-1,2-dicarboxylate To a solution of Va (135 g, 0.634 mol) in dry MeOH (1000 mL) was added NaN$_3$ (41.5 g, 0.634 mol) at room temperature. The reaction mixture was heated to 40° C. and stirred for 18 h. The reaction was concentrated in vacuo to remove most of the solvent below 30° C. The residue was poured into 500 mL of water and extracted with CH$_2$Cl$_2$ (200 mL×4). The combined organics were washed with brine (100 mL), dried over sodium sulfate, filtered and concentrated in vacuo which gave the title compound Vb as a white solid (140.5 g, 90.5%).

Preparation of compound Vc: 1-tert-Butyl 2-methyl (2S,4S)-4-{[tert-butyl(dimethyl)silyl]oxy}pyrrolidine-1,2-dicarboxylate To a solution of Vb (90 g, 0.36 mol) and imidazole (50 g, 0.734 mol) in dry DMF (1 L) was added TBSCI (82.7 g, 0.551 mol) in portions at 0° C. After the addition, the reaction was allowed to warm up to room temperature and stirred overnight. The reaction was poured into 1 L of water and extracted with ethyl acetate (300 mL×5). The combined organics was washed with brine (200 mL), dried over sodium sulfate, filtered and concentrated in vacuo which gave the title compound Vc as colorless oil which was used in next step without further purification (125.5 g).

Preparation of compound Vd: tert-Butyl (2S,4S)-4-{[tert-butyl(dimethyl)silyl]oxy}-2-(hydroxymethyl)pyrrolidine-1-carboxylate To a suspension of LiAlH4 (38 g, 1.0 mol) in dry THF (1 L) was added dropwise a solution of Vc (180 g, 0.5 mol) in dry THF (1 L) at −20° C. under nitrogen. After the addition, the reaction was kept at −20° C. and stirred for 3 h. The reaction was quenched by added dropwise 10% of NaOH aqueous. The precipitate solid was filtered off and the filtrate was concentrated in vacuo which gave the title compound Vd as light yellow oil (86.5 g, 52.2%).

Preparation of compound Ve: tert-Butyl (2S,4S)-4-{[tert-butyl(dimethyl)silyl]oxy}-2-(methoxymethyl)pyrrolidine-1-carboxylate To a solution of Vd (35 g, 0.106 mol) in dry THF (500 mL) was added NaH (6.4 g, 0.159 mol) in portions at 0° C. under nitrogen. The mixture was stirred at this temperature for 1 h. MeI was added dropwise to this mixture at 0° C. The reaction mixture was allowed to warm up to room temperature and stirred overnight. The reaction was poured into ice/water with stirring and extracted with ethyl acetate (200 mL×4). The combined organics was washed with brine (150 mL), dried over sodium sulfate, filtered and concentrated in vacuo. The residue was purified by column chromatography (petroleum ether:ethyl acetate=50:1~10:1) which gave the title compound Ve as light yellow oil (20 g, 54.8%).

Preparation of compound Vf: tert-Butyl (2S,4S)-4-hydroxy-2-(methoxymethyl)pyrrolidine-1-carboxylate A solution of Ve (31 g, 89.72 mmol) and TBAF (47 g, 0.179 mol) in THF (400 mL) was heated to reflux for 24 h. The reaction was concentrated in vacuo and the residue was purified by flash column chromatography (petroleum ether:ethyl acetate=30:1~10:1) which gave the title compound Vf (20.2 g, 97.35%) as light yellow oil.

Preparation of compound Vg: tert-Butyl (2S,4R)-4-azido-2-(methoxymethyl)pyrrolidine-1-carboxylate To a solution of Vf (20 g, 86.47 mmol) and PPh$_3$ (27.2 g, 0.104 mol) in dry THF (200 mL) was added dropwise DIAD (21 g, 0.104 mol) at 0° C. under nitrogen. Then DPPA (28.6 g, 0.104 mol) was added dropwise. After the addition, the reaction was allowed to warm up to room temperature and stirred overnight. TLC (petroleum ether:ethyl acetate=4:1) showed the reaction was complete. The reaction was concentrated in vacuo below 30° C. The residue was purified by column chromatography (petroleum ether:ethyl acetate=100:1~20:1) which gave the title compound Vg (15.1 g, 67.7%) as light yellow oil.

A mixture of Vg (15 g, 58.6 mmol) and Pd(OH)$_2$/C (2.0 g) in MeOH (200 mL) was hydrogenated under H$_2$ (25 psi, room temperature) for 48 h. The mixture was filtered through a Celite pad. The filtrate was concentrated in vacuo and the residue was purified by column chromatography (CH$_2$Cl$_2$:MeOH=100:1~15:1) which gave the title compound V (9.8 g, 72.8%) as brown oil.

Example VI tert-Butyl (2S,4R)-4-amino-2-(ethoxymethyl)pyrrolidine-1-carboxylate

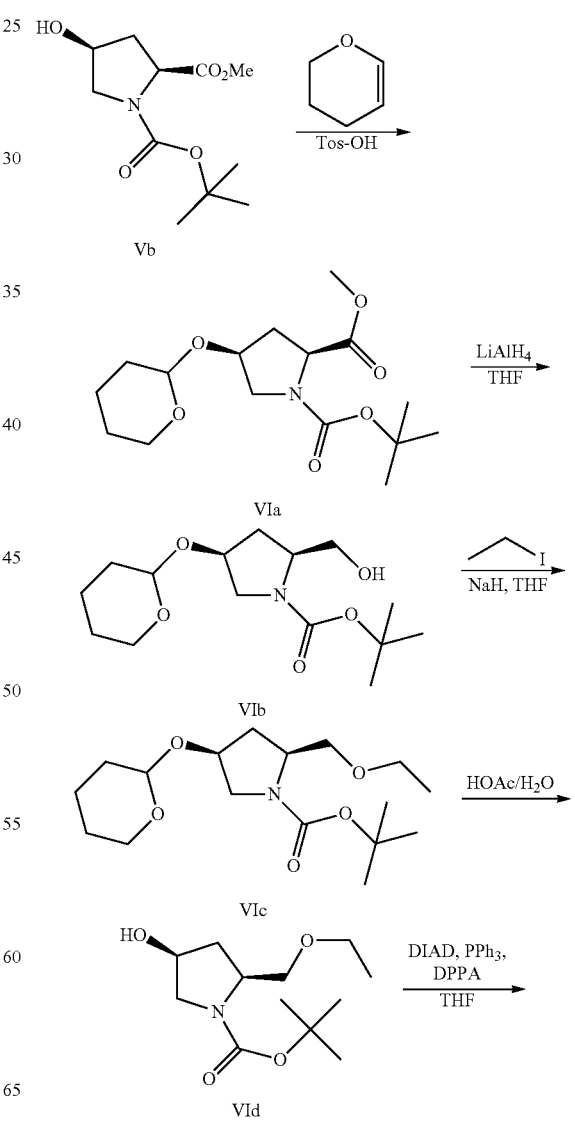

-continued

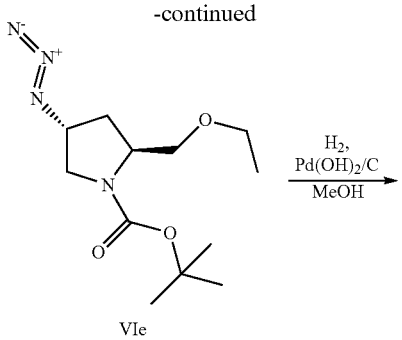

VIe

VI

Preparation of compound VIa: 1-tert-Butyl 2-methyl (2S,4S)-4-(tetrahydro-2H-pyran-2-yloxy)pyrrolidine-1,2-dicarboxylate A solution of Vb (170 g, 0.694 mol), 3,4-dihydro-2H-pyran (174.9 g, 2.082 mol) and Tos-OH (4.0 g) in dry ether (2 L) was stirred at room temperature for 3 h. The reaction was concentrated in vacuo which gave the title compound VIa (239.5 g) as yellow oil which was used in next step without further purification.

Preparation of compound VIb: tert-Butyl (2S,4S)-2-(hydroxymethyl)-4-(tetrahydro-2H-pyran-2-yloxy)pyrrolidine-1-carboxylate To a suspension of LiAlH$_4$ (34.9 g, 0.917 mol) in dry THF (1000 mL) was added dropwise a solution of VIa (150 g, 0.459 mol) in dry THF (1000 mL) at −20° C. under nitrogen. After the addition, the reaction was kept at −20° C. and stirred for 3 h. The reaction was quenched by added dropwise 10% of NaOH aqueous. The precipitate solid was filtered off and the filtrate was concentrated in vacuo. The residue was purified by flash column chromatography (petroleum ether:ethyl acetate=50:1~5:1) which gave the title compound VIb (105 g, 76.5%) as light yellow oil.

Preparation of compound VIc: tert-Butyl (2S,4S)-2-(ethoxymethyl)-4-(tetrahydro-2H-pyran-2-yloxy)pyrrolidine-1-carboxylate To a solution of VIb (50 g, 0.166 mol) in dry THF (600 mL) was added NaH (13.3 g, 0.332 mol) in portions at 0° C. under nitrogen. The mixture was stirred at this temperature for 1 h. Iodo-ethane (77.2 g, 0.498 mol) was added dropwise to this mixture at 0° C. The reaction mixture was allowed to warm up to room temperature and stirred overnight. The reaction was poured into ice/water with stirring and extracted with ethyl acetate (200 mL×5). The combined organics was washed with brine (100 mL), dried over sodium sulfate, filtered and concentrated in vacuo which gave the title compound VIc (51.5 g) as brown oil, which was used in next step without further purification.

Preparation of compound VId: tert-Butyl (2S,4S)-2-(ethoxymethyl)-4-hydroxypyrrolidine-1-carboxylate A solution of VId (51.0 g, 0.155 mol) in HOAc/H$_2$O (1:1, 500 mL) was heated to 40° C. and stirred overnight. The reaction was basified with solid NaHCO$_3$ to pH ~8 and extracted with ethyl acetate (200 mL×5). The combined organics was washed with brine (100 mL) and dried over sodium sulfate, filtered and concentrated in vacuo. The residue was purified by column chromatography (petroleum ether:ethyl acetate=30:1~10:1) which gave the title compound VId (20.6 g, 54.2%) as brown oil.

Preparation of compound VIe: tert-Butyl (2S,4R)-4-azido-2-(ethoxymethyl)pyrrolidine-1-carboxylate To a solution of VId (22 g, 89.8 mmol) and PPh$_3$ (28.2 g, 108 mmol) in dry THF (400 mL) was added dropwise DIAD (21.8 g, 108 mmol) at 0° C. under nitrogen. Then DPPA (29.6 g, 108 mmol) was added dropwise. After the addition, the reaction was allowed to warm up to room temperature and stirred overnight. The reaction was concentrated in vacuo below 30° C. The residue was purified by column chromatography (petroleum ether:ethyl acetate=100:1~10:1) which gave the title compound VIe (15.4 g, 63.6%) as colorless oil.

A mixture of VIe (15 g, 55.6 mmol) and Pd(OH)$_2$/C (2.0 g) in MeOH (200 mL) was hydrogenated under H$_2$ (25 psi, room temperature) for 5 h. The mixture was filtered through a celite pad. The filtrate was concentrated in vacuo and the residue was purified by column chromatography (CH$_2$Cl$_2$:MeOH=100:1~20:1) which gave the title compound VI (11.05 g, 81.5%) as brown oil.

Example VII (3R,4R)-3-Amino-4-methyl-piperidine-1-carboxylic acid tert-butyl ester

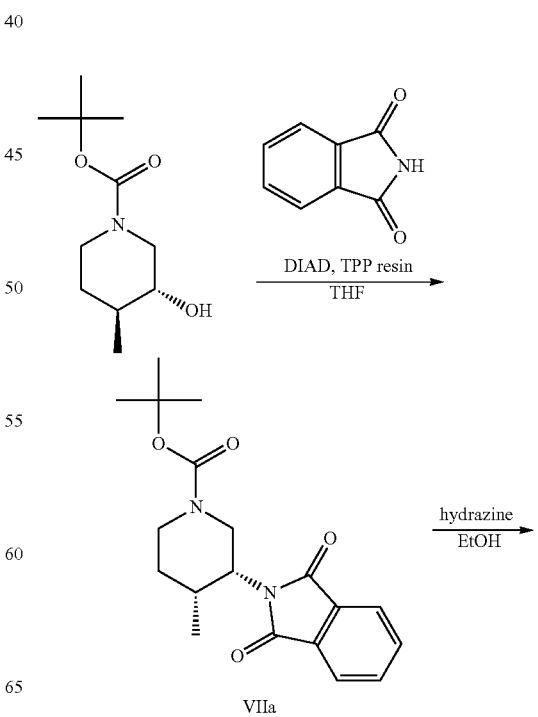

VIIa

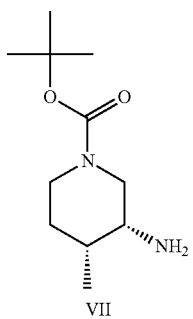

VII

Preparation of compound VIIa: (3R,4R)-3-(1,3-Di-oxo-1,3-dihydro-isoindol-2-yl)-4-methyl-piperidine-1-carboxylic acid tert-butyl ester To a solution of trans-3-Hydroxy-4-methyl-piperidine-1-carboxylic acid tert-butyl ester (1.78 g, 8.28 mmol) (WO 01/87838), phthalimide (1.46 g, 9.94 mmol) and TPP-resin (4.14 g) in anhydrous THF (30 ml) at 23° C. was added DIAD (2.4 ml, 12.4 mmol). The reaction mixture was stirred at 23° C. for 48 h. then the resin was filtered off and the filtrate was concentrated under reduced pressure to give an oil. The crude oil was purified by flash chromatography using silica gel (0-50% EtOAc-Heptane) which gave the title compound VIIa (1.6 g, 47% yield).

A solution of the VIIa (1.6 g) in EtOH (15 ml) was treated with hydrazine hydrate (2.3 ml, 46 mmol) and the resulting mixture was heated to 80° C. for 12 h. The reaction mixture was then concentrated under reduced pressure to an oil and purified by flash chromatography using silica gel, eluting with 30-100% EtOAc in heptane which gave the title compound VII as a colorless oil. 1H NMR (400 MHz, CDCl3 0.95 (d, J=6.82 Hz, 3H) 1.16-1.34 (m, 2H) 1.45 (s, 9H) 1.71 (d, J=3.54 Hz, 1H) 2.84 (br. s., 2H) 2.99 (d, J=12.88 Hz, 1H) 3.76-3.86 (m, 1H) 3.85-4.01 (m, 1H). LCMS: M+1=215.

Example VIII (3R,5R)-3-Amino-5-hydroxy-piperidine-1-carboxylic acid benzyl ester

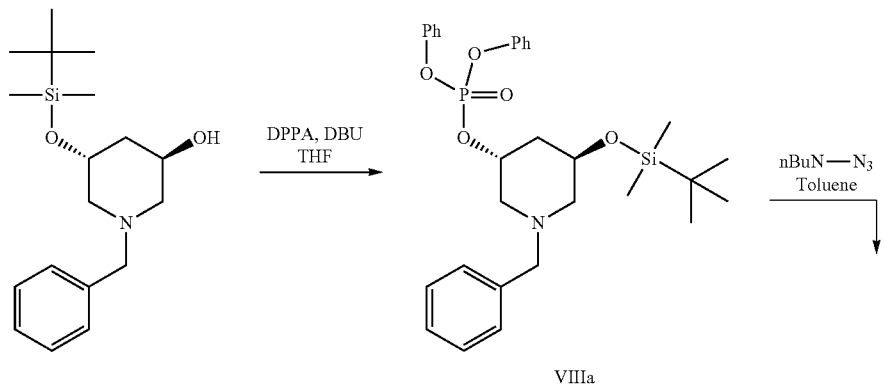

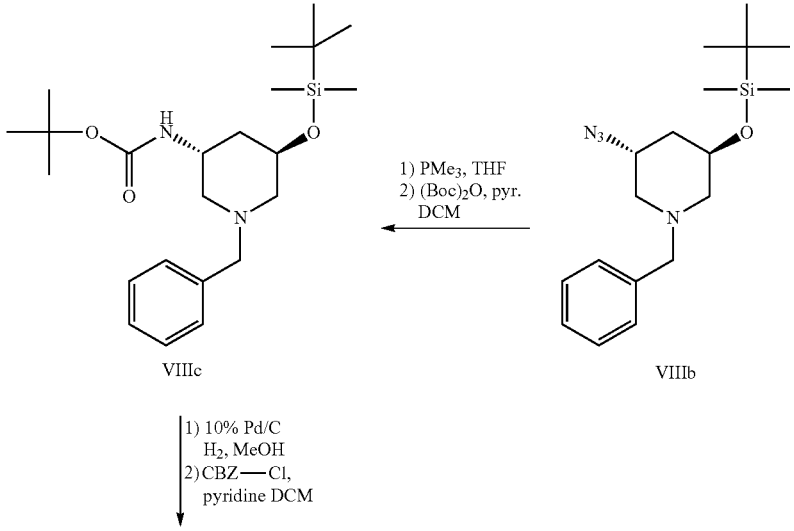

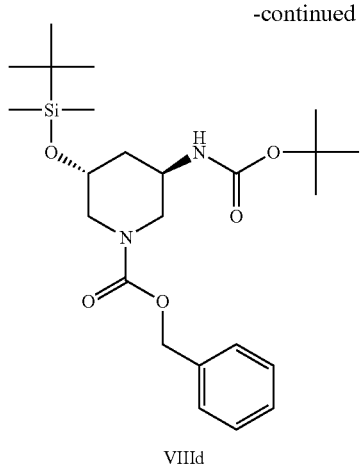

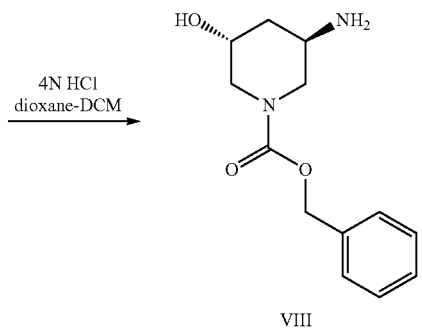

VIIId → VIII

4N HCl
dioxane-DCM

Preparation of compound VIIIa: Phosphoric acid (3R,5R)-1-benzyl-5-(tert-butyl-dimethyl-silanyloxy)-piperidin-3-yl ester diphenyl ester To a solution of (3R,5R)-1-Benzyl-5-(tert-butyl-dimethyl-silanyloxy)-piperidin-3-ol (322 mg, 1 mmol) in THF (3.3 ml) cooled to 0 C was added DBU (164 ul, 1.1 mmol) followed by diphenyl phosphoryl azide (237 ul, 1.1 mmol). The reaction was allowed to stir at 23 C for 18 hours. The reaction mixture was quenched with saturated sodium bicarbonate (1 ml) then extracted with EtOAc (10 ml). The EtOAc phase was washed with brine then dried with Na2SO4 and concentrated under reduced pressure. The crude product was purified by flash chromatography on silica gel (0-60% EtOAc-heptane) which gave the title compound VIIIa as a clear oil (2.8 g, 81%). 1H NMR (400 MHz, CHLOROFORM-d)-0.01 (d, J=4.29 Hz, 6H) 0.85 (s, 9H) 1.54-1.74 (m, 1H) 1.96-2.18 (m, 2H) 2.41 (d, J=12.13 Hz, 1H) 2.64-2.91 (m, 2H) 3.40-3.74 (m, 2H) 4.07 (ddd, J=8.21, 4.29, 4.17 Hz, 1H) 4.95 (d, J=2.78 Hz, 1H) 7.12-7.46 (m, 15H). LCMS: M+1=554

Preparation of compound VIIIb: (3R,5R)-3-Azido-1-benzyl-5-(tert-butyl-dimethyl-silanyloxy)-piperidine A solution of VIIIa (1.1 g, 2.0 mmol) in toluene (6.7 ml) was treated with tetrabutylammonium azide (1.14 g, 4 mmol) at 100 C for 18 hours. The crude reaction mixture was concentrated under reduced pressure to an oil and purified by flash chromatography on silica gel (0-40% EtOAc-heptane) which gave the title compound VIIIb as a clear oil (466 mg, 67% yield). 1H NMR (400 MHz, CHLOROFORM-d) 0.05 (d, J=8.59 Hz, 6H) 0.89 (s, 9H) 1.53-1.71 (m, 1H) 1.88 (d, J=11.12 Hz, 1H) 2.11-2.25 (m, 1H) 2.43 (d, J=11.12 Hz, 1H) 2.54-2.77 (m, 2H) 3.46-3.71 (m, 2H) 3.82 (br. s., 1H) 4.05 (dt, J=7.77, 3.82 Hz, 1H) 7.33 (d, J=4.04 Hz, 5H). LCMS: M+H=347.

Preparation of compound VIIIc: [(3R,5R)-1-Benzyl-5-(tert-butyl-dimethyl-silanyloxy)-piperidin-3-yl]-carbamic acid tert-butyl ester A solution of VIIIb (430 mg, 1.24 mmol) in THF (6.2 ml) was treated with H2O (3 drops) and a 1M solution of trimethyl phosphine in toluene (3.72 ml, 3.72 mmol). The reaction mixture was stirred at 23 C for 18 hours then concentrated to an oil under reduced pressure. The crude oil was dissolved in DCM (5 ml), cooled to 0 C, then treated with pyridine (125 ul) and Boc2O (297 mg) for 5 hours. The reaction mixture was diluted with water (5 ml) and DCM (5 ml). The DCM layer was washed with brine then dried with Na2SO4 and concentrated under reduced pressure to an oil. The crude oil was purified by flash chromatography on silica gel (0-60% EtOAc-heptane) to give the title compound VIIIc as a clear oil (394 mg, 75% yield). LCMS: M+H=421.

Preparation of compound VIIId: (3R,5R)-3-tert-Butoxycarbonylamino-5-(tert-butyl-dimethyl-silanyloxy)-piperidine-1-carboxylic acid benzyl ester A mixture of VIIIc (394 mg, 0.937 mol) and 10% Pd/C (40 mg) in EtOH (10 ml) was hydrogenated at 1 atm. and 23 C using a balloon. After 18 hours the reaction mixture was filtered through celite then concentrated under reduced pressure to an oil. The crude oil was dissolved in DCM (5 ml), then cooled to 0 C. Pyridine (103 ul) was added, followed by CBZ—Cl (144 ul). After 5 hours the reaction mixture was quenched with saturated NaHCO3 then partitioned between dichloromethane and water. The organic phase was washed with brine, dried with Na2SO4 then concentrated under reduced pressure to an oil. The crude oil was purified by flash chromatography using silica gel (0-50% EtOAc-Heptane) to give the title compound VIIId as a colorless oil. (304 mg, 70% yield). LCMS: M+1−Boc=365.

A solution of VIIId (101 mg, 0.217 mmol) in DCM (1 ml) was treated with 4N HCl in dioxane (0.5 ml, 2 mmol). The resulting mixture was stirred at 23 C for 6 hours then concentrated under reduced pressure to an oil. The crude oil was partitioned between ethyl acetate (10 ml) and water (3 ml). The aqueous phase was neutralized with saturated sodium bicarbonate (1 ml). The phases were separated and the organic was washed with brine (3 ml) then dried with Na2SO4 and concentrated under reduced pressure to give the title compound VIII as a colorless oil. (56 mg, 92% yield). LCMS: M+H=251

Example IX (3R,4R)-3-Amino-4-fluoromethyl-pyrrolidine-1-carboxylic acid benzyl ester

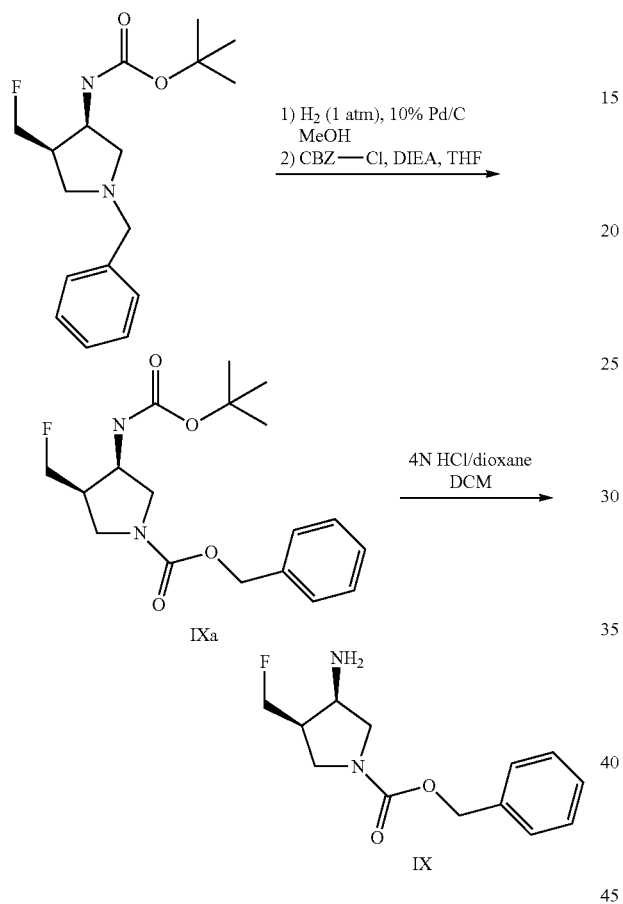

Preparation of compound IXa: (3R,4R)-3-tert-Butoxycarbonylamino-4-fluoromethyl-pyrrolidine-1-carboxylic acid benzyl ester A solution of ((3R,4R)-1-Benzyl-4-fluoromethyl-pyrrolidin-3-yl)-carbamic acid tert-butyl ester (1 g, 3.24 mmol) in methanol (20 mL) was hydrogenated at 1 atm with 10% palladium on carbon (100 mg) for 24 hours. He crude reaction mixture was filter through celite then concentrate to an oil. The crude amine was dissolved in dichloromethane (8 ml) then cooled to 0 C and diisopropylethylamine (619 ul, 3.57 mmol) was added followed by benzyl chloroformate (507 ul, 3.57 mmol, 1.1 equiv.). The crude reaction was concentrated to an oil then purified by silica gel chromatography eluting with 0-20% EtOAc in Heptane which gave the title compound IXa of as a colorless oil (811 mg). 1H NMR (400 MHz, CHLOROFORM-d) 1.45 (s, 9H) 2.67 (br. s., 1H) 3.24-3.49 (m, 2H) 3.63-3.80 (m, 2H) 4.27-4.53 (m, 2H) 4.53-4.66 (m, 1H) 4.70 (dd, J=9.73, 4.93 Hz, 1H) 5.14 (br. s., 2H) 7.37 (br. s., 5H); LCMS: M+1−Boc=253.

To a solution of IXa (811 mg, 2.30 mmol) in dichloromethane (7.6 ml) at 23 C was added 4N HCl in dioxane (2.88 ml, 11.5 mmol). The resulting mixture was stirred for 3 hours. The crude reaction mixture was concentrated to an oil then partitioned between saturated sodium bicarbonate and ethyl acetate. The ethyl acetate layer was washed with brine, dried with sodium sulfate and concentrated to give the title compound IX as a clear oil (526 mg). 1H NMR (400 MHz, CHLOROFORM-d) 2.46-2.65 (m, 1H) 3.22-3.41 (m, 2H) 3.55-3.66 (m, 2H) 3.66-3.73 (m, 1H) 4.45-4.76 (m, 2H) 5.05-5.22 (m, 2H) 7.37 (d, J=4.55 Hz, 5H); LCMS: M+1=253.

Example X tert-butyl (2R,4R)-4-amino-2-methylpyrrolidine-1-carboxylate

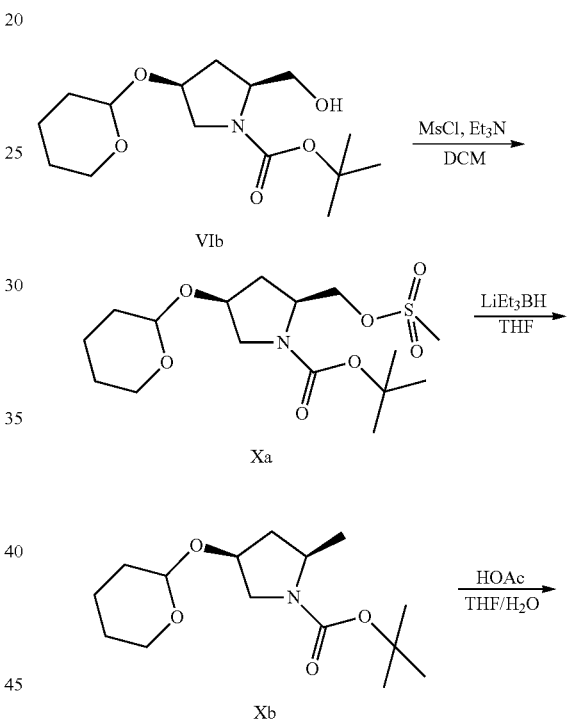

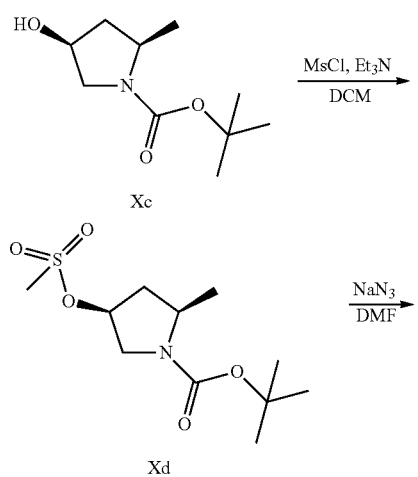

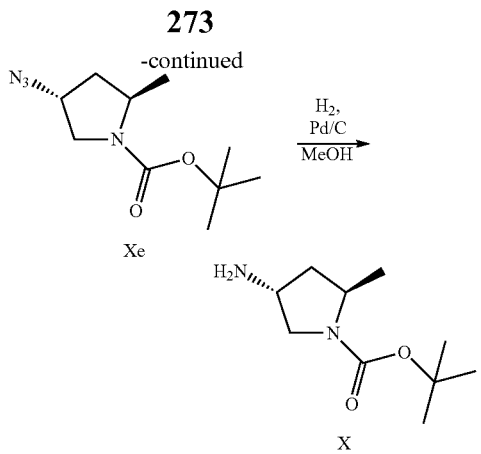

Preparation of compound Xa: tert-butyl (2S,4S)-2-{[(methylsulfonyl)oxy]methyl}-4-(tetrahydro-2H-pyran-2-yloxy)pyrrolidine-1-carboxylate To a solution of VIb (70.0 g, 0.232 mol) and Et3N (47.0 g, 0.465 mol) in dry DCM (170 mL) was added dropwise MsCl (40.0 g, 0.349 mol) at 0° C. under N2 gas. After the addition, the reaction mixture was stirred at room temperature for 1 hour. The reaction mixture was diluted with EtOAc (500 mL) and then washed with 5% aqueous citric acid (300 mL×3), 5% aqueous Na2CO3 (300 mL×3) and brine (300 mL×3) in sequence. The organic layer was dried over Na2SO4 and concentrated in vacuum which gave the title compound Xa (90.0 g, 80%) as a yellow oil.

Preparation of compound Xb: tert-butyl (2R,4S)-2-methyl-4-(tetrahydro-2H-pyran-2-yloxy)pyrrolidine-1-carboxylate A solution of Xa (32.0 g, 0.084 mol) in THF (60 mL) was added dropwise LiEt3BH/THF (1.0 M, 370 mL) at 0° C. over 1 hour. After addition, the reaction was stirred at room temperature for 4 hours. The reaction mixture was quenched with ice-water, then extracted with EtOAc (300 mL×3). The combined organic layers were washed with 5% citric acid aqueous solution (500 mL×3), saturated aqueous Na2CO3 (500 mL×3) and brine (500 mL×3) in sequences, dried over Na2SO4 and concentrated in vacuum to give a residue, which was purified by column chromatography (silica gel, petroleum ether/EtOAc 10:1) which gave the title compound Xb (15.0 g, 66%) as colorless oil.

Preparation of compound Xc: tert-butyl (2R,4S)-4-hydroxy-2-methylpyrrolidine-1-carboxylate A solution of Xb (15.0 g, 0.053 mol) in HOAc/THF/H2O (1:1:1, 300 mL) was refluxed for 2 hours. The reaction mixture was neutralized with solid NaHCO3 to pH ~7 and then extracted with EtOAc (100 mL×3). The combined organic layers were washed with brine (100 mL×3), dried over Na2SO4 and concentrated in vacuum to yield residue, which was purified by column chromatography (silica gel, petroleum ether/EtOAc 10:1) which gave the title compound Xc (8.2 g, 77%) as a white solid.

Preparation of compound Xd: tert-butyl (2R,4S)-2-methyl-4-[(methylsulfonyl)oxy]pyrrolidine-1-carboxylate To a solution of Xc (9.5 g, 0.047 mol) and Et3N (9.5 g, 0.095 mol) in dry DCM (60 mL) was added dropwise MsCl (8.1 g, 0.071 mol) at 0 C under N2 gas. After the addition, the reaction mixture was stirred at room temperature overnight. The reaction mixture was diluted with EtOAc (500 mL) and then filtered. The filtrate was washed with 5% aqueous citric acid (200 mL×3), 5% aqueous Na2CO3 (200 mL×3) and brine (200 mL×3) in sequence, then dried over Na2SO4 and concentrated in vacuum which gave the title compound Xd (12.6 g, 94%) as an orange oil.

Preparation of compound Xe: tert-butyl (2R,4R)-4-azido-2-methylpyrrolidine-1-carboxylate A solution of Xd (13.2 g, 0.047 mol) and NaN3 (6.1 g, 0.095 mol) in DMF (200 mL) was stirred at 80° C. under N2 gas for two hours. The reaction mixture was poured into 5% aqueous NaHCO3 (400 mL). The mixture was extracted with ether (200 mL×3). The combined organic layers were washed with brine (150 mL×3), dried over Na2SO4 and concentrated in vacuum. Et2O was displaced with methanol (150 mL×3) which gave a solution of the title compound Xe in methanol (~100 mL), which was used for next step without further purification.

A mixture of Xe and 10% Pd/C (1.5 g) in methanol (100 mL) was hydrogenated under H2 (50 psi) at room temperature for two hours. The reaction mixture was filtered and the filtrate was concentrated in vacuum which gave the title compound X (7.8 g, 90%) as yellow oil. 1H NMR (400 MHz, CDCl3): 3.99-3.81 (m, 1H), 3.53-3.47 (m, 2H), 3.09-2.90 (m, 1H), 1.79-1.68 (m, 2H), 1.39 (s, 9H), 1.18-1.09 (d, 2H); LCMS: M+H=201.

Example XI (3R,4R)-3-Amino-4-hydroxymethyl-pyrrolidine-1-carboxylic acid tert-butyl ester

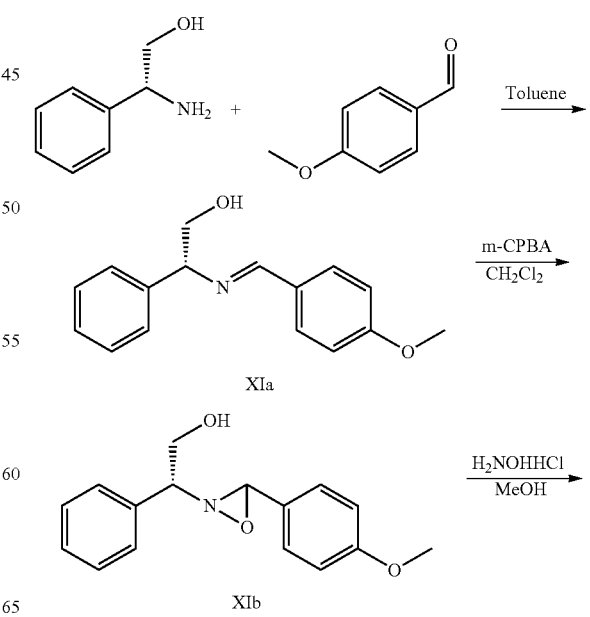

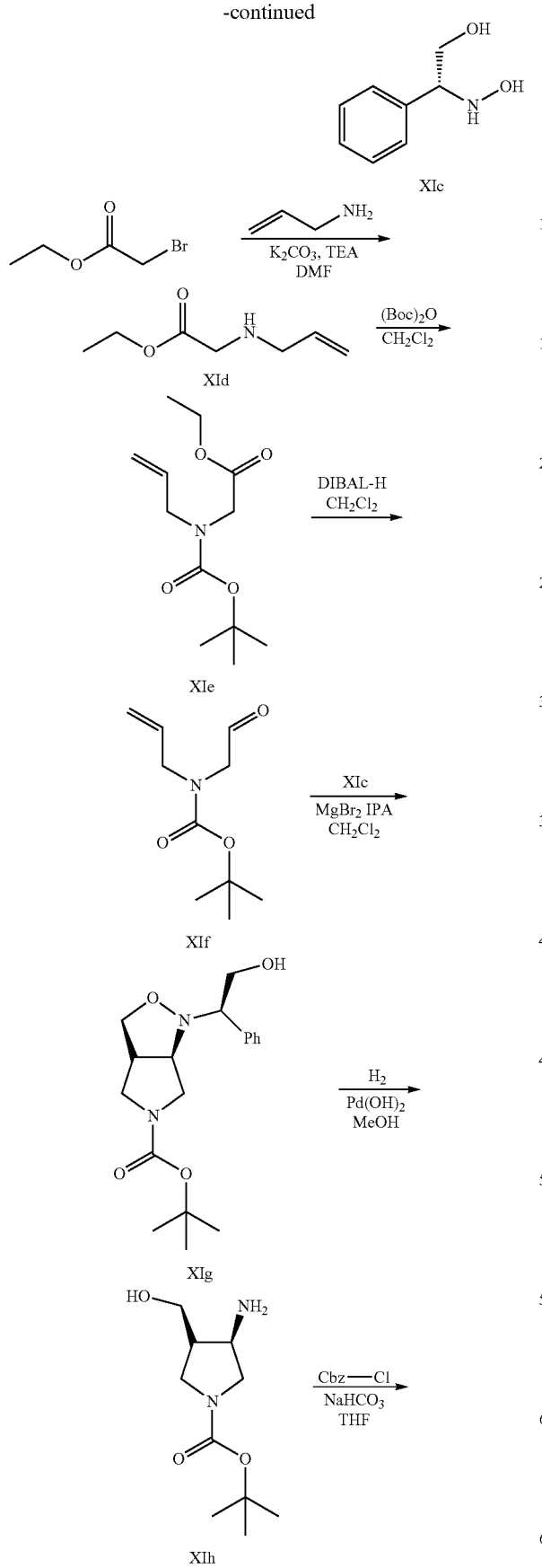
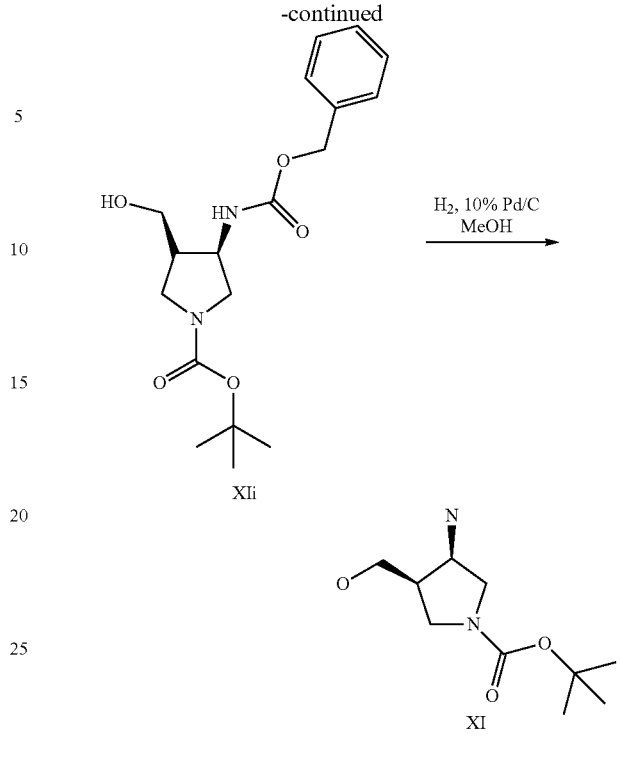

Preparation of compound XIa: (2R)-2-{[(E)-(4-methoxyphenyl)methylidene]amino}-2-phenylethanol A solution of (2R)-2-amino-2-phenylethanol (148 g, 1.08 mol) and 4-methoxybenzaldehyde (147 g, 1.08 mol) in toluene (2 L) was heated at reflux to remove water by Dean-Stark trap for 3 hr. The mixture was concentrated and the residue was dried which gave the title compound XIa (265 g, 96%) as a white solid, which was used for next reaction without further purification.

Preparation of compound XIb: (2R)-2-[3-(4-methoxyphenyl)oxaziridin-2-yl]-2-phenylethanol A solution of XIa (265 g, 1.03 mol) in CH2Cl2 (2 L) was cooled to 0° C. and stirred using a machine stirrer. To the cold mixture was added m-CPBA (267 g, 1.55 mol) in portions over about 0.5 hr. After the addition, the resulting mixture was stirred at 0° C. for an additional 0.5 hr. The solids were then removed by vacuum filtration and the solids were rinsed with $CH_2Cl_2$. The filtrate was washed with 10% aq. K2CO3, dried over MgSO4, filtered and concentrated which gave the title compound XIb (279.4 g, 100%) as a yellow oil, which was used for next reaction without further purification.

Preparation of compound XIc: (2R)-2-(hydroxyamino)-2-phenylethanol

XIb (279.4 g, 1.03 mol) was dissolved in MeOH (2 L), and hydroxylamine hydrochloride (143.2 g, 2.06 mol) was added in one portion. After the addition, the mixture was stirred at room temperature overnight. Conc. HCl (175 mL) was added dropwise to the reaction mixture and concentrated. The residue was diluted with water (210 mL) and extracted with EtOAc (6×2 L) until no more organic material could be extracted. The aqueous layer was based to pH=9 by careful addition of solid Na2CO3. The aqueous solution was extracted with CHCl2 (3×1 L), the combined organic extracts were dried over MgSO4, filtered and concentrated. The residue was re-crystallized from EtOAc/Hexane (1:1, 200 mL) which gave the title compound XIc (37 g, 23.4%) as a pale white solid.

Preparation of compound XId: ethyl N-prop-2-en-1-ylglycinate

To an ice cold solution of K2CO3 (331.7 g, 2.4 mol), NaI (360 g, 2.4 mol), DMF (1 L), triethylamine (484.8 g, 4.8 mol) and prop-2-en-1-amine (82 g, 1.44 mol) was slowly added a solution of ethyl bromoacetate (200 g, 1.2 mol) in DMF (100 mL) via addition funnel over 0.5 hr. The ice bath was removed upon completion of addition, and the mixture was stirred at room temperature overnight. The mixture was filtered and rinsed with Et2O. Cold saturated NaCl aq. (2 L) was added to filtrate and the mixture was extracted with Et2O (1 L*3). The combined organic extracts were dried over Na2SO4, filtered and concentrated which gave the title compound XId (150 g, 87.3%) as a yellow oil, which was directly utilized for next reaction without further purification.

Preparation of compound XIe: ethyl N-(tert-butoxycarbonyl)-N-prop-2-en-1-ylglycinate To a solution of XId (150 g, 1.05 mol) in MeOH (2 L) was added triethylamine (106 g, 1.05 moL), the solution was cooled to 0° C. and Boc2O (229 g, 1.05 mol) was added dropwise over about 0.5 h. After the addition, the mixture was stirred at room temperature overnight. The mixture was concentrated and the residue was diluted with EtOAc (1 L). The mixture was washed sequentially with water and sat. aq. NaCl, dried over Na2SO4 and concentrated. The residue was purified by distillation under reduced pressure (b.p. ~100° C./0.5 mm Hg) which gave the title compound XIe (180 g, 70%) as a clear colorless oil.

Preparation of compound XIf: tert-butyl (2-oxoethyl)prop-2-en-1-ylcarbamate

To a solution of XIe (87 g, 0.358 mol) in CH2Cl2 (1 L) was added dropwise a solution of DIBAL-H (715 mL of 1.0 M in CH2Cl2, 0.715 mol) over 1 hr at −78° C. After the addition, the mixture was further stirred at −78° C. for 2 hours and quenched by addition of sat. aq. NH$_4$Cl (100 mL) and 2 N HCl (350 mL). The mixture was extracted with CH$_2$Cl$_2$ (1 L×2). The combined organic extracts were washed with sat. aq. NaCl, dried over Na2SO4, filtered and concentrated. The residue was purified by distillation under reduced pressure (b.p. ~90° C./0.5 mm Hg) which gave the title compound XIf (45 g, 63.1%) as a light yellow oil.

Preparation of compound XIg: tert-butyl (3aR,6aR)-1-[(1R)-2-hydroxy-1-phenylethyl]tetrahydro-1H-pyrrolo[3,4-c]isoxazole-5(3H)-carboxylate To a solution of XIc (26 g, 0.17 mol) in CH$_2$Cl$_2$ (560 mL) was added MgBr2 (45 g, 0.17 mol). The resulting mixture was stirred at room temperature for 30 min and isopropanol (10.2 g, 0.17 mol) was added. The mixture was stirred at room temperature for 10 min, a solution of XIf (34.7 g, 0.17 mol) in CH$_2$Cl$_2$ (140 mL) was added dropwise. The resulting mixture was heated at 35° C. overnight. The reaction was poured into a solution of ice/sat. aq. NaHCO3 (1 L) and subsequently diluted with CH$_2$Cl$_2$ (1 L). The phases were separated, and the organic extract was washed with sat. aq. NaCl, dried over Na2SO4, filtered and concentrated. The crude product was purified by column chromatography (petroleum ether: EtOAc=2:1) which gave the title compound XIg (30 g, 52.9%) as a light yellow oil.

Preparation of compound XIh: tert-butyl (3R,4R)-3-amino-4-(hydroxymethyl)pyrrolidine-1-carboxylate A Parr reaction vessel was charged with XIg (30 g, 90 mmol), acetic acid (30 mL), MeOH (360 mL), water (150 mL) and 20% Pd(OH)$_2$/C (8.4 g, 12.5 mol %). The reaction vessel was purged with N2, then hydrogenated under H2 (50 Psi) for 48 h. The mixture was filtered through Celite and the filter cake was rinsed with MeOH. The filtrate was concentrated and the residue was dried in vacuo which gave the title compound XIh (19 g, 100%) as an oil, which was used for next reaction without further purification.

Preparation of compound XIi: (3R,4R)-3-Benzyloxycarbonylamino-4-hydroxymethyl-pyrrolidine-1-carboxylic acid tert-butyl ester XIh (19 g, 0.09 mol) was dissolved in THF—H2O (V/V 2:1, 750 mL). The mixture was cooled to 0° C. and solid NaHCO3 (30.2 g, 0.36 mol) was added, followed by benzyl chloroformate (18.4 g, 0.108 mol). The resulting mixture was stirred at room temperature for 2 hours, then poured into 1 N HCl/ice (1 L). The mixture was extracted with EtOAc (3×1 L). The combined organic extracts were washed with water, sat. aq. NaCl, dried over Na2SO4, filtered and concentrated. The residue was purified by column chromatography (petroleum ether:EtOAc=2:1) which gave the title compound XIi (12 g, 38%) as a white solid.

A mixture of XIi (701 mg, 2 mmol) and 10% palladium on carbon (70 mg) in methanol (5 ml) was hydrogenated at 1 atm and 23 C. TLC (1:1) EtOAc-Heptanes indicated that the reaction was complete. The crude reaction mixture was filtered through celite then concentrated to give the title compound XI (220 mg) as a white solid.

Biological Testing, Ki Data and Cellular Assay Data $K_i$ Determination $K_i$ determination, spectrophotometric based assay: CHK1 inhibitors were serially diluted in DMSO and an aliquot of these dilutions was added to a solution containing 1 nM of CHK1 (kinase domain) in a 50 mM Tris.HCl buffer, pH 7.5 containing 25 mM MgCl$_2$, 400 mM NaCl, 80 ug/mL pyruvate kinase, 40 ug/mL lactate dehydrogenase, 4 mM phosphoenolpyruvate, 200 uM NADH and 2.5% DMSO (upon inhibitor addition). After 15 min pre-incubation, the enzymatic reaction was initiated by the simultaneous addition of Syntide 2 peptide (125 uM, final concentration) and ATP (150 uM, final concentration). The kinase-catalyzed production of ADP from ATP that accompanied phosphoryl transfer to the substrate Syntide 2 was coupled to the oxidation of NADH through the activities of pyruvate kinase and lactate dehydrogenase. NADH conversion to NAD$^+$ was monitored by the decrease in absorbance at 340 nm ($\epsilon$=6.22 cm$^{-1}$ mM$^{-1}$) using a microplate reader from Molecular Devices Spectormax Plus (Sunnyvale, Calif.) or BMG LABTECH Inc (Offenburg, Germany).

The inhibition of CHK1 was analyzed by fitting the data to the following equation to determine $K_{iapp}$:

$$Vi = Vo \cdot \left(1 - \left(\frac{[E]o + [I]o + K_i(1 + So/K_m) - \sqrt{([E]o + [I]o + K_i(1 + So/K_m))^2 - 4 \cdot [E]o \cdot [I]o}}{2 \cdot [E]o}\right)\right)$$

where [E]o and [I]o are the active enzyme and inhibitor concentration, respectively; $K_i$ is the inhibition binding constant and Km the Michaelis-Menten constant for ATP; $V_i$ and $V_o$ are the rates of substrate oxidation in the presence of and in the absence of inhibitor, respectively.

EC50 Determination (Cellular Assay)

The Histone H3 phosphorylation ELISA assay detects cells entering mitosis and represents the primary in vitro cell-based assay used to measure the cellular potency of compounds in abrogating the $G_2$ check point induced by DNA damage in HeLa cells or MiaPaCa cells. The candidate substances were assayed for potency in their ability to inhibit camptothecin-induced $G_2$ arrest, as measured by an increase in Histone H3 phosphorylation on Ser10, a marker of entry into mitosis.

The PathScan Phospho-Histone H3 (Ser10) Sandwich ELISA kit was used (Cell Signaling, #7155) and the assay was performed according to manufacturer recommendations. Tissue culture plates were seeded with HeLa cells or MiaPaCa Cells and allowed to attach overnight. The cells were then treated with camptothecin to induce DNA damage for 8 hrs. Candidate substances or diluent were then added in the presence of nocodozole for 16 hours. Cells were then lysed with buffer from Assay Designs (#80-1114) supplemented with protease inhibitors and frozen overnight. The fresh whole cell lysates were then thawed and added to the ELISA plate with shaking for 3 hours. Between all subsequent steps plates were washed 4 times with PBST. Biotinylated phospho Histone H3 (ser10) detection antibody was added for 1 hour, followed by addition of horseradish peroxidase-linked streptavidin secondary antibody for 1 hour. Color development of the antibody was performed with addition of TMB substrate and incubation for 2 minutes on a plate shaker. Stop solution was added and plates were read with absorbance at 450 nM on a spectrophotometer. EC50 values were calculated by sigmoid curve fitting using a four-parameter analysis.

CHK-1 Kinase Domain Ki data and CHK-1 cellular assay EC50 data of the compounds of Examples 1-299 are shown below. Under the "Ki" column, data entries in the format of "%" are percent inhibition data where no Ki data is available. Data entry under the "EC50" column with an * are data obtained using Mia Paca-2 cells rather than HeLa cells. Data is not available where noted as n/a.

TABLE 3

Ki and EC50 value of the compounds.

| Example No. | Ki (uM) | EC50 (uM) |
|---|---|---|
| 1 | 0.0132 | 0.0703 |
| 2 | 0.00324 | 0.0343 |
| 3 | 0% | 0.486 |
| 4 | 0.00774 | 0.0928* |
| 5 | 0.00249 | 0.0183* |
| 6 | 0.00254 | 0.0318 |
| 7 | 0.00165 | 0.0167* |
| 8 | 16.7% | n/a |
| 9 | 0.131 | 10 |
| 10 | 0.0236 | 0.244 |
| 11 | 101% | 0.0621 |
| 12 | 0.0275 | 0.0684 |
| 13 | 0.0128 | 0.513* |
| 14 | 0.0336 | 4.21* |
| 15 | 43.5% | 10 |
| 16 | 0.0194 | 0.0811* |
| 17 | 0.00641 | 0.0595* |
| 18 | 0.00123 | 0.0191* |
| 19 | 0.167 | 10* |
| 20 | 0.93 | 10* |
| 21 | 0.00602 | 0.0688* |
| 22 | n/a | n/a |
| 23 | 36.1% | 10 |
| 24 | 0.00638 | 0.178* |
| 25 | 0.0702 | 10 |
| 26 | 63.9 | n/a |
| 27 | 0.0539 | 5.58 |
| 28 | 0.00477 | 0.205 |
| 29 | 0.00551 | 0.0868* |
| 30 | 0.147 | 0.634 |
| 31 | 0.0273 | 0.183 |
| 32 | n/a | n/a |
| 33 | 0.00100 | 0.00727* |
| 34 | 0.00338 | 0.0290 |
| 35 | 0.00388 | 0.0409 |
| 36 | n/a | n/a |
| 37 | 0.00203 | 0.0210* |
| 38 | 0.0080 | 0.0400 |
| 39 | 0.0170 | 0.677 |
| 40 | 0.00443 | 0.104 |
| 41 | 0.007 | 0.0258 |
| 42 | 0.007 | 0.0293 |
| 43 | 0.00669 | 0.0646 |
| 44 | 0.00251 | 0.0210 |
| 45 | 0.585 | n/a |
| 46 | 29.7% | 7.97 |
| 47 | 0.0246 | 0.0522 |
| 48 | 0.165 | 0.600 |
| 49 | 0.0117 | 0.142 |
| 50 | 0.0174 | 0.148 |
| 51 | 0.00960 | 0.0956 |
| 52 | 0.00955 | 0.0729 |
| 53 | 0.037 | 0.459 |
| 54 | 0.118 | 1.11 |
| 55 | 0.023 | 0.229 |
| 56 | 0.0112 | 0.126 |
| 57 | 0.00609 | 0.373 |
| 58 | 0% | n/a |
| 59 | 0.00300 | 0.00909 |
| 60 | 1.00 | 8.32 |
| 61 | 0.0379 | 0.119 |
| 62 | 0.0735 | 0.694 |
| 63 | 35.5% | n/a |
| 64 | 1.11 | 10 |
| 65 | 0.0330 | 0.501 |
| 66 | 0.0127 | 0.344 |
| 67 | 0.0800 | 0.507 |
| 68 | 0% | n/a |
| 69 | 0.60% | n/a |
| 70 | 0% | n/a |
| 71 | 0% | n/a |
| 72 | 1.4% | n/a |
| 73 | 0% | n/a |
| 74 | 5.8% | n/a |
| 75 | 6.7% | n/a |
| 76 | 1.6% | n/a |
| 77 | 0% | n/a |
| 78 | 0.0371 | 3.56 |
| 79 | 0.00568 | 0.184 |
| 80 | 1.00 | n/a |
| 81 | 1.00 | n/a |
| 82 | 1.00 | n/a |
| 83 | 1.00 | n/a |
| 84 | 1.00 | n/a |
| 85 | 0.0131 | 0.795 |

TABLE 3-continued

Ki and EC50 value of the compounds.

| Example No. | Ki (uM) | EC50 (uM) |
|---|---|---|
| 86 | 0.00168 | 0.295* |
| 87 | 0.00863 | 0.127* |
| 88 | 0.0907 | 10 |
| 89 | 0.261 | 10 |
| 90 | 0.0705 | 10 |
| 91 | 0.0187 | 0.497 |
| 92 | 0.0875 | 10 |
| 93 | 0.0890 | 3.33 |
| 94 | 0.0206 | 0.370 |
| 95 | 0.0375 | 10 |
| 96 | 0.00270 | 0.0243 |
| 97 | 0.00862 | 0.151 |
| 98 | 1.00 | 10 |
| 99 | 0.0284 | 10 |
| 100 | 0.0146 | 3.53 |
| 101 | 0.0554 | 10 |
| 102 | 0.00310 | 10 |
| 103 | 0.0265 | 0.0696 |
| 104 | 0.0364 | 10 |
| 105 | 0.0206 | 10 |
| 106 | 0.0218 | 0.271 |
| 107 | 0.00285 | 0.0316 |
| 108 | 0.0102 | 0.0470 |
| 109 | 0.0284 | 0.190 |
| 110 | 0.0173 | 0.589* |
| 111 | 0.00363 | 0.0224 |
| 112 | 0.0127 | 1.11 |
| 113 | 95.5% | 0.103 |
| 114 | 0.0123 | 0.230 |
| 115 | 0.00330 | 0.169 |
| 116 | 0.00197 | 0.0203 |
| 117 | 0.000802 | 0.0329 |
| 118 | 0.00527 | 1.11 |
| 119 | 0.00538 | 0.0267 |
| 120 | 0.0343 | 0.686* |
| 121 | 16.5% | 10 |
| 122 | 0.0110 | 1.06 |
| 123 | 0.00322 | 0.0229* |
| 124 | 0.00229 | 10 |
| 125 | 0.000663 | 0.0350 |
| 126 | 0.00588 | 0.140 |
| 127 | 0.00891 | 1.06 |
| 128 | 0.00179 | 0.172 |
| 129 | 0.000929 | 0.0108* |
| 130 | 0.00486 | 0.139* |
| 131 | 0% | 10 |
| 132 | 18.3% | 10 |
| 133 | 0.0214 | 10 |
| 134 | 0% | 10 |
| 135 | 0.0126 | 0.208* |
| 136 | 0.0520 | 0.966 |
| 137 | 0.00240 | 0.256* |
| 138 | 0.142 | 0.188 |
| 139 | 0.00970 | 10 |
| 140 | 0.00107 | 0.0192 |
| 141 | 0.0100 | 0.0778 |
| 142 | 0.00149 | 0.125* |
| 143 | 0.00111 | 0.119 |
| 144 | 0.00318 | 0.167* |
| 145 | 0.0081 | 0.389 |
| 146 | 0.0190 | 0.493 |
| 147 | 0.0129 | 0.295 |
| 148 | 104% | 10 |
| 149 | 0.00677 | 10 |
| 150 | 0.00591 | 0.284 |
| 151 | 0.00107 | 0.0787 |
| 152 | 0.00147 | 0.00560 |
| 153 | 2.2% | n/a |
| 154 | 0.00390 | 0.602* |
| 155 | 0.00100 | 0.0461* |
| 156 | 0.0284 | 0.314 |
| 157 | 0.0217 | 0.0733* |
| 158 | 0.0498 | 0.129* |
| 159 | 0.0208 | 0.166 |
| 160 | 0.00107 | 0.0257* |
| 161 | 0.00147 | 0.00566* |
| 162 | 30 | 0.321* |
| 163 | 0.0140 | 0.248* |
| 164 | 0.0184 | 10 |
| 165 | 0.00109 | 0.123 |
| 166 | 0.00479 | 0.123 |
| 167 | 0.101 | 10 |
| 168 | 0.0227 | 10 |
| 169 | 45.9% | 1.85 |
| 170 | 0.0111 | 0.414 |
| 171 | 21.7% | 10 |
| 172 | 0.178 | 10 |
| 173 | 0.0237 | 10 |
| 174 | 0.0169 | 10 |
| 175 | 0.0137 | 0.197 |
| 176 | 0.00954 | 0.0112 |
| 177 | 49.1% | 10 |
| 178 | 0.00201 | 0.0312 |
| 179 | 29.1% | 0.294 |
| 180 | 0.00150 | 10 |
| 181 | 0.00720 | 0.0261* |
| 182 | 98.9% | n/a |
| 183 | 0.00540 | 0.0530 |
| 184 | 109% | 0.0664 |
| 185 | 0.00540 | 0.0664 |
| 186 | 0.0240 | 0.664 |
| 187 | n/a | n/a |
| 188 | 0.0578 | 0.663* |
| 189 | 0.0179 | 0.626* |
| 190 | 0.156 | 1.32 |
| 191 | 0.00470 | 5.07 |
| 192 | 0.0292 | 0.187* |
| 193 | 0.0265 | 0.102 |
| 194 | 0.0136 | 0.00776 |
| 195 | 0.0734 | 0.0785 |
| 196 | 0.0320 | 0.0168 |
| 197 | 0.00305 | 0.00482* |
| 198 | 0.00109 | 0.0234 |
| 199 | 0.00782 | 0.106* |
| 200 | 26.1% | 0.127* |
| 201 | 0.00488 | 0.0489 |
| 202 | 0.0184 | 0.0194 |
| 203 | 0.00409 | 0.134* |
| 204 | 0.0545 | 0.0749* |
| 205 | 0.0383 | 0.0552* |
| 206 | 0.0482 | 0.240* |
| 207 | 21% | n/a |
| 208 | 0.195 | n/a |
| 209 | 0.00130 | 0.123 |
| 210 | 0.00285 | n/a |
| 211 | 0.00254 | 0.00459* |
| 212 | n/a | n/a |
| 213 | 0.00358 | 10 |
| 214 | 0.000935 | 0.0122* |
| 215 | 0.00678 | 0.0358 |
| 216 | 0.0155 | 0.0358 |
| 217 | 0.00699 | 0.0364* |
| 218 | 0.00512 | 10 |
| 219 | 48.4% | 0.979 |
| 220 | 17.9% | n/a |
| 221 | 0.00334 | 0.370 |
| 222 | 42.5% | 10 |
| 223 | 0.0681 | 0.329 |
| 224 | 0.00239 | 0.0303 |
| 225 | 0.0179 | 0.0649* |
| 226 | 0.00460 | 0.00717* |
| 227 | 0.0920 | 1.00* |
| 228 | 0.00650 | 0.0245* |
| 229 | 0.00440 | 0.00975* |
| 230 | 0.00920 | 0.0768* |
| 231 | 0.0286 | 20* |
| 232 | 0.00260 | 0.100* |
| 233 | 0.00340 | 0.0755* |
| 234 | 0.00250 | 0.0899* |
| 235 | 0.00680 | 0.0679* |
| 236 | 0.0876 | 0.479* |
| 237 | 0.00298 | 0.0467* |

TABLE 3-continued

Ki and EC50 value of the compounds.

| Example No. | Ki (uM) | EC50 (uM) |
|---|---|---|
| 238 | 0.00490 | 0.0871* |
| 239 | 0.0722 | 0.201* |
| 240 | 0.0616 | 0.171* |
| 241 | 0.0450 | 0.201* |
| 242 | 0.0280 | 0.129* |
| 243 | 0.0248 | 0.172* |
| 244 | 0.0159 | 0.0603* |
| 245 | 0.00472 | 0.0859* |
| 246 | 0.0353 | 0.229 |
| 247 | 0.192 | 1.11* |
| 248 | 0.0453 | 10 |
| 249 | 0.00450 | 0.0322 |
| 250 | 0.0488 | 1.62* |
| 251 | 0.0100 | 0.255* |
| 252 | 0.0693 | 1.11* |
| 253 | 0.0856 | 1.03* |
| 254 | 0.0283 | 0.542* |
| 255 | 0.0345 | 0.597* |
| 256 | 0.00126 | 0.0537* |
| 257 | 0.0126 | 0.166* |
| 258 | 0.00438 | 0.0984* |
| 259 | 0.00382 | 0.0388* |
| 260 | 0.233 | 0.549* |
| 261 | 0.0149 | 0.0370* |
| 262 | 0.0564 | 0.303 |
| 263 | 0.374 | n/a |
| 264 | n/a | n/a |
| 265 | 0.00537 | 0.244* |
| 266 | 0.0787 | 0.548* |
| 267 | 27.0 | 10* |
| 268 | 0.0658 | 1.48* |
| 269 | 0.00976 | 0.0730* |
| 270 | n/a | n/a |
| 271 | 0.118 | 4.77* |
| 272 | 0.0408 | 2.01* |
| 273 | n/a | n/a |
| 274 | n/a | n/a |
| 275 | n/a | n/a |
| 276 | n/a | n/a |
| 277 | n/a | n/a |
| 278 | n/a | n/a |
| 279 | n/a | n/a |
| 280 | n/a | n/a |
| 281 | n/a | n/a |
| 282 | n/a | n/a |
| 283 | n/a | n/a |
| 284 | n/a | n/a |
| 285 | 0.0213 | 0.0910* |
| 286 | n/a | n/a |
| 287 | n/a | n/a |
| 288 | n/a | n/a |
| 289 | n/a | n/a |
| 290 | n/a | n/a |
| 291 | n/a | n/a |
| 292 | n/a | n/a |
| 293 | n/a | n/a |
| 294 | n/a | n/a |
| 295 | n/a | n/a |
| 296 | 0.334 | 4.08 |
| 297 | 0.105 | n/a |
| 298 | 0.00527 | n/a |
| 299 | 0.00411 | n/a |

The invention claimed is:

1. A compound of formula (I),

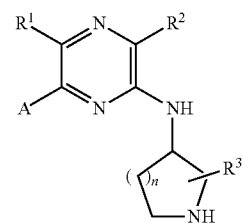

wherein,
n is 0, 1 or 2;
A is of the structure

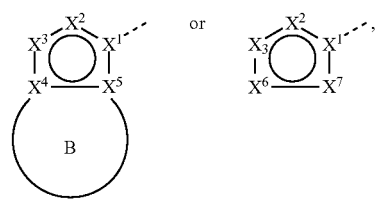

and A is optionally further substituted with 1-6 $R^4$;
$X^1$, $X^2$, $X^3$, $X^4$ and $X^5$ form a 5 member heteroaryl having 1-4 nitrogen ring atoms;
$X^1$, $X^2$, $X^3$, $X^6$ and $X^7$ form a 5 member heteroaryl having 1-4 nitrogen ring atoms;
$X^1$ is N or C; $X^2$ is N, NH or CH; $X^3$ is N; each of $X^4$ and $X^5$ is independently N or C; each of $X^6$ and $X^7$ is independently N, NH or CH;
B together with $X^4$ and $X^5$ form a ring selected from phenyl, 5-6 member heteroaryl, 5-6 member heterocyclyl, $C_5$-$C_6$ cycloalkyl and $C_5$-$C_6$ cycloalkenyl, each of said 5-6 member heteroaryl and 5-6 member heterocyclyl has 1-3 ring heteroatoms selected from N, O and S;
each of $R^1$ and $R^2$ is independently selected from hydrogen, fluorine, chlorine, —CN, —$OR^b$, —N($R^b$)$_2$, and $C_1$-$C_3$ alkyl optionally substituted with 1-6 groups selected from fluorine, chlorine and —CN;
$R^3$ represents 1-6 optional substituents independently selected from the group consisting of -oxo- and $R^o$;
two $R^3$ attached to the same ring atom, together with the ring atom to which they are attached, may form a ring selected from $C_3$-$C_6$ cycloalkyl, $C_5$-$C_6$ cycloalkenyl and 3-6 member heterocyclyl; each of said $C_3$-$C_6$ cycloalkyl, $C_5$-$C_6$ cycloalkenyl and 3-6 member heterocyclyl is optionally further substituted with 1-5 groups selected from -oxo- and $R^w$;
two $R^3$ attached to two adjacent ring atoms, together with the ring atoms attached to, may form a fused ring selected from $C_3$-$C_6$ cycloalkyl, $C_5$-$C_6$ cycloalkenyl, 3-6 member heterocyclyl, phenyl and 5-6 member heteroaryl; said $C_3$-$C_6$ cycloalkyl, $C_5$-$C_6$ cycloalkenyl, 3-6 member heterocyclyl, phenyl and 5-6 member heteroaryl is optionally further substituted with 1-5 groups selected from oxo and $R^w$;
two $R^3$ attached to, two different ring atoms with at least one ring atom in between, may form a $C_1$-$C_4$ alkylene, a 2-4 member heteroalkylene, or a diradical selected from the group consisting of:

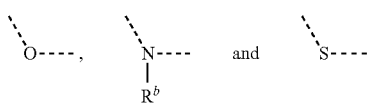

such C₁-C₄ alkylene, 2-4 member heteroalkylene and diradical together with the azetidinyl (when n is 0), pyrrolidinyl (when n is 1) or the piperidinyl (when n is 2) form a bicyclic bridged ring system, said bicyclic bridged ring system having a total of 6-9 ring atoms with 1-3 of the ring atoms selected from O, N and S; the C₁-C₄ alkylene or a 1-4 member heteroalkylene is optionally further substituted with 1-5 groups selected from -oxo- and R$^w$;

each R⁴ is independently R⁰;

each R⁰ is independently selected from the group consisting of (a) fluorine, chlorine and —CN; (b) C₁-C₆ alkyl, C₂-C₆ alkenyl and C₂-C₆ alkynyl, each of which is optionally further substituted with 1-6 groups selected from fluorine, chlorine and CN; (c) C₃-C₆ cycloalkyl, -L-(C₃-C₆ cycloalkyl), 4-6 member heterocyclyl, -L-(4-6 member heterocyclyl), phenyl, -L-phenyl, 5-6 member heteroaryl, -L-(5-6 member heteroaryl), C₅-C₆ cycloalkenyl, -L-(C₅-C₆ cycloalkenyl), wherein each C₃-C₆ cycloalkyl, phenyl, 5-6 member heteroaryl, 4-6 member heterocyclyl and C₅-C₆ cycloalkenyl is independently optionally further substituted with 1-6 R$^x$; (d) —N(Ra)₂, -L-N(R$^a$)₂; (e) —OR$^a$, -L-OR$^a$; (f) —O-L-N(R$^a$)₂, —N(R$^b$)-L-OR$^a$, -L-O-L-N(R$^a$)₂, -L-N(R$^b$)-L-OR$^a$; (g) —C(O)R$^a$, —C(O)OR$^a$, —C(O)N(R$^a$)₂, -L-C(O)R$^a$, -L-C(O)OR$^a$, -L-C(O)N(R$^a$)₂; (h) —N(R$^b$)-(L)$_p$-C(O)R$^a$, —N(R$^b$)-(L)$_p$-C(O)OR$^a$, —N(R$^b$)-(L)$_p$-C(O)N(R$^a$)₂, -L-N(R$^b$)-(L)$_p$-C(O)R$^a$, -L-N(R$^b$)-(L)$_p$-C(O)OR$^a$, -L-N(R$^b$)-(L)$_p$-C(O)N(R$^a$)₂; (i) —O-(L)$_p$-C(O)R$^a$, —O-(L)$_p$-C(O)N(R$^a$)₂, —O-(L)$_p$-C(O)O—R$^a$, -L-O-(L)$_p$-C(O)R$^a$, -L-O-(L)$_p$-C(O)N(R$^a$)₂-L-O-(L)$_p$-C(O)O—R$^a$; (j) —S(O)₂R$^a$, —S(O)₂OR$^a$, —S(O)₂N(R$^a$)₂, -L-S(O)₂R$^a$, -L-S(O)₂OR$^a$, -L-S(O)₂N(R$^a$)₂; (k) —O-(L)$_p$-S(O)₂R$^a$, )—O-(L)$_p$-S(O)₂O—R$^a$, —O-(L)$_p$-S(O)₂N(R$^a$)₂, -L-O-(L)$_p$-S(O)₂R$^a$, -L-O-(L)$_p$-S(O)₂O—R$^{a''}$)-L-O-(L)$_p$-S(O)₂N(R$^a$)₂; (l) —N(R$^b$)-(L)$_p$-S(O)₂R$^a$, —N(R$^b$)-(L)$_p$-S(O)₂O—R$^a$, —N(R$^b$)-(L)$_p$-S(O)₂N(R$^a$)₂, -L-N(R$^b$)-(L)$_p$-S(O)₂R$^a$, -L-N(R$^b$)-(L)$_p$-S(O)₂O—R$^{a''}$)-L-N(R$^b$)-(L)$_p$-S(O)₂N(R$^a$)₂; and (m) —C(R$^a$)=N—CN, -L-C(R$^a$)=N—CN;

each R$^a$ is independently selected from the group consisting of: (a) hydrogen, C₁-C₆ alkyl and C₁-C₆ perfluoroalkyl; (b) C₁-C₆ alkyl further substituted by 1-2 groups selected from fluorine, chlorine, —CN, —OR$^b$ and —N(R$^b$)₂; (c) C₂-C₆ alkenyl and C₂-C₆ alkynyl, each of which is optionally further substituted by 1-3 groups selected from fluorine, chlorine, —CN, —OR$^b$ and —N(R$^b$)₂; (d) —(C₁-C₆ alkylene)$_p$-(C₃-C₆ cycloalkyl), —(C₁-C₆ alkylene)$_p$-phenyl, —(C₁-C₆ alkylene)$_p$-(5-6 member heteroaryl), —(C₁-C₆ alkylene)$_p$-(4-6 member heterocyclyl), —(C₁-C₆ alkylene)$_p$-(C₅-C₆ cycloalkenyl), wherein each C₁-C₆ alkylene is optionally further substituted with 1-3 groups selected from fluorine, chlorine and —CN, wherein each of said C₃-C₆ cycloalkyl, phenyl, 5-6 member heteroaryl, 4-6 member heterocyclyl and C₅-C₆ cycloalkenyl is independently optionally further substituted with 1-3 R$^y$;

or two R$^a$ connected to the same nitrogen form a 3-10 member heterocyclyl or 5-10 member heteroaryl, said 3-10 member heterocyclyl and said 5-10 member heteroaryl is optionally further substituted with 1-3 R$^z$;

each L is independently C₁-C₆ alkylene, C₂-C₆ alkenylene or C₂-C₆ alkynylene, and each L is optionally further substituted with 1-3 groups selected from fluorine, chlorine, OH and —CN;

each R$^w$, R$^x$, R$^y$ and R$^z$ is independently selected from the group consisting of (i) fluorine, chlorine, —CN, —OR$^b$, C₁-C₆ alkyl, C₁-C₃ perfluoroalkyl, C₂-C₆ alkenyl, C₂-C₆ alkynyl and —N(R$^b$)₂; (ii) C₁-C₆ alkyl further substituted with 1-2 groups selected from fluorine, chlorine, —CN, —OR$^b$ and —N(R$^b$)₂; (iii) —C(O)—R$^b$, —C(O)OR$^b$, —C(O)—N(R$^b$)₂; (iv) —N(R$^b$)—C(O)—R$^b$, —N(R$^b$)—C(O)OR$^b$, —N(R$^b$)—C(O)—N(R$^b$)₂; (v) —O—C(O)—R$^b$, —O—C(O)OR$^b$, —O—C(O)—N(R$^b$)₂; (vi) —S(O)₂—R$^b$, —S(O)₂—O—R$^b$—S(O)₂—N(R$^b$)₂; (vii) —N(R$^b$)—S(O)₂—R$^b$, —N(R$^b$)—S(O)₂—O—R$^b$, —N(R$^b$)—S(O)₂—N(R$^b$)₂; and (viii) —O—S(O)₂—R$^b$, —O—S(O)₂—O—R$^b$—O—S(O)₂—N(R$^b$)₂;

each R$^b$ is independently selected from the group consisting of hydrogen, C₁-C₃ alkyl, C₁-C₃ perfluoroalkyl and C₁-C₃ alkyl further substituted by 1-2 groups selected from fluorine, chlorine and CN;

each p is independently 0 or 1;

or a pharmaceutically acceptable salt thereof.

2. The compound or salt of claim 1, wherein n is 2 and the compound is of formula II,

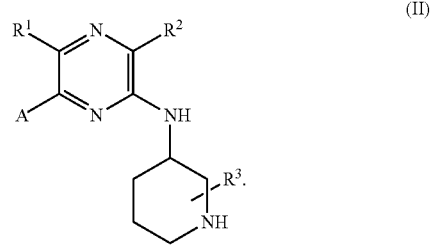

3. The compound or salt of claim 1, wherein n is 1 and the compound is of formula IV,

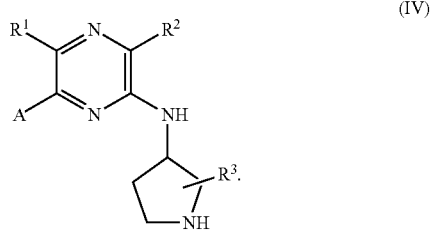

4. The compound or salt of claim 1, wherein

A is a heteroaryl selected from the group consisting of

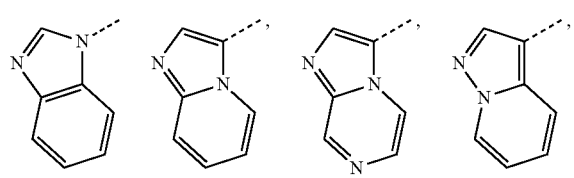

-continued

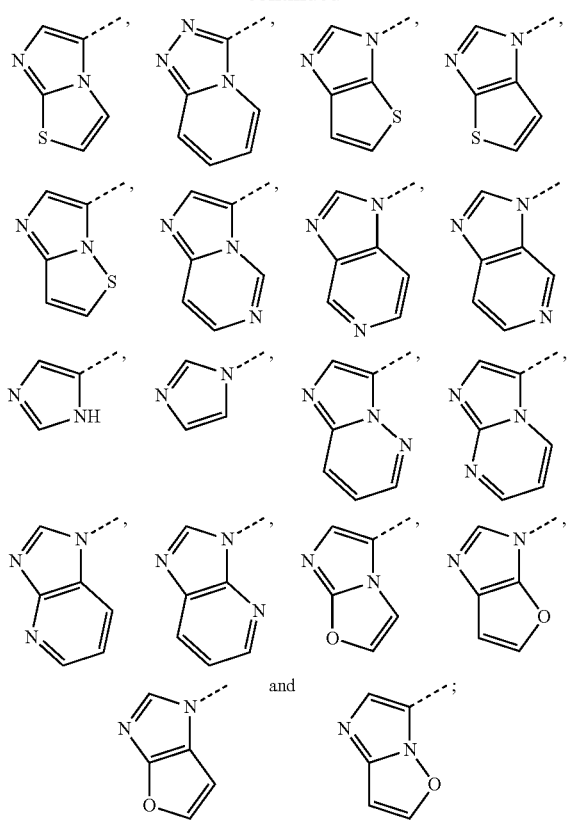

and A is optionally further substituted with 1-5 R⁴;

each of R¹ and R² is independently selected from hydrogen, fluorine, chlorine, —CN, —OR$^b$, —N(R$^b$)², and C₁-C₃ alkyl optionally substituted with 1-6 groups selected from fluorine, chlorine and —CN;

R³ represents 1-6 optional substituents independently selected from the group consisting of -oxo- and R⁰;

each R⁴ is independently R⁰;

each R⁰ is independently selected from the group consisting of (a) fluorine, chlorine and —CN; (b) C₁-C₆ alkyl, optionally further substituted with 1-6 groups selected from fluorine, chlorine and CN; (c) C₃-C₆ cycloalkyl, -L-(C₃-C₆ cycloalkyl), 4-6 member heterocyclyl, -L-(4-6 member heterocyclyl), wherein each C₃-C₆ cycloalkyl and 4-6 member heterocyclyl is independently optionally further substituted with 1-6 R$^x$; (d) —N(R$^a$)₂, -L-N(R$^a$)₂; (e) —OR$^a$, -L-OR$^a$; and (g) —C(O)R$^a$, —C(O)OR$^a$, —C(O)N(R$^a$)₂, -L-C(O)R$^a$, -L-C(O)OR$^a$, -L-C(O)N(R$^a$)₂;

each R$^a$ is independently selected from the group consisting of (a) hydrogen, C₁-C₆ alkyl and C₁-C₆ perfluoroalkyl; (b) C₁-C₆ alkyl further substituted by 1-2 groups selected from fluorine, chlorine, —CN, —OR$^b$ and —N(R$^b$)₂; (d) —(C₁-C₆ alkylene)$_p$-(C₃-C₆ cycloalkyl), —(C₁-C₆ alkylene)$_p$-(4-6 member heterocyclyl), wherein each C₁-C₆ alkylene is optionally further substituted with 1-3 groups selected from fluorine, chlorine and —CN, wherein each of said C₃-C₆ cycloalkyl and 4-6 member heterocyclyl is independently optionally further substituted with 1-3 R$^y$;

or two R$^a$ connected to the same nitrogen form a 3-10 member heterocyclyl or 5-10 member heteroaryl, said 3-10 member heterocyclyl and said 5-10 member heteroaryl is optionally further substituted with 1-3 R$^z$;

each L is independently C₁-C₆ alkylene optionally further substituted with 1-3 groups selected from fluorine, chlorine, OH and —CN;

each R$^w$, R$^x$, R$^y$ and R$^z$ is independently selected from the group consisting of (i) fluorine, chlorine, —CN, —OR$^b$, C₁-C₆ alkyl, C₁-C₃ perfluoroalkyl, C₂-C₆ alkenyl, C₂-C₆ alkynyl and —N(R$^b$)₂; (ii) C₁-C₆ alkyl further substituted with 1-2 groups selected from fluorine, chlorine, —CN, —OR$^b$ and —N(R$^b$)₂; (iii) —C(O)—R$^b$, —C(O)OR$^b$, —C(O)—N(R$^b$)₂; and each R$^b$ is independently selected from the group consisting of hydrogen, C₁-C₃ alkyl, C₁-C₃ perfluoroalkyl and C₁-C₃ alkyl further substituted by 1-2 groups selected from fluorine, chlorine and CN.

5. The compound or salt of claim 1, wherein R¹ is hydrogen.

6. The compound or salt of claim 1, wherein, n is 1 or 2;

A is a heteroaryl selected from the group consisting of

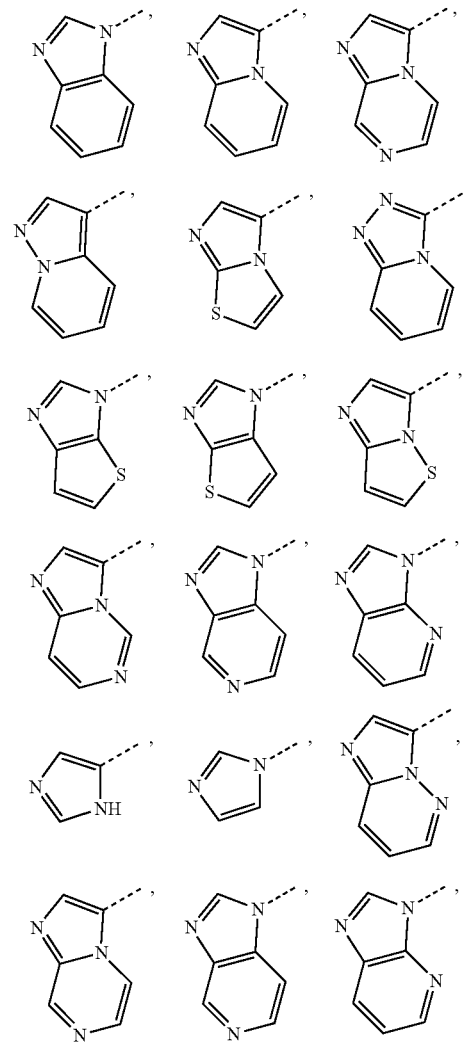

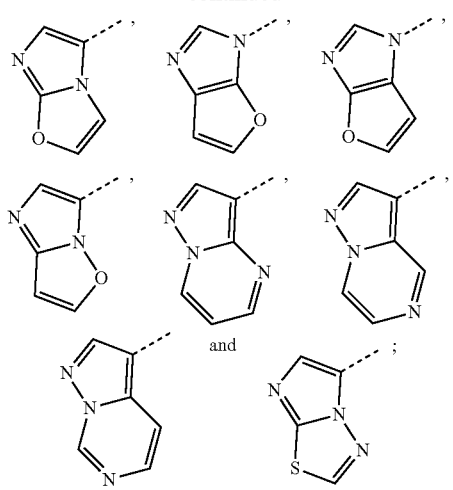

A is optionally further substituted with 1-5 $R^4$;
$R^1$ is hydrogen;
$R^2$ is selected from hydrogen, fluorine, chlorine, —CN, —$OR^b$ and $C_1$-$C_3$ alkyl;
$R^3$ represents 1-6 optional substituents independently selected from the group consisting of -oxo- and $R^0$; furthermore, when n is 2, two $R^3$ attached to two different ring atoms with at least one ring atom in between, may form a $C_1$-$C_4$ alkylene, a 2-4 member heteroalkylene, or a diradical selected from the group consisting of:

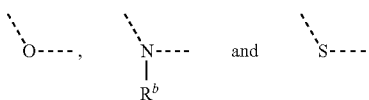

such $C_1$-$C_4$ alkylene, 2-4 member heteroalkylene and diradical together with the piperidinyl (when n is 2) form a bicyclic bridged ring system, said bicyclic bridged ring system having a total of 6-9 ring atoms with 1-3 of the ring atoms selected from N, O and S; the $C_1$-$C_4$ alkylene or a 1-4 member heteroalkylene is optionally further substituted with 1-5 groups selected from -oxo- and $R^w$;
  each $R^4$ is independently $R^0$;
  each $R^0$ is independently selected from the group consisting of (a) fluorine, chlorine and —CN; (b) $C_1$-$C_6$ alkyl, $C_2$-$C_6$ alkenyl and $C_2$-$C_6$ alkynyl, each of which is optionally further substituted with 1-6 groups selected from fluorine, chlorine and CN; (c) $C_3$-$C_6$ cycloalkyl, -L-($C_3$-$C_6$ cycloalkyl), 4-6 member heterocyclyl, -L-(4-6 member heterocyclyl), wherein each $C_3$-$C_6$ cycloalkyl and 4-6 member heterocyclyl is optionally further substituted with 1-6 $R^x$; (d) —N($R^a$)$_2$, -L-N($R^a$)$_2$; (e) —$OR^a$, -L-$OR^a$; and (f) —C(O)$R^a$, —C(O)$OR^a$, —C(O)N($R^a$)$_2$, -L-C(O)$R^a$, -L-C(O)$OR^a$, -L-C(O)N($R^a$)$_2$;
  each $R^a$ is independently selected from the group consisting of (a) hydrogen, $C_1$-$C_6$ alkyl and $C_1$-$C_6$ perfluoroalkyl; and (b) $C_1$-$C_6$ alkyl further substituted by 1-2 groups selected from fluorine, chlorine, —CN, —$OR^b$ and —N($R^b$)$_2$; (c) —($C_1$-$C_6$ alkylene)$_p$-($C_3$-$C_6$ cycloalkyl), —($C_1$-$C_6$ alkylene)$_p$-(4-6 member heterocyclyl), wherein each $C_1$-$C_6$ alkylene is optionally further substituted with 1-3 groups selected from fluorine, chlorine and —CN, wherein each of said $C_3$-$C_6$ cycloalkyl, 4-6 member heterocyclyl is independently optionally further substituted with 1-3 $R^y$;
  or two $R^a$ connected to the same nitrogen form a 3-10 member heterocyclyl or 5-10 member heteroaryl, said 3-10 member heterocyclyl and said 5-10 member heteroaryl is optionally further substituted with 1-3 $R^z$;
  each L is independently $C_1$-$C_6$ alkylene and each L is optionally further substituted with 1-3 groups selected from fluorine, chlorine, OH and —CN;
  each $R^w$, $R^x$, $R^y$ and $R^z$ is independently selected from the group consisting of (i) fluorine, chlorine, —CN, —$OR^b$, $C_1$-$C_6$ alkyl, $C_1$-$C_3$ perfluoroalkyl and —N($R^b$)$_2$; (ii) $C_1$-$C_6$ alkyl further substituted with 1-2 groups selected from fluorine, chlorine, —CN, —$OR^b$ and —N($R^b$)$_2$;
  each $R^b$ is independently selected from the group consisting of hydrogen, $C_1$-$C_3$ alkyl, $C_1$-$C_3$ perfluoroalkyl and $C_1$-$C_3$ alkyl further substituted by 1-2 groups selected from fluorine, chlorine and CN; and
  each p is independently 0 or 1.

7. The compound or salt of claim 1, wherein,
n is 1 or 2;
A is a heteroaryl selected from the group consisting of

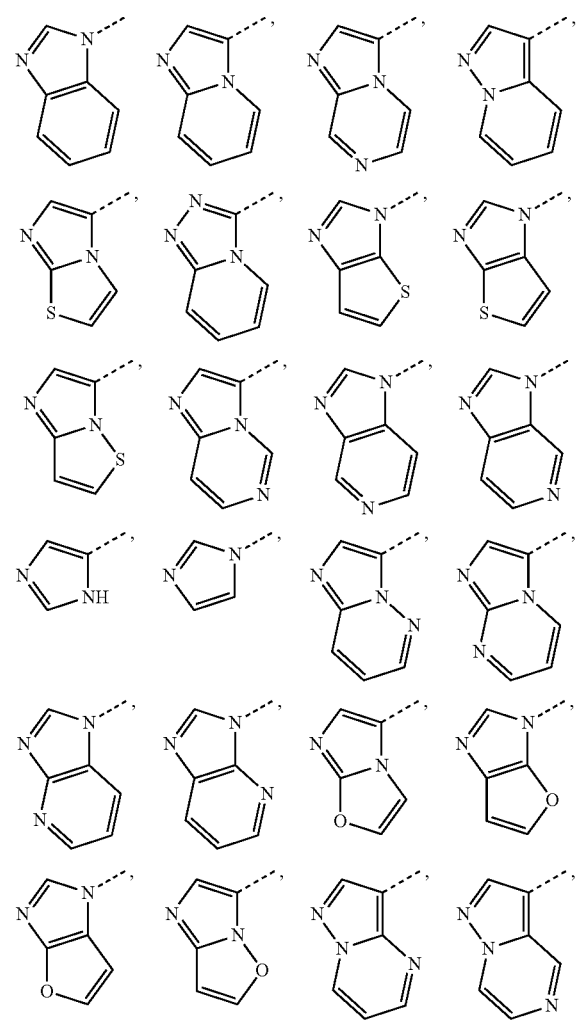

-continued

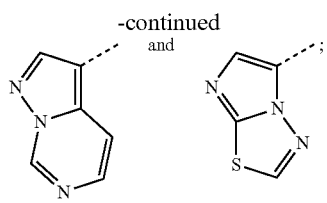
and

A is optionally further substituted with 1-5 $R^4$;
$R^1$ is hydrogen;
$R^2$ is selected from hydrogen, fluorine, chlorine, —CN, —$OR^b$ and $C_1$-$C_3$ alkyl;
$R^3$ represents 1-6 optional substituents independently selected from the group consisting of -oxo- and $R^0$;
each $R^4$ is independently $R^0$;
each $R^0$ is independently selected from the group consisting of (a) fluorine, chlorine and —CN; (b) $C_1$-$C_6$ alkyl optionally further substituted with 1-6 groups selected from fluorine, chlorine and CN; (c) $C_3$-$C_6$ cycloalkyl, -L-($C_3$-$C_6$ cycloalkyl), 4-6 member heterocyclyl, -L-(4-6 member heterocyclyl), wherein each $C_3$-$C_6$ cycloalkyl and 4-6 member heterocyclyl is optionally further substituted with 1-6 $R^x$; (d) —$OR^a$, -L-$OR^a$; and (e) —C(O)N($R^a$)$_2$, -L-C(O)N($R^a$)$_2$;
each $R^a$ is independently selected from the group consisting of (a) hydrogen, $C_1$-$C_6$ alkyl and $C_1$-$C_6$ perfluoroalkyl; and (b) $C_1$-$C_6$ alkyl further substituted by 1-2 groups selected from fluorine, chlorine, —CN, —$OR^b$ and —N($R^b$)$_2$; (c) —($C_1$-$C_6$ alkylene)$_p$-($C_3$-$C_6$ cycloalkyl), —($C_1$-$C_6$ alkylene)$_p$-(4-6 member heterocyclyl), wherein each $C_1$-$C_6$ alkylene is optionally further substituted with 1-3 groups selected from fluorine, chlorine and —CN, wherein each of said $C_3$-$C_6$ cycloalkyl, 4-6 member heterocyclyl is independently optionally further substituted with 1-3 $R^y$;
or two $R^a$ connected to the same nitrogen form a 3-10 member heterocyclyl or 5-10 member heteroaryl, said 3-10 member heterocyclyl and said 5-10 member heteroaryl is optionally further substituted with 1-3 $R^z$;
each L is independently $C_1$-$C_6$ alkylene and each L is optionally further substituted with 1-3 groups selected from fluorine, chlorine, OH and —CN;
each $R^w$, $R^x$, $R^y$ and $R^z$ is independently selected from the group consisting of (i) fluorine, chlorine, —CN, —$OR^b$ and $C_1$-$C_6$ alkyl; (ii) $C_1$-$C_6$ alkyl further substituted with 1-2 groups selected from fluorine, chlorine and —CN;
each $R^b$ is independently selected from the group consisting of hydrogen and $C_1$-$C_3$ alkyl; and
each p is independently 0 or 1.

8. The compound or salt of claim 1, wherein $R^1$ is hydrogen and $R^2$ is hydrogen.

9. The compound or salt of claim 1, wherein A is further substituted with 1-3 $R^4$ selected from the group consisting of
(a) fluorine, chlorine and —CN; and
(b) $C_1$-$C_6$ alkyl, optionally further substituted with 1-6 groups selected from fluorine, chlorine and CN.

10. The compound or salt of claim 1, wherein each $R^a$ is independently selected from the group consisting of hydrogen, $C_1$-$C_6$ alkyl, $C_1$-$C_6$ perfluoroalkyl and $C_1$-$C_6$ alkyl further substituted by 1-2 groups selected from fluorine, chlorine, —CN, —$OR^b$ and —N($R^b$)$_2$.

11. The compound or salt of claim 1, wherein each L is —$C_1$-$C_6$ alkylene, and L is optionally further substituted.

12. The compound or salt of claim 1, wherein each $R^w$, $R^x$, $R^y$ and $R^z$ is independently selected from the group consisting of fluorine, chlorine, —CN and $C_1$-$C_6$ alkyl.

13. The compound or salt of claim 1, wherein each $R^b$ is independently selected from the group consisting of hydrogen and $C_1$-$C_3$ alkyl.

14. The compound or salt of claim 1, wherein each $R^3$ is independently selected from the group consisting of -oxo-, fluorine, chlorine, $C_1$-$C_3$ alkyl, $C_1$-$C_3$ alkoxy, and $CF_3$.

15. The compound or salt of claim 1, wherein each $R^3$ is independently selected from the group consisting of -oxo- and
(a) fluorine, chlorine and —CN;
(b) $C_1$-$C_6$ alkyl, $C_2$-$C_6$ alkenyl and $C_2$-$C_6$ alkynyl, each of which is optionally further substituted with 1-6 groups selected from fluorine, chlorine and CN;
further more, two $R^3$ attached to, two different ring atoms with at least one ring atom in between, may form a $C_1$-$C_4$ alkylene, a 2-4 member heteroalkylene, or a diradical selected from the group consisting of:

$$\diagdown O \text{----}, \quad \diagdown \underset{R^b}{N} \text{----} \quad \text{and} \quad \diagdown S \text{----}$$

such $C_1$-$C_4$ alkylene, 2-4 member heteroalkylene and diradical together with the azetidinyl (when n is 0), pyrrolidinyl (when n is 1) or the piperidinyl (when n is 2) form a bicyclic bridged ring system, said bicyclic bridged ring system having a total of 6-9 ring atoms with 1-3 of the ring atoms selected from O, N and S; and the $C_1$-$C_4$ alkylene or a 1-4 member heteroalkylene is optionally further substituted with 1-5 groups selected from -oxo- and $R^w$.

16. The compound or salt of claim 1, wherein each p is 0.

17. The compound or salt of claim 1, wherein each p is 1.

18. A pharmaceutical composition comprising the compound or salt of claim 1, and a pharmaceutically acceptable carrier.

* * * * *

UNITED STATES PATENT AND TRADEMARK OFFICE
CERTIFICATE OF CORRECTION

PATENT NO. : 8,518,952 B2  
APPLICATION NO. : 13/057558  
DATED : August 27, 2013  
INVENTOR(S) : Braganza et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 220 days.

Signed and Sealed this  
Twenty-fourth Day of February, 2015

Michelle K. Lee  
*Deputy Director of the United States Patent and Trademark Office*